United States Patent
Schaffer et al.

(10) Patent No.: US 9,580,720 B2
(45) Date of Patent: Feb. 28, 2017

(54) CELLS AND METHODS FOR PRODUCING RHAMNOLIPIDS

(71) Applicant: EVONIK DEGUSSA GMBH, Essen (DE)

(72) Inventors: Steffen Schaffer, Herten (DE); Mirja Wessel, Bochum (DE); Anja Thiessenhusen, Muenster (DE); Nadine Stein, Recklinghausen (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 14/642,879

(22) Filed: Mar. 10, 2015

(65) Prior Publication Data

US 2015/0247151 A1 Sep. 3, 2015

Related U.S. Application Data

(62) Division of application No. 13/812,625, filed as application No. PCT/EP2011/062441 on Jul. 2, 2011, now Pat. No. 9,005,928.

(30) Foreign Application Priority Data

Jul. 28, 2010 (DE) .................. 10 2010 032 484

(51) Int. Cl.

| | | |
|---|---|---|
| C12N 15/78 | (2006.01) | |
| A01N 43/16 | (2006.01) | |
| C12N 9/10 | (2006.01) | |
| C12P 19/44 | (2006.01) | |
| C12N 9/14 | (2006.01) | |
| C12N 15/52 | (2006.01) | |
| C12N 15/70 | (2006.01) | |
| C12N 15/77 | (2006.01) | |

(52) U.S. Cl.
CPC ............. *C12N 15/78* (2013.01); *A01N 43/16* (2013.01); *C12N 9/1051* (2013.01); *C12N 9/14* (2013.01); *C12N 15/52* (2013.01); *C12N 15/70* (2013.01); *C12N 15/77* (2013.01); *C12P 19/44* (2013.01); *C12Y 306/04013* (2013.01); *Y02P 20/52* (2015.11)

(58) Field of Classification Search
None
See application file for complete search history.

(56) References Cited

U.S. PATENT DOCUMENTS

| | | |
|---|---|---|
| 4,601,893 A | 7/1986 | Cardinal |
| 5,175,108 A | 12/1992 | Bachmann et al. |
| 6,136,576 A | 10/2000 | Diaz-Torres et al. |
| 7,118,904 B2 | 10/2006 | Mockel et al. |
| 2007/0020624 A1 | 1/2007 | Rubenfield et al. |

FOREIGN PATENT DOCUMENTS

| | | |
|---|---|---|
| DE | 100 31 999 A1 | 4/2001 |
| EP | 0 473 869 A2 | 3/1992 |
| EP | 1 083 225 A1 | 3/2001 |
| GB | 1009370 | 11/1965 |
| WO | 96/15246 A1 | 5/1996 |
| WO | WO 2004/050882 A1 | 6/2004 |
| WO | WO 2004/083385 A1 | 9/2004 |

OTHER PUBLICATIONS

Nelson et al. Uniprot Accession No. Q88LZ3 (Oct. 31, 2006).*
Nelson et al. Uniprot Accession No. Q88LZ1 (Oct. 31, 2006).*
Nelson et al. Uniprot Accession No. Q88LZ4 (Oct. 31, 2006).*
Nelson et al. Uniprot Accession No. Q88LZ2 (Oct. 31, 2006).*
Rahim, et al., Mol. Mocrobiol. (2001) 40(3), pp. 708-718.
Ochsner, et al., J. Biol. Chem. (1994) 269 (31), pp. 19787-19795.
Ochsner, Urs A. et al., "Production of Pseudomonas aeruginosa Rhamnolipid Biosurfactants in Heterologous Hosts", Applied and Environmental Microbiology (Sep. 1995), vol. 61, No. 9, pp. 3503-3506.
Fang, Xiangdong et al., "Final Report: Bio-Engineering High Performance Microbial Strains for MEOR by Directed Protein Evolution Technology", Oil & Natural Gas Technology (Jul. 2, 2008), prepared for U.S. Dept. of Energy, National Energy Technology Laboratory, pp. II-V, 1-90.
"Pseudomonas aeruginosa rhamnosyl transferase genes and regulatory protein gene, complete cds.", XP002657937, retrieved from EBI accession No. EM_PRO: L28170, (May 5, 1994).
International Search Report dated Oct. 7, 2011 issued in PCT/EP2011/062441.
Lohaus, C., et al., "Proteomforschung" Biospektrum, 1998, vol. 5, pp. 32-39.
Rodriguez, R. L., et al., "Vectors: a survey of molecular cloning vectors and their uses", 1987, pp. 179-204, Butterworths Publishers, Stoneham, Massachusetts.
http://web.archive.org/web/20071210070444/http://www3.dsmz.de/species/bacteria.htm, printed on Dec. 3, 2013.
http://web.archive.org/web/20071026085918/http://www3.dsmz.de/species/yeasts.htm, printed on Dec. 3, 2013.
http://web.archive.org/web/20071210070449/http://www3.dsmz.de/species/fungi.htm, printed on Dec. 3, 2013.
Huisman, G. W., et al., "Metabolism of Poly(3-hydroxyalkanoates) (PHAs) by Pseudomonas oleovorans", The Journal of Biological Chemistry, Feb. 5, 1991, vol. 266, No. 4, pp. 2191-2198.
Liebl, W. et al., High efficiency electroporation of intact Corynebacterium glutamicum cells, FEMS Microbiology, (1989), Letters 65, pp. 299-304.
Altschul, S.F. et al., "Basic Local Alignment Search Tool", J. Mol. Biol., Oct. 1990, vol. 215, No. 3, pp. 403-410.
Cha, M. et al., "Heterologous production of Pseudomonas aeruginosa EMS1 biosurfactant Pseudomonas putida", May 2008, Biosource Technology, vol. 99, No. 7, pp. 2192-2199.
Rehm, B.H.A. et al., "Role of Fatty Acid De Novo Biosynthesis in Polyhydroxyalkanoic Acid (PHA) and Rhamnolipid Synthesis by Pseudomonads: Establishment of the Transacylase (Pha-G)-Mediated Pathway for PHA Biosynthesis in *Escherichia coli*", Applied and Environmental Microbiology, Jul. 2001, vol. 67, No. 7, pp. 3102-3109.

(Continued)

*Primary Examiner* — Nashaat Nashed
(74) *Attorney, Agent, or Firm* — Scully Scott Murphy and Presser; Frank Digiglio

(57) ABSTRACT

This invention relates to cells and nucleic acids and also use thereof for producing rhamnolipids, and also methods for producing rhamnolipids.

11 Claims, 3 Drawing Sheets

(56) References Cited

OTHER PUBLICATIONS

Devereux, J. et al., "A Comprehensive set of Sequence Analysis Programs for the VAX", Nuclei Acids Research, Jan. 1984, vol. 12, No. 1, pp. 387-395.
Kovach, M.E. et al., "Four new derivatives of the broad-host-range cloning vector pBBR1MCS, carrying different antibiotic-resistance cassettes", Gene, Dec. 1, 1995, vol. 166, No. 1, pp. 175-176.
Iwasaki, K. et al., "Transformation of Pseudomonas putida by Electroporation", Biosci. Biotechnol. Biochem., May 1994, vol. 58, No. 5, pp. 851-854.
Ben-Bassat, A., et al., Processing of the Initiation Methionine from Proteins: Properties of the Escherichia coli Methionine Aminopeptidase and its Gene Structure, Journal of Bacteriology, Feb. 1987, vol. 169, No. 2, pp. 751-757.
Sahin-Toth, M., et al. "Cysteine scanning mutagenesis of the N-terminal 32 amino acid residues in the lactose permease of Escherichia coli", Protein Science, Feb. 1994, vol. 3, No. 2, pp. 240-247.
Ouyang, S., et al., "Construction of pha-Operon-Defined Knockout Mutants of Pseudomonas putida KT2442 and their Applications in Poly(hydroxyalkanoate) Production", Macromol. Biosci, Feb. 12, 2007, vol. 7, No. 2, pp. 227-233.
Singh, B., et al., "Characterization of a Pseudomonas putida transporter (AatJMQP) required for acidic amino acid uptake: biochemical properties and regulation by the Aau two-component system", Microbiology, Mar. 2008, vol. 154 (Pt. 3), pp. 797-809.
Dubeau, D., et al., "Burkholderia thailandensis harbors two identical rhl gene clusters responsible for the biosynthesis of rhamnolipds", BMC Microbiology, Dec. 17, 2009, vol. 9, No. 263, pp. 1-12.
Jensen, P.R., et al., "Artificial Promoters for Metabolic Optimization", Biotechnology and Bioengineering, Apr. 20/May 5, 1998, Issue 2-3, pp. 191-195.
Reinscheid, D.J., et al., "Stable Expression of hom-1-thrB in Corynebacterium glutamicum and Its Effect on the Carbon Flux to Threonine and Related Amino Acids", Applied and Environmental Microbiology, Jan. 1994, vol. 60, No. 1, pp. 126-132.
Labarre, J., et al., Gene Replacement, Integration, and Amplification at the gdhA Locus of Corynebacterium glutamicum, Journal of Bacteriology, Feb. 1993, vol. 175, No. 4, pp. 1001-1007.
Schafer, A., et al., "Increased Fertility of Corynebacterium glutamicum Recipients Intergeneric Matings with Escherichia coli after Stress Exposure", Applied and Environmental Microbiology, Feb. 1994, vol. 60, No. 2, pp. 756-759.
Freedberg, W.B., et al., "Three Kinds of Controls Affecting the Expression of the glp Regulon in Escherichia coli", Journal of Bacteriology, Sep. 1973, vol. 115, No. 3, pp. 816-823.
Ray, W.K., et al., "Characterization of a 12-Kilodalton Rhodanese Encoded by glpE of Escherichia coli and Its Interaction with Thioredoxin", Journal of Bacteriology, Apr. 2000, vol. 182, No. 8, pp. 2277-2284.
Malumbres, M., et al., "Codon preference in Corynebacteria", Gene, Nov. 30, 1993, vol. 134, No. 1, pp. 15-24.
O'Regan, M., et al., "Cloning and nucleotide sequence of the phosphoenolpyruvate carboxylase-coding gene of Corynebacterium glutamicum ATCC13032", Gene, Apr. 30, 1989, vol. 77, No. 2, pp. 237-251.
Eikmanns, B.J., et al., "A family of Corynebacterium glutamicum/ Escherichia coli shuttle vectors for cloning, controlled gene expression, and promoter probing", Gene, Jun. 15, 1991, vol. 102, No. 1, pp. 93-98.
Guerrero, C., et al., "Directed mutagenesis of a regulatory palindromic sequence upstream from the Brevibacterium lactofermentum tryotophan operon", Gene, Jan. 28, 1994, vol. 138, No. 1-2, pp. 35-41.
Donahue, J.L., et al., "Purification and Characterization of glpX-Encoded Fructose 1,6-Bisphosphatase, a New Enzyme of the Glycerol 3-Phosphate Regulon of Escherichia coli", Journal of Bacteriology, Oct. 2000, vol. 182, No. 19, pp. 5624-5627.

Wilson, M.J., et al., "Analysis of Promoters Recognized by PvdS, an Extracytoplasmic-Function Sigma Factor Protein from Pseudomonas aeruginosa", Journal of Bacteriology, Mar. 2001, vol. 183, No. 6, pp. 2151-2155.
Lottspeich, F., "Proteomanalyse—ein Weg zur Funktionsanalyse von Proteinen", Angew. Chem., Sep. 3, 1999, vol. 111,No. 17, pp. 2630-2647.
Tsuchiya, M., et al., Genetic Control Systems of Escherichia coli Can Confer Inducible Expression of Cloned Genes in Coryneform Bacteria, Bio/technology, Apr. 1988, vol. 6, pp. 428-430.
Lee, Y., et al., "Inactivation of the Pseudomonas putida KT2440 dsbA gene promotes extracellular matrix production and biofilm formation", FEMS Microbiol. Lett., Aug. 2009, vol. 297, pp. 38-48.
Tauch, A., et al., "Corynebacterium glutamicum DNA is subjected to methylation-restriction in Escherichia coli", FEMS Microbiol. Lett., Nov. 1, 1994, vol. 123, No. 3, pp. 343-348.
Dunican, L.K., et al., "High Frequency Transformation of Whole Cells of Amino Acid Producing Coryneform Bacteria Using High Voltage Electroporation", Bio/technology, Oct. 1989, vol. 7, pp. 1067-1070.
Thierbach, G., et al., "Transformation of spheroplasts and protoplasts of Corynebacterium glutamicum", Appl. Microbiol. Biotechnol., Oct. 1988, vol. 29, pp. 356-362.
Schwarzer, A., et al., "Manipulation of Corynebacterium glutamicum by Gene Disruption and Replacement", Bio/technology, Jan. 1991, vol. 9, pp. 84-87.
Martin, J.F., et al., "Cloning Systems in Amino Acid-Producing Corynebacteria", Bio/technology, Feb. 1987, vol. 5, pp. 137-146.
Ren, Q., et al., "Mutants of Pseudomonas putida affected in poly-3-hydroxyalkanoate synthesis", Appl. Microbiol. Biotechnol., Jun. 1998, vol. 49, pp. 743-750.
Hochuli, E., et al., "Genetic Approach to Facilitate Purification of Recombinant Proteins with a Novel Metal Chelate Adsorbent", Bio/Technology, Nov. 1988, pp. 1321-1325.
Hermann, T., et al., "Proteome analysis of Corynebacterium glutamicum", Electrophoresis, May 2001, vol. 22, No. 9, pp. 1712-1723.
De Eugenio, L.I., et al., The turnover of medium-chain-length polyhydroxyalkanoates in Pseudomonas putida KT2442 and the fundamental role of PhaZ depolymerase for the metabolic balance:, Environmental Microbiology, Jan. 2010, vol. 12, No. 1, pp. 207-221.
Leitermann, F., et al., "Rhamnolipids", Handbook of Hydrocarbon and Lipid Microbiology, Jan. 1, 2010, vol. 4, pp. 3037-3051.
Goeddel, D.V., "Systems for Heterologous Gene Expression", Methods in Enzymology, Jun. 11, 1990, vol. 185, pp. 3-7.
Cabrera-Vlaaldares, N., et al. "Monorhamnolipids and 3-(3-hydroxyalkanoyloxy) alkanoic acids (HAAs) production using Escherichia coli as a heterologous host)" Appl Microbiol Bootechnol 73:187-194 (2006).
Kornfeld, S., et al., "The Enzymatic Synthesis of Thymidine-linked Sugars" The Journal of Biological Chemistry 236(6):1761-1794 (1961).
Rahim, R., et al., "Involvement of the rml locus in core oligosaccharide and O polysaccharide assembly in Pseudomonas aeruginosa" Microbiology 146:2803-2814 (2000).
Boels, Ingeborg C., et al., "Identification and Functional Chracterization of the Lactococcus lactis rfb Operon, Required for dTDP-Rhamnose Biosynthesis", Journal of Bacteriology, Mar. 2004, pp. 1239-1248.
C.P. Chou, Engineering cell physiology to enhance recombinant protein production in Escherichia coli. Appl Microbiol Biotechnol (2007) 76:521-532.
K. Terpe, Overview of bacterial expression systems for heterologous protein production: from molecular and biochemical fundamentals to commercial systems. Appl Microbiol Biotechnol (2006) 72:211-222.
Retallack et al. Reliable protein production in a Pseudomonas fluorescens expression system. Protein Expression and Purification. 81:2, (2012) 157-165.

(56) References Cited

OTHER PUBLICATIONS

Brinkrolf, et al. The transcriptional regulatory repertoire of Corynebacterium glutamicum: Reconstruction of the network controlling pathways involved in lysine and glutamate production. Journal of Biotechnology 149 (2010) 173-182.

* cited by examiner

SEQUENCE LISTING

```
<160> NUMBER OF SEQ ID NOS: 92

<210> SEQ ID NO 1
<211> LENGTH: 888
<212> TYPE: DNA
<213> ORGANISM: Pseudomonas aeruginosa
<220> FEATURE:
<221> NAME/KEY: CDS
<222> LOCATION: (1)..(888)

<400> SEQUENCE: 1 atg cgg cgc gaa agt ctg ttg gta tcg gtt tgc aag ggc ctg cgg gta        48
Met Arg Arg Glu Ser Leu Leu Val Ser Val Cys Lys Gly Leu Arg Val
1               5                   10                  15 cat gtc gag cgc gtt ggg cag gat ccc ggg cgc agc acg gtg atg ctg        96
His Val Glu Arg Val Gly Gln Asp Pro Gly Arg Ser Thr Val Met Leu
            20                  25                  30 gtc aac ggc gcg atg gcg acc acc gcc tcg ttc gcc cgg acc tgc aag       144
Val Asn Gly Ala Met Ala Thr Thr Ala Ser Phe Ala Arg Thr Cys Lys
        35                  40                  45 tgc ctg gcc gaa cat ttc aac gtg gtg ctg ttc gac ctg ccc ttc gcc       192
Cys Leu Ala Glu His Phe Asn Val Val Leu Phe Asp Leu Pro Phe Ala
    50                  55                  60 ggg cag tcg cgt cag cac aac ccg cag cgg ggg ttg atc acc aag gac       240
Gly Gln Ser Arg Gln His Asn Pro Gln Arg Gly Leu Ile Thr Lys Asp
65                  70                  75                  80 gac gag gtg gaa atc ctc ctg gcg ctg atc gag cgc ttc gag gtc aat       288
Asp Glu Val Glu Ile Leu Leu Ala Leu Ile Glu Arg Phe Glu Val Asn
                85                  90                  95
```

| | | |
|---|---|---|
| cac ctg gtc tcc gcg tcc tgg ggc ggt atc tcc acg ctg ctg gcg ctg<br>His Leu Val Ser Ala Ser Trp Gly Gly Ile Ser Thr Leu Leu Ala Leu<br>               100                       105                       110 | | 336 |
| tcg cgc aat ccg cgc ggc atc cgc agc tcg gtg gtg atg gca ttc gcc<br>Ser Arg Asn Pro Arg Gly Ile Arg Ser Ser Val Val Met Ala Phe Ala<br>         115                       120                       125 | | 384 |
| cct gga ctg aac cag gcg atg ctc gac tac gtc ggg cgg gcg cag gcg<br>Pro Gly Leu Asn Gln Ala Met Leu Asp Tyr Val Gly Arg Ala Gln Ala<br>130                       135                       140 | | 432 |
| ctg atc gag ctg gac gac aag tcg gcg atc ggc cat ctg ctc aac gag<br>Leu Ile Glu Leu Asp Asp Lys Ser Ala Ile Gly His Leu Leu Asn Glu<br>145                       150                       155                       160 | | 480 |
| acc gtc ggc aaa tac ctg ccg ccg cgc ctg aaa gcc agc aac cat cag<br>Thr Val Gly Lys Tyr Leu Pro Pro Arg Leu Lys Ala Ser Asn His Gln<br>                   165                       170                       175 | | 528 |
| cac atg gct tcg ctg gcc acc ggc gaa tac gag cag gcg cgc ttt cac<br>His Met Ala Ser Leu Ala Thr Gly Glu Tyr Glu Gln Ala Arg Phe His<br>         180                       185                       190 | | 576 |
| atc gac cag gtg ctg gcg ctc aac gat cgg ggc tac ctg gct tgc ctg<br>Ile Asp Gln Val Leu Ala Leu Asn Asp Arg Gly Tyr Leu Ala Cys Leu<br>195                       200                       205 | | 624 |
| gag cgg atc cag agc cac gtg cat ttc atc aac ggc agc tgg gac gaa<br>Glu Arg Ile Gln Ser His Val His Phe Ile Asn Gly Ser Trp Asp Glu<br>210                       215                       220 | | 672 |
| tac acc acc gcc gag gac gcc cgc cag ttc cgc gac tac ctg ccg cac<br>Tyr Thr Thr Ala Glu Asp Ala Arg Gln Phe Arg Asp Tyr Leu Pro His<br>225                       230                       235                       240 | | 720 |
| tgc agt ttc tcg cgg gtg gag ggc acc ggg cat ttc ctc gac ctg gag<br>Cys Ser Phe Ser Arg Val Glu Gly Thr Gly His Phe Leu Asp Leu Glu<br>                   245                       250                       255 | | 768 |
| tcc aag ctg gcc gcg gta cgc gtg cac cgc gcc ctg ctc gag cac ctg<br>Ser Lys Leu Ala Ala Val Arg Val His Arg Ala Leu Leu Glu His Leu<br>         260                       265                       270 | | 816 |
| ctg aag caa ccg gag ccg cag cgg gcg gaa cgc gcg gcg gga ttc cac<br>Leu Lys Gln Pro Glu Pro Gln Arg Ala Glu Arg Ala Ala Gly Phe His<br>               275                       280                       285 | | 864 |
| gag atg gcc atc ggc tac gcc tga<br>Glu Met Ala Ile Gly Tyr Ala<br>         290                       295 | | 888 |

<210> SEQ ID NO 2
<211> LENGTH: 295
<212> TYPE: PRT
<213> ORGANISM: Pseudomonas aeruginosa

<400> SEQUENCE: 2

Met Arg Arg Glu Ser Leu Leu Val Ser Val Cys Lys Gly Leu Arg Val
1                   5                       10                       15

His Val Glu Arg Val Gly Gln Asp Pro Gly Arg Ser Thr Val Met Leu
                   20                       25                       30

Val Asn Gly Ala Met Ala Thr Thr Ala Ser Phe Ala Arg Thr Cys Lys
         35                       40                       45

Cys Leu Ala Glu His Phe Asn Val Val Leu Phe Asp Leu Pro Phe Ala
50                       55                       60

Gly Gln Ser Arg Gln His Asn Pro Gln Arg Gly Leu Ile Thr Lys Asp
65                   70                       75                       80

Asp Glu Val Glu Ile Leu Leu Ala Leu Ile Glu Arg Phe Glu Val Asn
                   85                       90                       95

```
His Leu Val Ser Ala Ser Trp Gly Gly Ile Ser Thr Leu Leu Ala Leu
                100                 105                 110

Ser Arg Asn Pro Arg Gly Ile Arg Ser Ser Val Val Met Ala Phe Ala
            115                 120                 125

Pro Gly Leu Asn Gln Ala Met Leu Asp Tyr Val Gly Arg Ala Gln Ala
        130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
290                 295

<210> SEQ ID NO 3
<211> LENGTH: 1281
<212> TYPE: DNA
<213> ORGANISM: Pseudomonas aeruginosa
<220> FEATURE:
<221> NAME/KEY: CDS
<222> LOCATION: (1)..(1281)

<400> SEQUENCE: 3 atg cac gcc atc ctc atc gcc atc ggc tcg gcc ggc gac gta ttt ccc      48
Met His Ala Ile Leu Ile Ala Ile Gly Ser Ala Gly Asp Val Phe Pro
1               5                   10                  15 ttc atc ggc ctg gcc cgg acc ctg aaa ttg cgc ggg cac cgc gtg agc      96
Phe Ile Gly Leu Ala Arg Thr Leu Lys Leu Arg Gly His Arg Val Ser
            20                  25                  30 ctc tgc acc atc ccg gtg ttt cgc gac gcg gtg gag cag cac ggc atc     144
Leu Cys Thr Ile Pro Val Phe Arg Asp Ala Val Glu Gln His Gly Ile
        35                  40                  45 gcg ttc gtc ccg ctg agc gac gaa ctg acc tac cgc cgg acc atg ggc     192
Ala Phe Val Pro Leu Ser Asp Glu Leu Thr Tyr Arg Arg Thr Met Gly
    50                  55                  60 gat ccg cgc ctg tgg gac ccc aag acg tcc ttc ggc gtg ctc tgg caa     240
Asp Pro Arg Leu Trp Asp Pro Lys Thr Ser Phe Gly Val Leu Trp Gln
65                  70                  75                  80 acc atc gcc ggg atg atc gag ccg gtc tac gag tac gtc tcg gcg cag     288
Thr Ile Ala Gly Met Ile Glu Pro Val Tyr Glu Tyr Val Ser Ala Gln
                85                  90                  95 cgc cat gac gac atc gtg gtg gtc ggc tcg ctc tgg gcg ctg ggc gca     336
Arg His Asp Asp Ile Val Val Val Gly Ser Leu Trp Ala Leu Gly Ala
            100                 105                 110 cgc atc gct cac gag aag tac ggg att ccc tac ctg tcc gcg cag gtc     384
```

```
Arg Ile Ala His Glu Lys Tyr Gly Ile Pro Tyr Leu Ser Ala Gln Val
        115                 120                 125 tcg cca tcg acc ttg ttg tcg gcg cac ctg ccg ccg gta cac ccc aag        432
Ser Pro Ser Thr Leu Leu Ser Ala His Leu Pro Pro Val His Pro Lys
        130                 135                 140 ttc aac gtg ccc gag cag atg ccg ctg gcg atg cgc aag ctg ctc tgg        480
Phe Asn Val Pro Glu Gln Met Pro Leu Ala Met Arg Lys Leu Leu Trp
145                 150                 155                 160 cgc tgc atc gag cgc ttc aag ctg gat cgc acc tgc gcg ccg gat atc        528
Arg Cys Ile Glu Arg Phe Lys Leu Asp Arg Thr Cys Ala Pro Asp Ile
                165                 170                 175 aac gcg gtg cgg cgc aag gtc ggc ctg gag acg ccg gtg aag cgc atc        576
Asn Ala Val Arg Arg Lys Val Gly Leu Glu Thr Pro Val Lys Arg Ile
            180                 185                 190 ttc acc caa tgg atg cat tcg ccg cag ggc gtg gtc tgc ctg ttc ccg        624
Phe Thr Gln Trp Met His Ser Pro Gln Gly Val Val Cys Leu Phe Pro
        195                 200                 205 gcc tgg ttc gcg ccg ccc cag cag gat tgg ccg caa ccc ctg cac atg        672
Ala Trp Phe Ala Pro Pro Gln Gln Asp Trp Pro Gln Pro Leu His Met
210                 215                 220 acc ggc ttc ccg ctg ttc gac ggc agt atc ccg ggg acc ccg ctc gac        720
Thr Gly Phe Pro Leu Phe Asp Gly Ser Ile Pro Gly Thr Pro Leu Asp
225                 230                 235                 240 gac gaa ctg caa cgc ttt ctc gat cag ggc agc cgg ccg ctg gtg ttc        768
Asp Glu Leu Gln Arg Phe Leu Asp Gln Gly Ser Arg Pro Leu Val Phe
                245                 250                 255 acc cag ggc tcg acc gaa cac ctg cag ggc gac ttc tac gcc atg gcc        816
Thr Gln Gly Ser Thr Glu His Leu Gln Gly Asp Phe Tyr Ala Met Ala
            260                 265                 270 ctg cgc gcg ctg gaa cgc ctc ggc gcg cgt ggg atc ttc ctc acc ggc        864
Leu Arg Ala Leu Glu Arg Leu Gly Ala Arg Gly Ile Phe Leu Thr Gly
        275                 280                 285 gcc ggc cag gaa ccg ctg cgc ggc ttg ccg aac cac gtg ctg cag cgc        912
Ala Gly Gln Glu Pro Leu Arg Gly Leu Pro Asn His Val Leu Gln Arg
290                 295                 300 gcc tac gcg cca ctg gga gcc ttg ctg cca tcg tgc gcc ggg ctg gtc        960
Ala Tyr Ala Pro Leu Gly Ala Leu Leu Pro Ser Cys Ala Gly Leu Val
305                 310                 315                 320 cat ccg ggc ggt atc ggc gcc atg agc ctg gcc ttg gcg gcg ggg gtg       1008
His Pro Gly Gly Ile Gly Ala Met Ser Leu Ala Leu Ala Ala Gly Val
                325                 330                 335 ccg cag gtg ctg ctg ccc tgc gcc cac gac cag ttc gac aat gcc gaa       1056
Pro Gln Val Leu Leu Pro Cys Ala His Asp Gln Phe Asp Asn Ala Glu
            340                 345                 350 cgg ctg gtc cgg ctc ggc tgc ggg atg cgc ctg ggc gtg cca ttg cgc       1104
Arg Leu Val Arg Leu Gly Cys Gly Met Arg Leu Gly Val Pro Leu Arg
        355                 360                 365 gag cag gag ttg cgc ggg gcg ctg tgg cgc ttg ctc gag gac ccg gcc       1152
Glu Gln Glu Leu Arg Gly Ala Leu Trp Arg Leu Leu Glu Asp Pro Ala
370                 375                 380 atg gcg gcg gcc tgt cgg cgt ttc atg gaa ttg tca caa ccg cac agt       1200
Met Ala Ala Ala Cys Arg Arg Phe Met Glu Leu Ser Gln Pro His Ser
385                 390                 395                 400 atc gct tgc ggt aaa gcg gcc cag gtg gtc gaa cgt tgt cat agg gag       1248
Ile Ala Cys Gly Lys Ala Ala Gln Val Val Glu Arg Cys His Arg Glu
                405                 410                 415 ggg gat gcg cga tgg ctg aag gct gcg tcc tga                           1281
Gly Asp Ala Arg Trp Leu Lys Ala Ala Ser
            420                 425
```

<210> SEQ ID NO 4
<211> LENGTH: 426
<212> TYPE: PRT
<213> ORGANISM: Pseudomonas aeruginosa

<400> SEQUENCE: 4

```
Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
            20                  25                  30

Leu Cys Thr Ile Pro Val Phe Arg Asp Ala Val Glu Gln His Gly Ile
        35                  40                  45

Ala Phe Val Pro Leu Ser Asp Glu Leu Thr Tyr Arg Arg Thr Met Gly
    50                  55                  60

Asp Pro Arg Leu Trp Asp Pro Lys Thr Ser Phe Gly Val Leu Trp Gln
65                  70                  75                  80

Thr Ile Ala Gly Met Ile Glu Pro Val Tyr Glu Tyr Val Ser Ala Gln
                85                  90                  95

Arg His Asp Asp Ile Val Val Gly Ser Leu Trp Ala Leu Gly Ala
            100                 105                 110

Arg Ile Ala His Glu Lys Tyr Gly Ile Pro Tyr Leu Ser Ala Gln Val
        115                 120                 125

Ser Pro Ser Thr Leu Leu Ser Ala His Leu Pro Pro Val His Pro Lys
    130                 135                 140

Phe Asn Val Pro Glu Gln Met Pro Leu Ala Met Arg Lys Leu Leu Trp
145                 150                 155                 160

Arg Cys Ile Glu Arg Phe Lys Leu Asp Arg Thr Cys Ala Pro Asp Ile
                165                 170                 175

Asn Ala Val Arg Arg Lys Val Gly Leu Glu Thr Pro Val Lys Arg Ile
            180                 185                 190

Phe Thr Gln Trp Met His Ser Pro Gln Gly Val Val Cys Leu Phe Pro
        195                 200                 205

Ala Trp Phe Ala Pro Pro Gln Gln Asp Trp Pro Gln Pro Leu His Met
    210                 215                 220

Thr Gly Phe Pro Leu Phe Asp Gly Ser Ile Pro Gly Thr Pro Leu Asp
225                 230                 235                 240

Asp Glu Leu Gln Arg Phe Leu Asp Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Gly Ala Arg Gly Ile Phe Leu Thr Gly
        275                 280                 285

Ala Gly Gln Glu Pro Leu Arg Gly Leu Pro Asn His Val Leu Gln Arg
    290                 295                 300

Ala Tyr Ala Pro Leu Gly Ala Leu Leu Pro Ser Cys Ala Gly Leu Val
305                 310                 315                 320

His Pro Gly Gly Ile Gly Ala Met Ser Leu Ala Leu Ala Ala Gly Val
                325                 330                 335

Pro Gln Val Leu Leu Pro Cys Ala His Asp Gln Phe Asp Asn Ala Glu
            340                 345                 350

Arg Leu Val Arg Leu Gly Cys Gly Met Arg Leu Gly Val Pro Leu Arg
        355                 360                 365

Glu Gln Glu Leu Arg Gly Ala Leu Trp Arg Leu Leu Glu Asp Pro Ala
    370                 375                 380
```

```
Met Ala Ala Ala Cys Arg Arg Phe Met Glu Leu Ser Gln Pro His Ser
385                 390                 395                 400

Ile Ala Cys Gly Lys Ala Ala Gln Val Val Glu Arg Cys His Arg Glu
            405                 410                 415

Gly Asp Ala Arg Trp Leu Lys Ala Ala Ser
        420                 425

<210> SEQ ID NO 5
<211> LENGTH: 978
<212> TYPE: DNA
<213> ORGANISM: Pseudomonas aeruginosa
<220> FEATURE:
<221> NAME/KEY: CDS
<222> LOCATION: (1)..(978)

<400> SEQUENCE: 5
```

| Codons | AA | Pos |
|---|---|---|
| atg gac cgg ata gac atg ggc gtg ctg gtg gta ctg ttc aat cct ggc | Met Asp Arg Ile Asp Met Gly Val Leu Val Val Leu Phe Asn Pro Gly | 48 |
| | 1             5              10             15 | |
| gac gac gac ctg gaa cac ctt ggc gaa ctg gcg gcg gcg ttt ccg caa | Asp Asp Asp Leu Glu His Leu Gly Glu Leu Ala Ala Ala Phe Pro Gln | 96 |
| | 20             25             30 | |
| ctg cgc ttc ctt gcc gtc gac aac tca ccg cac agc gat ccg cag cgc | Leu Arg Phe Leu Ala Val Asp Asn Ser Pro His Ser Asp Pro Gln Arg | 144 |
| | 35             40             45 | |
| aat gcc cgg ctg cgc ggg caa ggc atc gcc gtg ctg cac cac ggc aac | Asn Ala Arg Leu Arg Gly Gln Gly Ile Ala Val Leu His His Gly Asn | 192 |
| | 50             55             60 | |
| cgg cag ggc atc gcc ggc gcc ttc aac cag gga ctc gac gcg cta ttc | Arg Gln Gly Ile Ala Gly Ala Phe Asn Gln Gly Leu Asp Ala Leu Phe | 240 |
| 65             70             75             80 | | |
| cgg cgt ggc gtg cag ggt gtg ctg ctc gac cag gac tcc cgt ccc | Arg Arg Gly Val Gln Gly Val Leu Leu Leu Asp Gln Asp Ser Arg Pro | 288 |
| | 85             90             95 | |
| ggc ggc gcc ttc ctc gcc gcc cag tgg cgc aac ctg cag gcg cgc aac | Gly Gly Ala Phe Leu Ala Ala Gln Trp Arg Asn Leu Gln Ala Arg Asn | 336 |
| | 100             105             110 | |
| ggt cag gcc tgc ctg ctc ggc cca cgg atc ttc gac cgg ggt gac cgg | Gly Gln Ala Cys Leu Leu Gly Pro Arg Ile Phe Asp Arg Gly Asp Arg | 384 |
| | 115             120             125 | |
| cgc ttc ctg ccg gcc atc cat ctc gac gga ctg acg ctc agg caa ttg | Arg Phe Leu Pro Ala Ile His Leu Asp Gly Leu Thr Leu Arg Gln Leu | 432 |
| | 130             135             140 | |
| tct ctg gac ggc ctg acg acc ccg cag cgc acc tcg ttc ctg atc tcc | Ser Leu Asp Gly Leu Thr Thr Pro Gln Arg Thr Ser Phe Leu Ile Ser | 480 |
| 145             150             155             160 | | |
| tcc ggc tgc ctg ctg acc cgc gag gcc tac cag cgc ctc ggc cac ttc | Ser Gly Cys Leu Leu Thr Arg Glu Ala Tyr Gln Arg Leu Gly His Phe | 528 |
| | 165             170             175 | |
| gac gag gaa ctg ttc atc gac cac gtg gac acc gaa tac agc ctg cgc | Asp Glu Glu Leu Phe Ile Asp His Val Asp Thr Glu Tyr Ser Leu Arg | 576 |
| | 180             185             190 | |
| gcc cag gcg ctg gac gtg ccc ctg tac gtc gac ccg cgg ctg gtc ctc | Ala Gln Ala Leu Asp Val Pro Leu Tyr Val Asp Pro Arg Leu Val Leu | 624 |
| | 195             200             205 | |
| gag cac cgc atc ggc acg cgc aag acc cgc cgc ctc ggc ggt ctc agc | Glu His Arg Ile Gly Thr Arg Lys Thr Arg Arg Leu Gly Gly Leu Ser | 672 |
| | 210             215             220 | |
| ctc agc gcg atg aac cac gcc ccg ctg cgc cgc tac tac ctg gcg cgc | Leu Ser Ala Met Asn His Ala Pro Leu Arg Arg Tyr Tyr Leu Ala Arg | 720 |

```
                  225                 230                 235                 240
aac ggc ctg ctg gtc ctg cgc cgc tac gcc cgg tcc tcg ccg ctg gcc       768
Asn Gly Leu Leu Val Leu Arg Arg Tyr Ala Arg Ser Ser Pro Leu Ala
                    245                 250                 255 ctg ctg gcg aac ctg ccg acc ctg acc cag ggc ctc gcg gtg ctc ctg       816
Leu Leu Ala Asn Leu Pro Thr Leu Thr Gln Gly Leu Ala Val Leu Leu
                260                 265                 270 ctc gaa cgc gac aag ctg ctc aag ctg cgc tgc ctg ggc tgg ggc ctg       864
Leu Glu Arg Asp Lys Leu Leu Lys Leu Arg Cys Leu Gly Trp Gly Leu
            275                 280                 285 tgg gac ggc ctg cgg gga cgc ggc ggc gcg ctg gag acc aac cgc ccg       912
Trp Asp Gly Leu Arg Gly Arg Gly Gly Ala Leu Glu Thr Asn Arg Pro
        290                 295                 300 cgc ctg ctg aag cgc ctc gcc ggc ccg gcc gtg gcg tcc gta gct tcc       960
Arg Leu Leu Lys Arg Leu Ala Gly Pro Ala Val Ala Ser Val Ala Ser
305                 310                 315                 320 ggc aag gcc aag gcc tag                                               978
Gly Lys Ala Lys Ala
                325

<210> SEQ ID NO 6
<211> LENGTH: 325
<212> TYPE: PRT
<213> ORGANISM: Pseudomonas aeruginosa

<400> SEQUENCE: 6

Met Asp Arg Ile Asp Met Gly Val Leu Val Leu Phe Asn Pro Gly
1               5                   10                  15

Asp Asp Asp Leu Glu His Leu Gly Glu Leu Ala Ala Ala Phe Pro Gln
                20                  25                  30

Leu Arg Phe Leu Ala Val Asp Asn Ser Pro His Ser Asp Pro Gln Arg
            35                  40                  45

Asn Ala Arg Leu Arg Gly Gln Gly Ile Ala Val Leu His His Gly Asn
        50                  55                  60

Arg Gln Gly Ile Ala Gly Ala Phe Asn Gln Gly Leu Asp Ala Leu Phe
65                  70                  75                  80

Arg Arg Gly Val Gln Gly Val Leu Leu Leu Asp Gln Asp Ser Arg Pro
                85                  90                  95

Gly Gly Ala Phe Leu Ala Ala Gln Trp Arg Asn Leu Gln Ala Arg Asn
            100                 105                 110

Gly Gln Ala Cys Leu Leu Gly Pro Arg Ile Phe Asp Arg Gly Asp Arg
        115                 120                 125

Arg Phe Leu Pro Ala Ile His Leu Asp Gly Leu Thr Leu Arg Gln Leu
130                 135                 140

Ser Leu Asp Gly Leu Thr Thr Pro Gln Arg Thr Ser Phe Leu Ile Ser
145                 150                 155                 160

Ser Gly Cys Leu Leu Thr Arg Glu Ala Tyr Gln Arg Leu Gly His Phe
                165                 170                 175

Asp Glu Glu Leu Phe Ile Asp His Val Asp Thr Glu Tyr Ser Leu Arg
            180                 185                 190

Ala Gln Ala Leu Asp Val Pro Leu Tyr Val Asp Pro Arg Leu Val Leu
        195                 200                 205

Glu His Arg Ile Gly Thr Arg Lys Thr Arg Arg Leu Gly Gly Leu Ser
    210                 215                 220

Leu Ser Ala Met Asn His Ala Pro Leu Arg Arg Tyr Tyr Leu Ala Arg
225                 230                 235                 240
```

-continued

```
Asn Gly Leu Leu Val Leu Arg Arg Tyr Ala Arg Ser Ser Pro Leu Ala
            245                 250                 255

Leu Leu Ala Asn Leu Pro Thr Leu Thr Gln Gly Leu Ala Val Leu Leu
        260                 265                 270

Leu Glu Arg Asp Lys Leu Leu Lys Leu Arg Cys Leu Gly Trp Gly Leu
    275                 280                 285

Trp Asp Gly Leu Arg Gly Arg Gly Ala Leu Glu Thr Asn Arg Pro
290                 295                 300

Arg Leu Leu Lys Arg Leu Ala Gly Pro Ala Val Ala Ser Val Ala Ser
305                 310                 315                 320

Gly Lys Ala Lys Ala
            325
```

<210> SEQ ID NO 7
<211> LENGTH: 1269
<212> TYPE: DNA
<213> ORGANISM: Pseudomonas aeruginosa
<220> FEATURE:
<221> NAME/KEY: CDS
<222> LOCATION: (1)..(1269)

<400> SEQUENCE: 7

| | | |
|---|---|---|
| gtg tcc acg acc agc ctc tgc ccc tcc gcc acg cgg gaa cac ggt ccc<br>Val Ser Thr Thr Ser Leu Cys Pro Ser Ala Thr Arg Glu His Gly Pro<br>1               5                   10                  15 | 48 |
| ggc gcg aaa cgc gtc ctg cct ctg ctg ttc ctc acc tgc ctg ctg gat<br>Gly Ala Lys Arg Val Leu Pro Leu Leu Phe Leu Thr Cys Leu Leu Asp<br>            20                  25                  30 | 96 |
| gcc gct ggc gtc ggc ctg atc gtg ccc ctg ccg acg ctg atc ggc<br>Ala Ala Gly Val Gly Leu Ile Val Pro Leu Leu Pro Thr Leu Ile Gly<br>        35                  40                  45 | 144 |
| agc gtg gcg ccg ctg gcg gtc cgc gac gcg gcc acc tgg ggc gcc gcc<br>Ser Val Ala Pro Leu Ala Val Arg Asp Ala Ala Thr Trp Gly Ala Ala<br>    50                  55                  60 | 192 |
| ctg gtg atg acc ttc gcg ctg ctg caa ttg ttc ttt tcg ccg gtc ctc<br>Leu Val Met Thr Phe Ala Leu Leu Gln Leu Phe Phe Ser Pro Val Leu<br>65                  70                  75                  80 | 240 |
| ggc agc ctc agc gac cgc ttc gga cgc cgc ccc gtc ctg gtc ctg gcg<br>Gly Ser Leu Ser Asp Arg Phe Gly Arg Arg Pro Val Leu Val Leu Ala<br>            85                  90                  95 | 288 |
| atg ctc ggc ttc gcc ctc agc tat ctg ctg ctg gcg ctg gcc gac agc<br>Met Leu Gly Phe Ala Leu Ser Tyr Leu Leu Leu Ala Leu Ala Asp Ser<br>        100                 105                 110 | 336 |
| ctc tgg atg ctg ttc ctc ggt cgc gcg ctg gcc ggg ctc acc ggc gcc<br>Leu Trp Met Leu Phe Leu Gly Arg Ala Leu Ala Gly Leu Thr Gly Ala<br>    115                 120                 125 | 384 |
| agc gtg gcc acc gcg atg gcc tgc gcg gct gac ctc ggc acg cac ggg<br>Ser Val Ala Thr Ala Met Ala Cys Ala Ala Asp Leu Gly Thr His Gly<br>130                 135                 140 | 432 |
| cag cgc acc cgg cac ttc ggc tgg ctg tac gcc ggc ctc gcc ctg ggc<br>Gln Arg Thr Arg His Phe Gly Trp Leu Tyr Ala Gly Leu Ala Leu Gly<br>145                 150                 155                 160 | 480 |
| atg atc ctc ggc ccc gcc ctc ggt ggg ctg ctg gcg gtg cac ggc acg<br>Met Ile Leu Gly Pro Ala Leu Gly Gly Leu Leu Ala Val His Gly Thr<br>            165                 170                 175 | 528 |
| acg ctg ccg ctg ttg ctg gcc gcc ggc ctg tgc ctg ctc aac gcc ctg<br>Thr Leu Pro Leu Leu Leu Ala Ala Gly Leu Cys Leu Leu Asn Ala Leu<br>        180                 185                 190 | 576 |
| ctc gcc ggc ctg ttc ctc gag gaa acc ctg ccc ccg acg cga cgc cgc<br>Leu Ala Gly Leu Phe Leu Glu Glu Thr Leu Pro Pro Thr Arg Arg Arg | 624 |

-continued

```
              195                 200                 205
cgc ctg gac ccg agg cgg atg aat gcc ttg cgc tcg atc agc ggc ctg      672
Arg Leu Asp Pro Arg Arg Met Asn Ala Leu Arg Ser Ile Ser Gly Leu
    210                 215                 220 gct cgg caa ccg ggg gtc gga cgc ctg ctg gcg gtg ctt gcc ctg gta      720
Ala Arg Gln Pro Gly Val Gly Arg Leu Leu Ala Val Leu Ala Leu Val
225                 230                 235                 240 ttc ctc ggc ttg cag gcg gtg atg gtg gtc tgg ccg ttc ttc gtg atc      768
Phe Leu Gly Leu Gln Ala Val Met Val Val Trp Pro Phe Phe Val Ile
                245                 250                 255 gag aag ttt cac tgg agc agc gcc tgg atc ggc tac tcg ctg gcc ctc      816
Glu Lys Phe His Trp Ser Ser Ala Trp Ile Gly Tyr Ser Leu Ala Leu
            260                 265                 270 tac ggc gtg ctc gcg gtg ctc gcc cag acc ctc ggc gtg aac ctc tgc      864
Tyr Gly Val Leu Ala Val Leu Ala Gln Thr Leu Gly Val Asn Leu Cys
        275                 280                 285 aag cgg cgc ctg gac gac gcc cgc ctg ctg cgc ctg ggc ctc gcc ctg      912
Lys Arg Arg Leu Asp Asp Ala Arg Leu Leu Arg Leu Gly Leu Ala Leu
    290                 295                 300 caa ggc tgc ggc ctg ctg ctg ttc gcc ctg gtc gac tcg tca ttc tgg      960
Gln Gly Cys Gly Leu Leu Leu Phe Ala Leu Val Asp Ser Ser Phe Trp
305                 310                 315                 320 ctg gtc tgc gcg ctg ctg ccc ttc gcg ctc ggc agc ctc gcc acc ccg     1008
Leu Val Cys Ala Leu Leu Pro Phe Ala Leu Gly Ser Leu Ala Thr Pro
                325                 330                 335 gcc atg cag ggg ctg ctc tcg gcc cgc gtg ccg gtc gac cgc cag ggc     1056
Ala Met Gln Gly Leu Leu Ser Ala Arg Val Pro Val Asp Arg Gln Gly
            340                 345                 350 gag ttg cag ggc gtg ctg agc agc ctg atg agc ctc gcc gcg atc gtc     1104
Glu Leu Gln Gly Val Leu Ser Ser Leu Met Ser Leu Ala Ala Ile Val
        355                 360                 365 ggt ccg ccg ctg atg agc ggc ctg ttc cac tgg ggc agc ggt ccg ctc     1152
Gly Pro Pro Leu Met Ser Gly Leu Phe His Trp Gly Ser Gly Pro Leu
    370                 375                 380 gcg ccg ctg ccc ctg gcc ggc gcg cca ttc ctc gcc ggc gcc ctt ctc     1200
Ala Pro Leu Pro Leu Ala Gly Ala Pro Phe Leu Ala Gly Ala Leu Leu
385                 390                 395                 400 gtt ctg gcc ggg ctg gtc ctg gcc tgg caa ctt cga cct acg gga gaa     1248
Val Leu Ala Gly Leu Val Leu Ala Trp Gln Leu Arg Pro Thr Gly Glu
                405                 410                 415 gaa cga tca tgg acc gga tag                                         1269
Glu Arg Ser Trp Thr Gly
            420
```

<210> SEQ ID NO 8
<211> LENGTH: 422
<212> TYPE: PRT
<213> ORGANISM: Pseudomonas aeruginosa

<400> SEQUENCE: 8

Val Ser Thr Thr Ser Leu Cys Pro Ser Ala Thr Arg Glu His Gly Pro
1               5                   10                  15

Gly Ala Lys Arg Val Leu Pro Leu Leu Phe Leu Thr Cys Leu Leu Asp
            20                  25                  30

Ala Ala Gly Val Gly Leu Ile Val Pro Leu Leu Pro Thr Leu Ile Gly
        35                  40                  45

Ser Val Ala Pro Leu Ala Val Arg Asp Ala Ala Thr Trp Gly Ala Ala
    50                  55                  60

Leu Val Met Thr Phe Ala Leu Leu Gln Leu Phe Phe Ser Pro Val Leu

```
                65                  70                  75                  80
Gly Ser Leu Ser Asp Arg Phe Gly Arg Arg Pro Val Leu Val Leu Ala
                    85                  90                  95
Met Leu Gly Phe Ala Leu Ser Tyr Leu Leu Ala Leu Ala Asp Ser
                100                 105                 110
Leu Trp Met Leu Phe Leu Gly Arg Ala Leu Ala Gly Leu Thr Gly Ala
                115                 120                 125
Ser Val Ala Thr Ala Met Ala Cys Ala Ala Asp Leu Gly Thr His Gly
            130                 135                 140
Gln Arg Thr Arg His Phe Gly Trp Leu Tyr Ala Gly Leu Ala Leu Gly
145                 150                 155                 160
Met Ile Leu Gly Pro Ala Leu Gly Gly Leu Leu Ala Val His Gly Thr
                165                 170                 175
Thr Leu Pro Leu Leu Leu Ala Ala Gly Leu Cys Leu Leu Asn Ala Leu
                180                 185                 190
Leu Ala Gly Leu Phe Leu Glu Glu Thr Leu Pro Pro Thr Arg Arg Arg
                195                 200                 205
Arg Leu Asp Pro Arg Arg Met Asn Ala Leu Arg Ser Ile Ser Gly Leu
            210                 215                 220
Ala Arg Gln Pro Gly Val Gly Arg Leu Leu Ala Val Leu Ala Leu Val
225                 230                 235                 240
Phe Leu Gly Leu Gln Ala Val Met Val Val Trp Pro Phe Phe Val Ile
                245                 250                 255
Glu Lys Phe His Trp Ser Ser Ala Trp Ile Gly Tyr Ser Leu Ala Leu
                260                 265                 270
Tyr Gly Val Leu Ala Val Leu Ala Gln Thr Leu Gly Val Asn Leu Cys
            275                 280                 285
Lys Arg Arg Leu Asp Asp Ala Arg Leu Leu Arg Leu Gly Leu Ala Leu
            290                 295                 300
Gln Gly Cys Gly Leu Leu Leu Phe Ala Leu Val Asp Ser Ser Phe Trp
305                 310                 315                 320
Leu Val Cys Ala Leu Leu Pro Phe Ala Leu Gly Ser Leu Ala Thr Pro
                325                 330                 335
Ala Met Gln Gly Leu Leu Ser Ala Arg Val Pro Val Asp Arg Gln Gly
            340                 345                 350
Glu Leu Gln Gly Val Leu Ser Ser Leu Met Ser Leu Ala Ala Ile Val
            355                 360                 365
Gly Pro Pro Leu Met Ser Gly Leu Phe His Trp Gly Ser Gly Pro Leu
        370                 375                 380
Ala Pro Leu Pro Leu Ala Gly Ala Pro Phe Leu Ala Gly Ala Leu Leu
385                 390                 395                 400
Val Leu Ala Gly Leu Val Leu Ala Trp Gln Leu Arg Pro Thr Gly Glu
                405                 410                 415
Glu Arg Ser Trp Thr Gly
            420

<210> SEQ ID NO 9
<211> LENGTH: 882
<212> TYPE: DNA
<213> ORGANISM: Pseudomonas putida
<220> FEATURE:
<221> NAME/KEY: CDS
<222> LOCATION: (1)..(882)

<400> SEQUENCE: 9
```

```
atg gct cgt aaa gga att att ctg gcc ggt tcg ggt aca cgc ctg        48
Met Ala Arg Lys Gly Ile Ile Leu Ala Gly Ser Gly Thr Arg Leu
 1               5                  10                  15 cat ccg gcc aca ctt tcg gtt tcg aag cag ctg ctg ccg gtg tat gac    96
His Pro Ala Thr Leu Ser Val Ser Lys Gln Leu Leu Pro Val Tyr Asp
                20                  25                  30 aaa ccg atg atc tac tac ccg ctg agc acc ctg ctc gct ggt atc       144
Lys Pro Met Ile Tyr Tyr Pro Leu Ser Thr Leu Leu Ala Gly Ile
            35                  40                  45 cgg gac atc ctg atc att tcc acc ccg cag gac acc ccg cgc ttc gaa   192
Arg Asp Ile Leu Ile Ile Ser Thr Pro Gln Asp Thr Pro Arg Phe Glu
50                  55                  60 cag ctg ctg ggc gat ggc agc cag tgg ggc ctg aac ctg tca tac gca   240
Gln Leu Leu Gly Asp Gly Ser Gln Trp Gly Leu Asn Leu Ser Tyr Ala
65                  70                  75                  80 ata caa cca agc ccg gat ggc ttg gcg caa gcg ttc acc atc ggc gct   288
Ile Gln Pro Ser Pro Asp Gly Leu Ala Gln Ala Phe Thr Ile Gly Ala
                85                  90                  95 gac ttc atc ggt aac gac cct tct gcg ttg gtt ctc ggt gac aat att   336
Asp Phe Ile Gly Asn Asp Pro Ser Ala Leu Val Leu Gly Asp Asn Ile
            100                 105                 110 ttc tac ggc cat gac ttc cag gca ctg cta ttg aac gca gat aaa cgt   384
Phe Tyr Gly His Asp Phe Gln Ala Leu Leu Leu Asn Ala Asp Lys Arg
        115                 120                 125 gaa tcc ggt gct tca gta ttc gct tat cat gtt cat gac cca gaa cgc   432
Glu Ser Gly Ala Ser Val Phe Ala Tyr His Val His Asp Pro Glu Arg
130                 135                 140 tat ggc gta gcg gag ttt gac gat agc ggt cgc gta ttg tcg ctg gaa   480
Tyr Gly Val Ala Glu Phe Asp Asp Ser Gly Arg Val Leu Ser Leu Glu
145                 150                 155                 160 gaa aaa ccg gca gtt cca aag tct agc tat gcg gtc acc ggc ctg tat   528
Glu Lys Pro Ala Val Pro Lys Ser Ser Tyr Ala Val Thr Gly Leu Tyr
                165                 170                 175 ttc tat gac aat cag gta gtc aat ctg gct cgc gag ctg aag cct tcc   576
Phe Tyr Asp Asn Gln Val Val Asn Leu Ala Arg Glu Leu Lys Pro Ser
            180                 185                 190 cca cgt ggc gag ctg gaa atc acc gac ctc aac aac ctt tac ttg cag   624
Pro Arg Gly Glu Leu Glu Ile Thr Asp Leu Asn Asn Leu Tyr Leu Gln
        195                 200                 205 cag cag cag ttg cag gtc gaa atc atg ggc cgt ggc tat gcg tgg ctc   672
Gln Gln Gln Leu Gln Val Glu Ile Met Gly Arg Gly Tyr Ala Trp Leu
    210                 215                 220 gac acc ggc acg cac gac agt ctg ctg gag gct agc cag tac atc gca   720
Asp Thr Gly Thr His Asp Ser Leu Leu Glu Ala Ser Gln Tyr Ile Ala
225                 230                 235                 240 acc atg gag cgc cgt cag ggc ttg aaa gtc gcc tgc cct gag gaa att   768
Thr Met Glu Arg Arg Gln Gly Leu Lys Val Ala Cys Pro Glu Glu Ile
                245                 250                 255 tgc tac cgc gct ggc tgg atc aac gct gag caa ctc gag tgc ctg gct   816
Cys Tyr Arg Ala Gly Trp Ile Asn Ala Glu Gln Leu Glu Cys Leu Ala
            260                 265                 270 caa cca ctg ctg aaa aac ggt tat ggc aag tat ctg cag aac ttg ctg   864
Gln Pro Leu Leu Lys Asn Gly Tyr Gly Lys Tyr Leu Gln Asn Leu Leu
        275                 280                 285 aaa gag aag gtg ttc tga                                           882
Lys Glu Lys Val Phe
    290

<210> SEQ ID NO 10
<211> LENGTH: 293
```

<212> TYPE: PRT
<213> ORGANISM: Pseudomonas putida

<400> SEQUENCE: 10

```
Met Ala Arg Lys Gly Ile Ile Leu Ala Gly Gly Ser Gly Thr Arg Leu
1               5                   10                  15

His Pro Ala Thr Leu Ser Val Ser Lys Gln Leu Pro Val Tyr Asp
            20                  25                  30

Lys Pro Met Ile Tyr Tyr Pro Leu Ser Thr Leu Leu Ala Gly Ile
            35                  40                  45

Arg Asp Ile Leu Ile Ile Ser Thr Pro Gln Asp Thr Pro Arg Phe Glu
50                  55                  60

Gln Leu Leu Gly Asp Gly Ser Gln Trp Gly Leu Asn Leu Ser Tyr Ala
65                  70                  75                  80

Ile Gln Pro Ser Pro Asp Gly Leu Ala Gln Ala Phe Thr Ile Gly Ala
                85                  90                  95

Asp Phe Ile Gly Asn Asp Pro Ser Ala Leu Val Leu Gly Asp Asn Ile
            100                 105                 110

Phe Tyr Gly His Asp Phe Gln Ala Leu Leu Asn Ala Asp Lys Arg
            115                 120                 125

Glu Ser Gly Ala Ser Val Phe Ala Tyr His Val His Asp Pro Glu Arg
130                 135                 140

Tyr Gly Val Ala Glu Phe Asp Asp Ser Gly Arg Val Leu Ser Leu Glu
145                 150                 155                 160

Glu Lys Pro Ala Val Pro Lys Ser Ser Tyr Ala Val Thr Gly Leu Tyr
                165                 170                 175

Phe Tyr Asp Asn Gln Val Val Asn Leu Ala Arg Glu Leu Lys Pro Ser
            180                 185                 190

Pro Arg Gly Glu Leu Glu Ile Thr Asp Leu Asn Asn Leu Tyr Leu Gln
            195                 200                 205

Gln Gln Gln Leu Gln Val Glu Ile Met Gly Arg Gly Tyr Ala Trp Leu
        210                 215                 220

Asp Thr Gly Thr His Asp Ser Leu Leu Glu Ala Ser Gln Tyr Ile Ala
225                 230                 235                 240

Thr Met Glu Arg Arg Gln Gly Leu Lys Val Ala Cys Pro Glu Glu Ile
                245                 250                 255

Cys Tyr Arg Ala Gly Trp Ile Asn Ala Glu Gln Leu Gly Cys Leu Ala
            260                 265                 270

Gln Pro Leu Leu Lys Asn Gly Tyr Gly Lys Tyr Leu Gln Asn Leu Leu
            275                 280                 285

Lys Glu Lys Val Phe
290
```

<210> SEQ ID NO 11
<211> LENGTH: 1101
<212> TYPE: DNA
<213> ORGANISM: Pseudomonas putida
<220> FEATURE:
<221> NAME/KEY: CDS
<222> LOCATION: (1)..(1101)

<400> SEQUENCE: 11

```
atg att cta gta aca ggc gga gcc ggc ttc atc ggc tca aat ttc gta    48
Met Ile Leu Val Thr Gly Gly Ala Gly Phe Ile Gly Ser Asn Phe Val
1               5                   10                  15 ctg caa tgg tgt gcg cac aat gag gaa ccc gtc ctc aac ctc gac gcc    96
Leu Gln Trp Cys Ala His Asn Glu Glu Pro Val Leu Asn Leu Asp Ala
```

|  |  |  |  |  |  |  |  |  |  |  |  |  |  |  |  |  |
|---|---|---|---|---|---|---|---|---|---|---|---|---|---|---|---|---|
| | | 20 | | | | 25 | | | | | 30 | | | | | |
| ctg | acc | tac | gca | ggc | aac | ctg | gcc | aac | ctg | cag | ccg | ctg | gaa | ggc | aac | 144 |
| Leu | Thr | Tyr | Ala | Gly | Asn | Leu | Ala | Asn | Leu | Gln | Pro | Leu | Glu | Gly | Asn | |
| | | 35 | | | | 40 | | | | | 45 | | | | | |
| cct | cag | cat | cgc | ttt | gtg | caa | ggc | aat | att | tgc | gat | gct | gcg | ctt | ctg | 192 |
| Pro | Gln | His | Arg | Phe | Val | Gln | Gly | Asn | Ile | Cys | Asp | Ala | Ala | Leu | Leu | |
| | 50 | | | | | 55 | | | | | 60 | | | | | |
| acc | aag | ctg | ttc | gca | gag | cac | cgc | ccg | cgc | gcc | gtg | gtt | cac | ttc | gcg | 240 |
| Thr | Lys | Leu | Phe | Ala | Glu | His | Arg | Pro | Arg | Ala | Val | Val | His | Phe | Ala | |
| 65 | | | | | 70 | | | | | 75 | | | | | 80 | |
| gcg | gaa | tcc | cat | gta | gac | cgc | tca | atc | acc | ggc | ccc | gaa | gcg | ttt | gtc | 288 |
| Ala | Glu | Ser | His | Val | Asp | Arg | Ser | Ile | Thr | Gly | Pro | Glu | Ala | Phe | Val | |
| | | | | 85 | | | | | 90 | | | | | 95 | | |
| gaa | acc | aac | gtg | atg | ggc | acg | ttt | cgc | ttg | ctt | gaa | gcc | gcc | cgg | gcg | 336 |
| Glu | Thr | Asn | Val | Met | Gly | Thr | Phe | Arg | Leu | Leu | Glu | Ala | Ala | Arg | Ala | |
| | | | 100 | | | | | 105 | | | | | 110 | | | |
| cat | tgg | aat | agt | ttg | gaa | ggt | gca | gag | aag | gag | gcc | ttc | cgt | ttc | ctc | 384 |
| His | Trp | Asn | Ser | Leu | Glu | Gly | Ala | Glu | Lys | Glu | Ala | Phe | Arg | Phe | Leu | |
| | | | | 115 | | | | | 120 | | | | | 125 | | |
| cat | gtc | tct | acc | gac | gaa | gtc | tac | ggc | aca | cta | ggg | cca | aac | gac | ccg | 432 |
| His | Val | Ser | Thr | Asp | Glu | Val | Tyr | Gly | Thr | Leu | Gly | Pro | Asn | Asp | Pro | |
| | 130 | | | | | 135 | | | | | 140 | | | | | |
| gcg | ttc | acc | gaa | acc | acg | ccg | tac | gcg | ccg | aac | agc | cca | tac | tcc | gcc | 480 |
| Ala | Phe | Thr | Glu | Thr | Thr | Pro | Tyr | Ala | Pro | Asn | Ser | Pro | Tyr | Ser | Ala | |
| 145 | | | | | 150 | | | | | 155 | | | | | 160 | |
| agc | aag | gca | gcc | agc | gac | cat | ctg | gta | cgc | tcg | tat | ttc | cat | acc | tac | 528 |
| Ser | Lys | Ala | Ala | Ser | Asp | His | Leu | Val | Arg | Ser | Tyr | Phe | His | Thr | Tyr | |
| | | | | 165 | | | | | 170 | | | | | 175 | | |
| ggc | atg | ccg | gta | ctc | act | acc | aac | tgc | tcc | aac | aat | tac | ggg | ccg | ctc | 576 |
| Gly | Met | Pro | Val | Leu | Thr | Thr | Asn | Cys | Ser | Asn | Asn | Tyr | Gly | Pro | Leu | |
| | | | 180 | | | | | 185 | | | | | 190 | | | |
| cac | ttc | ccg | gaa | aaa | ctg | atc | ccg | ctg | atg | atc | gtc | aac | gca | ctc | gcc | 624 |
| His | Phe | Pro | Glu | Lys | Leu | Ile | Pro | Leu | Met | Ile | Val | Asn | Ala | Leu | Ala | |
| | | | | 195 | | | | | 200 | | | | | 205 | | |
| ggt | aag | gcg | ctg | cct | gtc | tat | ggc | gac | ggc | cag | caa | atc | cgc | gac | tgg | 672 |
| Gly | Lys | Ala | Leu | Pro | Val | Tyr | Gly | Asp | Gly | Gln | Gln | Ile | Arg | Asp | Trp | |
| | 210 | | | | | 215 | | | | | 220 | | | | | |
| ctg | tat | gtc | gaa | gat | cac | tgc | tcg | ggc | atc | cgt | cgc | gta | ctg | gaa | gcc | 720 |
| Leu | Tyr | Val | Glu | Asp | His | Cys | Ser | Gly | Ile | Arg | Arg | Val | Leu | Glu | Ala | |
| 225 | | | | | 230 | | | | | 235 | | | | | 240 | |
| ggt | gcg | ttc | ggc | gag | acg | tac | aat | att | ggc | ggc | tgg | aat | gaa | aaa | gcc | 768 |
| Gly | Ala | Phe | Gly | Glu | Thr | Tyr | Asn | Ile | Gly | Gly | Trp | Asn | Glu | Lys | Ala | |
| | | | | 245 | | | | | 250 | | | | | 255 | | |
| aac | att | gac | att | gtg | cgt | aca | ctc | tgc | agc | ctt | ctc | gac | gag | atg | gca | 816 |
| Asn | Ile | Asp | Ile | Val | Arg | Thr | Leu | Cys | Ser | Leu | Leu | Asp | Glu | Met | Ala | |
| | | | 260 | | | | | 265 | | | | | 270 | | | |
| cct | gcg | gca | tcg | cgc | cag | gta | atc | aat | cag | aag | acc | ggc | gag | cct | gtc | 864 |
| Pro | Ala | Ala | Ser | Arg | Gln | Val | Ile | Asn | Gln | Lys | Thr | Gly | Glu | Pro | Val | |
| | | 275 | | | | | 280 | | | | | 285 | | | | |
| gaa | cag | tat | gca | gaa | ctc | atc | gcc | tac | gta | acc | gac | cgc | cca | ggc | cat | 912 |
| Glu | Gln | Tyr | Ala | Glu | Leu | Ile | Ala | Tyr | Val | Thr | Asp | Arg | Pro | Gly | His | |
| | 290 | | | | | 295 | | | | | 300 | | | | | |
| gac | cgc | cgt | tat | gcc | atc | gat | gca | cgc | aag | atc | gag | cgg | gag | ctc | ggc | 960 |
| Asp | Arg | Arg | Tyr | Ala | Ile | Asp | Ala | Arg | Lys | Ile | Glu | Arg | Glu | Leu | Gly | |
| 305 | | | | | 310 | | | | | 315 | | | | | 320 | |
| tgg | aaa | cct | gcc | gaa | acc | ttc | gag | acg | ggc | att | cga | aag | aca | gtc | gct | 1008 |
| Trp | Lys | Pro | Ala | Glu | Thr | Phe | Glu | Thr | Gly | Ile | Arg | Lys | Thr | Val | Ala | |
| | | | | 325 | | | | | 330 | | | | | 335 | | |
| tgg | tac | ttg | gcc | aac | cag | aaa | tgg | gta | aaa | ggt | gtc | atg | gac | ggc | agc | 1056 |

Trp Tyr Leu Ala Asn Gln Lys Trp Val Lys Gly Val Met Asp Gly Ser
                340                 345                 350 tac cgt gac tgg gtg gca caa caa tac ggg gca aat aaa gcg tga        1101
Tyr Arg Asp Trp Val Ala Gln Gln Tyr Gly Ala Asn Lys Ala
            355                 360                 365

<210> SEQ ID NO 12
<211> LENGTH: 366
<212> TYPE: PRT
<213> ORGANISM: Pseudomonas putida

<400> SEQUENCE: 12

Met Ile Leu Val Thr Gly Gly Ala Gly Phe Ile Gly Ser Asn Phe Val
1               5                   10                  15

Leu Gln Trp Cys Ala His Asn Glu Glu Pro Val Leu Asn Leu Asp Ala
            20                  25                  30

Leu Thr Tyr Ala Gly Asn Leu Ala Asn Leu Gln Pro Leu Glu Gly Asn
        35                  40                  45

Pro Gln His Arg Phe Val Gln Gly Asn Ile Cys Asp Ala Ala Leu Leu
    50                  55                  60

Thr Lys Leu Phe Ala Glu His Arg Pro Arg Ala Val Val His Phe Ala
65                  70                  75                  80

Ala Glu Ser His Val Asp Arg Ser Ile Thr Gly Pro Glu Ala Phe Val
                85                  90                  95

Glu Thr Asn Val Met Gly Thr Phe Arg Leu Leu Glu Ala Ala Arg Ala
            100                 105                 110

His Trp Asn Ser Leu Glu Gly Ala Glu Lys Glu Ala Phe Arg Phe Leu
        115                 120                 125

His Val Ser Thr Asp Glu Val Tyr Gly Thr Leu Gly Pro Asn Asp Pro
    130                 135                 140

Ala Phe Thr Glu Thr Thr Pro Tyr Ala Pro Asn Ser Pro Tyr Ser Ala
145                 150                 155                 160

Ser Lys Ala Ala Ser Asp His Leu Val Arg Ser Tyr Phe His Thr Tyr
                165                 170                 175

Gly Met Pro Val Leu Thr Thr Asn Cys Ser Asn Asn Tyr Gly Pro Leu
            180                 185                 190

His Phe Pro Glu Lys Leu Ile Pro Leu Met Ile Val Asn Ala Leu Ala
        195                 200                 205

Gly Lys Ala Leu Pro Val Tyr Gly Asp Gly Gln Gln Ile Arg Asp Trp
    210                 215                 220

Leu Tyr Val Glu Asp His Cys Ser Gly Ile Arg Arg Val Leu Glu Ala
225                 230                 235                 240

Gly Ala Phe Gly Glu Thr Tyr Asn Ile Gly Gly Trp Asn Glu Lys Ala
                245                 250                 255

Asn Ile Asp Ile Val Arg Thr Leu Cys Ser Leu Leu Asp Glu Met Ala
            260                 265                 270

Pro Ala Ala Ser Arg Gln Val Ile Asn Gln Lys Thr Gly Glu Pro Val
        275                 280                 285

Glu Gln Tyr Ala Glu Leu Ile Ala Tyr Val Thr Asp Arg Pro Gly His
    290                 295                 300

Asp Arg Arg Tyr Ala Ile Asp Ala Arg Lys Ile Glu Arg Glu Leu Gly
305                 310                 315                 320

Trp Lys Pro Ala Glu Thr Phe Glu Thr Gly Ile Arg Lys Thr Val Ala
                325                 330                 335

Trp Tyr Leu Ala Asn Gln Lys Trp Val Lys Gly Val Met Asp Gly Ser

```
              340                 345                 350
Tyr Arg Asp Trp Val Ala Gln Gln Tyr Gly Ala Asn Lys Ala
            355                 360                 365

<210> SEQ ID NO 13
<211> LENGTH: 549
<212> TYPE: DNA
<213> ORGANISM: Pseudomonas putida
<220> FEATURE:
<221> NAME/KEY: CDS
<222> LOCATION: (1)..(549)

<400> SEQUENCE: 13 atg caa gcc att ccg ctg gat atc ccc gaa gtc gtg ctg ttt acc ccc        48
Met Gln Ala Ile Pro Leu Asp Ile Pro Glu Val Val Leu Phe Thr Pro
1               5                  10                  15 aag gtt ttt ggc gac gaa cgt ggt ttc ttc tac gag agc ttc aac gcc        96
Lys Val Phe Gly Asp Glu Arg Gly Phe Phe Tyr Glu Ser Phe Asn Ala
                20                  25                  30 cgt gtt ttc agc gaa gtg acc ggc ctg cag ccc gac ttc gta caa gac       144
Arg Val Phe Ser Glu Val Thr Gly Leu Gln Pro Asp Phe Val Gln Asp
            35                  40                  45 aac cac tcg cgc tcg gta aaa ggc gtg ctc cgt ggc ctg cac tat cag       192
Asn His Ser Arg Ser Val Lys Gly Val Leu Arg Gly Leu His Tyr Gln
    50                  55                  60 ctg gca cct cac gcc cag ggc aag ctg gtg cgt gtg gtg caa ggc gaa       240
Leu Ala Pro His Ala Gln Gly Lys Leu Val Arg Val Val Gln Gly Glu
65                  70                  75                  80 gtc ttc gat gtt gcg gtg gat atc cgt cgc tcg tcc aca acc ttc ggt       288
Val Phe Asp Val Ala Val Asp Ile Arg Arg Ser Ser Thr Thr Phe Gly
                85                  90                  95 aaa tgg gta ggt gcg gtg ttg tcg gcc gag aac aag aac cag ctg tgg       336
Lys Trp Val Gly Ala Val Leu Ser Ala Glu Asn Lys Asn Gln Leu Trp
                100                 105                 110 atc ccg cca ggg ttc gca cac ggg ttc gtc acg ttg agt gaa acc gca       384
Ile Pro Pro Gly Phe Ala His Gly Phe Val Thr Leu Ser Glu Thr Ala
            115                 120                 125 gag ttc ctc tac aag acc acc gac ttc tac tcg ccg cag tgc gag cgc       432
Glu Phe Leu Tyr Lys Thr Thr Asp Phe Tyr Ser Pro Gln Cys Glu Arg
        130                 135                 140 tgc att gcc tgg aat gat ccg gca gtg ggt atc gaa tgg ccc atc gac       480
Cys Ile Ala Trp Asn Asp Pro Ala Val Gly Ile Glu Trp Pro Ile Asp
145                 150                 155                 160 tcc gta cca agc ttg tct ggc aag gac cag ctt ggg gtc gca ttg gct       528
Ser Val Pro Ser Leu Ser Gly Lys Asp Gln Leu Gly Val Ala Leu Ala
                165                 170                 175 gac gcc gaa ctg ttc gac taa                                           549
Asp Ala Glu Leu Phe Asp
            180

<210> SEQ ID NO 14
<211> LENGTH: 182
<212> TYPE: PRT
<213> ORGANISM: Pseudomonas putida

<400> SEQUENCE: 14

Met Gln Ala Ile Pro Leu Asp Ile Pro Glu Val Val Leu Phe Thr Pro
1               5                  10                  15

Lys Val Phe Gly Asp Glu Arg Gly Phe Phe Tyr Glu Ser Phe Asn Ala
                20                  25                  30

Arg Val Phe Ser Glu Val Thr Gly Leu Gln Pro Asp Phe Val Gln Asp
```

```
                 35                  40                  45
Asn His Ser Arg Ser Val Lys Gly Val Leu Arg Gly Leu His Tyr Gln
 50                  55                  60

Leu Ala Pro His Ala Gln Gly Lys Leu Val Arg Val Gln Gly Glu
 65                  70                  75                  80

Val Phe Asp Val Ala Val Asp Ile Arg Ser Ser Thr Thr Phe Gly
                 85                  90                  95

Lys Trp Val Gly Ala Val Leu Ser Ala Glu Asn Lys Asn Gln Leu Trp
             100                 105                 110

Ile Pro Pro Gly Phe Ala His Gly Phe Val Thr Leu Ser Glu Thr Ala
             115                 120                 125

Glu Phe Leu Tyr Lys Thr Thr Asp Phe Tyr Ser Pro Gln Cys Glu Arg
 130                 135                 140

Cys Ile Ala Trp Asn Asp Pro Ala Val Gly Ile Glu Trp Pro Ile Asp
 145                 150                 155                 160

Ser Val Pro Ser Leu Ser Gly Lys Asp Gln Leu Gly Val Ala Leu Ala
                 165                 170                 175

Asp Ala Glu Leu Phe Asp
             180

<210> SEQ ID NO 15
<211> LENGTH: 903
<212> TYPE: DNA
<213> ORGANISM: Pseudomonas putida
<220> FEATURE:
<221> NAME/KEY: CDS
<222> LOCATION: (1)..(903)

<400> SEQUENCE: 15 gtg aaa atc ctg ctg ttg ggg aaa aac ggg caa gta ggc tgg gag cta       48
Val Lys Ile Leu Leu Leu Gly Lys Asn Gly Gln Val Gly Trp Glu Leu
 1               5                  10                  15 cag cgc gcc ttg gcg ccg ctg ggt gag gtc att gcg ctg gat cgt cag       96
Gln Arg Ala Leu Ala Pro Leu Gly Glu Val Ile Ala Leu Asp Arg Gln
             20                  25                  30 ggg gcc gag ggc tta tgt ggc gac ttg tcc aac ctg gac ggc ttg gcc      144
Gly Ala Glu Gly Leu Cys Gly Asp Leu Ser Asn Leu Asp Gly Leu Ala
         35                  40                  45 gct acg att cgt cag ctg gcg ccg gac gtg atc gtc aac gct gct gcc      192
Ala Thr Ile Arg Gln Leu Ala Pro Asp Val Ile Val Asn Ala Ala Ala
 50                  55                  60 tac act gca gtg gat aaa gct gag agc gat cag gca ctg gct gca atg      240
Tyr Thr Ala Val Asp Lys Ala Glu Ser Asp Gln Ala Leu Ala Ala Met
 65                  70                  75                  80 atc aat gcc gcg gct cct gct gta tta gca cgt gaa aca gca gct ttg      288
Ile Asn Ala Ala Ala Pro Ala Val Leu Ala Arg Glu Thr Ala Ala Leu
                 85                  90                  95 ggc gcc tgg ttg att cac tat tcc acc gat tat gta ttt gac ggc agc      336
Gly Ala Trp Leu Ile His Tyr Ser Thr Asp Tyr Val Phe Asp Gly Ser
             100                 105                 110 ggc agt cag cgc tgg gag gaa act gcg cct acc ggc ccc ctt tcg gtc      384
Gly Ser Gln Arg Trp Glu Glu Thr Ala Pro Thr Gly Pro Leu Ser Val
         115                 120                 125 tac ggc cgg acc aag ctg gaa ggc gag cat gcc att ctc gcc agc ggc      432
Tyr Gly Arg Thr Lys Leu Glu Gly Glu His Ala Ile Leu Ala Ser Gly
 130                 135                 140 gcc aag gcc gtg gta ctg cgc acc agc tgg gtg tat gct gcg cgc ggg      480
Ala Lys Ala Val Val Leu Arg Thr Ser Trp Val Tyr Ala Ala Arg Gly
145                 150                 155                 160
```

```
cac aat ttt gcc aag acc atg ctg cgc ctg gcg gcg gag cgt gag acg       528
His Asn Phe Ala Lys Thr Met Leu Arg Leu Ala Ala Glu Arg Glu Thr
            165                 170                 175 ttg agc gtg gta gca gac caa ttt ggc gca ccc acg ggc gct gac ctg       576
Leu Ser Val Val Ala Asp Gln Phe Gly Ala Pro Thr Gly Ala Asp Leu
        180                 185                 190 atc gcc gac gtt act gca cac atc ctg cgg caa atc ttc aat ggg caa       624
Ile Ala Asp Val Thr Ala His Ile Leu Arg Gln Ile Phe Asn Gly Gln
    195                 200                 205 gac aac cgt cac ctg gca ggg att tac cac ttg gct gcg tcc ggt gaa       672
Asp Asn Arg His Leu Ala Gly Ile Tyr His Leu Ala Ala Ser Gly Glu
210                 215                 220 acc tct tgg cat ggt ttt gct cag ttc gtg ctg gcg cat gct caa cgc       720
Thr Ser Trp His Gly Phe Ala Gln Phe Val Leu Ala His Ala Gln Arg
225                 230                 235                 240 act ggc gta gcg ctg aaa gtg aca gct gat aag gtt gcc gca atc agc       768
Thr Gly Val Ala Leu Lys Val Thr Ala Asp Lys Val Ala Ala Ile Ser
            245                 250                 255 acc gaa gct tat cca gta cct gca cca cgt ccg cgc aac tcg cgc ctg       816
Thr Glu Ala Tyr Pro Val Pro Ala Pro Arg Pro Arg Asn Ser Arg Leu
        260                 265                 270 gca ctg ggc aaa ctg gaa aac acg ttc aat ttc aaa atg ccg ctt tgg       864
Ala Leu Gly Lys Leu Glu Asn Thr Phe Asn Phe Lys Met Pro Leu Trp
    275                 280                 285 gag caa ggc gtg caa cgt atg ctg gac gaa atc cag taa                    903
Glu Gln Gly Val Gln Arg Met Leu Asp Glu Ile Gln
290                 295                 300

<210> SEQ ID NO 16
<211> LENGTH: 300
<212> TYPE: PRT
<213> ORGANISM: Pseudomonas putida

<400> SEQUENCE: 16

Val Lys Ile Leu Leu Gly Lys Asn Gly Gln Val Gly Trp Glu Leu
1               5                   10                  15

Gln Arg Ala Leu Ala Pro Leu Gly Glu Val Ile Ala Leu Asp Arg Gln
            20                  25                  30

Gly Ala Glu Gly Leu Cys Gly Asp Leu Ser Asn Leu Asp Gly Leu Ala
        35                  40                  45

Ala Thr Ile Arg Gln Leu Ala Pro Asp Val Ile Val Asn Ala Ala Ala
    50                  55                  60

Tyr Thr Ala Val Asp Lys Ala Glu Ser Asp Gln Ala Leu Ala Ala Met
65                  70                  75                  80

Ile Asn Ala Ala Ala Pro Ala Val Leu Ala Arg Glu Thr Ala Ala Leu
                85                  90                  95

Gly Ala Trp Leu Ile His Tyr Ser Thr Asp Tyr Val Phe Asp Gly Ser
            100                 105                 110

Gly Ser Gln Arg Trp Glu Glu Thr Ala Pro Thr Gly Pro Leu Ser Val
        115                 120                 125

Tyr Gly Arg Thr Lys Leu Glu Gly Glu His Ala Ile Leu Ala Ser Gly
    130                 135                 140

Ala Lys Ala Val Val Leu Arg Thr Ser Trp Val Tyr Ala Ala Arg Gly
145                 150                 155                 160

His Asn Phe Ala Lys Thr Met Leu Arg Leu Ala Ala Glu Arg Glu Thr
                165                 170                 175

Leu Ser Val Val Ala Asp Gln Phe Gly Ala Pro Thr Gly Ala Asp Leu
```

```
                180                 185                 190
Ile Ala Asp Val Thr Ala His Ile Leu Arg Gln Ile Phe Asn Gly Gln
                    195                 200                 205

Asp Asn Arg His Leu Ala Gly Ile Tyr His Leu Ala Ala Ser Gly Glu
            210                 215                 220

Thr Ser Trp His Gly Phe Ala Gln Phe Val Leu Ala His Ala Gln Arg
225                 230                 235                 240

Thr Gly Val Ala Leu Lys Val Thr Ala Asp Lys Val Ala Ala Ile Ser
                245                 250                 255

Thr Glu Ala Tyr Pro Val Pro Ala Pro Arg Pro Arg Asn Ser Arg Leu
            260                 265                 270

Ala Leu Gly Lys Leu Glu Asn Thr Phe Asn Phe Lys Met Pro Leu Trp
        275                 280                 285

Glu Gln Gly Val Gln Arg Met Leu Asp Glu Ile Gln
    290                 295                 300

<210> SEQ ID NO 17
<211> LENGTH: 1041
<212> TYPE: DNA
<213> ORGANISM: Burkholderia thailandensis
<220> FEATURE:
<221> NAME/KEY: CDS
<222> LOCATION: (1)..(1041)

<400> SEQUENCE: 17 atg cgc ggt tcc ggc gag tgg gta gcc gct gcg gcg cgc gtg agg c

```
                Phe Leu Asn Asp Ala Met Thr Asp Tyr Val Thr Arg Ala Arg Asp His
                                180                 185                 190 atc gcg gcg ggg gag aac ctg aag gcg gcg cag ttg ctc aac gac acg        624
Ile Ala Ala Gly Glu Asn Leu Lys Ala Ala Gln Leu Leu Asn Asp Thr
            195                 200                 205 gtg ggg cgc tac ctg ccg cgg atc atg aag ctg tac aac tac cgg tat        672
Val Gly Arg Tyr Leu Pro Arg Ile Met Lys Leu Tyr Asn Tyr Arg Tyr
210                 215                 220 ctg acg aag ctg ccg cgc acc gag cag gac cag gtg gcg ttc cac gtc        720
Leu Thr Lys Leu Pro Arg Thr Glu Gln Asp Gln Val Ala Phe His Val
225                 230                 235                 240 gac cag atc ctg tcg atg cgg ccg gag cag tac ctg ccg gaa ttc cgc        768
Asp Gln Ile Leu Ser Met Arg Pro Glu Gln Tyr Leu Pro Glu Phe Arg
                245                 250                 255 cag atc ggc tgc gcg gtg aag ttc atc aac ggc gag ctg gac gag tac        816
Gln Ile Gly Cys Ala Val Lys Phe Ile Asn Gly Glu Leu Asp Glu Tyr
                260                 265                 270 acg acg gcg tcg gac gtg cgg cgg ctg gcg gcc tac gtg cgg cgc gcg        864
Thr Thr Ala Ser Asp Val Arg Arg Leu Ala Ala Tyr Val Arg Arg Ala
            275                 280                 285 gag ttc gcg acg atc cgg cag gcg ggg cac ttc ctg gac ctc gag ggg        912
Glu Phe Ala Thr Ile Arg Gln Ala Gly His Phe Leu Asp Leu Glu Gly
290                 295                 300 cgt cag cag cag gag cag ctt cgc gcg gcg atc ctg ggc ttc ttc ggc        960
Arg Gln Gln Gln Glu Gln Leu Arg Ala Ala Ile Leu Gly Phe Phe Gly
305                 310                 315                 320 gac gag cgg gcg agc gcg gcg cgc gac gac gcg cag gac gag acg ctc       1008
Asp Glu Arg Ala Ser Ala Ala Arg Asp Asp Ala Gln Asp Glu Thr Leu
                325                 330                 335 gcg ccg ctc ggt cag ttg ccg gcg ctg tcg tag                           1041
Ala Pro Leu Gly Gln Leu Pro Ala Leu Ser
                340                 345

<210> SEQ ID NO 18
<211> LENGTH: 346
<212> TYPE: PRT
<213> ORGANISM: Burkholderia thailandensis

<400> SEQUENCE: 18

Met Arg Gly Ser Gly Glu Trp Val Ala Ala Ala Arg Val Arg Gln
1               5                   10                  15

Gly Gly Gln Ile Ala Arg Glu Gly Gly Tyr Val Glu Ala Ser Ile Lys
                20                  25                  30

Gly Ala Gly Ser Ala His Leu Pro Ser Arg Cys Gly Arg Tyr Ala Met
            35                  40                  45

Pro Ile Glu Lys Gln Val Val Ala Leu Pro Ser Gly Leu Lys Val His
50                  55                  60

Val Glu Arg His Val Phe Asp Pro Ala Phe Glu Thr Val Ile Leu Val
65                  70                  75                  80

Asn Gly Ala Leu Ala Thr Thr Ser Phe Gly Gln Thr Ile Arg Tyr
                85                  90                  95

Leu Gly Glu Arg Val Asn Ala Val Cys Phe Asp Leu Pro Tyr Ala Gly
                100                 105                 110

Gln Ser Arg Gln His Asn Pro Gly Glu Tyr Ile Leu Thr Lys Asp Asp
            115                 120                 125

Glu Val Glu Ile Leu Leu His Leu Ala Glu Arg Phe Glu Pro Ser Phe
130                 135                 140

Leu Leu Ser Val Ser Trp Gly Gly Val Ala Ser Leu Phe Ala Leu Ala
```

```
                145                 150                 155                 160
Arg Gly Cys Ala Ser Val Arg Arg Ala Val Ile Ala Ser Phe Ser Pro
                165                 170                 175

Phe Leu Asn Asp Ala Met Thr Asp Tyr Val Thr Arg Ala Arg Asp His
                180                 185                 190

Ile Ala Ala Gly Glu Asn Leu Lys Ala Ala Gln Leu Leu Asn Asp Thr
                195                 200                 205

Val Gly Arg Tyr Leu Pro Arg Ile Met Lys Leu Tyr Asn Tyr Arg Tyr
                210                 215                 220

Leu Thr Lys Leu Pro Arg Thr Glu Gln Asp Gln Val Ala Phe His Val
225                 230                 235                 240

Asp Gln Ile Leu Ser Met Arg Pro Glu Gln Tyr Leu Pro Glu Phe Arg
                245                 250                 255

Gln Ile Gly Cys Ala Val Lys Phe Ile Asn Gly Glu Leu Asp Glu Tyr
                260                 265                 270

Thr Thr Ala Ser Asp Val Arg Arg Leu Ala Ala T

```
                115                   120                   125
gtg cgg gcg atg gcg gac ccg gcg ctg tgg gat ccg cgc acg tcg ttc         432
Val Arg Ala Met Ala Asp Pro Ala Leu Trp Asp Pro Arg Thr Ser Phe
        130                   135                   140 aag acg ctg tgg cgg gtg atc gcg ccg gtg gtg agg ccg cac ttc gag         480
Lys Thr Leu Trp Arg Val Ile Ala Pro Val Val Arg Pro His Phe Glu
145                   150                   155                   160 gtg ctg cgc gcg ctg agc gac gcg gac acg gtg ctg gtg ggc acg ctg         528
Val Leu Arg Ala Leu Ser Asp Ala Asp Thr Val Leu Val Gly Thr Leu
                165                   170                   175 tgg gcg ttc tcg gcg cgg ctg atg cag gag cgc ttc ggc acg cgg tac         576
Trp Ala Phe Ser Ala Arg Leu Met Gln Glu Arg Phe Gly Thr Arg Tyr
        180                   185                   190 gtg tcg gtg cag gtg tcg ccg tcg acg ctg ctg tcg gcg cat gcg ccg         624
Val Ser Val Gln Val Ser Pro Ser Thr Leu Leu Ser Ala His Ala Pro
195                   200                   205 ccg acg cac aag cgg ctg acg atc ccg aag ggc ctg ccg ctg gcg gtg         672
Pro Thr His Lys Arg Leu Thr Ile Pro Lys Gly Leu Pro Leu Ala Val
        210                   215                   220 aag gcg ggg ctg atg acg ctg atc gag cgg cag gtg ctg gac cgg gtg         720
Lys Ala Gly Leu Met Thr Leu Ile Glu Arg Gln Val Leu Asp Arg Val
225                   230                   235                   240 tgc ggc ccg gag ctg aac gcg gcg cgg cag gcg ctg ggc ctg gcg ccg         768
Cys Gly Pro Glu Leu Asn Ala Ala Arg Gln Ala Leu Gly Leu Ala Pro
                245                   250                   255 gcg aag cgg atc ctg ggc cgg tgg ctg cat tcg acg gac ggg gtg ctg         816
Ala Lys Arg Ile Leu Gly Arg Trp Leu His Ser Thr Asp Gly Val Leu
        260                   265                   270 tgc ctg ttt ccg tcg tgg ttc gcg ccg gcg cag ccg gac tgg ccg gcg         864
Cys Leu Phe Pro Ser Trp Phe Ala Pro Ala Gln Pro Asp Trp Pro Ala
        275                   280                   285 aac cac ctg caa agc ggg ttt ccg ctg ttc aac gac gcg ggt ccg gcg         912
Asn His Leu Gln Ser Gly Phe Pro Leu Phe Asn Asp Ala Gly Pro Ala
        290                   295                   300 cag gcg gat gcg gag ctg gag gcg ttc gtc gcg tcg ggc gag gcg ccg         960
Gln Ala Asp Ala Glu Leu Glu Ala Phe Val Ala Ser Gly Glu Ala Pro
305                   310                   315                   320 gtg gtg ttc acg gcg ggc tcg acg ctg gtg gac ggc cgc acg tat gag        1008
Val Val Phe Thr Ala Gly Ser Thr Leu Val Asp Gly Arg Thr Tyr Glu
                325                   330                   335 cac gcg gtg acg cag gtg ctg cag gcc acg ggg gtg cgg ggg att ctg        1056
His Ala Val Thr Gln Val Leu Gln Ala Thr Gly Val Arg Gly Ile Leu
        340                   345                   350 ctc gcg ccg gat gcg ccg gat gcg ccg gcg gca tcg gac ggg gcg gcg        1104
Leu Ala Pro Asp Ala Pro Asp Ala Pro Ala Ala Ser Asp Gly Ala Ala
        355                   360                   365 ctg ctc aag cgc cgc tac gtg ccg ctc gcg gcg ttg ctg ccg cgc tgc        1152
Leu Leu Lys Arg Arg Tyr Val Pro Leu Ala Ala Leu Leu Pro Arg Cys
        370                   375                   380 cgg gcg ctg gtg cac cac ggg ggg atc ggg acg gcg tcg ctc gcg tac        1200
Arg Ala Leu Val His His Gly Gly Ile Gly Thr Ala Ser Leu Ala Tyr
385                   390                   395                   400 gcg gcg ggg gtg ccg cag gtg gtg acg ccg ttc gcg cac gac cag ttc        1248
Ala Ala Gly Val Pro Gln Val Val Thr Pro Phe Ala His Asp Gln Phe
                405                   410                   415 gac aac gcg cag cgg gtg gcg gcg agc ggc tgc ggg gtg cgg ctg gac        1296
Asp Asn Ala Gln Arg Val Ala Ala Ser Gly Cys Gly Val Arg Leu Asp
        420                   425                   430 gcg ccg gtg cgc ggc gag ccg ctc gcg cgg gcg ctg gcg cag gtg ctg        1344
```

```
                                                                              -continued Ala Pro Val Arg Gly Glu Pro Leu Ala Arg Ala Leu Ala Gln Val Leu
        435                 440                 445 ggc gac gcg gcg atg gcg gcg cgc tgc gcg cag gtg cgc gcg cgg atg     1392
Gly Asp Ala Ala Met Ala Ala Arg Cys Ala Gln Val Arg Ala Arg Met
450                 455                 460 gcg gcg gag ccg aac ggc tgc gac gcg gcg gcg cgc ttc atc gag cgc     1440
Ala Ala Glu Pro Asn Gly Cys Asp Ala Ala Ala Arg Phe Ile Glu Arg
465                 470                 475                 480 ttc gcg ccg ggc gtc gcg gcg cgg cgg gcg cag ccg gca tga             1482
Phe Ala Pro Gly Val Ala Ala Arg Arg Ala Gln Pro Ala
                485                 490

<210> SEQ ID NO 20
<211> LENGTH: 493
<212> TYPE: PRT
<213> ORGANISM: Burkholderia thailandensis

<400> SEQUENCE: 20

Met Asp Ala Gly Arg Ile Gly Leu His Asp Ala Ala Ala Gly Arg
1               5                   10                  15

Ile Gly Met Thr Glu Ala Phe Ala Ser Arg Ala Ar

```
Gln Ala Asp Ala Glu Leu Glu Ala Phe Val Ala Ser Gly Glu Ala Pro
305                 310                 315                 320

Val Val Phe Thr Ala Gly Ser Thr Leu Val Asp Gly Arg Thr Tyr Glu
                325                 330                 335

His Ala Val Thr Gln Val Leu Gln Ala Thr Gly Val Arg Gly Ile Leu
            340                 345                 350

Leu Ala Pro Asp Ala Pro Asp Ala Pro Ala Ala Ser Asp Gly Ala Ala
        355                 360                 365

Leu Leu Lys Arg Arg Tyr Val Pro Leu Ala Ala Leu Leu Pro Arg Cys
    370                 375                 380

Arg Ala Leu Val His His Gly Gly Ile Gly Thr Ala Ser Leu Ala Tyr
385                 390                 395                 400

Ala Ala Gly Val Pro Gln Val Val Thr Pro Phe Ala His Asp Gln Phe
                405                 410                 415

Asp Asn Ala Gln Arg Val Ala Ala Ser Gly Cys Gly Val Arg Leu Asp
            420                 425                 430

Ala Pro Val Arg Gly Glu Pro Leu Ala Arg Ala Leu Ala Gln Val Leu
        435                 440                 445

Gly Asp Ala Ala Met Ala Ala Arg Cys Ala Gln Val Arg Ala Arg Met
    450                 455                 460

Ala Ala Glu Pro Asn Gly Cys Asp Ala Ala Ala Arg Phe Ile Glu Arg
465                 470                 475                 480

Phe Ala Pro Gly Val Ala Ala Arg Arg Ala Gln Pro Ala
                485                 490

<210> SEQ ID NO 21
<211> LENGTH: 966
<212> TYPE: DNA
<213> ORGANISM: Burkholderia thailandensis
<220> FEATURE:
<221> NAME/KEY: CDS
<222> LOCATION: (1)..(966)

<400> SEQUENCE: 21 atg acg atc ctg ggg gcg ctg gtg att ctg tac gac ccg acg gac gag       48
Met Thr Ile Leu Gly Ala Leu Val Ile Leu Tyr Asp Pro Thr Asp Glu
1               5                   10                  15 cag ttg tcg ggg ctg gag gcg ctc gcg cgc gac agc gac gcg ctc gtg       96
Gln Leu Ser Gly Leu Glu Ala Leu Ala Arg Asp Ser Asp Ala Leu Val
            20                  25                  30 gtc gtg gac aac acg ccg cac gag cac gcg gcg gcg cgc gag cgg gtg      144
Val Val Asp Asn Thr Pro His Glu His Ala Ala Ala Arg Glu Arg Val
        35                  40                  45 cgt gcg ctg tcg gcg cgg acg aac acg gtg tgg cga cac cac ggc aac      192
Arg Ala Leu Ser Ala Arg Thr Asn Thr Val Trp Arg His His Gly Asn
    50                  55                  60 cgg ggc ggg gtc gcg ggc ggg tac aac gcg ggg ctg tcg gtg ctg ttc      240
Arg Gly Gly Val Ala Gly Gly Tyr Asn Ala Gly Leu Ser Val Leu Phe
65                  70                  75                  80 gcg cag ggc gtc gag gcg gtc gcg ctg ttc gac cag gac tcg acg gtg      288
Ala Gln Gly Val Glu Ala Val Ala Leu Phe Asp Gln Asp Ser Thr Val
                85                  90                  95 ccg gcc ggg tac ttc gag cgg atg cgc gag gcg tgc gcg caa ctg ggt      336
Pro Ala Gly Tyr Phe Glu Arg Met Arg Glu Ala Cys Ala Gln Leu Gly
            100                 105                 110 gag caa ccg ggc gcg cac gcg ggc gcg ttc atc gcg ggc ccg cgg atc      384
Glu Gln Pro Gly Ala His Ala Gly Ala Phe Ile Ala Gly Pro Arg Ile
        115                 120                 125
```

-continued

```
tac gac gcg aac gag cag cgc ttc ctg ccg gag ctg atg acg agc ggg      432
Tyr Asp Ala Asn Glu Gln Arg Phe Leu Pro Glu Leu Met Thr Ser Gly
    130                 135                 140 gtg acg gtg cgc cgc gtg cgg gtg gag ggc gag acg gcg ccg cag cgc      480
Val Thr Val Arg Arg Val Arg Val Glu Gly Glu Thr Ala Pro Gln Arg
145                 150                 155                 160 tgc gcg ttc ctg atc tcg tcg ggc agc gtg att tcg cgg gcc gcg tac      528
Cys Ala Phe Leu Ile Ser Ser Gly Ser Val Ile Ser Arg Ala Ala Tyr
                165                 170                 175 gcg cgg ctc ggt cga ttc gac gag gcg ctg ttc atc gat cac gtc gac      576
Ala Arg Leu Gly Arg Phe Asp Glu Ala Leu Phe Ile Asp His Val Asp
            180                 185                 190 acc gag tat tgc ctg cgc gcg ctc gcg cac aac gtg ccg ctg tac gtg      624
Thr Glu Tyr Cys Leu Arg Ala Leu Ala His Asn Val Pro Leu Tyr Val
        195                 200                 205 gtg ccg ccg ctc gtg ctg acg cac cgg atc ggc gcg cgg cgc cgg cac      672
Val Pro Pro Leu Val Leu Thr His Arg Ile Gly Ala Arg Arg Arg His
    210                 215                 220 aag gtg ggg ccg ttc gag ctg acg gcg atg cat cac ggg tgg ttg cgc      720
Lys Val Gly Pro Phe Glu Leu Thr Ala Met His His Gly Trp Leu Arg
225                 230                 235                 240 cga tac tac ggc gcg cgc aac gcg atg caa ctg ggg ctg cag tac ggc      768
Arg Tyr Tyr Gly Ala Arg Asn Ala Met Gln Leu Gly Leu Gln Tyr Gly
                245                 250                 255 ttg cgg ttt ccg gtg gcg ctg gtg ccg aat ctg ctg acg ata tgg cag      816
Leu Arg Phe Pro Val Ala Leu Val Pro Asn Leu Leu Thr Ile Trp Gln
            260                 265                 270 gtg atc cag gtg gtg ctg tgc gag cgg gag aag ggc gcg aag ctg cgc      864
Val Ile Gln Val Val Leu Cys Glu Arg Glu Lys Gly Ala Lys Leu Arg
        275                 280                 285 ggg atc gcg ctg ggc gtg ctc gac ggc ctg ttc ggg cgg ctg gga tcg      912
Gly Ile Ala Leu Gly Val Leu Asp Gly Leu Phe Gly Arg Leu Gly Ser
    290                 295                 300 ttc gac gat gcg cgc gcg ggc gcg gcg gcg cgc gag ccg gtg cgg cag      960
Phe Asp Asp Ala Arg Ala Gly Ala Ala Ala Arg Glu Pro Val Arg Gln
305                 310                 315                 320 gaa tga                                                              966
Glu

<210> SEQ ID NO 22
<211> LENGTH: 321
<212> TYPE: PRT
<213> ORGANISM: Burkholderia thailandensis

<400> SEQUENCE: 22

Met Thr Ile Leu Gly Ala Leu Val Ile Leu Tyr Asp Pro Thr Asp Glu
1               5                   10                  15

Gln Leu Ser Gly Leu Glu Ala Leu Ala Arg Asp Ser Asp Ala Leu Val
            20                  25                  30

Val Val Asp Asn Thr Pro His Glu His Ala Ala Ala Arg Glu Arg Val
        35                  40                  45

Arg Ala Leu Ser Ala Arg Thr Asn Thr Val Trp Arg His His Gly Asn
    50                  55                  60

Arg Gly Gly Val Ala Gly Gly Tyr Asn Ala Gly Leu Ser Val Leu Phe
65                  70                  75                  80

Ala Gln Gly Val Glu Ala Val Ala Leu Phe Asp Gln Asp Ser Thr Val
                85                  90                  95

Pro Ala Gly Tyr Phe Glu Arg Met Arg Glu Ala Cys Ala Gln Leu Gly
```

```
            100                 105                 110

Glu Gln Pro Gly Ala His Ala Gly Ala Phe Ile Ala Gly Pro Arg Ile
        115                 120                 125

Tyr Asp Ala Asn Glu Gln Arg Phe Leu Pro Glu Leu Met Thr Ser Gly
    130                 135                 140

Val Thr Val Arg Arg Val Arg Val Glu Gly Glu Thr Ala Pro Gln Arg
145                 150                 155                 160

Cys Ala Phe Leu Ile Ser Ser Gly Ser Val Ile Ser Arg Ala Ala Tyr
                165                 170                 175

Ala Arg Leu Gly Arg Phe Asp Glu Ala Leu Phe Ile Asp His Val Asp
            180                 185                 190

Thr Glu Tyr Cys Leu Arg Ala Leu Ala His Asn Val Pro Leu Tyr Val
        195                 200                 205

Val Pro Pro Leu Val Leu Thr His Arg Ile Gly Ala Arg Arg Arg His
    210                 215                 220

Lys Val Gly Pro Phe Glu Leu Thr Ala Met His His Gly Trp Leu Arg
225                 230                 235                 240

Arg Tyr Tyr Gly Ala Arg Asn Ala Met Gln Leu Gly Leu Gln Tyr Gly
                245                 250                 255

Leu Arg Phe Pro Val Ala Leu Val Pro Asn Leu Leu Thr Ile Trp Gln
            260                 265                 270

Val Ile Gln Val Val Leu Cys Glu Arg Glu Lys Gly Ala Lys Leu Arg
        275                 280                 285

Gly Ile Ala Leu Gly Val Leu Asp Gly Leu Phe Gly Arg Leu Gly Ser
    290                 295                 300

Phe Asp Asp Ala Arg Ala Gly Ala Ala Ala Arg Glu Pro Val Arg Gln
305                 310                 315                 320

Glu

<210> SEQ ID NO 23
<211> LENGTH: 1557
<212> TYPE: DNA
<213> ORGANISM: Burkholderia thailandensis
<220> FEATURE:
<221> NAME/KEY: CDS
<222> LOCATION: (1)..(1557)

<400> SEQUENCE: 23 atg tcg gcg gat cag gcg ggc gtt gcg ccg ccg gcg gcc gcc ccg ctg      48
Met Ser Ala Asp Gln Ala Gly Val Ala Pro Pro Ala Ala Ala Pro Leu
1               5                   10                  15 cgc ggc gcg aag ctc gcg ctg ctg acg ttc gcg ctg tcg ctc gcg acg      96
Arg Gly Ala Lys Leu Ala Leu Leu Thr Phe Ala Leu Ser Leu Ala Thr
            20                  25                  30 ttc atc gaa gtg ctg gat tcg acg gtg gcg aac gtg gcg gtg ccg gcg     144
Phe Ile Glu Val Leu Asp Ser Thr Val Ala Asn Val Ala Val Pro Ala
        35                  40                  45 atc tcg ggc agc ctc ggg gtg tcg aac agc cag ggc acg tgg gtg atc     192
Ile Ser Gly Ser Leu Gly Val Ser Asn Ser Gln Gly Thr Trp Val Ile
    50                  55                  60 agc tcg tac tcg gtg gcc gcg gcg atc gcg gtg ccg ctg acg ggg tgg     240
Ser Ser Tyr Ser Val Ala Ala Ala Ile Ala Val Pro Leu Thr Gly Trp
65                  70                  75                  80 ctt gcg cgg cgc gtg ggc gag ctg agg ctg ttc gtg gcg tcg gtg atc     288
Leu Ala Arg Arg Val Gly Glu Leu Arg Leu Phe Val Ala Ser Val Ile
                85                  90                  95 ctg ttc acg ctg acg tcg ctg ctg tgc ggg ctc gcg cgg gac ctg gag     336
```

```
Leu Phe Thr Leu Thr Ser Leu Leu Cys Gly Leu Ala Arg Asp Leu Glu
            100             105                 110 gtg ctg gtt gcg tgc cgg gcg ctg cag ggg ctg ttc tcg ggg ccg atg     384
Val Leu Val Ala Cys Arg Ala Leu Gln Gly Leu Phe Ser Gly Pro Met
            115             120                 125 gtg ccg ctg tcg cag acg atc ctg atg cgc gcg ttc ccg ccg gcg cgg     432
Val Pro Leu Ser Gln Thr Ile Leu Met Arg Ala Phe Pro Pro Ala Arg
            130             135                 140 cgc acg ctg gcg ctg gcg ctg tgg ggg atg acg gtg ctg ctc gcg ccg     480
Arg Thr Leu Ala Leu Ala Leu Trp Gly Met Thr Val Leu Leu Ala Pro
145             150                 155                 160 atc ttc ggg ccg gtg gtg ggc ggc tgg ctg atc gac aac ttc tcg tgg     528
Ile Phe Gly Pro Val Val Gly Gly Trp Leu Ile Asp Asn Phe Ser Trp
            165                 170                 175 ccg tgg atc ttc ctg atc aac ctg ccg atc ggg ctg ttc tcg ttc gcg     576
Pro Trp Ile Phe Leu Ile Asn Leu Pro Ile Gly Leu Phe Ser Phe Ala
            180             185                 190 gtg tgc acg ctg atg ctg cgc ccg cag gcg cag cgc ggc gag gcg agc     624
Val Cys Thr Leu Met Leu Arg Pro Gln Ala Gln Arg Gly Glu Ala Ser
            195             200                 205 ccg atc gac gcg ccg ggg atc gtg ctg ctg gtg atc ggg gtg ggc tcg     672
Pro Ile Asp Ala Pro Gly Ile Val Leu Leu Val Ile Gly Val Gly Ser
210             215                 220 ctg cag gcg atg ctg gac ctg ggg cac gac cgg ggc tgg ttc gat tcg     720
Leu Gln Ala Met Leu Asp Leu Gly His Asp Arg Gly Trp Phe Asp Ser
225             230                 235                 240 ccg ctg atc acg gcg ctg gcg atc gcg gcg ggg gtg tcg ctc gtg tcg     768
Pro Leu Ile Thr Ala Leu Ala Ile Ala Ala Gly Val Ser Leu Val Ser
            245             250                 255 ctg ctg atc tgg gag ctg ggc gag gcg cat ccg gtg gtg gat ctg agc     816
Leu Leu Ile Trp Glu Leu Gly Glu Ala His Pro Val Val Asp Leu Ser
            260             265                 270 ctg ttc cgg gag cgg acc ttc acg ttc tgc gtg gtg atc atc tcg ctg     864
Leu Phe Arg Glu Arg Thr Phe Thr Phe Cys Val Val Ile Ile Ser Leu
            275             280                 285 ggg atg atg agc ttc tcg gtg gtg ggg gtg gtg ttt ccg ctg tgg ctg     912
Gly Met Met Ser Phe Ser Val Val Gly Val Val Phe Pro Leu Trp Leu
            290             295                 300 cag gcg gtg atg gga tac acg gcg tac cag gcg ggg ctg gcg acg gcg     960
Gln Ala Val Met Gly Tyr Thr Ala Tyr Gln Ala Gly Leu Ala Thr Ala
305             310                 315                 320 tcg atg ggg gtg ctg gcg ctg gtg ttc tcg atc ctg gtg ggg ctg tac    1008
Ser Met Gly Val Leu Ala Leu Val Phe Ser Ile Leu Val Gly Leu Tyr
            325             330                 335 gcg agc cgg gtg gac gcg cgg gtg ctg gtg acg ttc ggg ttc ggg gtg    1056
Ala Ser Arg Val Asp Ala Arg Val Leu Val Thr Phe Gly Phe Gly Val
            340             345                 350 ttt gcg gcg gtg atg tgg tgg agc acg cac ttc acg ctg tcg atg acg    1104
Phe Ala Ala Val Met Trp Trp Ser Thr His Phe Thr Leu Ser Met Thr
            355             360                 365 ttc gcg cag gtg gtg acg ccg cgg ctg att cag ggg atg ggg ctg ccg    1152
Phe Ala Gln Val Val Thr Pro Arg Leu Ile Gln Gly Met Gly Leu Pro
            370             375                 380 tgc ttc ttc ata ccg ctg acg gcg gcg acg ctg tcg cgg gtg ccg gac    1200
Cys Phe Phe Ile Pro Leu Thr Ala Ala Thr Leu Ser Arg Val Pro Asp
385             390                 395                 400 gag aag ctg gcg gcg gcg tcg agc ctg tcg aac ttc ctg cgg acg ctg    1248
Glu Lys Leu Ala Ala Ala Ser Ser Leu Ser Asn Phe Leu Arg Thr Leu
            405             410                 415
```

```
tcg gcg gcg ttc ggc acg gcg ctg agc gtg acg tgg tgg gac aac cgg    1296
Ser Ala Ala Phe Gly Thr Ala Leu Ser Val Thr Trp Trp Asp Asn Arg
            420                 425                 430 gcg acg tac cac tac gcg gtg gtg tcg caa tcg gtg acg cgc gcc tcg    1344
Ala Thr Tyr His Tyr Ala Val Val Ser Gln Ser Val Thr Arg Ala Ser
        435                 440                 445 gag aac acg cag cgg tac gtg gac gcg ctg cac gcg atg ggg ctg cac    1392
Glu Asn Thr Gln Arg Tyr Val Asp Ala Leu His Ala Met Gly Leu His
    450                 455                 460 ggc gcg cgg gag ctg agc tcg ctg cac cag gtg gtg cgg cag cag gcg    1440
Gly Ala Arg Glu Leu Ser Ser Leu His Gln Val Val Arg Gln Gln Ala
465                 470                 475                 480 tac atg atg gcg acg aac gac atg ttc tac atg gcg agc gcg acg tgc    1488
Tyr Met Met Ala Thr Asn Asp Met Phe Tyr Met Ala Ser Ala Thr Cys
                485                 490                 495 ctg ctg ctg gcg ggg ctg atg tgg ctg acg cgg ccg aag cgg ggc gcg    1536
Leu Leu Leu Ala Gly Leu Met Trp Leu Thr Arg Pro Lys Arg Gly Ala
            500                 505                 510 gcg gcg gcg ctc ggg cac tga                                        1557
Ala Ala Ala Leu Gly His
        515
```

```
<210> SEQ ID NO 24
<211> LENGTH: 518
<212> TYPE: PRT
<213> ORGANISM: Burkholderia thailandensis

<400> SEQUENCE: 24

Met Ser Ala Asp Gln Ala Gly Val Ala Pro Pro Ala Ala Pro Leu
1

-continued

```
                225                 230                 235                 240
        Pro Leu Ile Thr Ala Leu Ala Ile Ala Ala Gly Val Ser Leu Val Ser
                        245                 250                 255

Leu Leu Ile Trp Glu Leu Gly Glu Ala His Pro Val Val Asp Leu Ser
                        260                 265                 270

Leu Phe Arg Glu Arg Thr Phe Thr Phe Cys Val Val Ile Ser Leu
                        275                 280                 285

Gly Met Met Ser Phe Ser Val Val Gly Val Val Phe Pro Leu Trp Leu
                        290                 295                 300

Gln Ala Val Met Gly Tyr Thr Ala Tyr Gln Ala Gly Leu Ala Thr Ala
        305                 310                 315                 320

Ser Met Gly Val Leu Ala Leu Val Phe Ser Ile Leu Val Gly Leu Tyr
                        325                 330                 335

Ala Ser Arg Val Asp Ala Arg Val Leu Val Thr Phe Gly Phe Gly Val
                        340                 345                 350

Phe Ala Ala Val Met Trp Trp Ser Thr His Phe Thr Leu Ser Met Thr
                        355                 360                 365

Phe Ala Gln Val Val Thr Pro Arg Leu Ile Gln Gly Met Gly Leu Pro
                        370                 375                 380

Cys Phe Phe Ile Pro Leu Thr Ala Ala Thr Leu Ser Arg Val Pro Asp
        385                 390                 395                 400

Glu Lys Leu Ala Ala Ser Ser Leu Ser Asn Phe Leu Arg Thr Leu
                        405                 410                 415

Ser Ala Ala Phe Gly Thr Ala Leu Ser Val Thr Trp Trp Asp Asn Arg
                        420                 425                 430

Ala Thr Tyr His Tyr Ala Val Val Ser Gln Ser Val Thr Arg Ala Ser
                        435                 440                 445

Glu Asn Thr Gln Arg Tyr Val Asp Ala Leu His Ala Met Gly Leu His
                        450                 455                 460

Gly Ala Arg Glu Leu Ser Ser Leu His Gln Val Val Arg Gln Gln Ala
        465                 470                 475                 480

Tyr Met Met Ala Thr Asn Asp Met Phe Tyr Met Ala Ser Ala Thr Cys
                        485                 490                 495

Leu Leu Leu Ala Gly Leu Met Trp Leu Thr Arg Pro Lys Arg Gly Ala
                        500                 505                 510

Ala Ala Ala Leu Gly His
                        515

<210> SEQ ID NO 25
<211> LENGTH: 1662
<212> TYPE: DNA
<213> ORGANISM: Burkholderia thailandensis
<220> FEATURE:
<221> NAME/KEY: CDS
<222> LOCATION: (1)..(1662)

<400> SEQUENCE: 25 atg cgc gcg cgg gcg cgg cgg cgc gcg agc cgg tgc ggc agg aat gaa      48
Met Arg Ala Arg Ala Arg Arg Ala Ser Arg Cys Gly Arg Asn Glu
1               5                   10                  15 cgg aac ggg ccg cag cgg gat acc gga aag caa gaa gga cgc atc ata      96
Arg Asn Gly Pro Gln Arg Asp Thr Gly Lys Gln Glu Gly Arg Ile Ile
            20                  25                  30 cga atg acg cag aca gca acg caa gca gcc act cgc gcg atg atc gcg     144
Arg Met Thr Gln Thr Ala Thr Gln Ala Ala Thr Arg Ala Met Ile Ala
        35                  40                  45
```

-continued

| | | |
|---|---|---|
| aca gga agc cgc gcg gcg cgc cgg ctc gcg gca gcc gcg ctc gcg tgg<br>Thr Gly Ser Arg Ala Ala Arg Arg Leu Ala Ala Ala Ala Leu Ala Trp<br>    50                          55                        60 | | 192 |
| gcg ctc gcc ggc tgc gtg ccg tcg ggc ttc gag ccg gcg ctc gcg ccg<br>Ala Leu Ala Gly Cys Val Pro Ser Gly Phe Glu Pro Ala Leu Ala Pro<br>65                      70                        75                        80 | | 240 |
| cgc acg ccg ggc gac gac gcg ctc gcg cac acg gcg ggg ggc gcc gcg<br>Arg Thr Pro Gly Asp Asp Ala Leu Ala His Thr Ala Gly Gly Ala Ala<br>                        85                          90                        95 | | 288 |
| cac ggc gca tgg ccg agc ccc gac tgg gtc cgg cag ctc ggc gat ccg<br>His Gly Ala Trp Pro Ser Pro Asp Trp Val Arg Gln Leu Gly Asp Pro<br>              100                        105                        110 | | 336 |
| caa ctc gac gcg ctc gtc gac gag gcg ctg cgg cag aac ccg acg ctg<br>Gln Leu Asp Ala Leu Val Asp Glu Ala Leu Arg Gln Asn Pro Thr Leu<br>            115                        120                        125 | | 384 |
| cag gcc gcg cag gcg cgc atc ggc gtc gcg cag tcg cag ctg cag cag<br>Gln Ala Ala Gln Ala Arg Ile Gly Val Ala Gln Ser Gln Leu Gln Gln<br>130                      135                        140 | | 432 |
| ttc gaa tcg ctg acg ggg ctc acc gcg acg gcg ggc gcg tcg ctc tcc<br>Phe Glu Ser Leu Thr Gly Leu Thr Ala Thr Ala Gly Ala Ser Leu Ser<br>145                     150                        155                        160 | | 480 |
| aag gcg cac gtg ccg cgc tcg ggc ggc acc atc aat acg acg ttc aac<br>Lys Ala His Val Pro Arg Ser Gly Gly Thr Ile Asn Thr Thr Phe Asn<br>              165                        170                        175 | | 528 |
| ggc ttg ccg gtg tcg gtg ccg ctc gtc ggc gaa tcg gtg gtg tcg tcg<br>Gly Leu Pro Val Ser Val Pro Leu Val Gly Glu Ser Val Val Ser Ser<br>                        180                        185                        190 | | 576 |
| tcg tcg ctg ttc gtc ggg ctg aac tat cag ctg gac ctg tgg ggc aag<br>Ser Ser Leu Phe Val Gly Leu Asn Tyr Gln Leu Asp Leu Trp Gly Lys<br>            195                        200                        205 | | 624 |
| aac gcg gcg gcc acg cgc ggg ctg ctg tcg atg cgc gat gcg gcg cgc<br>Asn Ala Ala Ala Thr Arg Gly Leu Leu Ser Met Arg Asp Ala Ala Arg<br>210                      215                        220 | | 672 |
| gtg gag gcc gag cag gcg cgg ctc gcg ctg tcg gtg gcg atc gtg acg<br>Val Glu Ala Glu Gln Ala Arg Leu Ala Leu Ser Val Ala Ile Val Thr<br>225                     230                        235                        240 | | 720 |
| ctg tac ggc gag ctg gac cgc gcg tat gcg ctg cgc gag ctg ctg cag<br>Leu Tyr Gly Glu Leu Asp Arg Ala Tyr Ala Leu Arg Glu Leu Leu Gln<br>              245                        250                        255 | | 768 |
| cag aag cgc cgc gcg agc gag cag gtg gag acg gtg ctg cgc gag cgc<br>Gln Lys Arg Arg Ala Ser Glu Gln Val Glu Thr Val Leu Arg Glu Arg<br>            260                        265                        270 | | 816 |
| gcg gcg cgc ggg atc gac aac ggc tac gat gcg gac gac gcg gcg ctc<br>Ala Ala Arg Gly Ile Asp Asn Gly Tyr Asp Ala Asp Asp Ala Ala Leu<br>        275                        280                        285 | | 864 |
| aag cgg ggc aag ctg ctc gag cag ctc gcg ctg acc gac gag cag atc<br>Lys Arg Gly Lys Leu Leu Glu Gln Leu Ala Leu Thr Asp Glu Gln Ile<br>290                      295                        300 | | 912 |
| cag ttg cag aag ctg caa ctg ggg gtg ctg agc ggg cgg ggg ccg gag<br>Gln Leu Gln Lys Leu Gln Leu Gly Val Leu Ser Gly Arg Gly Pro Glu<br>305                     310                        315                        320 | | 960 |
| cgc ggg ctg tcg ctc gcg cgg ccg aag ctc gcg ccg ctc gcg gac gcg<br>Arg Gly Leu Ser Leu Ala Arg Pro Lys Leu Ala Pro Leu Ala Asp Ala<br>              325                        330                        335 | | 1008 |
| ccg ctg ccg gcg cgg ctg ccg gcc ggg ctg ctg ggg cgg cgg ccg gac<br>Pro Leu Pro Ala Arg Leu Pro Ala Gly Leu Leu Gly Arg Arg Pro Asp<br>            340                        345                        350 | | 1056 |
| atc gtc gcg gcg cgg ctg cgg gtg gag gcg gcg tac gcg gcg atc gac<br>Ile Val Ala Ala Arg Leu Arg Val Glu Ala Ala Tyr Ala Ala Ile Asp<br>355                      360                        365 | | 1104 |

-continued

```
ggc acg cgc gcg tcg ttc tac ccg gac gtg aac ctg gcg gcg ctg ggc        1152
Gly Thr Arg Ala Ser Phe Tyr Pro Asp Val Asn Leu Ala Ala Leu Gly
        370                 375                 380 ggg ctg ttc gcg ctc acg ccg gcg tcg ctg ttc aag cac gat gcg ctg        1200
Gly Leu Phe Ala Leu Thr Pro Ala Ser Leu Phe Lys His Asp Ala Leu
385                 390                 395                 400 ggg ggc tcg atc ggt ccg gcg ctg tcg ctg ccg atc ttc gat cgc ggc        1248
Gly Gly Ser Ile Gly Pro Ala Leu Ser Leu Pro Ile Phe Asp Arg Gly
                405                 410                 415 cgg ctg aag gcg aag ctg ggg ggc gac gtg gcg aac gcg gac gtg gcg        1296
Arg Leu Lys Ala Lys Leu Gly Gly Asp Val Ala Asn Ala Asp Val Ala
        420                 425                 430 ctg gcg ctg tac aac cag acg gtg gat gcg gcg ctg ggc gag gtg gcg        1344
Leu Ala Leu Tyr Asn Gln Thr Val Asp Ala Ala Leu Gly Glu Val Ala
            435                 440                 445 cgg cag ttg acg tcg ctg tcg acg gtg gat gcg ctg ctc gag gcg cag        1392
Arg Gln Leu Thr Ser Leu Ser Thr Val Asp Ala Leu Leu Glu Ala Gln
450                 455                 460 cag cag gcg gtg cgc tcg gcg cag cgg atg gtg gcg ctg gcg cag gac        1440
Gln Gln Ala Val Arg Ser Ala Gln Arg Met Val Ala Leu Ala Gln Asp
465                 470                 475                 480 cgg cac cgg cgg ggg atg ggg atg cgc aag gac gtg aac gtg gcg aag        1488
Arg His Arg Arg Gly Met Gly Met Arg Lys Asp Val Asn Val Ala Lys
                485                 490                 495 ctg acg ctg ctg gac gag cgt gcg cac gtg atc gag ctg cag gcg cgg        1536
Leu Thr Leu Leu Asp Glu Arg Ala His Val Ile Glu Leu Gln Ala Arg
            500                 505                 510 cgg cgg acg ctg cgg gtg ggg ctg atc ggg gcg ctg ggc ggc ggc ttc        1584
Arg Arg Thr Leu Arg Val Gly Leu Ile Gly Ala Leu Gly Gly Gly Phe
        515                 520                 525 gac gcg cgg ccg gcg ggc ggc gcg ccg ctc gcg cag ggc aag ccg ttc        1632
Asp Ala Arg Pro Ala Gly Gly Ala Pro Leu Ala Gln Gly Lys Pro Phe
530                 535                 540 gcg gcg gcg agc gac agg ccg ccc gat tga                                1662
Ala Ala Ala Ser Asp Arg Pro Pro Asp
545                 550
```

<210> SEQ ID NO 26
<211> LENGTH: 553
<212> TYPE: PRT
<213> ORGANISM: Burkholderia thailandensis

<400> SEQUENCE: 26

```
Met Arg Ala Arg Ala Arg Arg Ala Ser Arg Cys Gly Arg Asn Glu
1               5                   10                  15

Arg Asn Gly Pro Gln Arg Asp Thr Gly Lys Gln Glu Gly Arg Ile Ile
                20                  25                  30

Arg Met Thr Gln Thr Ala Thr Gln Ala Ala Thr Arg Ala Met Ile Ala
        35                  40                  45

Thr Gly Ser Arg Ala Ala Arg Arg Leu Ala Ala Ala Leu Ala Trp
    50                  55                  60

Ala Leu Ala Gly Cys Val Pro Ser Gly Phe Glu Pro Ala Leu Ala Pro
65                  70                  75                  80

Arg Thr Pro Gly Asp Asp Ala Leu Ala His Thr Ala Gly Gly Ala Ala
                85                  90                  95

His Gly Ala Trp Pro Ser Pro Asp Trp Val Arg Gln Leu Gly Asp Pro
            100                 105                 110

Gln Leu Asp Ala Leu Val Asp Glu Ala Leu Arg Gln Asn Pro Thr Leu
```

```
            115                 120                 125
Gln Ala Gln Ala Arg Ile Gly Val Ala Gln Ser Gln Leu Gln Gln
    130                 135                 140
Phe Glu Ser Leu Thr Gly Leu Thr Ala Thr Ala Gly Ala Ser Leu Ser
145                 150                 155                 160
Lys Ala His Val Pro Arg Ser Gly Gly Thr Ile Asn Thr Thr Phe Asn
                165                 170                 175
Gly Leu Pro Val Ser Val Pro Leu Val Gly Glu Ser Val Ser Ser
                180                 185                 190
Ser Ser Leu Phe Val Gly Leu Asn Tyr Gln Leu Asp Leu Trp Gly Lys
            195                 200                 205
Asn Ala Ala Thr Arg Gly Leu Leu Ser Met Arg Asp Ala Ala Arg
210                 215                 220
Val Glu Ala Glu Gln Ala Arg Leu Ala Leu Ser Val Ala Ile Val Thr
225                 230                 235                 240
Leu Tyr Gly Glu Leu Asp Arg Ala Tyr Ala Leu Arg Glu Leu Leu Gln
                245                 250                 255
Gln Lys Arg Arg Ala Ser Glu Gln Val Glu Thr Val Leu Arg Glu Arg
                260                 265                 270
Ala Ala Arg Gly Ile Asp Asn Gly Tyr Asp Ala Asp Ala Ala Leu
            275                 280                 285
Lys Arg Gly Lys Leu Leu Glu Gln Leu Ala Leu Thr Asp Glu Gln Ile
            290                 295                 300
Gln Leu Gln Lys Leu Gln Leu Gly Val Leu Ser Gly Arg Gly Pro Glu
305                 310                 315                 320
Arg Gly Leu Ser Leu Ala Arg Pro Lys Leu Ala Pro Leu Ala Asp Ala
                325                 330                 335
Pro Leu Pro Ala Arg Leu Pro Ala Gly Leu Leu Gly Arg Arg Pro Asp
                340                 345                 350
Ile Val Ala Ala Arg Leu Arg Val Glu Ala Ala Tyr Ala Ala Ile Asp
            355                 360                 365
Gly Thr Arg Ala Ser Phe Tyr Pro Asp Val Asn Leu Ala Ala Leu Gly
    370                 375                 380
Gly Leu Phe Ala Leu Thr Pro Ala Ser Leu Phe Lys His Asp Ala Leu
385                 390                 395                 400
Gly Gly Ser Ile Gly Pro Ala Leu Ser Leu Pro Ile Phe Asp Arg Gly
                405                 410                 415
Arg Leu Lys Ala Lys Leu Gly Gly Asp Val Ala Asn Ala Asp Val Ala
                420                 425                 430
Leu Ala Leu Tyr Asn Gln Thr Val Asp Ala Ala Leu Gly Glu Val Ala
            435                 440                 445
Arg Gln Leu Thr Ser Leu Ser Thr Val Asp Ala Ala Leu Leu Glu Ala Gln
    450                 455                 460
Gln Gln Ala Val Arg Ser Ala Gln Arg Met Val Ala Leu Ala Gln Asp
465                 470                 475                 480
Arg His Arg Arg Gly Met Gly Met Arg Lys Asp Val Asn Val Ala Lys
                485                 490                 495
Leu Thr Leu Leu Asp Glu Arg Ala His Val Ile Glu Leu Gln Ala Arg
                500                 505                 510
Arg Arg Thr Leu Arg Val Gly Leu Ile Gly Ala Leu Gly Gly Gly Phe
            515                 520                 525
Asp Ala Arg Pro Ala Gly Gly Ala Pro Leu Ala Gln Gly Lys Pro Phe
    530                 535                 540
```

```
Ala Ala Ala Ser Asp Arg Pro Pro Asp
545                 550

<210> SEQ ID NO 27
<211> LENGTH: 1401
<212> TYPE: DNA
<213> ORGANISM: Burkholderia thailandensis
<220> FEATURE:
<221> NAME/KEY: CDS
<222> LOCATION: (1)..(1401)

<400> SEQUENCE: 27 atg cgg ccc gaa gcc acc gac acc cga aga cac cga cac caa cgc cac      48
Met Arg Pro Glu Ala Thr Asp Thr Arg Arg His Arg His Gln Arg His
1               5                   10                  15 ctt cac cgt gta cac gag cga ttc aac cga cac cgc

```
gca ggc gca gct gga ggc ggc gcg cgc gct ggg cag cga gcg gcc ggt      816
Ala Gly Ala Ala Gly Gly Gly Ala Arg Ala Gly Gln Arg Ala Ala Gly
            260                 265                 270 cga gca gaa ccc ggc ggt gca gca ggc ggc cgc gca gtt caa gct ggc      864
Arg Ala Glu Pro Gly Gly Ala Ala Gly Gly Arg Ala Val Gln Ala Gly
        275                 280                 285 gta ccg gaa cct gag gcg cac gac gat cgt gtc gcc ggt gga cgg cac      912
Val Pro Glu Pro Glu Ala His Asp Asp Arg Val Ala Gly Gly Arg His
    290                 295                 300 ggt cgg tca gcg gtc ggt gca gat cgg tca gca ggt ggg gcc ggg ggt      960
Gly Arg Ser Ala Val Gly Ala Asp Arg Ser Ala Gly Gly Ala Gly Gly
305                 310                 315                 320 gcc gct gat gtc ggt ggt gca gtt gcg gca ggt gtg ggt gga ggc gaa     1008
Ala Ala Asp Val Gly Gly Ala Val Ala Ala Gly Val Gly Gly Gly Glu
                325                 330                 335 ctt caa gga agg gca gat ccg gca cat gcg ggt ggg cca gcc ggt gcg     1056
Leu Gln Gly Arg Ala Asp Pro Ala His Ala Gly Gly Pro Ala Gly Ala
            340                 345                 350 gct cga atc gga cct gta cgg cgc gcg ggt gac gta cca cgg ccg ggt     1104
Ala Arg Ile Gly Pro Val Arg Arg Ala Gly Asp Val Pro Arg Pro Gly
        355                 360                 365 gga ggg ggt ctc ggc ggg cac ggg cag cgc gtt ctc gat gct gcc gtc     1152
Gly Gly Gly Leu Gly Gly His Gly Gln Arg Val Leu Asp Ala Ala Val
    370                 375                 380 gca gaa cgc ggc ggg gaa ctg gat caa ggt ggt gca gcg cct gcc ggt     1200
Ala Glu Arg Gly Gly Glu Leu Asp Gln Gly Gly Ala Ala Pro Ala Gly
385                 390                 395                 400 ggt gat ctc gct gga gcc gtc gga gct ggc ggc gca ccc gct gcg ggt     1248
Gly Asp Leu Ala Gly Ala Val Gly Ala Gly Gly Ala Pro Ala Ala Gly
                405                 410                 415 ggg gct gtc gat gcg cgc gac ggt gga gac gaa ggt gcg tgg cgg ccg     1296
Gly Ala Val Asp Ala Arg Asp Gly Gly Asp Glu Gly Ala Trp Arg Pro
            420                 425                 430 cct gct cga cgg cga cgc gcc gct gcc ggg gct gcg cac gcg ggt gca     1344
Pro Ala Arg Arg Arg Arg Ala Ala Ala Gly Ala Ala His Ala Gly Ala
        435                 440                 445 cga agc gca ggc ggg cga ggc cga ggc cgc ggc ttc ggc agt gat tcg     1392
Arg Ser Ala Gly Gly Arg Gly Arg Gly Arg Gly Phe Gly Ser Asp Ser
    450                 455                 460 gga gaa tga                                                         1401
Gly Glu
465

<210> SEQ ID NO 28
<211> LENGTH: 466
<212> TYPE: PRT
<213> ORGANISM: Burkholderia thailandensis

<400> SEQUENCE: 28

Met Arg Pro Glu Ala Thr Asp Thr Arg Arg His Arg His Gln Arg His
1               5                   10                  15

Leu His Arg Val His Glu Arg Phe Asn Arg His Arg Pro Arg Ala Ser
            20                  25                  30

Lys Pro Val Gly Pro Ile Arg Asp Gly Leu Arg Ala Gly Pro Ala Val
        35                  40                  45

Ala Gly Arg Arg His Arg His His Ala Arg Glu Asp Leu Glu Arg Tyr
    50                  55                  60

Arg His Arg Tyr Pro Ala Arg Glu Gly Ala His Arg Ser Gly Arg Pro
65                  70                  75                  80
```

Arg Arg Arg Ala Arg Ala Arg Ala Gly Ala Ala Arg Ile Ala
                85                  90                  95

Ser Ala Ala Gly Ser Arg Gly Asp Ala Arg Arg Ala Pro Arg Asp Ala
            100                 105                 110

Pro Pro Ala Leu Arg Ala Val Leu Arg Ala Ala Gly Ala Gly Arg Ala
        115                 120                 125

Asp Arg Gly Ala Leu Leu Val Arg Arg Ala Leu Gln Arg Gly Asp
    130                 135                 140

Gly Arg Arg Val Arg Gly Arg Gln Arg Gly Ala Asp Arg Ala Asp
145                 150                 155                 160

Pro Gly Asp Gly Asp Arg Arg Ala Gly Gly His Ala Ala Gly Glu
            165                 170                 175

Gly Gly Ala Gly Ala Gly Glu Ala Arg Arg Gly Arg Val Gly Gly
        180                 185                 190

Val Arg Ala Gly Ala Gly Ala Ala Arg Ala Gly Gly Ala Ala Gly Gly
    195                 200                 205

Glu His Ala Ala Leu Asp Gly Asp Val Arg Gly Asp Gly Glu Gly Ala
    210                 215                 220

Arg Gly Gly Pro Glu Ala Cys Ala Ala Gly Val Ser Gly Gly Thr Gly
225                 230                 235                 240

Ala Ala Lys Val Val Ala Gly Glu Arg Ala Gly Gly Ala Gly Gly Gly
            245                 250                 255

Ala Gly Ala Ala Gly Gly Ala Arg Ala Ala Gly Gln Arg Ala Ala Gly
        260                 265                 270

Arg Ala Glu Pro Gly Ala Ala Gly Gly Arg Ala Val Gln Ala Gly
    275                 280                 285

Val Pro Glu Pro Glu Ala His Asp Asp Arg Val Ala Gly Gly Arg His
    290                 295                 300

Gly Arg Ser Ala Val Gly Ala Asp Arg Ser Ala Gly Gly Ala Gly Gly
305                 310                 315                 320

Ala Ala Asp Val Gly Gly Ala Val Ala Ala Gly Val Gly Gly Gly Glu
            325                 330                 335

Leu Gln Gly Arg Ala Asp Pro Ala His Ala Gly Gly Pro Ala Gly Ala
        340                 345                 350

Ala Arg Ile Gly Pro Val Arg Arg Ala Gly Asp Val Pro Arg Pro Gly
    355                 360                 365

Gly Gly Gly Leu Gly Gly His Gly Gln Arg Val Leu Asp Ala Ala Val
    370                 375                 380

Ala Glu Arg Gly Gly Glu Leu Asp Gln Gly Gly Ala Ala Pro Ala Gly
385                 390                 395                 400

Gly Asp Leu Ala Gly Ala Val Gly Ala Gly Gly Ala Pro Ala Ala Gly
            405                 410                 415

Gly Ala Val Asp Ala Arg Asp Gly Gly Asp Glu Gly Ala Trp Arg Pro
        420                 425                 430

Pro Ala Arg Arg Arg Ala Ala Ala Gly Ala Ala His Ala Gly Ala
    435                 440                 445

Arg Ser Ala Gly Gly Arg Gly Arg Gly Arg Gly Phe Gly Ser Asp Ser
450                 455                 460

Gly Glu
465

<210> SEQ ID NO 29
<211> LENGTH: 1680
<212> TYPE: DNA

```
<213> ORGANISM: Pseudomonas putida
<220> FEATURE:
<221> NAME/KEY: CDS
<222> LOCATION: (1)..(1680)

<400> SEQUENCE: 29 atg agt aac aag aac aac gat gag cta cag cgg cag gcc tcg gaa aac      48
Met Ser Asn Lys Asn Asn Asp Glu Leu Gln Arg Gln Ala Ser Glu Asn
1               5                   10                  15 acc atg ggg ctg aac ccg gtc atc ggc atc cgc cgc aag gac ctg ttg      96
Thr Met Gly Leu Asn Pro Val Ile Gly Ile Arg Arg Lys Asp Leu Leu
            20                  25                  30 agc tcg gca cgc acc gtg ctg cgc cag gcc gtg cgc caa ccg ctg cac     144
Ser Ser Ala Arg Thr Val Leu Arg Gln Ala Val Arg Gln Pro Leu His
        35                  40                  45 agc gcc aag cat gtg gct cac ttt ggc ctg gag ctg aag aac gtg ttg     192
Ser Ala Lys His Val Ala His Phe Gly Leu Glu Leu Lys Asn Val Leu
    50                  55                  60 ctg ggc aaa tcc agc ctg gcc ccg gac agc gac gac cgt cgc ttc aat     240
Leu Gly Lys Ser Ser Leu Ala Pro Asp Ser Asp Asp Arg Arg Phe Asn
65                  70                  75                  80 gac ccg gcc tgg agc aac aac ccg ctg tac cgc cgc tac ctg caa acc     288
Asp Pro Ala Trp Ser Asn Asn Pro Leu Tyr Arg Arg Tyr Leu Gln Thr
                85                  90                  95 tac ctg gcc tgg cgc aag gag ctg cag gac tgg gtg agc agc agc gac     336
Tyr Leu Ala Trp Arg Lys Glu Leu Gln Asp Trp Val Ser Ser Ser Asp
            100                 105                 110 ctg tcc ccc cag gac atc agc cgc ggc cag ttc gtc atc aac ctg atg     384
Leu Ser Pro Gln Asp Ile Ser Arg Gly Gln Phe Val Ile Asn Leu Met
        115                 120                 125 acc gag gcc atg gcg ccg acc aat acc ctg tcc aac ccg gct gcg gtc     432
Thr Glu Ala Met Ala Pro Thr Asn Thr Leu Ser Asn Pro Ala Ala Val
    130                 135                 140 aaa cgc ttc ttc gaa acc ggc ggc aag agc ctg ctc gat ggc ctg tcc     480
Lys Arg Phe Phe Glu Thr Gly Gly Lys Ser Leu Leu Asp Gly Leu Ser
145                 150                 155                 160 aac ctg gcc aag gac atg gtc aac aac ggc ggc atg ccc agc cag gtg     528
Asn Leu Ala Lys Asp Met Val Asn Asn Gly Gly Met Pro Ser Gln Val
                165                 170                 175 aac atg gat gcc ttc gaa gtg ggc aag aac ctg ggc acc agc gaa ggc     576
Asn Met Asp Ala Phe Glu Val Gly Lys Asn Leu Gly Thr Ser Glu Gly
            180                 185                 190 gcg gtg gtg tac cgc aac gat gtg ctg gaa ctg atc cag tac agc ccc     624
Ala Val Val Tyr Arg Asn Asp Val Leu Glu Leu Ile Gln Tyr Ser Pro
        195                 200                 205 atc acc gag cag gtg cat gcc cgt ccg ctg ctg gtg gtg cca ccg cag     672
Ile Thr Glu Gln Val His Ala Arg Pro Leu Leu Val Val Pro Pro Gln
    210                 215                 220 atc aac aag ttc tac gtg ttc gac ctc agc ccg gaa aag agc ctg gcg     720
Ile Asn Lys Phe Tyr Val Phe Asp Leu Ser Pro Glu Lys Ser Leu Ala
225                 230                 235                 240 cgc ttc tgc ctg cgc tcg cag cag cag acc ttc atc atc agc tgg cgc     768
Arg Phe Cys Leu Arg Ser Gln Gln Gln Thr Phe Ile Ile Ser Trp Arg
                245                 250                 255 aac ccg acc aag gcc cag cgt gaa tgg ggc ctg tcc acc tac atc gat     816
Asn Pro Thr Lys Ala Gln Arg Glu Trp Gly Leu Ser Thr Tyr Ile Asp
            260                 265                 270 gcg ctg aaa gaa gcc gtc gac gcg gtg ctg tcg att acc ggc agc aag     864
Ala Leu Lys Glu Ala Val Asp Ala Val Leu Ser Ile Thr Gly Ser Lys
        275                 280                 285
```

```
gac ctg aac atg ctc ggc gcc tgc tcc ggt ggc atc act tgt acc gca      912
Asp Leu Asn Met Leu Gly Ala Cys Ser Gly Gly Ile Thr Cys Thr Ala
    290             295                 300 ctg gtc ggg cac tat gcc gca ttg ggc gag aac aag gtc aac gcc ctg      960
Leu Val Gly His Tyr Ala Ala Leu Gly Glu Asn Lys Val Asn Ala Leu
305             310                 315                 320 acc gtg ctg gtc agc gtg ctg gac acc acc atg gac aac cag gtt gct     1008
Thr Val Leu Val Ser Val Leu Asp Thr Thr Met Asp Asn Gln Val Ala
                325                 330                 335 ttg ttt gtc gac gag cag acc ttg gag gcc gcc aag cgc cac tcc tat     1056
Leu Phe Val Asp Glu Gln Thr Leu Glu Ala Ala Lys Arg His Ser Tyr
            340                 345                 350 cag gcg ggc gtg ctg gaa ggc agc gaa atg gcc aag gtg ttc gcc tgg     1104
Gln Ala Gly Val Leu Glu Gly Ser Glu Met Ala Lys Val Phe Ala Trp
        355                 360                 365 atg cgc ccc aac gac ctg atc tgg aac tac tgg gta aac aac tac ctg     1152
Met Arg Pro Asn Asp Leu Ile Trp Asn Tyr Trp Val Asn Asn Tyr Leu
    370             375                 380 ctc ggc aat gag ccc ccc gtg ttc gac atc ctg ttc tgg aac aac gac     1200
Leu Gly Asn Glu Pro Pro Val Phe Asp Ile Leu Phe Trp Asn Asn Asp
385             390                 395                 400 acc acg cgc ctg ccg gcc gcc ttc cac ggc gac ctg atc gaa atg ttc     1248
Thr Thr Arg Leu Pro Ala Ala Phe His Gly Asp Leu Ile Glu Met Phe
                405                 410                 415 aag agc aac ccg ctg acc cgc ccc gac gcc ctg aaa gtg tgc ggc acc     1296
Lys Ser Asn Pro Leu Thr Arg Pro Asp Ala Leu Lys Val Cys Gly Thr
            420                 425                 430 gcg atc gac ctg aaa cag gtc aaa tgc gac atc tac agc ctc gcc ggc     1344
Ala Ile Asp Leu Lys Gln Val Lys Cys Asp Ile Tyr Ser Leu Ala Gly
        435                 440                 445 acc aac gac cac atc acc ccc tgg ccg tca tgc tac cgc tcg gca cat     1392
Thr Asn Asp His Ile Thr Pro Trp Pro Ser Cys Tyr Arg Ser Ala His
    450             455                 460 ctg ttc ggc ggc aag atc gaa ttc gta ctg tcc aac agc ggg cat atc     1440
Leu Phe Gly Gly Lys Ile Glu Phe Val Leu Ser Asn Ser Gly His Ile
465             470                 475                 480 cag agc atc ctc aac ccg ccg ggc aac ccg aag gca cgt ttc atg acc     1488
Gln Ser Ile Leu Asn Pro Pro Gly Asn Pro Lys Ala Arg Phe Met Thr
                485                 490                 495 ggt gcc gat cgc ccg ggt gac ccg gtg gcc tgg cag gaa aat gcc atc     1536
Gly Ala Asp Arg Pro Gly Asp Pro Val Ala Trp Gln Glu Asn Ala Ile
            500                 505                 510 aag cat gca gac tcc tgg tgg ctg cac tgg cag agt tgg ctg ggc gag     1584
Lys His Ala Asp Ser Trp Trp Leu His Trp Gln Ser Trp Leu Gly Glu
        515                 520                 525 cgt gcc ggc gcg ctg aaa aag gca ccg acc cgc ctg ggc aac cgt acc     1632
Arg Ala Gly Ala Leu Lys Lys Ala Pro Thr Arg Leu Gly Asn Arg Thr
    530             535                 540 tat gcc gcc ggc gaa gcc tcc cca ggc acc tac gtt cac gag cgt tga     1680
Tyr Ala Ala Gly Glu Ala Ser Pro Gly Thr Tyr Val His Glu Arg
545                 550                 555
```

<210> SEQ ID NO 30
<211> LENGTH: 559
<212> TYPE: PRT
<213> ORGANISM: Pseudomonas putida

<400> SEQUENCE: 30

```
Met Ser Asn Lys Asn Asn Asp Glu Leu Gln Arg Gln Ala Ser Glu Asn
1               5                   10                  15
```

```
Thr Met Gly Leu Asn Pro Val Ile Gly Ile Arg Arg Lys Asp Leu Leu
            20                  25                  30

Ser Ser Ala Arg Thr Val Leu Arg Gln Ala Val Arg Gln Pro Leu His
            35                  40                  45

Ser Ala Lys His Val Ala His Phe Gly Leu Glu Leu Lys Asn Val Leu
50                      55                  60

Leu Gly Lys Ser Ser Leu Ala Pro Asp Ser Asp Arg Arg Phe Asn
65                  70                  75                  80

Asp Pro Ala Trp Ser Asn Asn Pro Leu Tyr Arg Arg Tyr Leu Gln Thr
                85                  90                  95

Tyr Leu Ala Trp Arg Lys Glu Leu Gln Asp Trp Val Ser Ser Ser Asp
            100                 105                 110

Leu Ser Pro Gln Asp Ile Ser Arg Gly Gln Phe Val Ile Asn Leu Met
            115                 120                 125

Thr Glu Ala Met Ala Pro Thr Asn Thr Leu Ser Asn Pro Ala Ala Val
    130                 135                 140

Lys Arg Phe Phe Glu Thr Gly Gly Lys Ser Leu Leu Asp Gly Leu Ser
145                 150                 155                 160

Asn Leu Ala Lys Asp Met Val Asn Asn Gly Gly Met Pro Ser Gln Val
            165                 170                 175

Asn Met Asp Ala Phe Glu Val Gly Lys Asn Leu Gly Thr Ser Glu Gly
            180                 185                 190

Ala Val Val Tyr Arg Asn Asp Val Leu Glu Leu Ile Gln Tyr Ser Pro
            195                 200                 205

Ile Thr Glu Gln Val His Ala Arg Pro Leu Leu Val Val Pro Pro Gln
    210                 215                 220

Ile Asn Lys Phe Tyr Val Phe Asp Leu Ser Pro Glu Lys Ser Leu Ala
225                 230                 235                 240

Arg Phe Cys Leu Arg Ser Gln Gln Gln Thr Phe Ile Ile Ser Trp Arg
            245                 250                 255

Asn Pro Thr Lys Ala Gln Arg Glu Trp Gly Leu Ser Thr Tyr Ile Asp
            260                 265                 270

Ala Leu Lys Glu Ala Val Asp Ala Val Leu Ser Ile Thr Gly Ser Lys
            275                 280                 285

Asp Leu Asn Met Leu Gly Ala Cys Ser Gly Gly Ile Thr Cys Thr Ala
    290                 295                 300

Leu Val Gly His Tyr Ala Ala Leu Gly Glu Asn Lys Val Asn Ala Leu
305                 310                 315                 320

Thr Val Leu Val Ser Val Leu Asp Thr Thr Met Asp Asn Gln Val Ala
            325                 330                 335

Leu Phe Val Asp Glu Gln Thr Leu Glu Ala Ala Lys Arg His Ser Tyr
            340                 345                 350

Gln Ala Gly Val Leu Glu Gly Ser Glu Met Ala Lys Val Phe Ala Trp
            355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Met Phe
            405                 410                 415

Lys Ser Asn Pro Leu Thr Arg Pro Asp Ala Leu Lys Val Cys Gly Thr
            420                 425                 430

Ala Ile Asp Leu Lys Gln Val Lys Cys Asp Ile Tyr Ser Leu Ala Gly
```

-continued

```
                435                 440                 445
Thr Asn Asp His Ile Thr Pro Trp Pro Ser Cys Tyr Arg Ser Ala His
    450                 455                 460

Leu Phe Gly Gly Lys Ile Glu Phe Val Leu Ser Asn Ser Gly His Ile
465                 470                 475                 480

Gln Ser Ile Leu Asn Pro Pro Gly Asn Pro Lys Ala Arg Phe Met Thr
                485                 490                 495

Gly Ala Asp Arg Pro Gly Asp Pro Val Ala Trp Gln Glu Asn Ala Ile
                500                 505                 510

Lys His Ala Asp Ser Trp Trp Leu His Trp Gln Ser Trp Leu Gly Glu
                515                 520                 525

Arg Ala Gly Ala Leu Lys Lys Ala Pro Thr Arg Leu Gly Asn Arg Thr
                530                 535                 540

Tyr Ala Ala Gly Glu Ala Ser Pro Gly Thr Tyr Val His Glu Arg
545                 550                 555

<210> SEQ ID NO 31
<211> LENGTH: 1683
<212> TYPE: DNA
<213> ORGANISM: Pseudomonas putida
<220> FEATURE:
<221> NAME/KEY: CDS
<222> LOCATION: (1)..(1683)

<400> SEQUENCE: 31 atg aca gac aaa ccg gcc aaa gga tcg aca acg ctc ccc gcc acc cgc      48
Met Thr Asp Lys Pro Ala Lys Gly Ser Thr Thr Leu Pro Ala Thr Arg
1               5                   10                  15 atg aac gtg cag aac gcc atc ctc ggc ctg cgc ggc cgc gac ctg ctt      96
Met Asn Val Gln Asn Ala Ile Leu Gly Leu Arg Gly Arg Asp Leu Leu
                20                  25                  30 tcc acg ctg cgc aac gtc ggc cgc cac ggc ctg cgc cac ccg ctg cat     144
Ser Thr Leu Arg Asn Val Gly Arg His Gly Leu Arg His Pro Leu His
            35                  40                  45 acc gcg cat cat ctg ctg gcg ctt ggc ggg cag ttg ggg cgg gtg atg     192
Thr Ala His His Leu Leu Ala Leu Gly Gly Gln Leu Gly Arg Val Met
        50                  55                  60 ctg ggg gac acg ccc tac cag ccg aac ccg cgt gac gca cgc ttc agt     240
Leu Gly Asp Thr Pro Tyr Gln Pro Asn Pro Arg Asp Ala Arg Phe Ser
65                  70                  75                  80 gac ccg acc tgg agc cag aac ccg ttc tac cgc cgc ggc ctg caa gcc     288
Asp Pro Thr Trp Ser Gln Asn Pro Phe Tyr Arg Arg Gly Leu Gln Ala
                85                  90                  95 tat ctg gcc tgg cag aag cag aca cgc cag tgg atc gat gaa agc cat     336
Tyr Leu Ala Trp Gln Lys Gln Thr Arg Gln Trp Ile Asp Glu Ser His
                100                 105                 110 ttg aac gac gat gat cga gcc cgc gcc cac ttc ctg ttc aac ctg atc     384
Leu Asn Asp Asp Asp Arg Ala Arg Ala His Phe Leu Phe Asn Leu Ile
            115                 120                 125 aac gat gcg ctg gcg ccc agc aac tca ctg ctc aat ccg cag gcg gtc     432
Asn Asp Ala Leu Ala Pro Ser Asn Ser Leu Leu Asn Pro Gln Ala Val
        130                 135                 140 aag ggg ctg ttc aac acc ggc ggc cag agc ctg gtg cgc ggc gtg gct     480
Lys Gly Leu Phe Asn Thr Gly Gly Gln Ser Leu Val Arg Gly Val Ala
145                 150                 155                 160 cac ctg ctc gac gac ctg cgt cac aac gat ggg ctg cct cgt cag gtg     528
His Leu Leu Asp Asp Leu Arg His Asn Asp Gly Leu Pro Arg Gln Val
                165                 170                 175 gac gag cgc gcc ttc gaa gtg ggc gtt aac ctg gcc gca acc cct ggc     576
```

```
                Asp Glu Arg Ala Phe Glu Val Gly Val Asn Leu Ala Ala Thr Pro Gly
                            180                 185                 190 gca gtg gta ttt cgc aac gag ctg ctg gag ctg atc cag tac tcg ccg        624
Ala Val Val Phe Arg Asn Glu Leu Leu Glu Leu Ile Gln Tyr Ser Pro
            195                 200                 205 atg agc gaa aag cag cac gca cgc cca ctg ctg gtc gtg ccg cct cag        672
Met Ser Glu Lys Gln His Ala Arg Pro Leu Leu Val Val Pro Pro Gln
210                 215                 220 atc aac agg ttc tac atc ttc gac ctc agc gcg acc aac agc ttc gtc        720
Ile Asn Arg Phe Tyr Ile Phe Asp Leu Ser Ala Thr Asn Ser Phe Val
225                 230                 235                 240 cag tac atg ctc aaa agc ggc ttg cag gtg ttc atg gtc agc tgg agc        768
Gln Tyr Met Leu Lys Ser Gly Leu Gln Val Phe Met Val Ser Trp Ser
                245                 250                 255 aac ccc gac cca cgc cac cgt gaa tgg ggc ctt tcc agc tat gtg caa        816
Asn Pro Asp Pro Arg His Arg Glu Trp Gly Leu Ser Ser Tyr Val Gln
            260                 265                 270 gcc ctg gag gaa gcg ctc aat gcc tgc cgc agt atc agc ggc aac cgc        864
Ala Leu Glu Glu Ala Leu Asn Ala Cys Arg Ser Ile Ser Gly Asn Arg
        275                 280                 285 gac ccc aac ctg atg ggt gcc tgt gcc ggc ggc ctg acc atg gcc gca        912
Asp Pro Asn Leu Met Gly Ala Cys Ala Gly Gly Leu Thr Met Ala Ala
290                 295                 300 ctg caa ggc cat ctg caa gcc aag aag caa ttg cgc cgg gtg cgc agt        960
Leu Gln Gly His Leu Gln Ala Lys Lys Gln Leu Arg Arg Val Arg Ser
305                 310                 315                 320 gcc acg tat ctg gtc agc ttg ctg gac agc aag ttc gaa agc ccg gcc       1008
Ala Thr Tyr Leu Val Ser Leu Leu Asp Ser Lys Phe Glu Ser Pro Ala
                325                 330                 335 agc ctg ttc gcc gat gag cag acc atc gaa gcg gcc aag cga cgc tcc       1056
Ser Leu Phe Ala Asp Glu Gln Thr Ile Glu Ala Ala Lys Arg Arg Ser
            340                 345                 350 tat cag cgt ggc gtg ctg gac ggt ggt gaa gtg gcg cgg atc ttc gcc       1104
Tyr Gln Arg Gly Val Leu Asp Gly Gly Glu Val Ala Arg Ile Phe Ala
        355                 360                 365 tgg atg cgg ccc aac gac ctg atc tgg aac tac tgg gta aac aac tac       1152
Trp Met Arg Pro Asn Asp Leu Ile Trp Asn Tyr Trp Val Asn Asn Tyr
370                 375                 380 ctg ctc ggc aag aca ccg cct gcg ttc gac atc ctg tac tgg aat gcc       1200
Leu Leu Gly Lys Thr Pro Pro Ala Phe Asp Ile Leu Tyr Trp Asn Ala
385                 390                 395                 400 gac agc acg cgc ctg ccc gcc gcg ctg cat ggc gac ctg ctg gag ttt       1248
Asp Ser Thr Arg Leu Pro Ala Ala Leu His Gly Asp Leu Leu Glu Phe
                405                 410                 415 ttc aag ctc aac ccc ttg acc tac gcg tcc ggg ctg gag gtg tgc ggt       1296
Phe Lys Leu Asn Pro Leu Thr Tyr Ala Ser Gly Leu Glu Val Cys Gly
            420                 425                 430 acg ccg atc gac ctg cag cag gtc aat atc gac agc ttt acc gtg gcc       1344
Thr Pro Ile Asp Leu Gln Gln Val Asn Ile Asp Ser Phe Thr Val Ala
        435                 440                 445 ggc agc aac gac cac atc aca cca tgg gat gcg gtg tac cgc tcg gcc       1392
Gly Ser Asn Asp His Ile Thr Pro Trp Asp Ala Val Tyr Arg Ser Ala
450                 455                 460 ttg ctg ctg ggt ggc gag cgg cgc ttc gtg ctg gcc aac agc ggg cat       1440
Leu Leu Leu Gly Gly Glu Arg Arg Phe Val Leu Ala Asn Ser Gly His
465                 470                 475                 480 atc cag agc atc atc aac ccg cca ggc aac ccc aag gcc tac tac ctg       1488
Ile Gln Ser Ile Ile Asn Pro Pro Gly Asn Pro Lys Ala Tyr Tyr Leu
                485                 490                 495
```

| | | | | | | | | | | | | | | | |
|---|---|---|---|---|---|---|---|---|---|---|---|---|---|---|---|
| gcc | aac | ccc | aag | ctg | agc | agc | gac | cca | cgc | gcc | tgg | ttc | cac | gac | gcc |
| Ala | Asn | Pro | Lys | Leu | Ser | Ser | Asp | Pro | Arg | Ala | Trp | Phe | His | Asp | Ala |
|     |     |     | 500 |     |     |     |     | 505 |     |     |     |     | 510 |     |     |

1536

| | | | | | | | | | | | | | | | |
|---|---|---|---|---|---|---|---|---|---|---|---|---|---|---|---|
| aag | cgc | agt | gaa | ggc | agc | tgg | tgg | ccg | ttg | tgg | ctg | gag | tgg | atc | acc |
| Lys | Arg | Ser | Glu | Gly | Ser | Trp | Trp | Pro | Leu | Trp | Leu | Glu | Trp | Ile | Thr |
|     |     | 515 |     |     |     |     | 520 |     |     |     |     | 525 |     |     |     |

1584

| | | | | | | | | | | | | | | | |
|---|---|---|---|---|---|---|---|---|---|---|---|---|---|---|---|
| gca | cgc | tcc | ggc | ctg | ctc | aag | gca | ccg | cgt | act | gaa | ctg | ggc | aac | gcc |
| Ala | Arg | Ser | Gly | Leu | Leu | Lys | Ala | Pro | Arg | Thr | Glu | Leu | Gly | Asn | Ala |
|     | 530 |     |     |     |     | 535 |     |     |     |     | 540 |     |     |     |     |

1632

| | | | | | | | | | | | | | | | |
|---|---|---|---|---|---|---|---|---|---|---|---|---|---|---|---|
| act | tac | cca | ctg | cta | ggc | ccc | gcg | cca | ggc | acc | tac | gtg | ctg | acc | cga |
| Thr | Tyr | Pro | Leu | Leu | Gly | Pro | Ala | Pro | Gly | Thr | Tyr | Val | Leu | Thr | Arg |
| 545 |     |     |     |     | 550 |     |     |     |     | 555 |     |     |     |     | 560 |

1680 tga    1683

<210> SEQ ID NO 32
<211> LENGTH: 560
<212> TYPE: PRT
<213> ORGANISM: Pseudomonas putida

<400> SEQUENCE: 32

Met Thr Asp Lys Pro Ala Lys Gly Ser Thr Thr Leu Pro Ala Thr Arg
1               5                   10                  15

Met Asn Val Gln Asn Ala Ile Leu Gly Leu Arg Gly Arg Asp Leu Leu
                20                  25                  30

Ser Thr Leu Arg Asn Val Gly Arg His Gly Leu Arg His Pro Leu His
            35                  40                  45

Thr Ala His His Leu Leu Ala Leu Gly Gly Gln Leu Gly Arg Val Met
        50                  55                  60

Leu Gly Asp Thr Pro Tyr Gln Pro Asn Pro Arg Asp Ala Arg Phe Ser
65                  70                  75                  80

Asp Pro Thr Trp Ser Gln Asn Pro Phe Tyr Arg Arg Gly Leu Gln Ala
                85                  90                  95

Tyr Leu Ala Trp Gln Lys Gln Thr Arg Gln Trp Ile Asp Glu Ser His
            100                 105                 110

Leu Asn Asp Asp Arg Ala Arg Ala His Phe Leu Phe Asn Leu Ile
        115                 120                 125

Asn Asp Ala Leu Ala Pro Ser Asn Ser Leu Leu Asn Pro Gln Ala Val
130                 135                 140

Lys Gly Leu Phe Asn Thr Gly Gly Gln Ser Leu Val Arg Gly Val Ala
145                 150                 155                 160

His Leu Leu Asp Asp Leu Arg His Asn Asp Gly Leu Pro Arg Gln Val
                165                 170                 175

Asp Glu Arg Ala Phe Glu Val Gly Val Asn Leu Ala Ala Thr Pro Gly
            180                 185                 190

Ala Val Val Phe Arg Asn Glu Leu Leu Glu Leu Ile Gln Tyr Ser Pro
        195                 200                 205

Met Ser Glu Lys Gln His Ala Arg Pro Leu Leu Val Val Pro Pro Gln
    210                 215                 220

Ile Asn Arg Phe Tyr Ile Phe Asp Leu Ser Ala Thr Asn Ser Phe Val
225                 230                 235                 240

Gln Tyr Met Leu Lys Ser Gly Leu Gln Val Phe Met Val Ser Trp Ser
                245                 250                 255

Asn Pro Asp Pro Arg His Arg Glu Trp Gly Leu Ser Ser Tyr Val Gln
            260                 265                 270

Ala Leu Glu Glu Ala Leu Asn Ala Cys Arg Ser Ile Ser Gly Asn Arg
        275                 280                 285

```
Asp Pro Asn Leu Met Gly Ala Cys Ala Gly Gly Leu Thr Met Ala Ala
    290                 295                 300

Leu Gln Gly His Leu Gln Ala Lys Lys Gln Leu Arg Arg Val Arg Ser
305                 310                 315                 320

Ala Thr Tyr Leu Val Ser Leu Leu Asp Ser Lys Phe Glu Ser Pro Ala
                325                 330                 335

Ser Leu Phe Ala Asp Glu Gln Thr Ile Glu Ala Ala Lys Arg Arg Ser
            340                 345                 350

Tyr Gln Arg Gly Val Leu Asp Gly Gly Glu Val Ala Arg Ile Phe Ala
        355                 360                 365

Trp Met Arg Pro Asn Asp Leu Ile Trp Asn Tyr Trp Val Asn Asn Tyr
    370                 375                 380

Leu Leu Gly Lys Thr Pro Pro Ala Phe Asp Ile Leu Tyr Trp Asn Ala
385                 390                 395                 400

Asp Ser Thr Arg Leu Pro Ala Ala Leu His Gly Asp Leu Leu Glu Phe
                405                 410                 415

Phe Lys Leu Asn Pro Leu Thr Tyr Ala Ser Gly Leu Glu Val Cys Gly
            420                 425                 430

Thr Pro Ile Asp Leu Gln Gln Val Asn Ile Asp Ser Phe Thr Val Ala
        435                 440                 445

Gly Ser Asn Asp His Ile Thr Pro Trp Asp Ala Val Tyr Arg Ser Ala
    450                 455                 460

Leu Leu Leu Gly Gly Glu Arg Arg Phe Val Leu Ala Asn Ser Gly His
465                 470                 475                 480

Ile Gln Ser Ile Ile Asn Pro Pro Gly Asn Pro Lys Ala Tyr Tyr Leu
                485                 490                 495

Ala Asn Pro Lys Leu Ser Ser Asp Pro Arg Ala Trp Phe His Asp Ala
            500                 505                 510

Lys Arg Ser Glu Gly Ser Trp Trp Pro Leu Trp Leu Glu Trp Ile Thr
        515                 520                 525

Ala Arg Ser Gly Leu Leu Lys Ala Pro Arg Thr Glu Leu Gly Asn Ala
    530                 535                 540

Thr Tyr Pro Leu Leu Gly Pro Ala Pro Gly Thr Tyr Val Leu Thr Arg
545                 550                 555                 560
```

<210> SEQ ID NO 33
<211> LENGTH: 888
<212> TYPE: DNA
<213> ORGANISM: Pseudomonas putida
<220> FEATURE:
<221> NAME/KEY: CDS
<222> LOCATION: (1)..(888)

<400> SEQUENCE: 33

```
atg agg cca gaa atc gct gta ctt gat atc caa ggt cag tat cgg gtt      48
Met Arg Pro Glu Ile Ala Val Leu Asp Ile Gln Gly Gln Tyr Arg Val
1               5                   10                  15 tac acg gag ttc tat cgc gcg gat gcg gcc gaa aac acg atc atc ctg      96
Tyr Thr Glu Phe Tyr Arg Ala Asp Ala Ala Glu Asn Thr Ile Ile Leu
                20                  25                  30 atc aac ggc tcg ctg gcc acc acg gcc tcg ttc gcc cag acg gta cgt     144
Ile Asn Gly Ser Leu Ala Thr Thr Ala Ser Phe Ala Gln Thr Val Arg
            35                  40                  45 aac ctg cac cca cag ttc aac gtg gtt ctg ttc gac cag ccg tat tca     192
Asn Leu His Pro Gln Phe Asn Val Val Leu Phe Asp Gln Pro Tyr Ser
        50                  55                  60
```

| | | |
|---|---|---|
| ggc aag tcc aag ccg cac aac cgt cag gaa cgg ctg atc agc aag gag<br>Gly Lys Ser Lys Pro His Asn Arg Gln Glu Arg Leu Ile Ser Lys Glu<br>65                                  70                        75                            80 | 240 |
| acc gag gcg cat atc ctc ctt gag ctg atc gag cac ttc cag gca gac<br>Thr Glu Ala His Ile Leu Leu Glu Leu Ile Glu His Phe Gln Ala Asp<br>                                   85                        90                        95 | 288 |
| cac gtg atg tct ttt tcg tgg ggt ggc gca agc acg ctg ctg gcg ctg<br>His Val Met Ser Phe Ser Trp Gly Gly Ala Ser Thr Leu Leu Ala Leu<br>                          100                      105                      110 | 336 |
| gcg cac cag ccg cgg tac gtg aag aag gca gtg gtg agt tcg ttc tcg<br>Ala His Gln Pro Arg Tyr Val Lys Lys Ala Val Val Ser Ser Phe Ser<br>               115                      120                      125 | 384 |
| cca gtg atc aac gag cca atg cgc gac tat ctg gac cgt ggc tgc cag<br>Pro Val Ile Asn Glu Pro Met Arg Asp Tyr Leu Asp Arg Gly Cys Gln<br>130                                135                      140 | 432 |
| tac ctg gcc gcc tgc gac cgt tat cag gtc ggc aac ctg gtc aat gac<br>Tyr Leu Ala Ala Cys Asp Arg Tyr Gln Val Gly Asn Leu Val Asn Asp<br>145                              150                      155                      160 | 480 |
| acc atc ggc aag cac ttg ccg tcg ctg ctc aaa cgc ttc aac tac cgc<br>Thr Ile Gly Lys His Leu Pro Ser Leu Leu Lys Arg Phe Asn Tyr Arg<br>                                 165                      170                      175 | 528 |
| cat gtg agc agc ctg gac agc cac gag tac gca cag atg cac ttc cac<br>His Val Ser Ser Leu Asp Ser His Glu Tyr Ala Gln Met His Phe His<br>             180                      185                      190 | 576 |
| atc aac caa gtg ctg gag cac gac ctg gaa cgt gcg ctg caa ggc gcg<br>Ile Asn Gln Val Leu Glu His Asp Leu Glu Arg Ala Leu Gln Gly Ala<br>          195                      200                      205 | 624 |
| cgc aat atc aac atc ccg gtg ttg ttc atc aac ggc gaa cgc gac gag<br>Arg Asn Ile Asn Ile Pro Val Leu Phe Ile Asn Gly Glu Arg Asp Glu<br>210                                215                      220 | 672 |
| tac acc acg gtc gaa gat gcg cgg cag ttc agc aag cat gtg ggc aga<br>Tyr Thr Thr Val Glu Asp Ala Arg Gln Phe Ser Lys His Val Gly Arg<br>225                                230                      235                      240 | 720 |
| agc cag ttc agc gtg atc cgc gat gcg ggc cac ttc ctg gac atg gag<br>Ser Gln Phe Ser Val Ile Arg Asp Ala Gly His Phe Leu Asp Met Glu<br>                                 245                      250                      255 | 768 |
| aac aag acc gcc tgc gag aac acc cgc agt gtc atg ctg ggg ttc ctc<br>Asn Lys Thr Ala Cys Glu Asn Thr Arg Ser Val Met Leu Gly Phe Leu<br>             260                      265                      270 | 816 |
| aag cca acc gtg cgt gaa ccc cgc caa cgt tac caa ccc gtg caa cag<br>Lys Pro Thr Val Arg Glu Pro Arg Gln Arg Tyr Gln Pro Val Gln Gln<br>          275                      280                      285 | 864 |
| ggg cag cat gca ttg gcc atc tga<br>Gly Gln His Ala Leu Ala Ile<br>290                                295 | 888 |

```
<210> SEQ ID NO 34
<211> LENGTH: 295
<212> TYPE: PRT
<213> ORGANISM: Pseudomonas putida

<400> SEQUENCE: 34
```

Met Arg Pro Glu Ile Ala Val Leu Asp Ile Gln Gly Gln Tyr Arg Val
1                  5                        10                        15

Tyr Thr Glu Phe Tyr Arg Ala Asp Ala Ala Glu Asn Thr Ile Ile Leu
                    20                        25                        30

Ile Asn Gly Ser Leu Ala Thr Thr Ala Ser Phe Ala Gln Thr Val Arg
                        35                        40                        45

Asn Leu His Pro Gln Phe Asn Val Val Leu Phe Asp Gln Pro Tyr Ser
        50                        55                        60

```
Gly Lys Ser Lys Pro His Asn Arg Gln Glu Arg Leu Ile Ser Lys Glu
 65                  70                  75                  80

Thr Glu Ala His Ile Leu Leu Glu Leu Ile Glu His Phe Gln Ala Asp
                 85                  90                  95

His Val Met Ser Phe Ser Trp Gly Gly Ala Ser Thr Leu Leu Ala Leu
            100                 105                 110

Ala His Gln Pro Arg Tyr Val Lys Lys Ala Val Val Ser Ser Phe Ser
        115                 120                 125

Pro Val Ile Asn Glu Pro Met Arg Asp Tyr Leu Asp Arg Gly Cys Gln
    130                 135                 140

Tyr Leu Ala Ala Cys Asp Arg Tyr Gln Val Gly Asn Leu Val Asn Asp
145                 150                 155                 160

Thr Ile Gly Lys His Leu Pro Ser Leu Leu Lys Arg Phe Asn Tyr Arg
                165                 170                 175

His Val Ser Ser Leu Asp Ser His Glu Tyr Ala Gln Met His Phe His
            180                 185                 190

Ile Asn Gln Val Leu Glu His Asp Leu Glu Arg Ala Leu Gln Gly Ala
        195                 200                 205

Arg Asn Ile Asn Ile Pro Val Leu Phe Ile Asn Gly Glu Arg Asp Glu
    210                 215                 220

Tyr Thr Thr Val Glu Asp Ala Arg Gln Phe Ser Lys His Val Gly Arg
225                 230                 235                 240

Ser Gln Phe Ser Val Ile Arg Asp Ala Gly His Phe Leu Asp Met Glu
                245                 250                 255

Asn Lys Thr Ala Cys Glu Asn Thr Arg Ser Val Met Leu Gly Phe Leu
            260                 265                 270

Lys Pro Thr Val Arg Glu Pro Arg Gln Arg Tyr Gln Pro Val Gln Gln
        275                 280                 285

Gly Gln His Ala Leu Ala Ile
    290                 295

<210> SEQ ID NO 35
<211> LENGTH: 903
<212> TYPE: DNA
<213> ORGANISM: Pseudomonas aeruginosa
<220> FEATURE:
<221> NAME/KEY: CDS
<222> LOCATION: (1)..(903)

<400> SEQUENCE: 35 atg agg ccg gaa aca gcc atc atc gag atc cac ggg caa tac agg att      48
Met Arg Pro Glu Thr Ala Ile Ile Glu Ile His Gly Gln Tyr Arg Ile
 1               5                  10                  15 cac acc gag ttc tac ggc aac ccc gcg gcg cag caa acc atc atc ctg      96
His Thr Glu Phe Tyr Gly Asn Pro Ala Ala Gln Gln Thr Ile Ile Leu
                20                  25                  30 gtc aac ggc tcg ctg tcg acc aca gcg tcc ttc gcc cag acc gtg aag     144
Val Asn Gly Ser Leu Ser Thr Thr Ala Ser Phe Ala Gln Thr Val Lys
            35                  40                  45 tac ctg cag ccg cat tac aac gtg gtg ctc tac gac cag ccg tat gcc     192
Tyr Leu Gln Pro His Tyr Asn Val Val Leu Tyr Asp Gln Pro Tyr Ala
        50                  55                  60 ggc cag tcc aaa ccc cat aac gaa aac cac acg ccg atc agc aag gaa     240
Gly Gln Ser Lys Pro His Asn Glu Asn His Thr Pro Ile Ser Lys Glu
 65                  70                  75                  80 tgc gag gcc agg atc ctg ctg gaa ctg atc gaa cgc ttc cgt gcc gag     288
Cys Glu Ala Arg Ile Leu Leu Glu Leu Ile Glu Arg Phe Arg Ala Glu
```

```
gta gtg atg tcg ttc tcg tgg ggc ggc gtc gcc acc ctg ctg gcc ctg      336
Val Val Met Ser Phe Ser Trp Gly Gly Val Ala Thr Leu Leu Ala Leu
        100                 105                 110 gcg caa cgt ccc gga cgg atc cgc agg gcg gtg gtc aac tca ttc tcg      384
Ala Gln Arg Pro Gly Arg Ile Arg Arg Ala Val Val Asn Ser Phe Ser
            115                 120                 125 cct cag ctc aac ccg gcc atg ctc gac tac ctg cat cgc ggc ctc gac      432
Pro Gln Leu Asn Pro Ala Met Leu Asp Tyr Leu His Arg Gly Leu Asp
    130                 135                 140 tac ctc gcc gcc tgc gat cgc acc cag atc ggc aac ctg gtc aac gaa      480
Tyr Leu Ala Ala Cys Asp Arg Thr Gln Ile Gly Asn Leu Val Asn Glu
145                 150                 155                 160 acc atc ggc cgc tac ctg cca cag ttg ttc aag cgc tac aac ttc cgc      528
Thr Ile Gly Arg Tyr Leu Pro Gln Leu Phe Lys Arg Tyr Asn Phe Arg
                165                 170                 175 cac gtc agc agc ctg gac gag cac gaa tac cac cag atg cac ttc cat      576
His Val Ser Ser Leu Asp Glu His Glu Tyr His Gln Met His Phe His
            180                 185                 190 atc cgc gaa gtg ctg cgc ctg aac gcc gat agc tat acc gag agc ttc      624
Ile Arg Glu Val Leu Arg Leu Asn Ala Asp Ser Tyr Thr Glu Ser Phe
        195                 200                 205 gcc ggc atc gag atc ccg atg ctg ttc atg aac ggc gag ctg gac atc      672
Ala Gly Ile Glu Ile Pro Met Leu Phe Met Asn Gly Glu Leu Asp Ile
    210                 215                 220 tac acc acg ccc cac gaa gcc cgc cag ttc ggc caa ctg atc cgc ggc      720
Tyr Thr Thr Pro His Glu Ala Arg Gln Phe Gly Gln Leu Ile Arg Gly
225                 230                 235                 240 gcg gaa ttc cac acc atc cgc aat gcc ggc cac ttc atc gac gtc gag      768
Ala Glu Phe His Thr Ile Arg Asn Ala Gly His Phe Ile Asp Val Glu
                245                 250                 255 cac aag gcc gcc tgg cag cag acc cag gac gcc ctg ctg gcc ttc ctc      816
His Lys Ala Ala Trp Gln Gln Thr Gln Asp Ala Leu Leu Ala Phe Leu
            260                 265                 270 cgc ccg cag cgc acg cag ccg ctc aac ccg atc tac cgc ccc cag ccc      864
Arg Pro Gln Arg Thr Gln Pro Leu Asn Pro Ile Tyr Arg Pro Gln Pro
        275                 280                 285 aac ggc gcc agc gtc ccc ctc gcc gcc ctc gcc agc taa                  903
Asn Gly Ala Ser Val Pro Leu Ala Ala Leu Ala Ser
    290                 295                 300

<210> SEQ ID NO 36
<211> LENGTH: 300
<212> TYPE: PRT
<213> ORGANISM: Pseudomonas aeruginosa

<400> SEQUENCE: 36

Met Arg Pro Glu Thr Ala Ile Ile Glu Ile His Gly Gln Tyr Arg Ile
1               5                   10                  15

His Thr Glu Phe Tyr Gly Asn Pro Ala Ala Gln Gln Thr Ile Ile Leu
            20                  25                  30

Val Asn Gly Ser Leu Ser Thr Thr Ala Ser Phe Ala Gln Thr Val Lys
        35                  40                  45

Tyr Leu Gln Pro His Tyr Asn Val Val Leu Tyr Asp Gln Pro Tyr Ala
    50                  55                  60

Gly Gln Ser Lys Pro His Asn Glu Asn His Thr Pro Ile Ser Lys Glu
65                  70                  75                  80

Cys Glu Ala Arg Ile Leu Leu Glu Leu Ile Glu Arg Phe Arg Ala Glu
                85                  90                  95
```

```
Val Val Met Ser Phe Ser Trp Gly Gly Val Ala Thr Leu Leu Ala Leu
            100                 105                 110

Ala Gln Arg Pro Gly Arg Ile Arg Arg Ala Val Val Asn Ser Phe Ser
            115                 120                 125

Pro Gln Leu Asn Pro Ala Met Leu Asp Tyr Leu His Arg Gly Leu Asp
            130                 135                 140

Tyr Leu Ala Ala Cys Asp Arg Thr Gln Ile Gly Asn Leu Val Asn Glu
145                 150                 155                 160

Thr Ile Gly Arg Tyr Leu Pro Gln Leu Phe Lys Arg Tyr Asn Phe Arg
                165                 170                 175

His Val Ser Ser Leu Asp Glu His Glu Tyr His Gln Met His Phe His
            180                 185                 190

Ile Arg Glu Val Leu Arg Leu Asn Ala Asp Ser Tyr Thr Glu Ser Phe
            195                 200                 205

Ala Gly Ile Glu Ile Pro Met Leu Phe Met Asn Gly Glu Leu Asp Ile
            210                 215                 220

Tyr Thr Thr Pro His Glu Ala Arg Gln Phe Gly Gln Leu Ile Arg Gly
225                 230                 235                 240

Ala Glu Phe His Thr Ile Arg Asn Ala Gly His Phe Ile Asp Val Glu
                245                 250                 255

His Lys Ala Ala Trp Gln Gln Thr Gln Asp Ala Leu Leu Ala Phe Leu
            260                 265                 270

Arg Pro Gln Arg Thr Gln Pro Leu Asn Pro Ile Tyr Arg Pro Gln Pro
            275                 280                 285

Asn Gly Ala Ser Val Pro Leu Ala Ala Leu Ala Ser
            290                 295                 300

<210> SEQ ID NO 37
<211> LENGTH: 2310
<212> TYPE: DNA
<213> ORGANISM: Pseudomonas aeruginosa

<400> SEQUENCE: 37
```

| | | | | | |
|---|---|---|---|---|---|
| aggtaccaga | tctggcattt | ttgggaggtg | tgaaatgcgg | cgcgaaagtc | tgttggtatc | 60 |
| ggtttgcaag | ggcctgcggg | tacatgtcga | gcgcgttggg | caggatcccg | ggcgcagcac | 120 |
| ggtgatgctg | gtcaacggcg | cgatggcgac | caccgcctcg | ttcgcccgga | cctgcaagtg | 180 |
| cctggccgaa | catttcaacg | tggtgctgtt | cgacctgccc | ttcgccgggc | agtcgcgtca | 240 |
| gcacaacccg | cagcgggggt | tgatcaccaa | ggacgacgag | gtggaaatcc | tcctggcgct | 300 |
| gatcgagcgc | ttcgaggtca | atcacctggt | ctccgcgtcc | tggggcggta | tctccacgct | 360 |
| gctggcgctg | tcgcgcaatc | cgcgcggcat | ccgcagctcg | gtggtgatgg | cattcgcccc | 420 |
| tggactgaac | caggcgatgc | tcgactacgt | cgggcgggcg | caggcgctga | tcgagctgga | 480 |
| cgacaagtcg | gcgatcggcc | atctgctcaa | cgagaccgtc | ggcaaatacc | tgccgccgcg | 540 |
| cctgaaagcc | agcaaccatc | agcacatggc | ttcgctggcc | accggcgaat | acgagcaggc | 600 |
| gcgctttcac | atcgaccagg | tgctggcgct | caacgatcgg | ggctacctgg | cttgcctgga | 660 |
| gcggatccag | agccacgtgc | atttcatcaa | cggcagctgg | gacgaataca | ccaccgccga | 720 |
| ggacgcccgc | cagttccgcg | actacctgcc | gcactgcagt | ttctcgcggg | tggagggcac | 780 |
| cgggcatttc | ctcgacctgg | agtccaagct | ggccgcggta | cgcgtgcacc | gcgccctgct | 840 |
| cgagcacctg | ctgaagcaac | cggagccgca | gcgggcggaa | cgcgcggcgg | gattccacga | 900 |
| gatggccatc | ggctacgcct | gaacccttga | cctgcgaaga | cccggcctgg | ccgggctttg | 960 |

```
cggttgcata acgcacggag tagcaccatg cacgccatcc tcatcgccat cggctcggcc    1020
ggcgacgtat ttcccttcat cggcctggcc cggaccctga aattgcgcgg gcaccgcgtg    1080
agcctctgca ccatcccggt gtttcgcgac gcggtggagc agcacggcat cgcgttcgtc    1140
ccgctgagcg acgaactgac ctaccgccgg accatgggcg atccgcgcct gtgggacccc    1200
aagacgtcct tcggcgtgct ctggcaaacc atcgccggga tgatcgagcc ggtctacgag    1260
tacgtctcgg cgcagcgcca tgacgacatc gtggtggtcg gctcgctctg ggcgctgggc    1320
gcacgcatcg ctcacgagaa gtacgggatt ccctacctgt ccgcgcaggt ctcgccatcg    1380
accttgttgt cggcgcacct gccgccggta caccccaagt tcaacgtgcc cgagcagatg    1440
ccgctggcga tgcgcaagct gctctggcgc tgcatcgagc gcttcaagct ggatcgcacc    1500
tgcgcgccat atatcaacgc ggtgcggcgc aaggtcggcc tggagacgcc ggtgaagcgc    1560
atcttcaccc aatggatgca ttcgccgcag ggcgtggtct gcctgttccc ggcctggttc    1620
gcgccgcccc agcaggattg gccgcaaccc ctgcacatga ccggcttccc gctgttcgac    1680
ggcagtatcc cggggacccc gctcgacgac gaactgcaac gctttctcga tcagggcagc    1740
cggccgctgt tgttcaccca gggctcgacc gaacacctgc agggcgactt ctacgccatg    1800
gccctgcgcg cgctggaacg cctcggcgcg cgtgggatct tcctcaccgg cgccggccag    1860
gaaccgctgc gcggcttgcc gaaccacgtg ctgcagcgcg cctacgcgcc actgggagcc    1920
ttgctgccat cgtgcgccgg gctggtccat ccgggcggta tcggcgccat gagcctggcc    1980
ttggcggcgg ggtgccgca ggtgctgctg ccctgcgccc acgaccagtt cgacaatgcc    2040
gaacggctgg tccggctcgg ctgcgggatg cgcctgggcg tgccattgcg cgagcaggag    2100
ttgcgcgggg cgctgtggcg cttgctcgag gacccggcca tggcggcggc ctgtcggcgt    2160
ttcatggaat tgtcacaacc gcacagtatc gcttgcggta aagcggccca ggtggtcgaa    2220
cgttgtcata gggaggggga tgcgcgatgg ctgaaggctg cgtcctgaac ggtgctggca    2280
taacagatag ggttgcctct agagagctca                                    2310
```

<210> SEQ ID NO 38
<211> LENGTH: 7422
<212> TYPE: DNA
<213> ORGANISM: Artificial
<220> FEATURE:
<223> OTHER INFORMATION: Vector

<400> SEQUENCE: 38

```
ctcgggccgt ctcttgggct tgatcggcct tcttgcgcat ctcacgcgct cctgcggcgg     60
cctgtagggc aggctcatac ccctgccgaa ccgcttttgt cagccggtcg gccacggctt    120
ccggcgtctc aacgcgcttt gagattccca gcttttcggc caatccctgc ggtgcatagg    180
cgcgtggctc gaccgcttgc gggctgatgg tgacgtggcc cactggtggc cgctccaggg    240
cctcgtagaa cgcctgaatg cgcgtgtgac gtgccttgct gccctcgatg cccgttgca    300 gccctagatc ggccacagcg ccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgccccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt ctctggcagc aactcgcgca gtcggcccat cgcttcatcg gtgctgctgg    660
```

```
ccgcccagtg ctcgttctct ggcgtcctgc tggcgtcagc gttgggcgtc tcgcgctcgc      720
ggtaggcgtg cttgagactg gccgccacgt tgcccatttt cgccagcttc ttgcatcgca      780
tgatcgcgta tgccgccatg cctgcccctc ccttttggtg tccaaccggc tcgacggggg      840
cagcgcaagg cggtgcctcc ggcgggccac tcaatgcttg agtatactca ctagactttg      900
cttcgcaaag tcgtgaccgc ctacggcggc tgcggcgccc tacgggcttg ctctccgggc      960
ttcgccctgc gcggtcgctg cgctcccttg ccagcccgtg gatatgtgga cgatggccgc     1020
gagcggccac cggctggctc gcttcgctcg gcccgtggac aaccctgctg acaagctga      1080 tggacaggct gcgcctgccc acgagcttga ccacagggat tgcccaccgg ctacccagcc     1140
ttcgaccaca tacccaccgg ctccaactgc gcggcctgcg gccttgcccc atcaattttt     1200
ttaattttct ctggggaaaa gcctccggcc tgcggcctgc gcgcttcgct tgccggttgg     1260
acaccaagtg gaaggcgggt caaggctcgc gcagcgaccg cgcagcggct tggccttgac     1320
gcgcctggaa cgacccaagc ctatgcgagt gggggcagtc gaaggcgaag cccgcccgcc     1380 tgcccccga gcctcacggc ggcgagtgcg ggggttccaa gggggcagcg ccaccttggg      1440
caaggccgaa ggccgcgcag tcgatcaaca agccccggag gggccacttt ttgccggagg     1500
gggagccgcg ccgaaggcgt gggggaaccc cgcaggggtg cccttctttg ggcaccaaag     1560
aactagatat agggcgaaat gcgaaagact taaaaatcaa caacttaaaa aagggggta     1620 cgcaacagct cattgcggca cccccgcaa tagctcattg cgtaggttaa agaaaatctg     1680
taattgactg ccacttttac gcaacgcata attgttgtcg cgctgccgaa aagttgcagc     1740
tgattgcgca tggtgccgca accgtgcggc accctaccgc atggagataa gcatggccac     1800
gcagtccaga gaaatcggca ttcaagccaa gaacaagccc ggtcactggg tgcaaacgga     1860
acgcaaagcg catgaggcgt gggccgggct tattgcgagg aaacccacgg cggcaatgct     1920
gctgcatcac ctcgtggcgc agatgggcca ccagaacgcc gtggtggtca gccagaagac     1980
actttccaag ctcatcggac gttctttgcg gacggtccaa tacgcagtca aggacttggt     2040
ggccgagcgc tggatctccg tcgtgaagct caacggcccc ggcaccgtgt cggcctacgt     2100
ggtcaatgac cgcgtggcgt ggggccagcc ccgcgaccag ttgcgcctgt cggtgttcag     2160
tgccgccgtg gtggttgatc acgacgacca ggacgaatcg ctgttggggc atggcgacct     2220
gcgccgcatc ccgaccctgt atccgggcga gcagcaacta ccgaccggcc ccggcgagga     2280
gccgcccagc cagcccggca ttccgggcat ggaaccagac ctgccagcct tgaccgaaac     2340
ggaggaatgg gaacggcgcg ggcagcagcg cctgccgatg cccgatgagc cgtgttttct     2400
ggacgatggc gagccgttgg agccgccgac acgggtcacg ctgccgcgcc ggtagcactt     2460
gggttgcgca gcaacccgta agtgcgctgt tccagactat cggctgtagc cgcctcgccg     2520
ccctatacct tgtctgcctc cccgcgttgc gtcgcggtgc atggagccgg ccacctcga     2580 cctgaatgga agccggcggc acctcgctaa cggattcacc gtttttatca ggctctggga     2640
ggcagaataa atgatcatat cgtcaattat tacctccacg gggagagcct gagcaaactg     2700
gcctcaggca tttgagaagc acacggtcac actgcttccg gtagtcaata aaccggtaaa     2760
ccagcaatag acataagcgg ctatttaacg accctgccct gaaccgacga ccgggtcgaa     2820
tttgctttcg aatttctgcc attcatccgc ttattatcac ttattcaggc gtagcaccag     2880
gcgtttaagg gcaccaataa ctgccttaaa aaaattacgc cccgccctgc cactcatcgc     2940
agtcggccta ttggttaaaa aatgagctga tttaacaaaa atttaacgcg aattttaaca     3000
aaatattaac gcttacaatt tccattcgcc attcaggctg cgcaactgtt gggaagggcg     3060
```

```
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagaggcaac cctatctgtt atgccagcac cgttcaggac gcagccttca gccatcgcgc    3300
atcccctcc ctatgacaac gttcgaccac ctgggccgct ttaccgcaag cgatactgtg     3360
cggttgtgac aattccatga aacgccgaca ggccgccgcc atggccgggt cctcgagcaa    3420
gcgccacagc gccccgcgca actcctgctc gcgcaatggc acgcccaggc gcatcccgca    3480
gccgagccgg accagccgtt cggcattgtc gaactggtcg tgggcgcagg gcagcagcac    3540
ctgcggcacc cccgccgcca aggccaggct catggcgccg ataccgcccg gatggaccag    3600
cccggcgcac gatggcagca aggctcccag tggcgcgtag gcgcgctgca gcacgtggtt    3660
cggcaagccg cgcagcggtt cctggccggc gccggtgagg aagatcccac gcgcgccgag    3720
gcgttccagc gcgcgcaggg ccatggcgta gaagtcgccc tgcaggtgtt cggtcgagcc    3780
ctgggtgaac accagcggcc ggctgccctg atcgagaaag cgttgcagtt cgtcgtcgag    3840
cggggtcccc gggatactgc cgtcgaacag cgggaagccg gtcatgtgca ggggttgcgg    3900
ccaatcctgc tggggcggcg cgaaccaggc cgggaacagg cagaccacgc cctgcggcga    3960
atgcatccat tgggtgaaga tgcgcttcac cggcgtctcc aggccgacct tgcgccgcac    4020
cgcgttgata tccggcgcgc aggtgcgatc cagcttgaag cgctcgatgc agcgccagag    4080
cagcttgcgc atcgccagcg gcatctgctc gggcacgttg aacttggggt gtaccggcgg    4140
caggtgcgcc gacaacaagg tcgatggcga gacctgcgcg gacaggtagg gaatcccgta    4200
cttctcgtga gcgatgcgtg cgcccagcgc ccagagcgag ccgaccacca cgatgtcgtc    4260
atggcgctgc gccgagacgt actcgtagac cggctcgatc atcccggcga tggtttgcca    4320
gagcacgccg aaggacgtct tggggtccca caggcgcgga tcgcccatgg tccggcggta    4380
ggtcagttcg tcgctcagcg ggacgaacgc gatgccgtgc tgctccaccg cgtcgcgaaa    4440
caccgggatg gtgcagaggc tcacgcggtg cccgcgcaat ttcagggtcc gggccaggcc    4500
gatgaaggga aatacgtcgc cggccgagcc gatggcgatg aggatggcgt gcatggtgct    4560
actccgtgcg ttatgcaacc gcaaagcccg gccaggccgg gtcttcgcag gtcaagggtt    4620
caggcgtagc cgatggccat ctcgtggaat cccgccgcgc gttccgcccg ctgcggctcc    4680
ggttgcttca gcaggtgctc gagcagggcg cggtgcacgc gtaccgcggc cagcttggac    4740
tccaggtcga ggaaatgccc ggtgccctcc accgcgaga aactgcagtg cggcaggtag     4800
tcgcggaact ggcgggcgtc ctcggcggtg gtgtattcgt cccagctgcc gttgatgaaa    4860
tgcacgtggc tctggatccg ctccaggcaa gccaggtagc ccgatcgtt gagcgccagc     4920
acctggtcga tgtgaaagcg cgcctgctcg tattcgccgg tggccagcga agccatgtgc    4980
tgatggttgc tggctttcag gcgcggcggc aggtatttgc cgacggtctc gttgagcaga    5040
tggccgatcg ccgacttgtc gtccagctcg atcagcgcct gcgcccgccc gacgtagtcg    5100
agcatcgcct ggttcagtcc aggggcgaat gccatcacca ccgagctgcg gatgccgcgc    5160
ggattgcgcg acagcgccag cagcgtggag ataccgcccc aggacgcgga gaccaggtga    5220
ttgacctcga agcgctcgat cagcgccagg aggatttcca cctcgtcgtc cttggtgatc    5280
aaccccgct gcgggttgtg ctgacgcgac tgccgcgca agggcaggtc gaacagcacc       5340
acgttgaaat gttcggccag gcacttgcag gtccgggcga acgaggcggt ggtcgccatc    5400
```

-continued

```
gcgccgttga ccagcatcac cgtgctgcgc ccgggatcct gcccaacgcg ctcgacatgt      5460
acccgcaggc ccttgcaaac cgataccaac agactttcgc gccgcatttc acacctccca      5520
aaaatgccag atcccccggg ctgcaggaat tcgatatcaa gcttatcgat accgtcgacc      5580 tcgaggggg gcccggtacc cagcttttgt tccctttagt gagggttaat tgcgcgcttg       5640
gcgtaatcat ggtcatagct gtttcctgtg tgaaattgtt atccgctcac aattccacac      5700
aacatacgag ccggaagcat aaagtgtaaa gcctggggtg cctaatgagt gagctaactc      5760
acattaattg cgttgcgctc actgcccgct ttccagtcgg gaaacctgtc gtgccagctg      5820
cattaatgaa tcggccaacg cgcggggaga ggcggtttgc gtattgggcg catgcataaa      5880
aactgttgta attcattaag cattctgccg acatggaagc catcacaaac ggcatgatga      5940
acctgaatcg ccagcggcat cagcaccttg tcgccttgcg tataatattt gcccatgggg      6000
gtgggcgaag aactccagca tgagatcccc gcgctggagg atcatccagc cggcgtcccg      6060
gaaaacgatt ccgaagccca accttttcata aaggcggcg gtggaatcga aatctcgtga      6120
tggcaggttg ggcgtcgctt ggtcggtcat ttcgaacccc agagtcccgc tcagaagaac      6180
tcgtcaagaa ggcgatagaa ggcgatgcgc tgcgaatcgg gagcggcgat accgtaaagc      6240
acgaggaagc ggtcagccca ttcgccgcca agctcttcag caatatcacg ggtagccaac      6300
gctatgtcct gatagcggtc cgccacaccc agccggccac agtcgatgaa tccagaaaag      6360
cggccatttt ccaccatgat attcggcaag caggcatcgc catgggtcac gacgagatcc      6420
tcgccgtcgg catgcgcgc cttgagcctg gcgaacagtt cggctggcgc gagcccctga       6480
tgctcttcgt ccagatcatc ctgatcgaca agaccggctt ccatccgagt acgtgctcgc      6540
tcgatgcgat gtttcgcttg gtggtcgaat gggcaggtag ccggatcaag cgtatgcagc      6600
cgccgcattg catcagccat gatggatact ttctcggcag gagcaaggtg agatgacagg      6660
agatcctgcc ccggcacttc gcccaatagc agccagtccc ttcccgcttc agtgacaacg      6720
tcgagcacag ctgcgcaagg aacgcccgtc gtggccagcc acgatagccg cgctgcctcg      6780
tcctgcagtt cattcagggc accggacagg tcggtcttga caaaaagaac cgggcgcccc      6840
tgcgctgaca gccggaacac ggcggcatca gagcagccga ttgtctgttg tgcccagtca      6900
tagccgaata gcctctccac ccaagcggcc ggagaacctg cgtgcaatcc atcttgttca      6960
atcatgcgaa acgatcctca tcctgtctct tgatcagatc ttgatcccct gcgccatcag      7020
atccttggcg gcaagaaagc catccagttt actttgcagg gcttcccaac cttaccagag      7080
ggcgccccag ctggcaattc cggttcgctt gctgtccata aaaccgccca gtctagctat      7140
cgccatgtaa gcccactgca agctacctgc tttctctttg cgcttgcgtt ttcccttgtc      7200
cagatagccc agtagctgac attcatccca ggtggcactt ttcggggaaa tgtgcgcgcc      7260
cgcgttcctg ctggcgctgg gcctgtttct ggcgctggac ttcccgctgt tccgtcagca      7320
gcttttcgcc cacggccttg atgatcgcgc cggccttggc ctgcatatcc cgattcaacg      7380
gccccagggc gtccagaacg ggcttcaggc gctcccgaag gt                         7422
```

<210> SEQ ID NO 39
<211> LENGTH: 3294
<212> TYPE: DNA
<213> ORGANISM: Pseudomonas aeruginosa

<400> SEQUENCE: 39

```
aggtaccaga tctggcattt ttgggaggtg tgaaatgcgg cgcgaaagtc tgttggtatc       60
ggtttgcaag ggcctgcggg tacatgtcga gcgcgttggg caggatcccg ggcgcagcac      120
```

```
ggtgatgctg gtcaacggcg cgatggcgac caccgcctcg ttcgcccgga cctgcaagtg    180
cctggccgaa catttcaacg tggtgctgtt cgacctgccc ttcgccgggc agtcgcgtca    240
gcacaacccg cagcgggggt tgatcaccaa ggacgacgag gtggaaatcc tcctggcgct    300
gatcgagcgc ttcgaggtca atcacctggt ctccgcgtcc tggggcggta tctccacgct    360
gctggcgctg tcgcgcaatc cgcgcggcat ccgcagctcg gtggtgatgg cattcgcccc    420
tggactgaac caggcgatgc tcgactacgt cgggcgggcg caggcgctga tcgagctgga    480
cgacaagtcg gcgatcggcc atctgctcaa cgagaccgtc ggcaaatacc tgccgccgcg    540
cctgaaagcc agcaaccatc agcacatggc ttcgctggcc accggcgaat acgagcaggc    600
gcgctttcac atcgaccagg tgctggcgct caacgatcgg ggctacctgg cttgcctgga    660
gcggatccag agccacgtgc atttcatcaa cggcagctgg gacgaataca ccaccgccga    720
ggacgcccgc cagttccgcg actacctgcc gcactgcagt ttctcgcggg tggagggcac    780
cgggcatttc ctcgacctgg agtccaagct ggccgcggta cgcgtgcacc gcgccctgct    840
cgagcacctg ctgaagcaac cggagccgca gcgggcggaa cgcgcggcgg gattccacga    900
gatggccatc ggctacgcct gaacccttga cctgcgaaga cccggcctgg ccgggctttg    960
cggttgcata acgcacggag tagcaccatg cacgccatcc tcatcgccat cggctcggcc   1020
ggcgacgtat ttcccttcat cggcctggcc cggaccctga aattgcgcgg gcaccgcgtg   1080
agcctctgca ccatcccggt gtttcgcgac gcggtggagc agcacggcat cgcgttcgtc   1140
ccgctgagcg acgaactgac ctaccgccgg accatgggcg atccgcgcct gtgggacccc   1200
aagacgtcct tcggcgtgct ctggcaaacc atcgccggga tgatcgagcc ggtctacgag   1260
tacgtctcgg cgcagcgcca tgacgacatc gtggtggtcg gctcgctctg ggcgctgggc   1320
gcacgcatcg ctcacgagaa gtacgggatt ccctacctgt ccgcgcaggt ctcgccatcg   1380
accttgttgt cggcgcacct gccgccggta caccccaagt tcaacgtgcc cgagcagatg   1440
ccgctggcga tgcgcaagct gctctggcgc tgcatcgagc gcttcaagct ggatcgcacc   1500
tgcgcgccgg atatcaacgc ggtgcggcgc aaggtcggcc tggagacgcc ggtgaagcgc   1560
atcttcaccc aatggatgca ttcgccgcag ggcgtggtct gcctgttccc ggcctggttc   1620
gcgccgcccc agcaggattg gccgcaaccc ctgcacatga ccggcttccc gctgttcgac   1680
ggcagtatcc cggggacccc gctcgacgac gaactgcaac gctttctcga tcagggcagc   1740
cggccgctgg tgttcaccca gggctcgacc gaacacctgc agggcgactt ctacgccatg   1800
gccctgcgcg cgctggaacg cctcggcgcg cgtgggatct tcctcaccgg cgccggccag   1860
gaaccgctgc gcggcttgcc gaaccacgtg ctgcagcgcg cctacgcgcc actgggagcc   1920
ttgctgccat cgtgcgccgg gctggtccat ccgggcggta tcggcgccat gagcctggcc   1980
ttggcggcgg gggtgccgca ggtgctgctg ccctgcgccc acgaccagtt cgacaatgcc   2040
gaacggctgt ccggctcgg ctgcgggatg cgcctgggcg tgccattgcg cgagcaggag   2100
ttgcgcgggg cgctgtggcg cttgctcgag gacccggcca tggcggcggc ctgtcggcgt   2160
ttcatggaat tgtcacaacc gcacagtatc gcttgcggta aagcggccca ggtggtcgaa   2220
cgttgtcata gggagggga tgcgcgatgg ctgaaggctg cgtcctgacc tacggggaaa   2280
gaacgatcat ggaccggata gacatgggcg tgctggtggt actgttcaat cctggcgacg   2340
acgacctgga acaccttggc gaactggcgg cggcgtttcc gcaactgcgc ttccttgccg   2400
tcgacaactc accgcacagc gatccgcagc gcaatgcccg gctgcgcggg caaggcatcg   2460
```

| | | | | |
|---|---|---|---|---|
| ccgtgctgca | ccacggcaac | cggcagggca | tcgccggcgc | cttcaaccag ggactcgacg | 2520 |
| cgctattccg | gcgtggcgtg | cagggtgtgc | tgctgctcga | ccaggactcc cgtcccggcg | 2580 |
| gcgccttcct | cgccgcccag | tggcgcaacc | tgcaggcgcg | caacggtcag gcctgcctgc | 2640 |
| tcggcccacg | gatcttcgac | cggggtgacc | ggcgcttcct | gccggccatc catctcgacg | 2700 |
| gactgacgct | caggcaattg | tctctggacg | gcctgacgac | cccgcagcgc acctcgttcc | 2760 |
| tgatctcctc | cggctgcctg | ctgacccgcg | aggcctacca | cgcctcggc cacttcgacg | 2820 |
| aggaactgtt | catcgaccac | gtggacaccg | aatacagcct | gcgcgcccag gcgctggacg | 2880 |
| tgcccctgta | cgtcgacccg | cggctggtcc | tcgagcaccg | catcggcacg cgcaagaccc | 2940 |
| gccgcctcgg | cggtctcagc | ctcagcgcga | tgaaccacgc | cccgctgcgc cgctactacc | 3000 |
| tggcgcgcaa | cggcctgctg | gtcctgcgcc | gctacgcccg | gtcctcgccg ctggccctgc | 3060 |
| tggcgaacct | gccgaccctg | acccagggcc | tcgcggtgct | cctgctcgaa cgcgacaagc | 3120 |
| tgctcaagct | gcgctgcctg | ggctgggcc | tgtgggacgg | cctgcgggga cgcggcggcg | 3180 |
| cgctggagac | caaccgcccg | cgcctgctga | agcgcctcgc | cggcccggcc gtggcgtccg | 3240 |
| tagcttccgg | caaggccaag | gcctagtcgg | cgaaacgcat | tccctctaga gagc | 3294 |

<210> SEQ ID NO 40
<211> LENGTH: 8409
<212> TYPE: DNA
<213> ORGANISM: Artificial
<220> FEATURE:
<223> OTHER INFORMATION: Vector

<400> SEQUENCE: 40

| | | | | |
|---|---|---|---|---|
| accttcggga | gcgcctgaag | cccgttctgg | acgccctggg | gccgttgaat cgggatatgc | 60 |
| aggccaaggc | cgccgcgatc | atcaaggccg | tgggcgaaaa | gctgctgacg gaacagcggg | 120 |
| aagtccagcg | ccagaaacag | gcccagcgcc | agcaggaacg | cgggcgcgca catttccccg | 180 |
| aaaagtgcca | cctgggatga | atgtcagcta | ctgggctatc | tggacaaggg aaaacgcaag | 240 |
| cgcaaagaga | aagcaggtag | cttgcagtgg | gcttacatgg | cgatagctag actgggcggt | 300 |
| tttatggaca | gcaagcgaac | cggaattgcc | agctggggcg | ccctctggta aggttgggaa | 360 |
| gccctgcaaa | gtaaactgga | tggctttctt | gccgccaagg | atctgatggc gcagggatc | 420 |
| aagatctgat | caagagacag | gatgaggatc | gtttcgcatg | attgaacaag atggattgca | 480 |
| cgcaggttct | ccggccgctt | gggtggagag | gctattcggc | tatgactggg cacaacagac | 540 |
| aatcggctgc | tctgatgccg | ccgtgttccg | gctgtcagcg | caggggcgcc cggttctttt | 600 |
| tgtcaagacc | gacctgtccg | gtgccctgaa | tgaactgcag | gacgaggcag cgcggctatc | 660 |
| gtggctggcc | acgacgggcg | ttccttgcgc | agctgtgctc | gacgttgtca ctgaagcggg | 720 |
| aagggactgg | ctgctattgg | gcgaagtgcc | ggggcaggat | ctcctgtcat ctcaccttgc | 780 |
| tcctgccgag | aaagtatcca | tcatggctga | tgcaatgcgg | cggctgcata cgcttgatcc | 840 |
| ggctacctgc | ccattcgacc | accaagcgaa | acatcgcatc | gagcgagcac gtactcggat | 900 |
| ggaagccggt | cttgtcgatc | aggatgatct | ggacgaagag | catcagggc tcgcgccagc | 960 |
| cgaactgttc | gccaggctca | aggcgcgcat | gcccgacggc | gaggatctcg tcgtgaccca | 1020 |
| tggcgatgcc | tgcttgccga | atatcatggt | ggaaaatggc | cgcttttctg gattcatcga | 1080 |
| ctgtggccgg | ctgggtgtgg | cggaccgcta | tcaggacata | gcgttggcta cccgtgatat | 1140 |
| tgctgaagag | cttggcggcg | aatgggctga | ccgcttcctc | gtgctttacg gtatcgccgc | 1200 |
| tcccgattcg | cagcgcatcg | ccttctatcg | ccttcttgac | gagttcttct gagcgggact | 1260 |

```
ctggggttcg aaatgaccga ccaagcgacg cccaacctgc catcacgaga tttcgattcc    1320
accgccgcct tctatgaaag gttgggcttc ggaatcgttt tccgggacgc cggctggatg    1380
atcctccagc gcggggatct catgctggag ttcttcgccc accccatgg gcaaatatta    1440 tacgcaaggc gacaaggtgc tgatgccgct ggcgattcag gttcatcatg ccgtttgtga    1500
tggcttccat gtcggcagaa tgcttaatga attacaacag ttttatgca tgcgcccaat    1560 acgcaaaccg cctctccccg cgcgttggcc gattcattaa tgcagctggc acgacaggtt    1620
tcccgactgg aaagcgggca gtgagcgcaa cgcaattaat gtgagttagc tcactcatta    1680
ggcaccccag gctttacact ttatgcttcc ggctcgtatg ttgtgtggaa ttgtgagcgg    1740
ataacaattt cacacaggaa acagctatga ccatgattac gccaagcgcg caattaaccc    1800
tcactaaagg gaacaaaagc tgggtaccgg ccccccctc gaggtcgacg gtatcgataa    1860
gcttgatatc gaattcctgc agcccggggg atctggcatt tttgggaggt gtgaaatgcg    1920
gcgcgaaagt ctgttggtat cggtttgcaa gggcctgcgg gtacatgtcg agcgcgttgg    1980
gcaggatccc gggcgcagca cggtgatgct ggtcaacggc gcgatggcga ccaccgcctc    2040
gttcgcccgg acctgcaagt gcctggccga acatttcaac gtggtgctgt tcgacctgcc    2100
cttcgccggg cagtcgcgtc agcacaaccc gcagcggggg ttgatcacca aggacgacga    2160
ggtgaaaatc ctcctggcgc tgatcgagcg cttcgaggtc aatcacctgg tctccgcgtc    2220
ctggggcggt atctccacgc tgctggcgct gtcgcgcaat ccgcgcggca tccgcagctc    2280
ggtggtgatg gcattcgccc ctggactgaa ccaggcgatg ctcgactacg tcgggcgggc    2340
gcaggcgctg atcgagctgg acgacaagtc ggcgatcggc catctgctca acgagaccgt    2400
cggcaaatac ctgccgccgc gcctgaaagc cagcaaccat cagcacatgg cttcgctggc    2460
caccggcgaa tacgagcagg cgcgctttca catcgaccag gtgctggcgc tcaacgatcg    2520
gggctacctg gcttgcctgg agcggatcca gagccacgtg catttcatca acggcagctg    2580
ggacgaatac accaccgccg aggacgcccg ccagttccgc gactacctgc gcactgcag    2640 tttctcgcgg gtggagggca ccgggcattt cctcgacctg gagtccaagc tggccgcggt    2700
acgcgtgcac cgcgcccctgc tcgagcacct gctgaagcaa ccggagccgc agcgggcgga    2760
acgcgcggcg ggattccacg agatggccat cggctacgcc tgaacccttg acctgcgaag    2820 accccggcctg ccgggctttt gcggttgcat aacgcacgga gtagcaccat gcacgccatc    2880
ctcatcgcca tcggctcggc cggcgacgta tttcccttca tcggcctggc ccggaccctg    2940
aaattgcgcg gcaccgcgt gagcctctgc accatcccgg tgtttcgcga cgcggtggag    3000
cagcacggca tcgcgttcgt cccgctgagc gacgaactga cctaccgccg gaccatgggc    3060
gatccgcgcc tgtgggaccc caagacgtcc ttcgcgtgc tctggcaaac catcgccggg    3120
atgatcgagc cggtctacga gtacgtctcg gcgcagcgcc atgacgacat cgtggtggtc    3180
ggctcgctct gggcgctggg cgcacgcatc gctcacgaga agtacgggat tccctacctg    3240
tccgcgcagg tctcgccatc gaccttgttg tcggcgcacc tgccgccggt acaccccaag    3300
ttcaacgtgc ccgagcagat gccgctggcg atgcgcaagc tgctctggcg ctgcatcgag    3360
cgcttcaagc tggatcgcac ctgcgcgccg gatatcaacg cggtgcggcg caaggtcggc    3420
ctggagacgc cggtgaagcg catcttcacc caatggatgc attcgccgca gggcgtggtc    3480
tgcctgttcc cggcctggtt cgcgccgccc agcaggatt ggccgcaacc cctgcacatg    3540
accggcttcc cgctgttcga cggcagtatc ccggggaccc cgctcgacga cgaactgcaa    3600
```

-continued

```
cgctttctcg atcagggcag ccggccgctg gtgttcaccc agggctcgac cgaacacctg    3660
cagggcgact tctacgccat ggccctgcgc gcgctggaac gcctcggcgc gcgtgggatc    3720
ttcctcaccg gcgccggcca ggaaccgctg cgcggcttgc cgaaccacgt gctgcagcgc    3780
gcctacgcgc cactgggagc cttgctgcca tcgtgcgccg ggctggtcca tccgggcggt    3840
atcggcgcca tgagcctggc cttggcggcg ggggtgccgc aggtgctgct gccctgcgcc    3900
cacgaccagt tcgacaatgc cgaacggctg gtccggctcg gctgcgggat cgcctgggc    3960 gtgccattgc gcgagcagga gttgcgcggg gcgctgtggc gcttgctcga ggacccggcc    4020
atggcggcgg cctgtcggcg tttcatggaa ttgtcacaac cgcacagtat cgcttgcggt    4080
aaagcggccc aggtggtcga acgttgtcat agggaggggg atgcgcgatg gctgaaggct    4140
gcgtcctgac ctacgggaga agaacgatca tggaccggat agacatgggc gtgctggtgg    4200
tactgttcaa tcctggcgac gacgacctgg aacaccttgg cgaactggcg gcggcgtttc    4260
cgcaactgcg cttccttgcc gtcgacaact caccgcacag cgatccgcag cgcaatgccc    4320
ggctgcgcgg gcaaggcatc gccgtgctgc accacggcaa ccggcagggc atcgccggcg    4380
ccttcaacca gggactcgac gcgctattcc ggcgtggcgt gcagggtgtg ctgctgctcg    4440
accaggactc ccgtcccggc ggcgccttcc tcgccgccca gtggcgcaac ctgcaggcgc    4500
gcaacggtca ggcctgcctg ctcggcccac ggatcttcga ccggggtgac cggcgcttcc    4560
tgccggccat ccatctcgac ggactgacgc tcaggcaatt gtctctggac ggcctgacga    4620
ccccgcagcg cacctcgttc ctgatctcct ccggctgcct gctgacccgc gaggcctacc    4680
agcgcctcgg ccacttcgac gaggaactgt tcatcgacca cgtggacacc gaatacagcc    4740
tgcgcgccca ggcgctggac gtgccctgt acgtcgaccc gcggctggtc ctcgagcacc    4800
gcatcggcac gcgcaagacc cgccgcctcg gcggtctcag cctcagcgcg atgaaccacg    4860
ccccgctgcg ccgctactac ctggcgcgca acggcctgct ggtcctgcgc cgctacgccc    4920
ggtcctcgcc gctggccctg ctggcgaacc tgccgaccct gacccagggc ctcgcggtgc    4980
tcctgctcga acgcgacaag ctgctcaagc tgcgctgcct gggctggggc ctgtgggacg    5040
gcctgcgggg acgcggcggc gcgctggaga ccaaccgccc gcgcctgctg aagcgcctcg    5100
ccggcccggc cgtggcgtcc gtagcttccg gcaaggccaa ggcctagtcg gcgaaacgca    5160
ttccctctag agcggccgcc accgcggtgg agctccaatt cgccctatag tgagtcgtat    5220
tacgcgcgct cactggccgt cgttttacaa cgtcgtgact gggaaaaccc tggcgttacc    5280
caacttaatc gccttgcagc acatccccct ttcgccagct ggcgtaatag cgaagaggcc    5340
cgcaccgatc gcccttccca cagttgcgc agcctgaatg gcgaatggaa attgtaagcg    5400
ttaatatttt gttaaaattc gcgttaaatt tttgttaaat cagctcattt ttaaccaat    5460 aggccgactg cgatgagtgg cagggcgggg cgtaattttt ttaaggcagt tattggtgcc    5520
cttaaacgcc tggtgctacg cctgaataag tgataataag cggatgaatg gcagaaattc    5580
gaaagcaaat tcgacccggt cgtcggttca ggcagggtc gttaaatagc cgcttatgtc    5640
tattgctggt ttaccggttt attgactacc ggaagcagtg tgaccgtgtg cttctcaaat    5700
gcctgaggcc agtttgctca ggctctcccc gtggaggtaa taattgacga tatgatcatt    5760
tattctgcct cccagagcct gataaaaacg gtgaatccgt tagcgaggtg ccgccggctt    5820
ccattcaggt cgaggtggcc cggctccatg caccgcgacg caacgcgggg aggcagacaa    5880
ggtatagggc ggcgaggcgg ctacagccga tagtctggaa cagcgcactt acgggttgct    5940
gcgcaaccca agtgctaccg cgcggcagc gtgacccgtg tcggcggctc caacggctcg    6000
```

```
ccatcgtcca gaaaacacgg ctcatcgggc atcggcaggc gctgctgccc gcgccgttcc   6060
cattcctccg tttcggtcaa ggctggcagg tctggttcca tgcccggaat gccgggctgg   6120
ctgggcggct cctcgccggg gccggtcggt agttgctgct cgcccggata cagggtcggg   6180
atgcggcgca ggtcgccatg ccccaacagc gattcgtcct ggtcgtcgtg atcaaccacc   6240
acggcggcac tgaacaccga caggcgcaac tggtcgcggg gctggcccca cgccacgcgg   6300
tcattgacca cgtaggccga cacggtgccg gggccgttga gcttcacgac ggagatccag   6360
cgctcggcca ccaagtcctt gactgcgtat tggaccgtcc gcaaagaacg tccgatgagc   6420
ttggaaagtg tcttctggct gaccaccacg gcgttctggt ggcccatctg cgccacgagg   6480
tgatgcagca gcattgccgc cgtgggtttc ctcgcaataa gcccggccca cgcctcatgc   6540
gctttgcgtt ccgtttgcac ccagtgaccg ggcttgttct tggcttgaat gccgatttct   6600
ctggactgcg tggccatgct tatctccatg cggtagggtg ccgcacggtt gcggcaccat   6660
gcgcaatcag ctgcaacttt tcggcagcgc gacaacaatt atgcgttgcg taaaagtggc   6720
agtcaattac agattttctt taacctacgc aatgagctat tgcggggggt gccgcaatga   6780
gctgttgcgt acccccctTT tttaagttgt tgattttttaa gtctttcgca tttcgcccta   6840
tatctagttc tttggtgccc aaagaagggc acccctgcgg ggttcccccA cgccttcggc   6900
gcggctcccc ctccggcaaa aagtggcccc tcggggctt gttgatcgac tgcgcggcct   6960
tcggccttgc ccaaggtggc gctgcccct tggaaccccc gcactcgccg ccgtgaggct   7020
cggggggcag gcgggcgggc ttcgccttcg actgccccca ctcgcatagg cttgggtcgt   7080
tccaggcgcg tcaaggccaa gccgctgcgc ggtcgctgcg cgagccttga cccgccttcc   7140
acttggtgtc caaccggcaa gcgaagcgcg caggccgcag gccggaggct ttccccaga   7200
gaaaattaaa aaaattgatg gggcaaggcc gcaggccgcg cagttggagc cggtgggtat   7260
gtggtcgaag gctgggtagc cggtgggcaa tccctgtggt caagctcgtg ggcaggcgca   7320
gcctgtccat cagcttgtcc agcagggttg tccacgggcc gagcgaagcg agccagccgg   7380
tggccgctcg cggccatcgt ccacatatcc acgggctggc aagggagcgc agcgaccgcg   7440
cagggcgaag cccggagagc aagcccgtag ggcgccgcag ccgccgtagg cggtcacgac   7500
tttgcgaagc aaagtctagt gagtatactc aagcattgag tggcccgccg gaggcaccgc   7560
cttgcgctgc ccccgtcgag ccggttggac accaaaaggg aggggcaggc atggcggcat   7620
acgcgatcat gcgatgcaag aagctggcga aaatgggcaa cgtggcggcc agtctcaagc   7680
acgcctaccg cgagcgcgag acgcccaacg ctgacgccag caggacgcca gagaacgagc   7740
actgggcggc cagcagcacc gatgaagcga tgggccgact gcgcgagttg ctgccagaga   7800
agcggcgcaa ggacgctgtg ttggcggtcg agtacgtcat gacggccagc ccggaatggt   7860
ggaagtcggc cagccaagaa cagcaggcgg cgttcttcga gaaggcgcac aagtggctgg   7920
cggacaagta cggggcggat cgcatcgtga cggccagcat ccaccgtgac gaaaccagcc   7980
cgcacatgac cgcgttcgtg gtgccgctga cgcaggacgg caggctgtcg gccaaggagt   8040
tcatcggcaa caaagcgcag atgacccgcg accagaccac gtttgcggcc gctgtggccg   8100
atctagggct gcaacgggc atcgagggca gcaaggcacg tcacgcgc attcaggcgt   8160
tctacgaggc cctggagcgg ccaccagtgg gccacgtcac catcagcccg caagcggtcg   8220
agccacgcgc ctatgcaccg cagggattgg ccgaaaagct gggaatctca aagcgcgttg   8280
agacgccgga agccgtggcc gaccggctga caaaagcggt tcggcagggg tatgagcctg   8340
```

```
cctacaggc cgccgcagga gcgcgtgaga tgcgcaagaa ggccgatcaa gcccaagaga    8400
cggcccgag                                                           8409

<210> SEQ ID NO 41
<211> LENGTH: 3590
<212> TYPE: DNA
<213> ORGANISM: Pseudomonas aeruginosa

<400> SEQUENCE: 41
aggtaccaga tctggcattt ttgggaggtg tgaaatgcgg cgcgaaagtc tgttggtatc      60
ggtttgcaag ggcctgcggg tacatgtcga gcgcgttggg caggatcccg ggcgcagcac     120
ggtgatgctg gtcaacggcg cgatggcgac caccgcctcg ttcgcccgga cctgcaagtg     180
cctggccgaa catttcaacg tggtgctgtt cgacctgccc ttcgccgggc agtcgcgtca     240
gcacaacccg cagcgggggt tgatcaccaa ggacgacgag gtggaaatcc tcctggcgct     300
gatcgagcgc ttcgaggtca atcacctggt ctccgcgtcc tggggcggta tctccacgct     360
gctgcgcctg tcgcgcaatc cgcgcggcat ccgcagctcg gtggtgatgg cattcgcccc     420
tggactgaac caggcgatgc tcgactacgt cgggcgggcg caggcgctga tcgagctgga     480
cgacaagtcg gcgatcggcc atctgctcaa cgagaccgtc ggcaaatacc tgccgccgcg     540
cctgaaagcc agcaaccatc agcacatggc ttcgctggcc accggcgaat acgagcaggc     600
gcgctttcac atcgaccagg tgctggcgct caacgatcgg ggctacctgg cttgcctgga     660
gcggatccag agccacgtgc atttcatcaa cggcagctgg gacgaataca ccaccgccga     720
ggacgcccgc cagttccgcg actacctgcc gcactgcagt ttctcgcggg tggagggcac     780
cgggcatttc ctcgacctgg agtccaagct ggccgcggta cgcgtgcacc gcgccctgct     840
cgagcacctg ctgaagcaac cggagccgca gcgggcggaa cgcgcggcgg gattccacga     900
gatggccatc ggctacgcct gaacccttga cctgcgaaga cccggcctgg ccgggctttg     960
cggttgcata acgcacggag tagcaccatg cacgccatcc tcatcgccat cggctcggcc    1020
ggcgacgtat ttcccttcat cggcctggcc cggaccctga aattgcgcgg caccgcgtg    1080 agcctctgca ccatcccggt gtttcgcgac gcggtggagc agcacggcat cgcgttcgtc    1140
ccgctgagcg acgaactgac ctaccgccgg accatgggcg atccgcgcct gtgggacccc    1200
aagacgtcct tcggcgtgct ctggcaaacc atcgccggga tgatcgagcc ggtctacgag    1260
tacgtctcgg cgcagcgcca tgacgacatc gtggtggtcg gctcgctctg ggcgctgggc    1320
gcacgcatcg ctcacgagaa gtacgggatt ccctacctgt ccgcgcaggt ctcgccatcg    1380
accttgttgt cggcgcacct gccgccggta caccccaagt tcaacgtgcc cgagcagatg    1440
ccgctggcga tgcgcaagct gctctggcgc tgcatcgagc gcttcaagct ggatcgcacc    1500
tgcgcgccgg atatcaacgc ggtgcggcgc aaggtcggcc tggagacgcc ggtgaagcgc    1560
atcttcaccc aatggatgca ttcgccgcag ggcgtggtct gcctgttccc ggcctggttc    1620
gcgccgcccc agcaggattg gccgcaaccc ctgcacatga ccggcttccc gctgttcgac    1680
ggcagtatcc cggggacccc gctcgacgac gaactgcaac gctttctcga tcagggcagc    1740
cggccgctgt tgttcaccca gggctcgacc gaacacctgc agggcgactt ctacgccatg    1800
gccctgcgcg cgctggaacg cctcggcgcg cgtgggatct tcctcaccgg cgccggccag    1860
gaaccgctgc gcggcttgcc gaaccacgtg ctgcagcgcg cctacgcgcc actgggagcc    1920
ttgctgccat cgtgcgccgg gctggtccat ccggggcggta tcggcgccat gagcctggcc    1980
ttggcggcgg gggtgccgca ggtgctgctg ccctgcgccc acgaccagtt cgacaatgcc    2040
```

-continued

```
gaacggctgg tccggctcgg ctgcgggatg cgcctgggcg tgccattgcg cgagcaggag    2100
ttgcgcgggg cgctgtggcg cttgctcgag gacccggcca tggcggcggc ctgtcggcgt    2160
ttcatggaat tgtcacaacc gcacagtatc gcttgcggta aagcggccca ggtggtcgaa    2220
cgttgtcata gggaggggga tgcgcgatgg ctgaaggctg cgtcctgacg ccggaggat     2280 cctggcgtgt ccacgaccag cctctgcccc tccgccacgc gggaacacgg tcccggcgcg    2340
aaacgcgtcc tgcctctgct gttcctcacc tgcctgctgg atgccgctgg cgtcggcctg    2400
atcgtgcccc tgctgccgac gctgatcggc agcgtggcgc cgctggcggt ccgcgacgcg    2460
gccacctggg gcgccgccct ggtgatgacc ttcgcgctgc tgcaattgtt cttttcgccg    2520
gtcctcggca gcctcagcga ccgcttcgga cgccgccccg tcctggtcct ggcgatgctc    2580
ggcttcgccc tcagctatct gctgctgcg ctggccgaca gcctctggat gctgttcctc     2640
ggtcgcgcgc tggccgggct caccggcgcc agcgtggcca ccgcgatggc ctgcgcggct    2700
gacctcggca cgcacgggca gcgcacccgg cacttcggct ggctgtacgc cggcctcgcc    2760
ctgggcatga tcctcggccc cgccctcggt gggctgctgg cggtgcacgg cacgacgctg    2820
ccgctgttgc tggccgccgg cctgtgcctg ctcaacgccc tgctcgccgg cctgttcctc    2880
gaggaaaccc tgccccgac gcgacgccgc cgcctggacc cgaggcggat gaatgccttg     2940
cgctcgatca gcggcctggc tcggcaaccg ggggtcggac gcctgctggc ggtgcttgcc    3000
ctggtattcc tcggcttgca ggcggtgatg gtggtctggc cgttcttcgt gatcgagaag    3060
tttcactgga gcagcgcctg gatcggctac tcgctggccc tctacggcgt gctcgcggtg    3120
ctcgcccaga ccctcggcgt gaacctctgc aagcggcgcc tggacgacgc ccgcctgctg    3180
cgcctgggcc tcgccctgca aggtgcggc ctgctgctgt tcgccctggt cgactcgtca     3240
ttctggctgg tctgcgcgct gctgcccttc gcgctcggca gcctcgccac cccggccatg    3300
caggggctgc tctcggcccg cgtgccggtc gaccgccagg gcgagttgca gggcgtgctg    3360
agcagcctga tgagcctcgc cgcgatcgtc ggtccgccgc tgatgagcgg cctgttccac    3420
tggggcagcg gtccgctcgc gccgctgccc ctggccggcg cgccattcct cgccggcgcc    3480
cttctcgttc tggccgggct ggtcctggcc tggcaacttc gacctacggg agaagaacga    3540
tcatggaccg gatagacatg ggcgtgctgg tggtacttct agagagctca               3590
```

<210> SEQ ID NO 42
<211> LENGTH: 8702
<212> TYPE: DNA
<213> ORGANISM: Artificial
<220> FEATURE:
<223> OTHER INFORMATION: Vector

<400> SEQUENCE: 42

```
accttcggga gcgcctgaag cccgttctgg acgccctggg gccgttgaat cgggatatgc      60
aggccaaggc cgccgcgatc atcaaggccg tgggcgaaaa gctgctgacg gaacagcggg     120
aagtccagcg ccagaaacag gcccagcgcc agcaggaacg cgggcgcgca catttccccg     180
aaaagtgcca cctgggatga atgtcagcta ctgggctatc tggacaaggg aaaacgcaag    240
cgcaaagaga aagcaggtag cttgcagtgg gcttacatgg cgatagctag actgggcggt    300
tttatggaca gcaagcgaac cggaattgcc agctggggcg ccctctggta aggttgggaa    360
gccctgcaaa gtaaactgga tggctttctt gccgccaagg atctgatggc gcaggggatc    420
aagatctgat caagagacag gatgaggatc gtttcgcatg attgaacaag atggattgca    480
```

-continued

```
cgcaggttct ccggccgctt gggtggagag gctattcggc tatgactggg cacaacagac      540
aatcggctgc tctgatgccg ccgtgttccg gctgtcagcg caggggcgcc cggttctttt      600
tgtcaagacc gacctgtccg gtgccctgaa tgaactgcag gacgaggcag cgcggctatc      660
gtggctggcc acgacgggcg ttccttgcgc agctgtgctc gacgttgtca ctgaagcggg      720
aagggactgg ctgctattgg gcgaagtgcc ggggcaggat ctcctgtcat ctcaccttgc      780
tcctgccgag aaagtatcca tcatggctga tgcaatgcgg cggctgcata cgcttgatcc      840
ggctacctgc ccattcgacc accaagcgaa acatcgcatc gagcgagcac gtactcggat      900
ggaagccggt cttgtcgatc aggatgatct ggacgaagag catcaggggc tcgcgccagc      960
cgaactgttc gccaggctca aggcgcgcat gcccgacggc gaggatctcg tcgtgaccca     1020
tggcgatgcc tgcttgccga atatcatggt ggaaaatggc cgcttttctg gattcatcga     1080
ctgtggccgg ctgggtgtgg cggaccgcta tcaggacata gcgttggcta cccgtgatat     1140
tgctgaagag cttggcggcg aatgggctga ccgcttcctc gtgctttacg gtatcgccgc     1200
tcccgattcg cagcgcatcg ccttctatcg ccttcttgac gagttcttct gagcgggact     1260
ctggggttcg aaatgaccga ccaagcgacg cccaacctgc catcacgaga tttcgattcc     1320
accgccgcct tctatgaaag gttgggcttc ggaatcgttt tccgggacgc cggctggatg     1380
atcctccagc gcggggatct catgctggag ttcttcgccc accccatgg gcaaatatta     1440 tacgcaaggc gacaaggtgc tgatgccgct ggcgattcag gttcatcatg ccgtttgtga     1500
tggcttccat gtcggcagaa tgcttaatga attacaacag tttttatgca tgcgcccaat     1560
acgcaaaccg cctctccccg cgcgttggcc gattcattaa tgcagctggc acgacaggtt     1620
tcccgactgg aaagcgggca gtgagcgcaa cgcaattaat gtgagttagc tcactcatta     1680
ggcaccccag gctttacact ttatgcttcc ggctcgtatg ttgtgtggaa ttgtgagcgg     1740
ataacaattt cacacaggaa acagctatga ccatgattac gccaagcgcg caattaaccc     1800
tcactaaagg gaacaaaagc tgggtaccgg cccccctc gaggtcgacg gtatcgataa     1860
gcttgatatc gaattcctgc agcccggggg atctggcatt tttgggaggt gtgaaatgcg     1920
gcgcgaaagt ctgttggtat cggttttgcaa gggcctgcgg gtacatgtcg agcgcgttgg     1980
gcaggatccc gggcgcagca cggtgatgct ggtcaacggc gcgatggcga ccaccgcctc     2040
gttcgcccgg acctgcaagt gcctggccga acatttcaac gtggtgctgt tcgacctgcc     2100
cttcgccggg cagtcgcgtc agcacaaccc gcagcggggg ttgatcacca aggacgacga     2160
ggtgaaaatc ctcctggcgc tgatcgagcg cttcgaggtc aatcacctgg tctccgcgtc     2220
ctggggcggt atctccacgc tgctggcgct gtcgcgcaat ccgcgcggca tccgcagctc     2280
ggtggtgatg gcattcgccc ctggactgaa ccaggcgatg ctcgactacg tcgggcgggc     2340
gcaggcgctg atcgagctgg acgacaagtc ggcgatcggc catctgctca acgagaccgt     2400
cggcaaatac ctgccgccgc gcctgaaagc cagcaaccat cagcacatgg cttcgctggc     2460
caccggcgaa tacgagcagg cgcgctttca catcgaccag gtgctggcgc tcaacgatcg     2520
gggctacctg gcttgcctgg agcggatcca gagccacgtg catttcatca acggcagctg     2580
ggacgaatac accaccgccg aggacgcccg ccagttccgc gactacctgc cgcactgcag     2640
tttctcgcgg gtggagggca ccgggcattt cctcgacctg gagtccaagc tggccgcggt     2700
acgcgtgcac cgcgccctgc tcgagcacct gctgaagcaa ccggagccgc agcgggcgga     2760
acgcgcggcg ggattccacg agatggccat cggctacgcc tgaaccctg acctgcgaag     2820 acccggcctg gccgggcttt gcggttgcat aacgcacgga gtagcaccat gcacgccatc     2880
```

```
ctcatcgcca tcggctcggc cggcgacgta tttcccttca tcggcctggc ccggaccctg   2940
aaattgcgcg ggcaccgcgt gagcctctgc accatcccgg tgtttcgcga cgcggtggag   3000
cagcacggca tcgcgttcgt cccgctgagc gacgaactga cctaccgccg gaccatgggc   3060
gatccgcgcc tgtgggaccc caagacgtcc ttcggcgtgc tctggcaaac catcgccggg   3120
atgatcgagc cggtctacga gtacgtctcg gcgcagcgcc atgacgacat cgtggtggtc   3180
ggctcgctct gggcgctggg cgcacgcatc gctcacgaga gtacgggat tccctacctg   3240 tccgcgcagg tctcgccatc gaccttgttg tcggcgcacc tgccgccggt acaccccaag   3300
ttcaacgtgc ccgagcagat gccgctggcg atgcgcaagc tgctctggcg ctgcatcgag   3360
cgcttcaagc tggatcgcac ctgcgcgccg gatatcaacg cggtgcggcg caaggtcggc   3420
ctggagacgc cggtgaagcg catcttcacc caatggatgc attcgccgca gggcgtggtc   3480
tgcctgttcc cggcctggtt cgcgccgccc cagcaggatt ggccgcaacc cctgcacatg   3540
accggcttcc cgctgttcga cggcagtatc ccggggaccc cgctcgacga cgaactgcaa   3600
cgctttctcg atcagggcag ccggccgctg gtgttcaccc agggctcgac cgaacacctg   3660
cagggcgact tctacgccat ggccctgcgc gcgctggaac gcctcggcgc gcgtgggatc   3720
ttcctcaccg gcgccggcca ggaaccgctg cgcggcttgc cgaaccacgt gctgcagcgc   3780
gcctacgcgc cactgggagc cttgctgcca tcgtgcgccg ggctggtcca tccgggcggt   3840
atcggcgcca tgagcctggc cttggcggcg ggggtgccgc aggtgctgct gccctgcgcc   3900
cacgaccagt tcgacaatgc cgaacggctg gtccggctcg gctgcgggat gcgcctgggc   3960
gtgccattgc gcgagcagga gttgcgcggg gcgctgtggc gcttgctcga ggacccggcc   4020
atggcggcgg cctgtcggcg tttcatggaa ttgtcacaac cgcacagtat cgcttgcggt   4080
aaagcggccc aggtggtcga acgttgtcat agggaggggg atgcgcgatg gctgaaggct   4140
gcgtcctgac gccgggagga tcctggcgtg tccacgacca gcctctgccc ctccgccacg   4200
cgggaacacg gtcccggcgc gaaacgcgtc ctgcctctgc tgttcctcac ctgcctgctg   4260
gatgccgctg gcgtcggcct gatcgtgccc ctgctgccga cgctgatcgg cagcgtggcg   4320
ccgctggcgg tccgcgacgc ggccacctgg ggcgccgccc tggtgatgac cttcgcgctg   4380
ctgcaattgt tctttccgcc ggtcctcggc agcctcagcg accgcttcgg acgccgcccc   4440
gtcctggtcc tggcgatgct cggcttcgcc ctcagctatc tgctgctggc gctggccgac   4500
agcctctgga tgctgttcct cggtcgcgcg ctggccgggc tcaccggcgc cagcgtggcc   4560
accgcgatgg cctgcgcggc tgacctcggc acgcacgggc agcgcacccg gcacttcggc   4620
tggctgtacg ccggcctcgc cctgggcatg atcctcggcc ccgccctcgg tgggctgctg   4680
gcggtgcacg gcacgacgct gccgctgttg ctggccgccg gctgtgcct gctcaacgcc   4740 ctgctcgccg gcctgttcct cgaggaaacc ctgccccga cgcgacgccg ccgcctggac   4800
ccgaggcgga tgaatgcctt gcgctcgatc agcggcctgg ctcggcaacc gggggtcgga   4860
cgcctgctgg cggtgcttgc cctggtattc ctcggcttgc aggcggtgat ggtggtctgg   4920
ccgttcttcg tgatcgagaa gtttcactgg agcagcgcct ggatcggcta ctcgctggcc   4980
ctctacggcg tgctcgcggt gctcgcccag accctcggcg tgaacctctg caagcggcgc   5040
ctggacgacg cccgcctgct gcgcctgggc ctcgccctgc aaggctgcgg cctgctgctg   5100
ttcgccctgg tcgactcgtc attctggctg gtctgcgcgc tgctgccctt cgcgctcggc   5160
agcctcgcca ccccggccat gcaggggctg ctctcggccc gcgtgccggt cgaccgccag   5220
```

```
ggcgagttgc agggcgtgct gagcagcctg atgagcctcg ccgcgatcgt cggtccgccg    5280
ctgatgagcg gcctgttcca ctggggcagc ggtccgctcg cgccgctgcc cctggccggc    5340
gcgccattcc tcgccggcgc ccttctcgtt ctggccgggc tggtcctggc ctggcaactt    5400
cgacctacgg gagaagaacg atcatggacc ggatagacat gggcgtgctg gtggtacttc    5460
tagagcggcc gccaccgcgg tggagctcca attcgcccta gtgagtcg tattacgcgc       5520
gctcactggc cgtcgtttta caacgtcgtg actgggaaaa ccctggcgtt acccaactta    5580
atcgccttgc agcacatccc cctttcgcca gctggcgtaa tagcgaagag gcccgcaccg    5640
atcgccctc ccaacagttg cgcagcctga atggcgaatg gaaattgtaa gcgttaatat     5700
tttgttaaaa ttcgcgttaa attttttgtta aatcagctca ttttttaacc aataggccga   5760
ctgcgatgag tggcagggcg gggcgtaatt ttttaaggc agttattggt gcccttaaac     5820
gcctggtgct acgcctgaat aagtgataat aagcggatga atggcagaaa ttcgaaagca    5880
aattcgaccc ggtcgtcggt tcagggcagg gtcgttaaat agccgcttat gtctattgct    5940
ggtttaccgg tttattgact accggaagca gtgtgaccgt gtgcttctca aatgcctgag    6000
gccagtttgc tcaggctctc cccgtggagg taataattga cgatatgatc atttattctg    6060
cctcccagag cctgataaaa acggtgaatc cgttagcgag gtgccgccgg cttccattca    6120
ggtcgaggtg gcccggctcc atgcaccgcg acgcaacgcg gggaggcaga caaggtatag    6180
ggcggcgagg cggctacagc cgatagtctg aacagcgca cttacgggtt gctgcgcaac     6240
ccaagtgcta ccggcgcggc agcgtgaccc gtgtcggcgg ctccaacggc tcgccatcgt    6300
ccagaaaaca cggctcatcg ggcatcggca ggcgctgctg cccgcgccgt tcccattcct    6360
ccgtttcggt caaggctggc aggtctggtt ccatgcccgg aatgccgggc tggctgggcg    6420
gctcctcgcc ggggccggtc ggtagttgct gctcgcccgg atacagggtc gggatgcggc    6480
gcaggtcgcc atgccccaac agcgattcgt cctggtcgtc gtgatcaacc accacggcgg    6540
cactgaacac cgacaggcgc aactggtcgc ggggctggcc ccacgccacg cggtcattga    6600
ccacgtaggc cgacacggtg ccggggccgt tgagcttcac gacggagatc cagcgctcgg    6660
ccaccaagtc cttgactgcg tattggaccg tccgcaaaga acgtccgatg agcttggaaa    6720
gtgtcttctg gctgaccacc acggcgttct ggtggcccat ctgcgccacg aggtgatgca    6780
gcagcattgc cgccgtgggt ttcctcgcaa taagcccggc ccacgcctca tgcgctttgc    6840
gttccgtttg cacccagtga ccgggcttgt tcttggcttg aatgccgatt tctctggact    6900
gcgtggccat gcttatctcc atgcggtagg gtgccgcacg gttgcggcac catgcgcaat    6960
cagctgcaac ttttcggcag cgcgacaaca attatgcgtt gcgtaaaagt ggcagtcaat    7020
tacagatttt ctttaaccta cgcaatgagc tattgcgggg ggtgccgcaa tgagctgttg    7080
cgtacccccc tttttttaagt tgttgatttt taagtctttc gcatttcgcc ctatatctag    7140
ttctttggtg cccaaagaag ggcacccctg cggggttccc ccacgccttc ggcgcggctc    7200
cccctccggc aaaaagtggc ccctccgggg cttgttgatc gactgcgcgg ccttcggcct    7260
tgcccaaggt ggcgctgccc ccttggaacc cccgcactcg ccgccgtgag gctcgggggg    7320
caggcgggcg ggcttcgcct tcgactgccc ccactcgcat aggcttgggt cgttccaggc    7380
gcgtcaaggc caagccgctg cgcggtcgct gcgcgagcct tgacccgcct tccacttggt    7440
gtccaaccgg caagcgaagc gcgcaggcc caggccggag ctttttcccc agagaaaatt     7500
aaaaaaattg atggggcaag gccgcaggcc gcgcagttgg agccggtggg tatgtggtcg    7560
aaggctgggt agccggtggg caatccctgt ggtcaagctc gtgggcaggc gcagcctgtc    7620
```

```
catcagcttg tccagcaggg ttgtccacgg gccgagcgaa gcgagccagc cggtggccgc    7680
tcgcggccat cgtccacata tccacgggct ggcaagggag cgcagcgacc gcgcagggcg    7740
aagcccggag agcaagcccg tagggcgccg cagccgccgt aggcggtcac gactttgcga    7800
agcaaagtct agtgagtata ctcaagcatt gagtggcccg ccggaggcac cgccttgcgc    7860 tgccccgtc  gagccggttg acaccaaaa  gggaggggca ggcatggcgg catacgcgat    7920
catgcgatgc aagaagctgg cgaaaatggg caacgtggcg ccagtctca  agcacgccta    7980 ccgcgagcgc gagacgccca acgctgacgc cagcaggacg ccagagaacg agcactgggc    8040
ggccagcagc accgatgaag cgatgggccg actgcgcgag ttgctgccag agaagcggcg    8100
caaggacgct gtgttggcgg tcgagtacgt catgacggcc agcccggaat ggtggaagtc    8160
ggccagccaa gaacagcagg cggcgttctt cgagaaggcg cacaagtggc tggcggacaa    8220
gtacggggcg gatcgcatcg tgacggccag catccaccgt gacgaaacca gcccgcacat    8280
gaccgcgttc gtggtgccgc tgacgcagga cggcaggctg tcggccaagg agttcatcgg    8340
caacaaagcg cagatgaccc gcgaccagac cacgtttgcg gccgctgtgg ccgatctagg    8400
gctgcaacgg ggcatcgagg gcagcaaggc acgtcacacg cgcattcagg cgttctacga    8460
ggccctggag cggccaccag tgggccacgt caccatcagc ccgcaagcgg tcgagccacg    8520
cgcctatgca ccgcagggat tggccgaaaa gctgggaatc tcaaagcgcg ttgagacgcc    8580
ggaagccgtg gccgaccggc tgacaaaagc ggttcggcag gggtatgagc ctgccctaca    8640
ggccgccgca ggagcgcgtg agatgcgcaa gaaggccgat caagcccaag agacggcccg    8700
ag                                                                  8702
```

<210> SEQ ID NO 43
<211> LENGTH: 36
<212> TYPE: DNA
<213> ORGANISM: Artificial
<220> FEATURE:
<223> OTHER INFORMATION: Primer

<400> SEQUENCE: 43
tatatataga attcggctgc gctaccgcag cccttc                             36

<210> SEQ ID NO 44
<211> LENGTH: 34
<212> TYPE: DNA
<213> ORGANISM: Artificial
<220> FEATURE:
<223> OTHER INFORMATION: Primer

<400> SEQUENCE: 44
tatatatatc tagaattaat gcagctggca cgac                               34

<210> SEQ ID NO 45
<211> LENGTH: 8672
<212> TYPE: DNA
<213> ORGANISM: Artificial
<220> FEATURE:
<223> OTHER INFORMATION: Vector

<400> SEQUENCE: 45
ctcgggccgt ctcttgggct tgatcggcct tcttgcgcat ctcacgcgct cctgcggcgg    60
cctgtagggc aggctcatac ccctgccgaa ccgcttttgt cagccggtcg gcacggcttt    120
ccggcgtctc aacgcgcttt gagattccca gcttttcggc caatccctgc ggtgcatagg    180
```

```
cgcgtggctc gaccgcttgc gggctgatgg tgacgtggcc cactggtggc cgctccaggg    240
cctcgtagaa cgcctgaatg cgcgtgtgac gtgccttgct gccctcgatg ccccgttgca    300
gccctagatc ggccacagcg gccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgccccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt ctctggcagc aactcgcgca gtcggcccat cgcttcatcg gtgctgctgg    660
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcgcgcccc tacgggcttg ctctccgggc    960
ttcgccctgc gcggtcgctg cgctcccttg ccagcccgtg gatatgtgga cgatggccgc   1020
gagcggccac cggctggctc gcttcgctcg gcccgtggac aaccctgctg acaagctga    1080 tggacaggct gcgcctgccc acgagcttga ccacagggat tgcccaccgg ctacccagcc   1140
ttcgaccaca tacccaccgg ctccaactgc gcggcctgcg gccttgcccc atcaattttt   1200
ttaattttct ctggggaaaa gcctccggcc tgcggcctgc gcgcttcgct tgccggttgg   1260
acaccaagtg gaaggcgggt caaggctcgc gcagcgaccg cgcagcggct tggccttgac   1320
gcgcctggaa cgacccaagc ctatgcgagt gggggcagtc gaaggcgaag cccgcccgcc   1380 tgcccccga gcctcacggc ggcgagtgcg ggggttccaa gggggcagcg ccaccttggg   1440
caaggccgaa ggccgcgcag tcgatcaaca agccccggag gggccacttt tgccggagg    1500 gggagccgcg ccgaaggcgt gggggaaccc cgcaggggtg cccttctttg ggcaccaaag   1560
aactagatat agggcgaaat gcgaaagact taaaaatcaa caacttaaaa aagggggta    1620 cgcaacagct cattgcggca ccccccgcaa tagctcattg cgtaggttaa agaaaatctg   1680
taattgactg ccacttttac gcaacgcata attgttgtcg cgctgccgaa agttgcagc    1740 tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttgggc atggcgacct   2220 gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacggcgcg gcagcagcg cctgccgatg cccgatgagc cgtgttttct   2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520
ccctatacct tgtctgcctc cccgcgttgc gtcgcggtgc atggagccgg ccacctcga   2580
```

```
cctgaatgga agccggcggc acctcgctaa cggattcacc gttttatca ggctctggga    2640
ggcagaataa atgatcatat cgtcaattat tacctccacg gggagagcct gagcaaactg   2700
gcctcaggca tttgagaagc acacggtcac actgcttccg gtagtcaata aaccggtaaa   2760
ccagcaatag acataagcgg ctatttaacg accctgccct gaaccgacga ccgggtcgaa   2820
tttgctttcg aatttctgcc attcatccgc ttattatcac ttattcaggc gtagcaccag   2880
gcgtttaagg gcaccaataa ctgccttaaa aaaattacgc cccgccctgc cactcatcgc   2940
agtcggccta ttggttaaaa aatgagctga tttaacaaaa atttaacgcg aattttaaca   3000
aaatattaac gcttacaatt tccattcgcc attcaggctg cgcaactgtt gggaagggcg   3060
atcggtgcgg gcctcttcgc tattacgcca gctggcgaaa gggggatgtg ctgcaaggcg   3120
attaagttgg gtaacgccag ggttttccca gtcacgacgt tgtaaaacga cggccagtga   3180
gcgcgcgtaa tacgactcac tatagggcga attggagctc caccgcggtg gcggccgctc   3240
tagaactagt ggatccccg ggctgcagga attcggctgc gctaccgcag cccttctccg    3300
ctaaaaccgt tagtcgaaca gttcggcgtc agccaatgcg accccaagct ggtccttgcc   3360
agacaagctt ggtacggagt cgatgggcca ttcgatacc actgccggat cattccaggc    3420
aatgcagcgc tcgcactgcg gcgagtagaa gtcggtggtc ttgtagagga actctgcggt   3480
ttcactcaac gtgacgaacc cgtgtgcgaa ccctggcggg atccacagct ggttcttgtt   3540
ctcggccgac aacaccgcac ctacccattt accgaaggtt gtggacgagc gacggatatc   3600
caccgcaaca tcgaagactt cgccttgcac cacacgcacc agcttgccct gggcgtgagg   3660
tgccagctga tagtgcaggc cacggagcac gccttttacc gagcgcgagt ggttgtcttg   3720
tacgaagtcg ggctgcaggc cggtcacttc gctgaaaaca cgggcgttga agctctcgta   3780
gaagaaacca cgttcgtcgc caaaaacctt gggggtaaac agcacgactt cggggatatc   3840
cagcggaatg gcttgcatca gaacaccttc tctttcagca agttctgcag atacttgcca   3900
taaccgtttt tcagcagtgg ttgagccagg cactcgagtt gctcagcgtt gatccagcca   3960
gcgcggtagc aaatttcctc agggcaggcg actttcaagc cctgacgcg ctccatggtt    4020
gcgatgtact ggctagcctc cagcagactg tcgtgcgtgc cggtgtcgag ccacgcatag   4080
ccacggccca tgatttcgac ctgcaactgc tgctgctgca agtaaaggtt gttgaggtcg   4140
gtgatttcca gctcgccacg tggggaaggc ttcagctcgc gagccagatt gactacctga   4200
ttgtcataga aatacaggcc ggtgaccgca tagctagact ttggaactgc cggttttct    4260
tccagcgaca atacgcgacc gctatcgtca aactccgcta cgccatagcg ttctgggtca   4320
tgaacatgat aagcgaatac tgaagcaccg gattcacgtt tatctgcgtt caatagcagt   4380
gcctggaagt catggccgta gaaaatattg tcaccgagaa ccaacgcaga agggtcgtta   4440
ccgatgaagt cagcgccgat ggtgaacgct tgcgccaagc catccgggct tggttgtatt   4500
gcgtatgaca ggtcaggcc ccactggctg ccatcgccca gcagctgttc gaagcgcggg    4560
gtgtcctgcg gggtggaaat gatcaggatg tcccggatac cagcgagcag cagggtgctc   4620
agcgggtagt agatcatcgg tttgtcatac accggcagca gctgcttcga aaccgaaagt   4680
gtggccggat gcaggcgtgt acccgaaccg ccggccagaa taattccttt acgagccatg   4740
agagtcccta ttactggatt tcgtccagca tacgttgcac gccttgctcc caaagcggca   4800
ttttgaaatt gaacgtgttt tccagtttgc ccagtgccag gcgcgagttg cgcggacgtg   4860
gtgcaggtac tggataagct tcggtgctga ttgcggcaac cttatcagct gtcactttca   4920
```

```
gcgctacgcc agtgcgttga gcatgcgcca gcacgaactg agcaaaacca tgccaagagg    4980
tttcaccgga cgcagccaag tggtaaatcc ctgccaggtg acggttgtct tgcccattga    5040
agatttgccg caggatgtgt gcagtaacgt cggcgatcag gtcagcgccc gtgggtgcgc    5100
caaattggtc tgctaccacg ctcaacgtct cacgctccgc cgccaggcgc agcatggtct    5160
tggcaaaatt gtgcccgcgc gcagcataca cccagctggt gcgcagtacc acggccttgg    5220
cgccgctggc gagaatggca tgctcgcctt ccagcttggt ccggccgtag accgaaaggg    5280
ggccggtagg cgcagtttcc tcccagcgct gactgccgct gccgtcaaat acataatcgg    5340
tggaatagtg aatcaaccag gcgcccaaag ctgctgtttc acgtgctaat acagcaggag    5400
ccgcggcatt gatcattgca gccagtgcct gatcgctctc agctttatcc actgcagtgt    5460
aggcagcagc gttgacgatc acgtccggcg ccagctgacg aatcgtagcg ccaagccgt    5520 ccaggttgga caagtcgcca cataagccct cggcccctg acgatccagc gcaatgacct    5580
cacccagcgg cgccaaggcg cgctgtagct cccagcctac ttgcccgttt ttccccaaca    5640
gcaggatttt cacgctttat ttgccccgta ttgttgtgcc acccagtcac ggtagctgcc    5700
gtccatgaca ccttttaccc atttctggtt ggccaagtac caagcgactg tctttcgaat    5760
gcccgtctcg aaggtttcgg cagtttccag ccgagctccc gctcgatctt gcgtgcatcg    5820
atggcataac ggcggtcatg gcctgggcgg tcggttacgt aggcgatgag ttctgcatac    5880
tgttcgacag gctcgccggt cttctgattg attacctggc gcgatgccgc aggtgccatc    5940
tcgtcgagaa ggctgcagag tgtacgcaca atgtcaatgt tggcttttc attccagccg    6000 ccaatattgt acgtctcgcc gaacgcaccg gcttccagta cgcgacggat gcccgagcag    6060
tgatcttcga catacagcca gtcgcggatt tgctggccgt cgccatagac aggcagcgcc    6120
ttaccggcga gtgcgttgac gatcatcagc gggatcagtt tttccgggaa gtggagcggc    6180
ccgtaattgt tggagcagtt ggtagtgagt accggcatgc cgtaggtatg gaaatacgag    6240
cgtaccagat ggtcgctggc tgccttgctg gcggagtatg ggctgttcgg cgcgtacggc    6300
gtggtttcgg tgaacgccgg gtcgtttggc cctagtgtgc cgtagacttc gtcggtagag    6360
acatggagga aacggaaggc ctccttctct gcaccttcca aactattcca atgcgcccgg    6420
gcggcttcaa gcaagcgaaa cgtgcccatc acgttggttt cgacaaacgc ttcggggccg    6480
gtgattgagc ggtctacatg ggattccgcc gcgaagtgaa ccacggcgcg cgggcggtgc    6540
tctgcgaaca gcttggtcag aagcgcagca tcgcaaatat tgccttgcac aaagcgatgc    6600
tgagggttgc cttccagcgg ctgcaggttg gccaggttgc ctgcgtaggt cagggcgtcg    6660
aggttgagga cgggttcctc attgtgcgca caccattgca gtacgaaatt tgagccgatg    6720
aagccggctc cgcctgttac tagaatcata atttggctct aattggacaa aggtgttgt    6780 cgtagacaga tgacgcgaat tcgatatcaa gcttatcgat accgtcgacc tcgagggggg    6840
gcccggtacc cagcttttgt tccctttagt gagggttaat tgcgcgcttg gcgtaatcat    6900
ggtcatagct gtttcctgtg tgaaattgtt atccgctcac aattccacac aacatacgag    6960
ccggaagcat aaagtgtaaa gcctggggtg cctaatgagt gagctaactc acattaattg    7020
cgttgcgctc actgcccgct ttccagtcgg gaaacctgtc gtgccagctg cattaatgaa    7080
tcggccaacg cgcggggaga ggcggtttgc gtattgggcg catgcataaa aactgttgta    7140
attcattaag cattctgccg acatggaagc catcacaaac ggcatgatga acctgaatcg    7200
ccagcggcat cagcaccttg tcgccttgcg tataatattt gcccatgggg gtgggcgaag    7260
aactccagca tgagatcccc gcgctggagg atcatccagc cggcgtcccg gaaaacgatt    7320
```

```
ccgaagccca accttcata gaaggcggcg gtggaatcga aatctcgtga tggcaggttg    7380
ggcgtcgctt ggtcggtcat ttcgaacccc agagtcccgc tcagaagaac tcgtcaagaa    7440
ggcgatagaa ggcgatgcgc tgcgaatcgg gagcggcgat accgtaaagc acgaggaagc    7500
ggtcagccca ttcgccgcca agctcttcag caatatcacg ggtagccaac gctatgtcct    7560
gatagcggtc cgccacaccc agccggccac agtcgatgaa tccagaaaag cggccatttt    7620
ccaccatgat attcggcaag caggcatcgc catgggtcac gacgagatcc tcgccgtcgg    7680
gcatgcgcgc cttgagcctg gcgaacagtt cggctggcgc gagcccctga tgctcttcgt    7740
ccagatcatc ctgatcgaca agaccggctt ccatccgagt acgtgctcgc tcgatgcgat    7800
gtttcgcttg gtggtcgaat gggcaggtag ccggatcaag cgtatgcagc cgccgcattg    7860
catcagccat gatggatact ttctcggcag gagcaaggtg agatgacagg agatcctgcc    7920
ccggcacttc gcccaatagc agccagtccc ttcccgcttc agtgacaacg tcgagcacag    7980
ctgcgcaagg aacgcccgtc gtggccagcc acgatagccg cgctgcctcg tcctgcagtt    8040
cattcagggc accggacagg tcggtcttga caaaagaac cgggcgcccc tgcgctgaca    8100
gccggaacac ggcggcatca gagcagccga ttgtctgttg tgcccagtca tagccgaata    8160
gcctctccac ccaagcggcc ggagaacctg cgtgcaatcc atcttgttca atcatgcgaa    8220
acgatcctca tcctgtctct tgatcagatc ttgatcccct cgccatcag atccttggcg    8280 gcaagaaagc catccagttt actttgcagg gcttcccaac cttaccagag ggcgccccag    8340
ctggcaattc cggttcgctt gctgtccata aaaccgccca gtctagctat cgccatgtaa    8400
gcccactgca agctacctgc tttctctttg cgcttgcgtt ttcccttgtc cagatagccc    8460
agtagctgac attcatccca ggtggcactt tcggggaaa tgtgcgcgcc cgcgttcctg    8520
ctggcgctgg gcctgtttct ggcgctggac ttcccgctgt tccgtcagca gcttttcgcc    8580
cacggccttg atgatcgcgg cggccttggc ctgcatatcc cgattcaacg gccccagggc    8640
gtccagaacg ggcttcaggc gctcccgaag gt                                 8672
```

<210> SEQ ID NO 46
<211> LENGTH: 21
<212> TYPE: DNA
<213> ORGANISM: Artificial
<220> FEATURE:
<223> OTHER INFORMATION: Primer

<400> SEQUENCE: 46

```
ggccgctcta gaactagtgg a                                               21
```

<210> SEQ ID NO 47
<211> LENGTH: 12249
<212> TYPE: DNA
<213> ORGANISM: Artificial
<220> FEATURE:
<223> OTHER INFORMATION: Vector

<400> SEQUENCE: 47

```
ctcgggccgt ctcttgggct tgatcggcct tcttgcgcat ctcacgcgct cctgcggcgg     60
cctgtagggc aggctcatac ccctgccgaa ccgcttttgt cagccggtcg ccacggctt    120 ccggcgtctc aacgcgcttt gagattccca gcttttcggc caatccctgc ggtgcatagg    180
cgcgtggctc gaccgcttgc gggctgatgg tgacgtggcc cactggtggc cgctccaggg    240
cctcgtagaa cgcctgaatg cgcgtgtgac gtgccttgct gccctcgatg cccgttgca    300
```

```
gccctagatc ggccacagcg gccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgccccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt ctctggcagc aactcgcgca gtcggcccat cgcttcatcg gtgctgctgg    660
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcgcgccc tacgggcttg ctctccgggc    960
ttcgccctgc gcggtcgctg cgctcccttg ccagcccgtg gatatgtgga cgatggccgc   1020
gagcggccac cggctggctc gcttcgctcg gcccgtggac aaccctgctg gacaagctga   1080
tggacaggct gcgcctgccc acgagcttga ccacagggat tgcccaccgg ctacccagcc   1140
ttcgaccaca tacccaccgg ctccaactgc gcggcctgcg gccttgcccc atcaattttt   1200
ttaattttct ctggggaaaa gcctccggcc tgcggcctgc gcgcttcgct tgccggttgg   1260
acaccaagtg gaaggcgggt caaggctcgc gcagcgaccg cgcagcggct ggccttgac    1320
gcgcctggaa cgacccaagc ctatgcgagt gggggcagtc gaaggcgaag cccgcccgcc   1380
tgcccccga gcctcacggc ggcgagtgcg ggggttccaa gggggcagcg ccaccttggg    1440
caaggccgaa ggccgcgcag tcgatcaaca agccccggag gggccacttt tgccggagg    1500
gggagccgcg ccgaaggcgt gggggaaccc cgcaggggtg cccttctttg ggcaccaaag   1560
aactagatat agggcgaaat gcgaaagact taaaaatcaa caacttaaaa aagggggta    1620
cgcaacagct cattgcggca ccccccgcaa tagctcattg cgtaggttaa agaaaatctg   1680
taattgactg ccacttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgccagc cagcccggca ttccgggcat ggaaccagac ctgccagcct tgaccgaaac   2340
ggaggaatgg gaacggcgcg ggcagcagcg cctgccgatg cccgatgagc cgtgttttct   2400
ggacgatggc gagccgttgg agccgccgac acggtcacg ctgccgcgcc ggtagcactt    2460
gggttgcgca gcaacccgta agtgcgctgt tccagactat cggctgtagc cgcctcgccg   2520
ccctatacct tgtctgcctc cccgcgttgc gtcgcggtgc atggagccgg gccacctcga   2580
cctgaatgga agccggcggc acctcgctaa cggattcacc gttttatca ggctctggga    2640
ggcagaataa atgatcatat cgtcaattat tacctccacg gggagagcct gagcaaactg   2700
```

```
gcctcaggca tttgagaagc acacggtcac actgcttccg gtagtcaata aaccggtaaa  2760
ccagcaatag acataagcgg ctatttaacg accctgccct gaaccgacga ccgggtcgaa  2820
tttgctttcg aatttctgcc attcatccgc ttattatcac ttattcaggc gtagcaccag  2880
gcgtttaagg gcaccaataa ctgccttaaa aaaattacgc cccgccctgc cactcatcgc  2940
agtcggccta ttggttaaaa aatgagctga tttaacaaaa atttaacgcg aattttaaca  3000
aaatattaac gcttacaatt tccattcgcc attcaggctg cgcaactgtt gggaagggcg  3060
atcggtgcgg gcctcttcgc tattacgcca gctggcgaaa ggggatgtg ctgcaaggcg  3120
attaagttgg gtaacgccag gttttccca gtcacgacgt tgtaaaacga cggccagtga  3180
gcgcgcgtaa tacgactcac tatagggcga attggagctc caccgcggtg gcggccgctc  3240
tagaactagt ggatccccg gctgcagga attcggctgc gctaccgcag cccttctccg  3300
ctaaaaccgt tagtcgaaca gttcggcgtc agccaatgcg acccccaagct ggtccttgcc  3360
agacaagctt ggtacggagt cgatgggcca ttcgatccc actgccggat cattccaggc  3420
aatgcagcgc tcgcactgcg gcgagtagaa gtcggtggtc ttgtagagga actctgcggt  3480
ttcactcaac gtgacgaacc cgtgtgcgaa ccctggcggg atccacagct ggttcttgtt  3540
ctcggccgac aacaccgcac ctacccattt accgaaggtt gtggacgagc gacggatatc  3600
caccgcaaca tcgaagactt cgccttgcac cacacgcacc agcttgccct gggcgtgagg  3660
tgccagctga tagtgcaggc cacggagcac gccttttacc gagcgcgagt ggttgtcttg  3720
tacgaagtcg ggctgcaggc cggtcacttc gctgaaaaca cgggcgttga agctctcgta  3780
gaagaaacca cgttcgtcgc caaaaaccttt ggggtaaac agcacgactt cggggatatc  3840
cagcggaatg gcttgcatca gaacaccttc tctttcagca agttctgcag atacttgcca  3900
taaccgtttt tcagcagtgg ttgagccagg cactcgagtt gctcagcgtt gatccagcca  3960
gcgcggtagc aaatttcctc agggcaggcg actttcaagc cctgacgcg ctccatggtt  4020
gcgatgtact ggctagcctc cagcagactg tcgtgcgtgc cggtgtcgag ccacgcatag  4080
ccacggccca tgatttcgac ctgcaactgc tgctgctgca agtaaaggtt gttgaggtcg  4140
gtgatttcca gctcgccacg tggggaaggc ttcagctcgc gagccagatt gactacctga  4200
ttgtcataga aatacaggcc ggtgaccgca tagctagact ttggaactgc cggttttct  4260
tccagcgaca atacgcgacc gctatcgtca aactccgcta cgcctagcg ttctgggtca  4320
tgaacatgat aagcgaatac tgaagcaccg gattcacgtt tatctgcgtt caatagcagt  4380
gcctggaagt catggccgta gaaaatattg tcaccgagaa ccaacgcaga agggtcgtta  4440
ccgatgaagt cagcgccgat ggtgaacgct tgcgccaagc catccgggct tggttgtatt  4500
gcgtatgaca ggttcaggcc ccactggctg ccatcgccca gcagctgttc gaagcgcggg  4560
gtgtcctgcg gggtggaaat gatcaggatg tcccggatac cagcgagcag cagggtgctc  4620
agcgggtagt agatcatcgg tttgtcatac accggcagca gctgcttcga aaccgaaagt  4680
gtggccggat gcaggcgtgt acccgaaccg ccggccagaa taattccttt acgagccatg  4740
agagtcccta ttactggatt tcgtccagca tacgttgcac gccttgctcc caaagcggca  4800
ttttgaaatt gaacgtgttt tccagtttgc ccagtgccag gcgcgagttg cgcggacgtg  4860
gtgcaggtac tggataagct tcggtgctga ttgcggcaac cttatcagct gtcactttca  4920
gcgctacgcc agtgcgttga gcatgcgcca gcacgaactg agcaaaacca tgccaagagg  4980
tttcaccgga cgcagccaag tggtaaatcc ctgccaggtg acggttgtct tgcccattga  5040
```

```
agatttgccg caggatgtgt gcagtaacgt cggcgatcag gtcagcgccc gtgggtgcgc   5100
caaattggtc tgctaccacg ctcaacgtct cacgctccgc cgccaggcgc agcatggtct   5160
tggcaaaatt gtgcccgcgc gcagcataca cccagctggt gcgcagtacc acggccttgg   5220
cgccgctggc gagaatggca tgctcgcctt ccagcttggt ccggccgtag accgaaaggg   5280
ggccggtagg cgcagtttcc tcccagcgct gactgccgct gccgtcaaat acataatcgg   5340
tggaatagtg aatcaaccag gcgcccaaag ctgctgtttc acgtgctaat acagcaggag   5400
ccgcggcatt gatcattgca gccagtgcct gatcgctctc agctttatcc actgcagtgt   5460
aggcagcagc gttgacgatc acgtccggcg ccagctgacg aatcgtagcg gccaagccgt   5520
ccaggttgga caagtcgcca cataagccct cggcccctg acgatccagc gcaatgacct   5580
cacccagcgg cgccaaggcg cgctgtagct cccagcctac ttgcccgttt ttccccaaca   5640
gcaggatttt cacgctttat tgccccgta ttgttgtgcc acccagtcac ggtagctgcc   5700
gtccatgaca ccttttaccc atttctggtt ggccaagtac caagcgactg tctttcgaat   5760
gcccgtctcg aaggtttcgg caggtttcca gccgagctcc cgctcgatct tgcgtgcatc   5820
gatggcataa cggcggtcat ggcctgggcg gtcggttacg taggcgatga gttctgcata   5880
ctgttcgaca ggctcgccgg tcttctgatt gattacctgg cgcgatgccg caggtgccat   5940
ctcgtcgaga aggctgcaga gtgtacgcac aatgtcaatg ttggctttt cattccagcc   6000 gccaatattg tacgtctcgc cgaacgcacc ggcttccagt acgcgacgga tgcccgagca   6060
gtgatcttcg acatacagcc agtcgcggat ttgctggccg tcgccataga caggcagcgc   6120
cttaccggcg agtgcgttga cgatcatcag cgggatcagt ttttccggga agtggagcgg   6180
cccgtaattg ttggagcagt tggtagtgag taccggcatg ccgtaggtat ggaaatacga   6240
gcgtaccaga tggtcgctgg ctgccttgct ggcggagtat gggctgttcg gcgcgtacgg   6300
cgtggtttcg gtgaacgccg ggtcgtttgg ccctagtgtg ccgtagactt cgtcggtaga   6360
gacatggagg aaacggaagg cctccttctc tgcaccttcc aaactattcc aatgcgcccg   6420
ggcggcttca agcaagcgaa acgtgcccat cacgttggtt tcgacaaacg cttcggggcc   6480
ggtgattgag cggtctacat gggattccgc cgcgaagtga accacggcgc gcgggcggtg   6540
ctctgcgaac agcttggtca gaagcgcagc atcgcaaata ttgccttgca caaagcgatg   6600
ctgagggttg ccttccagcg gctgcaggtt ggccaggttg cctgcgtagg tcagggcgtc   6660
gaggttgagg acgggttcct cattgtgcgc acaccattgc agtacgaaat ttgagccgat   6720
gaagccggct ccgcctgtta ctagaatcat aatttggctc taattggaca aaaggtgttg   6780
tcgtagacag atgacgcgaa ttcgatatca agcttatcga taccgtcgac ctcgaggggg   6840
ggcccggtac ccagcttttg ttccctttag tgagggttaa ttgcgcgctt ggcgtaatca   6900
tggtcatagc tgtttcctgt gtgaaattgt tatccgctca caattccaca caacatacga   6960 gccgaagca taaagtgtaa agcctggggt gcctaatgag tgagctaact cacattaatt   7020
gcgttgcgct cactgcccgc tttccagtcg ggaaacctgt cgtgccagct gcattaattc   7080
tagagggaat gcgtttcgcc gactaggcct tggccttgcc ggaagctacg gacgccacgg   7140
ccgggccggc gaggcgcttc agcaggcgcg ggcggttggt ctccagcgcg ccgccgcgtc   7200
cccgcaggcc gtcccacagg ccccagccca ggcagcgcag cttgagcagc ttgtcgcgtt   7260
cgagcaggag caccgcgagg ccctgggtca gggtcggcag gttcgccagc agggccagcg   7320
gcgaggaccg ggcgtagcgg cgcaggacca gcaggccgtt gcgcgccagg tagtagcggc   7380
gcagcggggc gtggttcatc gcgctgaggc tgagaccgcc gaggcggcgg gtcttgcgcg   7440
```

```
tgccgatgcg gtgctcgagg accagccgcg ggtcgacgta caggggcacg tccagcgcct    7500
gggcgcgcag gctgtattcg gtgtccacgt ggtcgatgaa cagttcctcg tcgaagtggc    7560
cgaggcgctg gtaggcctcg cgggtcagca ggcagccgga ggagatcagg aacgaggtgc    7620
gctgcggggt cgtcaggccg tccagagaca attgcctgag cgtcagtccg tcgagatgga    7680
tggccggcag gaagcgccgg tcaccccggt cgaagatccg tgggccgagc aggcaggcct    7740
gaccgttgcg cgcctgcagg ttgcgccact gggcggcgag gaaggcgccg ccgggacggg    7800
agtcctggtc gagcagcagc acaccctgca cgccacgccg gaatagcgcg tcgagtccct    7860
ggttgaaggc gccggcgatg ccctgccggt tgccgtggtg cagcacggcg atgcctttgcc   7920 cgcgcagccg ggcattgcgc tgcggatcgc tgtgcggtga gttgtcgacg gcaaggaagc    7980
gcagttgcgg aaacgccgcc gccagttcgc caaggtgttc caggtcgtcg tcgccaggat    8040
tgaacagtac caccagcacg cccatgtcta tccggtccat gatcgttctt ctcccgtagg    8100
tcaggacgca gccttcagcc atcgcgcatc cccctcccta tgacaacgtt cgaccacctg    8160
ggccgcttta ccgcaagcga tactgtgcgg ttgtgacaat tccatgaaac gccgacaggc    8220
cgccgccatg gccgggtcct cgagcaagcg ccacagcgcc ccgcgcaact cctgctcgcg    8280
caatggcacg cccaggcgca tcccgcagcc gagccggacc agccgttcgg cattgtcgaa    8340
ctggtcgtgg gcgcagggca gcagcacctg cggcaccccc gccgcaagg ccaggctcat     8400 ggcgccgata ccgcccggat ggaccagccc ggcgcacgat ggcagcaagg ctcccagtgg    8460
cgcgtaggcg cgctgcagca cgtggttcgg caagccgcgc agcggttcct ggccggcgcc    8520
ggtgaggaag atcccacgcg cgccgaggcg ttccagcgcg cgcagggcca tggcgtagaa    8580
gtcgccctgc aggtgttcgg tcgagccctg ggtgaacacc agcggccggc tgccctgatc    8640
gagaaagcgt tgcagttcgt cgtcgagcgg ggtccccggg atactgccgt cgaacagcgg    8700
gaagccggtc atgtgcaggg gttgcggcca atcctgctgg ggcggcgcga accaggccgg    8760
gaacaggcag accacgccct gcggcgaatg catccattgg gtgaagatgc gcttcaccgg    8820
cgtctccagg ccgaccttgc gccgcaccgc gttgatatcc ggcgcgcagg tgcgatccag    8880
cttgaagcgc tcgatgcagc gccagagcag cttgcgcatc gccagcggca tctgctcggg    8940
cacgttgaac ttggggtgta ccggcggcag gtgcgccgac aacaaggtcg atggcgagac    9000
ctgcgcggac aggtagggaa tcccgtactt ctcgtgagcg atgcgtgcgc ccagcgccca    9060
gagcgagccg accaccacga tgtcgtcatg gcgctgcgcc gagacgtact cgtagaccgg    9120
ctcgatcatc ccggcgatgg tttgccagag cacgccgaag gacgtcttgg ggtcccacag    9180
gcgcggatcg cccatggtcc ggcggtaggt cagttcgtcg ctcagcggga cgaacgcgat    9240
gccgtgctgc tccaccgcgt cgcgaaacac cgggatggtg cagaggctca cgcggtgccc    9300
gcgcaatttc agggtccggg ccaggccgat gaagggaaat acgtcgccgg ccgagccgat    9360
ggcgatgagg atggcgtgca tggtgctact ccgtgcgtta tgcaaccgca aagcccggcc    9420
aggccgggtc ttcgcaggtc aagggttcag gcgtagccga tggccatctc gtggaatccc    9480
gccgcgcgtt ccgcccgctg cggctccggt tgcttcagca ggtgctcgag cagggcgcgg    9540
tgcacgcgta ccgcggccag cttggactcc aggtcgagga aatgcccggt gcctccacc    9600 cgcgagaaac tgcagtgcgg caggtagtcg cggaactggc gggcgtcctc ggcggtggtg    9660
tattcgtccc agctgccgtt gatgaaatgc acgtggctct ggatccgctc caggcaagcc    9720
aggtagcccc gatcgttgag cgccagcacc tggtcgatgt gaaagcgcgc ctgctcgtat    9780
```

```
tcgccggtgg ccagcgaagc catgtgctga tggttgctgg ctttcaggcg cggcggcagg    9840
tatttgccga cggtctcgtt gagcagatgg ccgatcgccg acttgtcgtc cagctcgatc    9900
agcgcctgcg cccgcccgac gtagtcgagc atcgcctggt tcagtccagg ggcgaatgcc    9960
atcaccaccg agctgcggat gccgcgcgga ttgcgcgaca cgccagcag cgtggagata    10020 ccgccccagg acgcggagac caggtgattg acctcgaagc gctcgatcag cgccaggagg    10080
atttccacct cgtcgtcctt ggtgatcaac ccccgctgcg ggttgtgctg acgcgactgc    10140
ccggcgaagg gcaggtcgaa cagcaccacg ttgaaatgtt cggccaggca cttgcaggtc    10200
cgggcgaacg aggcggtggt cgccatcgcg ccgttgacca gcatcaccgt gctgcgcccg    10260
ggatcctgcc caacgcgctc gacatgtacc cgcaggccct tgcaaaccga taccaacaga    10320
ctttcgcgcc gcatttcaca cctcccaaaa atgccagatc ccccgggctg caggaattcg    10380
atatcaagct tatcgatacc gtcgacctcg agggggggcc cggtacccag cttttgttcc    10440
ctttagtgag ggttaattgc gcgcttggcg taatcatggt catagctgtt tcctgtgtga    10500
aattgttatc cgctcacaat tccacacaac atacgagccg gaagcataaa gtgtaaagcc    10560
tggggtgcct aatgagtgag ctaactcaca ttaattgcgt tgcgctcact gcccgctttc    10620
cagtcgggaa acctgtcgtg ccagctgcat taatgaatcg gccaacgcgc ggggagaggc    10680
ggtttgcgta ttgggcgcat gcataaaaac tgttgtaatt cattaagcat tctgccgaca    10740
tggaagccat cacaaacggc atgatgaacc tgaatcgcca gcggcatcag caccttgtcg    10800
ccttgcgtat aatatttgcc catggggtg ggcgaagaac tccagcatga tccccgcgc    10860 ctggaggatc atccagccgg cgtcccggaa aacgattccg aagcccaacc tttcatagaa    10920
ggcggcggtg gaatcgaaat ctcgtgatgg caggttgggc gtcgcttggt cggtcatttc    10980 gaacccaga gtcccgctca gaagaactcg tcaagaaggc gatagaaggc gatgcgctgc    11040
gaatcgggag cggcgatacc gtaaagcacg aggaagcggt cagcccattc gccgccaagc    11100
tcttcagcaa tatcacgggt agccaacgct atgtcctgat agcggtccgc cacacccagc    11160
cggccacagt cgatgaatcc agaaaagcgg ccattttcca ccatgatatt cggcaagcag    11220
gcatcgccat gggtcacgac gagatcctcg ccgtcgggca tgcgcgcctt gagcctggcg    11280
aacagttcgg ctggcgcgag cccctgatgc tcttcgtcca gatcatcctg atcgacaaga    11340
ccggcttcca tccgagtacg tgctcgctcg atgcgatgtt tcgcttggtg gtcgaatggg    11400
caggtagccg gatcaagcgt atgcagccgc cgcattgcat cagccatgat ggatactttc    11460
tcggcaggag caaggtgaga tgacaggaga tcctgccccg gcacttcgcc caatagcagc    11520
cagtcccttc ccgcttcagt gacaacgtcg agcacagctg cgcaaggaac gcccgtcgtg    11580 gccagcacg atagccgcgc tgcctcgtcc tgcagttcat tcagggcacc ggacaggtcg    11640
gtcttgacaa aaagaaccgg gcgcccctgc gctgacagcc ggaacacggc ggcatcagag    11700
cagccgattg tctgttgtgc ccagtcatag ccgaatagcc tctccaccca agcggccgga    11760
gaacctgcgt gcaatccatc ttgttcaatc atgcgaaacg atcctcatcc tgtctcttga    11820
tcagatcttg atccctgcg ccatcagatc cttggcggca agaaagccat ccagtttact    11880
ttgcagggct tcccaacctt accagagggc gccccagctg gcaattccgg ttcgcttgct    11940
gtccataaaa ccgcccagtc tagctatcgc catgtaagcc cactgcaagc tacctgcttt    12000
ctctttgcgc ttgcgttttc ccttgtccag atagcccagt agctgacatt catcccaggt    12060 ggcactttc ggggaaatgt gcgcgcccgc gttcctgctg gcgctgggcc tgtttctggc    12120
gctggacttc ccgctgttcc gtcagcagct tttcgcccac ggccttgatg atcgcggcgg    12180
```

```
<210> SEQ ID NO 48
<211> LENGTH: 37
<212> TYPE: DNA
<213> ORGANISM: Artificial
<220> FEATURE:
<223> OTHER INFORMATION: Primer

<400> SEQUENCE: 48
tatatataga attcgcgtca tctgtctacg acaacac                              37

<210> SEQ ID NO 49
<211> LENGTH: 5144
<212> TYPE: DNA
<213> ORGANISM: Artificial
<220> FEATURE:
<223> OTHER INFORMATION: Vector

<400> SEQUENCE: 49
ctcgggccgt ctcttgggct tgatcggcct tcttgcgcat ctcacgcgct cctgcggcgg      60
cctgtagggc aggctcatac ccctgccgaa ccgcttttgt cagccggtcg gccacggctt     120
ccggcgtctc aacgcgcttt gagattccca gcttttcggc caatccctgc ggtgcatagg     180
cgcgtggctc gaccgcttgc gggctgatgg tgacgtggcc cactggtggc cgctccaggg     240
cctcgtagaa cgcctgaatg cgcgtgtgac gtgccttgct gccctcgatg ccccgttgca     300
gccctagatc ggccacagcg gccgcaaacg tggtctggtc gcgggtcatc tgcgctttgt     360
tgccgatgaa ctccttggcc gacagcctgc cgtcctgcgt cagcggcacc acgaacgcgg     420
tcatgtgcgg gctggtttcg tcacggtgga tgctggccgt cacgatgcga tccgccccgt     480
acttgtccgc cagccacttg tgcgccttct cgaagaacgc cgcctgctgt tcttggctgg     540
ccgacttcca ccattccggg ctggccgtca tgacgtactc gaccgccaac acagcgtcct     600
tgcgccgctt ctctggcagc aactcgcgca gtcggcccat cgcttcatcg gtgctgctgg     660
ccgcccagtg ctcgttctct ggcgtcctgc tggcgtcagc gttgggcgtc tcgcgctcgc     720
ggtaggcgtg cttgagactg gccgccacgt tgcccatttt cgccagcttc ttgcatcgca     780
tgatcgcgta tgccgccatg cctgcccctc ccttttggtg tccaaccggc tcgacggggg     840
cagcgcaagg cggtgcctcc ggcgggccac tcaatgcttg agtatactca ctagactttg     900
cttcgcaaag tcgtgaccgc ctacggcggc tgcggcgccc tacgggcttg ctctccgggc     960
ttcgccctgc gcggtcgctg cgctcccttg ccagcccgtg gatatgtgga cgatggccgc    1020
gagcggccac cggctggctc gcttcgctcg cccgtggac aaccctgctg acaagctga     1080 tggacaggct gcgcctgccc acgagcttga ccacagggat gcccaccgg ctacccagcc    1140 ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt ggggcagtc gaaggcgaag cccgcccgcc    1380
tgcccccgga gcctcacggc ggcgagtgcg ggggttccaa gggggcagcg ccaccttggg    1440
caaggccgaa ggccgcgcag tcgatcaaca gccccggag gggccactt ttgcggagg     1500 gggagccgcg ccgaaggcgt gggggaaccc cgcagggg tg cccttcttg ggcaccaaag    1560
```

```
aactagatat agggcgaaat gcgaaagact taaaaatcaa caacttaaaa aaggggggta   1620
cgcaacagct cattgcggca cccccgcaa  tagctcattg cgtaggttaa agaaaatctg   1680
taattgactg ccacttttac gcaacgcata attgttgtcg cgctgccgaa aagttgcagc   1740
tgattgcgca tggtgccgca accgtgcggc accctaccgc atggagataa gcatggccac   1800
gcagtccaga gaaatcggca ttcaagccaa gaacaagccc ggtcactggg tgcaaacgga   1860
acgcaaagcg catgaggcgt gggccgggct tattgcgagg aaacccacgg cggcaatgct   1920
gctgcatcac ctcgtggcgc agatgggcca ccagaacgcc gtggtggtca gccagaagac   1980
actttccaag ctcatcggac gttctttgcg gacggtccaa tacgcagtca aggacttggt   2040
ggccgagcgc tggatctccg tcgtgaagct caacggcccc ggcaccgtgt cggcctacgt   2100
ggtcaatgac cgcgtggcgt ggggccagcc ccgcgaccag ttgcgcctgt cggtgttcag   2160
tgccgccgtg gtggttgatc acgacgacca ggacgaatcg ctgttggggc atggcgacct   2220
gcgccgcatc ccgaccctgt atccgggcga gcagcaacta ccgaccggcc ccggcgagga   2280
gccgcccagc cagcccggca ttccgggcat ggaaccagac ctgccagcct tgaccgaaac   2340
ggaggaatgg gaacggcgcg ggcagcagcg cctgccgatg cccgatgagc cgtgttttct   2400
ggacgatggc gagccgttgg agccgccgac acgggtcacg ctgccgcgcc ggtagcactt   2460
gggttgcgca gcaacccgta agtgcgctgt tccagactat cggctgtagc cgcctcgccg   2520 ccctataccct tgtctgcctc cccgcgttgc gtcgcggtgc atggagccgg ccacctcga   2580 cctgaatgga agccggcggc acctcgctaa cggattcacc gttttatca ggctctggga    2640 ggcagaataa atgatcatat cgtcaattat tacctccacg gggagagcct gagcaaactg   2700
gcctcaggca tttgagaagc acacggtcac actgcttccg gtagtcaata accggtaaa    2760 ccagcaatag acataagcgg ctatttaacg accctgccct gaaccgacga ccgggtcgaa   2820
tttgctttcg aatttctgcc attcatccgc ttattatcac ttattcaggc gtagcaccag   2880
gcgtttaagg gcaccaataa ctgccttaaa aaaattacgc cccgccctgc cactcatcgc   2940
agtcggccta ttggttaaaa aatgagctga tttaacaaaa atttaacgcg aattttaaca   3000
aaatattaac gcttacaatt tccattcgcc attcaggctg cgcaactgtt gggaagggcg   3060
atcggtgcgg gcctcttcgc tattacgcca gctggcgaaa gggggatgtg ctgcaaggcg   3120
attaagttgg gtaacgccag gttttccca  gtcacgacgt tgtaaaacga cggccagtga   3180
gcgcgcgtaa tacgactcac tatagggcga attggagctc caccgcggtg gcggccgctc   3240
tagaactagt ggatccccg  ggctgcagga attcgatatc aagcttatcg ataccgtcga   3300
cctcgagggg gggcccggta cccagctttt gttcccttta gtgagggtta attgcgcgct   3360
tggcgtaatc atggtcatag ctgtttcctg tgtgaaattg ttatccgctc acaattccac   3420
acaacatacg agccggaagc ataaagtgta aagcctgggg tgcctaatga gtgagctaac   3480
tcacattaat tgcgttgcgc tcactgcccg ctttccagtc gggaaacctg tcgtgccagc   3540
tgcattaatg aatcggccaa cgcgcgggga gaggcggttt gcgtattggg cgcatgcata   3600
aaaactgttg taattcatta agcattctgc cgacatggaa gccatcacaa acggcatgat   3660
gaacctgaat cgccagcggc atcagcacct tgtcgccttg cgtataatat ttgcccatgg   3720
gggtgggcga agaactccag catgagatcc ccgcgctgga ggatcatcca gccggcgtcc   3780
cggaaaacga ttccgaagcc caaccttta  tagaaggcgg cggtggaatc gaaatctcgt   3840 gatgcaggt  tgggcgtcgc ttggtcggtc atttcgaacc ccagagtccc gctcagaaga   3900
actcgtcaag aaggcgatag aaggcgatgc gctgcgaatc gggagcggcg ataccgtaaa   3960
```

```
gcacgaggaa gcggtcagcc cattcgccgc caagctcttc agcaatatca cgggtagcca   4020
acgctatgtc ctgatagcgg tccgccacac ccagccggcc acagtcgatg aatccagaaa   4080
agcggccatt ttccaccatg atattcggca agcaggcatc gccatgggtc acgacgagat   4140
cctcgccgtc gggcatgcgc gccttgagcc tggcgaacag ttcggctggc gcgagcccct   4200
gatgctcttc gtccagatca tcctgatcga caagaccggc ttccatccga gtacgtgctc   4260
gctcgatgcg atgtttcgct tggtggtcga atgggcaggt agccggatca agcgtatgca   4320
gccgccgcat tgcatcagcc atgatggata ctttctcggc aggagcaagg tgagatgaca   4380
ggagatcctg ccccggcact cgcccaata gcagccagtc ccttcccgct tcagtgacaa   4440
cgtcgagcac agctgcgcaa ggaacgcccg tcgtggccag ccacgatagc cgcgctgcct   4500
cgtcctgcag ttcattcagg gcaccggaca ggtcggtctt gacaaaaaga accgggcgcc   4560
cctgcgctga cagccggaac acggcggcat cagagcagcc gattgtctgt tgtgcccagt   4620
catagccgaa tagcctctcc acccaagcgg ccggagaacc tgcgtgcaat ccatcttgtt   4680
caatcatgcg aaacgatcct catcctgtct cttgatcaga tcttgatccc ctgcgccatc   4740
agatccttgg cggcaagaaa gccatccagt ttactttgca gggcttccca accttaccag   4800
agggcgcccc agctggcaat tccggttcgc ttgctgtcca taaaaccgcc cagtctagct   4860
atcgccatgt aagcccactg caagctacct gctttctctt tgcgcttgcg ttttcccttg   4920
tccagatagc ccagtagctg acattcatcc caggtggcac ttttcgggga aatgtgcgcg   4980
cccgcgttcc tgctggcgct gggcctgttt ctggcgctgg acttcccgct gttccgtcag   5040
cagcttttcg cccacggcct tgatgatcgc ggcggccttg gcctgcatat cccgattcaa   5100
cggccccagg gcgtccagaa cgggcttcag gcgctcccga aggt               5144
```

<210> SEQ ID NO 50
<211> LENGTH: 4549
<212> TYPE: DNA
<213> ORGANISM: Pseudomonas aeruginosa

<400> SEQUENCE: 50

```
ggtaccagat ctggcatttt tgggaggtgt gaaatgcggc gcgaaagtct gttggtatcg     60
gtttgcaagg gcctgcgggt acatgtcgag cgcgttgggc aggatcccgg gcgcagcacg    120
gtgatgctgg tcaacggcgc gatggcgacc accgcctcgt tcgcccggac ctgcaagtgc    180
ctggccgaac atttcaacgt ggtgctgttc gacctgccct tcgccgggca gtcgcgtcag    240
cacaacccgc agcgggggtt gatcaccaag gacgacgagg tggaaatcct cctggcgctg    300
atcgagcgct tcgaggtcaa tcacctggtc tccgcgtcct ggggcggtat ctccacgctg    360
ctggcgctgt cgcgcaatcc gcgcggcatc cgcagctcgg tggtgatggc attcgccact    420
ggactgaacc aggcgatgct cgactacgtc gggcgggcgc aggcgctgat cgagctggac    480
gacaagtcgg cgatcggcca tctgctcaac gagaccgtcg gcaaatacct gccgccgcgc    540
ctgaaagcca gcaaccatca gcacatggct tcgctggcca ccggcgaata cgagcaggcg    600
cgctttcaca tcgaccaggt gctggcgctc aacgatcggg gctacctggc ttgcctggag    660
cggatccaga gccacgtgca tttcatcaac ggcagctggg acgaatacac caccgccgag    720 gacgccgcc agttccgcga ctacctgccg cactgcagtt tctcgcgggt ggagggcacc    780
gggcatttcc tcgacctgga gtccaagctg gccgcggtac gcgtgcaccg cgccctgctc    840
gagcacctgc tgaagcaacc ggagccgcag cgggcggaac gcgcggcggg attccacgag    900
```

```
atggccatcg gctacgcctg aacccttgac ctgcgaagac ccggcctggc cgggctttgc    960
ggttgcataa cgcacggagt agcaccatgc acgccatcct catcgccatc ggctcggccg   1020
gcgacgtatt tcccttcatc ggcctggccc ggaccctgaa attgcgcggg caccgcgtga   1080
gcctctgcac catcccggtg tttcgcgacg cggtggagca gcacggcatc gcgttcgtcc   1140
cgctgagcga cgaactgacc taccgccgga ccatgggcga tccgcgcctg tgggacccca   1200
agacgtcctt cggcgtgctc tggcaaacca tcgccgggat gatcgagccg gtctacgagt   1260
acgtctcggc gcagcgccat gacgacatcg tggtggtcgg ctcgctctgg gcgctgggcg   1320
cacgcatcgc tcacgagaag tacgggattc cctacctgtc cgcgcaggtc tcgccatcga   1380
ccttgttgtc ggcgcacctg ccgccggtac accccaagtt caacgtgccc gagcagatgc   1440
cgctggcgat gcgcaagctg ctctggcgct gcatcgagcg cttcaagctg gatcgcacct   1500
gcgcgccgga tatcaacgcg gtgcggcgca aggtcggcct ggagacgccg gtgaagcgca   1560
tcttcaccca atggatgcat cgccgcagg gcgtggtctg cctgttcccg gcctggttcg   1620
cgccgcccca gcaggattgg ccgcaacccc tgcacatgac cggcttcccg ctgttcgacg   1680
gcagtatccc ggggaccccg ctcgacgacg aactgcaacg cttcctgat cagggcagcc   1740
ggccgctggt gttcacccag ggctcgaccg aacacctgca gggcgacttc tacgccatgg   1800
ccctgcgcgc gctggaacgc ctcggcgcgc gtgggatctt cctcaccggc gccggccagg   1860
aaccgctgcg cggcttgccg aaccacgtgc tgcagcgcgc ctacgcgcca ctgggagcct   1920
tgctgccatc gtgcgccggg ctggtccatc cgggcggtat cggcgccatg agcctggcct   1980
tggcggcggg ggtgccgcag gtgctgctgc cctgcgccca cgaccagttc gacaatgccg   2040
aacggctggt ccggctcggc tgcgggatgc gcctgggcgt gccattgcgc gagcaggagt   2100
tgcgcggggc gctgtggcgc ttgctcgagg accggccat ggcggcggcc tgtcggcgtt   2160
tcatggaatt gtcacaaccg cacagtatcg cttgcggtaa agcggcccag gtggtcgaac   2220
gttgtcatag ggaggggat gcgcgatggc tgaaggctgc gtcctgacgc cgggaggatc   2280
ctggcgtgtc cacgaccagc ctctgcccct ccgccacgcg ggaacacggt cccggcgcga   2340
aacgcgtcct gcctctgctg ttcctcacct gcctgctgga tgccgctggc gtcggcctga   2400
tcgtgcccct gctgccgacg ctgatcggca gcgtggcgcc gctgcggtc cgcgacgcgg   2460
ccacctgggg cgccgccctg gtgatgacct tcgcgctgct gcaattgttc ttttcgccgg   2520
tcctcggcag cctcagcgac cgcttcggac gccgccccgt cctggtcctg gcgatgctcg   2580
gcttcgccct cagctatctg ctgctggcgc tggccgacag cctctggatg ctgttcctcg   2640
gtcgcgcgct ggccgggctc accggcgcca gcgtggccac cgcgatggcc tgcgcggctg   2700
acctcggcac gcacgggcag cgcacccggc acttcggctg gctgtacgcc ggcctcgccc   2760
tgggcatgat cctcggcccc gccctcggtg ggctgctggc ggtgcacggc acgacgctgc   2820
cgctgttgct ggccgccggc ctgtgcctgc tcaacgccct gctcgccggc ctgttcctcg   2880
aggaaaccct gcccccgacg cgacgccgcc gcctggaccc gaggcggatg aatgccttgc   2940
gctcgatcag cggcctggct cggcaaccgg gggtcggacg cctgctggcg gtgcttgccc   3000
tggtattcct cggcttgcag gcggtgatgg tggtctggcc gttcttcgtg atcgagaagt   3060
ttcactggag cagcgcctgg atcggctact cgctggccct ctacggcgtg ctcgcggtgc   3120
tcgcccagac cctcggcgtg aacctctgca agcggcgcct ggacgacgcc cgcctgctgc   3180
gcctgggcct cgcccgcaa ggctgcggcc tgctgctgtt cgcccggtc gactcgtcat   3240
tctggctggt ctgcgcgctg ctgcccttcg cgctcggcag cctcgccacc ccggccatgc   3300
```

| | |
|---|---|
| agggggctgct ctcggcccgc gtgccggtcg accgccaggg cgagttgcag ggcgtgctga | 3360 |
| gcagcctgat gagcctcgcc gcgatcgtcg gtccgccgct gatgagcggc ctgttccact | 3420 |
| ggggcagcgg tccgctcgcg ccgctgcccc tggccggcgc gccattcctc gccggcgccc | 3480 |
| ttctcgttct ggccgggctg gtcctggcct ggcaacttcg acctacggga gaagaacgat | 3540 |
| catggaccgg atagacatgg gcgtgctggt ggtactgttc aatcctggcg acgacgacct | 3600 |
| ggaacacctt ggcgaactgg cggcggcgtt ccgcaactg cgcttccttg ccgtcgacaa | 3660 |
| ctcaccgcac agcgatccgc agcgcaatgc ccggctgcgc gggcaaggca tcgccgtgct | 3720 |
| gcaccacggc aaccggcagg gcatcgccgg cgccttcaac cagggactcg acgcgctatt | 3780 |
| ccggcgtggc gtgcagggtg tgctgctgct cgaccaggac tcccgtcccg gcggcgcctt | 3840 |
| cctcgccgcc cagtggcgca acctgcaggc gcgcaacggt caggcctgcc tgctcggccc | 3900 |
| acggatcttc gaccggggtg accggcgctt cctgccggcc atccatctcg acggactgac | 3960 |
| gctcaggcaa ttgtctctgg acggcctgac gaccccgcag cgcacctcgt tcctgatctc | 4020 |
| ctccggctgc ctgctgaccc gcgaggccta ccagcgcctc ggccacttcg acgaggaact | 4080 |
| gttcatcgac cacgtggaca ccgaatacag cctgcgcgcc caggcgctgg acgtgccct | 4140 |
| gtacgtcgac ccgcggctgg tcctcgagca ccgcatcggc acgcgcaaga cccgccgcct | 4200 |
| cggcggtctc agcctcagcg cgatgaacca cgccccgctg cgccgctact acctggcgcg | 4260 |
| caacggcctg ctggtcctgc gccgctacgc ccggtcctcg ccgctggccc tgctggcgaa | 4320 |
| cctgccgacc ctgacccagg gcctcgcggt gctcctgctc gaacgcgaca gctgctcaa | 4380 |
| gctgcgctgc ctgggctggg gcctgtggga cggcctgcgg ggacgcggcg gcgcgctgga | 4440 |
| gaccaaccgc ccgcgcctgc tgaagcgcct cgccggcccg gccgtggcgt ccgtagcttc | 4500 |
| cggcaaggcc aaggcctagt cggcgaaacg cattccctct agagagctc | 4549 |

<210> SEQ ID NO 51
<211> LENGTH: 9663
<212> TYPE: DNA
<213> ORGANISM: Artificial Sequence
<220> FEATURE:
<223> OTHER INFORMATION: vector

<400> SEQUENCE: 51

| | |
|---|---|
| ctcgggccgt ctcttgggct tgatcggcct tcttgcgcat ctcacgcgct cctgcggcgg | 60 |
| cctgtagggc aggctcatac ccctgccgaa ccgcttttgt cagccggtcg gccacggctt | 120 |
| ccggcgtctc aacgcgcttt gagattccca gcttttcggc caatccctgc ggtgcatagg | 180 |
| cgcgtggctc gaccgcttgc gggctgatgg tgacgtggcc cactggtggc cgctccaggg | 240 |
| cctcgtagaa cgcctgaatg cgcgtgtgac gtgccttgct gccctcgatg ccccgttgca | 300 |
| gccctagatc ggccacagcg gccgcaaacg tggtctggtc gcgggtcatc tgcgctttgt | 360 |
| tgccgatgaa ctccttggcc gacagcctgc cgtcctgcgt cagcggcacc acgaacgcgg | 420 |
| tcatgtgcgg gctggtttcg tcacggtgga tgctggccgt cacgatgcga tccgccccgt | 480 |
| acttgtccgc cagccacttg tgcgccttct cgaagaacgc cgcctgctgt tcttggctgg | 540 |
| ccgacttcca ccattccggg ctggccgtca tgacgtactc gaccgccaac acagcgtcct | 600 |
| tgcgccgctt ctctggcagc aactcgcgca gtcggcccat cgcttcatcg gtgctgctgg | 660 |
| ccgcccagtg ctcgttctct ggcgtcctgc tggcgtcagc gttgggcgtc tcgcgctcgc | 720 |
| ggtaggcgtg cttgagactg gccgccacgt tgccccatttt cgccagcttc ttgcatcgca | 780 |

```
tgatcgcgta tgccgccatg cctgcccctc ccttttggtg tccaaccggc tcgacggggg      840
cagcgcaagg cggtgcctcc ggcgggccac tcaatgcttg agtatactca ctagactttg      900
cttcgcaaag tcgtgaccgc ctacggcggc tgcggcgccc tacgggcttg ctctccgggc      960
ttcgccctgc gcggtcgctg cgctcccttg ccagccgtg gatatgtgga cgatggccgc      1020
gagcggccac cggctggctc gcttcgctcg gcccgtggac aaccctgctg acaagctga      1080 tggacaggct gcgcctgccc acgagcttga ccacagggat tgcccaccgg ctacccagcc     1140
ttcgaccaca tacccaccgg ctccaactgc gcggcctgcg gccttgcccc atcaattttt     1200
ttaattttct ctggggaaaa gcctccggcc tgcggcctgc gcgcttcgct tgccggttgg     1260
acaccaagtg gaaggcgggt caaggctcgc gcagcgaccg cgcagcggct tggccttgac     1320
gcgcctggaa cgacccaagc ctatgcgagt gggggcagtc gaaggcgaag cccgcccgcc     1380
tgccccccga gcctcacggc ggcgagtgcg ggggttccaa gggggcagcg ccaccttggg     1440
caaggccgaa ggccgcgcag tcgatcaaca agccccggag gggccacttt tgccggagg     1500 gggagccgcg ccgaaggcgt gggggaaccc cgcaggggtg cccttctttg ggcaccaaag     1560
aactagatat agggcgaaat gcgaaagact taaaaatcaa caacttaaaa aaggggggta     1620
cgcaacagct cattgcggca cccccgcaa tagctcattg cgtaggttaa agaaaatctg     1680
taattgactg ccacttttac gcaacgcata attgttgtcg cgctgccgaa aagttgcagc     1740
tgattgcgca tggtgccgca accgtgcggc accctaccgc atggagataa gcatggccac     1800
gcagtccaga gaaatcggca ttcaagccaa gaacaagccc ggtcactggg tgcaaacgga     1860
acgcaaagcg catgaggcgt gggccgggct tattgcgagg aaacccacgg cggcaatgct     1920
gctgcatcac ctcgtggcgc agatgggcca ccagaacgcc gtggtggtca gccagaagac     1980
actttccaag ctcatcggac gttctttgcg gacggtccaa tacgcagtca aggacttggt     2040
ggccgagcgc tggatctccg tcgtgaagct caacggcccc ggcaccgtgt cggcctacgt     2100
ggtcaatgac cgcgtggcgt ggggccagcc ccgcgaccag ttgcgcctgt cggtgttcag     2160
tgccgccgtg gtggttgatc acgacgacca ggacgaatcg ctgttggggc atggcgacct     2220
gcgccgcatc ccgaccctgt atccgggcga gcagcaacta ccgaccggcc ccggcgagga     2280
gccgcccagc cagcccggca ttccgggcat ggaaccagac ctgccagcct tgaccgaaac     2340
ggaggaatgg gaacgcgcg ggcagcagcg cctgccgatg cccgatgagc cgtgtttct      2400 ggacgatggc gagccgttgg agccgccgac acgggtcacg ctgccgcgcc ggtagcactt     2460
gggttgcgca gcaacccgta agtgcgctgt tccagactat cggctgtagc cgcctcgccg     2520
ccctatacct tgtctgcctc cccgcgttgc gtcgcggtgc atggagccgg ccacctcga     2580 cctgaatgga agccggcggc acctcgctaa cggattcacc gttttatca ggctctggga     2640 ggcagaataa atgatcatat cgtcaattat acctccacg gggagagcct gagcaaactg     2700
gcctcaggca tttgagaagc acacggtcac actgcttccg gtagtcaata aaccggtaaa     2760
ccagcaatag acataagcgg ctatttaacg accctgccct gaaccgacga ccgggtcgaa     2820
tttgctttcg aatttctgcc attcatccgc ttattatcac ttattcaggc gtagcaccag     2880
gcgtttaagg gcaccaataa ctgccttaaa aaaattacgc cccgccctgc cactcatcgc     2940
agtcggccta ttggttaaaa aatgagctga tttaacaaaa atttaacgcg aattttaaca     3000
aaatattaac gcttacaatt tccattcgcc attcaggctg cgcaactgtt gggaagggcg     3060
atcggtgcgg gcctcttcgc tattacgcca gctggcgaaa gggggatgtg ctgcaaggcg     3120
attaagttgg gtaacgccag ggttttccca gtcacgacgt tgtaaaacga cggccagtga     3180
```

```
gcgcgcgtaa tacgactcac tatagggcga attggagctc caccgcggtg gcggccgctc   3240
tagagggaat gcgtttcgcc gactaggcct tggccttgcc ggaagctacg gacgccacgg   3300
ccgggccggc gaggcgcttc agcaggcgcg ggcggttggt ctccagcgcg ccgccgcgtc   3360
cccgcaggcc gtcccacagg ccccagccca ggcagcgcag cttgagcagc ttgtcgcgtt   3420
cgagcaggag caccgcgagg ccctgggtca gggtcggcag gttcgccagc agggccagcg   3480
gcgaggaccg ggcgtagcgg cgcaggacca gcaggccgtt gcgcgccagg tagtagcggc   3540
gcagcggggc gtggttcatc gcgctgaggc tgagaccgcc gaggcggcgg gtcttgcgcg   3600
tgccgatgcg gtgctcgagg accagccgcg ggtcgacgta caggggcacg tccagcgcct   3660
gggcgcgcag gctgtattcg gtgtccacgt ggtcgatgaa cagttcctcg tcgaagtggc   3720
cgaggcgctg gtaggcctcg cgggtcagca ggcagccgga ggagatcagg aacgaggtgc   3780
gctgcggggt cgtcaggccg tccagagaca attgcctgag cgtcagtccg tcgagatgga   3840
tggccggcag gaagcgccgg tcaccccggt cgaagatccg tgggccgagc aggcaggcct   3900
gaccgttgcg cgcctgcagg ttgcgccact gggcggcgag gaaggcgccg ccgggacggg   3960
agtcctggtc gagcagcagc acaccctgca cgccacgccg gaatagcgcg tcgagtccct   4020
ggttgaaggc gccggcgatg ccctgccggt tgccgtggtg cagcacggcg atgccttgcc   4080
cgcgcagccg ggcattgcgc tgcggatcgc tgtgcggtga gttgtcgacg gcaaggaagc   4140
gcagttgcgg aaacgccgcc gccagttcgc caaggtgttc caggtcgtcg tcgccaggat   4200
tgaacagtac caccagcacg cccatgtcta tccggtccat gatcgttctt ctcccgtagg   4260
tcgaagttgc caggccagga ccagcccggc cagaacgaga agggcgccgg cgaggaatgg   4320
cgcgccggcc aggggcagcg gcgcgagcgg accgctgccc cagtggaaca ggccgctcat   4380
cagcggcgga ccgacgatcg cggcgaggct catcaggctg ctcagcacgc cctgcaactc   4440
gccctggcgg tcgaccggca cgcggggccga gagcagcccc tgcatggccg gggtggcgag   4500
gctgccgagc gcgaagggca gcagcgcgca gaccagccag aatgacgagt cgaccagggc   4560
gaacagcagc aggccgcagc cttgcagggc gaggcccagg cgcagcaggc gggcgtcgtc   4620
caggcgccgc ttgcagaggt tcacgccgag ggtctgggcg agcaccgcga gcacgccgta   4680
gagggccagc gagtagccga tccaggcgct gctccagtga aacttctcga tcacgaagaa   4740
cggccagacc accatcaccg cctgcaagcc gaggaatacc agggcaagca ccgccagcag   4800
gcgtccgacc cccggttgcc gagccaggcc gctgatcgag cgcaaggcat tcatccgcct   4860
cgggtccagg cggcggcgtc gcgtcggggg caggggtttcc tcgaggaaca ggccggcgag   4920
cagggcgttg agcaggcaca ggccggcggc cagcaacagc ggcagcgtcg tgccgtgcac   4980
cgccagcagc ccaccgaggg cggggccgag gatcatgccc agggcgaggc cggcgtacag   5040
ccagccgaag tgccgggtgc gctgcccgtg cgtgccgagg tcagccgcgc aggccatcgc   5100
ggtggccacg ctggcgccgg tgagcccggc cagcgcgcga ccgaggaaca gcatccagag   5160
gctgtcggcc agcgccagca gcagatagct gagggcgaag ccgagcatcg ccaggaccag   5220
gacggggcgg cgtccgaagc ggtcgctgag gctgccgagg accggcgaaa agaacaattg   5280
cagcagcgcg aaggtcatca ccagggcggc gccccaggtg gccgcgtcgc ggaccgccag   5340
cggcgccacg ctgccgatca gcgtcggcag caggggcacg atcaggccga cgccagcggc   5400
atccagcagg caggtgagga acagcagagg caggacgcgt ttcgcgccgg gaccgtgttc   5460
ccgcgtggcg gaggggcaga ggctggtcgt ggacacgcca ggatcctccc ggcgtcagga   5520
```

```
cgcagccttc agccatcgcg catccccctc cctatgacaa cgttcgacca cctgggccgc    5580
tttaccgcaa gcgatactgt gcggttgtga caattccatg aaacgccgac aggccgccgc    5640
catggccggg tcctcgagca agcgccacag cgccccgcgc aactcctgct cgcgcaatgg    5700
cacgcccagg cgcatcccgc agccgagccg gaccagccgt tcggcattgt cgaactggtc    5760
gtgggcgcag ggcagcagca cctgcggcac ccccgccgcc aaggccaggc tcatggcgcc    5820
gataccgccc ggatggacca gcccggcgca cgatggcagc aaggctccca gtggcgcgta    5880
ggcgcgctgc agcacgtggt tcggcaagcc gcgcagcggt tcctggccgg cgccggtgag    5940
gaagatccca cgcgcgccga ggcgttccag cgcgcgcagg gccatggcgt agaagtcgcc    6000
ctgcaggtgt tcggtcgagc cctgggtgaa caccagcggc cggctgccct gatcgagaaa    6060
gcgttgcagt tcgtcgtcga gcggggtccc cgggatactg ccgtcgaaca gcggaagcc     6120 ggtcatgtgc aggggttgcg gccaatcctg ctggggcggc gcgaaccagg ccgggaacag    6180
gcagaccacg ccctgcggcg aatgcatcca ttgggtgaag atgcgcttca ccggcgtctc    6240
caggccgacc ttgcgccgca ccgcgttgat atccggcgcg caggtgcgat ccagcttgaa    6300
gcgctcgatg cagcgccaga gcagcttgcg catcgccagc ggcatctgct cgggcacgtt    6360
gaacttgggg tgtaccggcg gcaggtgcgc cgacaacaag gtcgatggcg agacctgcgc    6420
ggacaggtag ggaatcccgt acttctcgtg agcgatgcgt gcgcccagcg cccagagcga    6480
gccgaccacc acgatgtcgt catggcgctg cgccgagacg tactcgtaga ccggctcgat    6540
catcccggcg atggtttgcc agagcacgcc gaaggacgtc ttggggtccc acaggcgcgg    6600
atcgcccatg gtccggcggt aggtcagttc gtcgctcagc gggacgaacg cgatgccgtg    6660
ctgctccacc gcgtcgcgaa acaccgggat ggtgcagagg ctcacgcggt gcccgcgcaa    6720
tttcagggtc cgggccaggc cgatgaaggg aaatacgtcg ccggccgagc cgatggcgat    6780
gaggatggcg tgcatggtgc tactccgtgc gttatgcaac cgcaaagccc ggccaggccg    6840
ggtcttcgca ggtcaagggt tcaggcgtag ccgatggcca tctcgtggaa tcccgccgcg    6900
cgttccgccc gctgcggctc cggttgcttc agcaggtgct cgagcagggc gcggtgcacg    6960
cgtaccgcgg ccagcttgga ctccaggtcg aggaaatgcc cggtgccctc cacccgcgag    7020
aaactgcagt gcggcaggta gtcgcggaac tggcgggcgt cctcggcggt ggtgtattcg    7080
tcccagctgc cgttgatgaa atgcacgtgg ctctggatcc gctccaggca agccaggtag    7140
ccccgatcgt tgagcgccag cacctggtcg atgtgaaagc gcgcctgctc gtattcgccg    7200
gtggccagcg aagccatgtg ctgatggttg ctggctttca ggcgcggcgg caggtatttg    7260
ccgacggtct cgttgagcag atggccgatc gccgacttgt cgtccagctc gatcagcgcc    7320
tgcgcccgcc cgacgtagtc gagcatcgcc tggttcagtc caggggcgaa tgccatcacc    7380
accgagctgc ggatgccgcg cggattgcgc gacagcgcca gcagcgtgga gataccgccc    7440
caggacgcgg agaccaggtg attgacctcg aagcgctcga tcagcgccag gaggatttcc    7500
acctcgtcgt ccttggtgat caaccccgc tgcgggttgt gctgacgcga ctgcccggcg    7560
aagggcaggt cgaacagcac cacgttgaaa tgttcggcca ggcacttgca ggtccgggcg    7620
aacgaggcgg tggtcgccat cgcgccgttg accagcatca ccgtgctgcg cccgggatcc    7680
tgcccaacgc gctcgacatg tacccgcagg cccttgcaaa ccgataccaa cagactttcg    7740
cgccgcattt cacacctccc aaaaatgcca gatcccccgg gctgcaggaa ttcgatatca    7800
agcttatcga taccgtcgac ctcgaggggg ggcccggtac ccagcttttg ttccctttag    7860
tgagggttaa ttgcgcgctt ggcgtaatca tggtcatagc tgtttcctgt gtgaaattgt    7920
```

```
tatccgctca caattccaca caacatacga gccggaagca taaagtgtaa agcctggggt    7980
gcctaatgag tgagctaact cacattaatt gcgttgcgct cactgcccgc tttccagtcg    8040
ggaaacctgt cgtgccagct gcattaatga atcggccaac gcgcgggag aggcggtttg     8100
cgtattgggc gcatgcataa aaactgttgt aattcattaa gcattctgcc gacatggaag    8160
ccatcacaaa cggcatgatg aacctgaatc gccagcggca tcagcacctt gtcgccttgc    8220
gtataatatt tgcccatggg ggtgggcgaa gaactccagc atgagatccc cgcgctggag    8280
gatcatccag ccggcgtccc ggaaaacgat tccgaagccc aacctttcat agaaggcggc    8340
ggtggaatcg aaatctcgtg atggcaggtt gggcgtcgct tggtcggtca tttcgaaccc    8400
cagagtcccg ctcagaagaa ctcgtcaaga aggcgataga aggcgatgcg ctgcgaatcg    8460
ggagcggcga taccgtaaag cacgaggaag cggtcagccc attcgccgcc aagctcttca    8520
gcaatatcac gggtagccaa cgctatgtcc tgatagcggt ccgccacacc cagccggcca    8580
cagtcgatga atccagaaaa gcggccattt tccaccatga tattcggcaa gcaggcatcg    8640
ccatgggtca cgacgagatc ctcgccgtcg gcatgcgcg ccttgagcct ggcgaacagt     8700
tcggctggcg cgagcccctg atgctcttcg tccagatcat cctgatcgac aagaccggct    8760
tccatccgag tacgtgctcg ctcgatgcga tgtttcgctt ggtggtcgaa tgggcaggta    8820
gccggatcaa gcgtatgcag ccgccgcatt gcatcagcca tgatggatac tttctcggca    8880
ggagcaaggt gagatgacag gagatcctgc cccggcactt cgcccaatag cagccagtcc    8940
cttcccgctt cagtgacaac gtcgagcaca gctgcgcaag gaacgcccgt cgtggccagc    9000
cacgatagcc gcgctgcctc gtcctgcagt tcattcaggg caccggacag gtcggtcttg    9060
acaaaaagaa ccgggcgccc ctgcgctgac agccggaaca cggcggcatc agagcagccg    9120
attgtctgtt gtgcccagtc atagccgaat agcctctcca cccaagcggc cggagaacct    9180
gcgtgcaatc catcttgttc aatcatgcga aacgatcctc atcctgtctc ttgatcagat    9240
cttgatcccc tgcgccatca gatccttggc ggcaagaaag ccatccagtt tactttgcag    9300
ggcttcccaa ccttaccaga gggcgcccca gctggcaatt ccggttcgct tgctgtccat    9360
aaaaccgccc agtctagcta tcgccatgta agcccactgc aagctacctg ctttctcttt    9420
gcgcttgcgt tttcccttgt ccagatagcc cagtagctga cattcatccc aggtggcact    9480
tttcggggaa atgtgcgcgc ccgcgttcct gctggcgctg ggcctgtttc tggcgctgga    9540
cttcccgctg ttccgtcagc agcttttcgc ccacggcctt gatgatcgcg gcggccttgg    9600
cctgcatatc ccgattcaac ggccccaggg cgtccagaac gggcttcagg cgctcccgaa    9660
ggt                                                                  9663
```

<210> SEQ ID NO 52  
<211> LENGTH: 9793  
<212> TYPE: DNA  
<213> ORGANISM: Artificial Sequence  
<220> FEATURE:  
<223> OTHER INFORMATION: vector

<400> SEQUENCE: 52

```
gatctggcat ttttgggagg tgtgaaatgc ggcgcgaaag tctgttggta tcggtttgca      60
agggcctgcg ggtacatgtc gagcgcgttg ggcaggatcc cgggcgcagc acggtgatgc     120
tggtcaacgg cgcgatggcg accaccgcct cgttcgcccg gacctgcaag tgcctggccg    180
aacatttcaa cgtggtgctg ttcgacctgc ccttcgccgg gcagtcgcgt cagcacaacc    240
```

| | |
|---|---|
| cgcagcgggg gttgatcacc aaggacgacg aggtggaaat cctcctggcg ctgatcgagc | 300 |
| gcttcgaggt caatcacctg gtctccgcgt cctggggcgg tatctccacg ctgctggcgc | 360 |
| tgtcgcgcaa tccgcgcggc atccgcagct cggtggtgat ggcattcgcc cctggactga | 420 |
| accaggcgat gctcgactac gtcgggcggg cgcaggcgct gatcgagctg gacgacaagt | 480 |
| cggcgatcgg ccatctgctc aacgagaccg tcggcaaata cctgccgccg cgcctgaaag | 540 |
| ccagcaacca tcagcacatg gcttcgctgg ccaccggcga atacgagcag gcgcgctttc | 600 |
| acatcgacca ggtgctggcg ctcaacgatc ggggctacct ggcttgcctg gagcggatcc | 660 |
| agagccacgt gcatttcatc aacggcagct gggacgaata caccaccgcc gaggacgccc | 720 |
| gccagttccg cgactacctg ccgcactgca gtttctcgcg ggtggagggc accgggcatt | 780 |
| tcctcgacct ggagtccaag ctggccgcgc tacgcgtgca ccgcgccctg ctcgagcacc | 840 |
| tgctgaagca accggagccg cagcgggcgg aacgcgcggc gggattccac gagatggcca | 900 |
| tcggctacgc ctgaacccct tgacctgcgaa gaccccggcct ggccgggctt tgcggttgca | 960 |
| taacgcacgg agtagcacca tgcacgcat cctcatcgcc atcggctcgg ccggcgacgt | 1020 |
| atttcccttc atcggcctgg cccggaccct gaaattgcgc gggcaccgcg tgagcctctg | 1080 |
| caccatcccg gtgtttcgcg acgcggtgga gcagcacgga atcgcgttcg tcccgctgag | 1140 |
| cgacgaactg acctaccgcc ggaccatggg cgatccgcgc ctgtgggacc caagacgtc | 1200 |
| cttcggcgtg ctctggcaaa ccatcgccgg gatgatcgag ccggtctacg agtacgtctc | 1260 |
| ggcgcagcgc catgacgaca tcgtggtggt cggctcgctc tgggcgctgg gcgcacgcat | 1320 |
| cgctcacgag aagtacggga ttccctacct gtccgcgcag gtctcgccat cgaccttgtt | 1380 |
| gtcggcgcac ctgccgccgg tacaccccaa gttcaacgtg cccgagcaga tgccgctggc | 1440 |
| gatgcgcaag ctgctctggc gctgcatcga gcgcttcaag ctggatcgca cctgcgcgcc | 1500 |
| ggatatcaac gcggtgcggc gcaaggtcgg cctggagacg ccggtgaagc gcatcttcac | 1560 |
| ccaatggatg cattcgccgc agggcgtggt ctgcctgttc ccggcctggt tcgcgccgcc | 1620 |
| ccagcaggat tggccgcaac ccctgcacat gaccggcttc ccgctgttcg acggcagtat | 1680 |
| cccgggggacc ccgctcgacg acgaactgca acgctttctc gatcagggca gccggccgct | 1740 |
| ggtgttcacc cagggctcga ccgaacacct gcagggcgac ttctacgcca tggccctgcg | 1800 |
| cgcgctggaa cgcctcggcg cgcgtgggat cttcctcacc ggcgccggcc aggaaccgct | 1860 |
| gcgcggcttg ccgaaccacg tgctgcagcg cgcctacgcg ccactgggag ccttgctgcc | 1920 |
| atcgtgcgcc gggctggtcc atcgggcgg tatcggcgcc atgagcctgg ccttggcggc | 1980 |
| gggggtgccg caggtgctgc tgccctgcgc ccacgaccag ttcgacaatg ccgaacggct | 2040 |
| ggtccggctc ggctgcggga tgcgcctggg cgtgccattg cgcagcagg agttgcgcgg | 2100 |
| ggcgctgtgg cgcttgctcg aggacccggc catggcggcg gcctgtcggc gtttcatgga | 2160 |
| attgtcacaa ccgcacagta tcgcttgcgg taaagcggcc caggtggtcg aacgttgtca | 2220 |
| tagggagggg gatgcgcgat ggctgaaggc tgcgtcctga acggtgctgg cataacagat | 2280 |
| agggttgcct ctagagtcga cctgcaggca tgcaagcttg gctgttttgg cggatgagag | 2340 |
| aagattttca gcctgataca gattaaatca gaacgcagaa gcggtctgat aaaacagaat | 2400 |
| ttgcctggcg gcagtagcgc ggtggtccca cctgacccca tgccgaactc agaagtgaaa | 2460 |
| cgccgtagcg ccgatggtag tgtggggtct ccccatgcga gagtagggaa ctgccaggca | 2520 |
| tcaaataaaa cgaaaggctc agtcgaaaga ctgggccttt cgttttatct gttgtttgtc | 2580 |
| ggtgaacgct ctcctgagta ggacaaatcc gccgggagcg atttgaacg ttgcgaagca | 2640 |

```
acggcccgga gggtggcggg caggacgccc gccataaact gccaggcatc aaattaagca   2700
gaaggccatc ctgacggatg gccttttttgc gtttctacaa actcttttg tttattttc   2760
taaatacatt caaatatgta tccgctcatg ctccttcgtc ggtgtcgtcg ccggatggtc   2820
tgcggtggtg ctcagcgtgg agacgcgcac cgtcacggac ccccatcaat cctgcctatt   2880
tgccacgttt aacaaggtag ttaagcgttc atttacgaag aaaacacgat aagctgcaca   2940
aatacctgaa aaagttgaac gccccgtgag cgggaactca cagggcgtcg gctaacccc   3000
agtcatcagc tgggagaaag cactcaagac atgactctag ccgatccgca ggacacagtc   3060
acagctagcg cgtggaaatt gtccgccgat ctgttcgaca cccaccccga agctatgcgc   3120
tgcggctcac gcggctggac ggcagaagat cgccgcgaac tgctcgctca cctgggacgc   3180
gaaagcttcc agggcagcaa gacaagagat ttcgcgagcg cctggattaa aaacccggat   3240
accggcgaaa cccaaccaaa gctctaccgg gctggctcaa aagcgctgac gcggtgccag   3300
tacgttgcgc tgacgcacgc gcaacatgcc gcggtgatcg tgcttgacat cgatgtgccc   3360
agccaccagg ccggcgggaa gattgagcac gtaaacccgc aggtctacgc gattttagag   3420
aaatgggcac gcctagaaaa agcgccggct tggatcggcg tgaatccgct gagcgggaaa   3480
tgccagctca tctggctcat tgacccggtg tatgccgcag caggtaaaac cagcccaaat   3540
atgcgcctgc tggctgcaac gacggaagaa atgactcgtg ttttcggcgc tgaccaggct   3600
ttttcgcata ggctgagccg gtggccgctg cacgtctcag acgatccgac agcctataaa   3660
tggcactgcc agcatgatcg tgtggatcgg ctggccgacc taatgagat tgctcgaacg   3720
atgaccggat cacagaagcc gaaaaagtac attgagcagg acttttccag cggacgcgcc   3780
cgcattgaag cggcacaacg cgccaccgca gaagccaagg cgctagcgat tttggacgcg   3840
agcctgccga gcgccctgga cgcgtccggc gacctgatcg acggcgtgcg agtgctctgg   3900
acaaatccag agcgagcgcg cgacgagacc gcgtttcgcc acgcgttgac cgtgggatac   3960
cagctcaaag ctgctggtga gcgcctaaaa gatgccaaga tcatcgacgc gtatgaagtg   4020
gcgtacaacg ttgcccaggc ggtcggtgca gacggccggg agccggatct tcccgccatg   4080
cgtgatcgcc tgacgatggc gcgtcgtgtg cgcggctacg tggctaaagg ccagccagtc   4140
gtccctgctc gtcgggtgga aacgcagagc agccgagggc ggaaagctct agcgacgatg   4200
gggcgacggg gcgcagctac atcgaatgca cgcagatggg ctgacccaga agtaagtat   4260
gcgcaggaga cgcgacagcg attagcggaa gcaaacaaac gccgagaaat gacaggcgag   4320
ttgctcgaac ttcgcgtcaa aactgcgatc ctggatgccc gttctcaatc ggttgctgat   4380
ccctcgactc gtgagcttgc aggcgaacta ggtgtcagtg aaaggcgcat ccaacaagtc   4440
agaaaggcac ttgaatgga agctaaacgc ggccgtccac gggctgaaaa ctaataaacg   4500
aaacaccgtc agcagaaaac ggttccccc tttaggggtc ccgtccttgc tctggctctc   4560
acttgccctc accctccgct atccacgggc tgaaaactaa taaacgaaac accgtcagca   4620
gaaaacggtt ccccccttt agggtgtctc gctcctagct ctgatccctc cccggttcct   4680
ccccggcctg attttaagg ggggctcacg ctgtcggcag agaacggttc cccgccttct   4740
gctctggctc ttcctcgact ccctccccct caaaaatctc ctcgagatcc tggagacctt   4800
tttggagcta gcgcgttgct gcttcgcacc aacttgctca tgatgatttt cattttttgct   4860
tgtgtgcttt ttgggttga accctccaaa gaggggaaac caggggcaca cctcatgcac   4920
taaagtgccg cttcgctggt cagggtgaaa tcacctggaa aaaagtgcg gtaaccgctg   4980
```

```
cgcttggcgt tttttctggg caagaagtct cgcaggtttt cgcaggagtg ccggaagaaa    5040
ttatcagaat tggggctaga atttttaacg aacgttcgtt ataatggtgt catgaccttc    5100
acgacgaagt accaaaactg gcctgaagca tcagcggtgg atctctccga tgtcgcgctg    5160
gagtccgacg cactcgatgc cgccgtcgat ttaaaaacgg tgatcggatt tttccgcgcc    5220
ctcgatacga cagacgcgcc agcatcacgc gactgggcaa gtgccgcgag cgacctagaa    5280
acgcttgtgg ccgaccttga agagctggcg gacgagctgc gtgctcggca gcgccaggag    5340
gacgcgcagt agtggaggat cgcatcagct gcgcctactg cggtggcctg atcccacccc    5400
ggcctgaccc acgaggacgg cgcgcaaaat actgctcaga cgcgtgtcgt gccgcagcca    5460
gccgcgagcg cgccaacaag cgccacgccc aggaggtcga agccgcacgt cgaccgcgtg    5520
tagtgcgtgg cggaaacttc ttgcgtttcg caagagaaat gcgtcccatt tctcgtcgga    5580
ctcggggaag gaagcgtgat gctctcggtc aagcacgtcg ctcgccagcg ctgcgaggag    5640
ttcggccttc gtgcggaagt gccagtagag gccgggctgc tgtacctgta agtgagccgc    5700
cagcgcgcga gtggtgaagc catcgagccc agtctcgtcg agcacctgcc gggccccgag    5760
caacacggac gtgcggtcga gacgcttccg gtggtgagtc atagttgcac tttatcatcg    5820
ataactttat cttagataaa gtgactgctc gctactctca tctgactgct cgctactctc    5880
atcgtggaat cctgacagcc gtgctcatca cggcgaccct cgatgctgca gggctgggcc    5940
tcgtgatgcc gatcttgcct acccttctcg accaggtcgg tgccccgac gacatgatcc    6000 cactgcacgt cggactactg acagcgctct atgcgatcat gcagtttctt tgcgccccga    6060
tccttggccg actctctgac cgtttcggac gccgccgcgt gcttgtcgcc tccctcgcag    6120
gcgcgacgat cgactacctc gtgctcgcac tgacggacac gctgtgggtc ttttacctcg    6180
cccgcgcggt tgcaggcatt accggcgcca cgaacgccgt caccgcgacg gtgatcgccg    6240
acattactcc gccggatcag cgcgcaaaac gctacgggtg gctcggcgca tgctacggcg    6300
gtggcatgat cgcgggtccc gccattggcg gtcttttcgg cggggtctca ccgcatctgc    6360
cattcctcgt cgccgccgcg ctcgccggaa tcaccctcgt actcagcgcg agtcttctgc    6420
gtgagacgcg gccaccgggc agcaacggct cgcacgcaca gcaacccggt acggcgaagc    6480
gaaccgcagt gccggggatg cttatccttc tcgcagtctt cggcatcgtg cagttcatcg    6540
gccaagcacc aggctccacc tgggtgctct tcacgcagca gcgcctcgac tggaaccccg    6600
tcgaagtcgg cgtttcgcta tccatcttcg gaatggtgca agtattcgtg caggcggcac    6660
tgaccggacg catcgtgtcc cggatcggcg agacccgggc gatcctcgtc ggtatcgccg    6720
cagacgccat tgggctcatc ggccttgccc tcatcgccag cacatgggcg atgctaccga    6780
tcctcgcagc gctcggactc ggcagcatca cgttgcccgc actgcagacg ctgctctcga    6840
gacgcgcgcc cgagcagcag cagggacgcc tgcagggaac acttgcaagc ctgaacagcc    6900
tcacctcgat catcggcccg gtcaccttca ccggcatttt cgcactcacc gaacgaatg    6960 cagacggcac cctctggatc tgcgccgcag cgctctacgt tctctgcgcc ctcctgatga    7020
tccgtgagac atgcgcctca cggcgatctc gataaccgcg ctaaggtgcc atcccgatgc    7080
gacgggatcg ctctgccacc agtcaagtct cccgtagccg gtatgagcat gaccaaaatc    7140
ccttaacgtg agttttcgtt ccactgagcg tcagacccg tagaaaagat caaaggatct    7200
tcttgagatc ctttttttct gcgcgtaatc tgctgcttgc aaacaaaaaa accaccgcta    7260
ccagcggtgg tttgtttgcc ggatcaagag ctaccaactc tttttccgaa ggtaactggc    7320
ttcagcagag cgcagatacc aaatactgtc cttctagtgt agccgtagtt aggccaccac    7380
```

```
ttcaagaact ctgtagcacc gcctacatac ctcgctctgc taatcctgtt accagtggct    7440
gctgccagtg gcgataagtc gtgtcttacc gggttggact caagacgata gttaccggat    7500
aaggcgcagc ggtcgggctg aacggggggt tcgtgcacac agcccagctt ggagcgaacg    7560
acctacaccg aactgagata cctacagcgt gagctatgag aaagcgccac gcttcccgaa    7620
gggagaaagg cggacaggta tccggtaagc ggcagggtcg aacaggaga gcgcacgagg     7680 gagcttccag ggggaaacgc ctggtatctt tatagtcctg tcgggtttcg ccacctctga    7740
cttgagcgtc gattttgtg atgctcgtca ggggggcgga gcctatggaa aaacgccagc     7800
aacgcggcct tttacggtt cctggccttt gctggcctt ttgctcacat gttctttcct       7860
gcgttatccc ctgattctgt ggataaccgt attaccgcct ttgagtgagc tgataccgct    7920
cgccgcagcc gaacgaccga gcgcagcgag tcagtgagcg aggaagcgga agagcgcctg    7980
atgcggtatt ttctccttac gcatctgtgc ggtatttcac accgcatatg gtgcactctc    8040
agtacaatct gctctgatgc cgcatagtta agccagtata cactccgcta tcgctacgtg    8100
actgggtcat ggctgcgccc cgacacccgc caacacccgc tgacgcgccc tgacgggctt    8160
gtctgctccc ggcatccgct tacagacaag ctgtgaccgt ctccgggagc tgcatgtgtc    8220
agaggttttc accgtcatca ccgaaacgcg cgaggcagca gatcaattcg cgcgcgaagg    8280
cgaagcggca tgcatttacg ttgacaccat cgaatggtgc aaaaccttc gcggtatggc     8340 atgatagcgc ccggaagaga gtcaattcag ggtggtgaat gtgaaaccag taacgttata    8400
cgatgtcgca gagtatgccg gtgtctctta tcagaccgtt tcccgcgtgg tgaaccaggc    8460
cagccacgtt tctgcgaaaa cgcgggaaaa agtggaagcg gcgatggcgg agctgaatta    8520
cattcccaac cgcgtggcac aacaactggc gggcaaacag tcgttgctga ttggcgttgc    8580
cacctccagt ctggccctgc acgcgccgtc gcaaattgtc gcggcgatta atctcgcgc     8640 cgatcaactg ggtgccagcg tggtggtgtc gatggtagaa cgaagcggcg tcgaagcctg    8700
taaagcggcg gtgcacaatc ttctcgcgca acgcgtcagt gggctgatca ttaactatcc    8760
gctggatgac caggatgcca ttgctgtgga agctgcctgc actaatgttc cggcgttatt    8820
tcttgatgtc tctgaccaga cacccatcaa cagtattatt ttctcccatg aagacggtac    8880
gcgactgggc gtggagcatc tggtcgcatt gggtcaccag caaatcgcgc tgttagcggg    8940
cccattaagt tctgtctcgg cgcgtctgcg tctggctggc tggcataaat atctcactcg    9000
caatcaaatt cagccgatag cggaacggga aggcgactgg agtgccatgt ccggttttca    9060
acaaaccatg caaatgctga atgagggcat cgttcccact gcgatgctgg ttgccaacga    9120
tcagatggcg ctgggcgcaa tgcgcgccat taccgagtcc gggctgcgcg ttggtgcgga    9180
tatctcggta gtgggatacg acgataccga agacagctca tgttatatcc cgccgtcaac    9240
caccatcaaa caggattttc gcctgctggg gcaaaccagc gtggaccgct tgctgcaact    9300
ctctcagggc caggcggtga agggcaatca gctgttgccc gtctcactgg tgaaaagaaa    9360
aaccaccctg gcgcccaata cgcaaaccgc ctctccccgc gcgttggccg attcattaat    9420
gcagctggca cgacaggttt cccgactgga aagcgggcag tgagcgcaac gcaattaatg    9480
tgagttagcg cgaattgatc tggtttgaca gcttatcatc gactgcacgg tgcaccaatg    9540
cttctggcgt caggcagcca tcggaagctg tggtatggct gtgcaggtcg taaatcactg    9600
cataattcgt gtcgctcaag gcgcactccc gttctggata tgttttttg cgccgacatc     9660 ataacggttc tggcaaatat tctgaaatga gctgttgaca attaatcatc cggctcgtat    9720
```

-continued

| | |
|---|---:|
| aatgtgtgga attgtgagcg gataacaatt tcacacagga acagaccat ggaattcgag | 9780 |
| ctcggtaccc ggg | 9793 |

<210> SEQ ID NO 53
<211> LENGTH: 10780
<212> TYPE: DNA
<213> ORGANISM: Artificial Sequence
<220> FEATURE:
<223> OTHER INFORMATION: vector

<400> SEQUENCE: 53

| | |
|---|---:|
| gatctggcat ttttgggagg tgtgaaatgc ggcgcgaaag tctgttggta tcggtttgca | 60 |
| agggcctgcg ggtacatgtc gagcgcgttg ggcaggatcc cgggcgcagc acggtgatgc | 120 |
| tggtcaacgg cgcgatggcg accaccgcct cgttcgcccg gacctgcaag tgcctggccg | 180 |
| aacatttcaa cgtggtgctg ttcgacctgc ccttcgccgg gcagtcgcgt cagcacaacc | 240 |
| cgcagcgggg gttgatcacc aaggacgacg aggtggaaat cctcctggcg ctgatcgagc | 300 |
| gcttcgaggt caatcacctg gtctccgcgt cctgggcgg tatctccacg ctgctggcgc | 360 |
| tgtcgcgcaa tccgcgcggc atccgcagct cggtggtgat ggcattcgcc cctggactga | 420 |
| accaggcgat gctcgactac gtcgggcggg cgcaggcgct gatcgagctg gacgacaagt | 480 |
| cggcgatcgg ccatctgctc aacgagaccg tcggcaaata cctgccgccg cgcctgaaag | 540 |
| ccagcaacca tcagcacatg gcttcgctgg ccaccggcga atacgagcag gcgcgctttc | 600 |
| acatcgacca ggtgctggcg ctcaacgatc ggggctacct ggcttgcctg gagcggatcc | 660 |
| agagccacgt gcatttcatc aacggcagct gggacgaata caccaccgcc gaggacgccc | 720 |
| gccagttccg cgactacctg ccgcactgca gtttctcgcg ggtggagggc accgggcatt | 780 |
| tcctcgacct ggagtccaag ctggccgcg tacgcgtgca ccgcgccctg ctcgagcacc | 840 |
| tgctgaagca accggagccg cagcgggcgg aacgcgcggc gggattccac gagatggcca | 900 |
| tcggctacgc ctgaacccctt gacctgcgaa gacccgcct ggccgggctt gcgcgttgca | 960 |
| taacgcacgg agtagcacca tgcacgccat cctcatcgcc atcggctcgg ccggcgacgt | 1020 |
| atttcccttc atcggcctgg cccggaccct gaaattgcgc gggcaccgcg tgagcctctg | 1080 |
| caccatcccg gtgtttcgcg acgcggtgga gcagcacggc atcgcgttcg tcccgctgag | 1140 |
| cgacgaactg acctaccgcc ggaccatggg cgatccgcgc ctgtgggacc ccaagacgtc | 1200 |
| cttcggcgtg ctctggcaaa ccatcgccgg gatgatcgag ccggtctacg agtacgtctc | 1260 |
| ggcgcagcgc catgacgaca tcgtggtggt cggctcgctc tgggcgctgg gcgcacgcat | 1320 |
| cgctcacgag aagtacggga ttccctacct gtccgcgcag gtctcgccat cgaccttgtt | 1380 |
| gtcggcgcac ctgccgccgg tacacccccaa gttcaacgtg cccgagcaga tgccgctggc | 1440 |
| gatgcgcaag ctgctctggc gctgcatcga gcgcttcaag ctggatcgca cctgcgcgcc | 1500 |
| ggatatcaac gcggtgcggc gcaaggtcgg cctggagacg ccggtgaagc gcatcttcac | 1560 |
| ccaatggatg cattcgccgc agggcgtggt ctgcctgttc ccggcctggt tcgcgccgcc | 1620 |
| ccagcaggat tggccgcaac ccctgcacat gaccggcttc ccgctgttcg acggcagtat | 1680 |
| cccgggggacc ccgtcgacg acgaactgca acgctttctc gatcagggca gccggccgct | 1740 |
| ggtgttcacc cagggctcga ccgaacacct gcagggcgac ttctacgcca tggccctgcg | 1800 |
| cgcgctggaa cgcctcggcg cgcgtgggat cttcctcacc ggcgccggcc aggaaccgct | 1860 |
| gcgcggcttg ccgaaccacg tgctgcagcg cgcctacgcg ccactgggag ccttgctgcc | 1920 |
| atcgtgcgcc gggctggtcc atccgggcgg tatcggcgcc atgagcctgg ccttggcggc | 1980 |

```
gggggtgccg caggtgctgc tgccctgcgc ccacgaccag ttcgacaatg ccgaacggct    2040
ggtccggctc ggctgcggga tgcgcctggg cgtgccattg cgcgagcagg agttgcgcgg    2100
ggcgctgtgg cgcttgctcg aggacccggc catggcggcg gcctgtcggc gtttcatgga    2160
attgtcacaa ccgcacagta tcgcttgcgg taaagcggcc caggtggtcg aacgttgtca    2220
tagggagggg gatgcgcgat ggctgaaggc tgcgtcctga cctacgggag aagaacgatc    2280
atggaccgga tagacatggg cgtgctggtg gtactgttca atcctggcga cgacgacctg    2340
gaacaccttg gcgaactggc ggcggcgttt ccgcaactgc gcttccttgc cgtcgacaac    2400
tcaccgcaca gcgatccgca gcgcaatgcc cggctgcgcg ggcaaggcat cgccgtgctg    2460
caccacggca accggcaggg catcgccggc gccttcaacc agggactcga cgcgctattc    2520
cggcgtggcg tgcagggtgt gctgctgctc gaccaggact cccgtcccgg cggcgccttc    2580
ctcgccgccc agtggcgcaa cctgcaggcg cgcaacggtc aggcctgcct gctcggccca    2640
cggatcttcg accggggtga ccggcgcttc ctgccggcca tccatctcga cggactgacg    2700
ctcaggcaat tgtctctgga cggcctgacg accccgcagc gcacctcgtt cctgatctcc    2760
tccggctgcc tgctgacccg cgaggcctac cagcgcctcg gccacttcga cgaggaactg    2820
ttcatcgacc acgtggacac cgaatacagc ctgcgcgccc aggcgctgga cgtgcccctg    2880
tacgtcgacc cgcggctggt cctcgagcac cgcatcggca cgcgcaagac ccgccgcctc    2940
ggcggtctca gcctcagcgc gatgaaccac gccccgctgc cgctactact cctggcgcgc    3000
aacggcctgc tggtcctgcg ccgctacgcc cggtcctcgc cgctggccct gctggcgaac    3060
ctgccgaccc tgacccaggg cctcgcggtg ctcctgctcg aacgcgacaa gctgctcaag    3120
ctgcgctgcc tgggctgggg cctgtgggac ggcctgcggg gacgcggcgg cgcgctggag    3180
accaaccgcc cgcgcctgct gaagcgcctc gccggcccgg ccgtggcgtc cgtagcttcc    3240
ggcaaggcca aggcctagtc ggcgaaacgc attccctcta gagtcgacct gcaggcatgc    3300
aagcttggct gttttggcgg atgagagaag attttcagcc tgatacagat taaatcagaa    3360
cgcagaagcg gtctgataaa acagaatttg cctggcggca gtagcgcggt ggtcccacct    3420 gacccccatgc cgaactcaga agtgaaacgc cgtagcgccg atggtagtgt ggggtctccc    3480
catgcgagag tagggaactg ccaggcatca aataaaacga aaggctcagt cgaaagactg    3540
ggcctttcgt tttatctgtt gtttgtcggt gaacgctctc ctgagtagga caaatccgcc    3600
gggagcggat ttgaacgttg cgaagcaacg gcccggaggg tggcgggcag gacgcccgcc    3660
ataaactgcc aggcatcaaa ttaagcagaa ggccatcctg acggatggcc tttttgcgtt    3720
tctacaaact cttttttgttt attttttctaa atacattcaa atatgtatcc gctcatgctc    3780
cttcgtcggt gtcgtcgccg gatggtctgc ggtggtgctc agcgtggaga cgcgcaccgt    3840
cacggacccc catcaatcct gcctatttgc cacgtttaac aaggtagtta agcgttcatt    3900
tacgaagaaa acacgataag ctgcacaaat acctgaaaaa gttgaacgcc ccgtgagcgg    3960
gaactcacag ggcgtcggct aaccccagt catcagctgg gagaaagcac tcaagacatg    4020
actctagccg atccgcagga cacagtcaca gctagcgcgt ggaaattgtc cgccgatctg    4080
ttcgacaccc accccgaagc tatgcgctgc ggctcacgcg gctggacggc agaagatcgc    4140
cgcgaactgc tcgctcacct gggacgcgaa agcttccagg gcagcaagac aagagatttc    4200
gcgagcgcct ggattaaaaa cccggatacc ggcgaaaccc aaccaaagct ctaccgggct    4260
ggctcaaaag cgctgacgcg gtgccagtac gttgcgctga cgcacgcgca acatgccgcg    4320
```

```
gtgatcgtgc ttgacatcga tgtgcccagc caccaggccg gcgggaagat tgagcacgta    4380
aacccgcagg tctacgcgat tttagagaaa tgggcacgcc tagaaaaagc gccggcttgg    4440
atcggcgtga atccgctgag cgggaaatgc cagctcatct ggctcattga cccggtgtat    4500
gccgcagcag gtaaaaccag cccaaatatg cgcctgctgg ctgcaacgac ggaagaaatg    4560
actcgtgttt tcggcgctga ccaggctttt tcgcataggc tgagccggtg gccgctgcac    4620
gtctcagacg atccgacagc ctataaatgg cactgccagc atgatcgtgt ggatcggctg    4680
gccgacctaa tggagattgc tcgaacgatg accggatcac agaagccgaa aaagtacatt    4740
gagcaggact tttccagcgg acgcgcccgc attgaagcgg cacaacgcgc caccgcagaa    4800
gccaaggcgc tagcgatttt ggacgcgagc ctgccgagcg ccctggacgc gtccggcgac    4860
ctgatcgacg gcgtgcgagt gctctggaca aatccagagc gagcgcgcga cgagaccgcg    4920
tttcgccacg cgttgaccgt gggataccag ctcaaagctg ctggtgagcg cctaaaagat    4980
gccaagatca tcgacgcgta tgaagtggcg tacaacgttg cccaggcggt cggtgcagac    5040
ggccgggagc cggatcttcc cgccatgcgt gatcgcctga cgatggcgcg tcgtgtgcgc    5100
ggctacgtgg ctaaaggcca gccagtcgtc cctgctcgtc gggtggaaac gcagagcagc    5160
cgagggcgga aagctctagc gacgatgggg cgacggggcg cagctacatc gaatgcacgc    5220
agatgggctg acccagaaag taagtatgcg caggagacgc gacagcgatt agcggaagca    5280
aacaaacgcc gagaaatgac aggcgagttg ctcgaacttc gcgtcaaaac tgcgatcctg    5340
gatgcccgtt ctcaatcggt tgctgatccc tcgactcgtg agcttgcagg cgaactaggt    5400
gtcagtgaaa ggcgcatcca acaagtcaga aaggcacttg gaatgaagc taaacgcggc    5460 cgtccacggg ctgaaaacta ataaacgaaa caccgtcagc agaaaacggt tccccccttt    5520
aggggtcccg tccttgctct ggctctcact tgccctcacc ctccgctatc cacgggctga    5580
aaactaataa cgaaacaccc gtcagcagaa aacggttccc cccctttagg gtgtctcgct    5640
cctagctctg atccctcccc ggttcctccc cggcctgatt tttaagggg gctcacgctg    5700 tcggcagaga acggttcccc gccttctgct ctggctcttc ctcgactccc tccccctcaa    5760
aaatctcctc gagatcctgg agacctttttt ggagctagcg cgttgctgct tcgcaccaac    5820
ttgctcatga tgattttcat ttttgcttgt gtgcttttttt gggttgaacc ctccaaagag    5880
gggaaaccag gggcacacct catgcactaa agtgccgctt cgctggtcag ggtgaaatca    5940
cctggaaaaa aagtgcggta accgctgcgc ttggcgtttt ttctgggcaa gaagtctcgc    6000
aggttttcgc aggagtgccg gaagaaatta tcagaattgg ggctagaatt tttaacgaac    6060
gttcgttata atggtgtcat gaccttcacg acgaagtacc aaaactggcc tgaagcatca    6120
gcggtggatc tctccgatgt cgcgctggag tccgacgcac tcgatgccgc cgtcgattta    6180
aaaacggtga tcggattttt ccgcgccctc gatacgacag acgcgccagc atcacgcgac    6240
tgggcaagtg ccgcgagcga cctagaaacg cttgtggccg accttgaaga gctgccgac    6300 gagctgcgtg ctcggcagcg ccaggaggac gcgcagtagt ggaggatcgc atcagctgcg    6360
cctactgcgg tggcctgatc ccaccccggc ctgacccacg aggacggcgc gcaaaatact    6420
gctcagacgc gtgtcgtgcc gcagccagcc gcgagcgcgc caacaagcgc cacgcccagg    6480
aggtcgaagc cgcacgtcga ccgcgtgtag tgcgtggcgg aaacttcttg cgtttcgcaa    6540
gagaaatgcg tcccatttct cgtcggactc ggggaaggaa gcgtgatgct ctcggtcaag    6600
cacgtcgctc gccagcgctg cgaggagttc ggccttcgtg cggaagtgcc agtagaggcc    6660
gggctgctgt acctgtaagt gagccgccag cgcgcgagtg gtgaagccat cgagcccagt    6720
```

```
ctcgtcgagc acctgccggg ccccgagcaa cacggacgtg cggtcgagac gcttccggtg    6780
gtgagtcata gttgcacttt atcatcgata actttatctt agataaagtg actgctcgct    6840
actctcatct gactgctcgc tactctcatc gtggaatcct gacagccgtg ctcatcacgg    6900
cgaccctcga tgctgcaggg ctgggcctcg tgatgccgat cttgcctacc cttctcgacc    6960
aggtcggtgc ccccgacgac atgatcccac tgcacgtcgg actactgaca gcgctctatg    7020
cgatcatgca gtttctttgc gccccgatcc ttggccgact ctctgaccgt ttcggacgcc    7080
gccgcgtgct tgtcgcctcc ctcgcaggcg cgacgatcga ctacctcgtg ctcgcactga    7140
cggacacgct gtgggtcttt tacctcgccc gcgcggttgc aggcattacc ggcgccacga    7200
acgccgtcac cgcgacggtg atcgccgaca ttactccgcc ggatcagcgc gcaaaacgct    7260
acgggtggct cggcgcatgc tacggcgtg gcatgatcgc gggtcccgcc attggcggtc    7320
ttttcggcgg ggtctcaccg catctgccat tcctcgtcgc cgccgcgctc gccggaatca    7380
ccctcgtact cagcgcgagt cttctgcgtg agacgcggcc accgggcagc aacggctcgc    7440
acgcacagca acccggtacg gcgaagcgaa ccgcagtgcc ggggatgctt atccttctcg    7500
cagtcttcgg catcgtgcag ttcatcggcc aagcaccagg ctccacctgg gtgctcttca    7560
cgcagcagcg cctcgactgg aaccccgtcg aagtcggcgt ttcgctatcc atcttcggaa    7620
tggtgcaagt attcgtgcag gcggcactga ccggacgcat cgtgtcccgg atcggcgaga    7680
cccgggcgat cctcgtcggt atcgccgcag acgccattgg gctcatcggc cttgccctca    7740
tcgccagcac atgggcgatg ctaccgatcc tcgcagcgct cggactcggc agcatcacgt    7800
tgcccgcact gcagacgctg ctctcgagac gcgcgcccga gcagcagcag gacgcctgc    7860 agggaacact tgcaagcctg aacagcctca cctcgatcat cggcccggtc accttcaccg    7920
gcattttcgc actcacccga acgaatgcag acggcaccct ctggatctgc gccgcagcgc    7980
tctacgttct ctgcgccctc ctgatgatcc gtgagacatg cgcctcacgg cgatctcgat    8040
aaccgcgcta aggtgccatc ccgatgcgac gggatcgctc tgccaccagt caagtctccc    8100
gtagccggta tgagcatgac caaaatccct taacgtgagt tttcgttcca ctgagcgtca    8160
gaccccgtag aaaagatcaa aggatcttct tgagatcctt ttttctgcg cgtaatctgc    8220 tgcttgcaaa caaaaaaacc accgctacca gcggtggttt gtttgccgga tcaagagcta    8280
ccaactcttt ttccgaaggt aactggcttc agcagagcgc agataccaaa tactgtcctt    8340
ctagtgtagc cgtagttagg ccaccacttc aagaactctg tagcaccgcc tacatacctc    8400
gctctgctaa tcctgttacc agtggctgct gccagtggcg ataagtcgtg tcttaccggg    8460
ttggactcaa gacgatagtt accggataag cgcagcggt cgggctgaac gggggttcg    8520 tgcacacagc ccagcttgga gcgaacgacc tacaccgaac tgagatacct acagcgtgag    8580
ctatgagaaa gcgccacgct tcccgaaggg agaaaggcgg acaggtatcc ggtaagcggc    8640
agggtcggaa caggagagcg cacgagggag cttccagggg gaaacgcctg gtatctttat    8700
agtcctgtcg ggtttcgcca cctctgactt gagcgtcgat ttttgtgatg ctcgtcaggg    8760
gggcggagcc tatggaaaaa cgccagcaac gcggcctttt tacggttcct ggccttttgc    8820
tggccttttg ctcacatgtt ctttcctgcg ttatccctg attctgtgga taaccgtatt    8880
accgcctttg agtgagctga taccgctcgc cgcagccgaa cgaccgagcg cagcgagtca    8940
gtgagcgagg aagcggaaga gcgcctgatg cggtattttc tccttacgca tctgtgcggt    9000
atttcacacc gcatatggtg cactctcagt acaatctgct ctgatgccgc atagttaagc    9060
```

| | |
|---|---|
| cagtatacac tccgctatcg ctacgtgact gggtcatggc tgcgccccga cacccgccaa | 9120 |
| cacccgctga cgcgccctga cgggcttgtc tgctcccggc atccgcttac agacaagctg | 9180 |
| tgaccgtctc cgggagctgc atgtgtcaga ggttttcacc gtcatcaccg aaacgcgcga | 9240 |
| ggcagcagat caattcgcgc gcgaaggcga agcggcatgc atttacgttg acaccatcga | 9300 |
| atggtgcaaa acctttcgcg gtatggcatg atagcgcccg aagagagtc aattcagggt | 9360 |
| ggtgaatgtg aaaccagtaa cgttatacga tgtcgcagag tatgccggtg tctcttatca | 9420 |
| gaccgtttcc cgcgtggtga accaggccag ccacgtttct gcgaaacgc gggaaaaagt | 9480 |
| ggaagcggcg atggcggagc tgaattacat tcccaaccgc gtggcacaac aactggcggg | 9540 |
| caaacagtcg ttgctgattg gcgttgccac ctccagtctg gccctgcacg cgccgtcgca | 9600 |
| aattgtcgcg gcgattaaat ctcgcgccga tcaactgggt gccagcgtgg tggtgtcgat | 9660 |
| ggtagaacga agcggcgtcg aagcctgtaa agcggcggtg cacaatcttc tcgcgcaacg | 9720 |
| cgtcagtggg ctgatcatta actatccgct ggatgaccag gatgccattg ctgtggaagc | 9780 |
| tgcctgcact aatgttccgg cgttatttct tgatgtctct gaccagacac ccatcaacag | 9840 |
| tattattttc tcccatgaag acggtacgcg actgggcgtg gagcatctgg tcgcattggg | 9900 |
| tcaccagcaa atcgcgctgt tagcgggccc attaagttct gtctcggcgc gtctgcgtct | 9960 |
| ggctggctgg cataaatatc tcactcgcaa tcaaattcag ccgatagcgg aacgggaagg | 10020 |
| cgactggagt gccatgtccg ttttcaaca accatgcaa atgctgaatg agggcatcgt | 10080 |
| tcccactgcg atgctggttg ccaacgatca gatggcgctg ggcgcaatgc gcgccattac | 10140 |
| cgagtccggg ctgcgcgttg gtgcggatat ctcggtagtg ggatacgacg ataccgaaga | 10200 |
| cagctcatgt tatatcccgc cgtcaaccac catcaaacag gattttcgcc tgctggggca | 10260 |
| aaccagcgtg gaccgcttgc tgcaactctc tcagggccag gcggtgaagg caatcagct | 10320 |
| gttgcccgtc tcactggtga aaagaaaaac cacccggcg cccaatacgc aaaccgcctc | 10380 |
| tccccgcgcg ttggccgatt cattaatgca gctggcacga caggtttccc gactggaaag | 10440 |
| cgggcagtga gcgcaacgca attaatgtga gttagcgcga attgatctgg tttgacagct | 10500 |
| tatcatcgac tgcacggtgc accaatgctt ctggcgtcag gcagccatcg gaagctgtgg | 10560 |
| tatggctgtg caggtcgtaa atcactgcat aattcgtgtc gctcaaggcg cactcccgtt | 10620 |
| ctggataatg tttttgcgc cgacatcata acggttctgg caaatattct gaaatgagct | 10680 |
| gttgacaatt aatcatccgg ctcgtataat gtgtggaatt gtgagcggat aacaatttca | 10740 |
| cacaggaaac agaccatgga attcgagctc ggtacccggg | 10780 |

<210> SEQ ID NO 54
<211> LENGTH: 11073
<212> TYPE: DNA
<213> ORGANISM: Artificial Sequence
<220> FEATURE:
<223> OTHER INFORMATION: vector

<400> SEQUENCE: 54

| | |
|---|---|
| gatctggcat ttttgggagg tgtgaaatgc ggcgcgaaag tctgttggta tcggtttgca | 60 |
| agggcctgcg ggtacatgtc gagcgcgttg ggcaggatcc cgggcgcagc acggtgatgc | 120 |
| tggtcaacgg cgcgatggcg accaccgcct cgttcgcccg gacctgcaag tgcctggccg | 180 |
| aacatttcaa cgtggtgctg ttcgacctgc ccttcgccgg gcagtcgcgt cagcacaacc | 240 |
| cgcagcgggg gttgatcacc aaggacgacg aggtggaaat cctcctggcg ctgatcgagc | 300 |
| gcttcgaggt caatcacctg gtctccgcgt cctggggcgg tatctccacg ctgctggcgc | 360 |

```
tgtcgcgcaa tccgcgcggc atccgcagct cggtggtgat ggcattcgcc cctggactga    420
accaggcgat gctcgactac gtcgggcggg cgcaggcgct gatcgagctg acgacaagt     480 cggcgatcgg ccatctgctc aacgagaccg tcggcaaata cctgccgccg cgcctgaaag    540
ccagcaacca tcagcacatg gcttcgctgg ccaccggcga atacgagcag gcgcgctttc    600
acatcgacca ggtgctggcg ctcaacgatc ggggctacct ggcttgcctg agcggatcc     660 agagccacgt gcatttcatc aacggcagct gggacgaata caccaccgcc gaggacgccc    720
gccagttccg cgactacctg ccgcactgca gtttctcgcg ggtggagggc accgggcatt    780
tcctcgacct ggagtccaag ctggccgcgg tacgcgtgca ccgcgccctg ctcgagcacc    840
tgctgaagca accggagccg cagcgggcgg aacgcgcggc gggattccac gagatggcca    900
tcggctacgc ctgaaccctt gacctgcgaa gacccgccct ggccgggctt tgcggttgca    960
taacgcacgg agtagcacca tgcacgccat cctcatcgcc atcggctcgg ccggcgacgt   1020
atttcccttc atcggcctgg cccggaccct gaaattgcgc gggcaccgcg tgagcctctg   1080
caccatcccg gtgtttcgcg acgcggtgga gcagcacggc atcgcgttcg tcccgctgag   1140
cgacgaactg acctaccgcc ggaccatggg cgatccgcgc ctgtgggacc caagacgtc    1200 cttcggcgtg ctctggcaaa ccatcgccgg gatgatcgag ccggtctacg agtacgtctc   1260
ggcgcagcgc catgacgaca tcgtggtggt cggctcgctc tgggcgctgg gcgcacgcat   1320
cgctcacgag aagtacggga ttccctacct gtccgcgcag gtctcgccat cgaccttgtt   1380
gtcggcgcac ctgccgccgg tacacccccaa gttcaacgtg cccgagcaga tgccgctggc   1440
gatgcgcaag ctgctctggc gctgcatcga gcgcttcaag ctggatcgca cctgcgcgcc   1500
ggatatcaac gcggtgcggc gcaaggtcgg cctggagacg ccggtgaagc gcatcttcac   1560
ccaatggatg cattcgccgc agggcgtggt ctgcctgttc ccggcctggt tcgcgccgcc   1620
ccagcaggat tggccgcaac ccctgcacat gaccggcttc ccgctgttcg acggcagtat   1680 cccgggggacc ccgctcgacg acgaactgca acgctttctc gatcagggca gccggccgct   1740
ggtgttcacc cagggctcga ccgaacacct gcagggcgac ttctacgcca tggccctgcg   1800
cgcgctggaa cgcctcggcg cgcgtgggat cttcctcacc ggcgccggcc aggaaccgct   1860
gcgcggcttg ccgaaccacg tgctgcagcg cgcctacgcg ccactgggag ccttgctgcc   1920
atcgtgcgcc gggctggtcc atccgggcgg tatcggcgcc atgagcctgg ccttggcggc   1980
gggggtgccg caggtgctgc tgccctgcgc ccacgaccag ttcgacaatg ccgaacggct   2040
ggtccggctc ggctgcggga tgcgcctggg cgtgccattg cgcgagcagg agttgcgcgg   2100
ggcgctgtgg cgcttgctcg aggacccggc catggcggcg cctgtcggc gtttcatgga   2160 attgtcacaa ccgcacagta tcgcttgcgg taaagcggcc caggtggtcg aacgttgtca   2220
tagggagggg gatgcgcgat ggctgaaggc tgcgtcctga cgccgggagg atcctggcgt   2280
gtccacgacc agcctctgcc cctccgccac gcgggaacac ggtccggcg cgaaacgcgt    2340 cctgcctctg ctgttcctca cctgcctgct ggatgccgct ggcgtcggcc tgatcgtgcc   2400
cctgctgccg acgctgatcg gcagcgtggc ggcgctggcg gtccgcgacg cggccacctg   2460
gggcgccgcc ctggtgatga ccttcgcgct gctgcaattg ttcttttcgc cggtcctcgg   2520
cagcctcagc gaccgcttcg acgccgccc cgtcctggtc ctggcgatgc tcggcttcgc   2580
cctcagctat ctgctgctgg cgctggccga cagcctctgg atgctgttcc tcggtcgcgc   2640
gctggccggg ctcaccggcg ccagcgtggc caccgcgatg gcctgcgcgg ctgacctcgg   2700
```

| | |
|---|---:|
| cacgcacggg cagcgcaccc ggcacttcgg ctggctgtac gccggcctcg ccctgggcat | 2760 |
| gatcctcggc cccgccctcg gtgggctgct ggcggtgcac ggcacgacgc tgccgctgtt | 2820 |
| gctggccgcc ggcctgtgcc tgctcaacgc cctgctcgcc ggcctgttcc tcgaggaaac | 2880 |
| cctgcccccg acgcgacgcc gccgcctgga cccgaggcgg atgaatgcct tgcgctcgat | 2940 |
| cagcggcctg gctcggcaac cggggtcgg acgcctgctg gcggtgcttg ccctggtatt | 3000 |
| cctcggcttg caggcggtga tggtggtctg gccgttcttc gtgatcgaga agtttcactg | 3060 |
| gagcagcgcc tggatcggct actcgctggc cctctacggc gtgctcgcgg tgctcgccca | 3120 |
| gaccctcggc gtgaacctct gcaagcggcg cctggacgac gcccgcctgc tgcgcctggg | 3180 |
| cctcgccctg caaggctgcg gcctgctgct gttcgccctg gtcgactcgt cattctggct | 3240 |
| ggtctgcgcg ctgctgccct tcgcgctcgg cagcctcgcc accccggcca tgcaggggct | 3300 |
| gctctcggcc cgcgtgccgg tcgaccgcca gggcgagttg cagggcgtgc tgagcagcct | 3360 |
| gatgagcctc gccgcgatcg tcggtccgcc gctgatgagc ggcctgttcc actggggcag | 3420 |
| cggtccgctc gcgccgctgc ccctggccgg cgcgccattc ctcgccggcg cccttctcgt | 3480 |
| tctggccggg ctggtcctgg cctggcaact tcgacctacg ggagaagaac gatcatggac | 3540 |
| cggatagaca tgggcgtgct ggtggtactt ctagagtcga cctgcaggca tgcaagcttg | 3600 |
| gctgttttgg cggatgagag aagattttca gcctgataca gattaaatca gaacgcagaa | 3660 |
| gcggtctgat aaaacagaat ttgcctggcg gcagtagcgc ggtggtccca cctgacccca | 3720 |
| tgccgaactc agaagtgaaa cgccgtagcg ccgatggtag tgtggggtct ccccatgcga | 3780 |
| gagtagggaa ctgccaggca tcaaataaaa cgaaaggctc agtcgaaaga ctgggccttt | 3840 |
| cgttttatct gttgtttgtc ggtgaacgct ctcctgagta ggacaaatcc gccgggagcg | 3900 |
| gatttgaacg ttgcgaagca acggcccgga gggtggcggg caggacgccc gccataaact | 3960 |
| gccaggcatc aaattaagca gaaggccatc ctgacggatg ccttttttgc gtttctacaa | 4020 |
| actcttttg tttattttc taaatacatt caaatatgta tccgctcatg ctccttcgtc | 4080 |
| ggtgtcgtcg ccggatggtc tgcggtggtg ctcagcgtgg agacgcgcac cgtcacggac | 4140 |
| ccccatcaat cctgcctatt tgccacgttt aacaaggtag ttaagcgttc atttacgaag | 4200 |
| aaaacacgat aagctgcaca aatacctgaa aaagttgaac gccccgtgag cgggaactca | 4260 |
| cagggcgtcg gctaaccccc agtcatcagc tgggagaaag cactcaagac atgactctag | 4320 |
| ccgatccgca ggacacagtc acagctagcg cgtggaaatt gtccgccgat ctgttcgaca | 4380 |
| cccaccccga agctatgcgc tgcggctcac gcggctggac ggcagaagat cgccgcgaac | 4440 |
| tgctcgctca cctgggacgc gaaagcttcc agggcagcaa gacaagagat tcgcgagcg | 4500 |
| cctggattaa aaacccggat accggcgaaa cccaaccaaa gctctaccgg ctggctcaa | 4560 |
| aagcgctgac gcggtgccag tacgttgcgc tgacgcacgc gcaacatgcc gcggtgatcg | 4620 |
| tgcttgacat cgatgtgccc agccaccagg ccggcgggaa gattgagcac gtaaacccgc | 4680 |
| aggtctacgc gattttagag aaatgggcac gcctagaaaa agcgccggct tggatcggcg | 4740 |
| tgaatccgct gagcgggaaa tgccagctca tctggctcat tgacccggtg tatgccgcag | 4800 |
| caggtaaaac cagcccaaat atgcgcctgc tggctgcaac gacggaagaa atgactcgtg | 4860 |
| ttttcggcgc tgaccaggct ttttcgcata ggctgagccg gtggccgctg cacgtctcag | 4920 |
| acgatccgac agcctataaa tggcactgcc agcatgatcg tgtggatcgg ctggccgacc | 4980 |
| taatggagat tgctcgaacg atgaccggat cacagaagcc gaaaaagtac attgagcagg | 5040 |
| acttttccag cggacgcgcc cgcattgaag cggcacaacg cgccaccgca gaagccaagg | 5100 |

```
cgctagcgat tttggacgcg agcctgccga gcgccctgga cgcgtccggc gacctgatcg   5160
acggcgtgcg agtgctctgg acaaatccag agcgagcgcg cgacgagacc gcgtttcgcc   5220
acgcgttgac cgtgggatac cagctcaaag ctgctggtga gcgcctaaaa gatgccaaga   5280
tcatcgacgc gtatgaagtg gcgtacaacg ttgcccaggc ggtcggtgca gacggccggg   5340
agccggatct tcccgccatg cgtgatcgcc tgacgatggc gcgtcgtgtg cgcggctacg   5400
tggctaaagg ccagccagtc gtccctgctc gtcgggtgga aacgcagagc agccgagggc   5460
ggaaagctct agcgacgatg gggcgacggg gcgcagctac atcgaatgca cgcagatggg   5520
ctgacccaga aagtaagtat gcgcaggaga cgcgacagcg attagcggaa gcaaacaaac   5580
gccgagaaat gacaggcgag ttgctcgaac ttcgcgtcaa aactgcgatc ctggatgccc   5640
gttctcaatc ggttgctgat ccctcgactc gtgagcttgc aggcgaacta ggtgtcagtg   5700
aaaggcgcat ccaacaagtc agaaaggcac ttggaatgga agctaaacgc ggccgtccac   5760
gggctgaaaa ctaataaacg aaacaccgtc agcagaaaac ggttcccccc tttaggggtc   5820
ccgtccttgc tctggctctc acttgccctc accctccgct atccacgggc tgaaaactaa   5880
taaacgaaac accgtcagca gaaaacggtt ccccccttt agggtgtctc gctcctagct   5940
ctgatccctc cccggttcct ccccggcctg atttttaagg ggggctcacg ctgtcggcag   6000
agaacggttc cccgccttct gctctggctc ttcctcgact ccctccccct caaaaatctc   6060
ctcgagatcc tggagacctt tttggagcta gcgcgttgct gcttcgcacc aacttgctca   6120
tgatgatttt catttttgct tgtgtgcttt tttgggttga accctccaaa gaggggaaac   6180
caggggcaca cctcatgcac taaagtgccg cttcgctggt cagggtgaaa tcacctggaa   6240
aaaaagtgcg gtaaccgctg cgcttggcgt tttttctggg caagaagtct cgcaggtttt   6300
cgcaggagtg ccggaagaaa ttatcagaat tggggctaga atttttaacg aacgttcgtt   6360
ataatggtgt catgaccttc acgacgaagt accaaaactg gcctgaagca tcagcggtgg   6420
atctctccga tgtcgcgctg gagtccgacg cactcgatgc cgccgtcgat ttaaaaacgg   6480
tgatcggatt tttccgcgcc ctcgatacga cagacgcgcc agcatcacgc gactgggcaa   6540
gtgccgcgag cgacctagaa acgcttgtgg ccgaccttga agagctggcc gacgagctgc   6600
gtgctcggca gcgccaggag gacgcgcagt agtggaggat cgcatcagct gcgcctactg   6660
cggtggcctg atcccacccc ggcctgaccc acgaggacgg cgcgcaaaat actgctcaga   6720
cgcgtgtcgt gccgcagcca gccgcgagcg cgccaacaag cgccacgccc aggaggtcga   6780
agccgcacgt cgaccgcgtg tagtgcgtgg cggaaacttc ttgcgtttcg caagagaaat   6840
gcgtcccatt tctcgtcgga ctcggggaag gaagcgtgat gctctcggtc aagcacgtcg   6900
ctcgccagcg ctgcgaggag ttcggccttc gtgcggaagt gccagtagag gccgggctgc   6960
tgtacctgta agtgagccgc cagcgcgcga gtggtgaagc catcgagccc agtctcgtcg   7020
agcacctgcc gggccccgag caacacggac gtgcggtcga gacgcttccg gtggtgagtc   7080
atagttgcac tttatcatcg ataactttat cttagataaa gtgactgctc gctactctca   7140
tctgactgct cgctactctc atcgtggaat cctgacagcc gtgctcatca cggcgaccct   7200
cgatgctgca gggctgggcc tcgtgatgcc gatcttgcct accttctcg accaggtcgg   7260 tgccccgac gacatgatcc cactgcacgt cggactactg acagcgctct atgcgatcat   7320
gcagtttctt tgcgccccga tccttggccg actctctgac cgtttcggac gccgccgcgt   7380
gcttgtcgcc tccctcgcag gcgcgacgat cgactacctc gtgctcgcac tgacggacac   7440
```

```
gctgtgggtc ttttacctcg cccgcgcggt tgcaggcatt accggcgcca cgaacgccgt    7500
caccgcgacg gtgatcgccg acattactcc gccggatcag cgcgcaaaac gctacgggtg    7560
gctcggcgca tgctacggcg gtggcatgat cgcgggtccc gccattggcg gtcttttcgg    7620
cggggtctca ccgcatctgc cattcctcgt cgccgccgcg ctcgccggaa tcaccctcgt    7680
actcagcgcg agtcttctgc gtgagacgcg gccaccgggc agcaacggct cgcacgcaca    7740
gcaacccggt acggcgaagc gaaccgcagt gccgggatg cttatccttc tcgcagtctt     7800
cggcatcgtg cagttcatcg ccaagcacc aggctccacc tgggtgctct tcacgcagca     7860
gcgcctcgac tggaaccccg tcgaagtcgg cgtttcgcta tccatcttcg gaatggtgca    7920
agtattcgtg caggcggcac tgaccggacg catcgtgtcc cggatcggcg agacccgggc    7980
gatcctcgtc ggtatcgccg cagacgccat tgggctcatc ggccttgccc tcatcgccag    8040
cacatgggcg atgctaccga tcctcgcagc gctcggactc ggcagcatca cgttgcccgc    8100
actgcagacg ctgctctcga cgcgcgcc cgagcagcag cagggacgcc tgcagggaac      8160
acttgcaagc ctgaacagcc tcacctcgat catcggcccg gtcaccttca ccggcatttt    8220
cgcactcacc cgaacgaatg cagacggcac cctctggatc tgcgccgcag cgctctacgt    8280
tctctgcgcc ctcctgatga tccgtgagac atgcgcctca cggcgatctc gataaccgcg    8340
ctaaggtgcc atcccgatgc gacgggatcg ctctgccacc agtcaagtct cccgtagccg    8400
gtatgagcat gaccaaaatc ccttaacgtg agttttcgtt ccactgagcg tcagaccccg    8460
tagaaaagat caaaggatct tcttgagatc cttttttct gcgcgtaatc tgctgcttgc      8520
aaacaaaaaa accaccgcta ccagcggtgg tttgtttgcc ggatcaagag ctaccaactc     8580 ttttccgaa ggtaactggc ttcagcagag cgcagatacc aaatactgtc cttctagtgt      8640
agccgtagtt aggccaccac ttcaagaact ctgtagcacc gcctacatac ctcgctctgc    8700
taatcctgtt accagtggct gctgccagtg gcgataagtc gtgtcttacc gggttggact    8760
caagacgata gttaccggat aaggcgcagc ggtcgggctg aacggggggt tcgtgcacac    8820
agcccagctt ggagcgaacg acctacaccg aactgagata cctacagcgt gagctatgag    8880
aaagcgccac gcttcccgaa gggagaaagg cggacaggta tccggtaagc ggcagggtcg    8940
gaacaggaga gcgcacgagg gagcttccag ggggaaacgc ctggtatctt tatagtcctg    9000
tcgggtttcg ccacctctga cttgagcgtc gatttttgtg atgctcgtca ggggggcgga    9060
gcctatggaa aaacgccagc aacgcggcct ttttacggtt cctggccttt tgctggcctt    9120
ttgctcacat gttctttcct gcgttatccc ctgattctgt ggataaccgt attaccgcct    9180
ttgagtgagc tgataccgct cgccgcagcc gaacgaccga gcgcagcgag tcagtgagcg    9240
aggaagcgga gagcgcctg atgcggtatt ttctccttac gcatctgtgc ggtatttcac     9300
accgcatatg gtgcactctc agtacaatct gctctgatgc cgcatagtta agccagtata    9360
cactccgcta tcgctacgtg actgggtcat ggctgcgccc cgacaccgc caacacccgc     9420 tgacgcgccc tgacgggctt gtctgctccc ggcatccgct tacagacaag ctgtgaccgt    9480
ctccgggagc tgcatgtgtc agaggttttc accgtcatca ccgaaacgcg cgaggcagca    9540
gatcaattcg cgcgcgaagg cgaagcggca tgcatttacg ttgacaccat cgaatggtgc    9600
aaaacctttc gcggtatggc atgatagcgc ccggaagaga gtcaattcag ggtggtgaat    9660
gtgaaaccag taacgttata cgatgtcgca gagtatgccg gtgtctctta tcagaccgtt    9720
tcccgcgtgg tgaaccaggc cagccacgtt tctgcgaaaa cgcgggaaaa agtggaagcg    9780
gcgatggcgg agctgaatta cattcccaac cgcgtggcac aacaactggc gggcaaacag    9840
```

| | |
|---|---|
| tcgttgctga ttggcgttgc cacctccagt ctggccctgc acgcgccgtc gcaaattgtc | 9900 |
| gcggcgatta atctcgcgc cgatcaactg ggtgccagcg tggtggtgtc gatggtagaa | 9960 |
| cgaagcggcg tcgaagcctg taaagcggcg gtgcacaatc ttctcgcgca acgcgtcagt | 10020 |
| gggctgatca ttaactatcc gctggatgac caggatgcca ttgctgtgga agctgcctgc | 10080 |
| actaatgttc cggcgttatt tcttgatgtc tctgaccaga cacccatcaa cagtattatt | 10140 |
| ttctcccatg aagacggtac gcgactgggc gtggagcatc tggtcgcatt gggtcaccag | 10200 |
| caaatcgcgc tgttagcggg cccattaagt tctgtctcgg cgcgtctgcg tctggctggc | 10260 |
| tggcataaat atctcactcg caatcaaatt cagccgatag cggaacggga aggcgactgg | 10320 |
| agtgccatgt ccggttttca acaaaccatg caaatgctga atgagggcat cgttcccact | 10380 |
| gcgatgctgg ttgccaacga tcagatgcg ctgggcgcaa tgcgcgccat taccgagtcc | 10440 |
| gggctgcgcg ttggtgcgga tatctcggta gtgggatacg acgataccga agacagctca | 10500 |
| tgttatatcc cgccgtcaac caccatcaaa caggattttc gcctgctggg gcaaaccagc | 10560 |
| gtggaccgct tgctgcaact ctctcagggc caggcggtga agggcaatca gctgttgccc | 10620 |
| gtctcactgg tgaaaagaaa aaccaccctg gcgcccaata cgcaaaccgc ctctccccgc | 10680 |
| gcgttggccg attcattaat gcagctggca cgacaggttt cccgactgga aagcgggcag | 10740 |
| tgagcgcaac gcaattaatg tgagttagcg cgaattgatc tggtttgaca gcttatcatc | 10800 |
| gactgcacgg tgcaccaatg cttctggcgt caggcagcca tcggaagctg tggtatggct | 10860 |
| gtgcaggtcg taaatcactg cataattcgt gtcgctcaag cgcactccc gttctggata | 10920 |
| atgtttttg cgccgacatc ataacggttc tggcaaatat tctgaaatga gctgttgaca | 10980 |
| attaatcatc cggctcgtat aatgtgtgga attgtgagcg gataacaatt tcacacagga | 11040 |
| aacagaccat ggaattcgag ctcggtaccc ggg | 11073 |

<210> SEQ ID NO 55
<211> LENGTH: 12263
<212> TYPE: DNA
<213> ORGANISM: Artificial Sequence
<220> FEATURE:
<223> OTHER INFORMATION: vector

<400> SEQUENCE: 55

| | |
|---|---|
| gatctggcat tttgggagg tgtgaaatgc ggcgcgaaag tctgttggta tcggtttgca | 60 |
| agggcctgcg ggtacatgtc gagcgcgttg ggcaggatcc cgggcgcagc acggtgatgc | 120 |
| tggtcaacgg cgcgatggcg accaccgcct cgttcgcccg gacctgcaag tgcctggccg | 180 |
| aacatttcaa cgtggtgctg ttcgacctgc ccttcgccgg gcagtcgcgt cagcacaacc | 240 |
| cgcagcgggg gttgatcacc aaggacgacg aggtggaaat cctcctggcg ctgatcgagc | 300 |
| gcttcgaggt caatcaccctg gtctccgcgt cctggggcgg tatctccacg ctgctggcgc | 360 |
| tgtcgcgcaa tccgcgcggc atccgcagct cggtggtgat ggcattcgcc cctgactga | 420 |
| accaggcgat gctcgactac gtcgggcggg cgcaggcgct gatcgagctg gacgacaagt | 480 |
| cggcgatcgg ccatctgctc aacgagaccg tcggcaaata cctgccgccg cgcctgaaag | 540 |
| ccagcaacca tcagcacatg gcttcgctgg ccaccggcga atacgagcag gcgcgctttc | 600 |
| acatcgacca ggtgctggcg ctcaacgatc ggggctacct ggcttgcctg agcggatcc | 660 |
| agagccacgt gcatttcatc aacgcagct gggacgaata caccaccgcc gaggacgcc | 720 |
| gccagttccg cgactacctg ccgcactgca gtttctcgcg ggtggagggc accgggcatt | 780 |

| | |
|---|---|
| tcctcgacct ggagtccaag ctggccgcgg tacgcgtgca ccgcgccctg ctcgagcacc | 840 |
| tgctgaagca accggagccg cagcgggcgg aacgcgcggc gggattccac gagatggcca | 900 |
| tcggctacgc ctgaacccett gacctgcgaa gacccggcct ggccgggctt tgcggttgca | 960 |
| taacgcacgg agtagcacca tgcacgccat cctcatcgcc atcggctcgg ccggcgacgt | 1020 |
| atttcccttc atcggcctgg cccggaccct gaaattgcgc gggcaccgcg tgagcctctg | 1080 |
| caccatcccg gtgtttcgcg acgcggtgga gcagcacggc atcgcgttcg tcccgctgag | 1140 |
| cgacgaactg acctaccgcc ggaccatggg cgatccgcgc ctgtgggacc ccaagacgtc | 1200 |
| cttcggcgtg ctctggcaaa ccatcgccgg gatgatcgag ccggtctacg agtacgtctc | 1260 |
| ggcgcagcgc catgacgaca tcgtggtggt cggctcgctc tgggcgctgg gcgcacgcat | 1320 |
| cgctcacgag aagtacggga ttccctacct gtccgcgcag gtctcgccat cgaccttgtt | 1380 |
| gtcggcgcac ctgccgccgg tacaccccaa gttcaacgtg cccgagcaga tgccgctggc | 1440 |
| gatgcgcaag ctgctctggc gctgcatcga gcgcttcaag ctggatcgca cctgcgcgcc | 1500 |
| ggatatcaac gcggtgcggc gcaaggtcgg cctggagacg ccggtgaagc gcatcttcac | 1560 |
| ccaatggatg cattcgccgc agggcgtggt ctgcctgttc ccggcctggt tcgcgccgcc | 1620 |
| ccagcaggat tggccgcaac ccctgcacat gaccggcttc ccgctgttcg acggcagtat | 1680 |
| cccgggggacc ccgctcgacg acgaactgca acgctttctc gatcagggca gccggccgct | 1740 |
| ggtgttcacc cagggctcga ccgaacacct gcagggcgac ttctacgcca tggccctgcg | 1800 |
| cgcgctggaa cgcctcggcg cgcgtgggat cttcctcacc ggcgccggcc aggaaccgct | 1860 |
| gcgcggcttg ccgaaccacg tgctgcagcg cgcctacgcg ccactgggag ccttgctgcc | 1920 |
| atcgtgcgcc gggctggtcc atccgggcgg tatcggcgcc atgagcctgg ccttggcggc | 1980 |
| gggggtgccg caggtgctgc tgccctgcgc ccacgaccag ttcgacaatg ccgaacggct | 2040 |
| ggtccggctc ggctgcggga tgcgcctggg cgtgccattg cgcgagcagg agttgcgcgg | 2100 |
| ggcgctgtgg cgcttgctcg aggacccggc catggcggcg cctgtcggc gtttcatgga | 2160 |
| attgtcacaa ccgcacagta tcgcttgcgg taaagcggcc caggtggtcg aacgttgtca | 2220 |
| tagggagggg gatgcgcgat ggctgaaggc tgcgtcctga cctacgggag aagaacgatc | 2280 |
| atggaccgga tagacatggg cgtgctggtg gtactgttca atcctggcga cgacgacctg | 2340 |
| gaacaccttg gcgaactggc ggcggcgttt ccgcaactgc gcttccttgc cgtcgacaac | 2400 |
| tcaccgcaca gcgatccgca gcgcaatgcc cggctgcgcg ggcaaggcat cgccgtgctg | 2460 |
| caccacggca accggcaggg catcgccggc gccttcaacc agggactcga cgcgctattc | 2520 |
| cggcgtggcg tgcagggtgt gctgctgctc gaccaggact cccgtcccgg cggcgccttc | 2580 |
| ctcgccgccc agtggcgcaa cctgcaggcg cgcaacggtc aggcctgcct gctcggccca | 2640 |
| cggatcttcg accggggtga ccggcgcttc ctgccggcca tccatctcga cggactgacg | 2700 |
| ctcaggcaat tgtctctgga cggcctgacg accccgcagc gcacctcgtt cctgatctcc | 2760 |
| tccggctgcc tgctgacccg cgaggcctac cagcgcctcg ccacttcga cgaggaactg | 2820 |
| ttcatcgacc acgtggacac cgaatacagc ctgcgcgccc aggcgctgga cgtgcccctg | 2880 |
| tacgtcgacc cgcggctggt cctcgagcac cgcatcggca cgcgcaagac ccgccgcctc | 2940 |
| ggcggtctca gcctcagcgc gatgaaccac gccccgctgc gccgctacta cctggcgcgc | 3000 |
| aacggcctgc tggtcctgcg ccgctacgcc cggtcctcgc cgctggccct gctggcgaac | 3060 |
| ctgccgaccc tgacccaggg cctcgcgtg tcctgctcg aacgcgacaa gctgctcaag | 3120 |
| ctgcgctgcc tgggctgggg cctgtgggac ggcctgcggg gacgcggcgg cgcgctggag | 3180 |

```
accaaccgcc cgcgcctgct gaagcgcctc gccggcccgg ccgtggcgtc cgtagcttcc    3240
ggcaaggcca aggcctagtc ggcgaaacgc attccctcta gatgagaggc cggcaaggat    3300
acccgactgg cgcacgggtc gcatcattat gacatcacgc cgcccgccgg cgttgccgcg    3360
accgttcgtc gaacctgtga attccggtag tttcccttgc cctcgctggc gtcccaagat    3420
caggatttcc tgtgttcgcc gggaggatcc tggcgtgtcc acgaccagcc tctgcccctc    3480
cgccacgcgg aaacacggtc ccggcgcgaa acgcgtcctg cctctgctgt tcctcacctg    3540
cctgctggat gccgctggcg tcggcctgat cgtgcccctg ctgccgacgc tgatcggcag    3600
cgtggcgccc ctggcggtcc gcgacgcggc cacctgggc gccgccctgg tgatgacctt    3660
cgcgctgctg caattgttct tttcgccggt cctcggcagc ctcagcgacc gcttcggacg    3720
ccgcccgtc ctggtcctgg cgatgctcgg cttcgccctc agctatctgc tgctggcgct    3780
ggccgacagc ctctggatgc tgttcctcgg tcgcgcgctg gccgggctca ccggcgccag    3840
cgtgccacc gcgatggcct gcgcggctga cctcggcacg cacgggcagc gcacccggca    3900
cttcggctgg ctgtacgccg gcctcgccct gggcatgatc ctcggccccg cctcggtgg    3960
gctgctggcg gtgcacggca cgacgctgcc gctgttgctg gccgccggcc tgtgcctgct    4020
caacgccctg ctcgccggcc tgttcctcga ggaaaccctg cccccgacgc gacgccgccg    4080
cctggacccg aggcggatga atgccttgcg ctcgatcagc ggcctggctc ggcaaccggg    4140
ggtcggacgc ctgctggcgg tgcttgccct ggtattcctc ggcttgcagg cggtgatggt    4200
ggtctggccg ttcttcgtga tcgagaagtt tcactggagc agcgcctgga tcggctactc    4260
gctggccctc tacggcgtgc tcgcggtgct cgcccagacc ctcggcgtga acctctgcaa    4320
gcggcgcctg gacgacgccc gcctgctgcg cctgggcctc gccctgcaag gctgcggcct    4380
gctgctgttc gccctggtcg actcgtcatt ctggctggtc tgcgcgctgc tgcccttcgc    4440
gctcggcagc ctcgccaccc cggccatgca ggggctgctc tcggcccgcg tgccggtcga    4500
ccgccagggc gagttgcagg gcgtgctgag cagcctgatg agcctcgccg cgatcgtcgg    4560
tccgccgctg atgagcggcc tgttccactg gggcagcggt ccgctcgcgc cgctgcccct    4620
ggccggcgcg ccattcctcg ccggcgccct tctcgttctg gccgggctgg tcctggcctg    4680
gcaacttcga cctacgggag aagaacgatc atggaccgga tagacatggg cgtgctggtg    4740
gtactgttca atcctggcgt ctagagtcga cctgcaggca tgcaagcttg gctgttttgg    4800
cggatgagag aagattttca gcctgataca gattaaatca gaacgcagaa gcggtctgat    4860
aaaacagaat ttgcctggcg gcagtagcgc ggtggtccca cctgacccca tgccgaactc    4920
agaagtgaaa cgccgtagcg ccgatggtag tgtgggtct ccccatgcga gagtagggaa    4980
ctgccaggca tcaaataaaa cgaaaggctc agtcgaaaga ctgggccttt cgttttatct    5040
gttgtttgtc ggtgaacgct ctcctgagta ggacaaatcc gccggagcg atttgaacg    5100
ttgcgaagca acgcccgga gggtggcggg caggacgccc gccataaact gccaggcatc    5160
aaattaagca gaaggccatc ctgacggatg cctttttgc gtttctacaa actctttttg    5220
tttatttttc taaatacatt caaatatgta tccgctcatg ctccttcgtc ggtgtcgtcg    5280
ccggatggtc tgcggtggtg ctcagcgtgg agacgcgcac cgtcacggac ccccatcaat    5340
cctgcctatt tgccacgttt aacaaggtag ttaagcgttc atttacgaag aaaacacgat    5400
aagctgcaca aatacctgaa aaagttgaac gccccgtgag cgggaactca cagggcgtcg    5460
gctaaccccc agtcatcagc tgggagaaag cactcaagac atgactctag ccgatccgca    5520
```

-continued

```
ggacacagtc acagctagcg cgtggaaatt gtccgccgat ctgttcgaca cccacccga   5580
agctatgcgc tgcggctcac gcggctggac ggcagaagat cgccgcgaac tgctcgctca   5640
cctgggacgc gaaagcttcc agggcagcaa gacaagagat ttcgcgagcg cctggattaa   5700
aaacccggat accggcgaaa cccaaccaaa gctctaccgg gctggctcaa aagcgctgac   5760
gcggtgccag tacgttgcgc tgacgcacgc gcaacatgcc gcggtgatcg tgcttgacat   5820
cgatgtgccc agccaccagg ccggcgggaa gattgagcac gtaaacccgc aggtctacgc   5880
gattttagag aaatgggcac gcctagaaaa agcgccggct tggatcggcg tgaatccgct   5940
gagcgggaaa tgccagctca tctggctcat tgacccggtg tatgccgcag caggtaaaac   6000
cagcccaaat atgcgcctgc tggctgcaac gacgaagaa atgactcgtg ttttcggcgc   6060
tgaccaggct ttttcgcata ggctgagccg gtggccgctg cacgtctcag acgatccgac   6120
agcctataaa tggcactgcc agcatgatcg tgtggatcgg ctggccgacc taatggagat   6180
tgctcgaacg atgaccggat cacagaagcc gaaaaagtac attgagcagg acttttccag   6240
cggacgcgcc cgcattgaag cggcacaacg cgccaccgca gaagccaagg cgctagcgat   6300
tttggacgcg agcctgccga gcgccctgga cgcgtccggc gacctgatcg acggcgtgcg   6360
agtgctctgg acaaatccag agcgagcgcg cgacgagacc gcgtttcgcc acgcgttgac   6420
cgtgggatac cagctcaaag ctgctggtga gcgcctaaaa gatgccaaga tcatcgacgc   6480
gtatgaagtg gcgtacaacg ttgcccaggc ggtcggtgca gacggccggg agccggatct   6540
tcccgccatg cgtgatcgcc tgacgatggc gcgtcgtgtg cgcggctacg tggctaaagg   6600
ccagccagtc gtccctgctc gtcgggtgga aacgcagagc agccgagggc ggaaagctct   6660
agcgacgatg gggcgacggg gcgcagctac atcgaatgca cgcagatggg ctgacccaga   6720
aagtaagtat gcgcaggaga cgcgacacg attagcggaa gcaaacaaac gccgagaaat   6780
gacaggcgag ttgctcgaac ttcgcgtcaa aactgcgatc ctggatgccc gttctcaatc   6840
ggttgctgat ccctcgactc gtgagcttgc aggcgaacta ggtgtcagtg aaggcgcat   6900
ccaacaagtc agaaaggcac ttggaatgga agctaaacgc ggccgtccac gggctgaaaa   6960
ctaataaacg aaacaccgtc agcagaaaac ggttccccc tttaggggtc ccgtccttgc   7020
tctggctctc acttgccctc accctccgct atccacgggc tgaaaactaa taaacgaaac   7080
accgtcagca gaaaacggtt ccccccttt agggtgtctc gctcctagct ctgatccctc   7140
cccggttcct ccccggcctg atttttaagg ggggctcacg ctgtcggcag agaacggttc   7200
cccgccttct gctctggctc ttcctcgact ccctccccct caaaaatctc ctcgagatcc   7260
tggagacctt tttggagcta gcgcgttgct gcttcgcacc aacttgctca tgatgatttt   7320
cattttgct tgtgtgcttt tttggggttga acctccaaa gaggggaaac caggggcaca   7380
cctcatgcac taaagtgccg cttcgctggt cagggtgaaa tcacctggaa aaaaagtgcg   7440
gtaaccgctg cgcttggcgt ttttctggg caagaagtct cgcaggtttt cgcaggagtg   7500
ccggaagaaa ttatcagaat tggggctaga atttttaacg aacgttcgtt ataatggtgt   7560
catgaccttc acgacgaagt accaaaactg gcctgaagca tcagcggtgg atctctccga   7620
tgtcgcgctg gagtccgacg cactcgatgc cgccgtcgat ttaaaaacgg tgatcggatt   7680
tttccgcgcc ctcgatacga cagacgcgcc agcatcacgc gactgggcaa gtgccgcgag   7740
cgacctagaa acgcttgtgg ccgaccttga agagctggcc gacagctgc gtgctcggca   7800
gcgcaggag gacgcgcagt agtggaggat cgcatcagct gcgcctactg cggtggcctg   7860
atcccacccc ggcctgaccc acgaggacgg cgcgcaaaat actgctcaga cgcgtgtcgt   7920
```

```
gccgcagcca gccgcgagcg cgccaacaag cgccacgccc aggaggtcga agccgcacgt    7980
cgaccgcgtg tagtgcgtgg cggaaacttc ttgcgtttcg caagagaaat gcgtcccatt    8040
tctcgtcgga ctcggggaag gaagcgtgat gctctcggtc aagcacgtcg ctcgccagcg    8100
ctgcgaggag ttcggccttc gtgcggaagt gccagtagag gccgggctgc tgtacctgta    8160
agtgagccgc cagcgcgcga gtggtgaagc catcgagccc agtctcgtcg agcacctgcc    8220
gggccccgag caacacggac gtgcggtcga gacgcttccg gtggtgagtc atagttgcac    8280
tttatcatcg ataactttat cttagataaa gtgactgctc gctactctca tctgactgct    8340
cgctactctc atcgtggaat cctgacagcc gtgctcatca cggcgaccct cgatgctgca    8400
gggctgggcc tcgtgatgcc gatcttgcct acccttctcg accaggtcgg tgccccgac     8460 gacatgatcc cactgcacgt cggactactg acagcgctct atgcgatcat gcagtttctt    8520 tgcgcccga tccttggccg actctctgac cgtttcggac gccgccgcgt gcttgtcgcc     8580
tccctcgcag gcgcgacgat cgactacctc gtgctcgcac tgacggacac gctgtgggtc    8640
ttttacctcg cccgcgcggt tgcaggcatt accggcgcca cgaacgccgt caccgcgacg    8700
gtgatcgccg acattactcc gccggatcag cgcgcaaaac gctacgggtg gctcggcgca    8760
tgctacggcg gtggcatgat cgcgggtccc gccattggcg gtcttttcgg cggggtctca    8820
ccgcatctgc cattcctcgt cgccgccgcg ctcgccggaa tcaccctcgt actcagcgcg    8880
agtcttctgc gtgagacgcg gccaccgggc agcaacggct cgcacgcaca gcaacccggt    8940
acggcgaagc gaaccgcagt gccggggatg cttatccttc tcgcagtctt cggcatcgtg    9000
cagttcatcg gccaagcacc aggctccacc tgggtgctct tcacgcagca gcgcctcgac    9060
tggaaccccg tcgaagtcgg cgtttcgcta tccatcttcg gaatggtgca agtattcgtg    9120
caggcggcac tgaccggacg catcgtgtcc cggatcggcg agacccgggc gatcctcgtc    9180
ggtatcgccg cagacgccat gggctcatc ggccttgccc tcatcgccag cacatgggcg     9240
atgctaccga tcctcgcagc gctcggactc ggcagcatca cgttgcccgc actgcagacg    9300
ctgctctcga gacgcgcgcc cgagcagcag cagggacgcc tgcagggaac acttgcaagc    9360
ctgaacagcc tcacctcgat catcggcccg gtcaccttca ccggcatttt cgcactcacc    9420
cgaacgaatg cagacggcac cctctggatc tgccgcag cgctctacgt tctctgcgcc      9480
ctcctgatga tccgtgagac atgcgcctca cggcgatctc gataaccgcg ctaaggtgcc    9540
atcccgatgc gacgggatcg ctctgccacc agtcaagtct cccgtagccg gtatgagcat    9600
gaccaaaatc ccttaacgtg agttttcgtt ccactgagcg tcagacccg tagaaaagat     9660 caaaggatct tcttgagatc cttttttct gcgcgtaatc tgctgcttgc aaacaaaaaa     9720
accaccgcta ccagcggtgg tttgtttgcc ggatcaagag ctaccaactc tttttccgaa    9780
ggtaactggc ttcagcagag cgcagatacc aaatactgtc cttctagtgt agccgtagtt    9840
aggccaccac ttcaagaact ctgtagcacc gcctacatac ctcgctctgc taatcctgtt    9900
accagtggct gctgccagtg gcgataagtc gtgtcttacc gggttggact caagacgata    9960
gttaccggat aaggcgcagc ggtcgggctg aacggggggt tcgtgcacac agcccagctt    10020
ggagcgaacg acctacaccg aactgagata cctacagcgt gagctatgag aaagcgccac    10080
gcttcccgaa gggagaaagg cggacaggta tccggtaagc ggcagggtcg aacaggaga    10140 gcgcacgagg gagcttccag ggggaaacgc ctggtatctt tatagtcctg tcgggtttcg    10200
ccacctctga cttgagcgtc gatttttgtg atgctcgtca ggggggcgga gcctatggaa    10260
```

| | | | | |
|---|---|---|---|---|
| aaacgccagc | aacgcggcct | ttttacggtt | cctggccttt | tgctggcctt | ttgctcacat | 10320 |
| gttctttcct | gcgttatccc | ctgattctgt | ggataaccgt | attaccgcct | ttgagtgagc | 10380 |
| tgataccgct | cgccgcagcc | gaacgaccga | gcgcagcgag | tcagtgagcg | aggaagcgga | 10440 |
| agagcgcctg | atgcggtatt | ttctccttac | gcatctgtgc | ggtatttcac | accgcatatg | 10500 |
| gtgcactctc | agtacaatct | gctctgatgc | cgcatagtta | agccagtata | cactccgcta | 10560 |
| tcgctacgtg | actgggtcat | ggctgcgccc | cgacacccgc | caacacccgc | tgacgcgccc | 10620 |
| tgacgggctt | gtctgctccc | ggcatccgct | tacagacaag | ctgtgaccgt | ctccgggagc | 10680 |
| tgcatgtgtc | agaggttttc | accgtcatca | ccgaaacgcg | cgaggcagca | gatcaattcg | 10740 |
| cgcgcgaagg | cgaagcggca | tgcatttacg | ttgacaccat | cgaatggtgc | aaaacctttc | 10800 |
| gcggtatggc | atgatagcgc | ccggaagaga | gtcaattcag | ggtggtgaat | gtgaaaccag | 10860 |
| taacgttata | cgatgtcgca | gagtatgccg | gtgtctctta | tcagaccgtt | tcccgcgtgg | 10920 |
| tgaaccaggc | cagccacgtt | tctgcgaaaa | cgcgggaaaa | agtggaagcg | gcgatggcgg | 10980 |
| agctgaatta | cattcccaac | cgcgtggcac | aacaactggc | gggcaaacag | tcgttgctga | 11040 |
| ttggcgttgc | cacctccagt | ctggccctgc | acgcgccgtc | gcaaattgtc | gcggcgatta | 11100 |
| aatctcgcgc | cgatcaactg | ggtgccagcg | tggtggtgtc | gatggtagaa | cgaagcggcg | 11160 |
| tcgaagcctg | taaagcggcg | gtgcacaatc | ttctcgcgca | acgcgtcagt | gggctgatca | 11220 |
| ttaactatcc | gctggatgac | caggatgcca | ttgctgtgga | agctgcctgc | actaatgttc | 11280 |
| cggcgttatt | tcttgatgtc | tctgaccaga | cacccatcaa | cagtattatt | ttctcccatg | 11340 |
| aagacggtac | gcgactgggc | gtggagcatc | tggtcgcatt | gggtcaccag | caaatcgcgc | 11400 |
| tgttagcggg | cccattaagt | tctgtctcgg | cgcgtctgcg | tctggctggc | tggcataaat | 11460 |
| atctcactcg | caatcaaatt | cagccgatag | cggaacggga | aggcgactgg | agtgccatgt | 11520 |
| ccggttttca | acaaaccatg | caaatgctga | atgagggcat | cgttcccact | gcgatgctgg | 11580 |
| ttgccaacga | tcagatggcg | ctgggcgcaa | tgcgcgccat | taccgagtcc | gggctgcgcg | 11640 |
| ttggtgcgga | tatctcggta | gtgggatacg | acgataccga | agacagctca | tgttatatcc | 11700 |
| cgccgtcaac | caccatcaaa | caggattttc | gcctgctggg | gcaaaccagc | gtggaccgct | 11760 |
| tgctgcaact | ctctcagggc | caggcggtga | agggcaatca | gctgttgccc | gtctcactgg | 11820 |
| tgaaaagaaa | aaccaccctg | gcgcccaata | cgcaaaccgc | ctctccccgc | gcgttggccg | 11880 |
| attcattaat | gcagctggca | cgacaggttt | cccgactgga | aagcgggcag | tgagcgcaac | 11940 |
| gcaattaatg | tgagttagcg | cgaattgatc | tggtttgaca | gcttatcatc | gactgcacgg | 12000 |
| tgcaccaatg | cttctggcgt | caggcagcca | tcggaagctg | tggtatggct | gtgcaggtcg | 12060 |
| taaatcactg | cataattcgt | gtcgctcaag | gcgcactccc | gttctggata | atgttttttg | 12120 |
| cgccgacatc | ataacggttc | tggcaaatat | tctgaaatga | gctgttgaca | attaatcatc | 12180 |
| cggctcgtat | aatgtgtgga | attgtgagcg | gataacaatt | tcacacagga | aacagaccat | 12240 |
| ggaattcgag | ctcggtaccc | ggg | | | | 12263 |

<210> SEQ ID NO 56
<211> LENGTH: 8471
<212> TYPE: DNA
<213> ORGANISM: Artificial Sequence
<220> FEATURE:
<223> OTHER INFORMATION: vector

<400> SEQUENCE: 56

| | | | | | | |
|---|---|---|---|---|---|---|
| aagcttgcat | gcctgcaggt | cgactctaga | ggatccccgg | gtaccgagct | cgaattcact | 60 |

```
ggccgtcgtt ttacagccaa gcttggctgt tttggcggat gagagaagat tttcagcctg    120
atacagatta aatcagaacg cagaagcggt ctgataaaac agaatttgcc tggcggcagt    180
agcgcggtgg tcccacctga ccccatgccg aactcagaag tgaaacgccg tagcgccgat    240
ggtagtgtgg ggtctcccca tgcgagagta gggaactgcc aggcatcaaa taaaacgaaa    300
ggctcagtcg aaagactggg cctttcgttt tatctgttgt ttgtcggtga acgctctcct    360
gagtaggaca atccgccgg gagcggattt gaacgttgcg aagcaacggc ccggagggtg    420
gcgggcagga cgcccgccat aaactgccag gcatcaaatt aagcagaagg ccatcctgac    480
ggatggcctt tttgcgtttc tacaaactct tttgtttatt tttctaaata cattcaaata    540
tgtatccgct catgagacaa taaccctgat aaatgcttca ataatattga aaaggaaga    600 gtatgagtat tcaacatttc cgtgtcgccc ttattccctt ttttgcggca ttttgccttc    660 ctgttttgc tcacccagaa acgctggtga agtaaaaga tgctgaagat cagttgggtg    720
cacgagtggg ttacatcgaa ctggatctca acagcggtaa gatccttgag agttttcgcc    780
ccgaagaacg ttttccaatg atgagcactt ttgatccccc tgcggcgtcg ctgatcgccc    840
tcgcgacgtt gtgcgggtgg cttgtccctg agggcgctgc gacagatagc taaaaatctg    900
cgtcaggatc gccgtagagc gcgcgtcgcg tcgattggag gcttccccttt tggttgacgg    960 tcttcaatcg ctctacggcg atcctgacgc tttttttgttg cgtaccgtcg atcgttttat   1020
ttctgtcgat cccgaaaaag tttttgcctt ttgtaaaaaa cttctcggtc gccccgcaaa   1080
ttttcgattc cagattttttt aaaaaccaag ccagaaatac gacacaccgt ttgcagataa   1140
tctgtctttc ggaaaaatca agtgcgatac aaaattttta gcacccctga gctgcgcaaa   1200
gtcccgcttc gtgaaaattt tcgtgccgcg tgattttccg ccaaaaactt taacgaacgt   1260
tcgttataat ggtgtcatga ccttcacgac gaagtaccaa aattggcccg aatcatcagc   1320
tatggatctc tctgatgtcg cgctggagtc gacgcgctc gatgctgccg tcgatttaaa   1380
aacggtgatc ggatttttcc gagctctcga tacgacggac gcgccagcat cacgagactg   1440
ggccagtgcc gcgagcgacc tagaaactct cgtggcggat cttgaggagc tggctgacga   1500
gctgcgtgct cggcagcgcc aggaggacgc acagtagtgg aggatcgaat cagttgcgcc   1560
tactgcggtg gcctgattcc tccccggcct gacccgcgag acggcgcgc aaaatattgc   1620 tcagatgcgt gtcgtgccgc agccagccgc gagcgcgcca acaaacgcca cgccgaggag   1680
ctggaggcgg ctaggtcgca aatggcgctg gaagtgcgtc ccccgagcga aattttggcc   1740
atggtcgtca cagagctgga agcggcagcg agaattatcc gcgatcgtgg cgcggtgccc   1800
gcaggcatga caaacatcgt aaatgccgcg tttcgtgtgg ccgtggccgc caggacgtg   1860 tcagcgccgc caccacctgc accgaatcgg cagcagcgtc cgcgcgtcgaa aaagcgcaca   1920 ggcggcaaga agcgataagc tgcacgaata cctgaaaaat gttgaacgcc ccgtgagcgg   1980
taactcacag ggcgtcggct aaccccccagt ccaaacctgg gagaaagcgc tcaaaaatga   2040
ctctagcgga ttcacgagac attgacacac cggcctggaa attttccgct gatctgttcg   2100
acacccatcc cgagctcgcg ctgcgatcac gtggctggac gagcgaagac cgccgcgaat   2160
tcctcgctca cctgggcaga gaaaatttcc agggcagcaa gacccgcgac ttcgccagcg   2220
cttggatcaa agacccggac acgggagaaa cacagccgaa gttataccga gttggttcaa   2280
aatcgcttgc ccggtgccag tatgttgctc tgacgcacgc gcagcacgca gccgtgcttg   2340
tcctggacat tgatgtgccg agccaccagg ccggcgggaa aatcgagcac gtaaaccccg   2400
```

```
aggtctacgc gattttggag cgctgggcac gcctggaaaa agcgccagct tggatcggcg    2460
tgaatccact gagcgggaaa tgccagctca tctggctcat tgatccggtg tatgccgcag    2520
caggcatgag cagcccgaat atgcgcctgc tggctgcaac gaccgaggaa atgacccgcg    2580
ttttcggcgc tgaccaggct ttttcacata ggctgagccg gtggccactg cacgtctccg    2640 acgatccac cgcgtaccgc tggcatgccc agcacaatcg cgtggatcgc ctagctgatc    2700
ttatggaggt tgctcgcatg atctcaggca cagaaaaacc taaaaaacgc tatgagcagg    2760
agttttctag cggacgggca cgtatcgaag cggcaagaaa agccactgcg gaagcaaaag    2820
cacttgccac gcttgaagca agcctgccga gcgccgctga agcgtctgga gagctgatcg    2880
acggcgtccg tgtcctctgg actgctccag ggcgtgccgc ccgtgatgag acggcttttc    2940
gccacgcttt gactgtggga taccagttaa aagcggctgg tgagcgccta aaagacacca    3000
agatcatcga cgcctacgag cgtgcctaca ccgtcgctca ggcggtcgga gcagacggcc    3060
gtgagcctga tctgccgccg atgcgtgacc gccagacgat ggcgcgacgt gtgcgcggct    3120
acgtcgctaa aggccagcca gtcgtccctg ctcgtcagac agagacgcag agcagccgag    3180
ggcgaaaagc tctggccact atgggaagac gtggcggtaa aaaggccgca gaacgctgga    3240
aagacccaaa cagtgagtac gcccgagcac agcgagaaaa actagctaag tccagtcaac    3300
gacaagctag gaaagctaaa ggaaatcgct tgaccattgc aggttggttt atgactgttg    3360
agggagagac tggctcgtgg ccgacaatca atgaagctat gtctgaattt agcgtgtcac    3420
gtcagaccgt gaatagagca cttaagtctg cgggcattga acttccacga ggacgccgta    3480
aagcttccca gtaaatgtgc catctcgtag gcagaaaacg gttcccccg taggggtctc    3540 tctcttggcc tcctttctag gtcgggctga ttgctcttga agctctctag gggggctcac    3600
accataggca gataacggtt ccccaccggc tcacctcgta agcgcacaag gactgctccc    3660
aaagatcttc aaagccactg ccgcgactcc gcttcgcgaa gccttgcccc gcggaaattt    3720
cctccaccga gttcgtgcac acccctatgc caagcttctt tcaccctaaa ttcgagagat    3780
tggattctta ccgtggaaat tcttcgcaaa atcgtcccc tgatcgccct gcgacgttg     3840 ctcgcggcgg tgccgctggt tgcgcttggc ttgaccgact tgatcctccg gcgttcagcc    3900
tgtgccacag ccgacaggat ggtgaccacc atttgcccca tatcaccgtc ggtactgatc    3960
ccgtcgtcaa taaccgaac cgctacaccc tgagcatcaa actctttat cagttggatc      4020 atgtcggcgg tgtcgcggcc aagacggtcg agcttcttca ccagaatgac atcaccttcc    4080
tccaccttca tcctcagcaa atccagccct tcccgatctg ttgaactgcc ggatgccttg    4140
tcggtaaaga tgcggttagc ttttacccct gcatctttga gcgctgaggt ctgcctcgtg    4200
aagaaggtgt tgctgactca taccaggcct gaatcgcccc atcatccagc cagaaagtga    4260
gggagccacg gttgatgaga gctttgttgt aggtggacca gttggtgatt ttgaacttt    4320 gctttgccac ggaacggtct gcgttgtcgg gaagatgcgt gatctgatcc ttcaactcag    4380
caaaagttcg atttattcaa caaagccgcc gtcccgtcaa gtcagcgtaa tgctctgcca    4440
gtgttacaac caattaacca attctgatta gaaaaactca tcgagcatca aatgaaactg    4500
caatttattc atatcaggat tatcaatacc atattttga aaaagccgtt tctgtaatga    4560
aggagaaaac tcaccgaggc agttccatag gatggcaaga tcctggtatc ggtctgcgat    4620
tccgactcgt ccaacatcaa tacaacctat taatttcccc tcgtcaaaaa taaggttatc    4680
aagtgagaaa tcaccatgag tgacgactga atccggtgag aatggcaaaa gcttatgcat    4740
ttctttccag acttgttcaa caggccagcc attacgctcg tcatcaaaat cactcgcatc    4800
```

```
aaccaaaccg ttattcattc gtgattgcgc ctgagcgaga cgaaatacgc gatcgctgtt    4860
aaaaggacaa ttacaaacag gaatcgaatg caaccggcgc aggaacactg ccagcgcatc    4920
aacaatattt tcacctgaat caggatattc ttctaatacc tggaatgctg ttttcccggg    4980
gatcgcagtg gtgagtaacc atgcatcatc aggagtacgg ataaaatgct tgatggtcgg    5040
aagaggcata aattccgtca gccagtttag tctgaccatc tcatctgtaa catcattggc    5100
aacgctacct ttgccatgtt tcagaaacaa ctctggcgca tcgggcttcc catacaatcg    5160
atagattgtc gcacctgatt gcccgacatt atcgcgagcc catttatacc catataaatc    5220
agcatccatg ttggaattta atcgcggcct cgagcaagac gtttcccgtt gaatatggct    5280
cataacaccc cttgtattac tgtttatgta agcagacagt tttattgttc atgatgatat    5340 attttttatct tgtgcaatgt aacatcagag attttgagac acaacgtggc tttgttgaat    5400
aaatcgaact tttgctgagt tgaaggatca gatcacgcat cttcccgaca acgcagaccg    5460
ttccgtggca aagcaaaagt tcaaaatcac caactggtcc acctacaaca aagctctcat    5520
caaccgtggc tccctcactt tctggctgga tgatgggggcg attcaggcct ggtatgagtc    5580
agcaacacct tcttcacgag gcagacctca gcgctagcgg agtgtatact ggcttactat    5640
gttggcactg atgagggtgt cagtgaagtg cttcatgtgg caggagaaaa aaggctgcac    5700
cggtgcgtca gcagaatatg tgatacagga tatattccgc ttcctcgctc actgactcgc    5760
tacgctcggt cgttcgactg cggcgagcgg aaatggctta cgaacggggc ggagatttcc    5820
tggaagatgc caggaagata cttaacaggg aagtgagagg gccgcggcaa agccgttttt    5880
ccataggctc cgccccctg acaagcatca cgaaatctga cgctcaaatc agtggtggcg    5940
aaacccgaca ggactataaa gataccaggc gtttccccct ggcggctccc tcgtgcgctc    6000
tcctgttcct gcctttcggt ttaccggtgt cattccgctg ttatggccgc gtttgtctca    6060
ttccacgcct gacactcagt tccgggtagg cagttcgctc caagctggac tgtatgcacg    6120 aacccccccgt tcagtccgac cgctgcgcct tatccggtaa ctatcgtctt gagtccaacc    6180
cggaaagaca tgcaaaagca ccactggcag cagccactgg taattgattt agaggagtta    6240
gtcttgaagt catgcgccgg ttaaggctaa actgaaagga caagttttgg tgactgcgct    6300
cctccaagcc agttacctcg gttcaaagag ttggtagctc agagaaccct cgaaaaaccg    6360
ccctgcaagg cggttttttc gttttcagag caagagatta cgcgcagacc aaaacgatct    6420
caagaagatc atcttattaa ggggtctgac gctcagtgga acgaaaactc acgttaaggg    6480
attttggtca tgagattatc aaaaaggatc ttcacctaga tccttttaaa ttaaaaatga    6540
agttttaaat caatctaaag tatatatgag taaacttggt ctgacagtta ccaatgctta    6600
atcagtgagg cacctatctc agcgatctgt ctatttcgtt catccatagt tgcctgactc    6660
cccgtcgtgt agataactac gatacgggag ggcttaccat ctggccccag tgctgcaatg    6720
ataccgcgag acccacgctc accggctcca gatttatcag caataaacca gccagccgga    6780
agggccgagc gcagaagtgg tcctgcaact ttatccgcct ccatccagtc tattaattgt    6840
tgccgggaag ctagagtaag tagttcgcca gttaatagtt tgcgcaacgt tgttgccatt    6900
gccgatgata agctgtcaaa catggcctgt cgcttgcggt attcggaatc ttgcacgccc    6960
tcgctcaagc cttcgtcact ggtcccgcca ccaaacgttt cggcgagaag caggccatta    7020
tcgccggcat ggcggccgac gcgcggggag aggcggtttg cgtattgggc gccagggtgg    7080
tttttctttt caccagtgag acgggcaaca gctgattgcc cttcaccgcc tggccctgag    7140
```

| | | |
|---|---|---|
| agagttgcag caagcggtcc acgctggttt gccccagcag gcgaaaatcc tgtttgatgg | 7200 | |
| tggttaacgg cgggatataa catgagctgt cttcggtatc gtcgtatccc actaccgaga | 7260 | |
| tatccgcacc aacgcgcagc ccggactcgg taatggcgcg cattgcgccc agcgccatct | 7320 | |
| gatcgttggc aaccagcatc gcagtgggaa cgatgccctc attcagcatt tgcatggttt | 7380 | |
| gttgaaaacc ggacatggca ctccagtcgc cttcccgttc cgctatcggc tgaatttgat | 7440 | |
| tgcgagtgag atatttatgc cagccagcca gacgcagacg cgccgagaca gaacttaatg | 7500 | |
| ggcccgctaa cagcgcgatt tgctggtgac ccaatgcgac cagatgctcc acgcccagtc | 7560 | |
| gcgtaccgtc ttcatgggag aaaataatac tgttgatggg tgtctggtca gagacatcaa | 7620 | |
| gaaataacgc cggaacatta gtgcaggcag cttccacagc aatggcatcc tggtcatcca | 7680 | |
| gcggatagtt aatgatcagc ccactgacgc gttgcgcgag aagattgtgc accgccgctt | 7740 | |
| tacaggcttc gacgccgctt cgttctacca tcgacaccac cacgctggca cccagttgat | 7800 | |
| cggcgcgaga tttaatcgcc gcgacaattt gcgacggcgc gtgcagggcc agactggagg | 7860 | |
| tggcaacgcc aatcagcaac gactgtttgc ccgccagttg ttgtgccacg cggttgggaa | 7920 | |
| tgtaattcag ctccgccatc gccgcttcca cttttcccg cgtttcgca gaaacgtggc | 7980 | |
| tggcctggtt caccacgcgg gaaacggtct gataagagac accggcatac tctgcgacat | 8040 | |
| cgtataacgt tactggtttc acattcacca ccctgaattg actctcttcc gggcgctatc | 8100 | |
| atgccatacc gcgaaaggtt ttgcaccatt cgatggtgtc aacgtaaatg catgccgctt | 8160 | |
| cgccttcgcg cgcgaattgc aagctgatcc gggcttatcg actgcacggt gcaccaatgc | 8220 | |
| ttctggcgtc aggcagccat cggaagctgt ggtatgctg tgcaggtcgt aaatcactgc | 8280 | |
| ataattcgtg tcgctcaagg cgcactcccg ttctggataa tgttttttgc gccgacatca | 8340 | |
| taacggttct ggcaaatatt ctgaaatgag ctgttgacaa ttaatcatcg gctcgtataa | 8400 | |
| tgtgtggaat tgtgagcgga taacaatttc acacaggaaa cagaattaaa agatatgacc | 8460 | |
| atgattacgc c | 8471 | |

<210> SEQ ID NO 57
<211> LENGTH: 12311
<212> TYPE: DNA
<213> ORGANISM: Artificial Sequence
<220> FEATURE:
<223> OTHER INFORMATION: vector

<400> SEQUENCE: 57

| | | |
|---|---|---|
| aagcttgcat gcctgcaggt cgactctaga attaatgcag ctggcacgac aggtttcccg | 60 | |
| actggaaagc gggcagtgag cgcaacgcaa ttaatgtgag ttagctcact cattaggcac | 120 | |
| cccaggcttt acactttatg cttccggctc gtatgttgtg tggaattgtg agcggataac | 180 | |
| aatttcacac aggaaacagc tatgaccatg attacgccaa gcgcgcaatt aaccctcact | 240 | |
| aaagggaaca aaagctgggt accgggcccc cctcgaggt cgacggtatc gataagcttg | 300 | |
| atatcgaatt cgcgtcatct gtctacgaca acacctttg tccaattaga gccaaattat | 360 | |
| gattctagta acaggcggag ccggcttcat cggctcaaat ttcgtactgc aatggtgtgc | 420 | |
| gcacaatgag gaacccgtcc tcaacctcga cgccctgacc tacgcaggca acctggccaa | 480 | |
| cctgcagccg ctggaaggca accctcagca tcgctttgtg caaggcaata tttgcgatgc | 540 | |
| tgcgcttctg accaagctgt cgcagagca ccgcccgcgc gccgtggttc acttcgcggc | 600 | |
| ggaatcccat gtagaccgct caatcaccgg ccccgaagcg tttgtcgaaa ccaacgtgat | 660 | |
| gggcacgttt cgcttgcttg aagccgcccg ggcgcattgg aatagtttgg aaggtgcaga | 720 | |

-continued

| | |
|---|---|
| gaaggaggcc ttccgtttcc tccatgtctc taccgacgaa gtctacggca cactagggcc | 780 |
| aaacgacccg gcgttcaccg aaaccacgcc gtacgcgccg aacagcccat actccgccag | 840 |
| caaggcagcc agcgaccatc tggtacgctc gtatttccat acctacggca tgccggtact | 900 |
| cactaccaac tgctccaaca attacgggcc gctccacttc ccggaaaaac tgatcccgct | 960 |
| gatgatcgtc aacgcactcg ccggtaaggc gctgcctgtc tatggcgacg ccagcaaat | 1020 |
| ccgcgactgg ctgtatgtcg aagatcactg ctcgggcatc cgtcgcgtac tggaagccgg | 1080 |
| tgcgttcggc gagacgtaca atattggcgg ctggaatgaa aaagccaaca ttgacattgt | 1140 |
| gcgtacactc tgcagccttc tcgacgagat ggcacctgcg gcatcgcgcc aggtaatcaa | 1200 |
| tcagaagacc ggcgagcctg tcaacagta tgcagaactc atcgcctacg taaccgaccg | 1260 |
| cccaggccat gaccgccgtt atgccatcga tgcacgcaag atcgagcggg agctcggctg | 1320 |
| gaaacctgcc gaaaccttcg agacgggcat tcgaaagaca gtcgcttggt acttggccaa | 1380 |
| ccagaaatgg gtaaaaggtg tcatggacgg cagctaccgt gactgggtgg cacaacaata | 1440 |
| cggggcaaat aaagcgtgaa atcctgctg ttggggaaaa acgggcaagt aggctgggag | 1500 |
| ctacagcgcg ccttggcgcc gctgggtgag gtcattgcgc tggatcgtca gggggccgag | 1560 |
| ggcttatgtg gcgacttgtc caacctggac ggcttggccg ctacgattcg tcagctggcg | 1620 |
| ccggacgtga tcgtcaacgc tgctgcctac actgcagtgg ataaagctga gagcgatcag | 1680 |
| gcactggctg caatgatcaa tgccgcggct cctgctgtat tagcacgtga acagcagct | 1740 |
| ttgggcgcct ggttgattca ctattccacc gattatgtat ttgacggcag cggcagtcag | 1800 |
| cgctgggagg aaactgcgcc taccggcccc ctttcggtct acgccggac caagctggaa | 1860 |
| ggcgagcatg ccattctcgc cagcggcgcc aaggccgtgg tactgcgcac cagctgggtg | 1920 |
| tatgctgcgc gcgggcacaa ttttgccaag accatgctgc gcctggcggc ggagcgtgag | 1980 |
| acgttgagcg tggtagcaga ccaatttggc gcacccacgg gcgctgacct gatcgccgac | 2040 |
| gttactgcac acatcctgcg gcaaatcttc aatgggcaag acaaccgtca cctggcaggg | 2100 |
| atttaccact tggctgcgtc cggtgaaacc tcttggcatg gttttgctca gttcgtgctg | 2160 |
| gcgcatgctc aacgcactgg cgtagcgctg aaagtgacag ctgataaggt tgccgcaatc | 2220 |
| agcaccgaag cttatccagt acctgcacca cgtccgcgca actcgcgcct ggcactgggc | 2280 |
| aaactggaaa acacgttcaa tttcaaaatg ccgctttggg agcaaggcgt gcaacgtatg | 2340 |
| ctggacgaaa tccagtaata gggactctca tggctcgtaa aggaattatt ctggccggcg | 2400 |
| gttcgggtac acgcctgcat ccggccacac tttcggtttc gaagcagctg ctgccggtgt | 2460 |
| atgacaaacc gatgatctac taccgctga gcaccctgct gctcgctggt atccgggaca | 2520 |
| tcctgatcat ttccaccccg caggacaccc cgcgcttcga acagctgctg ggcgatggca | 2580 |
| gccagtgggg cctgaacctg tcatacgcaa tacaaccaag cccggatggc ttggcgcaag | 2640 |
| cgttcaccat cggcgctgac ttcatcggta acgaccttc tgcgttggtt ctcggtgaca | 2700 |
| atattttcta cggccatgac ttccaggcac tgctattgaa cgcagataaa cgtgaatccg | 2760 |
| gtgcttcagt attcgcttat catgttcatg acccagaacg ctatggcgta gcggagtttg | 2820 |
| acgatagcgg tcgcgtattg tcgctggaag aaaaaccggc agttccaaag tctagctatg | 2880 |
| cggtcaccgg cctgtatttc tatgacaatc aggtagtcaa tctggctcgc gagctgaagc | 2940 |
| cttccccacg tggcgagctg gaaatcaccg acctcaacaa cctttacttg cagcagcagc | 3000 |
| agttgcaggt cgaaatcatg ggccgtggct atgcgtggct cgacaccggc acgcacgaca | 3060 |

```
gtctgctgga ggctagccag tacatcgcaa ccatggagcg ccgtcagggc ttgaaagtcg    3120
cctgccctga ggaaatttgc taccgcgctg gctggatcaa cgctgagcaa ctcgagtgcc    3180
tggctcaacc actgctgaaa aacggttatg gcaagtatct gcagaacttg ctgaaagaga    3240
aggtgttctg atgcaagcca ttccgctgga tatccccgaa gtcgtgctgt ttaccccccaa    3300
ggttttttggc gacgaacgtg gtttcttcta cgagagcttc aacgcccgtg ttttcagcga    3360
agtgaccggc ctgcagcccg acttcgtaca agacaaccac tcgcgctcgg taaaaggcgt    3420
gctccgtggc ctgcactatc agctggcacc tcacgcccag ggcaagctgg tgcgtgtggt    3480
gcaaggcgaa gtcttcgatg ttgcggtgga tatccgtcgc tcgtccacaa ccttcggtaa    3540
atgggtaggt gcggtgttgt cggccgagaa caagaaccag ctgtggatcc cgccagggtt    3600
cgcacacggg ttcgtcacgt tgagtgaaac cgcagagttc ctctacaaga ccaccgactt    3660
ctactcgccg cagtgcgagc gctgcattgc ctggaatgat ccggcagtgg gtatcgaatg    3720
gcccatcgac tccgtaccaa gcttgtctgg caaggaccag cttggggtcg cattggctga    3780
cgccgaactg ttcgactaac ggttttagcg gagaagggct gcggtagcgc agccgaattc    3840
ctgcagcccg ggggatccac tagttctaga ggatccccgg gtaccgagct cgaattcact    3900
ggccgtcgtt ttacagccaa gcttggctgt tttggcggat gagagaagat ttcagcctg    3960
atacagatta aatcagaacg cagaagcggt ctgataaaac agaatttgcc tggcggcagt    4020
agcgcggtgg tcccacctga ccccatgccg aactcagaag tgaaacgccg tagcgccgat    4080
ggtagtgtgg ggtctcccca tgcgagagta gggaactgcc aggcatcaaa taaaacgaaa    4140
ggctcagtca aaagactggg cctttcgttt tatctgttgt ttgtcggtga acgctctcct    4200
gagtaggaca aatccgccgg gagcggattt gaacgttgcg aagcaacggc ccggagggtg    4260
gcgggcagga cgcccgccat aaactgccag gcatcaaatt aagcagaagg ccatcctgac    4320
ggatggcctt tttgcgtttc tacaaactct tttgtttatt tttctaaata cattcaaata    4380
tgtatccgct catgagacaa taaccctgat aaatgcttca ataatattga aaaggaaga    4440
gtatgagtat tcaacatttc cgtgtcgccc ttattccctt ttttgcggca ttttgccttc    4500
ctgttttttgc tcacccagaa acgctggtga agtaaaaga tgctgaagat cagttgggtg    4560
cacgagtggg ttacatcgaa ctggatctca acagcggtaa gatccttgag agttttcgcc    4620
ccgaagaacg ttttccaatg atgagcactt tgatccccc tgcggcgtcg ctgatcgccc    4680
tcgcgacgtt gtgcgggtgg cttgtccctg agggcgctgc gacagatagc taaaaatctg    4740
cgtcaggatc gccgtagagc gcgcgtcgcg tcgattggag gcttcccctt tggttgacgg    4800
tcttcaatcg ctctacggcg atcctgacgc ttttttgttg cgtaccgtcg atcgttttat    4860
ttctgtcgat cccgaaaaag ttttttgcctt ttgtaaaaaa cttctcggtc gccccgcaaa    4920
ttttcgattc cagatttttt aaaaaccaag ccagaaatac gacacaccgt ttgcagataa    4980
tctgtctttc ggaaaaatca agtgcgatac aaaattttta gcacccctga ctgcgcaaa    5040
gtcccgcttc gtgaaaattt tcgtgccgcg tgattttccg ccaaaaactt taacgaacgt    5100
tcgttataat ggtgtcatga ccttcacgac gaagtaccaa aattggcccg aatcatcagc    5160
tatggatctc tctgatgtcg cgctggagtc cgacgcgctc gatgctgccg tcgatttaaa    5220
aacggtgatc ggattttttcc gagctctcga tacgacggac gcgccagcat cacgagactg    5280
ggccagtgcc gcgagcgacc tagaaactct cgtggcggat cttgaggagc tggctgacga    5340
gctgcgtgct cggcagcgcc aggaggacgc acagtagtgg aggatcgaat cagttgcgcc    5400
tactgcggtg gcctgattcc tccccggcct gacccgcgag gacggcgcgc aaaatattgc    5460
```

```
tcagatgcgt gtcgtgccgc agccagccgc gagcgcgcca acaaacgcca cgccgaggag   5520
ctggaggcgg ctaggtcgca aatggcgctg gaagtgcgtc ccccgagcga aattttggcc   5580
atggtcgtca cagagctgga agcggcagcg agaattatcc gcgatcgtgg cgcggtgccc   5640
gcaggcatga caaacatcgt aaatgccgcg tttcgtgtgg ccgtggccgc ccaggacgtg   5700
tcagcgccgc caccacctgc accgaatcgg cagcagcgtc gcgcgtcgaa aaagcgcaca   5760
ggcggcaaga agcgataagc tgcacgaata cctgaaaaat gttgaacgcc ccgtgagcgg   5820
taactcacag ggcgtcggct aaccccccagt ccaaacctgg gagaaagcgc tcaaaaatga   5880
ctctagcgga ttcacgagac attgacacac cggcctggaa attttccgct gatctgttcg   5940
acacccatcc cgagctcgcg ctgcgatcac gtggctggac gagcgaagac cgccgcgaat   6000
tcctcgctca cctgggcaga gaaaatttcc agggcagcaa gacccgcgac ttcgccagcg   6060
cttggatcaa agacccggac acgggagaaa cacagccgaa gttataccga gttggttcaa   6120
aatcgcttgc ccggtgccag tatgttgctc tgacgcacgc gcagcacgca gccgtgcttg   6180
tcctggacat tgatgtgccg agccaccagg ccggcgggaa aatcgagcac gtaaaccccg   6240
aggtctacgc gattttggag cgctgggcac gcctggaaaa agcgccagct tggatcggcg   6300
tgaatccact gagcgggaaa tgccagctca tctggctcat tgatccggtg tatgccgcag   6360
caggcatgag cagcccgaat atgcgcctgc tggctgcaac gaccgaggaa atgacccgcg   6420
ttttcggcgc tgaccaggct ttttcacata ggctgagccg gtggccactg cacgtctccg   6480
acgatcccac cgcgtaccgc tggcatgccc agcacaatcg cgtggatcgc ctagctgatc   6540
ttatggaggt tgctcgcatg atctcaggca cagaaaaacc taaaaaacgc tatgagcagg   6600
agttttctag cggacgggca cgtatcgaag cggcaagaaa agccactgcg gaagcaaaag   6660
cacttgccac gcttgaagca agcctgccga gcgccgctga agcgtctgga gagctgatcg   6720
acggcgtccg tgtcctctgg actgctccag ggcgtgccgc ccgtgatgag acggcttttc   6780
gccacgcttt gactgtggga taccagttaa aagcggctgg tgagcgccta aaagacacca   6840
agatcatcga cgcctacgag cgtgcctaca ccgtcgctca ggcggtcgga gcagacggcc   6900
gtgagcctga tctgccgccg atgcgtgacc gccagacgat ggcgcgacgt gtgcgcggct   6960
acgtcgctaa aggccagcca gtcgtccctg ctcgtcagac agagacgcag agcagccgag   7020
ggcgaaaagc tctggccact atgggaagac gtggcggtaa aaaggccgca gaacgctgga   7080
aagacccaaa cagtgagtac gcccgagcac agcgagaaaa actagctaag tccagtcaac   7140
gacaagctag gaaagctaaa ggaaatcgct tgaccattgc aggttggttt atgactgttg   7200
agggagagac tggctcgtgg ccgacaatca atgaagctat gtctgaattt agcgtgtcac   7260
gtcagaccgt gaatagagca cttaagtctg cgggcattga acttccacga ggacgccgta   7320
aagcttccca gtaaatgtgc catctcgtag gcagaaaacg gttcccccg tagggggtctc   7380
tctcttggcc tccttctag gtcgggctga ttgctcttga agctctctag gggggctcac   7440
accataggca gataacggtt ccccaccggc tcacctcgta agcgcacaag gactgctccc   7500
aaagatcttc aaagccactg ccgcgactcc gcttcgcgaa gccttgcccc gcggaaattt   7560
cctccaccga gttcgtgcac accctatgc caagcttctt tcacccctaaa ttcgagagat   7620
tggattctta ccgtggaaat tcttcgcaaa aatcgtcccc tgatcgccct tgcgacgttg   7680
ctcgcggcgg tgccgctggt tgcgcttggc ttgaccgact tgatcctccg gcgttcagcc   7740
tgtgccacag ccgacaggat ggtgaccacc atttgcccca tatcaccgtc ggtactgatc   7800
```

```
ccgtcgtcaa taaaccgaac cgctacaccc tgagcatcaa actctttat cagttggatc    7860
atgtcggcgg tgtcgcggcc aagacggtcg agcttcttca ccagaatgac atcaccttcc    7920
tccaccttca tcctcagcaa atccagccct tcccgatctg ttgaactgcc ggatgccttg    7980
tcggtaaaga tgcggttagc ttttacccct gcatctttga gcgctgaggt ctgcctcgtg    8040
aagaaggtgt tgctgactca taccaggcct gaatcgcccc atcatccagc cagaaagtga    8100
gggagccacg gttgatgaga gctttgttgt aggtggacca gttggtgatt ttgaactttt    8160
gctttgccac ggaacggtct cgttgtcgg gaagatgcgt gatctgatcc ttcaactcag    8220
caaaagttcg atttattcaa caaagccgcc gtcccgtcaa gtcagcgtaa tgctctgcca    8280
gtgttacaac caattaacca attctgatta gaaaaactca tcgagcatca aatgaaactg    8340
caatttattc atatcaggat tatcaatacc atattttga aaagccgtt tctgtaatga    8400
aggagaaaac tcaccgaggc agttccatag gatggcaaga tcctggtatc ggtctgcgat    8460
tccgactcgt ccaacatcaa tacaacctat taatttcccc tcgtcaaaaa taaggttatc    8520
aagtgagaaa tcaccatgag tgacgactga atccggtgag aatggcaaaa gcttatgcat    8580
ttctttccag acttgttcaa caggccagcc attacgctcg tcatcaaaat cactcgcatc    8640
aaccaaaccg ttattcattc gtgattgcgc ctgagcgaga cgaaatacgc gatcgctgtt    8700
aaaaggacaa ttacaaacag gaatcgaatg caaccggcgc aggaacactg ccagcgcatc    8760
aacaatattt tcacctgaat caggatattc ttctaatacc tggaatgctg ttttcccggg    8820
gatcgcagtg gtgagtaacc atgcatcatc aggagtacgg ataaaatgct tgatggtcgg    8880
aagaggcata aattccgtca gccagtttag tctgaccatc tcatctgtaa catcattggc    8940
aacgctacct ttgccatgtt tcagaaacaa ctctggcgca tcgggcttcc catacaatcg    9000
atagattgtc gcacctgatt gcccgacatt atcgcgagcc catttatacc catataaatc    9060
agcatccatg ttggaattta atcgcggcct cgagcaagac gtttcccgtt gaatatggct    9120
cataacaccc cttgtattac tgtttatgta agcagacagt tttattgttc atgatgatat    9180
atttttatct tgtgcaatgt aacatcagag attttgagac acaacgtggc tttgttgaat    9240
aaatcgaact tttgctgagt tgaaggatca gatcacgcat cttcccgaca acgcagaccg    9300
ttccgtggca aagcaaaagt tcaaaatcac caactggtcc acctacaaca agctctcat    9360
caaccgtggc tccctcactt tctggctgga tgatggggcg attcaggcct ggtatgagtc    9420
agcaacacct tcttcacgag gcagacctca gcgctagcgg agtgtatact ggcttactat    9480
gttggcactg atgagggtgt cagtgaagtg cttcatgtgg caggagaaaa aaggctgcac    9540
cggtgcgtca gcagaatatg tgatacagga tatattccgc ttcctcgctc actgactcgc    9600
tacgctcggt cgttcgactg cggcgagcgg aaatggctta cgaacggggc ggagatttcc    9660
tggaagatgc caggaagata cttaacaggg aagtgagagg gccgcggcaa agccgttttt    9720
ccataggctc cgcccccctg acaagcatca cgaaatctga cgctcaaatc agtggtggcg    9780
aaacccgaca ggactataaa gataccaggc gtttccccct ggcggctccc tcgtgcgctc    9840
tcctgttcct gcctttcggt ttaccggtgt cattccgctg ttatggccgc gtttgtctca    9900
ttccacgcct gacactcagt tccgggtagg cagttcgctc caagctggac tgtatgcacg    9960
aaccccccgt tcagtccgac cgctgcgcct atccggtaa ctatcgtctt gagtccaacc   10020
cggaaagaca tgcaaaagca ccactggcag cagccactgg taattgattt agaggagtta   10080
gtcttgaagt catgcgccgg ttaaggctaa actgaaagga caagtttggg tgactgcgct   10140
cctccaagcc agttacctcg gttcaaagag ttggtagctc agagaacctt cgaaaaaccg   10200
```

```
ccctgcaagg cggttttttc gttttcagag caagagatta cgcgcagacc aaaacgatct    10260
caagaagatc atcttattaa ggggtctgac gctcagtgga acgaaaactc acgttaaggg    10320
attttggtca tgagattatc aaaaaggatc ttcacctaga tccttttaaa ttaaaaatga    10380
agttttaaat caatctaaag tatatatgag taaacttggt ctgacagtta ccaatgctta    10440
atcagtgagg cacctatctc agcgatctgt ctatttcgtt catccatagt tgcctgactc    10500
cccgtcgtgt agataactac gatacgggag ggcttaccat ctggcccag tgctgcaatg     10560
ataccgcgag acccacgctc accggctcca gatttatcag caataaacca gccagccga     10620
agggccgagc gcagaagtgg tcctgcaact ttatccgcct ccatccagtc tattaattgt    10680
tgccgggaag ctagagtaag tagttcgcca gttaatagtt tgcgcaacgt tgttgccatt    10740
gccgatgata gctgtcaaa catggcctgt cgcttgcgt attcggaatc ttgcacgccc      10800
tcgctcaagc cttcgtcact ggtcccgcca ccaaacgttt cggcgagaag caggccatta    10860
tcgccggcat ggcggccgac gcgcgggag aggcggtttg cgtattgggc gccagggtgg     10920
tttttctttt caccagtgag acgggcaaca gctgattgcc cttcaccgcc tggccctgag    10980
agagttgcag caagcggtcc acgctggttt gccccagcag gcgaaaatcc tgtttgatgg    11040
tggttaacgg cgggatataa catgagctgt cttcggtatc gtcgtatccc actaccgaga    11100
tatccgcacc aacgcgcagc ccggactcgg taatggcgcg cattgcgccc agcgccatct    11160
gatcgttggc aaccagcatc gcagtgggaa cgatgccctc attcagcatt tgcatggttt    11220
gttgaaaacc ggacatggca ctccagtcgc cttcccgttc cgctatcggc tgaatttgat    11280
tgcgagtgag atatttatgc cagccagcca gacgcagacg cgccgagaca gaacttaatg    11340
ggcccgctaa cagcgcgatt tgctggtgac ccaatgcgac cagatgctcc acgcccagtc    11400
gcgtaccgtc ttcatgggag aaaataatac tgttgatggg tgtctggtca gagacatcaa    11460
gaaataacgc cggaacatta gtgcaggcag cttccacagc aatggcatcc tggtcatcca    11520
gcggatagtt aatgatcagc ccactgacgc gttgcgcgag aagattgtgc accgccgctt    11580
tacaggcttc gacgccgctt cgttctacca tcgacaccac cacgctgca cccagttgat     11640
cggcgcgaga tttaatcgcc gcgacaattt gcgacggcgc gtgcagggcc agactggagg    11700
tgcaacgcc aatcagcaac gactgtttgc ccgccagttg ttgtgccacg cggttgggaa     11760
tgtaattcag ctccgccatc gccgcttcca cttttttccg cgttttcgca gaaacgtggc    11820
tggcctggtt caccacgcgg gaaacggtct gataagagac accggcatac tctgcgacat    11880
cgtataacgt tactggtttc acattcacca ccctgaattg actctcttcc gggcgctatc    11940
atgccatacc gcgaaaggtt ttgcaccatt cgatggtgtc aacgtaaatg catgccgctt    12000
cgccttcgcg cgcgaattgc aagctgatcc gggcttatcg actgcacggt gcaccaatgc    12060
ttctggcgtc aggcagccat cggaagctgt ggtatggctg tgcaggtcgt aaatcactgc    12120
ataattcgtg tcgctcaagg cgcactcccg ttctggataa tgttttttgc gccgacatca    12180
taacggttct ggcaaatatt ctgaaatgag ctgttgacaa ttaatcatcg gctcgtataa    12240
tgtgtggaat tgtgagcgga taacaatttc acacaggaaa cagaattaaa agatatgacc    12300
atgattacgc c                                                         12311
```

<210> SEQ ID NO 58
<211> LENGTH: 9892
<212> TYPE: DNA
<213> ORGANISM: Artificial Sequence
<220> FEATURE:

<223> OTHER INFORMATION: vector

<400> SEQUENCE: 58

```
ctcgggccgt ctcttgggct tgatcggcct tcttgcgcat ctcacgcgct cctgcggcgg      60
cctgtagggc aggctcatac ccctgccgaa ccgcttttgt cagccggtcg gccacggctt     120
ccggcgtctc aacgcgcttt gagattccca gcttttcggc caatccctgc ggtgcatagg     180
cgcgtggctc gaccgcttgc gggctgatgg tgacgtggcc cactggtggc cgctccaggg     240
cctcgtagaa cgcctgaatg cgcgtgtgac gtgccttgct gccctcgatg cccgttgca     300
gccctagatc ggccacagcg gccgcaaacg tggtctggtc gcgggtcatc tgcgctttgt     360
tgccgatgaa ctccttggcc gacagcctgc cgtcctgcgt cagcggcacc acgaacgcgg     420
tcatgtgcgg gctggtttcg tcacggtgga tgctggccgt cacgatgcga tccgccccgt     480
acttgtccgc cagccacttg tgcgccttct cgaagaacgc cgcctgctgt tcttggctgg     540
ccgacttcca ccattccggg ctggccgtca tgacgtactc gaccgccaac acagcgtcct     600
tgcgccgctt ctctggcagc aactcgcgca gtcggcccat cgcttcatcg gtgctgctgg     660
ccgcccagtg ctcgttctct ggcgtcctgc tggcgtcagc gttgggcgtc tcgcgctcgc     720
ggtaggcgtg cttgagactg gccgccacgt tgcccatttt cgccagcttc ttgcatcgca     780
tgatcgcgta tgccgccatg cctgcccctc ccttttggtg tccaaccggc tcgacggggg     840
cagcgcaagg cggtgcctcc ggcgggccac tcaatgcttg agtatactca ctagactttg     900
cttcgcaaag tcgtgaccgc ctacggcggc tgcggcgccc tacgggcttg ctctccgggc     960
ttcgccctgc gcggtcgctg cgctcccttg ccagcccgtg gatatgtgga cgatggccgc    1020
gagcggccac cggctggctc gcttcgctcg gcccgtggac aaccctgctg gacaagctga    1080
tggacaggct gcgcctgccc acgagcttga ccacagggat gcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt ggggcagtc gaaggcgaag cccgcccgcc    1380
tgccccccga gcctcacggc ggcgagtgcg ggggttccaa gggggcagcg ccaccttggg    1440
caaggccgaa ggccgcgcag tcgatcaaca agccccggag gggccacttt ttgccggagg    1500
gggagccgcg ccgaaggcgt gggggaaccc cgcagggtg cccttctttg gcaccaaag    1560
aactagatat agggcgaaat gcgaaagact taaaaatcaa caacttaaaa aaggggggta    1620
cgcaacagct cattgcggca cccccgcaa tagctcattg cgtaggttaa agaaaatctg    1680
taattgactg ccacttttac gcaacgcata attgttgtcg cgctgccgaa aagttgcagc    1740
tgattgcgca tggtgccgca accgtgcggc accctaccgc atggagataa gcatggccac    1800
gcagtccaga gaaatcggca ttcaagccaa gaacaagccc ggtcactggg tgcaaacgga    1860
acgcaaagcg catgaggcgt gggccgggct tattgcgagg aaacccacgg cggcaatgct    1920
gctgcatcac ctcgtggcgc agatgggcca ccagaacgcc gtggtggtca gccagaagac    1980
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
tgccgccgtg gtggttgatc acgacgacca ggacgaatcg ctgttggggc atggcgacct    2220
gcgccgcatc ccgaccctgt atccgggcga gcagcaacta ccgaccggcc ccggcgagga    2280
```

```
gccgcccagc cagcccggca ttccgggcat ggaaccagac ctgccagcct tgaccgaaac    2340
ggaggaatgg gaacggcgcg ggcagcagcg cctgccgatg cccgatgagc cgtgttttct    2400
ggacgatggc gagccgttgg agccgccgac acgggtcacg ctgccgcgcc ggtagcactt    2460
gggttgcgca gcaacccgta agtgcgctgt tccagactat cggctgtagc cgcctcgccg    2520
ccctatacct tgtctgcctc cccgcgttgc gtcgcggtgc atggagccgg gccacctcga    2580
cctgaatgga agccggcggc acctcgctaa cggattcacc gtttttatca ggctctggga    2640
ggcagaataa atgatcatat cgtcaattat tacctccacg gggagagcct gagcaaactg    2700
gcctcaggca tttgagaagc acacggtcac actgcttccg gtagtcaata aaccggtaaa    2760
ccagcaatag acataagcgg ctatttaacg accctgccct gaaccgacga ccgggtcgaa    2820
tttgctttcg aatttctgcc attcatccgc ttattatcac ttattcaggc gtagcaccag    2880
gcgtttaagg gcaccaataa ctgccttaaa aaaattacgc cccgccctgc cactcatcgc    2940
agtcggccta ttggttaaaa aatgagctga tttaacaaaa atttaacgcg aattttaaca    3000
aaatattaac gcttacaatt tccattcgcc attcaggctg cgcaactgtt gggaagggcg    3060
atcggtgcgg gcctcttcgc tattacgcca gctggcgaaa gggggatgtg ctgcaaggcg    3120
attaagttgg gtaacgccag ggttttccca gtcacgacgt tgtaaaacga cggccagtga    3180
gcgcgcgtaa tacgactcac tatagggcga attggagctc caccgcggtg gcggccgctc    3240
tagacgccag gattgaacag taccaccagc acgcccatgt ctatccggtc catgatcgtt    3300
cttctcccgt aggtcgaagt tgccaggcca ggaccagccc ggccagaacg agaagggcgc    3360
cggcgaggaa tggcgcgccg gccaggggca gcggcgcgag cggaccgctg ccccagtgga    3420
acaggccgct catcagcggc ggaccgacga tcgcggcgag gctcatcagg ctgctcagca    3480
cgccctgcaa ctcgccctgg cggtcgaccg gcacgcgggc cgagagcagc cctgcatgg     3540 ccggggtggc gaggctgccg agcgcgaagg gcagcagcgc gcagaccagc cagaatgacg    3600
agtcgaccag ggcgaacagc agcaggccgc agccttgcag ggcgaggccc aggcgcagca    3660
ggcgggcgtc gtccaggcgc cgcttgcaga ggttcacgcc gagggtctgg gcagcaccg     3720 cgagcacgcc gtagagggcc agcgagtagc cgatccaggc gctgctccag tgaaacttct    3780
cgatcacgaa gaacggccag accaccatca ccgcctgcaa gccgaggaat accagggcaa    3840
gcaccgccag caggcgtccg accccggtt gccgagccag gccgctgatc gagcgcaagg     3900
cattcatccg cctcgggtcc aggcggcggc gtcgcgtcgg gggcagggtt cctcgagga     3960 acaggccggc gagcagggcg ttgagcaggc acaggccggc ggcagcaac agcggcagcg     4020 tcgtgccgtg caccgccagc agcccaccga gggcggggcc gaggatcatg cccagggcga    4080
ggccggcgta cagccagccg aagtgccggg tgcgctgccc gtgcgtgccg aggtcagccg    4140
cgcaggccat cgcggtggcc acgctggcgc cggtgagccc ggccagcgcg cgaccgagga    4200
acagcatcca gaggctgtcg gccagcgcca gcagcagata gctgagggcg aagccgagca    4260
tcgccaggac caggacgggg cggcgtccga agcggtcgct gaggctgccg aggaccggcg    4320
aaaagaacaa ttgcagcagc gcgaaggtca tcaccagggc ggcgcccag gtggccgcgt      4380 cgcggaccgc cagcggcgcc acgctgccga tcagcgtcgg cagcagggc acgatcaggc      4440 cgacgccagc ggcatccagc aggcaggtga ggaacagcag aggcaggacg cgtttcgcgc    4500
cgggaccgtg ttcccgcgtg gcggaggggc agaggctggt cgtggacacg ccaggatcct    4560
cccggcgaac acaggaaatc ctgatcttgg gacgccagcg agggcaaggg aaactaccgg    4620
```

```
aattcacagg ttcgacgaac ggtcgcggca acgccggcgg gcggcgtgat gtcataatga    4680
tgcgacccgt gcgccagtcg ggtatccttg ccggcctctc atctagaggg aatgcgtttc    4740
gccgactagg ccttggcctt gccggaagct acggacgcca cggccgggcc ggcgaggcgc    4800
ttcagcaggc gcggcggtt ggtctccagc gcgccgccgc gtccccgcag gccgtcccac     4860
aggccccagc ccaggcagcg cagcttgagc agcttgtcgc gttcgagcag gagcaccgcg    4920
aggccctggg tcagggtcgg caggttcgcc agcagggcca gcgcgagga ccggcgtag      4980 cggcgcagga ccagcaggcc gttgcgcgcc aggtagtagc ggcgcagcgg ggcgtggttc    5040
atcgcgctga ggctgagacc gccgaggcgg cgggtcttgc gcgtgccgat gcggtgctcg    5100
aggaccagcc gcgggtcgac gtacaggggc acgtccagcg cctgggcgcg caggctgtat    5160
tcggtgtcca cgtggtcgat gaacagttcc tcgtcgaagt ggccgaggcg ctggtaggcc    5220
tcgcgggtca gcaggcagcc ggaggagatc aggaacgagg tgcgctgcgg ggtcgtcagg    5280
ccgtccagag acaattgcct gagcgtcagt ccgtcgagat ggatggccgg caggaagcgc    5340
cggtcacccc ggtcgaagat ccgtgggccg agcaggcagg cctgaccgtt gcgcgcctgc    5400
aggttgcgcc actgggcggc gaggaaggcg ccgccgggac gggagtcctg gtcgagcagc    5460
agcacaccct gcacgccacg ccggaatagc gcgtcgagtc cctggttgaa ggcgccggcg    5520
atgccctgcc ggttgccgtg gtgcagcacg gcgatgcctt gcccgcgcag ccgggcattg    5580
cgctgcggat cgctgtgcgg tgagttgtcg acggcaagga agcgcagttg cggaaacgcc    5640
gccgccagtt cgccaaggtg ttccaggtcg tcgtcgccag gattgaacag taccaccagc    5700
acgcccatgt ctatccggtc catgatcgtt cttctcccgt aggtcaggac gcagccttca    5760
gccatcgcgc atccccctcc ctatgacaac gttcgaccac ctgggccgct ttaccgcaag    5820
cgatactgtg cggttgtgac aattccatga acgccgaca ggccgccgcc atggccgggt     5880
cctcgagcaa gcgccacagc gccccgcgca actcctgctc gcgcaatggc acgcccaggc    5940
gcatcccgca gccgagccgg accagccgtt cggcattgtc gaactggtcg tgggcgcagg    6000
gcagcagcac ctgcggcacc cccgccgcca aggccaggct catggcgccg ataccgcccg    6060
gatggaccag cccggcgcac gatggcagca aggctcccag tggcgcgtag gcgcgctgca    6120
gcacgtggtt cggcaagccg cgcagcggtt cctggccggc gccggtgagg aagatcccac    6180
gcgcgccgag gcgttccagc gcgcgcaggg ccatggcgta gaagtcgccc tgcaggtgtt    6240
cggtcgagcc ctgggtgaac accagcggcc ggctgccctg atcgagaaag cgttgcagtt    6300
cgtcgtcgag cggggtcccc gggatactgc cgtcgaacag cgggaagccg gtcatgtgca    6360
ggggttgcgg ccaatcctgc tggggcggcg cgaaccaggc cgggaacagg cagaccacgc    6420
cctgcggcga atgcatccat tgggtgaaga tgcgcttcac cggcgtctcc aggccgacct    6480
tgcgccgcac cgcgttgata tccggcgcgc aggtgcgatc cagcttgaag cgctcgatgc    6540
agcgccagag cagcttgcgc atcgccagcg gcatctgctc gggcacgttg aacttggggt    6600
gtaccggcgg caggtgcgcc gacaacaagg tcgatggcga gacctgcgcg acaggtagg    6660 gaatcccgta cttctcgtga gcgatgcgtg cgcccagcgc ccagagcgag ccgaccacca    6720
cgatgtcgtc atgcgctgc gccgagacgt actcgtagac cggctcgatc atccggcga     6780 tggtttgcca gagcacgccg aaggacgtct tggggtccca caggcgcgga tcgcccatgg    6840
tccggccgta ggtcagttcg tcgctcagcg ggacgaacgc gatgccgtgc tgctccaccg    6900
cgtcgcgaaa caccgggatg gtgcagaggc tcacgcggtg cccgcgcaat ttcagggtcc    6960
gggccaggcc gatgaaggga aatacgtcgc cggccgagcc gatggcgatg aggatggcgt    7020
```

```
gcatggtgct actccgtgcg ttatgcaacc gcaaagcccg gccaggccgg gtcttcgcag    7080
gtcaagggtt caggcgtagc cgatggccat ctcgtggaat cccgccgcgc gttccgcccg    7140
ctgcggctcc ggttgcttca gcaggtgctc gagcagggcg cggtgcacgc gtaccgcggc    7200
cagcttggac tccaggtcga ggaaatgccc ggtgccctcc acccgcgaga aactgcagtg    7260
cggcaggtag tcgcggaact ggcgggcgtc ctcggcggtg gtgtattcgt cccagctgcc    7320
gttgatgaaa tgcacgtggc tctggatccg ctccaggcaa gccaggtagc cccgatcgtt    7380
gagcgccagc acctggtcga tgtgaaagcg cgcctgctcg tattcgccgg tggccagcga    7440
agccatgtgc tgatggttgc tggctttcag gcgcggcggc aggtatttgc cgacggtctc    7500
gttgagcaga tggccgatcg ccgacttgtc gtccagctcg atcagcgcct gcgcccgccc    7560
gacgtagtcg agcatcgcct ggttcagtcc aggggcgaat gccatcacca ccgagctgcg    7620
gatgccgcgc ggattgcgcg acagcgccag cagcgtggag ataccgcccc aggacgcgga    7680
gaccaggtga ttgacctcga agcgctcgat cagcgccagg aggatttcca cctcgtcgtc    7740
cttggtgatc aaccccgct gcgggttgtg ctgacgcgac tgcccggcga agggcaggtc    7800
gaacagcacc acgttgaaat gttcggccag gcacttgcag gtccgggcga acgaggcggt    7860
ggtcgccatc gcgccgttga ccagcatcac cgtgctgcgc ccgggatcct gcccaacgcg    7920
ctcgacatgt acccgcaggc ccttgcaaac cgataccaac agactttcgc gccgcatttc    7980
acacctccca aaaatgccag atcccccggg ctgcaggaat tcgatatcaa gcttatcgat    8040
accgtcgacc tcgaggggggg gcccggtacc cagcttttgt tccctttagt gagggttaat    8100
tgcgcgcttg gcgtaatcat ggtcatagct gtttcctgtg tgaaattgtt atccgctcac    8160
aattccacac aacatacgag ccggaagcat aaagtgtaaa gcctggggtg cctaatgagt    8220
gagctaactc acattaattg cgttgcgctc actgcccgct ttccagtcgg gaaacctgtc    8280
gtgccagctg cattaatgaa tcggccaacg cgcggggaga ggcggtttgc gtattgggcg    8340
catgcataaa aactgttgta attcattaag cattctgccg acatggaagc catcacaaac    8400
ggcatgatga acctgaatcg ccagcggcat cagcaccttg tcgccttgcg tataatattt    8460
gcccatgggg gtgggcgaag aactccagca tgagatcccc gcgctggagg atcatccagc    8520
cggcgtcccg gaaaacgatt ccgaagccca acctttcata aaggcggcg gtggaatcga    8580 aatctcgtga tggcaggttg ggcgtcgctt ggtcggtcat ttcgaacccc agagtcccgc    8640
tcagaagaac tcgtcaagaa ggcgatagaa ggcgatgcgc tgcgaatcgg gagcggcgat    8700
accgtaaagc acgaggaagc ggtcagccca ttcgccgcca gctcttcag caatatcacg    8760 ggtagccaac gctatgtcct gatagcggtc cgccacaccc agccggccac agtcgatgaa    8820
tccagaaaag cggccatttt ccaccatgat attcggcaag caggcatcgc catgggtcac    8880
gacgagatcc tcgccgtcgg gcatgcgcgc cttgagcctg gcgaacagtt cggctggcgc    8940
gagcccctga tgctcttcgt ccagatcatc ctgatcgaca agaccggctt ccatccgagt    9000
acgtgctcgc tcgatgcgat gtttcgcttg gtggtcgaat gggcaggtag ccggatcaag    9060
cgtatgcagc cgccgcattg catcagccat gatggatact ttctcggcag gagcaaggtg    9120
agatgacagg agatcctgcc ccggcacttc gcccaatagc agccagtccc ttcccgcttc    9180
agtgacaacg tcgagcacag ctgcgcaagg aacgcccgtc gtggccagcc acgatagccg    9240
cgctgcctcg tcctgcagtt cattcagggc accggacagg tcggtcttga caaaaagaac    9300
cgggcgcccc tgcgctgaca gccggaacac ggcggcatca gagcagccga ttgtctgttg    9360
```

| | |
|---|---|
| tgcccagtca tagccgaata gcctctccac ccaagcggcc ggagaacctg cgtgcaatcc | 9420 |
| atcttgttca atcatgcgaa acgatcctca tcctgtctct tgatcagatc ttgatcccct | 9480 |
| gcgccatcag atccttggcg gcaagaaagc catccagttt actttgcagg gcttcccaac | 9540 |
| cttaccagag ggcgcccag ctggcaattc cggttcgctt gctgtccata aaaccgccca | 9600 |
| gtctagctat cgccatgtaa gcccactgca agctacctgc tttctctttg cgcttgcgtt | 9660 |
| ttcccttgtc cagatagccc agtagctgac attcatccca ggtggcactt ttcggggaaa | 9720 |
| tgtgcgcgcc cgcgttcctg ctggcgctgg gcctgtttct ggcgctggac ttcccgctgt | 9780 |
| tccgtcagca gcttttcgcc cacggccttg atgatcgcgg cggccttggc ctgcatatcc | 9840 |
| cgattcaacg gccccagggc gtccagaacg ggcttcaggc gctcccgaag gt | 9892 |

<210> SEQ ID NO 59
<211> LENGTH: 1477
<212> TYPE: DNA
<213> ORGANISM: Pseudomonas aeruginosa

<400> SEQUENCE: 59

| | |
|---|---|
| tgagaggccg gcaaggatac ccgactggcg cacgggtcgc atcattatga catcacgccg | 60 |
| cccgccggcg ttgccgcgac cgttcgtcga acctgtgaat tccggtagtt tcccttgccc | 120 |
| tcgctggcgt cccaagatca ggatttcctg tgttcgccgg aggatcctg gcgtgtccac | 180 |
| gaccagcctc tgcccctccg ccacgcggga acacggtccc ggcgcgaaac gcgtcctgcc | 240 |
| tctgctgttc ctcacctgcc tgctggatgc cgctggcgtc ggcctgatcg tgccctgct | 300 |
| gccgacgctg atcggcagcg tggcgccgct ggcggtccgc gacgcggcca cctggggcgc | 360 |
| cgccctggtg atgaccttcg cgctgctgca attgttcttt tcgccggtcc tcggcagcct | 420 |
| cagcgaccgc ttcggacgcc gcccgtcct ggtcctggcg atgctcggct tcgccctcag | 480 |
| ctatctgctg ctggcgctgg ccgacagcct ctggatgctg ttcctcggtc gcgcgctggc | 540 |
| cgggctcacc ggcgcagcg tggccaccgc gatggcctgc gcggctgacc tcggcacgca | 600 |
| cgggcagcgc acccggcact tcggctggct gtacgccggc ctcgccctgg gcatgatcct | 660 |
| cggcccccgcc ctcggtgggc tgctggcggt gcacggcacg acgctgccgc tgttgctggc | 720 |
| cgccggcctg tgcctgctca acgccctgct cgccggcctg ttcctcgagg aaaccctgcc | 780 |
| cccgacgcga cgccgccgcc tggacccgag gcggatgaat gccttgcgct cgatcagcgg | 840 |
| cctggctcgg caaccggggg tcggacgcct gctggcggtg cttgccctgg tattcctcgg | 900 |
| cttgcaggcg gtgatggtgg tctggccgtt cttcgtgatc gagaagtttc actgagcag | 960 |
| cgcctggatc ggctactcgc tggccctcta cggcgtgctc gcggtgctcg cccagaccct | 1020 |
| cggcgtgaac ctctgcaagc ggcgcctgga cgacgcccgc ctgctgcgcc tgggcctcgc | 1080 |
| cctgcaaggc tgcggcctgc tgctgttcgc cctggtcgac tcgtcattct ggctggtctg | 1140 |
| cgcgctgctg cccttcgcgc tcggcagcct cgccacccg gccatgcagg gctgctctc | 1200 |
| ggcccgcgtg ccggtcgacc gccagggcga gttgcaggc gtgctgagca gcctgatgag | 1260 |
| cctcgccgcg atcgtcggtc cgccgctgat gagcggcctg ttccactggg gcagcggtcc | 1320 |
| gctcgcgccc ctgccctgg ccggcgcgcc attcctcgcc ggcgccttc tcgttctggc | 1380 |
| cgggctggtc ctggcctggc aacttcgacc tacgggagaa gaacgatcat ggaccggata | 1440 |
| gacatgggcg tgctggtggt actgttcaat cctggcg | 1477 |

<210> SEQ ID NO 60
<211> LENGTH: 32

```
<212> TYPE: DNA
<213> ORGANISM: Artificial Sequence
<220> FEATURE:
<223> OTHER INFORMATION: primer

<400> SEQUENCE: 60
aggaaatcta gatgagaggc cggcaaggat ac                                    32

<210> SEQ ID NO 61
<211> LENGTH: 32
<212> TYPE: DNA
<213> ORGANISM: Artificial Sequence
<220> FEATURE:
<223> OTHER INFORMATION: primer

<400> SEQUENCE: 61
ccaggttcta gacgccagga ttgaacagta cc                                    32

<210> SEQ ID NO 62
<211> LENGTH: 7332
<212> TYPE: DNA
<213> ORGANISM: Artificial Sequence
<220> FEATURE:
<223> OTHER INFORMATION: vector

<400> SEQUENCE: 62
cgaaaatttt tgggaggtgt gaaatgcggc gcgaaagtct gttggtatcg gtttgcaagg      60
gcctgcgggt acatgtcgag cgcgttgggc aggatcccgg gcgcagcacg gtgatgctgg     120
tcaacggcgc gatggcgacc accgcctcgt cgcccggac ctgcaagtgc ctggccgaac     180
atttcaacgt ggtgctgttc gacctgccct cgccgggca gtcgcgtcag cacaacccgc     240
agcgcgggtt gatcaccaag gacgacgagg tggaaatcct cctggcgctg atcgagcgct     300
tcgaggtcaa tcacctggtc tccgcgtcct ggggcggtat ctccacgctg ctggcgctgt     360
cgcgcaatcc gcgcggcatc cgcagctcgg tggtgatggc attcgcccct ggactgaacc     420
aggcgatgct cgactacgtc gggcgggcgc aggcgctgat cgagctggac gacaagtcgg     480
cgatcggcca tctgctcaac gagaccgtcg gcaaatacct gccgcagcgc ctgaaagcca     540
gcaaccatca gcacatggct tcgctggcca ccggcgaata cgagcaggcg cgcttcaca     600 tcgaccaggt gctggcgctc aacgatcggg gctacttggc ttgcctggag cggatccaga     660
gccacgtgca tttcatcaac ggcagctggg acgaatacac caccgccgag gacgcccgcc     720
agttccgcga ctacctgccg cactgcagtt tctcgcgggt ggagggcacc gggcatttcc     780
tcgacctgga gtccaagctg gcagcggtac gcgtgcaccg cgccctgctc gagcacctgc     840
tgaagcaacc ggagccgcag cgggcggaac gcgcggcggg attccacgag atggccatcg     900
gctacgcctg aacccttgac ctgcgaagac ccggcctggc cggctttgc ggttgcataa     960 cgcacggagt agccccatgc acgccatcct catcgccatc ggctcggccg gcgacgtatt    1020
tcccttcatc ggcctggccc ggaccctgaa actgcgcggg caccgcgtga gcctctgcac    1080
catcccggtg tttcgcgacg cggtggagca gcacggcatc gcgttcgtcc gcctgagcga    1140
cgaactgacc taccgccgga ccatgggcga tccgcgcctg tgggaccca agacgtcctt    1200 cggcgtgctc tggcaagcca tcgccgggat gatcgagccg gtctacgagt acgtctcggc    1260
gcagcgccat gacgacatcg tggtggtcgg ctcgctatgg gcgctgggcg cacgcatcgc    1320
tcacgagaag tacgggattc cctacctgtc cgcgcaggtc tcgccatcga ccctgttgtc    1380
ggcgcacctg ccgccggtac accccaagtt caacgtgccc gagcagatgc cgctggcgat    1440
```

-continued

```
gcgcaagctg ctctggcgct gcatcgagcg cttcaagctg gatcgcacct gcgcgccgga    1500
gatcaacgcg gtgcgccgca aggtcggcct ggaaacgccg gtgaagcgca tcttcaccca    1560
atggatgcat tcgccgcagg gcgtggtctg cctgttcccg gcctggttcg cgccgcccca    1620
gcaggattgg ccgcaacccc tgcacatgac cggcttcccg ctgttcgacg gcagtatccc    1680
ggggaccccg ctcgacgacg aactgcaacg cttctctcgat cagggcagcc ggccgctggt    1740
gttcacccag ggctcgaccg aacacctgca gggcgacttc tacgccatgg ccctgcgcgc    1800
gctggaacgc ctcggcgcgc gtgggatctt cctcaccggc gccggccagg aaccgctgcg    1860
cggcttgccg aaccacgtgc tgcagcgcgc ctacgcgcca ctgggagcct tgctgccatc    1920
gtgcgccggg ctggtccatc cgggcggtat cggcgccatg agcctagcct ggcggcggg    1980
ggtgccgcag gtgctgctgc cctgtgccca cgaccagttc gacaatgccg aacggctggt    2040
ccggctcggc tgcgggatgc gcctgggcgt gccgttgcgc gagcaggagt tgcgcggggc    2100
gctgtgcgc ttgctcgagg acccggccat ggcggcggcc tgtcggcgtt tcatggaatt    2160
gtcacaaccg cacagtatcg cttgcggtaa agcggcccag gtggtcgaac gttgtcatag    2220
ggagggggat gctcgatggc tgaaggctgc gtcctgaacg gtctagagcg gccgccaccg    2280
cggtggagct ccaattcgcc ctatagtgag tcgtattacg cgcgctcact ggccgtcgtt    2340
ttacaacgtc gtgactggga aaaccctggc gttacccaac ttaatcgcct tgcagcacat    2400
ccccctttcg ccagctggcg taatagcgaa gaggcccgca ccgatcgccc ttcccaacag    2460
ttgcgcagcc tgaatggcga atggaaattg taagcgttaa tattttgtta aaattcgcgt    2520
taaattttg ttaaatcagc tcattttta accataggc cgactgcgat gagtggcagg    2580
gcggggcgta attttttaa ggcagttatt ggtgcccta aacgcctggt gctacgcctg    2640
aataagtgat aataagcgga tgaatggcag aaattcgaaa gcaaattcga cccggtcgtc    2700
ggttcagggc agggtcgtta aatagccgct tatgtctatt gctggtttac cggtttattg    2760
actaccggaa gcagtgtgac cgtgtgcttc tcaaatgcct gaggccagtt tgctcaggct    2820
ctccccgtgg aggtaataat tgacgatatg atcatttatt ctgcctccca gagcctgata    2880
aaaacggtga atccgttagc gaggtgccgc cggcttccat tcaggtcgag gtggcccggc    2940
tccatgcacc gcgacgcaac gcggggaggc agacaaggta tagggcggcg aggcggctac    3000
agccgatagt ctgaacagc gcacttacgg gttgctgcgc aacccaagtg ctaccggcgc    3060
ggcagcgtga cccgtgtcgg cggctccaac ggctcgccat cgtccagaaa acacggctca    3120
tcgggcatcg gcaggcgctg ctgcccgcgc cgttccatt cctccgttc ggtcaaggct    3180
ggcaggtctg gttccatgcc cggaatgccg ggctggctgg gcggctcctc gccggggccg    3240
gtcggtagtt gctgctcgcc cggatacagg gtcgggatgc ggcgcaggtc gccatgcccc    3300
aacagcgatt cgtcctggtc gtcgtgatca accaccacgg cggcactgaa caccgacagg    3360
cgcaactggt cgcggggctg gccccacgcc acgcggtcat tgaccacgta ggccgacacg    3420
gtgccggggc cgttgagctt cacgacggag atccagcgct cggccaccaa gtccttgact    3480
gcgtattgga ccgtccgcaa agaacgtccg atgagcttgg aaagtgtctt ctggctgacc    3540
accacgcgt tctggtggcc catctgcgcc acgaggtgat gcagcagcat gccgccgtg    3600
ggtttcctcg caataagccc ggcccacgcc tcatgcgctt tgcgttccgt ttgcacccag    3660
tgaccgggct tgttcttggc ttgaatgccg atttctctgg actgcgtggc catgcttatc    3720
tccatgcggt agggtgccgc acggttgcgg caccatgcgc aatcagctgc aacttttcgg    3780
cagcgcgaca acaattatgc gttgcgtaaa agtggcagtc aattacagat tttctttaac    3840
```

```
ctacgcaatg agctattgcg gggggtgccg caatgagctg ttgcgtaccc cccttttta   3900
agttgttgat ttttaagtct ttcgcatttc gccctatatc tagttcttg gtgcccaaag   3960
aagggcaccc ctgcggggtt ccccacgcc ttcggcgcgg ctccccctcc ggcaaaaagt   4020
ggcccctccg gggcttgttg atcgactgcg cggccttcgg ccttgcccaa ggtggcgctg   4080
ccccttgga accccgcac tcgccgccgt gaggctcggg gggcaggcgg gcgggcttcg   4140
ccttcgactg cccccactcg cataggcttg ggtcgttcca ggcgcgtcaa ggccaagccg   4200
ctgcgcggtc gctgcgcgag ccttgacccg ccttccactt ggtgtccaac cggcaagcga   4260
agcgcgcagg ccgcaggccg gaggcttttc cccagagaaa attaaaaaaa ttgatggggc   4320
aaggccgcag gccgcgcagt tggagccggt gggtatgtgg tcgaaggctg ggtagccggt   4380
gggcaatccc tgtggtcaag ctcgtgggca ggcgcagcct gtccatcagc ttgtccagca   4440
gggttgtcca cgggccgagc gaagcgagcc agccggtggc cgctcgcggc catcgtccac   4500
atatccacgg gctggcaagg gagcgcagcg accgcgcagg gcgaagcccg gagagcaagc   4560
ccgtagggcg ccgcagccgc cgtaggcggt cacgactttg cgaagcaaag tctagtgagt   4620
atactcaagc attgagtggc cgccggagg caccgccttg cgctgccccc gtcgagccgg   4680
ttggacacca aaagggaggg gcaggcatgg cggcatacgc gatcatgcga tgcaagaagc   4740
tggcgaaaat gggcaacgtg gcggccagtc tcaagcacgc ctaccgcgag cgcgagacgc   4800
ccaacgctga cgccagcagg acgccagaga acgagcactg ggcggccagc agcaccgatg   4860
aagcgatggg ccgactgcgc gagttgctgc cagagaagcg gcgcaaggac gctgtgttgg   4920
cggtcgagta cgtcatgacg gccagcccgg aatggtggaa gtcggccagc caagaacagc   4980
aggcggcgtt cttcgagaag gcgcacaagt ggctggcgga caagtacggg gcggatcgca   5040
tcgtgacggc cagcatccac cgtgacgaaa ccagcccgca catgaccgcg ttcgtggtgc   5100
cgctgacgca ggacggcagg ctgtcggcca aggagttcat cggcaacaaa gcgcagatga   5160
cccgcgacca gaccacgttt gcggccgctg tggccgatct agggctgcaa cggggcatcg   5220
agggcagcaa ggcacgtcac acgcgcattc aggcgttcta cgaggccctg gagcggccac   5280
cagtgggcca cgtcaccatc agcccgcaag cggtcgagcc acgcgcctat gcaccgcagg   5340
gattggccga aaagctggga atctcaaagc gcgttgagac gccggaagcc gtggccgacc   5400
ggctgacaaa agcggttcgg caggggtatg agcctgccct acaggccgcc gcaggagcgc   5460
gtgagatgcg caagaaggcc gatcaagccc aagagacggc ccgagacctt cgggagcgcc   5520
tgaagcccgt tctggacgcc ctgggccgt tgaatcggga tatgcaggcc aaggccgccg   5580
cgatcatcaa ggccgtgggc gaaaagctgc tgacggaaca gcgggaagtc cagcgccaga   5640
aacaggccca gcgccagcag gaacgcgggc gcgcacattt ccccgaaaag tgccacctgg   5700
gatgaatgtc agctactggg ctatctggac aagggaaaac gcaagcgcaa agagaaagca   5760
ggtagcttgc agtgggctta catggcgata gctagactgg gcggttttat ggacagcaag   5820
cgaaccggaa ttgccagctg gggcgccctc tggtaaggtt gggaagccct gcaaagtaaa   5880
ctggatggct tcttgccgc caaggatctg atggcgcagg ggatcaagat ctgatcaaga   5940
gacaggatga ggatcgtttc gcatgattga acaagatgga ttgcacgcag ttctccggc    6000
cgcttgggtg gagaggctat tcggctatga ctgggcacaa cagacaatcg gctgctctga   6060
tgccgccgtg ttccggctgt cagcgcaggg gcgcccggtt cttttgtca agaccgacct    6120
gtccggtgcc ctgaatgaac tgcaggacga ggcagcgcgg ctatcgtggc tggccacgac   6180
```

```
gggcgttcct tgcgcagctg tgctcgacgt tgtcactgaa gcgggaaggg actggctgct    6240
attgggcgaa gtgccggggc aggatctcct gtcatctcac cttgctcctg ccagaaaagt    6300
atccatcatg gctgatgcaa tgcggcggct gcatacgctt gatccggcta cctgcccatt    6360
cgaccaccaa gcgaaacatc gcatcgagcg agcacgtact cggatggaag ccggtcttgt    6420
cgatcaggat gatctggacg aagagcatca ggggctcgcg ccagccgaac tgttcgccag    6480
gctcaaggcg cgcatgcccg acggcgagga tctcgtcgtg acccatggcg atgcctgctt    6540
gccgaatatc atggtggaaa atggccgctt ttctggattc atcgactgtg gccggctggg    6600
tgtggcggac cgctatcagg acatagcgtt ggctacccgt gatattgctg aagagcttgg    6660
cggcgaatgg gctgaccgct tcctcgtgct ttacggtatc gccgctcccg attcgcagcg    6720
catcgccttc tatcgccttc ttgacgagtt cttctgagcg ggactctggg gttcgaaatg    6780
accgaccaag cgacgcccaa cctgccatca cgagatttcg attccaccgc cgccttctat    6840
gaaaggttgg gcttcggaat cgttttccgg gacgccggct ggatgatcct ccagcgcggg    6900
gatctcatgc tggagttctt cgcccacccc catgggcaaa tattatacgc aaggcgacaa    6960
ggtgctgatg ccgctggcga ttcaggttca tcatgccgtt tgtgatggct tccatgtcgg    7020
cagaatgctt aatgaattac aacagttttt atgcatgcgc caatacgca aaccgcctct    7080 ccccgcgcgt tggccgattc attaatgcag ctggcacgac aggtttcccg actggaaagc    7140
gggcagtgag cgcaacgcaa ttaatgtgag ttagctcact cattaggcac cccaggcttt    7200
acactttatg cttccggctc gtatgttgtg tggaattgtg agcggataac aatttcacac    7260
aggaaacagc tatgaccatg attacgccaa gcgcgcaatt aaccctcact aaagggaaca    7320
aaagctgggt ac                                                        7332
```

<210> SEQ ID NO 63  
<211> LENGTH: 7354  
<212> TYPE: DNA  
<213> ORGANISM: Artificial Sequence  
<220> FEATURE:  
<223> OTHER INFORMATION: vector

<400> SEQUENCE: 63

```
cgaattcaaa acttttttggg aggtgtgaga tgcggcgcga aagtctgttg gtaacggtat      60
gcaagggcct gcgggtacat gtcgagcgcg tggggcagga tcccgggcgc gacacggtga     120
tgctggtcaa cggcgcgatg gcgaccaccg cctcgttcgc ccggacctgc aagtgcctgg     180
ccgaacattt caacgtggtg ctgttcgacc tgcccttcgc cgggcagtcg cggcagcaca     240
atccgcagcg cggggttgatc accaaggacg acgaggtgga gattctcctg cgcgctgatcg    300 agcgcttcgc tgtcaaccac ctggtctcgg cctcctgggg cggcatctcc acgctgctgg     360
cgctgtcgcg caacccgcgc ggggtccgca gctcggtggt gatggcgttc cgcgccgggc     420
tgaaccaggc gatgctcgat tatgtcgggc gggcccagga actgatcgaa ctggacgaca     480
agtcggcgat cggccaccctg ctcaacgaga ccgtcggcaa gtacctgccg ccgcggctga    540
aggccagcaa ccatcagcac atggcctccc tggccactgg cgagtacgag caggcgcgtt     600
tccacatcga ccaggtgctg gcgctcaatg accgtggcta cctgagctgc tggggcaga     660 tccagagtca cgtgcatttc atcaacggca gctgggacga gtacaccacc gccgaggacg     720
cccgccagtt ccgcgattac ctgccgcatt gcagttttct gcgggtggaa ggcaccgggc     780
acttcctcga cctggagtcc aagctggcgg cggcgcgtgt gcaccgggcg ttgctcgagc     840
acctgctggc gcaaccggaa ccgtggcgct ccgagcaggc ggcgggattc cacgagatgg     900
```

```
ccatcggcta cgcctgaccc gtcgggatct gcgaaggccc ggcatggccg ggccttgccg    960
ttgcacaacg caaggagtag ccccatgcac gccattctca tcgccatcgg ttcggccggc   1020
gacgtgttcc ccttcatcgg cctggcccgc accctgaagt tgcgcggcca ccgcgtcagc   1080
ctgtgcacca ttccggtgtt tcgcgccgcg gtggagcagc acggcatcga gttcgtcccg   1140
ctcagcgacg aactgaccta ccgccggacc atgggcgacc cgcgcctgtg ggatccgaag   1200
acctcgttcg gagtgctctg gcaggccatc gccgggatga tcgagccggt ctacgagtac   1260
gtctgcgcac agcgccacga cgacatcgtg gtggtcggtt cgctgtgggc cctgggcgcg   1320
cggatcgccc atgagaaata cgggattccc tacctgtcgg tgcaggtctc gccgtcgacc   1380
ctgctgtcgg cgcacctgcc gccggtccac cccaggttca acgtgcccga gcaggtcccg   1440
ctggcgatgc gcaagttgct ctggcgctgc atcgaacgct tcaagctgga ccgcacctgc   1500
gccccggaga tcaacgcggt gcgccgcaag gtcggcctgg tcggcccggc gaagcgcatc   1560
ttcacccagt ggatgcattc gccacaggga gtgctctgcc tgttcccggc ctggttcgca   1620
ccgccccagc aggactggcc gcaaccgctg cacatgaccg gcttcccgct gttcgacggc   1680
agcgtcccgg ggaccgcct cgacgacgag ttgcagcgct tcctcgagca gggcagtcgg   1740
ccgctggtgt tcacccaggg ttcgaccgag cacctgcagg gagacttcta tgccatggcc   1800
ttgcgcgcgc tggagcgtct cggcgcccgc ggcatcttcc tcaccggcgc cggccaggag   1860
ccgctgcgtg gcttgccgag ccacgtgctg caacgctcgt acgtgccgtt ggggccttg    1920
ctgccggcgt gcgccgggct ggtccacccg gccggcatcg cgccatgag cctggcgctg   1980
gcggcggggg tgccgcaggt gctgctgcct tgcgcccacg accagttcga caacgccgaa   2040
cgcctggtcc gcctcggctg cggtatccgc ctgggcctgc cgctacgcga gcaggcgctg   2100
cgcgagtcgc tctggcgggct gctcgaggac ccggcgctgg cggcggcctg tcggcgtttc   2160
atggaattgt cacaaccgca cagtatcgct tgcggtaaag cggcccaagt ggtcgaacgt   2220
tgtcataggg aggggatgt gcgatggctg aaagccgcgt cctgagccgt gctggcagaa   2280
ttctctagag cggccgccac cgcggtggag ctccaattcg ccctatagtg agtcgtatta   2340
cgcgcgctca ctggccgtcg ttttacaacg tcgtgactgg gaaaaccctg gcgttaccca   2400
acttaatcgc cttgcagcac atcccccttt cgccagctgg cgtaatagcg aagaggcccg   2460
caccgatcgc ccttcccaac agttgcgcag cctgaatggc gaatgaaat tgtaagcgtt   2520
aatattttgt taaaattcgc gttaaatttt tgttaaatca gctcatttt taaccaatag   2580
gccgactgcg atgagtggca gggcggggcg taatttttt aaggcagtta ttggtgccct   2640
taaacgcctg gtgctacgcc tgaataagtg ataataagcg gatgaatggc agaaattcga   2700
aagcaaattc gacccggtcg tcggttcagg gcagggtcgt taaatagccg cttatgtcta   2760
ttgctggttt accggtttat tgactaccgg aagcagtgtg accgtgtgct tctcaaatgc   2820
ctgaggccag tttgctcagg ctctccccgt ggaggtaata attgacgata tgatcattta   2880
ttctgcctcc cagagcctga taaaaacggt gaatccgtta gcgaggtgcc gccggcttcc   2940
attcaggtcg aggtggcccg gctccatgca ccgcgacgca acgcggggag gcagacaagg   3000
tatagggcgg cgaggcggct acagccgata gtctggaaca gcgcacttac gggttgctgc   3060
gcaacccaag tgctaccggc gcggcagcgt gacccgtgtc ggcggctcca acggctcgcc   3120
atcgtccaga aaacacggct catcgggcat cggcaggcgc tgctgcccgc gccgttccca   3180
ttcctccgtt tcggtcaagg ctggcaggtc tggttccatg cccggaatgc cgggctggct   3240
```

```
gggcggctcc tcgccggggc cggtcggtag ttgctgctcg cccggataca gggtcgggat   3300
gcggcgcagg tcgccatgcc ccaacagcga ttcgtcctgg tcgtcgtgat caaccaccac   3360
ggcggcactg aacaccgaca ggcgcaactg gtcgcggggc tggccccacg ccacgcggtc   3420
attgaccacg taggccgaca cggtgccggg gccgttgagc ttcacgacgg agatccagcg   3480
ctcggccacc aagtccttga ctgcgtattg gaccgtccgc aaagaacgtc cgatgagctt   3540
ggaaagtgtc ttctggctga ccaccacggc gttctggtgg cccatctgcg ccacgaggtg   3600
atgcagcagc attgccgccg tgggtttcct cgcaataagc ccggcccacg cctcatgcgc   3660
tttgcgttcc gtttgcaccc agtgaccggg cttgttcttg gcttgaatgc cgatttctct   3720
ggactgcgtg gccatgctta tctccatgcg gtagggtgcc gcacggttgc ggcaccatgc   3780
gcaatcagct gcaacttttc ggcagcgcga caacaattat gcgttgcgta aaagtggcag   3840
tcaattacag attttcttta acctacgcaa tgagctattg cggggggtgc cgcaatgagc   3900
tgttgcgtac ccccctttt taagttgttg attttaagt ctttcgcatt tcgccctata   3960
tctagttctt tggtgcccaa agaagggcac ccctgcgggg ttcccccacg ccttcggcgc   4020
ggctccccct ccggcaaaaa gtggcccctc cggggcttgt tgatcgactg cgcggccttc   4080
ggccttgccc aaggtggcgc tgccccttg aaccccgc actcgccgcc gtgaggctcg   4140
gggggcaggc gggcgggctt cgccttcgac tgcccccact cgcataggct gggtcgttc   4200 caggcgcgtc aaggccaagc cgctgcgcgg tcgctgcgcg agccttgacc cgccttccac   4260
ttggtgtcca accggcaagc gaagcgcgca ggccgcaggc cggaggcttt tccccagaga   4320
aaattaaaaa aattgatggg gcaaggccgc aggccgcgca gttggagccg gtgggtatgt   4380
ggtcgaaggc tgggtagccg gtgggcaatc cctgtggtca agctcgtggg caggcgcagc   4440
ctgtccatca gcttgtccag cagggttgtc cacgggccga cgaagcgag ccagccggtg   4500 gccgctcgcg gccatcgtcc acatatccac gggctggcaa gggagcgcag cgaccgcgca   4560
gggcgaagcc cggagagcaa gcccgtaggg cgccgcagcc gccgtaggcg gtcacgactt   4620
tgcgaagcaa agtctagtga gtatactcaa gcattgagtg gcccgccgga ggcaccgcct   4680
tgcgctgccc ccgtcgagcc ggttggacac caaaagggag gggcaggcat ggcggcatac   4740
gcgatcatgc gatgcaagaa gctggcgaaa atgggcaacg tggcggccag tctcaagcac   4800
gcctaccgcg agcgcgagac gcccaacgct gacgccagca ggacgccaga gaacgagcac   4860
tgggcggcca gcagcaccga tgaagcgatg gccgactgc gcgagttgct gccagagaag   4920
cggcgcaagg acgctgtgtt ggcggtcgag tacgtcatga cggccagccc ggaatggtgg   4980
aagtcggcca gccaagaaca gcaggcggcg ttcttcgaga aggcgcacaa gtggctggcg   5040
gacaagtacg gggcggatcg catcgtgacg gccagcatcc accgtgacga aaccagcccg   5100
cacatgaccg cgttcgtggt gccgctgacg caggacggca ggctgtcggc caaggagttc   5160
atcggcaaca aagcgcagat gacccgcgac cagaccacgt ttgcggccgc tgtggccgat   5220
ctagggctgc aacgggcat cgagggcagc aaggcacgtc acacgcgcat tcaggcgttc   5280
tacgaggccc tggagcggcc accagtgggc cacgtcacca tcagcccgca agcggtcgag   5340
ccacgcgcct atgcaccgca gggattggcc gaaaagctgg gaatctcaaa gcgcgttgag   5400
acgccggaag ccgtggccga ccggctgaca aaagcggttc ggcaggggta tgagcctgcc   5460
ctacaggccg ccgcaggagc gcgtgagatg cgcaagaagg ccgatcaagc ccaagagacg   5520
gcccgagacc ttcgggagcg cctgaagccc gttctggacg ccctgggccc gttgaatcgg   5580
gatatgcagg ccaaggccgc cgcgatcatc aaggccgtgg gcgaaaagct gctgacggaa   5640
```

```
cagcgggaag tccagcgcca gaaacaggcc cagcgccagc aggaacgcgg gcgcgcacat    5700
ttccccgaaa agtgccacct gggatgaatg tcagctactg ggctatctgg acaagggaaa    5760
acgcaagcgc aaagagaaag caggtagctt gcagtgggct tacatggcga tagctagact    5820
gggcggtttt atggacagca agcgaaccgg aattgccagc tggggcgccc tctggtaagg    5880
ttgggaagcc ctgcaaagta aactggatgg ctttcttgcc gccaaggatc tgatggcgca    5940
ggggatcaag atctgatcaa gagacaggat gaggatcgtt tcgcatgatt gaacaagatg    6000
gattgcacgc aggttctccg gccgcttggg tggagaggct attcggctat gactgggcac    6060
aacagacaat cggctgctct gatgccgccg tgttccggct gtcagcgcag gggcgcccgg    6120 ttcttttgt caagaccgac ctgtccggtg ccctgaatga actgcaggac gaggcagcgc    6180
ggctatcgtg gctggccacg acgggcgttc cttgcgcagc tgtgctcgac gttgtcactg    6240
aagcgggaag ggactggctg ctattgggcg aagtgccggg gcaggatctc ctgtcatctc    6300
accttgctcc tgccgagaaa gtatccatca tggctgatgc aatgcggcgg ctgcatacgc    6360
ttgatccggc tacctgccca ttcgaccacc aagcgaaaca tcgcatcgag cgagcacgta    6420
ctcggatgga agccggtctt gtcgatcagg atgatctgga cgaagagcat caggggctcg    6480
cgccagccga actgttcgcc aggctcaagg cgcgcatgcc cgacggcgag gatctcgtcg    6540
tgacccatgg cgatgcctgc ttgccgaata tcatggtgga aaatggccgc ttttctggat    6600
tcatcgactg tggccggctg ggtgtggcgg accgctatca ggacatagcg ttggctaccc    6660
gtgatattgc tgaagagctt ggcggcgaat gggctgaccg cttcctcgtg ctttacggta    6720
tcgccgctcc cgattcgcag cgcatcgcct tctatcgcct tcttgacgag ttcttctgag    6780
cgggactctg gggttcgaaa tgaccgacca agcgacgccc aacctgccat cacgagattt    6840
cgattccacc gccgccttct atgaaaggtt gggcttcgga atcgttttcc gggacgccgg    6900
ctggatgatc ctccagcgcg ggatctcat gctggagttc ttcgcccacc cccatgggca    6960
aatattatac gcaaggcgac aaggtgctga tgccgctggc gattcaggtt catcatgccg    7020
tttgtgatgg cttccatgtc ggcagaatgc ttaatgaatt acaacagttt ttatgcatgc    7080
gcccaatacg caaaccgcct ctccccgcgc gttggccgat tcattaatgc agctggcacg    7140
acaggtttcc cgactggaaa gcgggcagtg agcgcaacgc aattaatgtg agttagctca    7200
ctcattaggc accccaggct ttacactta tgcttccggc tcgtatgttg tgtggaattg    7260
tgagcggata caatttcac acaggaaaca gctatgacca tgattacgcc aagcgcgcaa    7320
ttaaccctca ctaaagggaa caaaagctgg gtac                                7354

<210> SEQ ID NO 64
<211> LENGTH: 2298
<212> TYPE: DNA
<213> ORGANISM: Artificial Sequence
<220> FEATURE:
<223> OTHER INFORMATION: syn operon

<400> SEQUENCE: 64
aagcttgaat tcggtaccga aaatttttgg gaggtgtgaa atgcggcgcg aaagtctgtt      60
ggtatcggtt tgcaagggcc tgcgggtaca tgtcagcgc gttgggcagg atcccgggcg     120
cagcacggtg atgctggtca acggcgcgat ggcgaccacc gcctcgttcg cccggacctg     180
caagtgcctg gccgaacatt tcaacgtggt gctgttcgac ctgcccttcg ccgggcagtc     240
gcgtcagcac aacccgcagc gcgggttgat caccaaggac gacgaggtgg aaatcctcct     300
```

```
ggcgctgatc gagcgcttcg aggtcaatca cctggtctcc gcgtcctggg gcggtatctc    360
cacgctgctg gcgctgtcgc gcaatccgcg cggcatccgc agctcggtgg tgatggcatt    420
cgcccctgga ctgaaccagg cgatgctcga ctacgtcggg cgggcgcagg cgctgatcga    480
gctggacgac aagtcggcga tcggccatct gctcaacgag accgtcggca aatacctgcc    540
gcagcgcctg aaagccagca accatcagca catggcttcg ctggccaccg gcgaatacga    600
gcaggcgcgc tttcacatcg accaggtgct ggcgctcaac gatcgggct acttggcttg    660
cctggagcgg atccagagcc acgtgcattt catcaacggc agctgggacg aatacaccac    720
cgccgaggac gcccgccagt tccgcgacta cctgccgcac tgcagtttct cgcgggtgga    780
gggcaccggg catttcctcg acctggagtc caagctggca gcggtacgcg tgcaccgcgc    840
cctgctcgag cacctgctga agcaaccgga gccgcagcgg gcggaacgcg cggcgggatt    900
ccacgagatg gccatcggct acgcctgaac ccttgacctg cgaagacccg gctggccgg    960
gctttgcggt tgcataacgc acggagtagc cccatgcacg ccatcctcat cgccatcggc   1020
tcggccggcg acgtatttcc cttcatcggc ctggcccgga ccctgaaact gcgcgggcac   1080
cgcgtgagcc tctgcaccat cccggtgttt cgcgacgcgg tggagcagca cggcatcgcg   1140
ttcgtcccgc tgagcgacga actgacctac cgccggacca tgggcgatcc gcgcctgtgg   1200
gaccccaaga cgtccttcgg cgtgctctgg caagccatcg ccgggatgat cgagccggtc   1260
tacgagtacg tctcggcgca gcgccatgac gacatcgtgg tggtcggctc gctatgggcg   1320
ctgggcgcac gcatcgctca cgagaagtac gggattccct acctgtccgc gcaggtctcg   1380
ccatcgaccc tgttgtcggc gcacctgccg ccggtacacc ccaagttcaa cgtgcccgag   1440
cagatgccgc tggcgatgcg caagctgctc tggcgctgca tcgagcgctt caagctggat   1500
cgcacctgcg cgccggagat caacgcggtg cgccgcaagg tcggcctgga aacgccggtg   1560
aagcgcatct tcacccaatg gatgcattcg ccgcagggcg tggtctgcct gttcccggcc   1620
tggttcgcgc cgccccagca ggattggccg caacccctgc acatgaccgg cttcccgctg   1680
ttcgacggca gtatcccggg gaccccgctc gacgacgaac tgcaacgctt tctcgatcag   1740
ggcagccggc cgctggtgtt cacccagggc tcgaccgaac acctgcaggg cgacttctac   1800
gccatggccc tgcgcgcgct ggaacgcctc ggcgcgcgtg ggatcttcct caccggcgcc   1860
ggccaggaac cgctgcgcgg cttgccgaac cacgtgctgc agcgcgccta cgcgccactg   1920
ggagccttgc tgccatcgtg cgccgggctg gtccatccgg gcggtatcgg cgccatgagc   1980
ctagccttgg cggcggggt gccgcaggtg ctgctgccct gtgcccacga ccagttcgac   2040
aatgccgaac ggctggtccg gctcggctgc gggatgcgcc tgggcgtgcc gttgcgcgag   2100
caggagttgc gcggggcgct gtggcgcttg ctcgaggacc cggccatggc ggcggcctgt   2160
cggcgtttca tggaattgtc acaaccgcac agtatcgctt gcggtaaagc ggcccaggtg   2220
gtcgaacgtt gtcataggga gggggatgct cgatggctga aggctgcgtc ctgaacggtc   2280
tagagaattc ggcgcgcc                                                 2298
```

<210> SEQ ID NO 65
<211> LENGTH: 2302
<212> TYPE: DNA
<213> ORGANISM: Artificial Sequence
<220> FEATURE:
<223> OTHER INFORMATION: syn operon

<400> SEQUENCE: 65

```
ggtaccgaat tcaaaacttt ttgggaggtg tgagatgcgg cgcgaaagtc tgttggtaac    60
```

```
ggtatgcaag ggcctgcggg tacatgtcga gcgcgtgggg caggatcccg ggcgcgacac    120
ggtgatgctg gtcaacggcg cgatggcgac caccgcctcg ttcgcccgga cctgcaagtg    180
cctggccgaa catttcaacg tggtgctgtt cgacctgccc ttcgccgggc agtcgcggca    240
gcacaatccg cagcgcgggt tgatcaccaa ggacgacgag gtggagattc tcctggcgct    300
gatcgagcgc ttcgctgtca accacctggt ctcggcctcc tggggcggca tctccacgct    360
gctggcgctg tcgcgcaacc cgcgcggggt ccgcagctcg gtggtgatgg cgttcgcgcc    420
ggggctgaac caggcgatgc tcgattatgt cgggcgggcc caggaactga tcgaactgga    480
cgacaagtcg gcgatcggcc acctgctcaa cgagaccgtc ggcaagtacc tgccgccgcg    540
gctgaaggcc agcaaccatc agcacatggc ctccctggcc actggcgagt acgagcaggc    600
gcgtttccac atcgaccagg tgctggcgct caatgaccgt ggctacctga gctgcctggg    660
gcagatccag agtcacgtgc atttcatcaa cggcagctgg gacgagtaca ccaccgccga    720
ggacgcccgc cagttccgcg attacctgcc gcattgcagt ttttcgcggg tggaaggcac    780
cgggcacttc ctcgacctgg agtccaagct ggcggcggcg cgtgtgcacc gggcgttgct    840
cgagcacctg ctggcgcaac cggaaccgtg cgctccgag caggcggcgg gattccacga    900
gatggccatc ggctacgcct gacccgtcgg gatctgcgaa ggcccggcat ggccgggcct    960
tgccgttgca caacgcaagg agtagcccca tgcacgccat tctcatcgcc atcggttcgg   1020
ccggcgacgt gttccccttc atcggcctgg cccgcaccct gaagttgcgc ggccaccgcg   1080
tcagcctgtg caccattccg gtgtttcgcg ccgcggtgga gcagcacggc atcgagttcg   1140
tcccgctcag cgacgaactg acctaccgcc ggaccatggg cgacccgcgc ctgtgggatc   1200
cgaagacctc gttcggagtg ctctggcagg ccatcgccgg gatgatcgag ccggtctacg   1260
agtacgtctg cgcacagcgc cacgacgaca tcgtggtggt cggttcgctg tgggccctgg   1320
gcgcgcggat cgcccatgag aaatacggga ttccctacct gtcggtgcag gtctcgccgt   1380
cgaccctgct gtcggcgcac ctgccgccgg tccaccccag gttcaacgtg cccgagcagg   1440
tcccgctggc gatgcgcaag ttgctctggc gctgcatcga acgcttcaag ctggaccgca   1500
cctgcgcccc ggagatcaac gcggtgcgcc gcaaggtcgg cctggtcggc cggcgaagc    1560 gcatcttcac ccagtggatg cattcgccac agggagtgct ctgcctgttc ccggcctggt   1620
tcgcaccgcc ccagcaggac tggccgcaac cgctgcacat gaccggcttc ccgctgttcg   1680
acggcagcgt cccggggacc cgcctcgacg acgagttgca gcgcttcctc gagcagggca   1740
gtcggccgct ggtgttcacc cagggttcga ccgagcacct gcagggagac ttctatgcca   1800
tggccttgcg cgcgctggag cgtctcggcg cccgcggcat cttcctcacc ggcgccggcc   1860
aggagccgct gcgtggcttg ccgagccacg tgctgcaacg ctcgtacgtg ccgttggggg   1920
ccttgctgcc ggcgtgcgcc gggctggtcc accggccgg catcggcgcc atgagcctgg    1980 cgctggcgg ggggtgccg caggtgctgc tgccttgcgc ccacgaccag ttcgacaacg     2040
ccgaacgcct ggtccgcctc ggctgcggta tccgcctggg cctgccgcta cgcgagcagg   2100
cgctgcgcga gtcgctctgg cggctgctcg aggaccggc gctggcggcg cctgtcggc    2160 gtttcatgga attgtcacaa ccgcacagta tcgcttgcgg taaagcggcc caagtggtcg   2220
aacgttgtca tagggagggg gatgtgcgat ggctgaaagc cgcgtcctga gccgtgctgg   2280
cagaattctc tagaggcgcg cc                                            2302
```

<210> SEQ ID NO 66

<211> LENGTH: 8325
<212> TYPE: DNA
<213> ORGANISM: Artificial Sequence
<220> FEATURE:
<223> OTHER INFORMATION: vector

<400> SEQUENCE: 66

| | |
|---|---|
| ctagatacgg gagaagaacg atcatggacc ggatagacat gggcgtgctg gtggtgctgt | 60 |
| tcaatcctgg cgacgacgac ctggaacacc ttggcgaact ggcggcggcc tttccgcaac | 120 |
| tgcgcttcct cgccgtcgac aactcgccgc acagcgatcc gcagcgcaac gcccggctgc | 180 |
| gcgggcaagg catcgccgtg ctctaccacg gcaaccggca gggcatcgcc ggcgccttca | 240 |
| accaggggct cgacacgctg ttccggcgcg gcctgcaggg tgtgctgctg ctcgaccagg | 300 |
| actcccgtcc cggcggcgcc ttcctcgccg cccagtggcg caacctgcag gcatgcaacg | 360 |
| gccaggcctg cctgctcggc ccacggatct tcgaccgggg cgaccggcgc ttcctgccgg | 420 |
| ccatccacct cgacgggctg cgcgctcagg aactgtccct ggacggcctg acgacccac | 480 |
| agcgcacctc gttcctgatc tcctccggct gcctgctgac ccgcgaggcc taccagcgcc | 540 |
| tcggccactt cgacgaggaa ctgttcatcg accacgtgga caccgagtac agcctgcgcg | 600 |
| cccaggcgct ggacgtgccc ctgtacgtcg acccgcggct ggtcctcgag caccgcatcg | 660 |
| gcacgcgcaa gacccgccgc ctcggcggtc tcagcctcag cgcgatgaac cacgccccac | 720 |
| tgcgccgcta ctacctggcg cgcaacggcc tgctggtcct cgccgctac gcccggtcct | 780 |
| cgccgctggc cctgctggcg aacctgccga ccctgaccca gggcctcgcg gtgctcctgc | 840 |
| tcgaacgcga caagctgctc aagctgcgct gctgggctg gggcctgtgg acggcctgc | 900 |
| gggggcgcgg cggcgcgctg gagcgcaacc gcccgcgcct gctgaagcgc ctcgccggtc | 960 |
| cggcggtggc gcccacagtt cccggcaagg ccaaggccta gtcggcgaaa cgcattgagc | 1020 |
| tccaattcgc cctatagtga gtcgtattac gcgcgctcac tggccgtcgt tttacaacgt | 1080 |
| cgtgactggg aaaaccctgg cgttacccaa cttaatcgcc ttgcagcaca tcccccttc | 1140 |
| gccagctggc gtaatagcga agaggcccgc accgatcgcc cttcccaaca gttgcgcagc | 1200 |
| ctgaatggcg aatggaaatt gtaagcgtta atattttgtt aaaattcgcg ttaaattttt | 1260 |
| gttaaatcag ctcattttt aaccaatagg ccgactgcga tgagtggcag gcggggcgt | 1320 |
| aattttttta aggcagttat tggtgccctt aaacgcctgg tgctacgcct gaataagtga | 1380 |
| taataagcgg atgaatggca gaaattcgaa agcaaattcg acccggtcgt cggttcaggg | 1440 |
| cagggtcgtt aaatagccgc ttatgtctat tgctggttta ccggtttatt gactaccgga | 1500 |
| agcagtgtga ccgtgtgctt ctcaaatgcc tgaggccagt ttgctcaggc tctccccgtg | 1560 |
| gaggtaataa ttgacgatat gatcatttat tctgcctccc agagcctgat aaaaacggtg | 1620 |
| aatccgttag cgaggtgccg ccggcttcca ttcaggtcga ggtggcccgg ctccatgcac | 1680 |
| cgcgacgcaa cgcggggagg cagacaaggt atagggcggc gaggcggcta cagccgatag | 1740 |
| tctggaacag cgcacttacg ggttgctgcg caacccaagt gctaccggcg cggcagcgtg | 1800 |
| acccgtgtcg gcggctccaa cggctcgcca tcgtccagaa acacggctc atcgggcatc | 1860 |
| ggcaggcgct gctgcccgcg ccgttccat tcctccgttt cggtcaaggc tggcaggtct | 1920 |
| ggttccatgc ccggaatgcc gggctggctg gcggctcct cgccggggcc ggtcggtagt | 1980 |
| tgctgctcgc ccggatacag ggtcgggatg cggcgcaggt cgccatgccc caacagcgat | 2040 |
| tcgtcctggt cgtcgtgatc aaccaccacg gcggcactga acaccgacag gcgcaactgg | 2100 |
| tcgcggggct ggccccacgc cacgcggtca ttgaccacgt aggccgacac ggtgccgggg | 2160 |

```
ccgttgagct tcacgacgga gatccagcgc tcggccacca agtccttgac tgcgtattgg   2220
accgtccgca aagaacgtcc gatgagcttg gaaagtgtct tctggctgac cacccacggcg  2280
ttctggtggc ccatctgcgc cacgaggtga tgcagcagca ttgccgccgt gggtttcctc   2340
gcaataagcc cggcccacgc ctcatgcgct ttgcgttccg tttgcaccca gtgaccgggc   2400
ttgttcttgg cttgaatgcc gatttctctg gactgcgtgg ccatgcttat ctccatgcgg   2460
tagggtgccg cacggttgcg gcaccatgcg caatcagctg caacttttcg gcagcgcgac   2520
aacaattatg cgttgcgtaa aagtggcagt caattacaga ttttctttaa cctacgcaat   2580
gagctattgc ggggggtgcc gcaatgagct gttgcgtacc cccctttttt aagttgttga   2640
ttttttaagtc tttcgcattt cgccctatat ctagttcttt ggtgcccaaa aagggcacc   2700
cctgcgggt tcccccacgc cttcggcgcg gctcccctc cggcaaaaag tggcccctcc      2760
ggggcttgtt gatcgactgc gcggccttcg gccttgccca aggtggcgct gcccccttgg   2820
aaccccccgca ctcgccgccg tgaggctcgg ggggcaggcg ggcgggcttc gccttcgact  2880
gcccccactc gcataggctt gggtcgttcc aggcgcgtca aggccaagcc gctgcgcggt   2940
cgctgcgcga gccttgaccc gccttccact tggtgtccaa ccggcaagcg aagcgcgcag   3000
gccgcaggcc ggaggctttt ccccagagaa aattaaaaaa attgatgggg caaggccgca  3060
ggccgcgcag ttggagccgg tgggtatgtg gtcgaaggct gggtagccgg tgggcaatcc  3120
ctgtggtcaa gctcgtgggc aggcgcagcc tgtccatcag cttgtccagc agggttgtcc  3180
acgggccgag cgaagcgagc cagccggtgg ccgctcgcgg ccatcgtcca catatccacg  3240
ggctggcaag ggagcgcagc gaccgcgcag ggcgaagccc ggagagcaag cccgtagggc  3300
gccgcagccg ccgtaggcgg tcacgacttt gcgaagcaaa gtctagtgag tatactcaag  3360
cattgagtgg cccgccggag gcaccgcctt gcgctgcccc cgtcgagccg gttggacacc  3420
aaaagggagg ggcaggcatg gcggcatacg cgatcatgcg atgcaagaag ctggcgaaaa  3480
tgggcaacgt ggcggccagt ctcaagcacg cctaccgcga gcgcgagacg cccaacgctg  3540
acgccagcag gacgccagag aacgagcact gggcggccag cagcaccgat gaagcgatgg  3600
gccgactgcg cgagttgctg ccagagaagc ggcgcaagga cgctgtgttg gcggtcgagt  3660
acgtcatgac ggccagcccg gaatggtgga agtcggccag ccaagaacag caggcggcgt  3720
tcttcgagaa ggcgcacaag tggctggcgg acaagtacgg ggcggatcgc atcgtgacgg  3780
ccagcatcca ccgtgacgaa accagcccgc acatgaccgc gttcgtggtg ccgctgacgc  3840
aggacggcag gctgtcggcc aaggagttca tcggcaacaa agcgcagatg acccgcgacc  3900
agaccacgtt tgcggccgct gtggccgatc tagggctgca acggggcatc gagggcagca  3960
aggcacgtca cacgcgcatt caggcgttct acgaggccct ggagcggcca ccagtgggcc  4020
acgtcaccat cagcccgcaa gcggtcgagc cacgcgccta tgcaccgcag ggattggccg  4080
aaaagctggg aatctcaaag cgcgttgaga cgccggaagc cgtggccgac cggctgacaa  4140
aagcggttcg gcagggtat gagcctgccc tacaggccgc cgcaggagcg cgtgagatgc    4200
gcaagaaggc cgatcaagcc caagagacgg cccgagacct tcgggagcgc ctgaagcccg  4260
ttctggacgc cctgggccg ttgaatcggg atatgcaggc caaggccgcc gcgatcatca   4320
aggccgtggg cgaaaagctg ctgacggaac agcgggaagt ccagcgccag aaacaggccc  4380
agcgccagca ggaacgcggg cgcgcacatt tccccgaaaa gtgccacctg ggatgaatgt  4440
cagctactgg gctatctgga caagggaaaa cgcaagcgca aagagaaagc aggtagcttg  4500
```

```
cagtgggctt acatggcgat agctagactg ggcggtttta tggacagcaa gcgaaccgga   4560
attgccagct ggggcgccct ctggtaaggt tgggaagccc tgcaaagtaa actggatggc   4620
tttcttgccg ccaaggatct gatggcgcag gggatcaaga tctgatcaag agacaggatg   4680
aggatcgttt cgcatgattg aacaagatgg attgcacgca ggttctccgg ccgcttgggt   4740
ggagaggcta ttcggctatg actgggcaca acagacaatc ggctgctctg atgccgccgt   4800
gttccggctg tcagcgcagg ggcgcccggt tcttttgtc aagaccgacc tgtccggtgc   4860
cctgaatgaa ctgcaggacg aggcagcgcg gctatcgtgg ctggccacga cgggcgttcc   4920
ttgcgcagct gtgctcgacg ttgtcactga agcgggaagg gactggctgc tattgggcga   4980
agtgccgggg caggatctcc tgtcatctca ccttgctcct gccgagaaag tatccatcat   5040
ggctgatgca atgcggcggc tgcatacgct tgatccggct acctgcccat tcgaccacca   5100
agcgaaacat cgcatcgagc gagcacgtac tcggatggaa gccggtcttg tcgatcagga   5160
tgatctggac gaagagcatc aggggctcgc gccagccgaa ctgttcgcca ggctcaaggc   5220
gcgcatgccc gacggcgagg atctcgtcgt gacccatggc gatgcctgct tgccgaatat   5280
catggtggaa aatggccgct tttctggatt catcgactgt ggccggctgg gtgtggcgga   5340
ccgctatcag gacatagcgt tggctacccg tgatattgct gaagagcttg gcggcgaatg   5400
ggctgaccgc ttcctcgtgc tttacggtat cgccgctccc gattcgcagc gcatcgcctt   5460
ctatcgcctt cttgacgagt tcttctgagc gggactctgg ggttcgaaat gaccgaccaa   5520
gcgacgccca acctgccatc acgagatttc gattccaccg ccgccttcta tgaaaggttg   5580
ggcttcggaa tcgttttccg gacgccggc tggatgatcc tccagcgcgg ggatctcatg   5640
ctggagttct cgcccacccc catgggcaa atattatacg caaggcgaca aggtgctgat   5700
gccgctggcg attcaggttc atcatgccgt ttgtgatggc ttccatgtcg cagaatgct   5760
taatgaatta caacagtttt tatgcatgcg cccaatacgc aaaccgcctc tccccgcgcg   5820
ttggccgatt cattaatgca gctggcacga caggtttccc gactggaaag cgggcagtga   5880
gcgcaacgca attaatgtga gttagctcac tcattaggca ccccaggctt tacactttat   5940
gcttccggct cgtatgttgt gtggaattgt gagcggataa caatttcaca caggaaacag   6000
ctatgaccat gattacgcca agcgcgcaat taaccctcac taaagggaac aaaagctggg   6060
taccgaaaat ttttgggagg tgtgaaatgc ggcgcgaaag tctgttggta tcggtttgca   6120
agggcctgcg ggtacatgtc gagcgcgttg ggcaggatcc cgggcgcagc acggtgatgc   6180
tggtcaacgg cgcgatggcg accaccgcct cgttcgcccg gacctgcaag tgcctggccg   6240
aacatttcaa cgtggtgctg ttcgacctgc ccttcgccgg gcagtcgcgt cagcacaacc   6300
cgcagcgcgg gttgatcacc aaggacgacg aggtggaaat cctcctggcg ctgatcgagc   6360
gcttcgaggt caatcacctg gtctccgcgt cctggggcgg tatctccacg ctgctggcgc   6420
tgtcgcgcaa tccgcgcggc atccgcagct cggtggtgat ggcattcgcc ctgactga   6480
accaggcgat gctcgactac gtcgggcggg cgcaggcgct gatcgagctg acgacaagt   6540
cggcgatcgg ccatctgctc aacgagaccg tcggcaaata cctgccgcag cgcctgaaag   6600
ccagcaacca tcagcacatg gcttcgctgg ccaccggcga atacgagcag gcgcgctttc   6660
acatcgacca ggtgctggcg ctcaacgatc ggggctactt ggcttgcctg agcggatcc   6720
agagccacgt gcatttcatc aacggcagct gggacgaata caccaccgcc gaggacgccc   6780
gccagttccg cgactacctg ccgcactgca gtttctcgcg ggtggagggc accgggcatt   6840
tcctcgacct ggagtccaag ctggcagcgg tacgcgtgca ccgcgccctg ctcgagcacc   6900
```

| | |
|---|---:|
| tgctgaagca accggagccg cagcgggcgg aacgcgcggc gggattccac gagatggcca | 6960 |
| tcggctacgc ctgaacccttt gacctgcgaa gacccggcct ggccgggctt tgcggttgca | 7020 |
| taacgcacgg agtagcccca tgcacgccat cctcatcgcc atcggctcgg ccggcgacgt | 7080 |
| atttcccttc atcggcctgg cccggaccct gaaactgcgc gggcaccgcg tgagcctctg | 7140 |
| caccatcccg gtgtttcgcg acgcggtgga gcagcacggc atcgcgttcg tcccgctgag | 7200 |
| cgacgaactg acctaccgcc ggaccatggg cgatccgcgc ctgtgggacc caagacgtc | 7260 |
| cttcggcgtg ctctggcaag ccatcgccgg gatgatcgag ccggtctacg agtacgtctc | 7320 |
| ggcgcagcgc catgacgaca tcgtggtggt cggctcgcta tgggcgctgg gcgcacgcat | 7380 |
| cgctcacgag aagtacggga ttccctacct gtccgcgcag gtctcgccat cgaccctgtt | 7440 |
| gtcggcgcac ctgccgccgg tacacccaa gttcaacgtg cccgagcaga tgccgctggc | 7500 |
| gatgcgcaag ctgctctggc gctgcatcga gcgcttcaag ctggatcgca cctgcgcgcc | 7560 |
| ggagatcaac gcggtgcgcc gcaaggtcgg cctggaaacg ccggtgaagc gcatcttcac | 7620 |
| ccaatggatg cattcgccgc agggcgtggt ctgcctgttc ccggcctggt tcgcgccgcc | 7680 |
| ccagcaggat tggccgcaac ccctgcacat gaccggcttc ccgctgttcg acggcagtat | 7740 |
| cccggggacc ccgctcgacg acgaactgca acgctttctc gatcagggca gccggccgct | 7800 |
| ggtgttcacc cagggctcga ccgaacacct gcagggcgac ttctacgcca tggccctgcg | 7860 |
| cgcgctggaa cgcctcggcg cgcgtgggat cttcctcacc ggcgccggcc aggaaccgct | 7920 |
| gcgcggcttg ccgaaccacg tgctgcagcg cgcctacgcg ccactgggag ccttgctgcc | 7980 |
| atcgtgcgcc gggctggtcc atccgggcgg tatcggcgcc atgagcctag ccttggcggc | 8040 |
| gggggtgccg caggtgctgc tgccctgtgc ccacgaccag ttcgacaatg ccgaacggct | 8100 |
| ggtccggctc ggctgcggga tgcgcctggg cgtgccgttg cgcgagcagg agttgcgcgg | 8160 |
| ggcgctgtgg cgcttgctcg aggacccggc catggcggcg gcctgtcggc gtttcatgga | 8220 |
| attgtcacaa ccgcacagta tcgcttgcgg taaagcggcc caggtggtcg aacgttgtca | 8280 |
| tagggagggg gatgctcgat ggctgaaggc tgcgtcctga acggt | 8325 |

<210> SEQ ID NO 67
<211> LENGTH: 8335
<212> TYPE: DNA
<213> ORGANISM: Artificial Sequence
<220> FEATURE:
<223> OTHER INFORMATION: vector

<400> SEQUENCE: 67

| | |
|---|---:|
| ctagatacgg gagaagaacg atcatgacga tcctgggggc gctggtgatt ctgtacgacc | 60 |
| cgacggacga gcagttgtcg gggctggagg cgctcgcgcg cgacagcgac gcgctcgtgg | 120 |
| tcgtggacaa cacgccgcac gagcacgcgg cggcgcgcga gcgggtgcgt gcgctgtcgg | 180 |
| cgcggacgaa cacggtgtgg cgacaccacg gcaaccgggg cggggtcgcg ggcgggtaca | 240 |
| acgcggggct gtcggtgctg ttcgcgcagg gcgtcgaggc ggtcgcgctg ttcgaccagg | 300 |
| actcgacggt gccggccggg tacttcgagc ggatgcgcga ggcgtgcgcg caactgggtg | 360 |
| agcaaccggg cgcgcacgcg ggcgcgttca tcgcgggccc gcggatctac gacgcgaacg | 420 |
| agcagcgctt cctgccggag ctgatgacga gcggggtgac ggtgcgccgc gtgcgggtgg | 480 |
| agggcgagac ggcgccgcag cgctcgcgcgt tcctgatctc gtcgggcagc gtgatttcgc | 540 |
| gggccgcgta cgcgcggctc ggtcgattcg acgaggcgct gttcatcgat cacgtcgaca | 600 |

```
ccgagtattg cctgcgcgcg ctcgcgcaca acgtgccgct gtacgtggtg ccgccgctcg    660
tgctgacgca ccggatcggc gcgcggcgcc ggcacaaggt ggggccgttc gagctgacgg    720
cgatgcatca cgggtggttg cgccgatact acggcgcgcg caacgcgatg caactggggc    780
tgcagtacgg cttgcggttt ccggtggcgc tggtgccgaa tctgctgacg atatggcagg    840
tgatccaggt ggtgctgtgc gagcgggaga agggcgcgaa gctgcgcggg atcgcgctgg    900
gcgtgctcga cggcctgttc gggcggctgg gatcgttcga cgatgcgcgc gcgggcgcgg    960
cggcgcgcga gccggtgcgg caggaatgat cggcgaaacg cattgagctc caattcgccc   1020
tatagtgagt cgtattacgc gcgctcactg gccgtcgttt tacaacgtcg tgactgggaa   1080
aaccctggcg ttacccaact taatcgcctt gcagcacatc cccctttcgc cagctggcgt   1140
aatagcgaag aggcccgcac cgatcgccct cccaacagt tgcgcagcct gaatggcgaa   1200
tggaaattgt aagcgttaat attttgttaa aattcgcgtt aaattttgt taaatcagct   1260 cattttttaa ccaataggcc gactgcgatg agtggcaggg cggggcgtaa ttttttaag   1320 gcagttattg gtgcccttaa acgcctggtg ctacgcctga ataagtgata ataagcggat   1380
gaatggcaga aattcgaaag caaattcgac ccggtcgtcg gttcagggca gggtcgttaa   1440
atagccgctt atgtctattg ctggtttacc ggtttattga ctaccggaag cagtgtgacc   1500
gtgtgcttct caaatgcctg aggccagttt gctcaggctc tccccgtgga ggtaataatt   1560
gacgatatga tcatttattc tgcctcccag agcctgataa aaacggtgaa tccgttagcg   1620
aggtgccgcc ggcttccatt caggtcgagg tgcccggct ccatgcaccg cgacgcaacg   1680
cggggaggca gacaaggtat agggcggcga ggcggctaca gccgatagtc tggaacagcg   1740
cacttacggg ttgctgcgca acccaagtgc taccggcgcg gcagcgtgac ccgtgtcggc   1800
ggctccaacg gctcgccatc gtccagaaaa cacggctcat cgggcatcgg caggcgctgc   1860
tgcccgcgcc gttcccattc ctccgtttcg gtcaaggctg gcaggtctgg ttccatgccc   1920
ggaatgccgg gctggctggg cggctcctcg ccggggccgg tcggtagttg ctgctcgccc   1980
ggatacaggg tcgggatgcg gcgcaggtcg ccatgcccca acagcgattc gtcctggtcg   2040
tcgtgatcaa ccaccacggc ggcactgaac accgacaggc gcaactggtc gcggggctgg   2100
ccccacgcca cgcggtcatt gaccacgtag gccgacacgg tgccggggcc gttgagcttc   2160
acgacggaga tccagcgctc ggccaccaag tccttgactg cgtattggac cgtccgcaaa   2220
gaacgtccga tgagcttgga aagtgtcttc tggctgacca ccacggcgtt ctggtggccc   2280
atctgcgcca cgaggtgatg cagcagcatt gccgccgtgg gtttcctcgc aataagcccg   2340
gcccacgcct catgcgcttt gcgttccgtt tgcacccagt gaccgggctt gttcttggct   2400
tgaatgccga tttctctgga ctgcgtggcc atgcttatct ccatgcggta gggtgccgca   2460
cggttgcggc accatgcgca atcagctgca acttttcggc agcgcgacaa caattatgcg   2520
ttgcgtaaaa gtggcagtca attacagatt ttctttaacc tacgcaatga gctattgcgg   2580
ggggtgccgc aatgagctgt tgcgtacccc cctttttttaa gttgttgatt tttaagtctt   2640
tcgcatttcg ccctatatct agttctttgg tgcccaaaga agggcacccc tgcggggttc   2700
ccccacgcct tcgcgcggc tccccctccg gcaaaaagtg gcccctccgg ggcttgttga   2760
tcgactgcgc ggccttcggc cttgcccaag gtggcgctgc ccccttggaa ccccgcact   2820 cgccgccgtg aggctcgggg ggcaggcggg cgggcttcgc cttcgactgc ccccactcgc   2880
ataggcttgg gtcgttccag gcgcgtcaag gccaagccgc tgcgcggtcg ctgcgcgagc   2940
cttgacccgc cttccacttg gtgtccaacc ggcaagcgaa gcgcgcaggc cgcaggccgg   3000
```

-continued

```
aggcttttcc ccagagaaaa ttaaaaaaat tgatggggca aggccgcagg ccgcgcagtt    3060
ggagccggtg ggtatgtggt cgaaggctgg gtagccggtg ggcaatccct gtggtcaagc    3120
tcgtgggcag gcgcagcctg tccatcagct tgtccagcag ggttgtccac gggccgagcg    3180
aagcgagcca gccggtggcc gctcgcggcc atcgtccaca tatccacggg ctggcaaggg    3240
agcgcagcga ccgcgcaggg cgaagcccgg agagcaagcc cgtagggcgc cgcagccgcc    3300
gtaggcggtc acgactttgc gaagcaaagt ctagtgagta tactcaagca ttgagtggcc    3360
cgccggaggc accgccttgc gctgcccccg tcgagccggt tggacaccaa agggaggggg    3420
caggcatggc ggcatacgcg atcatgcgat gcaagaagct ggcgaaaatg ggcaacgtgg    3480
cggccagtct caagcacgcc taccgcgagc gcgagacgcc caacgctgac gccagcagga    3540
cgccagagaa cgagcactgg gcggccagca gcaccgatga agcgatgggc cgactgcgcg    3600
agttgctgcc agagaagcgg cgcaaggacg ctgtgttggc ggtcgagtac gtcatgacgg    3660
ccagcccgga atggtggaag tcggccagcc aagaacagca ggcggcgttc ttcgagaagg    3720
cgcacaagtg gctggcggac aagtacgggg cggatcgcat cgtgacggcc agcatccacc    3780
gtgacgaaac cagcccgcac atgaccgcgt tcgtggtgcc gctgacgcag gacggcaggc    3840
tgtcggccaa ggagttcatc ggcaacaaag cgcagatgac ccgcgaccag accacgtttg    3900
cggccgctgt ggccgatcta gggctgcaac ggggcatcga gggcagcaag gcacgtcaca    3960
cgcgcattca ggcgttctac gaggccctgg agcggccacc agtgggccac gtcaccatca    4020
gcccgcaagc ggtcgagcca cgcgcctatg caccgcaggg attggccgaa aagctgggaa    4080
tctcaaagcg cgttgagacg ccggaagccg tggccgaccg gctgacaaaa gcggttcggc    4140
aggggtatga gcctgcccta caggccgccg caggagcgcg tgagatgcgc aagaaggccg    4200
atcaagccca agagacggcc cgagaccttc gggagcgcct gaagcccgtt ctggacgccc    4260
tggggccgtt gaatcgggat atgcaggcca aggccgccgc gatcatcaag gccgtgggcg    4320
aaaagctgct gacggaacag cgggaagtcc agcgccagaa acaggcccag cgccagcagg    4380
aacgcgggcg cgcacatttc cccgaaaagt gccacctggg atgaatgtca gctactgggc    4440
tatctggaca agggaaaacg caagcgcaaa gagaaagcag gtagcttgca gtgggcttac    4500
atggcgatag ctagactggg cggttttatg gacagcaagc gaaccggaat tgccagctgg    4560
ggcgccctct ggtaaggttg ggaagccctg caaagtaaac tggatggctt tcttgccgcc    4620
aaggatctga tggcgcaggg gatcaagatc tgatcaagag acaggatgag gatcgtttcg    4680
catgattgaa caagatggat tgcacgcagg ttctccggcc gcttgggtgg agaggctatt    4740
cggctatgac tgggcacaac agacaatcgg ctgctctgat gccgccgtgt tccggctgtc    4800
agcgcagggg cgcccggttc tttttgtcaa gaccgacctg tccggtgccc tgaatgaact    4860
gcaggacgag gcagcgcggc tatcgtggct ggccacgacg ggcgttcctt gcgcagctgt    4920
gctcgacgtt gtcactgaag cgggaaggga ctggctgcta ttgggcgaag tgccggggca    4980
ggatctcctg tcatctcacc ttgctcctgc cgagaaagta tccatcatgg ctgatgcaat    5040
gcggcggctg catacgcttg atccggctac ctgcccattc gaccaccaag cgaaacatcg    5100
catcgagcga gcacgtactc ggatggaagc cggtcttgtc gatcaggatg atctggacga    5160
agagcatcag gggctcgcgc cagccgaact gttcgccagg ctcaaggcgc gcatgcccga    5220
cggcgaggat ctcgtcgtga cccatggcga tgcctgcttg ccgaatatca tggtggaaaa    5280
tggccgcttt tctggattca tcgactgtgg ccggctgggt gtggcggacc gctatcagga    5340
```

```
catagcgttg gctacccgtg atattgctga agagcttggc ggcgaatggg ctgaccgctt      5400
cctcgtgctt tacggtatcg ccgctcccga ttcgcagcgc atcgccttct atcgccttct      5460
tgacgagttc ttctgagcgg gactctgggg ttcgaaatga ccgaccaagc gacgcccaac      5520
ctgccatcac gagatttcga ttccaccgcc gccttctatg aaaggttggg cttcggaatc      5580
gttttccggg acgccggctg gatgatcctc cagcgcgggg atctcatgct ggagttcttc      5640
gcccaccccc atgggcaaat attatacgca aggcgacaag gtgctgatgc cgctggcgat      5700
tcaggttcat catgccgttt gtgatggctt ccatgtcggc agaatgctta atgaattaca      5760
acagttttta tgcatgcgcc caatacgcaa accgcctctc cccgcgcgtt ggccgattca      5820
ttaatgcagc tggcacgaca ggtttcccga ctggaaagcg ggcagtgagc gcaacgcaat      5880
taatgtgagt tagctcactc attaggcacc ccaggcttta cactttatgc ttccggctcg      5940
tatgttgtgt ggaattgtga gcggataaca atttcacaca ggaaacagct atgaccatga      6000
ttacgccaag cgcgcaatta accctcacta aagggaacaa aagctgggta ccgaattcaa      6060
aacttttggg gaggtgtgag atgcggcgcg aaagtctgtt ggtaacggta tgcaagggcc      6120
tgcgggtaca tgtcgagcgc gtggggcagg atcccgggcg cgacacggtg atgctggtca      6180
acggcgcgat ggcgaccacc gcctcgttcg cccggacctg caagtgcctg ccgaacatt       6240 tcaacgtggt gctgttcgac ctgcccttcg ccgggcagtc gcggcagcac aatccgcagc      6300
gcgggttgat caccaaggac gacgaggtgg agattctcct ggcgctgatc gagcgcttcg      6360
ctgtcaacca cctggtctcg gcctcctggg gcggcatctc cacgctgctg gcgctgtcgc      6420
gcaacccgcg cggggtccgc agctcggtgg tgatggcgtt cgcgccgggg ctgaaccagg      6480
cgatgctcga ttatgtcggg cgggcccagg aactgatcga actggacgac aagtcggcga      6540
tcggccacct gctcaacgag accgtcggca agtacctgcc gccgcggctg aaggccagca      6600
accatcagca catggcctcc ctggccactg gcgagtacga gcaggcgcgt ttccacatcg      6660
accaggtgct ggcgctcaat gaccgtggct acctgagctg cctggggcag atccagagtc      6720
acgtgcattt catcaacggc agctgggacg agtacaccac cgccgaggac gcccgccagt      6780
tccgcgatta cctgccgcat tgcagttttt cgcgggtgga aggcaccggg cacttcctcg      6840
acctggagtc caagctggcg gcggcgcgtg tgcaccgggc gttgctcgag cacctgctgg      6900
cgcaaccgga accgtggcgc tccgagcagg cggcggatt ccacgagatg gccatcggct       6960
acgcctgacc cgtcgggatc tgcgaaggcc cggcatggcc gggccttgcc gttgcacaac      7020
gcaaggagta gccccatgca cgccattctc atcgccatcg gttcggccgg cgacgtgttc      7080
cccttcatcg gcctggcccg cacccctgaag ttgcgcggcc accgcgtcag cctgtgcacc     7140
attccggtgt ttcgcgccgc ggtggagcag cacggcatcg agttcgtccc gctcagcgac      7200
gaactgacct accgccggac catgggcgac ccgcgcctgt gggatccgaa gacctcgttc      7260
ggagtgctct ggcaggccat cgccgggatg atcgagccgg tctacgagta cgtctgcgca      7320
cagcgccacg acgacatcgt ggtggtcggt tcgctgtggg ccctgggcgc gcggatcgcc      7380
catgagaaat acgggattcc ctacctgtcg gtgcaggtct cgccgtcgac cctgctgtcg      7440
gcgcacctgc cgccggtcca ccccaggttc aacgtgcccg agcaggtccc gctggcgatg      7500
cgcaagttgc tctggcgctg catcgaacgc ttcaagctgg accgcacctg cgccccggag      7560
atcaacgcgg tgcgccgcaa ggtcggcctg gtcggcccgg cgaagcgcat cttcacccag      7620
tggatgcatt cgccacaggg agtgctctgc ctgttcccgg cctggttcgc accgcccag       7680 caggactggc cgcaaccgct gcacatgacc ggcttcccgc tgttcgacgg cagcgtcccg      7740
```

-continued

```
gggacccgcc tcgacgacga gttgcagcgc ttcctcgagc agggcagtcg gccgctggtg    7800
ttcacccagg gttcgaccga gcacctgcag ggagacttct atgccatggc cttgcgcgcg    7860
ctggagcgtc tcggcgcccg cggcatcttc ctcaccggcg ccggccagga gccgctgcgt    7920
ggcttgccga gccacgtgct gcaacgctcg tacgtgccgt gggggccctt gctgccggcg    7980
tgcgccgggc tggtccaccc ggccggcatc ggcgccatga gcctggcgct ggcggcgggg    8040
gtgccgcagg tgctgctgcc ttgcgcccac gaccagttcg acaacgccga acgcctggtc    8100
cgcctcggct gcggtatccg cctgggcctg ccgctacgcg agcaggcgct gcgcgagtcg    8160
ctctggcggc tgctcgagga cccggcgctg cggcggcct gtcggcgttt catggaattg    8220
tcacaaccgc acagtatcgc ttgcggtaaa gcggcccaag tggtcgaacg ttgtcatagg    8280 gaggggatg tgcgatggct gaaagccgcg tcctgagccg tgctggcaga attct          8335
```

<210> SEQ ID NO 68
<211> LENGTH: 1023
<212> TYPE: DNA
<213> ORGANISM: Pseudomonas aeruginosa

<400> SEQUENCE: 68

```
tctagatacg ggagaagaac gatcatggac cggatagaca tgggcgtgct ggtggtgctg     60
ttcaatcctg cgacgacga cctggaacac cttggcgaac tggcggcggc ctttccgcaa    120
ctgcgcttcc tcgccgtcga caactcgccg cacagcgatc cgcagcgcaa cgcccggctg    180
cgcgggcaag gcatcgccgt gctctaccac ggcaaccggc agggcatcgc cggcgccttc    240
aaccaggggc tcgacacgct gttccggcgc ggcctgcagg gtgtgctgct gctcgaccag    300
gactcccgtc ccggcggcgc cttcctcgcc gcccagtggc gcaacctgca ggcatgcaac    360
ggccaggcct gcctgctcgg cccacggatc ttcgaccggg gcgaccggcg cttcctgccg    420
gccatccacc tcgacgggct ggcgctcagg caactgtccc tggacggcct gacgacccca    480
cagcgcacct cgttcctgat ctcctccggc tgcctgctga cccgcgaggc ctaccagcgc    540
ctcggccact tcgacgagga actgttcatc gaccacgtgg acaccgagta cagcctgcgc    600
gcccaggcgc tggacgtgcc cctgtacgtc gacccgcggc tggtcctcga gcaccgcatc    660
ggcacgcgca agacccgccg cctcggcggt ctcagcctca gcgcgatgaa ccacgcccca    720
ctgcgccgct actacctggc gcgcaacggc ctgctggtcc tgcgccgcta cgcccggtcc    780
tcgccgctgg ccctgctggc gaacctgccg accctgaccc agggcctcgc ggtgctcctg    840
ctcgaacgcg acaagctgct caagctgcgc tgcctgggct ggggcctgtg ggacggcctg    900
cgggggcgcg gcggcgcgct ggagcgcaac cgcccgcgcc tgctgaagcg cctcgccggt    960
ccggcggtgg cgcccacagt tcccggcaag gccaaggcct agtcggcgaa acgcattgag   1020
ctc                                                                 1023
```

<210> SEQ ID NO 69
<211> LENGTH: 13768
<212> TYPE: DNA
<213> ORGANISM: Artificial Sequence
<220> FEATURE:
<223> OTHER INFORMATION: vector

<400> SEQUENCE: 69

```
ctagaggtgg acggccgcac gtatgagcac gcggtgacgc aggtgctgca ggccacgggg     60
gtgcggggga ttctgctcgc gccggatgcg ccggatgcgc cggcggcatc ggacggggcg    120
```

```
gcgctgctca agcgccgcta cgtgccgctc gcggcgttgc tgccgcgctg ccgggcgctg    180
gtgcaccacg gggggatcgg gacgcgtcg ctcgcgtacg cggcggggt gccgcaggtg     240
gtgacgccgt tcgcgcacga ccagttcgac aacgcgcagc gggtggcggc gagcggctgc    300
ggggtgcggc tggacgcgcc ggtgcgcggc gagccgctcg cgcgggcgct ggcgcaggtg    360
ctgggcgacg cggcgatggc ggcgcgctgc gcgcaggtgc gcgcgcggat ggcggcggag    420
ccgaacggct gcgacgcggc ggcgcgcttc atcgagcgct tcgcgccggg cgtcgcggcg    480
cggcgggcgc agccggcatg agcgcgcagg cgatgtcggc ggatcaggcg ggcgttgcgc    540
cgccggcggc cgccccgctg cgcggcgcga agctcgcgct gctgacgttc gcgctgtcgc    600
tcgcgacgtt catcgaagtg ctggattcga cggtggcgaa cgtggcggtg ccggcgatct    660
cgggcagcct cggggtgtcg aacagccagg gcacgtgggt gatcagctcg tactcggtgg    720
ccgcggcgat cgcggtgccg ctgacggggt ggcttgcgcg gcgtgggc gagctgaggc      780
tgttcgtggc gtcggtgatc ctgttcacgc tgacgtcgct gctgtgcggg ctcgcgcggg    840
acctggaggt gctggttgcg tgccgggcgc tgcaggggc gttctcgggg ccgatggtgc     900
cgctgtcgca gacgatcctg atgcgcgcgt tcccgccggc gcggcgcacg ctggcgctgg    960
cgctgtgggg gatgacggtg ctgctcgcgc cgatcttcgg gccggtggtg ggcggctggc   1020
tgatcgacaa cttctcgtgg ccgtggatct tcctgatcaa cctgccgatc gggctgttct   1080
cgttcgcggt gtgcacgctg atgctgcgcc gcaggcgca gcgcggcgag gcgagcccga   1140
tcgacgcgcc ggggatcgtg ctgctggtga tcggggtggg ctcgctgcag gcgatgctgg   1200
acctggggca cgaccggggc tggttcgatt cgccgctgat cacggcgctg gcgatcgcgg   1260
cgggggtgtc gctcgtgtcg ctgctgatct gggagctggg cgaggcgcat ccggtggtgg   1320
atctgagcct gttccgggag cggaccttca cgttctgcgt ggtgatcatc tcgctgggga   1380
tgatgagctt ctcggtggtg ggggtggtgt ttccgctgtg gctgcaggcg gtgatgggat   1440
acacggcgta ccaggcgggg ctggcgacgg cgtcgatggg ggtgctggcg ctggtgttct   1500
cgatcctggt ggggctgtac gcgagccggg tggacgcgcg ggtgctggtg acgttcgggt   1560
tcggggtgtt gcggcggtg atgtggtgga gcacgcactt cacgcgtcg atgacgttcg    1620
cgcaggtggt gacgccgcgg ctgattcagg ggatggggct gccgtgcttc ttcataccgc   1680
tgacggcggc gacgctgtcg cgggtgccgg acgagaagct ggcggcggcg tcgagcctgt   1740
cgaacttcct gcggacgctg tcggcgcgt tcggcacggc gctgagcgtg acgtggtggg    1800
acaaccgggc gacgtaccac tacgcggtgg tgtcgcaatc ggtgacgcgc gcctcggaga   1860
acacgcagcg gtacgtggac gcgctgcacg cgatggggct gcacggcgcg cgggagctga   1920
gctcgctgca ccaggtggtg cggcagcagg cgtacatgat ggcgacgaac gacatgttct   1980
acatggcgag cgcgacgtgc ctgctgctgg cggggctgat gtggctgacg cggccgaagc   2040
ggggcgcggc ggcggcgctc gggcactgag gcgaggcatg tcgcgccccg catgacgaag   2100
gcgaaggaga agggcgatgc gccgaagtcc tggggacgcg gcgcgtcgat gcggcaacga   2160
agcgggcatt tcggcattcc gaaccaccaa agggaagagc gatgacgatc ctgggggcgc   2220
tggtgttcgg gcggctggga tcgttcgacg atgcgcgcgc gggcgcggcg gcgcgcgagc   2280
cggtgcggca ggaatgaacg gaacgggccg cagcgggata ccggaaagca agaaggacgc   2340
atcatacgaa tgacgcagac agcaacgcaa gcagccactc gcgcgatgat cgcgacagga   2400
agccgcgcg cgcgccggct cgcggcagcc gcgctcgcgt gggcgctcgc cggctgcgtg    2460
ccgtcgggct tcgagccggc gctcgcgccg cgcacgccgg gcgacgacgc gctcgcgcac   2520
```

```
acggcggggg gcgccgcgca cggcgcatgg ccgagcccg actgggtccg gcagctcggc    2580
gatccgcaac tcgacgcgct cgtcgacgag gcgctgcggc agaacccgac gctgcaggcc    2640
gcgcaggcgc gcatcggcgt cgcgcagtcg cagctgcagc agttcgaatc gctgacgggg    2700
ctcaccgcga cggcgggcgc gtcgctctcc aaggcgcacg tgccgcgctc gggcggcacc    2760
atcaatacga cgttcaacgg cttgccggtg tcggtgccgc tcgtcggcga atcggtggtg    2820
tcgtcgtcgt cgctgttcgt cgggctgaac tatcagctgg acctgtgggg caagaacgcg    2880
gcggccacgc gcgggctgct gtcgatgcgc gatgcggcgc gcgtggaggc cgagcaggcg    2940
cggctcgcgc tgtcggtggc gatcgtgacg ctgtacggcg agctggaccg cgcgtatgcg    3000
ctgcgcgagc tgctgcagca gaagcgccgc gcgagcgagc aggtggagac ggtgctgcgc    3060
gagcgcgcgg cgcgcgggat cgacaacggc tacgatgcgg acgacgcggc gctcaagcgg    3120
ggcaagctgc tcgagcagct cgcgctgacc gacgagcaga tccagttgca gaagctgcaa    3180
ctgggggtgc tgagcgggcg ggggccggag cgcgggctgt cgctcgcgcg gccgaagctc    3240
gcgccgctcg cggacgcgcc gctgccggcg cggctgccgg ccgggctgct ggggcggcgg    3300
ccggacatcg tcgcggcgcg gctgcgggtg gaggcggcgt acgcggcgat cgacggcacg    3360
cgcgcgtcgt tctacccgga cgtgaacctg gcggcgctgg gcgggctgtt cgcgctcacg    3420
ccggcgtcgc tgttcaagca cgatgcgctg ggggctcga tcggtccggc gctgtcgctg    3480
ccgatcttcg atcgcggccg gctgaaggcg aagctggggg gcgacgtggc gaacgcggac    3540
gtggcgctgg cgctgtacaa ccagacggtg gatgcggcgc tggcgaggt ggcgcggcag    3600 ttgacgtcgc tgtcgacggt ggatgcgctg ctcgaggcgc agcagcaggc ggtgcgctcg    3660
gcgcagcgga tggtggcgct ggcgcaggac cggcaccggc gggggatggg gatgcgcaag    3720
gacgtgaacg tggcgaagct gacgctgctg gacgagcgtg cgcacgtgat cgagctgcag    3780
gcgcggcggc ggacgctgcg ggtggggctg atcggggcgc tggcggcgg cttcgacgcg    3840 cggccggcgg gcggcgcgcc gctcgcgcag ggcaagccgt tcgcggcggc gagcgacagg    3900
ccgcccgatt gagcggcacg cacgcatgcg gcccgaagcc accgacaccc gaagacaccg    3960
acaccaacgc caccttcacc gtgtacacga gcgattcaac cgacaccgcc cccgagcatc    4020
gaagcccgtc gggccgatcc gcgacggctt gcgggccggc ccggccgttg ccggccggcg    4080
ccaccgacat cacgcacgcg aagaccttga acgataccgc caccgatacc ccgcgcgcga    4140
aggcgcccac cgatccggcc gccctcgacg gcgcgcacgc gcagcccgtg ccggcgcacg    4200
agcgcggatc gcctccgccg ccggaagccg cggcgacgct cgccgcgcgc cgcgcgacgc    4260
gccgccggcg cttcgcgctg ttcttcgggc tgctggcgct ggccgcgctg accgcggggc    4320
tctactggtt cgtcgccggg cgcttcagcg aggagacgga cgacgcgtac gtggccggca    4380
acgtggtgca gatcgccgcg cagatccagg ggacggtgac cgacgtgctg gtggcggaca    4440
cgcagcaggt gaaggcgggg caggcgctgg tgaagctcga cgacgcggac gcgtcggcgg    4500
cgttcgcgca ggcgcgggcg cagctcgcgc aggcggtgcg gcaggtggcg aacacgcggc    4560
tctcgatggg gatgtacgag gagacggtga aggcgcgcga ggcggacctg aagcttgcgc    4620
agcaggcgta tccggaggaa ctggcgcggc gaaagtcgtc gctggcgaac gcgcaggcgg    4680
cgctggcggg ggcgcaggcg cagctggagg cggcgcgcgc gctgggcagc gagcggccgg    4740
tcgagcagaa cccggcggtg cagcaggcgg ccgcgcagtt caagctggcg taccggaacc    4800
tgaggcgcac gacgatcgtg tcgccggtgg acggcacggt cggtcagcgg tcggtgcaga    4860
```

```
tcggtcagca ggtggggccg ggggtgccgc tgatgtcggt ggtgcagttg cggcaggtgt    4920
gggtggaggc gaacttcaag gaagggcaga tccggcacat gcgggtgggc cagccggtgc    4980
ggctcgaatc ggacctgtac ggcgcgcggg tgacgtacca cggccgggtg gaggggtct    5040 cggcgggcac gggcagcgcg ttctcgatgc tgccgtcgca gaacgcggcg gggaactgga    5100
tcaaggtggt gcagcgcctg ccggtggtga tctcgctgga gccgtcggag ctggcggcgc    5160
acccgctgcg ggtggggctg tcgatgcgcg cgacggtgga gacgaaggtg cgtggcggcc    5220
gcctgctcga cggcgacgcg ccgctgccgg ggctgcgcac gcgggtgcac gaagcgcagg    5280
cgggcgaggc cgaggccgcg gcttcggcag tgattcggga gaatgacggc cgcaggtgac    5340
gggcggttgc gggatcgctc tagagcggcc gccaccgcgg tggagctcca attcgcccta    5400
tagtgagtcg tattacgcgc gctcactggc cgtcgtttta caacgtcgtg actgggaaaa    5460
ccctggcgtt acccaactta atcgccttgc agcacatccc cctttcgcca gctggcgtaa    5520
tagcgaagag gcccgcaccg atcgcccttc ccaacagttg cgcagcctga atggcgaatg    5580
gaaattgtaa gcgttaatat tttgttaaaa ttcgcgttaa attttgtta aatcagctca    5640 ttttttaacc aataggccga ctgcgatgag tggcagggcg gggcgtaatt ttttttaaggc    5700 agttattggt gcccttaaac gcctggtgct acgcctgaat aagtgataat aagcggatga    5760
atggcagaaa ttcgaaagca aattcgaccc ggtcgtcggt tcagggcagg gtcgttaaat    5820
agccgcttat gtctattgct ggtttaccgg tttattgact accggaagca gtgtgaccgt    5880
gtgcttctca aatgcctgag gccagtttgc tcaggctctc cccgtggagg taataattga    5940
cgatatgatc atttattctg cctcccagag cctgataaaa acggtgaatc cgttagcgag    6000
gtgccgccgg cttccattca ggtcgaggtg gcccggctcc atgcaccgcg acgcaacgcg    6060
gggaggcaga caaggtatag gcggcgaggc ggctacagc cgatagtctg gaacagcgca    6120
cttacgggtt gctgcgcaac ccaagtgcta ccggcgcggc agcgtgaccc gtgtcggcgg    6180
ctccaacggc tcgccatcgt ccagaaaaca cggctcatcg ggcatcggca ggcgctgctg    6240
cccgcgccgt tccattcct ccgtttcggt caaggctggc aggtctggtt ccatgcccgg    6300
aatgccgggc tggctgggcg gctcctcgcc ggggccggtc ggtagttgct gctcgcccgg    6360
atacagggtc gggatgcggc gcaggtcgcc atgccccaac agcgattcgt cctggtcgtc    6420
gtgatcaacc accacggcgg cactgaacac cgacaggcgc aactggtcgc ggggctggcc    6480
ccacgccacg cggtcattga ccacgtaggc cgacacggtg ccggggccgt tgagcttcac    6540
gacggagatc cagcgctcgg ccaccaagtc cttgactgcg tattggaccg tccgcaaaga    6600
acgtccgatg agcttggaaa gtgtcttctg gctgaccacc acggcgttct ggtggcccat    6660
ctgcgccacg aggtgatgca gcagcattgc cgccgtgggt ttcctcgcaa taagcccggc    6720
ccacgcctca tgcgctttgc gttccgtttg cacccagtga ccgggcttgt tcttggcttg    6780
aatgccgatt tctctggact gcgtggccat gcttatctcc atgcggtagg gtgccgcacg    6840
gttgcggcac catgcgcaat cagctgcaac ttttcggcag cgcgacaaca attatgcgtt    6900
gcgtaaaagt ggcagtcaat tacagatttt ctttaaccta cgcaatgagc tattgcgggg    6960
ggtgccgcaa tgagctgttg cgtaccccc ttttttaagt tgttgatttt taagtctttc    7020
gcatttcgcc ctatatctag ttctttggtg cccaaagaag gcacccctg cggggttccc    7080 ccacgccttc ggcgcggctc cccctccggc aaaagtggc cctccgggg cttgttgatc    7140 gactgcgcg ccttcggcct tgcccaaggt ggcgctgccc ccttggaacc cccgcactcg    7200
ccgccgtgag gctcgggggg caggcgggcg ggcttcgcct tcgactgccc ccactcgcat    7260
```

```
aggcttgggt cgttccaggc gcgtcaaggc caagccgctg cgcggtcgct gcgcgagcct   7320
tgacccgcct tccacttggt gtccaaccgg caagcgaagc gcgcaggccg caggccggag   7380
gcttttcccc agagaaaatt aaaaaaattg atggggcaag ccgcaggcc gcgcagttgg    7440
agccggtggg tatgtggtcg aaggctgggt agccggtggg caatccctgt ggtcaagctc   7500
gtgggcaggc gcagcctgtc catcagcttg tccagcaggg ttgtccacgg gccgagcgaa   7560
gcgagccagc cggtggccgc tcgcggccat cgtccacata tccacgggct ggcaaggag   7620
cgcagcgacc gcgcagggcg aagcccggag agcaagcccg tagggcgccg cagccgccgt   7680
aggcggtcac gactttgcga agcaaagtct agtgagtata ctcaagcatt gagtggcccg   7740
ccggaggcac cgccttgcgc tgccccgtc gagccggttg acaccaaaa gggaggggca     7800
ggcatggcgg catacgcgat catgcgatgc aagaagctgg cgaaaatggg caacgtggcg   7860
gccagtctca agcacgccta ccgcgagcgc gagacgccca acgctgacgc cagcaggacg   7920
ccagagaacg agcactgggc ggccagcagc accgatgaag cgatgggccg actgcgcgag   7980
ttgctgccag agaagcggcg caaggacgct gtgttggcgg tcgagtacgt catgacggcc   8040
agcccggaat ggtggaagtc ggccagccaa gaacagcagg cggcgttctt cgagaaggcg   8100
cacaagtggc tggcggacaa gtacggggcg gatcgcatcg tgacggccag catccaccgt   8160
gacgaaacca gcccgcacat gaccgcgttc gtggtgccgc tgacgcagga cggcaggctg   8220
tcggccaagg agttcatcgg caacaaagcg cagatgaccc gcgaccagac cacgtttgcg   8280
gccgctgtgg ccgatctagg gctgcaacgg ggcatcgagg gcagcaaggc acgtcacacg   8340
cgcattcagg cgttctacga ggccctggag cggccaccag tgggccacgt caccatcagc   8400
ccgcaagcgg tcgagccacg cgcctatgca ccgcagggat tggccgaaaa gctgggaatc   8460
tcaaagcgcg ttgagacgcc ggaagccgtg gccgaccggc tgacaaaagc ggttcggcag   8520
gggtatgagc ctgccctaca ggccgccgca ggagcgcgtg agatgcgcaa gaaggccgat   8580
caagcccaag agacggcccg agaccttcgg gagcgcctga gcccgttcct ggacgccctg   8640
gggccgttga atcgggatat gcaggccaag gccgccgcga tcatcaaggc cgtgggcgaa   8700
aagctgctga cggaacagcg ggaagtccag cgccagaaac aggcccagcg ccagcaggaa   8760
cgcgggcgcg cacatttccc cgaaaagtgc cacctgggat gaatgtcagc tactgggcta   8820
tctggacaag ggaaaacgca agcgcaaaga gaaagcaggt agcttgcagt gggcttacat   8880
ggcgatagct agactgggcg gttttatgga cagcaagcga accggaattg ccagctgggg   8940
cgccctctgg taaggttggg aagccctgca agtaaactg gatggctttc ttgccgccaa    9000
ggatctgatg gcgcagggga tcaagatctg atcaagagac aggatgagga tcgtttcgca   9060
tgattgaaca agatggattg cacgcaggtt ctccggccgc ttgggtggag aggctattcg   9120
gctatgactg ggcacaacag acaatcggct gctctgatgc cgccgtgttc cggctgtcag   9180
cgcaggggcg cccggttctt tttgtcaaga ccgacctgtc cggtgccctg aatgaactgc   9240
aggacgaggc agcgcggcta tcgtggctgg ccacgacggg cgttccttgc gcagctgtgc   9300
tcgacgttgt cactgaagcg ggaagggact ggctgctatt gggcgaagtg ccggggcagg   9360
atctcctgtc atctcacctt gctcctgccg agaaagtatc catcatggct gatgcaatgc   9420
ggcggctgca tacgcttgat ccggctacct gcccattcga ccaccaagcg aaacatcgca   9480
tcgagcgagc acgtactcgg atggaagccg gtcttgtcga tcaggatgat ctggacgaag   9540
agcatcaggg gctcgcgcca gccgaactgt tcgccaggct caaggcgcgc atgcccgacg   9600
```

-continued

```
gcgaggatct cgtcgtgacc catggcgatg cctgcttgcc gaatatcatg gtggaaaatg   9660
gccgcttttc tggattcatc gactgtggcc ggctgggtgt ggcggaccgc tatcaggaca   9720
tagcgttggc tacccgtgat attgctgaag agcttggcgg cgaatgggct gaccgcttcc   9780
tcgtgcttta cggtatcgcc gctcccgatt cgcagcgcat cgccttctat cgccttcttg   9840
acgagttctt ctgagcggga ctctggggtt cgaaatgacc gaccaagcga cgcccaacct   9900
gccatcacga gatttcgatt ccaccgccgc cttctatgaa aggttgggct tcggaatcgt   9960
tttccgggac gccggctgga tgatcctcca gcgcgggat ctcatgctgg agttcttcgc   10020 ccaccccccat gggcaaatat tatacgcaag gcgacaaggt gctgatgccg ctggcgattc   10080
aggttcatca tgccgtttgt gatggcttcc atgtcggcag aatgcttaat gaattacaac   10140 agttttatg catgcgccca atacgcaaac cgcctctccc cgcgcgttgg ccgattcatt   10200
aatgcagctg gcacgacagg tttcccgact ggaaagcggg cagtgagcgc aacgcaatta   10260
atgtgagtta gctcactcat taggcacccc aggctttaca ctttatgctt ccggctcgta   10320
tgttgtgtgg aattgtgagc ggataacaat ttcacacagg aaacagctat gaccatgatt   10380
acgccaagcg cgcaattaac cctcactaaa gggaacaaaa gctgggtacc gggccccccc   10440
tcgaggtcga cggtatcgat aagcttgata tcgaattcct gcagcccggg ggatctggca   10500
tttttgggag gtgtgaaatg cggcgcgaaa gtctgttggt atcggtttgc aagggcctgc   10560
gggtacatgt cgagcgcgtt gggcaggatc ccgggcgcag cacggtgatg ctggtcaacg   10620
gcgcgatggc gaccaccgcc tcgttcgccc ggacctgcaa gtgcctggcc gaacatttca   10680
acgtggtgct gttcgacctg cccttcgccg ggcagtcgcg tcagcacaac ccgcagcggg   10740
ggttgatcac caaggacgac gaggtggaaa tcctcctggc gctgatcgag cgcttcgagg   10800
tcaatcacct ggtctccgcg tcctgggcg gtatctccac gctgctggcg ctgtcgcgca   10860
atccgcgcgg catccgcagc tcggtggtga tggcattcgc ccctggactg aaccaggcga   10920
tgctcgacta cgtcgggcgg gcgcaggcgc tgatcgagct ggacgacaag tcggcgatcg   10980
gccatctgct caacgagacc gtcggcaaat acctgccgcc gcgcctgaaa gccagcaacc   11040
atcagcacat ggcttcgctg ccaccggcg aatacgagca ggcgcgcttt cacatcgacc   11100
aggtgctggc gctcaacgat cggggctacc tggcttgcct ggagcggatc cagagccacg   11160
tgcatttcat caacgcagc tgggacgaat acaccaccgc cgaggacgcc cgccagttcc   11220
gcgactacct gccgcactgc agtttctcgc gggtggaggg caccgggcat ttcctcgacc   11280
tggagtccaa gctggccgcg gtacgcgtgc accgcgccct gctcgagcac ctgctgaagc   11340
aaccggagcc gcagcgggcg gaacgcgcgg cgggattcca cgagatggcc atcggctacg   11400
cctgaaccct tgacctgcga agacccggcc tggccgggct ttgcggttgc ataacgcacg   11460
gagtagcacc atgcacgcca tcctcatcgc catcggctcg gccggcgacg tatttcccatt   11520 catcggcctg gcccggaccc tgaaattgcg cgggcaccgc gtgagcctct gcaccatccc   11580
ggtgtttcgc gacgcggtgg agcagcacgg catcgcgttc gtcccgctga gcgacgaact   11640
gacctaccgc cggaccatgg gcgatccgcg cctgtgggac cccaagacgt ccttcggcgt   11700
gctctggcaa accatcgccg ggatgatcga gccggtctac gagtacgtct cggcgcagcg   11760
ccatgacgac atcgtggtgg tcggctcgct ctgggcgctg ggcgcacgca tcgctcacga   11820
gaagtacggg attccctacc tgtccgcgca ggtctcgcca tcgaccttgt tgtcggcgca   11880
cctgccgccg gtacacccca agttcaacgt gcccgagcag atgccgctgg cgatgcgcaa   11940
gctgctctgg cgctgcatcg agcgcttcaa gctggatcgc acctgcgcgc cggatatcaa   12000
```

```
cgcggtgcgg cgcaaggtcg gcctggagac gccggtgaag cgcatcttca cccaatggat   12060
gcattcgccg cagggcgtgg tctgcctgtt cccggcctgg ttcgcgccgc cccagcagga   12120
ttggccgcaa cccctgcaca tgaccggctt cccgctgttc gacggcagta tcccggggac   12180
cccgctcgac gacgaactgc aacgctttct cgatcagggc agccggccgc tggtgttcac   12240
ccagggctcg accgaacacc tgcagggcga cttctacgcc atggccctgc gcgcgctgga   12300
acgcctcggc gcgcgtggga tcttcctcac cggcgccggc caggaaccgc tgcgcggctt   12360
gccgaaccac gtgctgcagc gcgcctacgc gccactggga gccttgctgc atcgtgcgc   12420 cgggctggtc catccgggcg gtatcggcgc catgagcctg gccttggcgg cggggggtgcc   12480 gcaggtgctg ctgccctgcg cccacgacca gttcgacaat gccgaacggc tggtccggct   12540
cggctgcggg atgcgcctgg gcgtgccatt gcgcgagcag gagttgcgcg gggcgctgtg   12600
gcgcttgctc gaggacccgg ccatggcggc ggcctgtcgg cgtttcatgg aattgtcaca   12660
accgcacagt atcgcttgcg gtaaagcggc ccaggtggtc gaacgttgtc atagggaggg   12720
ggatgcgcga tggctgaagg ctgcgtcctg acctacggga gaagaacgat catggaccgg   12780
atagacatgg gcgtgctggt ggtactgttc aatcctggcg acgacgacct ggaacacctt   12840
ggcgaactgg cggcggcgtt tccgcaactg cgcttccttg ccgtcgacaa ctcaccgcac   12900
agcgatccgc agcgcaatgc ccggctgcgc gggcaaggca tcgccgtgct gcaccacggc   12960
aaccggcagg gcatcgccgg cgccttcaac cagggactcg acgcgctatt ccggcgtggc   13020
gtgcagggtg tgctgctgct cgaccaggac tcccgtcccg gcggcgcctt cctcgccgcc   13080
cagtggcgca acctgcaggc gcgcaacggt caggcctgcc tgctcggccc acggatcttc   13140 gaccgggtg accggcgctt cctgccggcc atccatctcg acggactgac gctcaggcaa   13200
ttgtctctgg acggcctgac gacccgcag cgcacctcgt tcctgatctc ctccggctgc   13260
ctgctgaccc gcgaggccta ccagcgcctc ggccacttcg acgaggaact gttcatcgac   13320
cacgtggaca ccgaatacag cctgcgcgcc caggcgctgg acgtgcccct gtacgtcgac   13380
ccgcggctgg tcctcgagca ccgcatcggc acgcgcaaga cccgccgcct cggcggtctc   13440
agcctcagcg cgatgaacca cgccccgctg cgccgctact acctggcgcg caacggcctg   13500
ctggtcctgc gccgctacgc ccggtcctcg ccgctggccc tgctggcgaa cctgccgacc   13560
ctgacccagg gcctcgcggt gctcctgctc gaacgcgaca agctgctcaa gctgcgctgc   13620
ctgggctggg gcctgtggga cggcctgcgg ggacgcggcg gcgcgctgga gaccaaccgc   13680
ccgcgcctgc tgaagcgcct cgccggcccg gccgtggcgt ccgtagcttc ggcaaggcc   13740 aaggcctagt cggcgaaacg cattccct                                      13768
```

<210> SEQ ID NO 70
<211> LENGTH: 5365
<212> TYPE: DNA
<213> ORGANISM: Artificial Sequence
<220> FEATURE:
<223> OTHER INFORMATION: synth operon

<400> SEQUENCE: 70

```
tctagaggtg gacggccgca cgtatgagca cgcggtgacg caggtgctgc aggccacggg     60
ggtgcggggg attctgctcg cgccggatgc gccggatgcg ccggcggcat cggacgggc    120 ggcgctgctc aagcgccgct acgtgccgct cgcggcgttg ctgccgcgct gccggcgct    180 ggtgcaccac gggggggatcg ggacggcgtc gctcgcgtac gcggcggggg tgccgcaggt    240
```

```
ggtgacgccg ttcgcgcacg accagttcga caacgcgcag cgggtggcgg cgagcggctg    300
cggggtgcgg ctggacgcgc cggtgcgcgg cgagccgctc gcgcgggcgc tggcgcaggt    360
gctgggcgac gcggcgatgg cggcgcgctg cgcgcaggtg cgcgcgcgga tggcggcgga    420
gccgaacggc tgcgacgcgg cggcgcgctt catcgagcgc ttcgcgccgg gcgtcgcggc    480
gcggcgggcg cagccggcat gagcgcgcag gcgatgtcgg cggatcaggc gggcgttgcg    540
ccgccggcgg ccgccccgct gcgcggcgcg aagctcgcgc tgctgacgtt cgcgctgtcg    600
ctcgcgacgt tcatcgaagt gctggattcg acggtggcga acgtggcggt gccggcgatc    660
tcgggcagcc tcggggtgtc gaacagccag ggcacgtggg tgatcagctc gtactcggtg    720
gccgcggcga tcgcggtgcc gctgacgggg tggcttgcgc ggcgcgtggg cgagctgagg    780
ctgttcgtgg cgtcggtgat cctgttcacg ctgacgtcgc tgctgtgcgg gctcgcgcgg    840
gacctggagg tgctggttgc gtgccgggcg ctgcaggggc tgttctcggg gccgatggtg    900
ccgctgtcgc agacgatcct gatgcgcgcg ttcccgccgg cgcggcgcac gctggcgctg    960
gcgctgtggg ggatgacggt gctgctcgcg ccgatcttcg gccggtggt gggcggctgg   1020
ctgatcgaca acttctcgtg gccgtggatc ttcctgatca acctgccgat cgggctgttc   1080
tcgttcgcgg tgtgcacgct gatgctgcgc ccgcaggcgc agcgcggcga ggcgagcccg   1140
atcgacgcgc cggggatcgt gctgctggtg atcggggtgg gctcgctgca ggcgatgctg   1200
gacctggggc acgaccgggg ctggttcgat tcgccgctga tcacggcgct ggcgatcgcg   1260
gcggggggtgt cgctcgtgtc gctgctgatc tgggagctgg gcgaggcgca tccggtggtg   1320
gatctgagcc tgttccggga gcggaccttc acgttctgcg tggtgatcat ctcgctgggg   1380
atgatgagct tctcggtggt gggggtggtg tttccgctgt ggctgcaggc ggtgatggga   1440
tacacgcgcgt accaggcggg gctggcgacg cgtcgatgg gggtgctggc gctggtgttc   1500
tcgatcctgg tggggctgta cgcgagccgg gtggacgcgc gggtgctggt gacgttcggg   1560
ttcggggtgt ttgcggcggt gatgtggtgg agcacgcact tcacgctgtc gatgacgttc   1620
gcgcaggtgg tgacgccgcg gctgattcag gggatggggc tgccgtgctt cttcataccg   1680
ctgacgcgcg cgacgctgtc gcgggtgccg gacgagaagc tggcggcggc gtcgagcctg   1740
tcgaacttcc tgcggacgct gtcggcggcg ttcggcacgg cgctgagcgt gacgtggtgg   1800
gacaaccggg cgacgtacca ctacgcggtg tgtcgcaat cggtgacgcg cgcctcggag   1860
aacacgcagc ggtacgtgga cgcgctgcac gcgatggggc tgcacggcgc gcgggagctg   1920
agctcgctgc accaggtggt gcggcagcag cgtacatga tggcgacgaa cgacatgttc   1980
tacatggcga gcgcgacgtg cctgctgctg gcggggctga tgtggctgac gcggccgaag   2040
cggggcgcgg cggcggcgct cgggcactga ggcgaggcat gtcgcgcccc gcatgacgaa   2100
ggcgaaggag aagggcgatg cgccgaagtc ctggggacgc ggcgcgtcga tgcggcaacg   2160
aagcgggcat ttcggcattc cgaaccacca aagggaagag cgatgacgat cctgggggcg   2220
ctggtgttcg ggcggctggg atcgttcgac gatgcgcgcg cgggcgcggc ggcgcgcgag   2280
ccggtgcggc aggaatgaac ggaacgggcc gcagcgggat accggaaagc aagaaggacg   2340
catcatacga atgacgcaga cagcaacgca agcagccact cgcgcgatga tcgcgacagg   2400
aagccgcgcg gcgcgccggc tcgcggcagc ccgcgctcgcg tgggcgctcg ccggctgcgt   2460
gccgtcgggc ttcgagccgg cgctcgcgcc gcgcacgccg ggcgacgacg cgctcgcgca   2520
cacggcgggg ggcgccgcgc acggcgcatg gccgagcccc gactgggtcc ggcagctcgg   2580
cgatccgcaa ctcgacgcgc tcgtcgacga ggcgctgcgg cagaacccga cgctgcaggc   2640
```

```
cgcgcaggcg cgcatcggcg tcgcgcagtc gcagctgcag cagttcgaat cgctgacggg    2700
gctcaccgcg acggcgggcg cgtcgctctc caaggcgcac gtgccgcgct cgggcggcac    2760
catcaatacg acgttcaacg gcttgccggt gtcggtgccg ctcgtcggcg aatcggtggt    2820
gtcgtcgtcg tcgctgttcg tcgggctgaa ctatcagctg gacctgtggg gcaagaacgc    2880
ggcggccacg cgcgggctgc tgtcgatgcg cgatgcggcg cgcgtggagg ccgagcaggc    2940
gcggctcgcg ctgtcggtgg cgatcgtgac gctgtacggc gagctggacc gcgcgtatgc    3000
gctgcgcgag ctgctgcagc agaagcgccg cgcgagcgag caggtggaga cggtgctgcg    3060
cgagcgcgcg gcgcgcggga tcgacaacgg ctacgatgcg gacgacgcgg cgctcaagcg    3120
gggcaagctg ctcgagcagc tcgcgctgac cgacgagcag atccagttgc agaagctgca    3180 actggggggtg ctgagcgggc gggggccgga gcgcgggctg tcgctcgcgc ggccgaagct    3240
cgcgccgctc gcggacgcgc cgctgccggc gcggctgccg gccgggctgc tggggcggcg    3300
gccggacatc gtcgcggcgc ggctgcgggt ggaggcggcg tacgcggcga tcgacggcac    3360
gcgcgcgtcg ttctacccgg acgtgaacct ggcggcgctg ggcgggctgt tcgcgctcac    3420
gccggcgtcg ctgttcaagc acgatgcgct gggggggctcg atcggtccgg cgctgtcgct    3480
gccgatcttc gatcgcggcc ggctgaaggc gaagctgggg ggcgacgtgg cgaacgcgga    3540
cgtggcgctg gcgctgtaca accagacggt ggatgcggcg ctgggcgagg tggcgcggca    3600
gttgacgtcg ctgtcgacgg tggatgcgct gctcgaggcg cagcagcagg cggtgcgctc    3660
ggcgcagcgg atggtggcgc tggcgcagga ccggcaccgg cggggatggg gatgcgcaa    3720 ggacgtgaac gtggcgaagc tgacgctgct ggacgagcgt gcgcacgtga tcgagctgca    3780
ggcgcggcgg cggacgctgc gggtggggct gatcggggcg ctgggcggcg gcttcgacgc    3840
gcggccggcg ggcggcgcgc cgctcgcgca gggcaagccg ttcgcggcgg cgagcgacag    3900
gccgcccgat tgagcggcac gcacgcatgc ggcccgaagc caccgacacc gaagacacc    3960 gacaccaacg ccaccttcac cgtgtacacg agcgattcaa ccgacaccgc ccccgagcat    4020
cgaagcccgt cgggccgatc cgcgacggct tgcgggccgg cccggccgtt gccggccggc    4080
gccaccgaca tcacgcacgc gaagaccttg aacgataccg ccaccgatac cccgcgcgcg    4140
aaggcgccca ccgatccggc cgccctcgac ggcgcgcacg cgcagcccgt gccggcgcac    4200
gagcgcggat cgcctccgcc gccggaagcc gcggcgacgc tcgccgcgcg ccgcgcgacg    4260
cgccgccggc gcttcgcgct gttcttcggg ctgctggcgc tggccgcgct gaccgcgggg    4320
ctctactggt tcgtcgccgg gcgcttcagc gaggagacgc acgacgcgta cgtgccggcc    4380
aacgtggtgc agatcgccgc gcagatccag gggacggtga ccgacgtgct ggtggcggac    4440
acgcagcagg tgaaggcggg gcaggcgctg gtgaagctcg acgacgcgga cgcgtcggcg    4500
gcgttcgcgc aggcgcgggc gcagctcgcg caggcggtgc ggcaggtggc gaacacgcgg    4560
ctctcgatgg ggatgtacga ggagacggtg aaggcgcgcg aggcggacct gaagcttgcg    4620
cagcaggcgt atccggagga actggcgcgg cgaaagtcgt cgctggcgaa cgcgcaggcg    4680
gcgctggcgg gggcgcaggc gcagctggag gcggcgcgcg cgctgggcag cgagcggccg    4740
gtcgagcaga acccggcggt gcagcaggcg gccgcgcagt tcaagctggc gtaccggaac    4800
ctgaggcgca cgacgatcgt gtcgccggtg gacggcacgg tcggtcagcg gtcggtgcag    4860
atcggtcagc aggtgggggcc gggggtgccg ctgatgtcgg tggtgcagtt gcggcaggtg    4920
tgggtggagg cgaacttcaa ggaagggcag atccggcaca tgcgggtggg ccagccggtg    4980
```

```
cggctcgaat cggacctgta cggcgcgcgg gtgacgtacc acggccgggt ggaggggggtc    5040 tcggcgggca cgggcagcgc gttctcgatg ctgccgtcgc agaacgcggc ggggaactgg    5100
atcaaggtgg tgcagcgcct gccggtggtg atctcgctgg agccgtcgga gctggcggcg    5160
cacccgctgc gggtggggct gtcgatgcgc gcgacggtgg agacgaaggt gcgtggcggc    5220
cgcctgctcg acggcgacgc gccgctgccg gggctgcgca cgcgggtgca cgaagcgcag    5280
gcgggcgagg ccgaggccgc ggcttcggca gtgattcggg agaatgacgg ccgcaggtga    5340
cgggcggttg cgggatcgct ctaga                                          5365
```

<210> SEQ ID NO 71
<211> LENGTH: 34
<212> TYPE: DNA
<213> ORGANISM: Artificial Sequence
<220> FEATURE:
<223> OTHER INFORMATION: primer

<400> SEQUENCE: 71

```
tatatataac cggtattaat gcagctggca cgac                                 34
```

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72

```
ggccgaccgg tactagtgga                                                 20
```

<210> SEQ ID NO 73
<211> LENGTH: 11960
<212> TYPE: DNA
<213> ORGANISM: Artificial Sequence
<220> FEATURE:
<223> OTHER INFORMATION: vector

<400> SEQUENCE: 73

```
accttcggga gcgcctgaag cccgttctgg acgccctggg gccgttgaat cgggatatgc     60
aggccaaggc cgccgcgatc atcaaggccg tgggcgaaaa gctgctgacg gaacagcggg    120
aagtccagcg ccagaaacag gcccagcgcc agcaggaacg cgggcgcgca catttccccg    180
aaaagtgcca cctgggatga atgtcagcta ctgggctatc tggacaaggg aaaacgcaag    240
cgcaaagaga aagcaggtag cttgcagtgg gcttacatgg cgatagctag actgggcggt    300
tttatggaca gcaagcgaac cggaattgcc agctggggcg ccctctggta aggttgggaa    360
gccctgcaaa gtaaactgga tggctttctt gccgccaagg atctgatggc gcaggggatc    420
aagatctgat caagagacag gatgaggatc gtttcgcatg attgaacaag atggattgca    480
cgcaggttct ccggccgctt gggtggagag gctattcggc tatgactggg cacaacagac    540
aatcggctgc tctgatgccg ccgtgttccg gctgtcagcg caggggcgcc cggttctttt    600
tgtcaagacc gacctgtccg gtgccctgaa tgaactgcag gacgaggcag cgcggctatc    660
gtggctggcc acgacgggcg ttccttgcgc agctgtgctc gacgttgtca ctgaagcggg    720
aagggactgg ctgctattgg gcgaagtgcc ggggcaggat ctcctgtcat ctcaccttgc    780
tcctgccgag aaagtatcca tcatggctga tgcaatgcgg cggctgcata cgcttgatcc    840
ggctacctgc ccattcgacc accaagcgaa acatcgcatc gagcgagcac gtactcggat    900
ggaagccggt cttgtcgatc aggatgatct ggacgaagag catcaggggc tcgcgccagc    960
```

```
cgaactgttc gccaggctca aggcgcgcat gcccgacggc gaggatctcg tcgtgaccca   1020
tggcgatgcc tgcttgccga atatcatggt ggaaaatggc cgcttttctg gattcatcga   1080
ctgtggccgg ctgggtgtgg cggaccgcta tcaggacata gcgttggcta cccgtgatat   1140
tgctgaagag cttggcggcg aatgggctga ccgcttcctc gtgctttacg gtatcgccgc   1200
tcccgattcg cagcgcatcg ccttctatcg ccttcttgac gagttcttct gagcgggact   1260
ctggggttcg aaatgaccga ccaagcgacg cccaacctgc catcacgaga tttcgattcc   1320
accgccgcct tctatgaaag gttgggcttc ggaatcgttt ccgggacgc cggctggatg    1380 atcctccagc gcggggatct catgctggag ttcttcgccc accccatgg gcaaatatta    1440 tacgcaaggc gacaaggtgc tgatgccgct ggcgattcag gttcatcatg ccgtttgtga   1500
tggcttccat gtcggcagaa tgcttaatga attacaacag tttttatgca tgcgcccaat   1560
acgcaaaccg cctctccccg cgcgttggcc gattcattaa tgcagctggc acgacaggtt   1620
tcccgactgg aaagcgggca gtgagcgcaa cgcaattaat gtgagttagc tcactcatta   1680
ggcaccccag gctttacact ttatgcttcc ggctcgtatg ttgtgtggaa ttgtgagcgg   1740
ataacaattt cacacaggaa acagctatga ccatgattac gccaagcgcg caattaaccc   1800
tcactaaagg gaacaaaagc tgggtaccgg ccccccctc gaggtcgacg gtatcgataa    1860
gctttgggag gtgtgaaatg cggcgcgaaa gtctgttggt atcggtttgc aagggcctgc   1920
gggtacatgt cgagcgcgtt gggcaggatc ccgggcgcag cacggtgatg ctggtcaacg   1980
gcgcgatggc gaccaccgcc tcgttcgccc ggacctgcaa gtgcctggcc gaacatttca   2040
acgtggtgct gttcgacctg cccttcgccg ggcagtcgcg tcagcacaac ccgcagcgcg   2100
ggttgatcac caaggacgac gaggtggaaa tcctcctggc gctgatcgag cgcttcgagg   2160
tcaatcacct ggtctccgcg tcctggggcg gtatctccac gctgctggcg ctgtcgcgca   2220
atccgcgcgg catccgcagc tcggtggtga tggcattcgc ccctggactg aaccaggcga   2280
tgctcgacta cgtcgggcgg gcgcaggcgc tgatcgagct ggacgacaag tcggcgatcg   2340
gccatctgct caacgagacc gtcggcaaat acctgccgca gcgcctgaaa gccagcaacc   2400
atcagcacat ggcttcgctg gccaccggcg aatacgagca ggcgcgcttt cacatcgacc   2460
aggtgctggc gctcaacgat cggggctact ggcttgcct ggagcggatc cagagccacg    2520
tgcatttcat caacggcagc tgggacgaat acaccaccgc cgaggacgcc cgccagttcc   2580
gcgactacct gccgcactgc agtttctcgc gggtggaggg caccgggcat ttcctcgacc   2640
tggagtccaa gctggcagcg gtacgcgtgc accgcgccct gctcgagcac ctgctgaagc   2700
aaccggagcc gcagcgggcg gaacgcgcgg cgggattcca cgagatggcc atcggctacg   2760
cctgaaccct tgacctgcga agacccgcc tggccgggct tgcggttgc ataacgcacg     2820 gagtagcccc atgcacgcca tcctcatcgc catcggctcg gccggcgacg tatttccctt   2880
catcggcctg gccggaccc tgaaactgcg cgggcaccgc gtgagcctct gcaccatccc    2940
ggtgtttcgc gacgcggtgg agcagcacgg catcgcgttc gtcccgctga cgacgaact    3000 gacctaccgc cggaccatgg gcgatccgcg cctgtgggac cccaagacgt ccttcggcgt   3060
gctctggcaa gccatcgccg ggatgatcga ccggtctac gagtacgtct cggcgcagcg    3120
ccatgacgac atcgtggtgg tcggctcgct atgggcgctg ggcgcacgca tcgctcacga   3180
gaagtacggg attccctacc tgtccgcgca ggtctcgcca tcgaccctgt tgtcggcgca   3240
cctgccgccg gtacacccca gttcaacgt gcccgagcag atgccgctgg cgatgcgcaa    3300
```

-continued

```
gctgctctgg cgctgcatcg agcgcttcaa gctggatcgc acctgcgcgc cggagatcaa    3360
cgcggtgcgc cgcaaggtcg gcctggaaac gccggtgaag cgcatcttca cccaatggat    3420
gcattcgccg cagggcgtgg tctgcctgtt cccggcctgg ttcgcgccgc cccagcagga    3480
ttggccgcaa cccctgcaca tgaccggctt cccgctgttc gacggcagta tcccggggac    3540
cccgctcgac gacgaactgc aacgctttct cgatcagggc agccggccgc tggtgttcac    3600
ccagggctcg accgaacacc tgcagggcga cttctacgcc atgggccctgc gcgcgctgga   3660
acgcctcggc gcgcgtggga tcttcctcac cggcgccggc caggaaccgc tgcgcggctt    3720
gccgaaccac gtgctgcagc gcgcctacgc gccactggga gccttgctgc catcgtgcgc    3780
cgggctggtc catccgggcg gtatcggcgc catgagccta gccttggcgg cggggggtgcc   3840
gcaggtgctg ctgccctgtg cccacgacca gttcgacaat gccgaacggc tggtccggct    3900
cggctgcggg atgcgcctgg gcgtgccgtt gcgcgagcag gagttgcgcg gggcgctgtg    3960
gcgcttgctc gaggacccgg ccatggcggc ggcctgtcgg cgtttcatgg aattgtcaca    4020
accgcacagt atcgcttgcg gtaaagcggc ccaggtggtc gaacgttgtc atagggaggg    4080
ggatgctcga tggctgaagg ctgcgtcctg aacggtgctg gcataacagt ctagagcggc    4140
cgccaccgcg gtggagctcc aattcgccct atagtgagtc gtattacgcg cgctcactgg    4200
ccgtcgtttt acaacgtcgt gactgggaaa accctggcgt tacccaactt aatcgccttg    4260
cagcacatcc ccctttcgcc agctggcgta atagcgaaga ggcccgcacc gatcgccctt    4320
cccaacagtt gcgcagcctg aatggcgaat ggaaattgta agcgttaata ttttgttaaa    4380
attgcgtta aattttttgtt aaatcagctc atttttttaac caataggccg actgcgatga    4440
gtggcagggc ggggcgtaat ttttttaagg cagttattgg tgcccttaaa cgcctggtgc    4500
tacgcctgaa taagtgataa taagcggatg aatggcagaa attcgaaagc aaattcgacc    4560
cggtcgtcgg ttcagggcag ggtcgttaaa tagccgctta tgtctattgc tggtttaccg    4620
gtaggtcaac tttcgcaaca tccggcttga ccataacggc gctgtcggcc gcattgagaa    4680
ctgcttcagc gataagctcc gcatcaccac tttcgtgcga agccgaggca taacggcctt    4740
cttgatgacc gaacgcatgc caatgctgtt cgagcgcatc gtccgtgagc gaagataggt    4800
ctgggtatcg attccgataa taagccagat ccagcacaaa tcgccttgag ccagtctttt    4860
tctgggggac gggcactgaa tttcccttaa catgcatgct cggctgcaca tctacgctcg    4920
gcaagccttc cttaacagac atttttcact ttcctatgaa tattcaagag cgccagaccg    4980
ctgaaacatg aagaatgacg tctaacctgc cgagccccga ggctattata attttttgttg   5040
ggttgttcaa catgaatgca agaactgcca tcactctaat tcctatttca ggaatactga    5100
caaataaaaa tgacactttc caaccccccgg aaacgaaccc gacttccaga tgcgcacccc    5160
gcgctgccat gcccagcgaa ctagagtccc aggatagcgg tagcttaagg ccctctagac    5220
ttgtcagcac ccagatttgt ctccgtgagt tgcatcgctc aaacaactgt tcttgcatg     5280
gacacctgac gactccctgt tgtgtctagg caaccatgag gtcaccttcc accgctgcaa    5340
cggctcctcc tcttccagcg tgagcagatc ggcacggtca gtaccggcac ccagcagtgt    5400
attttttcgac atcagggtgg tctaattccg gcagcgctag cagctcgcct tgcgttgccg    5460
gggcgaagtt tctcagcgtc atctgtctac gacaacacct tttgtccaat tagagccaaa    5520
ttatgattct agtaacaggc ggagccggct tcatcggctc aaatttcgta ctgcaatggt    5580
gtgcgcacaa tgaggaaccc gtcctcaacc tcgacgccct gacctacgca ggcaacctgg    5640
ccaacctgca gccgctggaa ggcaacccctc agcatcgctt tgtgcaaggc aatatttgcg    5700
```

```
atgctgcgct tctgaccaag ctgttcgcag agcaccgccc gcgcgccgtg gttcacttcg   5760
cggcggaatc ccatgtagac cgctcaatca ccggccccga agcgtttgtc gaaaccaacg   5820
tgatgggcac gtttcgcttg cttgaagccg cccggcgca ttggaatagt ttggaaggtg    5880
cagagaagga ggccttccgt ttcctccatg tctctaccga cgaagtctac ggcacactag   5940
ggccaaacga cccggcgttc accgaaacca cgccgtacgc gccgaacagc ccatactccg   6000
ccagcaaggc agccagcgac catctggtac gctcgtattt ccatacctac ggcatgccgg   6060
tactcactac caactgctcc aacaattacg ggccgctcca cttcccggaa aaactgatcc   6120
cgctgatgat cgtcaacgca ctcgccggta aggcgctgcc tgtctatggc gacggccagc   6180
aaatccgcga ctggctgtat gtcgaagatc actgctcggg catccgtcgc gtactggaag   6240
ccggtgcgtt cggcgagacg tacaatattg gcggctggaa tgaaaaagcc aacattgaca   6300
ttgtgcgtac actctgcagc cttctcgacg agatggcacc tgcggcatcg cgccaggtaa   6360
tcaatcagaa gaccggcgag cctgtcgaac agtatgcaga actcatcgcc tacgtaaccg   6420
accgcccagg ccatgaccgc cgttatgcca tcgatgcacg caagatcgag cgggagctcg   6480
gctggaaacc tgccgaaacc ttcgagacgg gcattcgaaa gacagtcgct tggtacttgg   6540
ccaaccagaa atgggtaaaa ggtgtcatgg acggcagcta ccgtgactgg gtggcacaac   6600
aatacgggga aaataaagcg tgaaaatcct gctgttgggg aaaaacgggc aagtaggctg   6660
ggagctacag cgcgccttgg cgccgctggg tgaggtcatt gcgctggatc gtcagggggc   6720
cgagggctta tgtggcgact tgtccaacct ggacggcttg gccgctacga ttcgtcagct   6780
ggcgccggac gtgatcgtca acgctgctgc ctacactgca gtggataaag ctgagagcga   6840
tcaggcactg gctgcaatga tcaatgccgc ggctcctgct gtattagcac gtgaaacagc   6900
agctttgggc gcctggttga ttcactattc caccgattat gtatttgacg gcagcggcag   6960
tcagcgctgg gaggaaactg cgcctaccgg ccccctttcg gtctacgccc ggaccaagct   7020
ggaaggcgag catgccattc tcgccagcgg cgccaaggcc gtggtactgc gcaccagctg   7080
ggtgtatgct gcgcgcgggc acaattttgc caagaccatg ctgcgcctgg cggcggagcg   7140
tgagacgttg agcgtggtag cagaccaatt tggcgcaccc acgggcgctg acctgatcgc   7200
cgacgttact gcacacatcc tgcggcaaat cttcaatggg caagacaacc gtcacctggc   7260
agggatttac cacttggctg cgtccggtga aacctcttgg catggttttg ctcagttcgt   7320
gctggcgcat gctcaacgca ctggcgtagc gctgaaagtg acagctgata aggttgccgc   7380
aatcagcacc gaagcttatc cagtacctgc accacgtccg cgcaactcgc gcctggcact   7440
gggcaaactg gaaaacacgt tcaatttcaa aatgccgctt gggagcaag gcgtgcaacg    7500
tatgctggac gaaatccagt aatagggact ctcatggctc gtaaggaat tattctggcc    7560
ggcggttcgg gtacacgcct gcatccggcc acactttcgg tttcgaagca gctgctgccg   7620
gtgtatgaca aaccgatgat ctactacccg ctgagcaccc tgctgctcgc tggtatccgg   7680
gacatcctga tcatttccac cccgcaggac accccgcgct tcgaacagct gctgggcgat   7740
ggcagccagt ggggcctgaa cctgtcatac gcaatacaac caagcccgga tggcttggcg   7800
caagcgttca ccatcggcgc tgacttcatc ggtaacgacc cttctgcgtt ggttctcggt   7860
gacaatattt tctacggcca tgacttccag gcactgctat tgaacgcaga taaacgtgaa   7920
tccggtgctt cagtattcgc ttatcatgtt catgacccag aacgctatgg cgtagcggag   7980
tttgacgata gcggtcgcgt attgtcgctg gaagaaaaac cggcagttcc aaagtctagc   8040
```

```
tatgcggtca ccggcctgta tttctatgac aatcaggtag tcaatctggc tcgcgagctg      8100
aagccttccc cacgtggcga gctggaaatc accgacctca acaaccttta cttgcagcag      8160
cagcagttgc aggtcgaaat catgggccgt ggctatgcgt ggctcgacac cggcacgcac      8220
gacagtctgc tggaggctag ccagtacatc gcaaccatgg agcgccgtca gggcttgaaa      8280
gtcgcctgcc ctgaggaaat tgctaccgc gctggctgga tcaacgctga gcaactcgag       8340
tgcctggctc aaccactgct gaaaaacggt tatggcaagt atctgcagaa cttgctgaaa      8400
gagaaggtgt tctgatgcaa gccattccgc tggatatccc cgaagtcgtg ctgtttaccc      8460
ccaaggtttt tggcgacgaa cgtggttttct tctacgagag cttcaacgcc cgtgttttca     8520
gcgaagtgac cggcctgcag cccgacttcg tacaagacaa ccactcgcgc tcggtaaaag      8580
gcgtgctccg tggcctgcac tatcagctgg cacctcacgc ccagggcaag ctggtgcgtg     8640
tggtgcaagg cgaagtcttc gatgttgcgg tggatatccg tcgctcgtcc acaaccttcg     8700
gtaaatgggt aggtgcggtg ttgtcggccg agaacaagaa ccagctgtgg atcccgccag     8760
ggttcgcaca cgggttcgtc acgttgagtg aaaccgcaga gttcctctac aagaccaccg     8820
acttctactc gccgcagtgc gagcgctgca ttgcctggaa tgatccggca gtgggtatcg     8880
aatggcccat cgactccgta ccaagcttgt ctggcaagga ccagcttggg gtcgcattgg     8940
ctgacgccga actgttcgac taacggtttt agcggagaag ggctgcggta gcgcagcctt      9000
gtctctgaac acatgccata ccgggtcttg ccgatagtgg cgttttcac acgccactaa      9060 gaagcaaccg ctgcatggcc tggcaaataa tcagaatttg ccccttcctt gtaggccatt      9120
tcccaaagat acccctgcgc ctgttttcca ttgcacacgt taaacgtgag acttagtctc      9180
gacccgtcgc tgccaaatca gtgaccggtt tattgactac cggaagcagt gtgaccgtgt     9240
gcttctcaaa tgcctgaggc cagtttgctc aggctctccc cgtggaggta ataattgacg     9300
atatgatcat ttattctgcc tcccagagcc tgataaaaac ggtgaatccg ttagcgaggt      9360
gccgccggct tccattcagg tcgaggtggc ccggctccat gcaccgcgac gcaacgcggg     9420
gaggcagaca aggtataggg cggcgaggcg gctacagccg atagtctgga acagcgcact     9480
tacgggttgc tgcgcaaccc aagtgctacc ggcgcggcag cgtgacccgt tcggcggct      9540 ccaacggctc gccatcgtcc agaaaacacg gctcatcggg catcggcagg cgctgctgcc     9600
cgcgccgttc ccattcctcc gtttcggtca aggctggcag gtctggttcc atgcccggaa     9660
tgccgggctg gctgggcggc tcctcgccgg ggccggtcgg tagttgctgc tcgcccggat     9720
acagggtcgg gatgcggcgc aggtcgccat gccccaacag cgattcgtcc tggtcgtcgt     9780
gatcaaccac cacggcggca ctgaacaccg acaggcgcaa ctggtcgcgg ggctggcccc     9840
acgccacgcg gtcattgacc acgtaggccg cacacggtgcc ggggccgttg agcttcacga    9900
cggagatcca gcgctcggcc accaagtcct tgactgcgta ttggaccgtc cgcaaagaac     9960
gtccgatgag cttggaaagt gtcttctggc tgaccaccac ggcgttctgg tggcccatct    10020
gcgccacgag gtgatgcagc agcattgccg ccgtgggttt cctcgcaata agcccggccc    10080
acgcctcatg cgctttgcgt tccgtttgca cccagtgacc gggcttgttc ttggcttgaa    10140
tgccgatttc tctggactgc gtggccatgc ttatctccat gcgtagggt gccgcacggt     10200 tgcggcacca tgcgcaatca gctgcaactt tcggcagcg cgacaacaat tatgcgttgc     10260
gtaaaagtgg cagtcaatta cagatttcct ttaacctacg caatgagcta ttgcggggg     10320 tgccgcaatg agctgttgcg taccccctt ttttaagttg ttgatttta agtctttcgc      10380 atttcgccct atatctagtt ctttggtgcc caaagaaggg caccctgcg gggttccccc     10440
```

```
acgccttcgg cgcggctccc cctccggcaa aaagtggccc ctccggggct tgttgatcga   10500
ctgcgcggcc ttcggccttg cccaaggtgg cgctgccccc ttggaacccc cgcactcgcc   10560
gccgtgaggc tcgggggggca ggcgggcggg cttcgccttc gactgccccc actcgcatag   10620
gcttgggtcg ttccaggcgc gtcaaggcca agccgctgcg cggtcgctgc gcgagccttg   10680
acccgccttc cacttggtgt ccaaccggca agcgaagcgc gcaggccgca ggccggaggc   10740
ttttccccag agaaaattaa aaaaattgat ggggcaaggc cgcaggccgc gcagttggag   10800
ccggtgggta tgtggtcgaa ggctgggtag ccggtgggca atccctgtgg tcaagctcgt   10860
gggcaggcgc agcctgtcca tcagcttgtc cagcagggtt gtccacgggc cgagcgaagc   10920
gagccagccg gtggccgctc gcggccatcg tccacatatc cacgggctgg caagggagcg   10980
cagcgaccgc gcagggcgaa gcccggagag caagcccgta gggcgccgca gccgccgtag   11040
gcggtcacga ctttgcgaag caaagtctag tgagtatact caagcattga gtggcccgcc   11100
ggaggcaccg ccttgcgctg cccccgtcga gccggttgga caccaaaagg gaggggcagg   11160
catggcggca tacgcgatca tgcgatgcaa gaagctggcg aaaatgggca acgtggcggc   11220
cagtctcaag cacgcctacc gcgagcgcga gacgcccaac gctgacgcca gcaggacgcc   11280
agagaacgag cactgggcgg ccagcagcac cgatgaagcg atgggccgac tgcgcgagtt   11340
gctgccagaa aagcggcgca aggacgctgt gttggcggtc gagtacgtca tgacggccag   11400
cccggaatgg tggaagtcgg ccagccaaga acagcaggcg gcgttcttcg agaaggcgca   11460
caagtggctg gcggacaagt acggggcgga tcgcatcgtg acggcagca tccaccgtga   11520
cgaaaccagc ccgcacatga ccgcgttcgt ggtgccgctg acgcaggacg gcaggctgtc   11580
ggccaaggag ttcatcggca acaaagcgca gatgacccgc gaccagacca cgtttgcggc   11640
cgctgtggcc gatctagggc tgcaacgggg catcgagggc agcaaggcac gtcacacgcg   11700
cattcaggcg ttctacgagg ccctggagcg gccaccagtg ggccacgtca ccatcagccc   11760
gcaagcggtc gagccacgcg cctatgcacc gcagggattg gccgaaaagc tgggaatctc   11820
aaagcgcgtt gagacgccgg aagccgtggc cgaccggctg acaaaagcgg ttcggcaggg   11880
gtatgagcct gccctacagg ccgccgcagg agcgcgtgag atgcgcaaga aggccgatca   11940
agcccaagag acggcccgag                                              11960
```

<210> SEQ ID NO 74
<211> LENGTH: 13289
<212> TYPE: DNA
<213> ORGANISM: Artificial Sequence
<220> FEATURE:
<223> OTHER INFORMATION: vector

<400> SEQUENCE: 74

```
ccggtcactg atttggcagc gacgggtcga gactaagtct cacgtttaac gtgtgcaatg     60
gaaacaggc gcaggggtat ctttgggaaa tggcctacaa ggaagggca aattctgatt      120
atttgccagg ccatgcagcg gttgcttctt agtggcgtgt gaaaaacgcc actatcggca     180
agacccggta tggcatgtgt tcagagacaa ggctgcgcta ccgcagccct tctccgctaa     240
aaccgttagt cgaacagttc ggcgtcagcc aatgcgaccc caagctggtc cttgccagac     300
aagcttggta cggagtcgat gggccattcg atacccactg ccggatcatt ccaggcaatg     360
cagcgctcgc actgcggcga gtagaagtcg gtggtcttgt agaggaactc tgcggtttca     420
ctcaacgtga cgaacccgtg tgcgaaccct ggcgggatcc acagctggtt cttgttctcg     480
```

```
gccgacaaca ccgcacctac ccatttaccg aaggttgtgg acgagcgacg atatccacc     540 gcaacatcga agacttcgcc ttgcaccaca cgcaccagct tgccctgggc gtgaggtgcc    600
agctgatagt gcaggccacg gagcacgcct tttaccgagc gcgagtggtt gtcttgtacg    660
aagtcgggct gcaggccggt cacttcgctg aaaacacggg cgttgaagct ctcgtagaag    720
aaaccacgtt cgtcgccaaa aaccttgggg gtaaacagca cgacttcggg gatatccagc    780
ggaatggctt gcatcagaac accttctctt tcagcaagtt ctgcagatac ttgccataac    840 cgttttcag cagtggttga gccaggcact cgagttgctc agcgttgatc cagccagcgc    900
ggtagcaaat ttcctcaggg caggcgactt caagccctg acggcgctcc atggttgcga    960
tgtactggct agcctccagc agactgtcgt gcgtgccggt gtcgagccac gcatagccac   1020
ggcccatgat ttcgacctgc aactgctgct gctgcaagta aaggttgttg aggtcggtga   1080
tttccagctc gccacgtggg gaaggcttca gctcgcgagc cagattgact acctgattgt   1140
catagaaata caggccggtg accgcatagc tagactttgg aactgccggt ttttcttcca   1200
gcgacaatac gcgaccgcta tcgtcaaact ccgctacgcc atagcgttct gggtcatgaa   1260
catgataagc gaatactgaa gcaccggatt cacgtttatc tgcgttcaat agcagtgcct   1320
ggaagtcatg gccgtagaaa atattgtcac cgagaaccaa cgcagaaggg tcgttaccga   1380
tgaagtcagc gccgatggtg aacgcttgcg ccaagccatc cgggcttggt tgtattgcgt   1440
atgacaggtt caggccccac tggctgccat cgcccagcag ctgttcgaag cgcggggtgt   1500
cctgcggggt ggaaatgatc aggatgtccc ggataccagc gagcagcagg gtgctcagcg   1560
ggtagtagat catcggtttg tcatacaccg gcagcagctg cttcgaaacc gaaagtgtgg   1620
ccggatgcag gcgtgtaccc gaaccgccgg ccagaataat tcctttacga gccatgagag   1680
tccctattac tggatttcgt ccagcatacg ttgcacgcct tgctcccaaa gcggcatttt   1740
gaaattgaac gtgttttcca gtttgcccag tgccaggcgc gagttgcgcg acgtggtgc    1800 aggtactgga taagcttcgg tgctgattgc ggcaaccta tcagctgtca ctttcagcgc    1860
tacgccagtg cgttgagcat gcgccagcac gaactgagca aaaccatgcc aagaggtttc    1920
accggacgca gccaagtggt aaatccctgc caggtgacgg ttgtcttgcc cattgaagat   1980
ttgccgcagg atgtgtgcag taacgtcggc gatcaggtca gcgcccgtgg gtgcgccaaa   2040
ttggtctgct accacgctca acgtctcacg ctccgccgcc aggcgcagca tggtcttggc   2100
aaaattgtgc ccgcgcgcag catacaccca gctggtgcgc agtaccacgg ccttggcgcc   2160
gctggcgaga atggcatgct cgccttccag cttggtccgg ccgtagaccg aaaggggggcc  2220 ggtaggcgca gtttcctccc agcgctgact gccgctgccg tcaaatacat aatcggtgga   2280
atagtgaatc aaccaggcgc ccaaagctgc tgtttcacgt gctaatacag caggagccgc   2340
ggcattgatc attgcagcca gtgcctgatc gctctcagct ttatccactg cagtgtaggc   2400
agcagcgttg acgatcacgt ccggcgccag ctgacgaatc gtagcggcca agccgtccag   2460
gttggacaag tcgccacata gccctcggc cccctgacga tccagcgcaa tgacctcacc    2520
cagcggcgcc aaggcgcgct gtagctccca gcctacttgc ccgttttcc ccaacagcag    2580 gatttcacg ctttatttgc cccgtattgt tgtgccaccc agtcacggta gctgccgtcc    2640
atgacacctt ttacccattt ctggttggcc aagtaccaag cgactgtctt tcgaatgccc   2700
gtctcgaagg tttcggcagg tttccagccg agctcccgct cgatcttgcg tgcatcgatg   2760
gcataacggc ggtcatggcc tgggcggtcg gttacgtagg cgatgagttc tgcatactgt   2820
tcgacaggct cgccggtctt ctgattgatt acctggcgcg atgccgcagg tgccatctcg   2880
```

```
tcgagaaggc tgcagagtgt acgcacaatg tcaatgttgg cttttcatt ccagccgcca    2940
atattgtacg tctcgccgaa cgcaccggct tccagtacgc gacggatgcc cgagcagtga    3000
tcttcgacat acagccagtc gcggatttgc tggccgtcgc catagacagg cagcgcctta    3060
ccggcgagtg cgttgacgat catcagcggg atcagttttt ccgggaagtg gagcggcccg    3120
taattgttgg agcagttggt agtgagtacc ggcatgccgt aggtatggaa atacgagcgt    3180
accagatggt cgctggctgc cttgctggcg gagtatgggc tgttcggcgc gtacggcgtg    3240
gtttcggtga acgccgggtc gtttggccct agtgtgccgt agacttcgtc ggtagagaca    3300
tggaggaaac ggaaggcctc cttctctgca ccttccaaac tattccaatg cgcccgggcg    3360
gcttcaagca agcgaaacgt gcccatcacg ttggtttcga caaacgcttc ggggccggtg    3420
attgagcggt ctacatggga ttccgccgcg aagtgaacca cggcgcgcgg gcggtgctct    3480
gcgaacagct tggtcagaag cgcagcatcg caaatattgc cttgcacaaa gcgatgctga    3540
gggttgcctt ccagcggctg caggttggcc aggttgcctg cgtaggtcag ggcgtcgagg    3600
ttgaggacgg gttcctcatt gtgcgcacac cattgcagta cgaaatttga gccgatgaag    3660
ccggctccgc ctgttactag aatcataatt tggctctaat tggacaaaag gtgttgtcgt    3720
agacagatga cgctgagaaa cttcgccccg gcaacgcaag gcgagctgct agcgctgccg    3780
gaattagacc accctgatgt cgaaaaatac actgctgggt gccggtactg accgtgccga    3840
tctgctcacg ctggaagagg aggagccgtt gcagcggtgg aaggtgacct catggttgcc    3900
tagacacaac agggagtcgt caggtgtcca tgcaagaaac agttgtttga gcgatgcaac    3960
tcacggagac aaatctgggt gctgacaagt ctagagggcc ttaagctacc gctatcctgg    4020
gactctagtt cgctgggcat ggcagcgcgg ggtgcgcatc tggaagtcgg gttcgtttcc    4080
ggggggttgga aagtgtcatt tttatttgtc agtattcctg aaataggaat tagagtgatg    4140
gcagttcttg cattcatgtt gaacaaccca acaaaaatta taatagcctc ggggctcggc    4200
aggttagacg tcattcttca tgtttcagcg gtctggcgct cttgaatatt cataggaaag    4260
tgaaaaatgt ctgttaagga aggcttgccg agcgtagatg tgcagccgag catgcatgtt    4320
aagggaaatt cagtgcccgt cccccagaaa aagactggct caaggcgatt tgtgctggat    4380
ctggcttatt atcggaatcg atacccagac ctatcttcgc tcacggacga tgcgctcgaa    4440
cagcattggc atgcgttcgg tcatcaagaa ggccgttatg cctcggcttc gcacgaaagt    4500
ggtgatgcgg agcttatcgc tgaagcagtt ctcaatgcgg ccgacagcgc cgttatggtc    4560
aagccggatg ttgcgaaagt tgacctaccg gtaaaccagc aatagacata agcggctatt    4620
taacgaccct gccctgaacc gacgaccggg tcgaatttgc tttcgaattt ctgccattca    4680
tccgcttatt atcacttatt caggcgtagc accaggcgtt taagggcacc aataactgcc    4740
ttaaaaaaat tacgccccgc cctgccactc atcgcagtcg gcctattggt taaaaaatga    4800
gctgatttaa caaaatttta acgcgaattt taacaaaata ttaacgctta caatttccat    4860
tcgccattca ggctgcgcaa ctgttgggaa gggcgatcgg tgcgggcctc ttcgctatta    4920
cgccagctgg cgaaaggggg atgtgctgca aggcgattaa gttgggtaac gccagggttt    4980
tcccagtcac gacgttgtaa aacgacggcc agtgagcgcg cgtaatacga ctcactatag    5040
ggcgaattgg agctccaccg cggtggcggc cgctctagaa gtaccaccag cacgcccatg    5100
tctatccggt ccatgatcgt tcttctcccg taggtcgaag ttgccaggcc aggaccagcc    5160
cggccagaac gagaagggcg ccggcgagga atggcgcgcc ggccaggggc agcggcgcga    5220
```

```
gcggaccgct gccccagtgg aacaggccgc tcatcagcgg cggaccgacg atcgcggcga    5280
ggctcatcag gctgctcagc acgccctgca actcgccctg gcggtcgacc ggcacgcggg    5340
ccgagagcag cccctgcatg gccggggtgg cgaggctgcc gagcgcgaag ggcagcagcg    5400
cgcagaccgc ccagaatgac gagtcgacca gggcgaacag cagcaggccg cagccttgca    5460
gggcgaggcc caggcgcagc aggcgggcgt cgtccaggcg ccgcttgcag aggttcacgc    5520
cgagggtctg ggcgagcacc gcgagcacgc cgtagagggc cagcgagtag ccgatccagg    5580
cgctgctcca gtgaaacttc tcgatcacga agaacggcca gaccaccatc accgcctgca    5640
agccgaggaa taccagggca agcaccgcca gcaggcgtcc gaccccggt tgccgagcca     5700
ggccgctgat cgagcgcaag gcattcatcc gcctcgggtc caggcggcgg cgtcgcgtcg    5760
ggggcagggt ttcctcgagg aacaggccgg cgagcagggc gttgagcagg cacaggccgg    5820
cggccagcaa cagcggcagc gtcgtgccgt gcaccgccag cagcccaccg agggcggggc    5880
cgaggatcat gcccagggcg aggccggcgt acagccagcc gaagtgccgg gtgcgctgcc    5940
cgtgcgtgcc gaggtcagcc gcgcaggcca tcgcggtggc cacgctggcg ccggtgagcc    6000
cggccagcgc gcgaccgagg aacagcatcc agaggctgtc ggccagcgcc agcagcagat    6060
agctgagggc gaagccgagc atcgccagga ccaggacggg gcggcgtccg aagcggtcgc    6120
tgaggctgcc gaggaccggc gaaaagaaca attgcagcag cgcgaaggtc atcaccaggg    6180
cggcgcccca ggtggccgcg tcgcggaccg ccagcggcgc cacgctgccg atcagcgtcg    6240
gcagcagggg cacgatcagg ccgacgccag cggcatccag caggcaggtg aggaacagca    6300
gaggcaggac gcgtttcgcg ccgggaccgt gttcccgcgt ggcggagggg cagaggctgg    6360
tcgtggacac gccaggatcc tcccggcgtc aggacgcagc cttcagccat cgcgcatccc    6420
cctccctatg acaacgttcg accacctggg ccgctttacc gcaagcgata ctgtgcggtt    6480
gtgacaattc catgaaacgc cgacaggccg ccgccatggc cgggtcctcg agcaagcgcc    6540
acagcgcccc gcgcaactcc tgctcgcgca atggcacgcc caggcgcatc ccgcagccga    6600
gccggaccag ccgttcggca ttgtcgaact ggtcgtgggc gcagggcagc agcacctgcg    6660
gcaccccgc cgcaaggcc aggctcatgg cgccgatacc gcccgatgg accagcccgg       6720
cgcacgatgg cagcaaggct cccagtggcg cgtaggcgcg ctgcagcacg tggttcggca    6780
agccgcgcag cggttcctgg ccggcgccgg tgaggaagat cccacgcgcg ccgaggcgtt    6840
ccagcgcgcg cagggccatg gcgtagaagt cgccctgcag gtgttcggtc gagccctggg    6900
tgaacaccag cggccggctg ccctgatcga gaaagcgttg cagttcgtcg tcgagcgggg    6960
tccccgggat actgccgtcg aacagcggga agccggtcat gtgcaggggt tgcggccaat    7020
cctgctgggg cggcgcgaac caggccggga acaggcagac cacgccctgc ggcgaatgca    7080
tccattgggt gaagatgcgc ttcaccggcg tctccaggcc gaccttgcgc cgcaccgcgt    7140
tgatatccgg cgcgcaggtg cgatccagct tgaagcgctc gatgcagcgc cagagcagct    7200
tgcgcatcgc cagcggcatc tgctcgggca cgttgaactt ggggtgtacc ggcggcaggt    7260
gcgccgacaa caaggtcgat ggcgagacct gcgcggacag gtagggaatc ccgtacttct    7320
cgtgagcgat gcgtgcgccc agcgcccaga gcgagccgac caccacgatg tcgtcatggc    7380
gctgcgccga gacgtactcg tagaccggct cgatcatccc ggcgatggtt tgccagagca    7440
cgccgaagga cgtcttgggg tcccacaggc gcggatcgcc catggtccgg cggtaggtca    7500
gttcgtcgct cagcgggacg aacgcgatgc cgtgctgctc caccgcgtcg cgaaacaccg    7560
ggatggtgca gaggctcacg cggtgcccgc gcaatttcag ggtccgggcc aggccgatga    7620
```

-continued

```
agggaaatac gtcgccggcc gagccgatgg cgatgaggat ggcgtgcatg gtgctactcc   7680
gtgcgttatg caaccgcaaa gcccggccag gccgggtctt cgcaggtcaa gggttcaggc   7740
gtagccgatg gccatctcgt ggaatcccgc cgcgcgttcc gcccgctgcg gctccggttg   7800
cttcagcagg tgctcgagca gggcgcggtg cacgcgtacc gcggccagct tggactccag   7860
gtcgaggaaa tgcccggtgc cctccacccg cgagaaactg cagtgcggca ggtagtcgcg   7920
gaactggcgg gcgtcctcgg cggtggtgta ttcgtcccag ctgccgttga tgaaatgcac   7980
gtggctctgg atccgctcca ggcaagccag gtagccccga tcgttgagcg ccagcacctg   8040
gtcgatgtga aagcgcgcct gctcgtattc gccggtggcc agcgaagcca tgtgctgatg   8100
gttgctggct ttcaggcgcg gcggcaggta tttgccgacg gtctcgttga gcagatggcc   8160
gatcgccgac ttgtcgtcca gctcgatcag cgcctgcgcc cgcccgacgt agtcgagcat   8220
cgcctggttc agtccagggg cgaatgccat caccaccgag ctgcggatgc cgcgcggatt   8280
gcgcgacagc gccagcagcg tggagatacc gccccaggac gcggagacca ggtgattgac   8340
ctcgaagcgc tcgatcagcg ccaggaggat ttccacctcg tcgtccttgg tgatcaaccc   8400
ccgctgcggg ttgtgctgac gcgactgccc ggcgaagggc aggtcgaaca gcaccacgtt   8460
gaaatgttcg gccaggcact gcaggtccgg ggcgaacgag gcggtggtcg ccatcgcgcc   8520
gttgaccagc atcaccgtgc tgcgcccggg atcctgccca acgcgctcga catgtacccg   8580
caggcccttg caaaccgata ccaacagact ttcgcgccgc atttcacacc tcccaaaaat   8640
gccagatccc ccgggctgca ggaattcgat atcaagctta tcgataccgt cgacctcgag   8700
ggggggcccg gtacccagct tttgttccct ttagtgaggg ttaattgcgc gcttggcgta   8760
atcatggtca tagctgtttc ctgtgtgaaa ttgttatccg ctcacaattc cacacaacat   8820
acgagccgga agcataaagt gtaaagcctg gggtgcctaa tgagtgagct aactcacatt   8880
aattgcgttg cgctcactgc ccgctttcca gtcgggaaac ctgtcgtgcc agctgcatta   8940
atgaatcggc caacgcgcgg ggagaggcgg tttgcgtatt gggcgcatgc ataaaaactg   9000
ttgtaattca ttaagcattc tgccgacatg gaagccatca caaacggcat gatgaacctg   9060
aatcgccagc ggcatcagca ccttgtcgcc ttgcgtataa tatttgccca tggggtggg   9120
cgaagaactc cagcatgaga tccccgcgct ggaggatcat ccagccggcg tcccggaaaa   9180
cgattccgaa gcccaacctt tcatagaagg cggcggtgga atcgaaatct cgtgatggca   9240
ggttgggcgt cgcttggtcg gtcatttcga accccagagt cccgctcaga gaactcgtc   9300
aagaaggcga tagaaggcga tgcgctgcga atcgggagcg gcgataccgt aaagcacgag   9360
gaagcggtca gcccattcgc cgccaagctc ttcagcaata tcacgggtag ccaacgctat   9420
gtcctgatag cggtccgcca cacccagccg gccacagtcg atgaatccag aaaagcggcc   9480
attttccacc atgatattcg gcaagcaggc atcgccatgg gtcacgacga tcctcgcc    9540
gtcgggcatg cgcgccttga gcctggcgaa cagttcggct ggcgcgagcc cctgatgctc   9600
ttcgtccaga tcatcctgat cgacaagacc ggcttccatc cgagtacgtg ctcgctcgat   9660
gcgatgtttc gcttggtggt cgaatgggca ggtagccgga tcaagcgtat gcagccgccg   9720
cattgcatca gccatgatgg atactttctc ggcaggagca aggtgagatg acaggagatc   9780
ctgccccggc acttcgccca atagcagcca gtcccttccc gcttcagtga caacgtcgag   9840
cacagctgcg caaggaacgc ccgtcgtggc cagccacgat agccgcgctg cctcgtcctg   9900
cagttcattc agggcaccgg acaggtcggt cttgacaaaa agaaccgggc gcccctgcgc   9960
```

```
tgacagccgg aacacggcgg catcagagca gccgattgtc tgttgtgccc agtcatagcc   10020
gaatagcctc tccacccaag cggccggaga acctgcgtgc aatccatctt gttcaatcat   10080
gcgaaacgat cctcatcctg tctcttgatc agatcttgat cccctgcgcc atcagatcct   10140
tggcggcaag aaagccatcc agtttacttt gcagggcttc ccaaccttac cagagggcgc   10200
cccagctggc aattccggtt cgcttgctgt ccataaaacc gcccagtcta gctatcgcca   10260
tgtaagccca ctgcaagcta cctgctttct ctttgcgctt gcgttttccc ttgtccagat   10320
agcccagtag ctgacattca tcccaggtgg cacttttcgg ggaaatgtgc gcgcccgcgt   10380
tcctgctggc gctgggcctg tttctggcgc tggacttccc gctgttccgt cagcagcttt   10440
tcgcccacgg ccttgatgat cgcggcggcc ttggcctgca tatcccgatt caacggcccc   10500
agggcgtcca gaacgggctt caggcgctcc gaaggtctc gggccgtctc ttgggcttga    10560
tcggccttct tgcgcatctc acgcgctcct gcggcggcct gtagggcagg ctcataccccc   10620 tgccgaaccg cttttgtcag ccggtcggcc acggcttccg gcgtctcaac gcgctttgag   10680
attcccagct tttcggccaa tccctgcggt gcataggcgc gtggctcgac cgcttgcggg   10740
ctgatggtga cgtggcccac tggtggccgc tccagggcct cgtagaacgc ctgaatgcgc   10800
gtgtgacgtg ccttgctgcc ctcgatgccc cgttgcagcc ctagatcggc cacagcggcc   10860
gcaaacgtgg tctggtcgcg ggtcatctgc gctttgttgc cgatgaactc cttggccgac   10920
agcctgccgt cctgcgtcag cggcaccacg aacgcggtca tgtgcgggct ggtttcgtca   10980
cggtggatgc tggccgtcac gatgcgatcc gccccgtact tgtccgccag ccacttgtgc   11040
gccttctcga agaacgccgc ctgctgttct tggctggccg acttccacca ttccgggctg   11100
gccgtcatga cgtactcgac cgccaacaca gcgtccttgc gccgcttctc tggcagcaac   11160
tcgcgcagtc ggcccatcgc ttcatcggtg ctgctggccg cccagtgctc gttctctggc   11220
gtcctgctgg cgtcagcgtt gggcgtctcg cgctcgcggt aggcgtgctt gagactggcc   11280
gccacgttgc ccattttcgc cagcttcttg catcgtgatga tcgcgtatgc cgccatgcct   11340
gcccctccct tttggtgtcc aaccggctcg acgggggcag cgcaaggcgg tgcctccggc   11400
gggccactca atgcttgagt atactcacta gactttgctt cgcaaagtcg tgaccgccta   11460
cggcggctgc ggcgccctac gggcttgctc tccgggcttc gccctgcgcg gtcgctgcgc   11520
tcccttgcca gcccgtggat atgtggacga tggccgcgag cggccaccgg ctggctcgct   11580
tcgctcggcc cgtggacaac cctgctggac aagctgatgg acaggctgcg cctgcccacg   11640
agcttgacca cagggattgc ccaccggcta cccagccttc gaccacatac ccaccggctc   11700
caactgcgcg gcctgcggcc ttgccccatc aattttttta attttctctg ggaaaagcc    11760 tccggcctgc ggcctgcgcg cttcgcttgc cggttggaca ccaagtggaa ggcgggtcaa   11820
ggctcgcgca gcgaccgcgc agcggcttgg ccttgacgcg cctggaacga cccaagccta   11880
tgcgagtggg ggcagtcgaa ggcgaagccc gccgcctgc cccccgagcc tcacggcggc    11940
gagtgcgggg gttccaaggg ggcagcgcca ccttgggcaa ggccgaaggc cgcgcagtcg   12000
atcaacaagc cccggagggg ccacttttg ccggaggggg agccgcgccg aaggcgtggg    12060
ggaaccccgc agggtgccc ttctttggc accaagaac tagatatagg gcgaaatgcg      12120
aaagacttaa aaatcaacaa cttaaaaaag gggggtacgc aacagctcat gcggcaccc    12180 cccgcaatag ctcattgcgt aggttaaaga aaatctgtaa ttgactgcca cttttacgca   12240
acgcataatt gttgtcgcgc tgccgaaaag ttgcagctga ttgcgcatgg tgccgcaacc   12300
gtgcggcacc ctaccgcatg gagataagca tggccacgca gtccagagaa atcggcattc   12360
```

-continued

```
aagccaagaa caagcccggt cactgggtgc aaacggaacg caaagcgcat gaggcgtggg    12420
ccgggcttat tgcgaggaaa cccacggcgg caatgctgct gcatcacctc gtggcgcaga    12480
tgggccacca gaacgccgtg gtggtcagcc agaagacact ttccaagctc atcggacgtt    12540
cttttgcgga ggtccaatac gcagtcaagg acttggtggc cgagcgctgg atctccgtcg    12600
tgaagctcaa cggccccggc accgtgtcgg cctacgtggt caatgaccgc gtggcgtggg    12660
gccagccccg cgaccagttg cgcctgtcgg tgttcagtgc cgccgtggtg gttgatcacg    12720
acgaccagga cgaatcgctg ttggggcatg gcgacctgcg ccgcatcccg accctgtatc    12780
cgggcgagca gcaactaccg accggccccg gcgaggagcc gccagccag cccggcattc     12840
cgggcatgga accagacctg ccagccttga ccgaaacgga ggaatgggaa cggcgcgggc    12900
agcagcgcct gccgatgccc gatgagccgt gttttctgga cgatggcgag ccgttggagc    12960
cgccgacacg ggtcacgctg ccgcgccggt agcacttggg ttgcgcagca acccgtaagt    13020
gcgctgttcc agactatcgg ctgtagccgc ctcgccgccc tataccttgt ctgcctcccc    13080
gcgttgcgtc gcggtgcatg gagccgggcc acctcgacct gaatggaagc cggcggcacc    13140
tcgctaacgg attcaccgtt tttatcaggc tctgggaggc agaataaatg atcatatcgt    13200
caattattac ctccacgggg agagcctgag caaactggcc tcaggcattt gagaagcaca    13260
cggtcacact gcttccggta gtcaataaa                                      13289
```

<210> SEQ ID NO 75
<211> LENGTH: 14250
<212> TYPE: DNA
<213> ORGANISM: Artificial Sequence
<220> FEATURE:
<223> OTHER INFORMATION: vector

<400> SEQUENCE: 75

```
ctcgggccgt ctcttgggct tgatcggcct tcttgcgcat ctcacgcgct cctgcggcgg      60
cctgtagggc aggctcatac ccctgccgaa ccgcttttgt cagccggtcg ccacggcttc    120
ccggcgtctc aacgcgcttt gagattccca gcttttcggc caatccctgc ggtgcatagg    180
cgcgtggctc gaccgcttgc gggctgatgg tgacgtggcc cactggtggc cgctccaggg    240
cctcgtagaa cgcctgaatg cgcgtgtgac gtgccttgct gccctcgatg ccccgttgca    300
gccctagatc ggccacagcg gccgcaaacg tggtctggtc gcgggtcatc tgcgctttgt    360
tgccgatgaa ctccttggcc gacagcctgc cgtcctgcgt cagcggcacc acgaacgcgg    420
tcatgtgcgg gctggtttcg tcacggtgga tgctggccgt cacgatgcga tccgccccgt    480
acttgtccgc cagccacttg tgcgccttct cgaagaacgc cgcctgctgt tcttggctgg    540
ccgacttcca ccattccggg ctggccgtca tgacgtactc gaccgccaac acagcgtcct    600
tgcgccgctt ctctggcagc aactcgcgca gtcgccccat cgcttcatcg gtgctgctgg    660
ccgcccagtg ctcgttctct ggcgtcctgc tggcgtcagc gttgggcgtc tcgcgctcgc    720
ggtaggcgtg cttgagactg gccgccacgt tgcccatttt cgccagcttc ttgcatcgca    780
tgatcgcgta tgccgccatg cctgcccctc ccttttggtg tccaaccggc tcgacggggg    840
cagcgcaagg cggtgcctcc ggcgggccac tcaatgcttg agtatactca ctagactttg    900
cttcgcaaag tcgtgaccgc ctacggcggc tgcggcgccc tacgggcttg ctctccgggc    960
ttcgccctgc gcggtcgctg cgctcccttg ccagcccgtg gatatgtgga cgatggccgc   1020
gagcggccac cggctggctc gcttcgctcg gcccgtggac aaccctgctg acaagctga    1080
```

```
tggacaggct gcgcctgccc acgagcttga ccacagggat tgcccaccgg ctacccagcc    1140
ttcgaccaca tacccaccgg ctccaactgc gcggcctgcg gccttgcccc atcaattttt    1200
ttaattttct ctggggaaaa gcctccggcc tgcggcctgc gcgcttcgct tgccggttgg    1260
acaccaagtg gaaggcgggt caaggctcgc gcagcgaccg cgcagcggct tggccttgac    1320
gcgcctggaa cgacccaagc ctatgcgagt gggggcagtc gaaggcgaag cccgcccgcc    1380
tgcccccga gcctcacggc ggcgagtgcg ggggttccaa gggggcagcg ccaccttggg     1440
caaggccgaa ggccgcgcag tcgatcaaca agccccggag gggccacttt tgccggagg     1500
gggagccgcg ccgaaggcgt gggggaaccc cgcagggggtg cccttctttg gcaccaaag    1560
aactagatat agggcgaaat gcgaaagact taaaaatcaa caacttaaaa aaggggggta    1620
cgcaacagct cattgcggca cccccgcaa tagctcattg cgtaggttaa agaaaatctg     1680
taattgactg ccacttttac gcaacgcata attgttgtcg cgctgccgaa aagttgcagc    1740
tgattgcgca tggtgccgca accgtgcggc accctaccgc atggagataa gcatggccac    1800
gcagtccaga gaaatcggca ttcaagccaa gaacaagccc ggtcactggg tgcaaacgga    1860
acgcaaagcg catgaggcgt gggccgggct tattgcgagg aaacccacgg cggcaatgct    1920
gctgcatcac ctcgtggcgc agatgggcca ccagaacgcc gtggtggtca gccagaagac    1980
actttccaag ctcatcggac gttctttgcg gacggtccaa tacgcagtca aggacttggt    2040
ggccgagcgc tggatctccg tcgtgaagct caacggcccc ggcaccgtgt cggcctacgt    2100
ggtcaatgac cgcgtggcgt ggggccagcc ccgcgaccag ttgcgcctgt cggtgttcag    2160
tgccgccgtg gtggttgatc acgacgacca ggacgaatcg ctgttggggc atggcgacct    2220
gcgccgcatc ccgaccctgt atccgggcga gcagcaacta ccgaccggcc ccggcgagga    2280
gccgcccagc cagcccggca ttccgggcat ggaaccagac ctgccagcct tgaccgaaac    2340
ggaggaatgg gaacggcgcg ggcagcagcg cctgccgatg cccgatgagc cgtgttttct    2400
ggacgatggc gagccgttgg agccgccgac acgggtcacg ctgccgcgcc ggtagcactt    2460
gggttgcgca gcaacccgta agtgcgctgt tccagactat cggctgtagc cgcctcgccg    2520
ccctatacct tgtctgcctc cccgcgttgc gtcgcggtgc atggagccgg gccacctcga    2580
cctgaatgga agccggcggc acctcgctaa cggattcacc gttttttatca ggctctggga    2640
ggcagaataa atgatcatat cgtcaattat tacctccacg gggagagcct gagcaaactg    2700
gcctcaggca tttgagaagc acacggtcac actgcttccg gtagtcaata aaccggtcac    2760
tgatttggca gcgacgggtc gagactaagt ctcacgttta acgtgtgcaa tggaaaacag    2820
gcgcaggggt atctttggga aatggcctac aaggaagggg caaattctga ttatttgcca    2880
ggccatgcag cggttgcttc ttagtggcgt gtgaaaaacg ccactatcgg caagacccgg    2940
tatggcatgt gttcagagac aaggctgcgc taccgcagcc cttctccgct aaaaccgtta    3000
gtcgaacagt tcggcgtcag ccaatgcgac cccaagctgg tccttgccag acaagcttgg    3060
tacgagtcg atgggccatt cgatacccac tgccggatca ttccaggcaa tgcagcgctc    3120
gcactgcggc gagtagaagt cggtggtctt gtagaggaac tctgcggttt cactcaacgt    3180
gacgaacccg tgtgcgaacc ctggcgggat ccacagctgg ttcttgttct cggccgacaa    3240
caccgcacct acccatttac cgaaggttgt ggacgagcga cggatatcca ccgcaacatc    3300
gaagacttcg ccttgcacca cacgcaccag cttgccctgg gcgtgaggtg ccagctgata    3360
gtgcaggcca cggagcacgc cttttaccga gcgcgagtgt ttgtcttgta cgaagtcggg    3420
ctgcaggccg gtcacttcgc tgaaaacacg ggcgttgaag ctctcgtaga agaaaccacg    3480
```

```
ttcgtcgcca aaaaccttgg gggtaaacag cacgacttcg gggatatcca gcggaatggc    3540
ttgcatcaga acaccttctc tttcagcaag ttctgcagat acttgccata accgttttc    3600
agcagtggtt gagccaggca ctcgagttgc tcagcgttga tccagccagc gcggtagcaa    3660
atttcctcag ggcaggcgac tttcaagccc tgacggcgct ccatggttgc gatgtactgg    3720
ctagcctcca gcagactgtc gtgcgtgccg gtgtcgagcc acgcatagcc acggcccatg    3780
atttcgacct gcaactgctg ctgctgcaag taaaggttgt tgaggtcggt gatttccagc    3840
tcgccacgtg gggaaggctt cagctcgcga gccagattga ctacctgatt gtcatagaaa    3900
tacaggccgt gaccgcata gctagacttt ggaactgccg ttttcttc cagcgacaat    3960
acgcgaccgc tatcgtcaaa ctccgctacg ccatagcgtt ctgggtcatg aacatgataa    4020
gcgaatactg aagcaccgga ttcacgttta tctgcgttca atagcagtgc ctggaagtca    4080
tggccgtaga aaatattgtc accgagaacc aacgcagaag ggtcgttacc gatgaagtca    4140
gcgccgatgg tgaacgcttg cgccaagcca tccgggcttg gttgtattgc gtatgacagg    4200
ttcaggcccc actggctgcc atcgcccagc agctgttcga agcgcgggt gtcctgcggg    4260
gtggaaatga tcaggatgtc ccggatacca gcgagcagca gggtgctcag cgggtagtag    4320
atcatcggtt tgtcatacac cggcagcagc tgcttcgaaa ccgaaagtgt ggccggatgc    4380
aggcgtgtac ccgaaccgcc ggccagaata attcctttac gagccatgag agtccctatt    4440
actggatttc gtccagcata cgttgcacgc cttgctccca aagcggcatt ttgaaattga    4500
acgtgttttc cagtttgccc agtgccaggc gcgagttgcg cggacgtggt gcaggtactg    4560
gataagcttc ggtgctgatt gcggcaacct tatcagctgt cactttcagc gctacgccag    4620
tgcgttgagc atgcgccagc acgaactgag caaaaccatg ccaagaggtt tcaccggacg    4680
cagccaagtg gtaaatccct gccaggtgac ggttgtcttg cccattgaag atttgccgca    4740
ggatgtgtgc agtaacgtcg gcgatcaggt cagcgcccgt gggtgcgcca aattggtctg    4800
ctaccacgct caacgtctca cgctccgccg ccaggcgcag catggtcttg gcaaaattgt    4860
gcccgcgcgc agcatacacc cagctggtgc gcagtaccac ggccttggcg ccgctggcga    4920
gaatggcatg ctcgccttcc agcttggtcc ggccgtagac cgaaaggggg ccggtaggcg    4980
cagtttcctc ccagcgctga ctgccgctgc cgtcaaatac ataatcggtg aatagtgaa    5040
tcaaccaggc gcccaaagct gctgtttcac gtgctaatac agcaggagcc gcggcattga    5100
tcattgcagc cagtgcctga tcgctctcag ctttatccac tgcagtgtag gcagcagcgt    5160
tgacgatcac gtccggcgcc agctgacgaa tcgtagcggc caagccgtcc aggttggaca    5220
agtcgccaca taagccctcg gcccctgac gatccagcgc aatgacctca cccagcggcg    5280
ccaaggcgcg ctgtagctcc cagcctactt gcccgttttt ccccaacagc aggattttca    5340
cgctttattt gccccgtatt gttgtgccac ccagtcacgg tagctgccgt ccatgacacc    5400
ttttacccat ttctgttgg ccaagtacca agcgactgtc tttcgaatgc ccgtctcgaa    5460
ggtttcggca ggtttccagc cgagctcccg ctcgatcttg cgtgcatcga tggcataacg    5520
gcggtcatgg cctgggcggt cggttacgta ggcgatgagt tctgcatact gttcgacagg    5580
ctcgccggtc ttctgattga ttacctggcg cgatgccgca ggtgccatct cgtcgagaag    5640
gctgcagagt gtacgcacaa tgtcaatgtt ggctttttca ttccagccgc caatattgta    5700
cgtctcgccg aacgcaccgg cttccagtac gcgacggatg cccgagcagt gatcttcgac    5760
atacagccag tcgcggattt gctggccgtc gccatagaca ggcagcgcct taccggcgag    5820
```

```
tgcgttgacg atcatcagcg ggatcagttt ttccgggaag tggagcggcc cgtaattgtt    5880
ggagcagttg gtagtgagta ccggcatgcc gtaggtatgg aaatacgagc gtaccagatg    5940
gtcgctggct gccttgctgg cggagtatgg gctgttcggc gcgtacggcg tggtttcggt    6000
gaacgccggt tcgtttggcc ctagtgtgcc gtagacttcg tcggtagaga catggaggaa    6060
acggaaggcc tccttctctg caccttccaa actattccaa tgcgcccggg cggcttcaag    6120
caagcgaaac gtgcccatca cgttggtttc gacaaacgct tcggggccgg tgattgagcg    6180
gtctacatgg gattccgccg cgaagtgaac cacggcgcgc gggcggtgct ctgcgaacag    6240
cttggtcaga agcgcagcat cgcaaatatt gccttgcaca aagcgatgct gagggttgcc    6300
ttccagcggc tgcaggttgg ccaggttgcc tgcgtaggtc agggcgtcga ggttgaggac    6360
gggttcctca ttgtgcgcac accattgcag tacgaaattt gagccgatga agccggctcc    6420
gcctgttact agaatcataa tttggctcta attggacaaa aggtgttgtc gtagacagat    6480
gacgctgaga aacttcgccc cggcaacgca aggcgagctg ctagcgctgc cggaattaga    6540
ccaccctgat gtcgaaaaat acactgctgg gtgccggtac tgaccgtgcc gatctgctca    6600
cgctggaaga ggaggagccg ttgcagcggt ggaaggtgac ctcatggttg cctagacaca    6660
acagggagtc gtcaggtgtc catgcaagaa acagttgttt gagcgatgca actcacggag    6720
acaaatctgg gtgctgacaa gtctagaggg ccttaagcta ccgctatcct gggactctag    6780
ttcgctgggc atggcagcgc ggggtgcgca tctggaagtc gggttcgttt ccggggttg     6840 gaaagtgtca ttttatttg tcagtattcc tgaaatagga attagagtga tggcagttct    6900
tgcattcatg ttgaacaacc caacaaaaat tataatagcc tcggggctcg gcaggttaga    6960
cgtcattctt catgtttcag cggtctggcg ctcttgaata ttcataggaa agtgaaaaat    7020
gtctgttaag gaaggcttgc cgagcgtaga tgtgcagccg agcatgcatg ttaagggaaa    7080
ttcagtgccc gtcccccaga aaaagactgg ctcaaggcga tttgtgctgg atctggctta    7140
ttatcggaat cgatacccag acctatcttc gctcacggac gatgcgctcg aacagcattg    7200
gcatgcgttc ggtcatcaag aaggccgtta tgcctcggct tcgcacgaaa gtggtgatgc    7260
ggagcttatc gctgaagcag ttctcaatgc ggccgacagc gccgttatgg tcaagccgga    7320
tgttgcgaaa gttgacctac cggtaaacca gcaatagaca taagcggcta tttaacgacc    7380
ctgccctgaa ccgacgaccg ggtcgaattt gctttcgaat ttctgccatt catccgctta    7440
ttatcactta ttcaggcgta gcaccaggcg tttaagggca ccaataactg ccttaaaaaa    7500
attacgcccc gccctgccac tcatcgcagt cggcctattg gttaaaaaat gagctgattt    7560
aacaaaaatt taacgcgaat tttaacaaaa tattaacgct tacaatttcc attcgccatt    7620
caggctgcgc aactgttggg aagggcgatc ggtgcgggcc tcttcgctat tacgccagct    7680
ggcgaaaggg ggatgtgctg caaggcgatt aagttgggta acgccagggt tttcccagtc    7740
acgacgttgt aaaacgacgg ccagtgagcg cgcgtaatac gactcactat agggcgaatt    7800
ggagctccac cgcggtggcg gccgctctag agggaatgcg tttcgccgac taggccttgg    7860
ccttgccgga agctacggac gccacggccg ggccggcgag gcgcttcagc aggcgcgggc    7920
ggttggtctc cagcgcgccg ccgcgtcccc gcaggccgtc ccacaggccc agcccaggc    7980 agcgcagctt gagcagcttg tcgcgttcga gcaggagcac cgcgaggccc tgggtcaggg    8040
tcggcaggtt cgccagcagg gccagcggcg aggaccgggc gtagcggcgc aggaccagca    8100
ggccgttgcg cgccaggtag tagcggcgca gcggggcgtg gttcatcgcg ctgaggctga    8160
gaccgccgag gcggcgggtc ttgcgcgtgc cgatgcggtg ctcgaggacc agccgcgggt    8220
```

```
cgacgtacag gggcacgtcc agcgcctggg cgcgcaggct gtattcggtg tccacgtggt    8280
cgatgaacag ttcctcgtcg aagtggccga ggcgctggta ggcctcgcgg gtcagcaggc    8340
agccggagga gatcaggaac gaggtgcgct gcggggtcgt caggccgtcc agagacaatt    8400
gcctgagcgt cagtccgtcg agatggatgg ccggcaggaa gcgccggtca ccccggtcga    8460
agatccgtgg gccgagcagg caggcctgac cgttgcgcgc ctgcaggttg cgccactggg    8520
cggcgaggaa ggcgccgccg ggacgggagt cctggtcgag cagcagcaca ccctgcacgc    8580
cacgccggaa tagcgcgtcg agtccctggt tgaaggcgcc ggcgatgccc tgccggttgc    8640
cgtggtgcag cacggcgatg ccttgcccgc gcagccgggc attgcgctgc ggatcgctgt    8700
gcggtgagtt gtcgacggca aggaagcgca gttgcggaaa cgccgccgcc agttcgccaa    8760
ggtgttccag gtcgtcgtcg ccaggattga acagtaccac cagcacgccc atgtctatcc    8820
ggtccatgat cgttcttctc ccgtaggtcg aagttgccag gccaggacca gcccggccag    8880
aacgagaagg gcgccggcga ggaatggcgc gccggccagg ggcagcggcg cgagcggacc    8940
gctgccccag tggaacaggc cgctcatcag cggcggaccg acgatcgcgg cgaggctcat    9000
caggctgctc agcacgccct gcaactcgcc ctggcggtcg accggcacgc gggccgagag    9060
cagcccctgc atggccgggg tggcgaggct gccgagcgcg aagggcagca gcgcgcagac    9120
cagccagaat gacgagtcga ccagggcgaa cagcagcagg ccgcagcctt gcagggcgag    9180
gcccaggcgc agcaggcggg cgtcgtccag gcgccgcttg cagaggttca cgccgagggt    9240
ctgggcgagc accgcgagca cgccgtagag ggccagcgag tagccgatcc aggcgctgct    9300
ccagtgaaac ttctcgatca cgaagaacgg ccagaccacc atcaccgcct gcaagccgag    9360
gaataccagg gcaagcaccg ccagcaggcg tccgaccccc ggttgccgag ccaggccgct    9420
gatcgagcgc aaggcattca tccgcctcgg gtccaggcgg cggcgtcgcg tcggggggcag    9480
ggtttcctcg aggaacaggc cggcgagcag ggcgttgagc aggcacaggc cggcggccag    9540
caacagcggc agcgtcgtgc cgtgcaccgc cagcagccca ccgagggcgg ggccgaggat    9600
catgcccagg gcgaggccgg cgtacagcca gccgaagtgc cgggtgcgct gcccgtgcgt    9660
gccgaggtca gccgcgcagg ccatcgcggt ggccacgctg gcgccggtga gcccggccag    9720
cgcgcgaccg aggaacagca tccagaggct gtcggccagc gccagcagca gatagctgag    9780
ggcgaagccg agcatcgcca ggaccaggac ggggcggcgt ccgaagcggt cgctgaggct    9840
gccgaggacc ggcgaaaaga acaattgcag cagcgcgaag gtcatcacca gggcggcgcc    9900
ccaggtggcc gcgtcgcgga ccgccagcgg cgccacgctg ccgatcagcg tcggcagcag    9960
gggcacgatc aggccgacgc cagcggcatc cagcaggcag gtgaggaaca gcagaggcag   10020
gacgcgtttc gcgccgggac cgtgttcccg cgtggcggag gggcagaggc tggtcgtgga   10080
cacgccagga tcctcccggc gtcaggacgc agccttcagc catcgcgcat ccccctccct   10140
atgacaacgt tcgaccacct gggccgcttt accgcaagcg atactgtgcg gttgtgacaa   10200
ttccatgaaa cgccgacagg ccgccgccat ggccgggtcc tcgagcaagc gccacagcgc   10260
cccgcgcaac tcctgctcgc gcaatggcac gcccaggcgc atcccgcagc cgagccggac   10320
cagccgttcg gcattgtcga actggtcgtg ggcgcagggc agcagcacct gcggcacccc   10380
cgccgccaag gccaggctca tggcgccgat accgcccgga tggaccagcc ggcgcacga   10440
tggcagcaag gctcccagtg gcgcgtaggc gcgctgcagc acgtggttcg gcaagccgcg   10500
cagcggttcc tggccggcgc cggtgaggaa gatcccacgc gcgccgaggc gttccagcgc   10560
```

```
gcgcagggcc atggcgtaga agtcgccctg caggtgttcg gtcgagccct gggtgaacac   10620
cagcggccgg ctgccctgat cgagaaagcg ttgcagttcg tcgtcgagcg gggtccccgg   10680
gatactgccg tcgaacagcg ggaagccggt catgtgcagg ggttgcggcc aatcctgctg   10740
gggcggcgcg aaccaggccg ggaacaggca gaccacgccc tgcggcgaat gcatccattg   10800
ggtgaagatg cgcttcaccg gcgtctccag gccgaccttg cgccgcaccg cgttgatatc   10860
cggcgcgcag gtgcgatcca gcttgaagcg ctcgatgcag cgccagagca gcttgcgcat   10920
cgccagcggc atctgctcgg gcacgttgaa cttggggtgt accggcggca ggtgcgccga   10980
caacaaggtc gatggcgaga cctgcgcgga caggtaggga atcccgtact tctcgtgagc   11040
gatgcgtgcg cccagcgccc agagcgagcc gaccaccacg atgtcgtcat ggcgctgcgc   11100
cgagacgtac tcgtagaccg gctcgatcat cccggcgatg gtttgccaga gcacgccgaa   11160
ggacgtcttg gggtcccaca ggcgcggatc gcccatggtc cggcggtagg tcagttcgtc   11220
gctcagcggg acgaacgcga tgccgtgctg ctccaccgcg tcgcgaaaca ccgggatggt   11280
gcagaggctc acgcggtgcc cgcgcaattt cagggtccgg gccaggccga tgaagggaaa   11340
tacgtcgccg gccgagccga tggcgatgag gatggcgtgc atggtgctac tccgtgcgtt   11400
atgcaaccgc aaagcccggc caggccgggt cttcgcaggt caagggttca ggcgtagccg   11460
atggccatct cgtggaatcc cgccgcgcgt tccgcccgct gcggctccgg ttgcttcagc   11520
aggtgctcga gcagggcgcg gtgcacgcgt accgcggcca gcttggactc caggtcgagg   11580
aaatgcccgg tgccctccac ccgcgagaaa ctgcagtgcg gcaggtagtc gcggaactgg   11640
cgggcgtcct cggcggtggt gtattcgtcc cagctgccgt tgatgaaatg cacgtggctc   11700
tggatccgct ccaggcaagc caggtagccc cgatcgttga gcgccagcac ctggtcgatg   11760
tgaaagcgcg cctgctcgta ttcgccggtg gccagcgaag ccatgtgctg atggttgctg   11820
gctttcaggc gcggcggcag gtatttgccg acggtctcgt tgagcagatg gccgatcgcc   11880
gacttgtcgt ccagctcgat cagcgcctgc gcccgcccga cgtagtcgag catcgcctgg   11940
ttcagtccag gggcgaatgc catcaccacc gagctgcgga tgccgcgcgg attgcgcgac   12000
agcgccagca gcgtggagat accgcccag gacgcggaga ccaggtgatt gacctcgaag   12060
cgctcgatca gcgccaggag gatttccacc tcgtcgtcct tggtgatcaa cccccgctgc   12120
gggttgtgct gacgcgactg cccggcgaag ggcaggtcga acagcaccac gttgaaatgt   12180
tcggccaggc acttgcaggt ccgggcgaac gaggcggtgg tcgccatcgc gccgttgacc   12240
agcatcaccg tgctgcgccc gggatcctgc ccaacgcgct cgacatgtac ccgcaggccc   12300
ttgcaaaccg ataccaacag actttcgcgc cgcatttcac acctcccaaa aatgccagat   12360 ccccgggct gcaggaattc gatatcaagc ttatcgatac cgtcgacctc gaggggggc   12420 ccggtaccca gcttttgttc cctttagtga gggttaattg cgcgcttggc gtaatcatgg   12480
tcatagctgt ttcctgtgtg aaattgttat ccgctcacaa ttccacacaa catacgagcc   12540
ggaagcataa agtgtaaagc ctgggtgcc taatgagtga gctaactcac attaattgcg   12600
ttgcgctcac tgcccgcttt ccagtcggga aacctgtcgt gccagctgca ttaatgaatc   12660
ggccaacgcg cggggagagg cggtttgcgt attgggcgca tgcataaaaa ctgttgtaat   12720
tcattaagca ttctgccgac atggaagcca tcacaaacgg catgatgaac ctgaatcgcc   12780
agcggcatca gcaccttgtc gccttgcgta taatatttgc ccatggggt gggcgaagaa   12840 ctccagcatg agatccccgc gctggaggat catccagccg cgtcccgga aaacgattcc   12900 gaagcccaac cttttcataga aggcggcggt ggaatcgaaa tctcgtgatg gcaggttggg   12960
```

```
cgtcgcttgg tcggtcattt cgaacccag  agtcccgctc agaagaactc gtcaagaagg    13020
cgatagaagg cgatgcgctg cgaatcggga gcggcgatac cgtaaagcac gaggaagcgg    13080
tcagcccatt cgccgccaag ctcttcagca atatcacggg tagccaacgc tatgtcctga    13140
tagcggtccg ccacacccag ccggccacag tcgatgaatc cagaaaagcg ccattttcc     13200 accatgatat tcggcaagca ggcatcgcca tgggtcacga cgagatcctc gccgtcgggc    13260
atgcgcgcct tgagcctggc gaacagttcg gctggcgcga gccctgatg  ctcttcgtcc    13320 agatcatcct gatcgacaag accggcttcc atccgagtac gtgctcgctc gatgcgatgt    13380
ttcgcttggt ggtcgaatgg gcaggtagcc ggatcaagcg tatgcagccg ccgcattgca    13440
tcagccatga tggatacttt ctcggcagga gcaaggtgag atgacaggag atcctgcccc    13500
ggcacttcgc ccaatagcag ccagtccctt cccgcttcag tgacaacgtc gagcacagct    13560
gcgcaaggaa cgcccgtcgt ggccagccac gatagccgcg ctgcctcgtc ctgcagttca    13620
ttcagggcac cggacaggtc ggtcttgaca aaaagaaccg ggcgccctg  cgctgacagc    13680 cggaacacgg cggcatcaga gcagccgatt gtctgttgtg cccagtcata gccgaatagc    13740
ctctccaccc aagcggccgg agaacctgcg tgcaatccat cttgttcaat catgcgaaac    13800
gatcctcatc ctgtctcttg atcagatctt gatcccctgc gccatcagat ccttggcggc    13860
aagaaagcca tccagtttac tttgcagggc ttcccaacct taccagaggg cgccccagct    13920
ggcaattccg gttcgcttgc tgtccataaa accgccagt  ctagctatcg ccatgtaagc    13980
ccactgcaag ctacctgctt tctctttgcg cttgcgtttt cccttgtcca gatagcccag    14040
tagctgacat tcatcccagg tggcactttt cggggaaatg tgcgcgcccg cgttcctgct    14100
ggcgctgggc ctgtttctgg cgctggactt cccgctgttc cgtcagcagc ttttcgccca    14160
cggccttgat gatcgcggcg gccttggcct gcatatcccg attcaacggc ccagggcgt    14220 ccagaacggg cttcaggcgc tcccgaaggt                                     14250
```

<210> SEQ ID NO 76
<211> LENGTH: 1011
<212> TYPE: DNA
<213> ORGANISM: Burkholderia thailandensis

<400> SEQUENCE: 76

```
tctagatacg ggagaagaac gatcatgacg atcctggggg cgctggtgat tctgtacgac     60
ccgacggacg agcagttgtc ggggctggag gcgctcgcgc gcgacagcga cgcgctcgtg    120
gtcgtggaca acacgccgca cgagcacgcg gcggcgcgcg agcgggtgcg tgcgctgtcg    180
gcgcggacga acacggtgtg gcgacaccac ggcaaccggg gcggggtcgc gggcgggtac    240
aacgcggggc tgtcggtgct gttcgcgcag ggcgtcgagg cggtcgcgct gttcgaccag    300
gactcgacgg tgccggccgg gtacttcgag cggatgcgcg aggcgtgcgc gcaactgggt    360
gagcaaccgg gcgcgcacgc gggcgcgttc atcgcgggcc cgcggatcta cgacgcgaac    420
gagcagcgct tcctgccgga gctgatgacg agcggggtga cggtgcgccg cgtgcgggtg    480
gagggcgaga cggcgccgca gcgctgcgcg ttcctgatct cgtcgggcag cgtgatttcg    540
cgggccgcgt acgcgcggct cggtcgattc gacgaggcgc tgttcatcga tcacgtcgac    600
accgagtatt gcctgcgcgc gctcgcgcac aacgtgccgc tgtacgtggt gccgccgctc    660
gtgctgacgc accggatcgg cgcgcggcgc cggcacaagg tggggccgtt cgagctgacg    720
gcgatgcatc acgggtggtt gcgccgatac tacggcgcgc gcaacgcgat gcaactgggg    780
```

```
ctgcagtacg gcttgcggtt tccggtggcg ctggtgccga atctgctgac gatatggcag      840
gtgatccagg tggtgctgtg cgagcgggag aagggcgcga agctgcgcgg gatcgcgctg      900
ggcgtgctcg acggcctgtt cgggcggctg ggatcgttcg acgatgcgcg cgcgggcgcg      960
gcggcgcgcg agccggtgcg gcaggaatga tcggcgaaac gcattgagct c              1011
```

```
<210> SEQ ID NO 77
<211> LENGTH: 888
<212> TYPE: DNA
<213> ORGANISM: Pseudomonas aeruginosa
<220> FEATURE:
<221> NAME/KEY: CDS
<222> LOCATION: (1)..(888)

<400> SEQUENCE: 77
```

| | | | | | | | | | | | | | | | | |
|---|---|---|---|---|---|---|---|---|---|---|---|---|---|---|---|---|
| atg | cgg | cgc | gaa | agt | ctg | ttg | gta | tcg | gtt | tgc | aag | ggc | ctg | cgg | gta | 48 |
| Met | Arg | Arg | Glu | Ser | Leu | Leu | Val | Ser | Val | Cys | Lys | Gly | Leu | Arg | Val | |
| 1 | | | | 5 | | | | | 10 | | | | | 15 | | |

| cat | gtc | gag | cgc | gtt | ggg | cag | gat | ccc | ggg | cgc | agc | acg | gtg | atg | ctg | 96 |
|---|---|---|---|---|---|---|---|---|---|---|---|---|---|---|---|---|
| His | Val | Glu | Arg | Val | Gly | Gln | Asp | Pro | Gly | Arg | Ser | Thr | Val | Met | Leu | |
| | | | 20 | | | | | 25 | | | | | 30 | | | |

| gtc | aac | ggc | gcg | atg | gcg | acc | acc | gcc | tcg | ttc | gcc | cgg | acc | tgc | aag | 144 |
|---|---|---|---|---|---|---|---|---|---|---|---|---|---|---|---|---|
| Val | Asn | Gly | Ala | Met | Ala | Thr | Thr | Ala | Ser | Phe | Ala | Arg | Thr | Cys | Lys | |
| | | 35 | | | | | 40 | | | | | 45 | | | | |

| tgc | ctg | gcc | gaa | cat | ttc | aac | gtg | gtg | ctg | ttc | gac | ctg | ccc | ttc | gcc | 192 |
|---|---|---|---|---|---|---|---|---|---|---|---|---|---|---|---|---|
| Cys | Leu | Ala | Glu | His | Phe | Asn | Val | Val | Leu | Phe | Asp | Leu | Pro | Phe | Ala | |
| 50 | | | | | 55 | | | | | 60 | | | | | | |

| ggg | cag | tcg | cgt | cag | cac | aac | ccg | cag | cgc | ggg | ttg | atc | acc | aag | gac | 240 |
|---|---|---|---|---|---|---|---|---|---|---|---|---|---|---|---|---|
| Gly | Gln | Ser | Arg | Gln | His | Asn | Pro | Gln | Arg | Gly | Leu | Ile | Thr | Lys | Asp | |
| 65 | | | | | 70 | | | | | 75 | | | | | 80 | |

| gac | gag | gtg | gaa | atc | ctc | ctg | gcg | ctg | atc | gag | cgc | ttc | gag | gtc | aat | 288 |
|---|---|---|---|---|---|---|---|---|---|---|---|---|---|---|---|---|
| Asp | Glu | Val | Glu | Ile | Leu | Leu | Ala | Leu | Ile | Glu | Arg | Phe | Glu | Val | Asn | |
| | | | | 85 | | | | | 90 | | | | | 95 | | |

| cac | ctg | gtc | tcc | gcg | tcg | tgg | ggc | ggt | atc | tcc | acg | ctg | ctg | gcg | ctg | 336 |
|---|---|---|---|---|---|---|---|---|---|---|---|---|---|---|---|---|
| His | Leu | Val | Ser | Ala | Ser | Trp | Gly | Gly | Ile | Ser | Thr | Leu | Leu | Ala | Leu | |
| | | | 100 | | | | | 105 | | | | | 110 | | | |

| tcg | cgc | aat | ccg | cgc | ggc | atc | cgc | agc | tcg | gtg | gtg | atg | gca | ttc | gcc | 384 |
|---|---|---|---|---|---|---|---|---|---|---|---|---|---|---|---|---|
| Ser | Arg | Asn | Pro | Arg | Gly | Ile | Arg | Ser | Ser | Val | Val | Met | Ala | Phe | Ala | |
| | | 115 | | | | | 120 | | | | | 125 | | | | |

| cct | gga | ctg | aac | cag | gcg | atg | ctc | gac | tac | gtc | ggg | cgg | gcg | cag | gcg | 432 |
|---|---|---|---|---|---|---|---|---|---|---|---|---|---|---|---|---|
| Pro | Gly | Leu | Asn | Gln | Ala | Met | Leu | Asp | Tyr | Val | Gly | Arg | Ala | Gln | Ala | |
| | 130 | | | | | 135 | | | | | 140 | | | | | |

| ctg | atc | gag | ctg | gac | gac | aag | tcg | gcg | atc | ggc | cat | ctg | ctc | aac | gag | 480 |
|---|---|---|---|---|---|---|---|---|---|---|---|---|---|---|---|---|
| Leu | Ile | Glu | Leu | Asp | Asp | Lys | Ser | Ala | Ile | Gly | His | Leu | Leu | Asn | Glu | |
| 145 | | | | | 150 | | | | | 155 | | | | | 160 | |

| acc | gtc | ggc | aaa | tac | ctg | ccg | ccg | cgc | ctg | aaa | gcc | agc | aac | cat | cag | 528 |
|---|---|---|---|---|---|---|---|---|---|---|---|---|---|---|---|---|
| Thr | Val | Gly | Lys | Tyr | Leu | Pro | Pro | Arg | Leu | Lys | Ala | Ser | Asn | His | Gln | |
| | | | | 165 | | | | | 170 | | | | | 175 | | |

| cac | atg | gct | tcg | ctg | gcc | acc | ggc | gaa | tac | gag | cag | gcg | cgc | ttt | cac | 576 |
|---|---|---|---|---|---|---|---|---|---|---|---|---|---|---|---|---|
| His | Met | Ala | Ser | Leu | Ala | Thr | Gly | Glu | Tyr | Glu | Gln | Ala | Arg | Phe | His | |
| | | | 180 | | | | | 185 | | | | | 190 | | | |

| atc | gac | cag | gtg | ctg | gcg | ctc | aac | gat | cgg | ggc | tac | ctg | gct | tgc | ctg | 624 |
|---|---|---|---|---|---|---|---|---|---|---|---|---|---|---|---|---|
| Ile | Asp | Gln | Val | Leu | Ala | Leu | Asn | Asp | Arg | Gly | Tyr | Leu | Ala | Cys | Leu | |
| | | 195 | | | | | 200 | | | | | 205 | | | | |

| gag | cgg | atc | cag | agc | cac | gtg | cat | ttc | atc | aac | ggc | agc | tgg | gac | gaa | 672 |
|---|---|---|---|---|---|---|---|---|---|---|---|---|---|---|---|---|
| Glu | Arg | Ile | Gln | Ser | His | Val | His | Phe | Ile | Asn | Gly | Ser | Trp | Asp | Glu | |
| | 210 | | | | | 215 | | | | | 220 | | | | | |

| tac | acc | acc | gcc | gag | gac | gcc | cgc | cag | ttc | cgc | gac | tac | ctg | ccg | cac | 720 |
|---|---|---|---|---|---|---|---|---|---|---|---|---|---|---|---|---|
| Tyr | Thr | Thr | Ala | Glu | Asp | Ala | Arg | Gln | Phe | Arg | Asp | Tyr | Leu | Pro | His | |
| 225 | | | | | 230 | | | | | 235 | | | | | 240 | |

```
tgc agt ttc tcg cgg gtg gag ggc acc ggg cat ttc ctc gac ctg gag    768
Cys Ser Phe Ser Arg Val Glu Gly Thr Gly His Phe Leu Asp Leu Glu
            245                 250                 255 tcc aag ctg gcc gcg gta cgc gtg cac cgc gcc ctg ctc gag cac ctg    816
Ser Lys Leu Ala Ala Val Arg Val His Arg Ala Leu Leu Glu His Leu
        260                 265                 270 ctg aag caa ccg gag ccg cag cgg gcg gaa cgc gcg gcg gga ttc cac    864
Leu Lys Gln Pro Glu Pro Gln Arg Ala Glu Arg Ala Ala Gly Phe His
    275                 280                 285 gag atg gcc atc ggc tac gcc tga                                    888
Glu Met Ala Ile Gly Tyr Ala
290                 295

<210> SEQ ID NO 78
<211> LENGTH: 295
<212> TYPE: PRT
<213> ORGANISM: Pseudomonas aeruginosa

<400> SEQUENCE: 78

Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295
```

<210> SEQ ID NO 79
<211> LENGTH: 888
<212> TYPE: DNA
<213> ORGANISM: Pseudomonas aeruginosa
<220> FEATURE:
<221> NAME/KEY: CDS
<222> LOCATION: (1)..(888)

<400> SEQUENCE: 79

| | | | | | | | | | | | | | | | | |
|---|---|---|---|---|---|---|---|---|---|---|---|---|---|---|---|---|
| atg | cgg | cgc | gaa | agt | ctg | ttg | gta | tcg | gtt | tgc | aag | ggc | ctg | cgg | gta | 48 |
| Met | Arg | Arg | Glu | Ser | Leu | Leu | Val | Ser | Val | Cys | Lys | Gly | Leu | Arg | Val | |
| 1 | | | | 5 | | | | | 10 | | | | | 15 | | |
| cat | gtc | gag | cgc | gtt | ggg | cag | gat | ccc | ggg | cgc | agc | acg | gtg | atg | ctg | 96 |
| His | Val | Glu | Arg | Val | Gly | Gln | Asp | Pro | Gly | Arg | Ser | Thr | Val | Met | Leu | |
| | | | 20 | | | | | 25 | | | | | 30 | | | |
| gtc | aac | ggc | gcg | atg | gcg | acc | acc | gcc | tcg | ttc | gcc | cgg | acc | tgc | aag | 144 |
| Val | Asn | Gly | Ala | Met | Ala | Thr | Thr | Ala | Ser | Phe | Ala | Arg | Thr | Cys | Lys | |
| | | 35 | | | | | 40 | | | | | 45 | | | | |
| tgc | ctg | gcc | gaa | cat | ttc | aac | gtg | gtg | ctg | ttc | gac | ctg | ccc | ttc | gcc | 192 |
| Cys | Leu | Ala | Glu | His | Phe | Asn | Val | Val | Leu | Phe | Asp | Leu | Pro | Phe | Ala | |
| 50 | | | | | 55 | | | | | 60 | | | | | | |
| ggg | cag | tcg | cgt | cag | cac | aac | ccg | cag | cgc | ggg | ttg | atc | acc | aag | gac | 240 |
| Gly | Gln | Ser | Arg | Gln | His | Asn | Pro | Gln | Arg | Gly | Leu | Ile | Thr | Lys | Asp | |
| 65 | | | | | 70 | | | | | 75 | | | | | 80 | |
| gac | gag | gtg | gaa | atc | ctc | ctg | gcg | ctg | atc | gag | cgc | ttc | gag | gtc | aat | 288 |
| Asp | Glu | Val | Glu | Ile | Leu | Leu | Ala | Leu | Ile | Glu | Arg | Phe | Glu | Val | Asn | |
| | | | | 85 | | | | | 90 | | | | | 95 | | |
| cac | ctg | gtc | tcc | gcg | tcc | tgg | ggc | ggt | atc | tcc | acg | ctg | ctg | gcg | ctg | 336 |
| His | Leu | Val | Ser | Ala | Ser | Trp | Gly | Gly | Ile | Ser | Thr | Leu | Leu | Ala | Leu | |
| | | | 100 | | | | | 105 | | | | | 110 | | | |
| tcg | cgc | aat | ccg | cgc | ggc | atc | cgc | agc | tcg | gtg | gtg | atg | gca | ttc | gcc | 384 |
| Ser | Arg | Asn | Pro | Arg | Gly | Ile | Arg | Ser | Ser | Val | Val | Met | Ala | Phe | Ala | |
| | | 115 | | | | | 120 | | | | | 125 | | | | |
| cct | gga | ctg | aac | cag | gcg | atg | ctc | gac | tac | gtc | ggg | cgg | gcg | cag | gcg | 432 |
| Pro | Gly | Leu | Asn | Gln | Ala | Met | Leu | Asp | Tyr | Val | Gly | Arg | Ala | Gln | Ala | |
| 130 | | | | | 135 | | | | | 140 | | | | | | |
| ctg | atc | gag | ctg | gac | gac | aag | tcg | gcg | atc | ggc | cat | ctg | ctc | aac | gag | 480 |
| Leu | Ile | Glu | Leu | Asp | Asp | Lys | Ser | Ala | Ile | Gly | His | Leu | Leu | Asn | Glu | |
| 145 | | | | | 150 | | | | | 155 | | | | | 160 | |
| acc | gtc | ggc | aaa | tac | ctg | ccg | cag | cgc | ctg | aaa | gcc | agc | aac | cat | cag | 528 |
| Thr | Val | Gly | Lys | Tyr | Leu | Pro | Gln | Arg | Leu | Lys | Ala | Ser | Asn | His | Gln | |
| | | | | 165 | | | | | 170 | | | | | 175 | | |
| cac | atg | gct | tcg | ctg | gcc | acc | ggc | gaa | tac | gag | cag | gcg | cgc | ttt | cac | 576 |
| His | Met | Ala | Ser | Leu | Ala | Thr | Gly | Glu | Tyr | Glu | Gln | Ala | Arg | Phe | His | |
| | | | 180 | | | | | 185 | | | | | 190 | | | |
| atc | gac | cag | gtg | ctg | gcg | ctc | aac | gat | cgg | ggc | tac | ttg | gct | tgc | ctg | 624 |
| Ile | Asp | Gln | Val | Leu | Ala | Leu | Asn | Asp | Arg | Gly | Tyr | Leu | Ala | Cys | Leu | |
| | | 195 | | | | | 200 | | | | | 205 | | | | |
| gag | cgg | atc | cag | agc | cac | gtg | cat | ttc | atc | aac | ggc | agc | tgg | gac | gaa | 672 |
| Glu | Arg | Ile | Gln | Ser | His | Val | His | Phe | Ile | Asn | Gly | Ser | Trp | Asp | Glu | |
| 210 | | | | | 215 | | | | | 220 | | | | | | |
| tac | acc | acc | gcc | gag | gac | gcc | cgc | cag | ttc | cgc | gac | tac | ctg | ccg | cac | 720 |
| Tyr | Thr | Thr | Ala | Glu | Asp | Ala | Arg | Gln | Phe | Arg | Asp | Tyr | Leu | Pro | His | |
| 225 | | | | | 230 | | | | | 235 | | | | | 240 | |
| tgc | agt | ttc | tcg | cgg | gtg | gag | ggc | acc | ggg | cat | ttc | ctc | gac | ctg | gag | 768 |
| Cys | Ser | Phe | Ser | Arg | Val | Glu | Gly | Thr | Gly | His | Phe | Leu | Asp | Leu | Glu | |
| | | | | 245 | | | | | 250 | | | | | 255 | | |
| tcc | aag | ctg | gca | gcg | gta | cgc | gtg | cac | cgc | gcc | ctg | ctc | gag | cac | ctg | 816 |
| Ser | Lys | Leu | Ala | Ala | Val | Arg | Val | His | Arg | Ala | Leu | Leu | Glu | His | Leu | |

```
                   260                 265                 270
ctg aag caa ccg gag ccg cag cgg gcg gaa cgc gcg gcg gga ttc cac        864
Leu Lys Gln Pro Glu Pro Gln Arg Ala Glu Arg Ala Ala Gly Phe His
        275                 280                 285 gag atg gcc atc ggc tac gcc tga                                        888
Glu Met Ala Ile Gly Tyr Ala
    290                 295

<210> SEQ ID NO 80
<211> LENGTH: 295
<212> TYPE: PRT
<213> ORGANISM: Pseudomonas aeruginosa

<400> SEQUENCE: 80

Met Arg Arg Glu Ser Leu Leu Val Ser Val Cys Lys Gly Leu Arg Val
1               5                   10                  15

His Val Glu Arg Val Gly Gln Asp Pro Gly Arg Ser Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Glu Val Asn
                85                  90                  95

His Leu Val Ser Ala Ser Trp Gly Gly Ile Ser Thr Leu Leu Ala Leu
            100                 105                 110

Ser Arg Asn Pro Arg Gly Ile Arg Ser Ser Val Val Met Ala Phe Ala
        115                 120                 125

Pro Gly Leu Asn Gln Ala Met Leu Asp Tyr Val Gly Arg Ala Gln Ala
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Gln Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ala Cys Leu
        195                 200                 205

Glu Arg Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Val Arg Val His Arg Ala Leu Leu Glu His Leu
            260                 265                 270

Leu Lys Gln Pro Glu Pro Gln Arg Ala Glu Arg Ala Ala Gly Phe His
        275                 280                 285

Glu Met Ala Ile Gly Tyr Ala
    290                 295

<210> SEQ ID NO 81
<211> LENGTH: 888
<212> TYPE: DNA
```

```
<213> ORGANISM: Pseudomonas aeruginosa
<220> FEATURE:
<221> NAME/KEY: CDS
<222> LOCATION: (1)..(888)

<400> SEQUENCE: 81 atg cgg cgc gaa agt ctg ttg gta acg gta tgc aag ggc ctg cgg gta      48
Met Arg Arg Glu Ser Leu Leu Val Thr Val Cys Lys Gly Leu Arg Val
1               5                   10                  15 cat gtc gag cgc gtg ggg cag gat ccc ggg cgc gac acg gtg atg ctg      96
His Val Glu Arg Val Gly Gln Asp Pro Gly Arg Asp Thr Val Met Leu
            20                  25                  30 gtc aac ggc gcg atg gcg acc acc gcc tcg ttc gcc cgg acc tgc aag     144
Val Asn Gly Ala Met Ala Thr Thr Ala Ser Phe Ala Arg Thr Cys Lys
        35                  40                  45 tgc ctg gcc gaa cat ttc aac gtg gtg ctg ttc gac ctg ccc ttc gcc     192
Cys Leu Ala Glu His Phe Asn Val Val Leu Phe Asp Leu Pro Phe Ala
50                  55                  60 ggg cag tcg cgg cag cac aat ccg cag cgc ggg ttg atc acc aag gac     240
Gly Gln Ser Arg Gln His Asn Pro Gln Arg Gly Leu Ile Thr Lys Asp
65                  70                  75                  80 gac gag gtg gag att ctc ctg gcg ctg atc gag cgc ttc gct gtc aac     288
Asp Glu Val Glu Ile Leu Leu Ala Leu Ile Glu Arg Phe Ala Val Asn
                85                  90                  95 cac ctg gtc tcg gcc tcc tgg ggc ggc atc tcc acg ctg ctg gcg ctg     336
His Leu Val Ser Ala Ser Trp Gly Gly Ile Ser Thr Leu Leu Ala Leu
            100                 105                 110 tcg cgc aac ccg cgc ggg gtc cgc agc tcg gtg gtg atg gcg ttc gcg     384
Ser Arg Asn Pro Arg Gly Val Arg Ser Ser Val Val Met Ala Phe Ala
        115                 120                 125 ccg ggg ctg aac cag gcg atg ctc gat tat gtc ggg cgg gcc cag gaa     432
Pro Gly Leu Asn Gln Ala Met Leu Asp Tyr Val Gly Arg Ala Gln Glu
130                 135                 140 ctg atc gaa ctg gac gac aag tcg gcg atc ggc cac ctg ctc aac gag     480
Leu Ile Glu Leu Asp Asp Lys Ser Ala Ile Gly His Leu Leu Asn Glu
145                 150                 155                 160 acc gtc ggc aag tac ctg ccg ccg cgg ctg aag gcc agc aac cat cag     528
Thr Val Gly Lys Tyr Leu Pro Pro Arg Leu Lys Ala Ser Asn His Gln
                165                 170                 175 cac atg gcc tcc ctg gcc act ggc gag tac gag cag gcg cgt ttc cac     576
His Met Ala Ser Leu Ala Thr Gly Glu Tyr Glu Gln Ala Arg Phe His
            180                 185                 190 atc gac cag gtg ctg gcg ctc aat gac cgt ggc tac ctg agc tgc ctg     624
Ile Asp Gln Val Leu Ala Leu Asn Asp Arg Gly Tyr Leu Ser Cys Leu
        195                 200                 205 ggg cag atc cag agt cac gtg cat ttc atc aac ggc agc tgg gac gag     672
Gly Gln Ile Gln Ser His Val His Phe Ile Asn Gly Ser Trp Asp Glu
210                 215                 220 tac acc acc gcc gag gac gcc cgc cag ttc cgc gat tac ctg ccg cat     720
Tyr Thr Thr Ala Glu Asp Ala Arg Gln Phe Arg Asp Tyr Leu Pro His
225                 230                 235                 240 tgc agt ttt tcg cgg gtg gaa ggc acc ggg cac ttc ctc gac ctg gag     768
Cys Ser Phe Ser Arg Val Glu Gly Thr Gly His Phe Leu Asp Leu Glu
                245                 250                 255 tcc aag ctg gcg gcg gcg cgt gtg cac cgg gcg ttg ctc gag cac ctg     816
Ser Lys Leu Ala Ala Ala Arg Val His Arg Ala Leu Leu Glu His Leu
            260                 265                 270 ctg gcg caa ccg gaa ccg tgg cgc tcc gag cag gcg gcg gga ttc cac     864
Leu Ala Gln Pro Glu Pro Trp Arg Ser Glu Gln Ala Ala Gly Phe His
        275                 280                 285
```

```
gag atg gcc atc ggc tac gcc tga                                              888
Glu Met Ala Ile Gly Tyr Ala
    290             295

<210> SEQ ID NO 82
<211> LENGTH: 295
<212> TYPE: PRT
<213> ORGANISM: Pseudomonas aeruginosa

<400> SEQUENCE: 82

Met Arg Arg Glu Ser Leu Leu Val Thr Val Cys Lys Gly Leu Arg Val
1               5                   10                  15

His Val Glu Arg Val Gly Gln Asp Pro Gly Arg Asp Thr Val Met Leu
            20                  25                  30

Val Asn Gly Ala Met Ala Thr Thr Ala Ser Phe Ala Arg Thr Cys Lys
        35                  40                  45

Cys Leu Ala Glu His Phe Asn Val Val Leu Phe Asp Leu Pro Phe Ala
    50                  55                  60

Gly Gln Ser Arg Gln His Asn Pro Gln Arg Gly Leu Ile Thr Lys Asp
65                  70                  75                  80

Asp Glu Val Glu Ile Leu Leu Ala Leu Ile Glu Arg Phe Ala Val Asn
                85                  90                  95

His Leu Val Ser Ala Ser Trp Gly Gly Ile Ser Thr Leu Leu Ala Leu
            100                 105                 110

Ser Arg Asn Pro Arg Gly Val Arg Ser Ser Val Val Met Ala Phe Ala
        115                 120                 125

Pro Gly Leu Asn Gln Ala Met Leu Asp Tyr Val Gly Arg Ala Gln Glu
    130                 135                 140

Leu Ile Glu Leu Asp Asp Lys Ser Ala Ile Gly His Leu Leu Asn Glu
145                 150                 155                 160

Thr Val Gly Lys Tyr Leu Pro Pro Arg Leu Lys Ala Ser Asn His Gln
                165                 170                 175

His Met Ala Ser Leu Ala Thr Gly Glu Tyr Glu Gln Ala Arg Phe His
            180                 185                 190

Ile Asp Gln Val Leu Ala Leu Asn Asp Arg Gly Tyr Leu Ser Cys Leu
        195                 200                 205

Gly Gln Ile Gln Ser His Val His Phe Ile Asn Gly Ser Trp Asp Glu
    210                 215                 220

Tyr Thr Thr Ala Glu Asp Ala Arg Gln Phe Arg Asp Tyr Leu Pro His
225                 230                 235                 240

Cys Ser Phe Ser Arg Val Glu Gly Thr Gly His Phe Leu Asp Leu Glu
                245                 250                 255

Ser Lys Leu Ala Ala Ala Arg Val His Arg Ala Leu Leu Glu His Leu
            260                 265                 270

Leu Ala Gln Pro Glu Pro Trp Arg Ser Glu Gln Ala Ala Gly Phe His
        275                 280                 285

Glu Met Ala Ile Gly Tyr Ala
    290             295

<210> SEQ ID NO 83
<211> LENGTH: 1281
<212> TYPE: DNA
<213> ORGANISM: Pseudomonas aeruginosa
<220> FEATURE:
<221> NAME/KEY: CDS
<222> LOCATION: (1)..(1281)

<400> SEQUENCE: 83
```

-continued

```
atg cac gcc att ctc atc gcc atc ggt tcg gcc ggc gac gtg ttc ccc     48
Met His Ala Ile Leu Ile Ala Ile Gly Ser Ala Gly Asp Val Phe Pro
1               5                   10                  15 ttc atc ggc ctg gcc cgc acc ctg aag ttg cgc ggc cac cgc gtc agc     96
Phe Ile Gly Leu Ala Arg Thr Leu Lys Leu Arg Gly His Arg Val Ser
            20                  25                  30 ctg tgc acc att ccg gtg ttt cgc gcc gcg gtg gag cag cac ggc atc    144
Leu Cys Thr Ile Pro Val Phe Arg Ala Ala Val Glu Gln His Gly Ile
        35                  40                  45 gag ttc gtc ccg ctc agc gac gaa ctg acc tac cgc cgg acc atg ggc    192
Glu Phe Val Pro Leu Ser Asp Glu Leu Thr Tyr Arg Arg Thr Met Gly
    50                  55                  60 gac ccg cgc ctg tgg gat ccg aag acc tcg ttc gga gtg ctc tgg cag    240
Asp Pro Arg Leu Trp Asp Pro Lys Thr Ser Phe Gly Val Leu Trp Gln
65                  70                  75                  80 gcc atc gcc ggg atg atc gag ccg gtc tac gag tac gtc tgc gca cag    288
Ala Ile Ala Gly Met Ile Glu Pro Val Tyr Glu Tyr Val Cys Ala Gln
                85                  90                  95 cgc cac gac gac atc gtg gtg gtc ggt tcg ctg tgg gcc ctg ggc gcg    336
Arg His Asp Asp Ile Val Val Val Gly Ser Leu Trp Ala Leu Gly Ala
            100                 105                 110 cgg atc gcc cat gag aaa tac ggg att ccc tac ctg tcg gtg cag gtc    384
Arg Ile Ala His Glu Lys Tyr Gly Ile Pro Tyr Leu Ser Val Gln Val
        115                 120                 125 tcg ccg tcg acc ctg ctg tcg gcg cac ctg ccg ccg gtc cac ccc agg    432
Ser Pro Ser Thr Leu Leu Ser Ala His Leu Pro Pro Val His Pro Arg
    130                 135                 140 ttc aac gtg ccc gag cag gtc ccg ctg gcg atg cgc aag ttg ctc tgg    480
Phe Asn Val Pro Glu Gln Val Pro Leu Ala Met Arg Lys Leu Leu Trp
145                 150                 155                 160 cgc tgc atc gaa cgc ttc aag ctg gac cgc acc tgc gcc ccg gag atc    528
Arg Cys Ile Glu Arg Phe Lys Leu Asp Arg Thr Cys Ala Pro Glu Ile
                165                 170                 175 aac gcg gtg cgc cgc aag gtc ggc ctg gtc ggc ccg gcg aag cgc atc    576
Asn Ala Val Arg Arg Lys Val Gly Leu Val Gly Pro Ala Lys Arg Ile
            180                 185                 190 ttc acc cag tgg atg cat tcg cca cag gga gtg ctc tgc ctg ttc ccg    624
Phe Thr Gln Trp Met His Ser Pro Gln Gly Val Leu Cys Leu Phe Pro
        195                 200                 205 gcc tgg ttc gca ccg ccc cag cag gac tgg ccg caa ccg ctg cac atg    672
Ala Trp Phe Ala Pro Pro Gln Gln Asp Trp Pro Gln Pro Leu His Met
    210                 215                 220 acc ggc ttc ccg ctg ttc gac ggc agc gtc ccg ggg acc cgc ctc gac    720
Thr Gly Phe Pro Leu Phe Asp Gly Ser Val Pro Gly Thr Arg Leu Asp
225                 230                 235                 240 gac gag ttg cag cgc ttc ctc gag cag ggc agt cgg ccg ctg gtg ttc    768
Asp Glu Leu Gln Arg Phe Leu Glu Gln Gly Ser Arg Pro Leu Val Phe
                245                 250                 255 acc cag ggt tcg acc gag cac ctg cag gga gac ttc tat gcc atg gcc    816
Thr Gln Gly Ser Thr Glu His Leu Gln Gly Asp Phe Tyr Ala Met Ala
            260                 265                 270 ttg cgc gcg ctg gag cgt ctc ggc gcc cgc ggc atc ttc ctc acc ggc    864
Leu Arg Ala Leu Glu Arg Leu Gly Ala Arg Gly Ile Phe Leu Thr Gly
        275                 280                 285 gcc ggc cag gag ccg ctg cgt ggc ttg ccg agc cac gtg ctg caa cgc    912
Ala Gly Gln Glu Pro Leu Arg Gly Leu Pro Ser His Val Leu Gln Arg
    290                 295                 300 tcg tac gtg ccg ttg ggg gcc ttg ctg ccg gcg tgc gcc ggg ctg gtc    960
Ser Tyr Val Pro Leu Gly Ala Leu Leu Pro Ala Cys Ala Gly Leu Val
```

```
305                 310                 315                 320
cac ccg gcc ggc atc ggc gcc atg agc ctg gcg ctg gcg gcg ggg gtg       1008
His Pro Ala Gly Ile Gly Ala Met Ser Leu Ala Leu Ala Ala Gly Val
            325                 330                 335 ccg cag gtg ctg ctg cct tgc gcc cac gac cag ttc gac aac gcc gaa       1056
Pro Gln Val Leu Leu Pro Cys Ala His Asp Gln Phe Asp Asn Ala Glu
            340                 345                 350 cgc ctg gtc cgc ctc ggc tgc ggt atc cgc ctg ggc ctg ccg cta cgc       1104
Arg Leu Val Arg Leu Gly Cys Gly Ile Arg Leu Gly Leu Pro Leu Arg
            355                 360                 365 gag cag gcg ctg cgc gag tcg ctc tgg cgg ctg ctc gag gac ccg gcg       1152
Glu Gln Ala Leu Arg Glu Ser Leu Trp Arg Leu Leu Glu Asp Pro Ala
        370                 375                 380 ctg gcg gcg gcc tgt cgg cgt ttc atg gaa ttg tca caa ccg cac agt       1200
Leu Ala Ala Ala Cys Arg Arg Phe Met Glu Leu Ser Gln Pro His Ser
385                 390                 395                 400 atc gct tgc ggt aaa gcg gcc caa gtg gtc gaa cgt tgt cat agg gag       1248
Ile Ala Cys Gly Lys Ala Ala Gln Val Val Glu Arg Cys His Arg Glu
                405                 410                 415 ggg gat gtg cga tgg ctg aaa gcc gcg tcc tga                           1281
Gly Asp Val Arg Trp Leu Lys Ala Ala Ser
                420                 425

<210> SEQ ID NO 84
<211> LENGTH: 426
<212> TYPE: PRT
<213> ORGANISM: Pseudomonas aeruginosa

<400> SEQUENCE: 84

Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
                20                  25                  30

Leu Cys Thr Ile Pro Val Phe Arg Ala Ala Val Glu Gln His Gly Ile
            35                  40                  45

Glu Phe Val Pro Leu Ser Asp Glu Leu Thr Tyr Arg Arg Thr Met Gly
        50                  55                  60

Asp Pro Arg Leu Trp Asp Pro Lys Thr Ser Phe Gly Val Leu Trp Gln
65                  70                  75                  80

Ala Ile Ala Gly Met Ile Glu Pro Val Tyr Glu Tyr Val Cys Ala Gln
                85                  90                  95

Arg His Asp Asp Ile Val Val Gly Ser Leu Trp Ala Leu Gly Ala
                100                 105                 110

Arg Ile Ala His Glu Lys Tyr Gly Ile Pro Tyr Leu Ser Val Gln Val
            115                 120                 125

Ser Pro Ser Thr Leu Leu Ser Ala His Leu Pro Val His Pro Arg
        130                 135                 140

Phe Asn Val Pro Glu Gln Val Pro Leu Ala Met Arg Lys Leu Leu Trp
145                 150                 155                 160

Arg Cys Ile Glu Arg Phe Lys Leu Asp Arg Thr Cys Ala Pro Glu Ile
                165                 170                 175

Asn Ala Val Arg Arg Lys Val Gly Leu Val Gly Pro Ala Lys Arg Ile
            180                 185                 190

Phe Thr Gln Trp Met His Ser Pro Gln Gly Val Leu Cys Leu Phe Pro
        195                 200                 205

Ala Trp Phe Ala Pro Pro Gln Gln Asp Trp Pro Gln Pro Leu His Met
    210                 215                 220
```

-continued

```
Thr Gly Phe Pro Leu Phe Asp Gly Ser Val Pro Thr Arg Leu Asp
225                 230                 235                 240

Asp Glu Leu Gln Arg Phe Leu Glu Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Gly Ala Arg Gly Ile Phe Leu Thr Gly
        275                 280                 285

Ala Gly Gln Glu Pro Leu Arg Gly Leu Pro Ser His Val Leu Gln Arg
    290                 295                 300

Ser Tyr Val Pro Leu Gly Ala Leu Leu Pro Ala Cys Ala Gly Leu Val
305                 310                 315                 320

His Pro Ala Gly Ile Gly Ala Met Ser Leu Ala Leu Ala Gly Val
                325                 330                 335

Pro Gln Val Leu Leu Pro Cys Ala His Asp Gln Phe Asp Asn Ala Glu
                340                 345                 350

Arg Leu Val Arg Leu Gly Cys Gly Ile Arg Leu Gly Leu Pro Leu Arg
            355                 360                 365

Glu Gln Ala Leu Arg Glu Ser Leu Trp Arg Leu Leu Glu Asp Pro Ala
        370                 375                 380

Leu Ala Ala Ala Cys Arg Arg Phe Met Glu Leu Ser Gln Pro His Ser
385                 390                 395                 400

Ile Ala Cys Gly Lys Ala Ala Gln Val Val Glu Arg Cys His Arg Glu
                405                 410                 415

Gly Asp Val Arg Trp Leu Lys Ala Ala Ser
                420                 425
```

<210> SEQ ID NO 85
<211> LENGTH: 1281
<212> TYPE: DNA
<213> ORGANISM: Pseudomonas aeruginosa
<220> FEATURE:
<221> NAME/KEY: CDS
<222> LOCATION: (1)..(1281)

<400> SEQUENCE: 85

```
atg cac gcc atc ctc atc gcc atc ggc tcg gcc ggc gac gta ttt ccc     48
Met His Ala Ile Leu Ile Ala Ile Gly Ser Ala Gly Asp Val Phe Pro
1               5                   10                  15 ttc atc ggc ctg gcc cgg acc ctg aaa ctg cgc ggg cac cgc gtg agc     96
Phe Ile Gly Leu Ala Arg Thr Leu Lys Leu Arg Gly His Arg Val Ser
                20                  25                  30 ctc tgc acc atc ccg gtg ttt cgc gac gcg gtg gag cag cac ggc atc    144
Leu Cys Thr Ile Pro Val Phe Arg Asp Ala Val Glu Gln His Gly Ile
            35                  40                  45 gcg ttc gtc ccg ctg agc gac gaa ctg acc tac cgc cgg acc atg ggc    192
Ala Phe Val Pro Leu Ser Asp Glu Leu Thr Tyr Arg Arg Thr Met Gly
        50                  55                  60 gat ccg cgc ctg tgg gac ccc aag acg tcc ttc ggc gtg ctc tgg caa    240
Asp Pro Arg Leu Trp Asp Pro Lys Thr Ser Phe Gly Val Leu Trp Gln
65                  70                  75                  80 gcc atc gcc ggg atg atc gag ccg gtc tac gag tac gtc tcg gcg cag    288
Ala Ile Ala Gly Met Ile Glu Pro Val Tyr Glu Tyr Val Ser Ala Gln
                85                  90                  95 cgc cat gac gac atc gtg gtg gtc ggc tcg cta tgg gcg ctg ggc gca    336
Arg His Asp Asp Ile Val Val Val Gly Ser Leu Trp Ala Leu Gly Ala
                100                 105                 110
```

| | | |
|---|---|---|
| cgc atc gct cac gag aag tac ggg att ccc tac ctg tcc gcg cag gtc<br>Arg Ile Ala His Glu Lys Tyr Gly Ile Pro Tyr Leu Ser Ala Gln Val<br>115                         120                 125 | 384 |
| tcg cca tcg acc ctg ttg tcg gcg cac ctg ccg ccg gta cac ccc aag<br>Ser Pro Ser Thr Leu Leu Ser Ala His Leu Pro Pro Val His Pro Lys<br>    130                     135                 140 | 432 |
| ttc aac gtg ccc gag cag atg ccg ctg gcg atg cgc aag ctg ctc tgg<br>Phe Asn Val Pro Glu Gln Met Pro Leu Ala Met Arg Lys Leu Leu Trp<br>145                         150                 155                 160 | 480 |
| cgc tgc atc gag cgc ttc aag ctg gat cgc acc tgc gcg ccg gag atc<br>Arg Cys Ile Glu Arg Phe Lys Leu Asp Arg Thr Cys Ala Pro Glu Ile<br>                 165                 170                 175 | 528 |
| aac gcg gtg cgc cgc aag gtc ggc ctg gaa acg ccg gtg aag cgc atc<br>Asn Ala Val Arg Arg Lys Val Gly Leu Glu Thr Pro Val Lys Arg Ile<br>               180                     185                 190 | 576 |
| ttc acc caa tgg atg cat tcg ccg cag ggc gtg gtc tgc ctg ttc ccg<br>Phe Thr Gln Trp Met His Ser Pro Gln Gly Val Val Cys Leu Phe Pro<br>             195                    200                205 | 624 |
| gcc tgg ttc gcg ccg ccc cag cag gat tgg ccg caa ccc ctg cac atg<br>Ala Trp Phe Ala Pro Pro Gln Gln Asp Trp Pro Gln Pro Leu His Met<br>210                         215                    220 | 672 |
| acc ggc ttc ccg ctg ttc gac ggc agt atc ccg ggg acc ccg ctc gac<br>Thr Gly Phe Pro Leu Phe Asp Gly Ser Ile Pro Gly Thr Pro Leu Asp<br>225                         230                 235                 240 | 720 |
| gac gaa ctg caa cgc ttt ctc gat cag ggc agc cgg ccg ctg gtg ttc<br>Asp Glu Leu Gln Arg Phe Leu Asp Gln Gly Ser Arg Pro Leu Val Phe<br>               245                     250                 255 | 768 |
| acc cag ggc tcg acc gaa cac ctg cag ggc gac ttc tac gcc atg gcc<br>Thr Gln Gly Ser Thr Glu His Leu Gln Gly Asp Phe Tyr Ala Met Ala<br>                 260                     265                 270 | 816 |
| ctg cgc gcg ctg gaa cgc ctc ggc gcg cgt ggg atc ttc ctc acc ggc<br>Leu Arg Ala Leu Glu Arg Leu Gly Ala Arg Gly Ile Phe Leu Thr Gly<br>               275                     280                 285 | 864 |
| gcc ggc cag gaa ccg ctg cgc ggc ttg ccg aac cac gtg ctg cag cgc<br>Ala Gly Gln Glu Pro Leu Arg Gly Leu Pro Asn His Val Leu Gln Arg<br>290                         295                 300 | 912 |
| gcc tac gcg cca ctg gga gcc ttg ctg cca tcg tgc gcc ggg ctg gtc<br>Ala Tyr Ala Pro Leu Gly Ala Leu Leu Pro Ser Cys Ala Gly Leu Val<br>305                         310                 315                 320 | 960 |
| cat ccg ggc ggt atc ggc gcc atg agc cta gcc ttg gcg gcg ggg gtg<br>His Pro Gly Gly Ile Gly Ala Met Ser Leu Ala Leu Ala Ala Gly Val<br>               325                     330                 335 | 1008 |
| ccg cag gtg ctg ctg ccc tgt gcc cac gac cag ttc gac aat gcc gaa<br>Pro Gln Val Leu Leu Pro Cys Ala His Asp Gln Phe Asp Asn Ala Glu<br>             340                     345                350 | 1056 |
| cgg ctg gtc cgg ctc ggc tgc ggg atg cgc ctg ggc gtg ccg ttg cgc<br>Arg Leu Val Arg Leu Gly Cys Gly Met Arg Leu Gly Val Pro Leu Arg<br>             355                     360                365 | 1104 |
| gag cag gag ttg cgc ggg gcg ctg tgg cgc ttg ctc gag gac ccg gcc<br>Glu Gln Glu Leu Arg Gly Ala Leu Trp Arg Leu Leu Glu Asp Pro Ala<br>370                         375                    380 | 1152 |
| atg gcg gcg gcc tgt cgg cgt ttc atg gaa ttg tca caa ccg cac agt<br>Met Ala Ala Ala Cys Arg Arg Phe Met Glu Leu Ser Gln Pro His Ser<br>385                         390                 395                 400 | 1200 |
| atc gct tgc ggt aaa gcg gcc cag gtg gtc gaa cgt tgt cat agg gag<br>Ile Ala Cys Gly Lys Ala Ala Gln Val Val Glu Arg Cys His Arg Glu<br>               405                     410                 415 | 1248 |
| ggg gat gct cga tgg ctg aag gct gcg tcc tga<br>Gly Asp Ala Arg Trp Leu Lys Ala Ala Ser<br>               420                     425 | 1281 |

<210> SEQ ID NO 86
<211> LENGTH: 426
<212> TYPE: PRT
<213> ORGANISM: Pseudomonas aeruginosa

<400> SEQUENCE: 86

```
Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
            20                  25                  30

Leu Cys Thr Ile Pro Val Phe Arg Asp Ala Val Glu Gln His Gly Ile
        35                  40                  45

Ala Phe Val Pro Leu Ser Asp Glu Leu Thr Tyr Arg Arg Thr Met Gly
    50                  55                  60

Asp Pro Arg Leu Trp Asp Pro Lys Thr Ser Phe Gly Val Leu Trp Gln
65                  70                  75                  80

Ala Ile Ala Gly Met Ile Glu Pro Val Tyr Glu Tyr Val Ser Ala Gln
                85                  90                  95

Arg His Asp Asp Ile Val Val Val Gly Ser Leu Trp Ala Leu Gly Ala
            100                 105                 110

Arg Ile Ala His Glu Lys Tyr Gly Ile Pro Tyr Leu Ser Ala Gln Val
        115                 120                 125

Ser Pro Ser Thr Leu Leu Ser Ala His Leu Pro Pro Val His Pro Lys
    130                 135                 140

Phe Asn Val Pro Glu Gln Met Pro Leu Ala Met Arg Lys Leu Leu Trp
145                 150                 155                 160

Arg Cys Ile Glu Arg Phe Lys Leu Asp Arg Thr Cys Ala Pro Glu Ile
                165                 170                 175

Asn Ala Val Arg Arg Lys Val Gly Leu Glu Thr Pro Val Lys Arg Ile
            180                 185                 190

Phe Thr Gln Trp Met His Ser Pro Gln Gly Val Val Cys Leu Phe Pro
        195                 200                 205

Ala Trp Phe Ala Pro Pro Gln Gln Asp Trp Pro Gln Pro Leu His Met
    210                 215                 220

Thr Gly Phe Pro Leu Phe Asp Gly Ser Ile Pro Gly Thr Pro Leu Asp
225                 230                 235                 240

Asp Glu Leu Gln Arg Phe Leu Asp Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Gly Ala Arg Gly Ile Phe Leu Thr Gly
        275                 280                 285

Ala Gly Gln Glu Pro Leu Arg Gly Leu Pro Asn His Val Leu Gln Arg
    290                 295                 300

Ala Tyr Ala Pro Leu Gly Ala Leu Leu Pro Ser Cys Ala Gly Leu Val
305                 310                 315                 320

His Pro Gly Gly Ile Gly Ala Met Ser Leu Ala Leu Ala Ala Gly Val
                325                 330                 335

Pro Gln Val Leu Leu Pro Cys Ala His Asp Gln Phe Asp Asn Ala Glu
            340                 345                 350

Arg Leu Val Arg Leu Gly Cys Gly Met Arg Leu Gly Val Pro Leu Arg
        355                 360                 365

Glu Gln Glu Leu Arg Gly Ala Leu Trp Arg Leu Leu Glu Asp Pro Ala
```

```
                370             375             380
Met Ala Ala Ala Cys Arg Arg Phe Met Glu Leu Ser Gln Pro His Ser
385             390             395             400

Ile Ala Cys Gly Lys Ala Ala Gln Val Val Glu Arg Cys His Arg Glu
            405             410             415

Gly Asp Ala Arg Trp Leu Lys Ala Ala Ser
            420             425

<210> SEQ ID NO 87
<211> LENGTH: 1281
<212> TYPE: DNA
<213> ORGANISM: Pseudomonas aeruginosa
<220> FEATURE:
<221> NAME/KEY: CDS
<222> LOCATION: (1)..(1281)

<400> SEQUENCE: 87 atg cac gcc atc ctc atc gcc atc ggc tcg gcc ggc gac gta ttt ccc      48
Met His Ala Ile Leu Ile Ala Ile Gly Ser Ala Gly Asp Val Phe Pro
1               5                   10                  15 ttc atc ggc ttg gcc cgg acc ctg aaa ttg cgc ggg cac cgc gtg agc      96
Phe Ile Gly Leu Ala Arg Thr Leu Lys Leu Arg Gly His Arg Val Ser
                20                  25                  30 ctc tgc acc atc ccg gtg ttt cgc gac gcg gtg gag cag cac ggc atc     144
Leu Cys Thr Ile Pro Val Phe Arg Asp Ala Val Glu Gln His Gly Ile
            35                  40                  45 gcg ttc gtc ccg ctg agc gac gaa ctg acc tac cgc cgg acc atg ggc     192
Ala Phe Val Pro Leu Ser Asp Glu Leu Thr Tyr Arg Arg Thr Met Gly
        50                  55                  60 gat ccg cgc ctg tgg gac ccc aag acg tcc ttc ggc gtg ctc tgg caa     240
Asp Pro Arg Leu Trp Asp Pro Lys Thr Ser Phe Gly Val Leu Trp Gln
65                  70                  75                  80 gcc atc gcc ggg atg atc gag ccg gtc tac gag tac gtc tcg gcg cag     288
Ala Ile Ala Gly Met Ile Glu Pro Val Tyr Glu Tyr Val Ser Ala Gln
                85                  90                  95 cgc cat gac gac atc gtg gtg gtc ggc tcg ctc tgg gcg ctg ggc gca     336
Arg His Asp Asp Ile Val Val Val Gly Ser Leu Trp Ala Leu Gly Ala
                100                 105                 110 cgc atc gct cac gag aag tac ggg att ccc tac ctg tcc gcg cag gtc     384
Arg Ile Ala His Glu Lys Tyr Gly Ile Pro Tyr Leu Ser Ala Gln Val
            115                 120                 125 tcg cca tcg acc ttg ttg tcg gcg cac ctg ccg ccg gta cac ccc aag     432
Ser Pro Ser Thr Leu Leu Ser Ala His Leu Pro Pro Val His Pro Lys
        130                 135                 140 ttc aac gtg ccc gag cag atg ccg ctg gcg atg cgc aag ctg ctc tgg     480
Phe Asn Val Pro Glu Gln Met Pro Leu Ala Met Arg Lys Leu Leu Trp
145                 150                 155                 160 cgc tgc atc gag cgc ttc aag ctg gat cgc acc tgc gcg ccg gag atc     528
Arg Cys Ile Glu Arg Phe Lys Leu Asp Arg Thr Cys Ala Pro Glu Ile
                165                 170                 175 aac gcg gtg cgc cgc aag gtc ggc ctg gag acg ccg gtg aag cgc atc     576
Asn Ala Val Arg Arg Lys Val Gly Leu Glu Thr Pro Val Lys Arg Ile
                180                 185                 190 ttc acc caa tgg atg cat tcg ccg cag ggc gtg gtc tgc ctg ttc ccg     624
Phe Thr Gln Trp Met His Ser Pro Gln Gly Val Val Cys Leu Phe Pro
            195                 200                 205 gcc tgg ttc gcg ccg ccc cag cag gat tgg ccg caa ccc ctg cac atg     672
Ala Trp Phe Ala Pro Pro Gln Gln Asp Trp Pro Gln Pro Leu His Met
        210                 215                 220 acc ggc ttc ccg ctg ttc gac ggc agt atc ccg ggg acc ccg ctc gac     720
Thr Gly Phe Pro Leu Phe Asp Gly Ser Ile Pro Gly Thr Pro Leu Asp
```

```
Thr Gly Phe Pro Leu Phe Asp Gly Ser Ile Pro Gly Thr Pro Leu Asp
225                 230                 235                 240 gac gaa ctg caa cgc ttt ctc gat cag ggc agc cgg ccg ctg gtg ttc    768
Asp Glu Leu Gln Arg Phe Leu Asp Gln Gly Ser Arg Pro Leu Val Phe
                245                 250                 255 acc cag ggc tcg acc gaa cac ctg cag ggc gac ttc tac gcc atg gcc    816
Thr Gln Gly Ser Thr Glu His Leu Gln Gly Asp Phe Tyr Ala Met Ala
            260                 265                 270 ctg cgc gcg ctg gaa cgc ctc ggc gcg cgt ggg atc ttc ctc acc ggc    864
Leu Arg Ala Leu Glu Arg Leu Gly Ala Arg Gly Ile Phe Leu Thr Gly
        275                 280                 285 gcc ggc cag gaa ccg ctg cgc ggc ttg ccg aat cac gtg ctg cag cgc    912
Ala Gly Gln Glu Pro Leu Arg Gly Leu Pro Asn His Val Leu Gln Arg
    290                 295                 300 gcc tac gcg cca ctg gga gcc ttg ctg cca tcg tgc gcc ggg ctg gtc    960
Ala Tyr Ala Pro Leu Gly Ala Leu Leu Pro Ser Cys Ala Gly Leu Val
305                 310                 315                 320 cat ccg ggc ggt atc ggc gcc atg agc ctg gcc ttg gcg gcg ggg gtg   1008
His Pro Gly Gly Ile Gly Ala Met Ser Leu Ala Leu Ala Ala Gly Val
                325                 330                 335 ccg cag gtg ctg ctg ccc tgc gcc cac gac cag ttc gac aat gcc gaa   1056
Pro Gln Val Leu Leu Pro Cys Ala His Asp Gln Phe Asp Asn Ala Glu
            340                 345                 350 cgg ctg gtc cgg ctc ggc tgc ggg atg cgc ctg ggc gtg ccg ttg cgc   1104
Arg Leu Val Arg Leu Gly Cys Gly Met Arg Leu Gly Val Pro Leu Arg
        355                 360                 365 gag cag gag ttg cgc ggg gcg ctg tgg cgc ttg ctc gag gac ccg gcc   1152
Glu Gln Glu Leu Arg Gly Ala Leu Trp Arg Leu Leu Glu Asp Pro Ala
    370                 375                 380 atg gcg gcg gcc tgt cgg cgt ttc atg gaa ttg tca caa ccg cac agt   1200
Met Ala Ala Ala Cys Arg Arg Phe Met Glu Leu Ser Gln Pro His Ser
385                 390                 395                 400 atc gct tgc ggt aaa gcg gcc cac gtg gtc gaa cgt tgt cat agg gag   1248
Ile Ala Cys Gly Lys Ala Ala His Val Val Glu Arg Cys His Arg Glu
                405                 410                 415 ggg gat gcg cga tgg ctg aag gct gcg tcc tga                       1281
Gly Asp Ala Arg Trp Leu Lys Ala Ala Ser
            420                 425
```

<210> SEQ ID NO 88
<211> LENGTH: 426
<212> TYPE: PRT
<213> ORGANISM: Pseudomonas aeruginosa

<400> SEQUENCE: 88

```
Met His Ala Ile Leu Ile Ala Ile Gly Ser Ala Gly Asp Val Phe Pro
1               5                   10                  15

Phe Ile Gly Leu Ala Arg Thr Leu Lys Leu Arg Gly His Arg Val Ser
                20                  25                  30

Leu Cys Thr Ile Pro Val Phe Arg Asp Ala Val Glu Gln His Gly Ile
            35                  40                  45

Ala Phe Val Pro Leu Ser Asp Glu Leu Thr Tyr Arg Arg Thr Met Gly
        50                  55                  60

Asp Pro Arg Leu Trp Asp Pro Lys Thr Ser Phe Gly Val Leu Trp Gln
65                  70                  75                  80

Ala Ile Ala Gly Met Ile Glu Pro Val Tyr Glu Tyr Val Ser Ala Gln
                85                  90                  95

Arg His Asp Asp Ile Val Val Gly Ser Leu Trp Ala Leu Gly Ala
            100                 105                 110
```

```
Arg Ile Ala His Glu Lys Tyr Gly Ile Pro Tyr Leu Ser Ala Gln Val
            115                 120                 125

Ser Pro Ser Thr Leu Leu Ser Ala His Leu Pro Pro Val His Pro Lys
    130                 135                 140

Phe Asn Val Pro Glu Gln Met Pro Leu Ala Met Arg Lys Leu Leu Trp
145                 150                 155                 160

Arg Cys Ile Glu Arg Phe Lys Leu Asp Arg Thr Cys Ala Pro Glu Ile
                165                 170                 175

Asn Ala Val Arg Arg Lys Val Gly Leu Glu Thr Pro Val Lys Arg Ile
            180                 185                 190

Phe Thr Gln Trp Met His Ser Pro Gln Gly Val Val Cys Leu Phe Pro
        195                 200                 205

Ala Trp Phe Ala Pro Pro Gln Gln Asp Trp Pro Gln Pro Leu His Met
    210                 215                 220

Thr Gly Phe Pro Leu Phe Asp Gly Ser Ile Pro Gly Thr Pro Leu Asp
225                 230                 235                 240

Asp Glu Leu Gln Arg Phe Leu Asp Gln Gly Ser Arg Pro Leu Val Phe
                245                 250                 255

Thr Gln Gly Ser Thr Glu His Leu Gln Gly Asp Phe Tyr Ala Met Ala
            260                 265                 270

Leu Arg Ala Leu Glu Arg Leu Gly Ala Arg Gly Ile Phe Leu Thr Gly
        275                 280                 285

Ala Gly Gln Glu Pro Leu Arg Gly Leu Pro Asn His Val Leu Gln Arg
    290                 295                 300

Ala Tyr Ala Pro Leu Gly Ala Leu Leu Pro Ser Cys Ala Gly Leu Val
305                 310                 315                 320

His Pro Gly Gly Ile Gly Ala Met Ser Leu Ala Leu Ala Ala Gly Val
                325                 330                 335

Pro Gln Val Leu Leu Pro Cys Ala His Asp Gln Phe Asp Asn Ala Glu
            340                 345                 350

Arg Leu Val Arg Leu Gly Cys Gly Met Arg Leu Gly Val Pro Leu Arg
        355                 360                 365

Glu Gln Glu Leu Arg Gly Ala Leu Trp Arg Leu Leu Glu Asp Pro Ala
    370                 375                 380

Met Ala Ala Ala Cys Arg Arg Phe Met Glu Leu Ser Gln Pro His Ser
385                 390                 395                 400

Ile Ala Cys Gly Lys Ala Ala His Val Val Glu Arg Cys His Arg Glu
                405                 410                 415

Gly Asp Ala Arg Trp Leu Lys Ala Ala Ser
            420                 425

<210> SEQ ID NO 89
<211> LENGTH: 978
<212> TYPE: DNA
<213> ORGANISM: Pseudomonas aeruginosa
<220> FEATURE:
<221> NAME/KEY: CDS
<222> LOCATION: (1)..(978)

<400> SEQUENCE: 89 atg gac cgg ata gac atg ggc gtg ctg gtg gtg ctg ttc aat cct ggc     48
Met Asp Arg Ile Asp Met Gly Val Leu Val Val Leu Phe Asn Pro Gly
1               5                   10                  15 gac gac gac ctg gaa cac ctt ggc gaa ctg gcg gcg gcc ttt ccg caa     96
Asp Asp Asp Leu Glu His Leu Gly Glu Leu Ala Ala Ala Phe Pro Gln
            20                  25                  30
```

-continued

```
ctg cgc ttc ctc gcc gtc gac aac tcg ccg cac agc gat ccg cag cgc      144
Leu Arg Phe Leu Ala Val Asp Asn Ser Pro His Ser Asp Pro Gln Arg
         35                  40                  45 aac gcc cgg ctg cgc ggg caa ggc atc gcc gtg ctc tac cac ggc aac      192
Asn Ala Arg Leu Arg Gly Gln Gly Ile Ala Val Leu Tyr His Gly Asn
 50                  55                  60 cgg cag ggc atc gcc ggc gcc ttc aac cag ggg ctc gac acg ctg ttc      240
Arg Gln Gly Ile Ala Gly Ala Phe Asn Gln Gly Leu Asp Thr Leu Phe
 65                  70                  75                  80 cgg cgc ggc ctg cag ggt gtg ctg ctc gac cag gac tcc cgt ccc          288
Arg Arg Gly Leu Gln Gly Val Leu Leu Asp Gln Asp Ser Arg Pro
             85                  90                  95 ggc ggc gcc ttc ctc gcc gcc cag tgg cgc aac ctg cag gca tgc aac      336
Gly Gly Ala Phe Leu Ala Ala Gln Trp Arg Asn Leu Gln Ala Cys Asn
                100                 105                 110 ggc cag gcc tgc ctg ctc ggc cca cgg atc ttc gac cgg ggc gac cgg      384
Gly Gln Ala Cys Leu Leu Gly Pro Arg Ile Phe Asp Arg Gly Asp Arg
            115                 120                 125 cgc ttc ctg ccg gcc atc cac ctc gac ggg ctg gcg ctc agg caa ctg      432
Arg Phe Leu Pro Ala Ile His Leu Asp Gly Leu Ala Leu Arg Gln Leu
130                 135                 140 tcc ctg gac ggc ctg acg acc cca cag cgc acc tcg ttc ctg atc tcc      480
Ser Leu Asp Gly Leu Thr Thr Pro Gln Arg Thr Ser Phe Leu Ile Ser
145                 150                 155                 160 tcc ggc tgc ctg ctg acc cgc gag gcc tac cag cgc ctc ggc cac ttc      528
Ser Gly Cys Leu Leu Thr Arg Glu Ala Tyr Gln Arg Leu Gly His Phe
                165                 170                 175 gac gag gaa ctg ttc atc gac cac gtg gac acc gag tac agc ctg cgc      576
Asp Glu Glu Leu Phe Ile Asp His Val Asp Thr Glu Tyr Ser Leu Arg
            180                 185                 190 gcc cag gcg ctg gac gtg ccc ctg tac gtc gac ccg cgg ctg gtc ctc      624
Ala Gln Ala Leu Asp Val Pro Leu Tyr Val Asp Pro Arg Leu Val Leu
        195                 200                 205 gag cac cgc atc ggc acg cgc aag acc cgc cgc ctc ggc ggt ctc agc      672
Glu His Arg Ile Gly Thr Arg Lys Thr Arg Arg Leu Gly Gly Leu Ser
210                 215                 220 ctc agc gcg atg aac cac gcc cca ctg cgc cgc tac tac ctg gcg cgc      720
Leu Ser Ala Met Asn His Ala Pro Leu Arg Arg Tyr Tyr Leu Ala Arg
225                 230                 235                 240 aac ggc ctg ctg gtc ctg cgc cgc tac gcc cgg tcc tcg ccg ctg gcc      768
Asn Gly Leu Leu Val Leu Arg Arg Tyr Ala Arg Ser Ser Pro Leu Ala
                245                 250                 255 ctg ctg gcg aac ctg ccg acc ctg acc cag ggc ctc gcg gtg ctc ctg      816
Leu Leu Ala Asn Leu Pro Thr Leu Thr Gln Gly Leu Ala Val Leu Leu
            260                 265                 270 ctc gaa cgc gac aag ctc ctc aag ctg cgc tgc ctg ggc tgg ggc ctg      864
Leu Glu Arg Asp Lys Leu Leu Lys Leu Arg Cys Leu Gly Trp Gly Leu
        275                 280                 285 tgg gac ggc ctg cgg ggg cgc ggc ggc gcg ctg gag cgc aac cgc ccg      912
Trp Asp Gly Leu Arg Gly Arg Gly Gly Ala Leu Glu Arg Asn Arg Pro
    290                 295                 300 cgc ctg ctg aag cgc ctc gcc ggt ccg gcg gtg gcg ccc aca gtt ccc      960
Arg Leu Leu Lys Arg Leu Ala Gly Pro Ala Val Ala Pro Thr Val Pro
305                 310                 315                 320 ggc aag gcc aag gcc tag                                              978
Gly Lys Ala Lys Ala
                325
```

<210> SEQ ID NO 90

```
<211> LENGTH: 325
<212> TYPE: PRT
<213> ORGANISM: Pseudomonas aeruginosa

<400> SEQUENCE: 90

Met Asp Arg Ile Asp Met Gly Val Leu Val Leu Phe Asn Pro Gly
1               5                   10                  15

Asp Asp Asp Leu Glu His Leu Gly Glu Leu Ala Ala Ala Phe Pro Gln
            20                  25                  30

Leu Arg Phe Leu Ala Val Asp Asn Ser Pro His Ser Asp Pro Gln Arg
        35                  40                  45

Asn Ala Arg Leu Arg Gly Gln Gly Ile Ala Val Leu Tyr His Gly Asn
    50                  55                  60

Arg Gln Gly Ile Ala Gly Ala Phe Asn Gln Gly Leu Asp Thr Leu Phe
65                  70                  75                  80

Arg Arg Gly Leu Gln Gly Val Leu Leu Leu Asp Gln Asp Ser Arg Pro
                85                  90                  95

Gly Gly Ala Phe Leu Ala Ala Gln Trp Arg Asn Leu Gln Ala Cys Asn
            100                 105                 110

Gly Gln Ala Cys Leu Leu Gly Pro Arg Ile Phe Asp Arg Gly Asp Arg
        115                 120                 125

Arg Phe Leu Pro Ala Ile His Leu Asp Gly Leu Ala Leu Arg Gln Leu
    130                 135                 140

Ser Leu Asp Gly Leu Thr Thr Pro Gln Arg Thr Ser Phe Leu Ile Ser
145                 150                 155                 160

Ser Gly Cys Leu Leu Thr Arg Glu Ala Tyr Gln Arg Leu Gly His Phe
                165                 170                 175

Asp Glu Glu Leu Phe Ile Asp His Val Asp Thr Glu Tyr Ser Leu Arg
            180                 185                 190

Ala Gln Ala Leu Asp Val Pro Leu Tyr Val Asp Pro Arg Leu Val Leu
        195                 200                 205

Glu His Arg Ile Gly Thr Arg Lys Thr Arg Arg Leu Gly Gly Leu Ser
    210                 215                 220

Leu Ser Ala Met Asn His Ala Pro Leu Arg Arg Tyr Tyr Leu Ala Arg
225                 230                 235                 240

Asn Gly Leu Leu Val Leu Arg Arg Tyr Ala Arg Ser Ser Pro Leu Ala
                245                 250                 255

Leu Leu Ala Asn Leu Pro Thr Leu Thr Gln Gly Leu Ala Val Leu Leu
            260                 265                 270

Leu Glu Arg Asp Lys Leu Leu Lys Leu Arg Cys Leu Gly Trp Gly Leu
        275                 280                 285

Trp Asp Gly Leu Arg Gly Arg Gly Ala Leu Glu Arg Asn Arg Pro
    290                 295                 300

Arg Leu Leu Lys Arg Leu Ala Gly Pro Ala Val Ala Pro Thr Val Pro
305                 310                 315                 320

Gly Lys Ala Lys Ala
                325

<210> SEQ ID NO 91
<211> LENGTH: 978
<212> TYPE: DNA
<213> ORGANISM: Pseudomonas aeruginosa
<220> FEATURE:
<221> NAME/KEY: CDS
<222> LOCATION: (1)..(978)

<400> SEQUENCE: 91
```

-continued

```
atg gac cgg ata gac atg ggc gtg ctg gtg gta ctg ttc aat cct ggc    48
Met Asp Arg Ile Asp Met Gly Val Leu Val Val Leu Phe Asn Pro Gly
1               5                   10                  15 gac gac gac ctg gaa cac ctt ggc gaa ctg gcg gcg gcg ttt ccg caa    96
Asp Asp Asp Leu Glu His Leu Gly Glu Leu Ala Ala Ala Phe Pro Gln
            20                  25                  30 ctg cgc ttc ctc gcc gtc gac aac tca ccg cac agc gat ccg cag cgc   144
Leu Arg Phe Leu Ala Val Asp Asn Ser Pro His Ser Asp Pro Gln Arg
        35                  40                  45 aat gcc cgg ctg cgc ggg caa ggc atc gcc gtg ctg cac cac ggc aac   192
Asn Ala Arg Leu Arg Gly Gln Gly Ile Ala Val Leu His His Gly Asn
    50                  55                  60 cgg cag ggc atc gcc ggc gcc ttc aac cag ggg ctc gac gcg ctg ttc   240
Arg Gln Gly Ile Ala Gly Ala Phe Asn Gln Gly Leu Asp Ala Leu Phe
65                  70                  75                  80 cgg cgt ggc gtg cag ggt gtg ctg ctc gac cag gac tcc cgt ccc       288
Arg Arg Gly Val Gln Gly Val Leu Leu Asp Gln Asp Ser Arg Pro
                85                  90                  95 ggc ggc gcc ttc ctc gcc gcc cag tgg cgc aac ctg cag gcg cgc aac   336
Gly Gly Ala Phe Leu Ala Ala Gln Trp Arg Asn Leu Gln Ala Arg Asn
            100                 105                 110 ggt cag gcc tgc ctg ctc ggc cca cgg atc ttc gac cgg ggt gac cgg   384
Gly Gln Ala Cys Leu Leu Gly Pro Arg Ile Phe Asp Arg Gly Asp Arg
        115                 120                 125 cgc ttc ctg ccg gcc atc cat ctc gac gga ctg acg ctc agg caa ttg   432
Arg Phe Leu Pro Ala Ile His Leu Asp Gly Leu Thr Leu Arg Gln Leu
    130                 135                 140 tct ctg gac ggc ctg acg acc ccg cag cgc acc tcg ttc ctg atc tcc   480
Ser Leu Asp Gly Leu Thr Thr Pro Gln Arg Thr Ser Phe Leu Ile Ser
145                 150                 155                 160 tcc ggc tgc ctg ctg acc cgc gag gcc tac cag cgc ctc ggc cac ttc   528
Ser Gly Cys Leu Leu Thr Arg Glu Ala Tyr Gln Arg Leu Gly His Phe
                165                 170                 175 gac gag gaa ctg ttc atc gac cac gtg gac acc gaa tac agc ctg cgc   576
Asp Glu Glu Leu Phe Ile Asp His Val Asp Thr Glu Tyr Ser Leu Arg
            180                 185                 190 gcc cag gcg ctg gac gtg ccc ctg tac gtc gac ccg cgg ctg gtc ctc   624
Ala Gln Ala Leu Asp Val Pro Leu Tyr Val Asp Pro Arg Leu Val Leu
        195                 200                 205 gag cac cgc atc ggc acg cgc aag acc cgc cgc ctc ggc ggt ctc agc   672
Glu His Arg Ile Gly Thr Arg Lys Thr Arg Arg Leu Gly Gly Leu Ser
    210                 215                 220 ctc agc gcg atg aac cac gcc ccg ctg cgc cgc tac tac ctg gcg cgc   720
Leu Ser Ala Met Asn His Ala Pro Leu Arg Arg Tyr Tyr Leu Ala Arg
225                 230                 235                 240 aac ggc ctg ctg gtc ctg cgc cgc tac gcc cgg tcc tcg ccg ctg gcc   768
Asn Gly Leu Leu Val Leu Arg Arg Tyr Ala Arg Ser Ser Pro Leu Ala
                245                 250                 255 ctg ctg gcg aac ctg ccg acc ctg acc cag ggc ctc gcg gtg ctc ctg   816
Leu Leu Ala Asn Leu Pro Thr Leu Thr Gln Gly Leu Ala Val Leu Leu
            260                 265                 270 ctc gaa cgc gac aag ctg ctc aag ctg cgc tgc ctg ggc tgg ggc ctg   864
Leu Glu Arg Asp Lys Leu Leu Lys Leu Arg Cys Leu Gly Trp Gly Leu
        275                 280                 285 tgg gac ggc ctg cgg gga cgc ggc ggc gcg ctg gag cgc aac cgc ccg   912
Trp Asp Gly Leu Arg Gly Arg Gly Gly Ala Leu Glu Arg Asn Arg Pro
    290                 295                 300 cgc ctg ctg aag cgc ctc gcc ggc ccg gcc gtg gcg tcc gta gct tcc   960
Arg Leu Leu Lys Arg Leu Ala Gly Pro Ala Val Ala Ser Val Ala Ser
```

```
                305                 310                 315                 320
ggc aag gcc aag gcc tag                                                           978
Gly Lys Ala Lys Ala
            325

<210> SEQ ID NO 92
<211> LENGTH: 325
<212> TYPE: PRT
<213> ORGANISM: Pseudomonas aeruginosa

<400> SEQUENCE: 92

Met Asp Arg Ile Asp Met Gly Val Leu Val Leu Phe Asn Pro Gly
1               5                   10                  15

Asp Asp Asp Leu Glu His Leu Gly Glu Leu Ala Ala Ala Phe Pro Gln
                20                  25                  30

Leu Arg Phe Leu Ala Val Asp Asn Ser Pro His Ser Asp Pro Gln Arg
            35                  40                  45

Asn Ala Arg Leu Arg Gly Gln Gly Ile Ala Val Leu His His Gly Asn
        50                  55                  60

Arg Gln Gly Ile Ala Gly Ala Phe Asn Gln Gly Leu Asp Ala Leu Phe
65                  70                  75                  80

Arg Arg Gly Val Gln Gly Val Leu Leu Leu Asp Gln Asp Ser Arg Pro
                85                  90                  95

Gly Gly Ala Phe Leu Ala Ala Gln Trp Arg Asn Leu Gln Ala Arg Asn
            100                 105                 110

Gly Gln Ala Cys Leu Leu Gly Pro Arg Ile Phe Asp Arg Gly Asp Arg
        115                 120                 125

Arg Phe Leu Pro Ala Ile His Leu Asp Gly Leu Thr Leu Arg Gln Leu
130                 135                 140

Ser Leu Asp Gly Leu Thr Thr Pro Gln Arg Thr Ser Phe Leu Ile Ser
145                 150                 155                 160

Ser Gly Cys Leu Leu Thr Arg Glu Ala Tyr Gln Arg Leu Gly His Phe
                165                 170                 175

Asp Glu Glu Leu Phe Ile Asp His Val Asp Thr Glu Tyr Ser Leu Arg
            180                 185                 190

Ala Gln Ala Leu Asp Val Pro Leu Tyr Val Asp Pro Arg Leu Val Leu
        195                 200                 205

Glu His Arg Ile Gly Thr Arg Lys Thr Arg Arg Leu Gly Gly Leu Ser
210                 215                 220

Leu Ser Ala Met Asn His Ala Pro Leu Arg Arg Tyr Tyr Leu Ala Arg
225                 230                 235                 240

Asn Gly Leu Leu Val Leu Arg Arg Tyr Ala Arg Ser Ser Pro Leu Ala
                245                 250                 255

Leu Leu Ala Asn Leu Pro Thr Leu Thr Gln Gly Leu Ala Val Leu Leu
            260                 265                 270

Leu Glu Arg Asp Lys Leu Leu Lys Leu Arg Cys Leu Gly Trp Gly Leu
        275                 280                 285

Trp Asp Gly Leu Arg Gly Arg Gly Gly Ala Leu Glu Arg Asn Arg Pro
290                 295                 300

Arg Leu Leu Lys Arg Leu Ala Gly Pro Ala Val Ala Ser Val Ala Ser
305                 310                 315                 320

Gly Lys Ala Lys Ala
            325
```

CELLS AND METHODS FOR PRODUCING RHAMNOLIPIDS

CROSS-REFERENCE TO RELATED APPLICATIONS

This application is a divisional application of U.S. patent application Ser. No. 13/812,625, filed Jan. 28, 2013, which is the National Phase of PCT/EP2011/062441, filed Jul. 20, 2011, which claims the benefit of German Application No. DE 102010032484 filed on Jul. 28, 2010, the contents of each of which is herein incorporated by reference in its entirety.

INCORPORATION BY REFERENCE OF SEQUENCE LISTING

The Sequence Listing in the ASCII text file, named as SequenceListing.txt of 547 KB, created on Dec. 10, 2012, and submitted to the United States Patent and Trademark Office via EFS-Web on Jan. 28, 2013, is incorporated herein by reference.

FIELD OF THE INVENTION

The invention relates to cells and nucleic acids and also use thereof for producing rhamnolipids, and also methods for producing rhamnolipids.

PRIOR ART

Surfactants are nowadays produced essentially based on the basis of petrochemical raw materials. The use of surfactants based on renewable raw materials is a suitable alternative on account of the foreseeable shortage of petrochemical raw materials and increasing demand for products that are based on renewable raw materials or are biodegradable.

Rhamnolipids consist of one (monorhamnosyl lipids) or two rhamnose radicals (dirhamnosyl lipids) and one or two 3-hydroxy fatty acid residues (see *Handbook of Hydrocarbon and Lipid Microbiology*, 2010, pages 3037-51). They have surface-active properties, which are needed in all sorts of applications for use as a surfactant (see Leitermann et al., 2009).

These lipids are nowadays produced using wild-type isolates of different human- and animal-pathogenic bacteria, in particular representatives of the genera *Pseudomonas* and *Burkholderia* (see *Handbook of Hydrocarbon and Lipid Microbiology*, 2010, pages 3037-51). The fact that these production organisms are able to cause diseases reduces the customer acceptance for the conventionally produced rhamnolipids very considerably. Moreover, higher safety requirements also have an effect on the production costs owing to increased capital expenditure and possibly additional working-up steps.

Although to some extent high product titers, and also space-time and/or carbon yields can be achieved with the aid of these production organisms, this requires the use of vegetable oils as the sole or co-substrate (see *Handbook of Hydrocarbon and Lipid Microbiology*, 2010, pages 3037-51). Vegetable oils, however, are comparatively expensive raw materials in comparison to other carbon sources, such as, for example, glucose, sucrose or polysaccharides such as, for example, starch, cellulose and hemicellulose, glycerol, CO, $CO_2$ or $CH_4$. Moreover, rhamnolipids distinguish themselves on account of their surfactant character in that they are susceptible to heavy foaming in fermentation processes. This is in particular the case if lipophilic substrates are employed. This problem is markedly reduced on use of water-soluble substrates such as, for example, glucose, sucrose, polysaccharides (starch, cellulose, hemicellulose) or glycerol. Finally, the properties of the rhamnolipids produced by the wild-type isolates can only be influenced to a restricted extent. Up to now, this takes place exclusively via the optimization of the process management (pH, oxygen supply, media composition, feeding strategies, nitrogen supply, temperature, choice of substrate, etc.). However, a very specific influence of certain product properties, such as, for example, the ratio of the various rhamnolipid species (number of rhamnose and 3-hydroxy fatty acid radicals) or chain length and degree of saturation of the 3-hydroxy fatty acid radicals would be desirable to be able to modulate the product properties relevant for the application.

Rhamnolipids, if they are to be employed in a large extent as surfactants in household, cleaning, cosmetic, food processing, pharmaceutical, plant protection and other applications, must appear to be in competition with the surfactants employed nowadays. These are high volume chemicals, which can be produced at very low costs, without obvious health risks for the customer and with clearly defined and modulatable product specifications. Therefore rhamnolipids must also be able to be produced at costs as low as possible, without health risks for the customer and with defined properties as far as possible.

Although rhamnolipids have already been produced in GRAS organisms (generally regarded as save) based on convenient carbon sources, such as, for example, glucose or glycerol, these are in this case exclusively monorhamnosyl lipids (Ochsner et al. Appl. Environ. Microbiol. 1995. 61(9): 3503-3506).

Cha et al. in Bioresour Technol. 2008. 99(7):2192-9, on the other hand, describe the production of monorhamnosyl lipids from soybean oil in *P. putida* by introduction of the genes rhlA and rhlB from *Pseudomonas aeruginosa*.

There is therefore an increasing need for the inexpensive and, from the health point of view, safe production of mono- and dirhamnosyl lipids having defined and modulatable properties. This modulation can be carried out, for example, by means of a balanced supply of the individual enzyme activities, which reduces the enrichment of monorhamnosyl lipids. This modulation, however, can also be carried out, for example, by the use of enzymes having certain properties, e.g. with respect to substrate specificity and thus, for example, the chain length of the hydroxy fatty acids incorporated in rhamnolipids.

The present invention therefore has the object of providing a possibility of producing rhamnolipids from readily accessible carbon sources using safe production hosts.

DESCRIPTION OF THE INVENTION

Surprisingly, it has been found that the cells and methods described below, in which these cells are employed, make a contribution to solving the stated object of the invention.

The present invention therefore relates to cells, which are able to form rhamnolipids and compared to their wild-type have at least one increased activity of a gene product of homologs of the gene products rhlA, rhlB and rhlC.

The invention further relates to a method for producing rhamnolipids using the aforementioned cells as a biocatalyst and simple carbon sources.

It is an advantage of the present invention that organisms can be employed that are non-pathogenic and simple to culture.

It is a further advantage that use of oils as the sole or co-substrate is not necessary. Another advantage is that with the aid of the invention rhamnolipids having defined and modulatable properties can be produced.

It is another advantage of the present invention that dirhamnosyl lipids can be produced.

A further advantage is that rhamnolipids can be produced with higher space-time and carbon yields than with cells without enhancement of these activities.

A contribution to achieving the object mentioned at the outset is made by a cell, preferably an isolated cell, which is able to form at least one rhamnolipid of the general formula (I) or its salt,

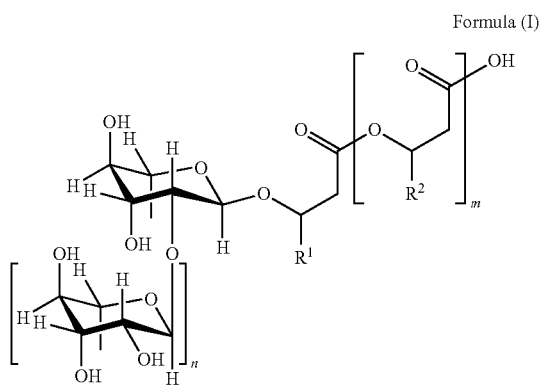

Formula (I)

wherein
m=2, 1 or 0, in particular 1 or 0,
n=1 or 0, in particular 1,
$R^1$ and $R^2$=independently of one another identical or different organic radical having 2 to 24, preferably 5 to 13 carbon atoms, in particular optionally branched, optionally substituted, in particular hydroxy-substituted, optionally unsaturated, in particular optionally mono-, di- or tri-unsaturated, alkyl radical, preferably that selected from the group consisting of pentenyl, heptenyl, nonenyl, undecenyl and tridecenyl and $(CH_2)_o$—$CH_3$ with o=1 to 23, preferably 4 to 12, characterized in that it has been genetically modified such that, compared to its wild-type, it has an increased activity of at least one of the enzymes $E_1$, $E_2$ and $E_3$, wherein the enzyme $E_1$ is able to catalyze the conversion of 3-hydroxyalkanoyl-ACP via 3-hydroxyalkanoyl-3-hydroxyalkanoic acid-ACP to hydroxyalkanoyl-3-hydroxyalkanoic acid, the enzyme $E_2$ is a rhamnosyltransferase I and is able to catalyze the conversion of dTDP-rhamnose and 3-hydroxyalkanoyl-3-hydroxyalkanoate to α-L-rhamnopyranosyl-3-hydroxyalkanoyl-3-hydroxyalkanoate and the enzyme $E_3$ is a rhamnosyltransferase II and is able to catalyze the conversion of dTDP-rhamnose and α-L-rhamnopyranosyl-3-hydroxyalkanoyl-3-hydroxyalkanoate to α-L-rhamnopyranosyl-(1-2)-α-L-rhamnopyranosyl-3-hydroxyalkanoyl-3-hydroxyalkanoate, wherein these enzymes $E_1$, $E_2$ and $E_3$ preferably are selected from the group consisting of
at least one enzyme $E_1$ selected from
an enzyme $E_{1a}$ having polypeptide sequence Seq ID No. 2 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 2 by deletion, insertion, substitution or a combination thereof and that still has at least 10%, preferably 50%, particularly preferably 80%, in particular more than 90% of the enzymatic activity of the enzyme having the reference sequence Seq ID No. 2, wherein enzymatic activity for an enzyme $E_{1a}$ is understood as meaning the ability preferably to convert 3-hydroxydecanoyl-ACP via 3-hydroxydecanoyl-3-hydroxydecanoic acid-ACP to hydroxydecanoyl-3-hydroxydecanoic acid,
an enzyme $E_{1b}$ having polypeptide sequence Seq ID No. 18 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 18 by deletion, insertion, substitution or a combination thereof and that still has at least 10%, preferably 50%, particularly preferably 80%, in particular more than 90% of the enzymatic activity of the enzyme having the reference sequence Seq ID No. 18, wherein enzymatic activity for an enzyme $E_{1b}$ is understood as meaning the ability preferably to convert 3-hydroxytetradecanoyl-ACP via 3-hydroxytetradecanoyl-3-hydroxytetradecanoic acid-ACP to hydroxytetradecanoyl-3-hydroxytetradecanoic acid,
an enzyme $E_{1c}$ having polypeptide sequence Seq ID No. 78 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 78 by deletion, insertion, substitution or a combination thereof and that still has at least 10%, preferably 50%, particularly preferably 80%, in particular more than 90% of the enzymatic activity of the enzyme having the reference sequence Seq ID No. 78, wherein enzymatic activity for an enzyme $E_{1c}$ is understood as meaning the ability preferably to convert 3-hydroxytetradecanoyl-ACP via 3-hydroxytetradecanoyl-3-hydroxytetradecanoic acid-ACP to hydroxytetradecanoyl-3-hydroxytetradecanoic acid,
an enzyme $E_{1d}$ having polypeptide sequence Seq ID No. 80 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 80 by deletion, insertion, substitution or a combination thereof and that still has at least 10%, preferably 50%, particularly preferably 80%, in particular more than 90% of the enzymatic activity of the enzyme having the reference sequence Seq ID No. 80, wherein enzymatic activity for an enzyme $E_{1d}$ is understood as meaning the ability preferably to convert 3-hydroxytetradecanoyl-ACP via 3-hydroxytetradecanoyl-3-hydroxytetradecanoic acid-ACP to hydroxytetradecanoyl-3-hydroxytetradecanoic acid, and
an enzyme $E_{1e}$ having polypeptide sequence Seq ID No. 82 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 82 by deletion, insertion, substitution or a combination thereof and that still has at least 10%, preferably 50%, particularly preferably 80%, in particular more than 90% of the enzymatic activity of the enzyme having the reference sequence Seq ID No. 82, wherein enzymatic activity for an enzyme $E_{1e}$ is understood as meaning the ability preferably to convert 3-hydroxytetradecanoyl-ACP via 3-hydroxytetradecanoyl-3-hydroxytetradecanoic acid-ACP to hydroxytetradecanoyl-3-hydroxytetradecanoic acid,
at least one enzyme $E_2$ having polypeptide sequence selected from
an enzyme $E_{2a}$ having polypeptide sequence Seq ID No. 4 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 4 by deletion, insertion, substitution or a combination thereof and that still has at least 10%, preferably 50%, particularly preferably 80%, in particular more than 90% of the enzymatic activity of the enzyme having the reference sequence Seq ID No. 4, wherein enzymatic activity for an enzyme $E_{2a}$ is understood as meaning the ability preferably to convert dTDP-rhamnose and 3-hydroxydecanoyl-3-hydroxydecanoic acid to α-L-rhamnopyranosyl-3-hydroxydecanoyl-3-hydroxydecanoic acid, an enzyme $E_{2b}$ having polypeptide sequence Seq ID No. 20 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 20 by deletion, insertion, substitution or a combination thereof and that still has at least 10%, preferably 50%, particularly preferably 80%, in particular more than 90% of the enzymatic activity of the enzyme having the reference sequence Seq ID No. 20, wherein enzymatic activity for an enzyme $E_{2b}$ is understood as meaning the ability preferably to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, an enzyme $E_{2c}$ having polypeptide sequence Seq ID No. 84 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 84 by deletion, insertion, substitution or a combination thereof and that still has at least 10%, preferably 50%, particularly preferably 80%, in particular more than 90% of the enzymatic activity of the enzyme having the reference sequence Seq ID No. 84, wherein enzymatic activity for an enzyme $E_{2c}$ is understood as meaning the ability preferably to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, an enzyme $E_{2d}$ having polypeptide sequence Seq ID No. 86 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 86 by deletion, insertion, substitution or a combination thereof and that still has at least 10%, preferably 50%, particularly preferably 80%, in particular more than 90% of the enzymatic activity of the enzyme having the reference sequence Seq ID No. 86, wherein enzymatic activity for an enzyme $E_{2d}$ is understood as meaning the ability preferably to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and an enzyme $E_{2e}$ having polypeptide sequence Seq ID No. 88 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 88 by deletion, insertion, substitution or a combination thereof and that still has at least 10%, preferably 50%, particularly preferably 80%, in particular more than 90% of the enzymatic activity of the enzyme having the reference sequence Seq ID No. 88, wherein enzymatic activity for an enzyme $E_{2e}$ is understood as meaning the ability preferably to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and at least one enzyme $E_3$ selected from an enzyme $E_{3a}$ having polypeptide sequence Seq ID No. 6 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 6 by deletion, insertion, substitution or a combination thereof and that still has at least 10%, preferably 50%, particularly preferably 80%, in particular more than 90% of the enzymatic activity of the enzyme having the reference sequence Seq ID No. 6, wherein enzymatic activity for an enzyme $E_{3a}$ is understood as meaning the ability preferably to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, an enzyme $E_{3b}$ having polypeptide sequence Seq ID No. 22 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 22 by deletion, insertion, substitution or a combination thereof and that still has at least 10%, preferably 50%, particularly preferably 80%, in particular more than 90% of the enzymatic activity of the enzyme having the reference sequence Seq ID No. 22, wherein enzymatic activity for an enzyme $E_{3b}$ is understood as meaning the ability preferably to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, an enzyme $E_{3c}$ having polypeptide sequence Seq ID No. 90 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 90 by deletion, insertion, substitution or a combination thereof and that still has at least 10%, preferably 50%, particularly preferably 80%, in particular more than 90% of the enzymatic activity of the enzyme having the reference sequence Seq ID No. 90, wherein enzymatic activity for an enzyme $E_{3c}$ is understood as meaning the ability preferably to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, and an enzyme $E_{3d}$ having polypeptide sequence Seq ID No. 92 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 92 by deletion, insertion, substitution or a combination thereof and that still has at least 10%, preferably 50%, particularly preferably 80%, in particular more than 92% of the enzymatic activity of the enzyme having the reference sequence Seq ID No. 92, wherein enzymatic activity for an enzyme $E_{3d}$ is understood as meaning the ability preferably to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid.

For general survey compare FIG. 1.

"Wild-type" of a cell herein designates a cell, the genome of which is present in a state as is formed naturally by evolution. The term is used both for the entire cell as well as for individual genes. The term "wild-type" therefore in particular does not include those cells or those genes, the gene sequences of which have been modified at least partially by man by means of recombinant methods.

The term "rhamnolipid" is understood in connection with the present invention as meaning a compound of the general formula (I) or its salt.

It is obvious that the activities actually indicated above for the enzymes $E_{1a}$ to $E_{3b}$ is only a special exemplary choice of a broader activity spectrum of the aforementioned enzymes; the respective activity mentioned is that for which a reliable measuring method is available in the case of a given enzyme. Thus it is obvious that an enzyme which a substrate having an unbranched, saturated $C_{10}$-alkyl radical likewise—even though optionally with decreased activity—will convert those substrates that contain a $C_6$- or $C_{16}$-alkyl radical, which can optionally also be branched or unsaturated.

The term "increased activity of an enzyme" is preferably to be understood as meaning increased intracellular activity.

The embodiments now following for increasing the enzyme activity in cells apply both for the increase in the activity of the enzyme $E_1$ to $E_3$ as well as for all subsequently mentioned enzymes, the activity of which can optionally be increased.

In principle, an increase in the enzymatic activity can be achieved by increasing the copy number of the gene sequence or the gene sequences which code for the enzyme, using a strong promoter or an improved ribosome binding site, attenuating a negative regulation of gene expression, for example by transcription regulators, or amplifying a positive regulation of gene expression, modifying the codon usage of the gene, in various ways increasing the half-life of the mRNA or of the enzyme, modifying the regulation of the expression of the gene or utilizing a gene or allele that codes for an appropriate enzyme having an increased activity and optionally combining these measures. According to the invention, genetically modified cells are produced, for example, by transformation, transduction, conjugation or a combination of these methods using a vector that contains the desired gene, an allele of this gene or parts thereof and optionally contains a promoter making possible the expression of the gene. Heterologous expression is in particular achieved by integration of the gene or the alleles in the chromosome of the cell or an extrachromosomally replicating vector.

DE-A-100 31 999 gives a general survey of the possibilities for increasing the enzyme activity in cells as exemplified by pyruvate carboxylase, which is inserted hereby as a reference and whose disclosure content with respect to the possibilities for increasing the enzyme activity in cells forms a part of the disclosure of the present invention.

The expression of the above and all subsequently mentioned enzymes or genes is detectable with the aid of 1- and 2-dimensional protein gel separation and subsequent optical identification of the protein concentration in the gel using appropriate analytical software. If the increase in an enzyme activity is based exclusively on an increase in the expression of the corresponding gene, the quantification of the increase in the enzyme activity can be determined in a simple manner by a comparison of the 1- or 2-dimensional protein separations between wild-type and genetically modified cell. A customary method for the preparation of the protein gels in the case of *coryneforme* bacteria and for the identification of the proteins is the procedure described by Hermann et al. (Electrophoresis, 22: 1712.23 (2001)). The protein concentration can likewise be analyzed by Western Blot hybridization using an antibody specific for the protein to be detected (Sambrook et al., Molecular Cloning: a laboratory manual, 2nd Ed. Cold Spring Harbor Laboratory Press, Cold Spring Harbor, N.Y. USA, 1989) and subsequent optical analysis using appropriate software for the concentration determination (Lohaus and Meyer (1989) Biospektrum, 5: 32-39; Lottspeich (1999) Angewandte Chemie 111: 2630-2647). The activity of DNA-binding proteins can be measured by means of DNA band shift assays (also called gel retardation) (Wilson et al. (2001) Journal of Bacteriology, 183: 2151-2155). The action of DNA-binding proteins on the expression of other genes can be detected by various well-described methods of the reporter gene assay (Sambrook et al., Molecular Cloning: a laboratory manual, 2nd Ed. Cold Spring Harbor Laboratory Press, Cold Spring Harbor, N.Y. USA, 1989). The intracellular enzymatic activities can be determined according to various described methods (Donahue et al. (2000) Journal of Bacteriology 182 (19): 5624-5627; Ray et al. (2000) Journal of Bacteriology 182 (8): 2277-2284; Freedberg et al. (1973) Journal of Bacteriology 115 (3): 816-823). If in the following embodiments no practical methods are indicated for the determination of the activity of a certain enzyme, the determination of the increase in the enzyme activity and also the determination of the decrease of an enzyme activity preferably take place by means of the methods described in Hermann et al., Electophoresis, 22: 1712-23 (2001), Lohaus et al., Biospektrum 5 32-39 (1998), Lottspeich, Angewandte Chemie 111: 2630-2647 (1999) and Wilson et al., Journal of Bacteriology 183: 2151-2155 (2001).

If the increase in the enzyme activity is accomplished by mutation of the endogenous gene, such mutations can be randomly produced either by conventional methods, such as, for example, by UV irradiation or by mutagenic chemicals, or selectively by means of genetic engineering methods such as deletion(s), insertion(s) and/or nucleotide exchange(s). Modified cells are obtained by these mutations. Particularly preferred mutants of enzymes are in particular also those enzymes that are no longer feedback-, product- or substrate-inhibitable or are so to a reduced degree at least in comparison to the wild-type enzyme.

If the increase in the enzyme activity is accomplished by increase in the synthesis of an enzyme, the copy number of the corresponding genes is increased or the promoter and regulation region or the ribosome binding site, which is situated upstream of the structural gene, is mutated. Expression cassettes, which are incorporated upstream of the structural gene, act in the same manner. It is additionally possible, by means of inducible promoters, to increase the expression at any desired point in time. In addition, however, also "enhancers" can be assigned to the enzyme gene as regulatory sequences, which likewise bring about increased gene expression by means of an improved interaction between RNA polymerase and DNA. As a result of measures for the prolongation of the lifetime of the mRNA, the expression is likewise improved. Furthermore, by prevention of the degradation of the enzyme protein the enzyme activity is likewise increased. The genes or gene constructs are present here either in plasmids having a different copy number or are integrated and amplified in the chromosome.

Alternatively, an overexpression of the genes concerned can furthermore be achieved by modification of the media composition and culture management. The person skilled in the art finds directions for this, inter alia, in Martin et al. (Bio/Technology 5, 137-146 (1987)), in Guerrero et al. (Genes 138, 35-41 (1994)), Tsuchiya and Morinaga (Bio/Technology 6, 428-430 (1988)), in Eikmanns et al. (Genes 102, 93-98 (1991)), in EP-A-0 472 869, in U.S. Pat. No. 4,601,893, in Schwarzer and Pühler (Bio/Technology 9, 84-87 (1991)), in Reinscheid et al. (Applied and Environmental Microbiology 60, 126-132 (1994)), in LaBarre et al. (Journal of Bacteriology 175, 1001-1007 (1993)), in WO-A-96/15246, in Malumbres et al. (Genes 134, 15-24 (1993)), in JP-A-10-229891, in Jensen and Hammer (Biotechnology and Bioengineering 58, 191-195 (1998)) and in known textbooks of genetics and molecular biology. The measures described above likewise lead, like the mutations, to genetically modified cells.

Episomal plasmids, for example, are employed for increasing the expression of the respective genes. Suitable plasmids or vectors are in principle all embodiments available for this purpose to the person skilled in the art. Such plasmids and vectors can be taken, for example, from the brochures of the companies Novagen, Promega, New England Biolabs, Clontech or Gibco BRL. Further preferred plasmids and vectors can be found in: Glover, D. M. (1985) DNA cloning: a practical approach, Vol. IRL Press Ltd., Oxford; Rodriguez, R. L. and Denhardt, D. T (eds) (1988) Vectors: a survey of molecular cloning vectors and their uses, 179-204, Butterworth, Stoneham; Goeddel, D. V. (1990) Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbor Laboratory Press, New York.

The plasmid vector, which contains the gene to be amplified, is then converted to the desired strain by conjugation or transformation. The method of conjugation is described, for example, in Schäfer et al., Applied and Environmental Microbiology 60: 756-759 (1994). Methods for transformation are described, for example, in Thierbach et al., Applied Microbiology and Biotechnology 29: 356-362 (1988), Dunican and Shivnan, Bio/Technology 7: 1067-1070 (1989) and Tauch et al., FEMS Microbiology Letters 123: 343-347 (1994). After homologous recombination by means of a "cross-over" event, the resulting strain contains at least two copies of the gene concerned.

Under the formulation used above and in the following embodiments "an activity of an enzyme $E_x$ increased in comparison to its wild-type" is preferably always to be understood as meaning an activity of the respective enzyme $E_x$ increased by a factor of at least 2, particularly preferably of at least 10, moreover preferably of at least 100, moreover still more preferably of at least 1,000 and most preferably of at least 10,000. Furthermore the cell according to the invention, which has "an increased activity of an enzyme $E_x$ compared to its wild-type", in particular also comprises a cell, whose wild-type contains no or at least no detectable activity of this enzyme $E_x$ and which shows a detectable activity of this enzyme $E_x$ only after increasing the enzyme activity, for example by overexpression. In this connection, the term "overexpression" or the formulation used in the following embodiments "increasing the expression" also comprises the case where a starting cell, for example a wild-type cell, has no or at least no detectable expression and a detectable synthesis of the enzyme $E_x$ is induced only by recombinant methods.

Changes of amino acid radicals of a given polypeptide sequence, which lead to no significant changes in the properties and function of the given polypeptide, are known to the person skilled in the art. Thus, for example, "conserved amino acids" can be mutually exchanged; examples of such suitable amino acid substitutions are: Ala for Ser; Arg for Lys; Asn for Gln or His; Asp for Glu; Cys for Ser; Gln for Asn; Glu for Asp; Gly for Pro; His for Asn or Gln; Ile for Leu or Val; Leu for Met or Val; Lys for Arg or Gln or Glu; Met for Leu or Ile; Phe for Met or Leu or Tyr; Ser for Thr; Thr for Ser; Trp for Tyr; Tyr for Trp or Phe; Val for Ile or Leu. It is likewise known that changes, particularly at the N- or C-terminus of a polypeptide, in the form of, for example, amino acid insertions or deletions often exert no significant influence on the function of the polypeptide.

The activity of an enzyme can be determined by disrupting cells which contain this activity in a manner known to the person skilled in the art, for example with the aid of a ball mill, a French press or of an ultrasonic disintegrator and subsequently separating off cells, cell debris and disruption aids, such as, for example, glass beads, by centrifugation for 10 minutes at 13,000 rpm and 4° C. Using the resulting cell-free crude extract, enzyme assays with subsequent LC-ESI-MS detection of the products can then be carried out. Alternatively, the enzyme can be enriched in the manner known to the person skilled in the art by chromatographic methods (such as nickel-nitrilotriacetic acid affinity chromatography, streptavidin affinity chromatography, gel filtration chromatography or ion-exchange chromatography) or else purified to homogeneity.

The activity of the enzyme $E_1$ is then determined using the samples obtained as described above in the following manner: A standard assay contains 100 μM E. coli ACP, 1 mM β-mercaptoethanol, 200 μM malonyl-coenzyme A, 40 μM octanoyl-coenzyme A (for $E_{1a}$) or dodecanoyl-coenzyme A (for $E_{1b}$), 100 μM NADPH, 2 μg of E. coli FabD, 2 μg of Mycobacterium tuberculosis FabH, 1 μg of E. coli FabG, 0.1 M sodium phosphate buffer, pH 7.0, and 5 μg of enzyme $E_1$ in a final volume of 120 μL. ACP, β-mercaptoethanol and sodium phosphate buffer are preincubated for 30 min at 37° C. to reduce the ACP completely. The reaction is started by addition of enzyme $E_1$. The reactions are stopped using 2 ml of water, which has been acidified with HCl to pH 2.0, and subsequently extracted twice with 2 ml of chloroform/methanol (2:1 (v:v)). Phase separation takes place by centrifugation (16,100 g, 5 min, RD. The lower organic phase is removed, evaporated completely in the vacuum centrifuge and the sediment is taken up in 50 μl of methanol. Undissolved constituents are sedimented by centrifugation (16, 100 g, 5 min, RT) and the sample is analyzed by means of LC-ESI-MS. The identification of the products takes place by analysis of the corresponding mass traces and the $MS^2$ spectra.

The activity of the enzyme $E_2$ is then determined as follows using the samples obtained as described above: a standard assay can consist of 185 μl of 10 mM tris-HCl (pH 7.5), 10 μl of 125 mM dTDP-rhamnose and 50 μl of protein crude extract (about 1 mg of total protein) or purified protein in solution (5 μg of purified protein). The reaction is started by the addition of 10 μl of 10 mM ethanolic solution of 3-hydroxydecanoyl-3-hydroxydecanoic acid (for $E_{2a}$) or 3-hydroxy-tetradecanoyl-3-hydroxytetradecanoic acid (for $E_{2b}$) and incubated for 1 h at 30° C. with shaking (600 rpm). Subsequently, the reaction is treated with 1 ml of acetone. Undissolved constituents are sedimented by centrifugation (16,100 g, 5 min, RD and the sample is analyzed by means of LC-ESI-MS. The identification of the products takes place by analysis of the corresponding mass traces and the $MS^2$ spectra.

The activity of the enzyme $E_3$ is then determined as follows using the samples obtained as described above: a standard assay can consist of 185 µl of 10 mM tris-HCl (pH 7.5), 10 µl of 125 mM of dTDP-rhamnose and 50 µl of protein crude extract (about 1 mg of total protein) or purified protein in solution (5 µg of purified protein). The reaction is started by the addition of 10 µl of 10 mM ethanolic solution of α-L-rhamnopyranosyl-3-hydroxydecanoyl-3-hydroxydecanoic acid (for $E_{3a}$) or α-L-rhamnopyranosyl-3-hydroxytetradecanoyl-3-hydroxytetradecanoic acid (for $E_{3b}$) and incubated for 1 h at 30° C. with shaking (600 rpm). Subsequently, the reaction is treated with 1 ml of acetone. Undissolved constituents are sedimented by centrifugation (16,100 g, 5 min, RT) and the sample is analyzed by means of LC-ESI-MS. The identification of the products takes place by analysis of the corresponding mass traces and the $MS^2$ spectra.

Cells according to the invention are preferred that have increased activities of the following enzyme combinations: $E_1$, $E_2$, $E_3$, $E_1E_2$, $E_1E_3$, $E_2E_3$ and $E_1E_2E_3$,
of which the combination
$E_2$, $E_2E_3$ and $E_1E_2E_3$, in particular $E_1E_2E_3$
is particularly preferred.

In a preferred embodiment of the cell according to the invention that has an increased activity of the enzyme combination $E_1E_2E_3$, n is preferably =1.

The cells according to the invention can be prokaryotes or eukaryotes. These can be mammalian cells (such as, for example, cells from man), plant cells or microorganisms such as yeasts, fungi or bacteria, wherein microorganisms are particularly preferred and bacteria and yeasts are most preferred.

Suitable bacteria, yeasts or fungi are in particular those bacteria, yeasts or fungi that are deposited in the Deutsche Sammlung von Mikroorganismen and Zellkulturen (German Collection of Microorganisms and Cell Cultures) GmbH (DSMZ), Brunswick, Germany, as listed on the DSMZ website.

Preferred cells according to the invention are those of the genera *Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium* and *Cupriavidus*, wherein *Aspergillus nidulans, Aspergillus niger, Alcaligenes latus, Bacillus megaterium, Bacillus subtilis, Brevibacterium flavum, Brevibacterium lactofermentum, Burkholderia andropogonis, B. brasilensis, B. caledonica, B. caribensis, B. caryophylli, B. fungorum, B. gladioli, B. glathei, B. glumae, B. graminis, B. hospita, B. kururiensis, B. phenazinium, B. phymatum, B. phytofirmans, B. plantarii, B. sacchari, B. singaporensis, B. sordidicola, B. terricola, B. tropica, B. tuberum, B. ubonensis, B. unamae, B. xenovorans, B. anthina, B. pyrrocinia, B. thailandensis, Candida blankii, Candida rugosa, Corynebacterium glutamicum, Corynebacterium efficiens, Escherichia coli, Hansenula polymorphs, Kluveromyces lactis, Methylobacterium extorquens, Paracoccus versutus, Pseudomonas argentinensis, P. borbori, P. citronellolis, P. flavescens, P. mendocina, P. nitroreducens, P. oleovorans, P. pseudoalcaligenes, P. resinovorans, P. straminea, P. aurantiaca, P. aureofaciens, P. chlororaphis, P. fragi, P. lundensis, P. taetrolens, P. antarctica, P. azotoformans, 'P. blatchfordae', P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. proteolytica, P. rhodesiae, P. synxantha, P. thivervalensis, P. tolaasii, P. veronii, P. denitrificans, P. pertucinogena, P. cremoricolorata, P. fulva, P. monteilii, P. mosselii, P. parafulva, P. putida, P. balearica, P. stutzeri, P. amygdali, P. avellanae, P. caricapapayae, P. cichorii, P. coronafaciens, P. ficuserectae, 'P. helianthi', P. meliae, P. savastanoi, P. syringae, P. tomato, P. viridiflava, P. abietaniphila, P. acidophila, P. agarici, P. alcaliphila, P. alkanolytica, P. amyloderamosa, P. asplenii, P. azotifigens, P. cannabina, P. coenobios, P. congelans, P. costantinii, P. cruciviae, P. delhiensis, P. excibis, P. extremorientalis, P. frederiksbergensis, P. fuscovaginae, P. gelidicola, P. grimontii, P. indica, P. jessenfi, P. jinjuensis, P. kilonensis, P. knackmussii, P. koreensis, P. lini, P. lutea, P. moraviensis, P. otitidis, P. pachastrellae, P. palleroniana, P. papaveris, P. peli, P. perolens, P. poae, P. pohangensis, P. psychrophila, P. psychrotolerans, P. rathonis, P. reptilivora, P. resiniphila, P. rhizosphaerae, P. rubescens, P. salomonii, P. segitis, P. septica, P. simiae, P. suis, P. thermotolerans, P. aeruginosa, P. tremae, P. trivialis, P. turbinellae, P. tuticorinensis, P. umsongensis, P. vancouverensis, P. vranovensis, P. xanthomarina, Ralstonia eutropha, Rhodospirillum rubrum, Rhodobacter sphaeroides, Saccharomyces cerevisiae, Yarrowia lipolytica* and *Zymomonas mobilis*,
in particular *Pseudomonas putida, Escherichia coli* and *Burkholderia thailandensis* are particularly preferred.

Preferred cells according to the invention are able as the wild-type to form no or no detectable amounts of rhamnolipids and as the wild-type moreover have preferably no or no detectable activity of the enzymes $E_1$, $E_2$ and $E_3$.

It is advantageous according to the invention if the cell according to the invention is a cell which is able as the wild-type to form polyhydroxyalkanoates having chain lengths of the mono-alkanoate of $C_6$ to $C_{16}$. Such cells are, for example, *Burkholderia* sp., *Burkholderia thailandensis, Pseudomonas* sp., *Pseudomonas putida, Pseudomonas aeruginosa, Pseudomonas oleovorans, Pseudomonas stutzeri, Pseudomonas fluorescens, Pseudomonas citronellolis, Pseudomonas resinovorans, Comamonas testosteroni, Aeromonas hydrophila, Cupriavidus necator, Alcaligenes latus* and *Ralstonia eutropha*. In this connection, preferred cells according to the invention are genetically modified such that, compared to their wild-type, they are able to form fewer polyhydroxyalkanoates.

Such cells are described, for example, in De Eugenio et al., Environ Microbiol. 2010. 12(1):207-21 and Rehm et al., Appl Environ Microbiol. 2001. 67(7):3102-9.

Such a cell, able to form fewer polyhydroxyalkanoates compared to its wild-type, is in particular characterized in that, compared to its wild-type, it has a decreased activity of at least one enzyme $E_9$ or $E_{10}$,
wherein $E_9$ represents a polyhydroxyalkanoate synthase, EC:2.3.1.-, in particular having polypeptide sequence Seq ID No. 30 or Seq ID No. 32 or having a polypeptide sequence in which up to 25%, preferably up to 20%, particularly preferably up to 15% in particular up to 10, 9, 8, 7, 6, 5, 4, 3, 2, 1% of the amino acid radicals compared to the respective reference sequence Seq ID No. 30 or Seq ID No. 32 are modified by deletion, insertion, substitution or a combination thereof and that still has at least 10%, preferably 50%, particularly preferably 80%, in particular more than 90% of the enzymatic activity of the enzyme having the respective reference sequence Seq ID No. 30 or Seq ID No. 32, wherein enzymatic activity for an enzyme $E_9$ is understood as meaning the ability to convert 3-hydroxy-alkanoyl-coenzyme A to poly-3-hydroxyalkanoic acid, in particular 3-hydroxytetradecanoyl-coenzyme A to poly-3-hydroxytetradecanoic acid, and $E_{10}$ represents a 3-hydroxyalkanoyl-ACP:coenzyme A transferase, in particular having polypeptide sequence Seq ID No. 34 or Seq ID No. 36 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the respective reference sequence Seq ID No. 34 or Seq ID No. 36 by deletion, insertion, substitution or a combination thereof and that still has at least 10%, preferably 50%, particularly preferably 80%, in particular more than 90% of the enzymatic activity of the enzyme having the respective reference sequence Seq ID No. 34 or Seq ID No. 36, wherein enzymatic activity for an enzyme $E_{10}$ is understood as meaning the ability to convert 3-hydroxyalkanoyl-ACP to 3-hydroxy-alkananoyl-coenzyme A, in particular 3-hydroxyalkananoyl-ACP to 3-hydroxytetradecanoyl-coenzyme A.

For a general survey compare FIG. 1.

The activity of the enzyme $E_9$ is then determined using the samples obtained as described above for the enzymes $E_1$ to $E_3$, by first mixing 560 μl of 100 mM tris/HCl, pH 7.5, 20 μl of 35 mM DTNB in DMSO and 20 μl of 41 mM 3-hydroxydecanoyl-coenzyme A. Subsequently, 5 μg of purified enzyme $E_9$ in 100 μl of tris/HCl, pH 7.5 are added, and subsequently the increase in the extinction at 412 nm (caused by addition of 5,5'-dithiobis(2-nitrobenzoate) (DTNB) to free SH groups) over time (ΔE/min) is recorded continuously for 1 min in a spectrophotometer.

The activity of the enzyme $E_{10}$ is then determined using the samples obtained as described above for the enzymes $E_1$ to $E_3$. The standard assay contains 3 mM $MgCl_2$, 40 μM hydroxydecanoyl-coenzyme A and 20 μM E. coli ACP in 50 mM tris-HCl, pH 7.5, in a total volume of 200 μl. The reaction is started by addition of 5 μg of purified enzyme $E_{10}$ in 50 μl of tris/HCl, pH 7.5 and incubated for 1 h at 30° C. The reaction is stopped by addition of 50% (w/v) trichloroacetic acid and 10 mg/ml of BSA (30 μl). Released coenzyme A is determined spectrophotometrically by recording the increase in the extinction at 412 nm, caused by addition of 5,5'-dithiobis(2-nitrobenzoate) (DTNB) to free SH groups, over time.

The formulation "decreased activity of an enzyme $E_x$" used is accordingly preferably understood as meaning an activity decreased by a factor of at least 0.5, particularly preferably of at least 0.1, moreover preferably of at least 0.01, moreover even more preferably of at least 0.001 and most preferably of at least 0.0001. The formulation "decreased activity" also comprises no detectable activity ("activity of zero"). The decrease in the activity of a certain enzyme can be effected, for example, by selective mutation or by other measures known to the person skilled in the art for decreasing the activity of a certain enzyme.

Methods for decreasing enzymatic activities in microorganisms are known to the person skilled in the art.

In particular, molecular biological techniques offer themselves here. The person skilled in the art finds instructions for the modification and decrease of protein expression and concomitant lowering of enzyme activity especially for Pseudomonas and Burkholderia, in particular for interrupting specific genes, for example, in Dubeau et al. 2009. BMC Microbiology 9:263; Singh & Röhm. Microbiology. 2008. 154:797-809 or Lee et al. FEMS Microbiol Lett. 2009. 297(1):38-48.

Cells preferred according to the invention are characterized in that the decrease in the enzymatic activity is achieved by modification of a gene comprising one of the said nucleic acid sequences, wherein the modification is selected from the group comprising, preferably consisting of, insertion of foreign DNA in the gene, deletion of at least parts of the gene, point mutations in the gene sequence, RNA interference (siRNA), antisense RNA or modification (insertion, deletion or point mutations) of regulatory sequences, such as, for example, promoters and terminators or of ribosome binding sites, which flank the gene.

Foreign DNA is to be understood in this connection as meaning any DNA sequence which is "foreign" to the gene (and not to the organism), i.e. endogenous DNA sequences can also function in this connection as "foreign DNA".

In this connection it is particularly preferred that the gene is interrupted by insertion of a selection marker gene, thus the foreign DNA is a selection marker gene, wherein preferably the insertion was effected by homologous recombination in the gene locus.

In a preferred embodiment of the cell according to the invention, the cells concerned are Pseudomonas putida cells, which have a decreased polyhydroxyalkanoate synthesis compared to their wild-type. Such cells are described, for example, in Ren et al., Journal Applied Microbiology and Biotechnology 1998 June, 49(6):743-50 as GPp121, GPp122, GPp123 and GPp124, in Huisman et al., J Biol Chem. 1991 Feb. 5; 266(4):2191-8 as GPp104 as well as in De Eugenio et al., Environ Microbial. 2010. 12(1):207-21 as KT42C1 and in Ouyang et al. Macromol Biosci. 2007. 7(2):227-33 as KTOY01 and KTOY02 and are preferred cells according to the invention.

For the case where the cell according to the invention is able to form a rhamnolipid having m=1, it is preferred that the radical

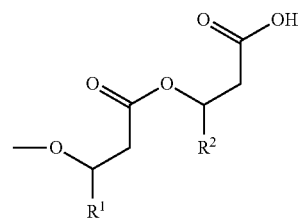

defined by means of $R^1$ and $R^2$ is derived from 3-hydroxyoctanoyl-3-hydroxyoctanoic acid, 3-hydroxyoctanoyl-3-hydroxydecanoic acid, 3-hydroxydecanoyl-3-hydroxyoctanoic acid, 3-hydroxyoctanoyl-3-hydroxydecenoic acid, 3-hydroxydecenoyl-3-hydroxyoctanoic acid, 3-hydroxyoctanoyl-3-hydroxydodecanoic acid, 3-hydroxydodecanoyl-3-hydroxyoctanoic acid, 3-hydroxyoctanoyl-3-hydroxydodecenoic acid, 3-hydroxydodecenoyl-3-hydroxyoctanoic acid, 3-hydroxydecanoyl-3-hydroxydecanoic acid, 3-hydroxydecenoyl-3-hydroxydecenoic acid, 3-hydroxydecenoyl-3-hydroxydecanoic acid, 3-hydroxydecanoyl-3-hydroxydecenoic acid, 3-hydroxydecenoyl-3-hydroxydodecanoic acid, 3-hydroxydodecanoyl-3-hydroxydecanoic acid, 3-hydroxydecanoyl-3-hydroxydodecenoic acid, 3-hydroxydodecenoyl-3-hydroxydecanoic acid, 3-hydroxydecanoyl-3-hydroxytetradecenoic acid, 3-hydroxytetradecanoyl-3-hydroxydecenoic acid, 3-hydroxydecenoyl-3-hydroxydecanoic acid, 3-hydroxydecanoyl-3-hydroxytetradecanoic acid, 3-hydroxytetradecanoyl-3- hydroxydecanoic acid, 3-hydroxydecanoyl-3-hydroxytetradecenoic acid, 3-hydroxytetradecenoyl-3-hydroxydecanoic acid, 3-hydroxydodecanoyl-3-hydroxydodecanoic acid, 3-hydroxydodecenoyl-3-hydroxydodecanoic acid, 3-hydroxydodecanoyl-3-hydroxydodecenoic acid, 3-hydroxydodecanoyl-3-hydroxytetradecanoic acid, 3-hydroxytetradecanoyl-3-hydroxydodecanoic acid, 3-hydroxytetradecanoyl-3-hydroxytetradecanoic acid, 3-hydroxyhexadecanoyl-3-hydroxytetradecanoic acid, 3-hydroxytetradecanoyl-3-hydroxyhexadecanoic acid or 3-hydroxyhexadecanoyl-3-hydroxyhexadecanoic acid.

It is obvious to the person skilled in the art that a cell according to the invention is also able to form mixtures of different rhamnolipids of the general formula (I).

In this connection, it is preferred that the cells according to the invention are able to form mixtures of rhamnolipids of the general formula (I), which are characterized in that in more than 80% by weight, preferably more than 90% by weight, particularly preferably more than 95% by weight of the rhamnolipids formed n is =1 and the radical defined by means of $R^1$ and $R^2$ is derived in less than 10% by weight, preferably less than 5% by weight, particularly preferably less than 2% by weight of the rhamnolipids formed, from 3-hydroxydecanoyl-3-hydroxyoctanoic acid or 3-hydroxyoctanoyl-3-hydroxydecanoic acid,
wherein the % by weight indicated refers to the sum of all rhamnolipids of the general formula (I) formed.

It is advantageous if the cell according to the invention has additionally been genetically modified with respect to $E_1$ to $E_3$ such that, compared to its wild-type, it has an increased activity as in each case specified below of at least one of the enzymes selected from the group consisting of
at least one enzyme $E_4$, a dTTP:α-D-glucose-1-phosphate thymidylyl transferase, EC 2.7.7.24, in particular one having polypeptide sequence Seq ID No. 10 or having a polypeptide sequence in which up to 25%, preferably up to 20%, particularly preferably up to 15% in particular up to 10, 9, 8, 7, 6, 5, 4, 3, 2, 1% of the amino acid radicals compared to the reference sequence Seq ID No. 10 are modified by deletion, insertion, substitution or a combination thereof and that still has at least 10%, preferably 50%, particularly preferably 80%, in particular more than 90% of the enzymatic activity of the enzyme having the reference sequence Seq ID No. 10, wherein enzymatic activity for an enzyme $E_4$ is understood as meaning the ability to convert α-D-glucose-1-phosphate and dTTP to dTDP-glucose,
at least one enzyme $E_5$, a dTTP-glucose-4,6-hydrolyase, EC 4.2.1.46, in particular one having polypeptide sequence Seq ID No. 12 or having a polypeptide sequence in which up to 25%, preferably up to 20%, particularly preferably up to 15% in particular up to 10, 9, 8, 7, 6, 5, 4, 3, 2, 1% of the amino acid radicals are modified compared to the reference sequence Seq ID No. 12 by deletion, insertion, substitution or a combination thereof and that still has at least 10%, preferably 50%, particularly preferably 80%, in particular more than 90% of the enzymatic activity of the enzyme having the reference sequence Seq ID No. 12, wherein enzymatic activity for an enzyme $E_5$ is understood as meaning the ability to convert dTDP-glucose to dTDP-4-dehydro-6-deoxy-D-glucose,
at least one enzyme $E_6$, a dTDP-4-dehydrorhamnose-3,5-epimerase, EC 5.1.3.13, in particular one having polypeptide sequence Seq ID No. 14 or having a polypeptide sequence in which up to 25%, preferably up to 20%, particularly preferably up to 15% in particular up to 10, 9, 8, 7, 6, 5, 4, 3, 2, 1% of the amino acid radicals compared to the reference sequence Seq ID No. 14 are modified by deletion, insertion, substitution or a combination thereof and that still has at least 10%, preferably 50%, particularly preferably 80%, in particular more than 90% of the enzymatic activity of the enzyme having the reference sequence Seq ID No. 14, wherein enzymatic activity for an enzyme $E_6$ is understood as meaning the ability to convert dTDP-4-dehydro-6-deoxy-D-glucose to dTDP-4-dehydro-6-deoxy-L-mannose and
at least one enzyme $E_7$, a dTDP-4-dehydrorhamnose reductase, EC 1.1.1.133, in particular one having polypeptide sequence Seq ID No. 16 or having a polypeptide sequence in which up to 25%, preferably up to 20%, particularly preferably up to 15% in particular up to 10, 9, 8, 7, 6, 5, 4, 3, 2, 1% of the amino acid radicals compared to the reference sequence Seq ID No. 16 are modified by deletion, insertion, substitution or a combination thereof and that still has at least 10%, preferably 50%, particularly preferably 80%, in particular more than 90% of the enzymatic activity of the enzyme having the reference sequence Seq ID No. 16, wherein enzymatic activity for an enzyme $E_7$ is understood as meaning the ability to convert dTDP-4-dehydro-6-deoxy-L-mannose to dTDP-6-deoxy-L-mannose.

The activity of the enzyme $E_4$ is determined using the samples obtained as above for the enzymes $E_1$ to $E_3$, by incubating α-D-glucose-1-phosphate (1.3 mM) with dTTP (5 mM) and 5 μg of purified enzyme $E_4$ in 50 μl of sodium phosphate buffer, pH 8.5 and stopping the reaction after 5, 10 and 20 min incubation at 30° C. by addition of 20 μl of chloroform. The mixture is then vortexed and centrifuged for 5 min at 16,000 g and room temperature. The aqueous phase is transferred to a new reaction vessel and the organic phase is extracted again with 80 μl of water. Both aqueous phases are combined and analyzed by means of HPLC. A Phenosphere ODS2 column (250×4.6 mm; Phenomenex, Torrance, USA) or a Spheresorb ODS2 column (250×4.6 mm; Waters, Milford, USA) is used here. The elution of the analytes takes place at a flow rate of 1 ml min$^{-1}$ using 0.5 M KH$_2$PO$_4$ (eluent A) for 15 min, followed by a linear gradient up to 80% eluent A and 20% methanol over a period of 14 min at a flow rate of 0.7 ml min$^{-1}$. Analytes which elute from the ODS2 columns are then injected into a Phenosphere SAX ion exchanger column (250×4.6 mm; Phenomenex, Torrance, USA) and the analytes are eluted using a flow rate of 1 ml min$^{-1}$ and a linear ammonium formate gradient (2 to 600 mM over 25 min). The quantification of dTDP-glucose then takes place by means of its UV absorption using a photodiode array detector (DAD). The absorption maximum of thymidine is at 267 nm. The calibration takes place by means of authentic nucleotide sugar (Sigma-Aldrich, Munich, USA).

The activity of the enzyme $E_5$ is then determined using the samples obtained as described above for the enzymes $E_1$ to $E_3$ by incubating dTDP-α-D-glucose (1.3 mM) with 5 μg of purified enzyme $E_5$ in 50 μl of sodium phosphate buffer, pH 8.5, and stopping the reaction after 5, 10 and 20 min incubation at 30° C. by addition of 20 μl of chloroform. The mixture is then vortexed and centrifuged for 5 min at 16,000 g and room temperature. The aqueous phase is transferred to a new reaction vessel and the organic phase is again extracted with 80 μl of water. Both aqueous phases are combined and analyzed by means of HPLC. A Phenosphere ODS2 column (250×4.6 mm; Phenomenex, Torrance, USA) or a Spheresorb ODS2 column (250×4.6 mm; Waters, Milford, USA) is used here. The elution of the analytes takes place at a flow rate of 1 ml min$^{-1}$ using 0.5 M KH$_2$PO$_4$ (eluent A) for 15 min, followed by a linear gradient of up to 80% eluent A and 20% methanol over a period of 14 min at a flow rate of 0.7 ml min$^{-1}$. Analytes which elute from the ODS2 columns are then injected into a Phenosphere SAX ion exchanger column (250×4.6 mm; Phenomenex, Torrance, USA) and the analytes are eluted using a flow rate of 1 ml min$^{-1}$ and a linear ammonium formate gradient (2 to 600 mM over 25 min). The quantification of dTDP-glucose and dTDP-4-dehydro-6-deoxy-D-glucose then takes place by means of their UV absorption using a photodiode array detector (DAD). The absorption maximum of thymidine is at 267 nm. The calibration takes place by means of authentic nucleotide sugar (Sigma-Aldrich, Munich, USA).

The activity of the enzyme $E_6$ is then determined using the samples obtained as described above for the enzymes $E_1$ to $E_3$, by first incubating dTDP-α-D-glucose (1.3 mM) with 5 μg of purified enzyme $E_5$ in 50 μl of sodium phosphate buffer, pH 8.5, for 10 min at 30° C. Subsequently, 0.5 μg of purified enzyme $E_6$ are added, and after 5, 10 and 20 min incubation at 30° C. the reaction is stopped by addition of 20 μl of chloroform. The mixture is then vortexed and centrifuged for 5 min at 16,000 g and room temperature. The aqueous phase is transferred to a new reaction vessel and the organic phase is again extracted with 80 μl of water. Both aqueous phases are combined and analyzed by means of HPLC. A Phenosphere ODS2 column (250×4.6 mm; Phenomenex, Torrance, USA) or a Spheresorb ODS2 column (250×4.6 mm; Waters, Milford, USA) is used here. The elution of the analytes takes place at a flow rate of 1 ml min$^{-1}$ using 0.5 M $KH_2PO_4$ (eluent A) for 15 min, followed by a linear gradient of up to 80% eluent A and 20% methanol over a period of 14 min at a flow rate of 0.7 ml min$^{-1}$. Analytes which elute from the ODS2 columns are then injected into a Phenosphere SAX ion exchanger column (250×4.6 mm; Phenomenex, Torrance, USA) and the analytes are eluted using a flow rate of 1 ml min$^{-1}$ and a linear ammonium formate gradient (2 to 600 mM over 25 min). The quantification of dTDP-glucose, dTDP-4-dehydro-6-deoxy-D-glucose and dTDP-6-deoxy-L-mannose then takes place by means of their UV absorption using a photodiode array detector (DAD). The absorption maximum of thymidine is at 267 nm. The calibration takes place by means of authentic nucleotide sugar (Sigma-Aldrich, Munich, USA).

The activity of the enzyme $E_7$ is then determined using the samples obtained as described above for the enzymes $E_1$ to $E_3$, by first incubating dTDP-α-D-glucose (1.3 mM) with 5 μg of purified enzyme $E_5$ in 50 μl of sodium phosphate buffer, pH 8.5, for 10 min at 30° C. Subsequently, 5 μg of purified enzyme $E_6$ and 0.5 μg of purified enzyme $E_7$ as well as NADPH (10 mM) are added, and after incubation at 30° C. for 5, 10 and 20 min the reaction is stopped by addition of 20 μl chloroform. The mixture is then vortexed and centrifuged for 5 min at 16,000 g and room temperature. The aqueous phase is transferred to a new reaction vessel and the organic phase is again extracted with 80 μl of water. Both aqueous phases are combined and analyzed by means of HPLC. A Phenosphere ODS2 column (250×4.6 mm; Phenomenex, Torrance, USA) or a Spheresorb ODS2 column (250×4.6 mm; Waters, Milford, USA) is used here. The elution of the analytes takes place at a flow rate of 1 ml min$^{-1}$ using 0.5 M $KH_2PO_4$ (eluent A) for 15 min, followed by a linear gradient of up to 80% eluent A and 20% methanol over a period of 14 min at a flow rate of 0.7 ml min$^{-1}$. Analytes which elute from the ODS2 columns are then injected into a Phenosphere SAX ion exchanger column (250×4.6 mm; Phenomenex, Torrance, USA) and the analytes are eluted using a flow rate of 1 ml min$^{-1}$ and a linear ammonium formate gradient (2 to 600 mM over 25 min). The quantification of dTDP-glucose, dTDP-4-dehydro-6-deoxy-D-glucose, dTDP-6-deoxy-L-mannose and dTDP-4-dehydro-6-deoxy-L-mannose then takes place by means of their UV absorption using a photodiode array detector (DAD). The absorption maximum of thymidine is 267 nm. The calibration takes place by means of authentic nucleotide sugar (Sigma-Aldrich, Munich, USA).

Cells according to the invention are preferred, which have increased activities of the following enzyme combinations: $E_4E_5$, $E_4E_6$, $E_4E_7$, $E_5E_6$, $E_5E_7$, $E_6E_7$, $E_4E_5E_6$, $E_4E_5E_7$, $E_5E_6E_7$, $E_4E_6E_7$, $E_4E_5E_6E_7$, of which the combination $E_4E_5E_6E_7$ is particularly preferred.

It can be advantageous according to the invention if the cell according to the invention has been genetically modified in the fatty acid biosynthesis such that the enzymatic reactions, which lead to the conversion of acyl-ACP and malonyl-coenzyme A to 3-ketoacyl-ACP and/or to the conversion of 3-ketoacyl-ACP to (R)-3-hydroxyalkanoyl-ACP, are increased. Additionally or alternatively it can be advantageous according to the invention if the cell according to the invention has been genetically modified in the fatty acid biosynthesis such that the enzymatic reactions, which lead to the conversion of (R)-3-hydroxyalkanoyl-ACP to trans-2-enoyl-ACP and/or to the conversion of trans-2-enoyl-ACP to acyl-ACP, are attenuated.

It can be just as advantageous if the cell according to the invention has been genetically modified in the β-oxidation of fatty acids such that the enzymatic reactions, which lead to the conversion of acyl-coenzyme A to trans-2-enoyl-coenzyme A and/or to the conversion of trans-2-enoyl-coenzyme A to (S)-3-hydroxyalkanoyl-coenzyme A, are increased. Additionally or alternatively, it can be advantageous according to the invention if the cell according to the invention in the β-oxidation of fatty acids has been genetically modified such that the enzymatic reactions, which lead to the conversion of (S)-3-hydroxyalkanoyl-coenzyme A to 3-ketoacyl-coenzyme A and/or to the conversion of 3-ketoacyl-coenzyme A to acyl-coenzyme A and acetyl-coenzyme A, are diminished.

For a general survey compare FIG. 1.

Since the cells according to the invention can be used advantageously for the production of rhamnolipids and since these lipids are subsequently optionally purified, it is advantageous if the cells according to the invention have an increased activity compared to their wild-type of at least an enzyme $E_8$, which catalyzes the export of a rhamnolipid of the general formula (I) from the cell into the surrounding medium.

Preferably, in this connection proteins $E_8$ are selected from the group consisting of an enzyme $E_8$ having polypeptide sequence Seq ID No. 8, Seq ID No. 24, Seq ID No. 26 or Seq ID No. 28 or having a polypeptide sequence in which up to 25%, preferably up to 20%, particularly preferably up to 15% in particular up to 10, 9, 8, 7, 6, 5, 4, 3, 2, 1% of the amino acid radicals are modified by deletion, insertion, substitution or a combination thereof compared to the respective reference sequence Seq ID No. 8, Seq ID No. 24, Seq ID No. 26 or Seq ID No. 28 and that still has at least 50%, preferably 65%, particularly preferably 80%, in particular more than 90% of the enzymatic activity of the enzyme having the respective reference sequence Seq ID No. 8, Seq ID No. 24, Seq ID No. 26 or Seq ID No. 28, wherein enzymatic activity for an enzyme $E_8$ is understood as meaning the ability to export a rhamnolipid of the general formula (I) from the cell into the surrounding medium.

A further, preferred embodiment of cells according to the invention is characterized in that it contains at least one of the nucleic acids or vectors according to the invention mentioned below.

Cells according to the invention can advantageously be used for the production of rhamnolipids. Thus a further subject of the invention is the use of cells according to the invention for the production of compounds of the general formula (I).

A further subject of the present invention is a method for producing rhamnolipids of the general formula (I),
wherein
m=2, 1 or 0, in particular 1 or 0,
n=1 or 0, in particular 1,
$R^1$ and $R^2$=independently of one another identical or different organic radical having 2 to 24, preferably 5 to 13 carbon atoms, in particular optionally branched, optionally substituted, in particular hydroxy-substituted, optionally unsaturated, in particular optionally mono-, di- or tri-unsaturated, alkyl radical, preferably that selected from the group consisting of pentenyl, heptenyl, nonenyl, undecenyl and tridecenyl and $(CH_2)_o$—$CH_3$ having o=1 to 23, preferably 4 to 12,
comprising the process steps
I) bringing into contact the cell according to the invention with a medium containing a carbon source
II) culturing the cell under conditions that make it possible for the cell to form rhamnolipid from the carbon source and
III) optionally isolating the rhamnolipids formed.

The genetically modified cells according to the invention can be brought into contact with the nutrient medium continuously or discontinuously in the batch process (batch culture) or in the fed-batch process (feed process) or repeated fed-batch process (repetitive feed process) for the purpose of the production of the abovementioned products and thus cultured. A semi-continuous process is also conceivable, as is described in GB-A-1009370. A summary of known culturing methods are described in the textbook of Chmiel ("Bioprozesstechnik 1. Einführung in die Bioverfahrenstechnik" [Bioprocess Technology 1. Introduction to the Bioprocess Technique] (Gustav Fischer Verlag, Stuttgart, 1991)) or in the textbook of Storhas ("Bioreaktoren and periphere Einrichtungen" [Bioreactors and Peripheral Devices], Vieweg Verlag, Brunswick/Wiesbaden, 1994).

The culture medium to be used must satisfy in a suitable manner the demands of the respective strains. Descriptions of culture media of different yeast strains are contained, for example, in "Nonconventional yeast in biotechnology" (Ed. Klaus Wolf, Springer-Verlag Berlin, 1996). The carbon source used can be carbohydrates such as, for example, glucose, sucrose, arabinose, xylose, lactose, fructose, maltose, molasses, starch, cellulose and hemicellulose, vegetable and animal oils and fats such as, for example, soybean oil, safflower oil, peanut oil, hempseed oil, jatropha oil, coconut fat, calabash oil, linseed oil, corn oil, poppyseed oil, evening primrose oil, olive oil, palm kernel oil, palm oil, rapeseed oil, sesame oil, sunflower oil, grapeseed oil, walnut oil, wheat germ oil and coconut oil, fatty acids, such as, for example, caprylic acid, capric acid, lauric acid, myristic acid, palmitic acid, palmitoleic acid, stearic acid, arachidonic acid, behenic acid, oleic acid, linoleic acid, linolenic acid, gamma-linolenic acid and its methyl or ethyl ester as well as fatty acid mixtures, mono-, di- and triglycerides containing the fatty acids just mentioned, alcohols such as, for example, glycerol, ethanol and methanol, hydrocarbons such as methane, carbon-containing gases and gas mixtures, such as $CO$, $CO_2$, synthesis or flue gas, amino acids such as L-glutamate or L-valine or organic acids such as, for example, acetic acid. These substances can be used individually or as a mixture. The use of carbohydrates, in particular of monosaccharides, oligosaccharides or polysaccharides, as the carbon source as is described in U.S. Pat. No. 601,494 and U.S. Pat. No. 6,136,576 as well as of hydrocarbons, in particular of alkanes, alkenes and alkynes as well as the monocarboxylic acids derived therefrom and the mono-, di and triglycerides derived from these monocarboxylic acids, as well as of glycerol and acetate, is particularly preferred. Mono-, di- and triglycerides containing the esterification products of glycerol with caprylic acid, capric acid, lauric acid, myristic acid, palmitic acid, palmitoleic acid, stearic acid, arachidonic acid, behenic acid, oleic acid, linoleic acid, linolenic acid and/or gamma-linolenic acid are very particularly preferred.

It is a great advantage of the present invention that the cells according to the invention are able to form rhamnolipids from the simplest carbon sources such as, for example, glucose, sucrose or glycerol, such that a provision of longer-chain C sources in the medium during the method according to the invention is not necessary. Thus it is advantageous in the case of lack of availability that the medium in step I) of the method according to the invention contains no or no detectable amounts of carboxylic acids having a chain length of greater than six carbon atoms or esters or glycerides derivable from these.

The nitrogen source used can be organic nitrogen-containing compounds such as peptones, yeast extract, meat extract, malt extract, cornsteep water, soybean meal and urea or inorganic compounds such as ammonium sulfate, ammonium chloride, ammonium phosphate, ammonium carbonate and ammonium nitrate, ammonia, ammonium hydroxide or ammonia water. The nitrogen sources can be used individually or as a mixture.

The phosphorus source used can be phosphoric acid, potassium dihydrogenphosphate or dipotassium hydrogenphosphate or the corresponding sodium-containing salts. The culture medium must furthermore contain salts of metals such as, for example, magnesium sulfate or iron sulfate, which are necessary for growth. Finally, essential growth promoters such as amino acids and vitamins can be employed additionally to the abovementioned substances. Suitable precursors can moreover be added to the culture medium. The said feedstocks can be added to the culture in the form of a single batch or fed in a suitable manner during culturing.

Basic compounds such as sodium hydroxide, potassium hydroxide, ammonia or ammonia water or acidic compounds such as phosphoric acid or sulfuric acid are suitably employed for pH control of the culture. Antifoam agents such as, for example, fatty acid polyglycol esters can be employed for the control of the foam development. Suitable selectively acting substances such as, for example, antibiotics can be added to the medium for maintaining the stability of plasmids. To maintain aerobic conditions, oxygen or oxygen-containing gas mixtures such as, for example, air are incorporated into the culture.

The temperature of the culture is normally more than 20° C., preferably more than 25° C., it can also be more than 40° C., wherein advantageously a culturing temperature of 95° C., particularly preferably 90° C. and most preferably 80° C. is not exceeded.

In step III) of the method according to the invention, the rhamnolipids formed by the cells can optionally be isolated from the cells and/or the nutrient medium, wherein for the isolation all methods known to the person skilled in the art for the isolation of low molecular weight substances from complex compositions are possible, such as, for example, filtration, extraction, adsorption (chromatography) or crystallization.

Moreover, the product phase contains residues of biomass and various impurities, such as oils, fatty acids and other nutrient media constituents. The separation of the impurities preferably takes place in a solvent-free process. Thus, for example, the product phase can be diluted with water to facilitate the adjustment of the pH. The product and aqueous phases can then be homogenized by converting the rhamnolipids into a water-soluble form by lowering or raising the pH by acids or alkalis. Potentially, the solubilization of the rhamnolipids in the aqueous phase can be assisted by incubation at higher temperatures, e.g. at 60 to 90° C., and constant mixing. By subsequent raising or lowering of the pH by alkalis or acids the rhamnolipids can then again be converted into a water-insoluble form, such that they can easily be separated from the aqueous phase. The product phase can then be washed once or several times with water to remove the water-soluble impurities.

Oil residues can be separated off, for example by extraction by means of suitable solvents advantageously by means of organic solvents. An alkane such as, for example, n-hexane is preferred as a solvent.

The separation of the product from the aqueous phase can be effected alternatively to the solvent-free process described above using a suitable solvent, e.g. an ester such as, for example, ethyl acetate or butyl acetate. The said extraction steps can be carried out in any desired sequence.

In this connection, solvents are preferably employed, in particular organic solvents. n-Pentanol is preferred as a solvent. A distillation, for example, takes place for the removal of the solvent. Subsequently, the lyophilized product can be further purified, for example by means of chromatographic methods. By way of example, at this point precipitation by means of suitable solvents, extraction by means of suitable solvents, complexation, for example by means of cyclodextrins or cyclodextrin derivatives, crystallization, purification or isolation by means of chromatographic methods or conversion of the rhamnolipids into easily separable derivatives may be mentioned.

The rhamnolipids that can be produced using the method according to the invention are likewise a subject of the present invention, in particular also the rhamnolipid mixtures described above, that can be produced using the method according to the invention.

The rhamnolipids and mixtures that can be produced using the method according to the invention can advantageously be employed in cleaning agents, in cosmetic or pharmaceutical formulations as well as in plant protection formulations.

Thus a further subject of the present invention is the use of the rhamnolipids obtained using the method according to the invention for the production of cosmetic, dermatological or pharmaceutical formulations, of plant protection formulations and of care and cleaning agents and surfactant concentrates.

The term "care agents" is understood here as meaning a formulation that fulfills the purpose of maintaining an article in its original form, reducing or avoiding the effects of external influences (e.g. time, light, temperature, pressure, pollution, chemical reaction with other reactive compounds coming into contact with the article) such as, for example, aging, pollution, material fatigue, or even improving desired positive properties of the article. For the last point, for example, an improved hair gloss or a greater elasticity of the article considered may be mentioned.

"Plant protection formulations" are to be understood as meaning those formulations that by the nature of their preparation are obviously used for plant protection; this is in particular the case if at least one compound from the classes consisting of the herbicides, fungicides, insecticides, acaricides, nematicides, protective substances against bird damage, plant nutrients and soil structure-improving agents is contained in the formulation.

According to the invention, rhamnolipids produced using the method according to the invention are preferably used in care and cleaning agents for housekeeping, industry, in particular for hard surfaces, leather or textiles.

A contribution to achieving the object is provided by an isolated nucleic acid, which contains at least in each case a sequence selected from the three groups [A1 to G1], [A2 to G2] and [A3 to G3],
wherein
the group [A1 to G1] consists of the following sequences:
A1a) a sequence according to Seq ID No. 1, wherein this sequence codes for a protein, which is able
to convert 3-hydroxydecanoyl-ACP via 3-hydroxydecanoyl-3-hydroxydecanoyl-ACP to 3-hydroxydecanoyl-3-hydroxydecanoic acid,
B1a) an intron-free sequence that is derived from a sequence according to A1a) and that encodes the same protein or peptide as the sequence according to Seq ID No. 1,
C1a) a sequence that encodes a protein or peptide that comprises the amino acid sequence according to Seq ID No. 2, and that is preferably able
to convert 3-hydroxydecanoyl-ACP via 3-hydroxydecanoyl-3-hydroxydecanoyl-ACP to 3-hydroxydecanoyl-3-hydroxydecanoic acid,
D1a) a sequence that is identical with a sequence according to one of the groups A1a) to
C1a), particularly preferably according to group A1a), to at least 70%, particularly preferably to at least 90%, moreover preferably to at least 95% and most preferably to at least 99%, wherein this sequence preferably codes for a protein or peptide, which is able to convert 3-hydroxydecanoyl-ACP via 3-hydroxydecanoyl-3-hydroxydecanoyl-ACP to 3-hydroxydecanoyl-3-hydroxydecanoic acid,
E1a) a sequence that hybridizes or, taking into consideration the degeneracy of the genetic code, would hybridize with the complementary strand of a sequence according to one of the groups A1a) to D1a), particularly preferably according to group A1a), wherein this sequence preferably codes for a protein or peptide, which is able
to convert 3-hydroxydecanoyl-ACP via 3-hydroxydecanoyl-3-hydroxydecanoyl-ACP to 3-hydroxydecanoyl-3-hydroxydecanoic acid,
F1a) a derivative of a sequence according to one of the groups A1a) to E1a), particularly preferably according to group A1a), obtained by substitution, addition, inversion and/or deletion of at least one base, preferably of at least 2 bases, moreover preferably of at least 5 bases and most preferably of at least 10 bases, but preferably of not more than 100 bases, particularly preferably of not more than 50 bases and most preferably of not more than 25 bases, wherein this derivative preferably codes for a protein or peptide, which is able
to convert 3-hydroxydecanoyl-ACP via 3-hydroxydecanoyl-3-hydroxydecanoyl-ACP to 3-hydroxydecanoyl-3-hydroxydecanoic acid, G1a) a complementary sequence to a sequence according to one of the groups A1a) to F1a), particularly preferably according to group A1a), A1b) a sequence according to Seq ID No. 17, wherein this sequence codes for a protein, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, B1b) an intron-free sequence that is derived from a sequence according to A1b) and that encodes the same protein or peptide as the sequence according to Seq ID No. 17, C1b) a sequence that encodes a protein or peptide that comprises the amino acid sequence according to Seq ID No. 18, and that preferably is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, D1b) a sequence that is identical with a sequence according to one of the groups A1b) to C1b), particularly preferably according to group A1b), to at least 70%, particularly preferably to at least 90%, moreover preferably to at least 95% and most preferably to at least 99%, wherein this sequence preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, E1b) a sequence that hybridizes or, taking into consideration the degeneracy of the genetic code, would hybridize with the complementary strand of a sequence according to one of the groups A1b) to D1b), particularly preferably according to group A1b), wherein this sequence preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, F1b) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A1b) to E1b), particularly preferably according to group A1b), wherein this derivative preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, and G1b) a complementary sequence to a sequence according to one of the groups A1b) to F1b), particularly preferably according to group A1b), and A1c) a sequence according to Seq ID No. 77, wherein this sequence codes for a protein, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, B1c) an intron-free sequence that is derived from a sequence according to A1c) and that encodes the same protein or peptide as the sequence according to Seq ID No. 77, C1c) a sequence that encodes a protein or peptide that comprises the amino acid sequence according to Seq ID No. 78, and that preferably is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, D1c) a sequence that is identical with a sequence according to one of the groups A1c) to C1c), particularly preferably according to group A1c), to at least 70%, particularly preferably to at least 90%, moreover preferably to at least 95% and most preferably to at least 99%, wherein this sequence preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, E1c) a sequence that hybridizes or, taking into consideration the degeneracy of the genetic code, would hybridize with the complementary strand of a sequence according to one of the groups A1c) to D1c), particularly preferably according to group A1c), wherein this sequence preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, F1c) a derivative obtained by substitution, addition, inversion and/or deletion of at least one base, preferably of at least 2 bases, moreover preferably of at least 5 bases and most preferably of at least 10 bases, but preferably of not more than 100 bases, particularly preferably of not more than 50 bases and most preferably of not more than 25 bases of a sequence according to one of the groups A1c) to E1c), particularly preferably according to group A1c), wherein this derivative preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, and G1c) a complementary sequence to a sequence according to one of the groups A1c) to F1c), particularly preferably according to group A1c), and A1d) a sequence according to Seq ID No. 79, wherein this sequence codes for a protein, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, B1d) an intron-free sequence that is derived from a sequence according to A1d) and that encodes the same protein or peptide as the sequence according to Seq ID No. 79, C1d) a sequence that encodes a protein or peptide that comprises the amino acid sequence according to Seq ID No. 80, and that preferably is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, D1d) a sequence that is identical with a sequence according to one of the groups A1d) to C1d), particularly preferably according to group A1d), to at least 70%, particularly preferably to at least 90%, moreover preferably to at least 95% and most preferably to at least 99%, wherein this sequence preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, E1d) a sequence that hybridizes or, taking into consideration the degeneracy of the genetic code, would hybridize with the complementary strand of a sequence according to one of the groups A1d) to D1d), particularly preferably according to group A1d), wherein this sequence preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, F1d) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A1d) to E1d), particularly preferably according to group A1d), wherein this derivative preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, and G1d) a complementary sequence to a sequence according to one of the groups A1d) to F1d), particularly preferably according to group A1d), and A1e) a sequence according to Seq ID No. 81, wherein this sequence codes for a protein, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, B1e) an intron-free sequence that is derived from a sequence according to A1e) and that encodes the same protein or peptide as the sequence according to Seq ID No. 81, C1e) a sequence that encodes a protein or peptide that comprises the amino acid sequence according to Seq ID No. 82, and that preferably is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, D1e) a sequence that is identical with a sequence according to one of the groups A1e) to C1e), particularly preferably according to group A1e), to at least 70%, particularly preferably to at least 90%, moreover preferably to at least 95% and most preferably to at least 99%, wherein this sequence preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, E1e) a sequence that hybridizes or, taking into consideration the degeneracy of the genetic code, would hybridize with the complementary strand of a sequence according to one of the groups A1e) to D1e), particularly preferably according to group A1e), wherein this sequence preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, F1e) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A1e) to E1e), particularly preferably according to group A1e), wherein this derivative preferably codes for a protein or peptide, which is able to convert 3-hydroxytetradecanoyl-ACP via 3-hydroxytetradecanoyl-3-hydroxytetradecanoyl-ACP to 3-hydroxytetradecanoyl-3-hydroxytetradecanoic acid, and G1e) a complementary sequence to a sequence according to one of the groups A1e) to F1e), particularly preferably according to group A1e), and the group [A2 to G2] consists of the following sequences:

A2a) a sequence according to Seq ID No. 3, wherein this sequence codes for a protein, which is able to convert dTDP-rhamnose and 3-hydroxydecanoyl-3-hydroxydecanoic acid to α-L-rhamnopyranosyl-3-hydroxydecanoyl-3-hydroxydecanoic acid, B2a) an intron-free sequence that is derived from a sequence according to A2a) and that encodes the same protein or peptide as the sequence according to Seq ID No. 3, C2a) a sequence that encodes a protein or peptide that comprises the amino acid sequence according to Seq ID No. 4, and which preferably is able to convert dTDP-rhamnose and 3-hydroxydecanoyl-3-hydroxydecanoic acid to α-L-rhamnopyranosyl-3-hydroxydecanoyl-3-hydroxydecanoic acid, D2a) a sequence that is identical with a sequence according to one of the groups A2a) to C2a), particularly preferably according to group A2a), to at least 80%, particularly preferably to at least 90%, moreover preferably to at least 95% and most preferably to at least 99%, wherein this sequence preferably codes for a protein or peptide, which is able to convert dTDP-rhamnose and 3-hydroxydecanoyl-3-hydroxydecanoic acid to α-L-rhamnopyranosyl-3-hydroxydecanoyl-3-hydroxydecanoic acid, E2a) a sequence that hybridizes or, taking into consideration the degeneracy of the genetic code, would hybridize with the complementary strand of a sequence according to one of the groups A2a) to D2a), particularly preferably according to group A2a), wherein this sequence preferably codes for a protein or peptide, which is able to convert dTDP-rhamnose and 3-hydroxydecanoyl-3-hydroxydecanoic acid to α-L-rhamnopyranosyl-3-hydroxydecanoyl-3-hydroxydecanoic acid, F2a) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A2a) to E2a), particularly preferably according to group A2a), wherein this derivative preferably codes for a protein or peptide, which is able to convert dTDP-rhamnose and 3-hydroxydecanoyl-3-hydroxydecanoic acid to α-L-rhamnopyranosyl-3-hydroxydecanoyl-3-hydroxydecanoic acid, G2a) a complementary sequence to a sequence according to one of the groups A2a) to F2a), particularly preferably according to group A2a), A2b) a sequence according to Seq ID No. 19, wherein this sequence codes for a protein, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, B2b) an intron-free sequence that is derived from a sequence according to A2b) and that encodes the same protein or peptide as the sequence according to Seq ID No. 19, C2b) a sequence that encodes a protein or peptide that comprises the amino acid sequence according to Seq ID No. 20, and which preferably is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, D2b) a sequence that is identical with a sequence according to one of the groups A2b) to C2b), particularly preferably according to group A2b), to at least 70%, particularly preferably to at least 90%, moreover preferably to at least 95% and most preferably to at least 99%, wherein this sequence preferably codes for a protein or peptide, which is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, E2b) a sequence that hybridizes or, taking into consideration the degeneracy of the genetic code, would hybridize with the complementary strand of a sequence according to one of the groups A2b) to D2b), particularly preferably according to group A2b), wherein this sequence preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
F2b) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A2b) to E2b), particularly preferably according to group A2b), wherein this derivative preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and
G2b) a complementary sequence to a sequence according to one of the groups A2b) to F2b), particularly preferably according to group A2b),
A2c) a sequence according to Seq ID No. 83, wherein this sequence codes for a protein, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
B2c) an intron-free sequence that is derived from a sequence according to A2c) and that encodes the same protein or peptide as the sequence according to Seq ID No. 83,
C2c) a sequence that encodes a protein or peptide that comprises the amino acid sequence according to Seq ID No. 84, and which preferably is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
D2c) a sequence that is identical with a sequence according to one of the groups A2c) to C2c), particularly preferably according to group A2c), to at least 70%, particularly preferably to at least 90%, moreover preferably to at least 95% and most preferably to at least 99%, wherein this sequence preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
E2c) a sequence that hybridizes or, taking into consideration the degeneracy of the genetic code, would hybridize with the complementary strand of a sequence according to one of the groups A2c) to D2c), particularly preferably according to group A2c), wherein this sequence preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
F2c) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A2c) to E2c), particularly preferably according to group A2c), wherein this derivative preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and
G2c) a complementary sequence to a sequence according to one of the groups A2c) to F2c), particularly preferably according to group A2c),
A2d) a sequence according to Seq ID No. 85, wherein this sequence codes for a protein, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
B2d) an intron-free sequence that is derived from a sequence according to A2d) and that encodes the same protein or peptide as the sequence according to Seq ID No. 85,
C2d) a sequence that encodes a protein or peptide that comprises the amino acid sequence according to Seq ID No. 86, and which preferably is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
D2d) a sequence that is identical with a sequence according to one of the groups A2d) to C2d), particularly preferably according to group A2d), to at least 70%, particularly preferably to at least 90%, moreover preferably to at least 95% and most preferably to at least 99%, wherein this sequence preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
E2d) a sequence that hybridizes or, taking into consideration the degeneracy of the genetic code, would hybridize with the complementary strand of a sequence according to one of the groups A2d) to D2d), particularly preferably according to group A2d), wherein this sequence preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
F2d) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A2d) to E2d), particularly preferably according to group A2d), wherein this derivative preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and
G2d) a complementary sequence to a sequence according to one of the groups A2d) to F2d), particularly preferably according to group A2d), and
A2e) a sequence according to Seq ID No. 87, wherein this sequence codes for a protein, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid,
B2e) an intron-free sequence that is derived from a sequence according to A2e) and that encodes the same protein or peptide as the sequence according to Seq ID No. 87,
C2e) a sequence that encodes a protein or peptide that comprises the amino acid sequence according to Seq ID No. 88, and which preferably is able to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, D2e) a sequence that is identical with a sequence according to one of the groups A2e) to C2e), particularly preferably according to group A2e), to at least 70%, particularly preferably to at least 90%, moreover preferably to at least 95% and most preferably to at least 99%, wherein this sequence preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, E2e) a sequence that hybridizes or, taking into consideration the degeneracy of the genetic code, would hybridize with the complementary strand of a sequence according to one of the groups A2e) to D2e), particularly preferably according to group A2e), wherein this sequence preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, F2e) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A2e) to E2e), particularly preferably according to group A2e), wherein this derivative preferably codes for a protein or peptide, which is able
to convert dTDP-rhamnose and 3-hydroxytetradecanoyl-3-hydroxytetradecanoic acid to α-L-rhamnopyranosyl-3-hydroxytetradecanoyl-3-hydroxytetradecanoic acid, and G2e) a complementary sequence to a sequence according to one of the groups A2e) to F2e), particularly preferably according to group A2e),
and
the group [A3 to G3] consists of the following sequences:
A3a) a sequence according to Seq ID No. 5, wherein this sequence codes for a protein, which is able
to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, B3a) an intron-free sequence that is derived from a sequence according to A3a) and that encodes the same protein or peptide as the sequence according to Seq ID No. 5, C3a) a sequence that encodes a protein or peptide that comprises the amino acid sequence according to Seq ID No. 6, and which preferably is able
to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, D3a) a sequence that is identical with a sequence according to one of the groups A3a) to C3a), particularly preferably according to group A3a), to at least 80%, particularly preferably to at least 90%, moreover preferably to at least 95% and most preferably to at least 99%, wherein this sequence preferably codes for a protein or peptide, which is able
to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, E3a) a sequence that hybridizes or, taking into consideration the degeneracy of the genetic code, would hybridize with the complementary strand of a sequence according to one of the groups A3a) to D3a), particularly preferably according to group A3a), wherein this sequence preferably codes for a protein or peptide, which is able
to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, F3a) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A3a) to E3a), particularly preferably according to group A3a), wherein this derivative preferably codes for a protein or peptide,
which is able
to convert dTDP-rhamnose and α-L-rhamnopyranosyl-3-hydroxydecanoyl-3-hydroxydecanoic acid to α-L-rhamnopyranosyl-(1-2)-α-L-rhamnopyranosyl-3-hydroxydecanoyl-3-hydroxydecanoic acid, G3a) a complementary sequence to a sequence according to one of the groups A3a) to F3a), particularly preferably according to group A3a), A3b) a sequence according to Seq ID No. 21, wherein this sequence codes for a protein, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, B3b) an intron-free sequence that is derived from a sequence according to A3b) and that encodes the same protein or peptide as the sequence according to Seq ID No. 21, C3b) a sequence that encodes a protein or peptide that comprises the amino acid sequence according to Seq ID No. 22, and which preferably is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, D3b) a sequence that is identical with a sequence according to one of the groups A3b) to C3b), particularly preferably according to group A3b), to at least 60%, particularly preferably to at least 90%, moreover preferably to at least 95% and most preferably to at least 99%, wherein this sequence preferably codes for a protein or peptide, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, E3b) a sequence that hybridizes or, taking into consideration the degeneracy of the genetic code, would hybridize with the complementary strand of a sequence according to one of the groups A3b) to D3b), particularly preferably according to group A3b), wherein this sequence preferably codes for a protein or peptide, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, F3b) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A3b) to E3b), particularly preferably according to group A3b), wherein this derivative preferably codes for a protein or peptide,
which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, and
G3b) a complementary sequence to a sequence according to one of the groups A3b) to F3b), particularly preferably according to group A3b),
A3c) a sequence according to Seq ID No. 89, wherein this sequence codes for a protein, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid,
B3c) an intron-free sequence that is derived from a sequence according to A3c) and that encodes the same protein or peptide as the sequence according to Seq ID No. 89,
C3c) a sequence that encodes a protein or peptide that comprises the amino acid sequence according to Seq ID No. 90, and which preferably is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid,
D3c) a sequence that is identical with a sequence according to one of the groups A3c) to C3c), particularly preferably according to group A3c), to at least 60%, particularly preferably to at least 90%, moreover preferably to at least 95% and most preferably to at least 99%, wherein this sequence preferably codes for a protein or peptide, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid,
E3c) a sequence that hybridizes or, taking into consideration the degeneracy of the genetic code, would hybridize with the complementary strand of a sequence according to one of the groups A3c) to D3c), particularly preferably according to group A3c), wherein this sequence preferably codes for a protein or peptide, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid,
F3c) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A3c) to E3c), particularly preferably according to group A3c), wherein this derivative preferably codes for a protein or peptide,
which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, and G3c) a complementary sequence to a sequence according to one of the groups A3c) to F3c), particularly preferably according to group A3c) and
A3d) a sequence according to Seq ID No. 91, wherein this sequence codes for a protein, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid,
B3d) an intron-free sequence that is derived from a sequence according to A3d) and that encodes the same protein or peptide as the sequence according to Seq ID No. 91,
C3d) a sequence that encodes a protein or peptide that comprises the amino acid sequence according to Seq ID No. 92, and which preferably is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid,
D3d) a sequence that is identical with a sequence according to one of the groups A3d) to C3d), particularly preferably according to group A3d), to at least 60%, particularly preferably to at least 90%, moreover preferably to at least 95% and most preferably to at least 99%, wherein this sequence preferably codes for a protein or peptide, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid,
E3d) a sequence that hybridizes or, taking into consideration the degeneracy of the genetic code, would hybridize with the complementary strand of a sequence according to one of the groups A3d) to D3d), particularly preferably according to group A3d), wherein this sequence preferably codes for a protein or peptide, which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid,
F3d) a derivative obtained by substitution, addition, inversion and/or deletion of at least one base, preferably of at least 2 bases, moreover preferably of at least 5 bases and most preferably at least 10 bases, but preferably of not more than 100 bases, particularly preferably of not more than 50 bases and most preferably of not more than 25 bases of a sequence according to one of the groups A3d) to E3d), particularly preferably according to group A3d), wherein this derivative preferably codes for a protein or peptide,
which is able
to convert dTDP-rhamnose and α-L-rhamnopyranosyl-3-hydroxytetradecanoyl-3-hydroxytetradecanoic acid to α-L-rhamnopyranosyl-(1-2)-α-L-rhamnopyranosyl-3-hydroxytetradecanoyl-3-hydroxytetradecanoic acid, and
G3d) a complementary sequence to a sequence according to one of the groups A3d) to F3d), particularly preferably according to group A3d).

The "nucleotide identity" or "amino acid identity" is determined here with the aid of known methods. Generally, specific computer programs having algorithms taking into consideration special requirements are used.

Preferred methods for the determination of the identity for the present produce the greatest agreement between the sequences to be compared. Computer programs for the determination of the identity comprise, but are not restricted to, the GCG program package, including GAP (Deveroy, J. et al., Nucleic Acid Research 12 (1984), page 387, Genetics Computer Group University of Wisconsin, Medicine (Wi)), and BLASTP, BLASTN and FASTA (Altschul, S. et al., Journal of Molecular Biology 215 (1990), pages 403-410). The BLAST program can be obtained from the National Center for Biotechnology Information (NCBI) and from further sources (BLAST handbook, Altschul S. et al., NCBI NLM NIH Bethesda ND 22894; Altschul S. et al., above).

The known Smith-Waterman algorithm can likewise be used for the determination of the nucleotide identity.

Preferred parameters for the determination of the "nucleotide identity" are, when using the BLASTN program (Altschul, S. et a, Journal of Molecular Biology 215 (1990), pages 403-410:
Expect Threshold: 10
Word size: 28
Match Score: 1
Mismatch Score: −2
Gap costs: Linear The above parameters are the default parameters in the nucleotide sequence comparison.

The GAP program is likewise suitable for use with the above parameters.

Preferred parameters for the determination of the "amino acid identity" are, when using the BLASTP program (Altschul, S. et al., Journal of Molecular Biology 215 (1990), pages 403-410:
Expect Threshold: 10
Word size: 3
Matrix: BLOSUM62
Gap costs: Existence: 11; Extension: 1
Compositional adjustments: Conditional compositional score matrix adjustment The above parameters are the default parameters in the amino acid sequence comparison. The GAP program is likewise suitable for use with the above parameters.

An identity of 60% according to the above algorithm means 60% identity in connection with the present invention. The same applies for higher identities.

The feature "sequence that hybridizes or, taking into consideration the degeneracy of the genetic code," would hybridize with the complementary strand of a sequence indicates a sequence that under preferably stringent conditions hybridizes, or would hybridize taking into consideration the degeneracy of the genetic code, with the complementary strand of a reference sequence. For example, the hybridizations can be carried out at 68° C. in 2×SSC or according to the protocol of the digoxigenin labeling kits of the company Boehringer (Mannheim). Preferred hybridization conditions are, for example, incubation at 65° C. overnight in 7% SDS, 1% BSA, 1 mM EDTA, 250 mM sodium phosphate buffer (pH 7.2) and subsequent washing at 65° C. with 2×SSC; 0.1% SDS.

The derivatives of the DNA isolated according to the invention, which according to alternatives F1), F2) or F3) can be obtained by substitution, addition, inversion and/or deletion of one or more bases of a sequence according to one of the groups A1) to E1), A2) to E2) and A3) to E3), include in particular those sequences which lead to conservative amino acid exchanges in the protein which they encode, such as, for example, to the exchange of glycine for alanine or of aspartic acid for glutamic acid. Such functionally neutral mutations are described as sense mutations and lead to no fundamental modification of the activity of the polypeptide. Furthermore, it is known that changes at the N- and/or C-terminus of a polypeptide do not significantly impair its function or can even stabilize this, so that also DNA sequences in which bases are attached at the 3'-end or at the 5'-end of the sequence containing the nucleic acids according to the invention are accordingly comprised by the present invention. The person skilled in the art finds information on this, inter alia, in Ben-Bassat et al. (Journal of Bacteriology 169:751-757 (1987)), in O'Regan et al. (Gene 77:237-251 (1989)), in Sahin-Toth et al. (Protein Sciences 3:240-247 (1994)), in Hochuli et al. (Bio/Technology 6:1321-1325 (1988)) and in known textbooks of genetics and molecular biology.

The nucleic acid according to the invention is preferably a vector, in particular an expression vector or a gene overexpression cassette. Suitable vectors are all vectors known to the person skilled in the art that are customarily employed for the inclusion of DNA into a host cell. These vectors can both replicate autonomously, as they have replication origins, such as, for example, those of the 2μ plasmid or ARS (autonomously replicating sequences) or integrate into the chromosomes (non-replicative plasmids). Vectors are also understood as meaning linear DNA fragments that have no replication origins at all, such as, for example, gene insertion or gene overexpression cassettes. Gene overexpression cassettes customarily consist of a marker, the genes to be overexpressed as well as regulatory regions relevant for the expression of the genes, such as, for example, promoters and terminators. Preferred vectors are selected from the group comprising plasmids and cassettes, such as, for example, E. coli yeast shuttle plasmids; expression vectors, gene insertion or gene overexpression cassettes are particularly preferred, in particular the vectors Seq ID No. 38, Seq ID No. 40, Seq ID No. 42, Seq ID No. 45 and Seq ID No. 47 described below.

According to a preferred embodiment of the vector according to the invention, the sequences of the groups [A1 to G1], [A2 to G2] and [A3 to G3] are under the control of at least one constitutive or regulatable promoter, which is suitable for the expression of the polypeptide encoded by these DNA sequences in the cell of a microorganism, preferably a bacteria, yeast or fungal cell, wherein *Aspergillus nidulans, Aspergillus niger, Alcaligenes latus, Bacillus megaterium, Bacillus subtilis, Brevibacterium flavum, Brevibacterium lactofermentum, Burkholderia andropogonis, B. brasilensis, B. caledonica, B. caribensis, B. caryophylli, B. fungorum, B. gladioli, B. glathei, B. glumae, B. graminis, B. hospita, B. kururiensis, B. phenazinium, B. phymatum, B. phytofirmans, B. plantarii, B. sacchari, B. singaporensis, B. sordidicola, B. terricola, B. tropica, B. tuberum, B. ubonensis, B. unamae, B. xenovorans, B. anthina, B. pyrrocinia, B. thailandensis, Candida blankii, Candida rugosa, Corynebacterium glutamicum, Corynebacterium efficiens, Escherichia coli, Hansenula polymorpha, Kluveromyces lactis, Methylobacterium extorquens, Paracoccus versutus, Pseudomonas argentinensis, P. borbori, P. citronellolis, P. flavescens, P. mendocina, P. nitroreducens, P. oleovorans, P. pseudoalcaligenes, P. resinovorans, P. straminea, P. aurantiaca, P. aureofaciens, P. chlororaphis, P. fragi, P. lundensis, P. taetrolens, P. antarctica, P. azotoformans, 'P. blatchfordae', P. brassicacearum, P. brenneri, P. cedrina, P. corrugata, P. fluorescens, P. gessardii, P. libanensis, P. mandelii, P. marginalis, P. mediterranea, P. meridiana, P. migulae, P. mucidolens, P. orientalis, P. panacis, P. proteolytica, P. rhodesiae, P. synxantha, P. thivervalensis, P. tolaasii, P. veronii, P. denitrificans, P. pertucinogena, P. cremoricolorata, P. fulva, P. monteilii, P. mosselii, P. parafulva, P. putida, P. balearica, P. stutzeri, P. amygdali, P. avellanae, P. caricapapayae, P. cichorii, P. coronafaciens, P. Ficuserectae, 'P. helianthi', P. meliae, P. savastanoi, P. syringae, P. tomato, P. viridiflava, P. abietaniphila, P. acidophila, P.* agarici, *P. alcaliphila*, *P. alkanolytica*, *P. amyloderamosa*, *P. asplenii*, *P. azotifigens*, *P. cannabina*, *P. coenobios*, *P. congelans*, *P. costantinii*, *P. cruciviae*, *P. delhiensis*, *P. excibis*, *P. extremorientalis*, *P. frederiksbergensis*, *P. fuscovaginae*, *P. gelidicola*, *P. grimontii*, *P. indica*, *P. jessenii*, *P. jinjuensis*, *P. kilonensis*, *P. knackmussii*, *P. koreensis*, *P. lini*, *P. lutea*, *P. moraviensis*, *P. otitidis*, *P. pachastrellae*, *P. palleroniana*, *P. papaveris*, *P. peli*, *P. perolens*, *P. poae*, *P. pohangensis*, *P. psychrophila*, *P. psychrotolerans*, *P. rathonis*, *P. reptilivora*, *P. resiniphila*, *P. rhizosphaerae*, *P. rubescens*, *P. salomonii*, *P. segitis*, *P. septica*, *P. simiae*, *P. suis*, *P. thermotolerans*, *P. aeruginosa*, *P. tremae*, *P. trivialis*, *P. turbinellae*, *P. tuticorinensis*, *P. umsongensis*, *P. vancouverensis*, *P. vranovensis*, *P. xanthomarina*, *Ralstonia eutropha*, *Rhodospirillum rubrum*, *Rhodobacter sphaeroides*, *Saccharomyces cerevisiae*, *Yarrowia lipolytica*, *Zymomonas mobilis*, in particular *Pseudomonas putida*, *Escherichia coli* and *Burkholderia thailandensis*, are particularly preferred. Examples of constitutive promoters are lac, lacUV5, tac, trc (in each case in the absence of the LacI repressor in the cells according to the invention), Ltet-O1 (in the absence of the TetR repressor in the cells according to the invention), T5 and gap. Examples of inducible promoters are lac, lacUV5, tac, trc (in each case in the presence of the LacI repressor in the cells according to the invention), Ltet-O1 (in the presence of the TetR repressor in the cells according to the invention), T5 (in combination with a lac operator and the presence of the LacI repressor in the cells according to the invention), SP6 and T7 (in the presence of the gene encoding the cognate RNA polymerase, whose expression, for its part, is regulated). The vector according to the invention should in addition to a promoter preferably comprise a ribosome binding site as well as a terminator. It is particularly preferred here that the nucleic acid according to the invention is incorporated in an expression cassette of the vector comprising the promoter, the ribosome binding site and the terminator. In addition to the abovementioned structural elements, the vector can additionally comprise selection genes known to the person skilled in the art.

All percentages (%) indicated are percentages by mass if not indicated otherwise. In the examples presented below, the present invention is described by way of example, without the invention, whose range of application results from the entire description and the claims, being intended to be restricted to the embodiments mentioned in the examples.

EXAMPLES

Figure 1:
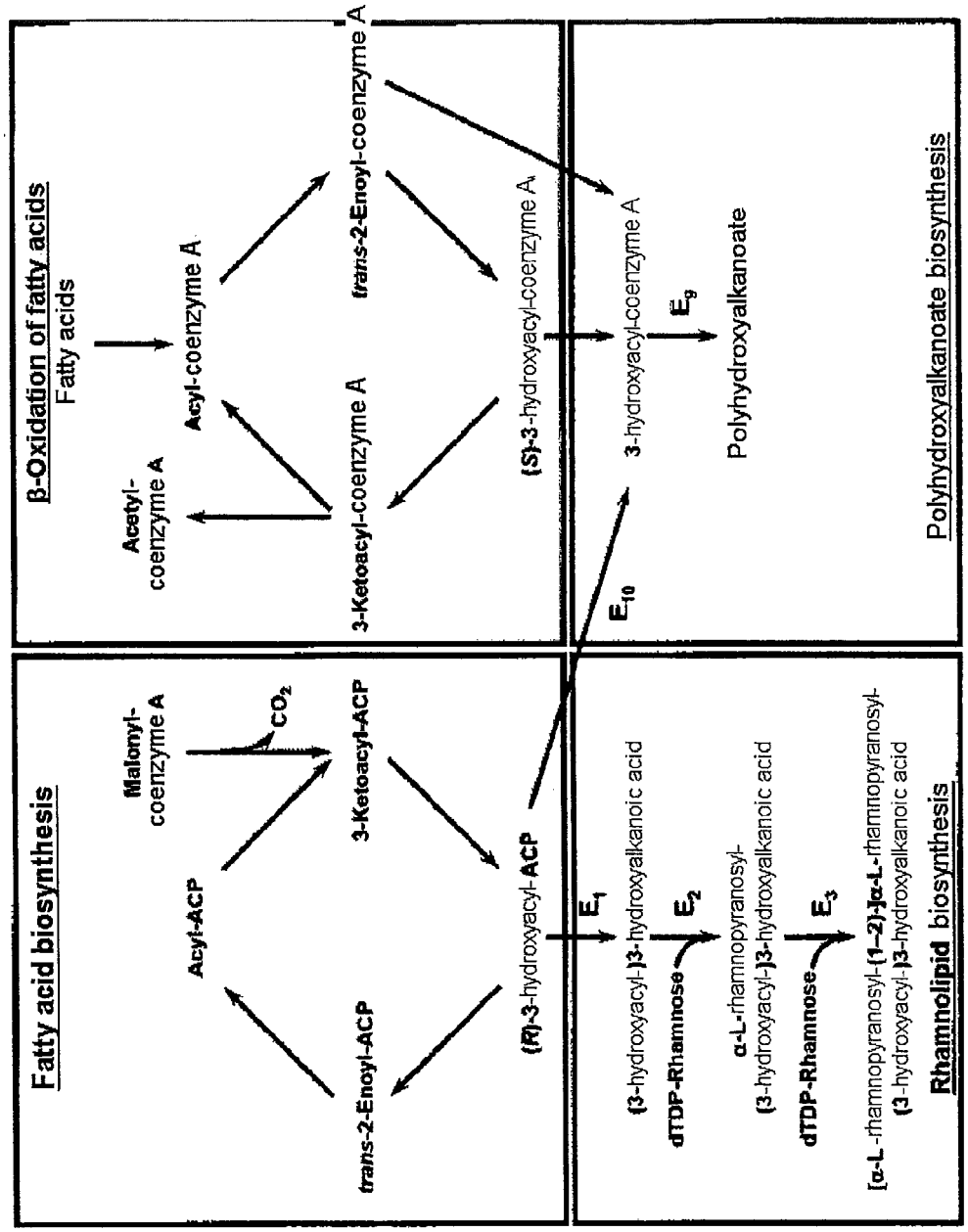
FIG. 1: Fatty acid biosynthesis, β-oxidation of fatty acids and linkage of these metabolic pathways with the biosynthesis of rhamnolipids (enzymes $E_1$, $E_2$ and $E_3$) and polyhydroxyalkanoates (enzymes $E_9$ and $E_{10}$). The carbon flows in fatty acid biosynthesis, β-oxidation of fatty acids, rhamnolipid biosynthesis and polyhydroxyalkanoate biosynthesis are shown. Consumption and formation of coenzymes, redox equivalents as well as nucleotides are not shown.

1. Construction of a Vector pBBR1MCS-2::AB for the Heterologous Expression of the *Pseudomonas aeruginosa* 1707 Genes rhlA and rhlB in *Pseudomonas putida*

For the heterologous expression of the *Pseudomonas aeruginosa* DSM1707 genes rhlA and rhlB, the plasmid pBBR1MCS-2::AB (Seq ID No. 38) was constructed. For this, the synthetic operon rhlAB (Seq ID No. 37) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::AB, the synthetic operon was cleaved from the vector by means of BglII and XbaI and subsequently ligated into the expression vector pBBR1MCS-2 (Seq ID No. 49) cleaved with BamHI and XbaI (described in Kovach et al., 1995: Four new derivatives of the broad host range cloning vector pBBR1MCS carrying different antibiotic-resistance cassettes. Gene, 166: 175-176). The resulting plasmid pBBR1MCS-2::AB (Seq ID No. 38) is 7422 base pairs in size. The ligation and the transformation of chemically competent *E. coli* DH5α cells (Gibco-BRL, Karlsruhe) took place in the manner known to the person skilled in the art. The authenticity of the insert was checked by DNA sequence analysis.

The transformation of *Pseudomonas putida* KT2440 and GPp104 using the vectors pBBR1MCS-2 (Seq ID No. 49) and pBBR1MCS-2::AB took place as previously described (Iwasaki et al. Biosci. Biotech. Biochem. 1994. 58(5):851-854). The plasmid DNA of 10 clones was isolated and analyzed. The strains obtained carrying the plasmids were named *P. putida* KT2440 pBBR1MCS-2, *P. putida* GPp104 pBBR1MCS-2, *P. putida* KT2440 pBBR1MCS-2::AB and *P. putida* GPp104 pBBR1MCS-2::AB.

2. Construction of a Vector pBBR1MCS-2::ABC for the Heterologous Expression of the *Pseudomonas aeruginosa* DSM1707 Genes rhlA, rhlB and rhlC in *Pseudomonas putida*

For the heterologous expression of the *Pseudomonas aeruginosa* DSM1707 genes rhlA, rhlB and rhlC, the plasmid pBBR1MCS-2::ABC (Seq ID No. 40) was constructed. For this, the synthetic operon rhlABC (Seq ID No. 39) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::ABC, the synthetic operon was cleaved from the vector by means of BglII and XbaI and subsequently ligated into the expression vector pBBR1MCS-2 (Seq ID No. 49) cleaved with BamHI and XbaI (Kovach et al., 1995: Four new derivatives of the broad host range cloning vector pBBR1MCS carrying different antibiotic-resistance cassettes. Gene, 166:175-176). The resulting plasmid pBBR1MCS-2::ABC (Seq ID No. 40) is 8409 base pairs in size. The ligation and the transformation of chemically competent *E. coli* DH5α cells (Gibco-BRL, Karlsruhe) took place in the manner known to the person skilled in the art. The authenticity of the insert was checked by DNA sequence analysis.

The transformation of *Pseudomonas putida* KT2440 and GPp104 using the vector pBBR1MCS-2::ABC took place as previously described (Iwasaki et al. Biosci. Biotech. Biochem. 1994. 58(5):851-854). The plasmid DNA of every 10 clones was isolated and analyzed. The strains obtained carrying the plasmids were named *P. putida* KT2440 pBBR1MCS-2::ABC and *P. putida* GPp104 pBBR1MCS-2::ABC.

3. Construction of a Vector pBBR1MCS-2::ABM for the Heterologous Expression of the *Pseudomonas aeruginosa* DSM1707 Genes rhlA, rhlB and pa1131 in *Pseudomonas putida*

For the heterologous expression of the *Pseudomonas aeruginosa* DSM1707 genes rhlA, rhlB and pa1131 the plasmid pBBR1MCS-2::ABM (Seq ID No. 42) was constructed. For this, the synthetic operon rhlAB-pa1131 (Seq ID No. 41) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::ABM the synthetic operon was cleaved from the vector by means of BglII and XbaI and subsequently ligated into the expression vector pBBR1MCS-2 (Seq ID No. 49) cleaved with BamHI and XbaI (Kovach et al., 1995: Four new derivatives of the broad host range cloning vector pBBR1MCS carrying different antibiotic-resistance cassettes. Gene, 166:175-176). The resulting plasmid pBBR1MCS-2::ABM (Seq ID No. 42) is 8702 base pairs in size. The ligation and the transformation of chemically competent *E. coli* DH5α cells (Gibco-BRL, Karlsruhe) took place in the manner known to the person skilled in the art. The authenticity of the insert was checked by DNA sequence analysis.

The transformation of *Pseudomonas putida* KT2440 and GPp104 using the vector pBBR1MCS-2::ABM took place as previously described (Iwasaki et al. Biosci. Biotech. Biochem. 1994. 58(5):851-854). The plasmid DNA of every 10 clones was isolated and analyzed. The strains obtained carrying the plasmids were named *P. putida* KT2440 pBBR1MCS-2::ABM and *P. putida* GPp104 pBBR1MCS-2::ABM.

4. Quantification of Rhamnolipid Production by Recombinant *P. putida* Strains

The recombinant strains *P. putida* KT2440 pBBR1MCS-2; *P. putida* KT2440 pBBR1MCS-2::AB; *P. putida* KT2440 pBBR1MCS-2::ABC; *P. putida* KT2440 pBBR1MCS-2::ABM; *P. putida* GPp104 pBBR1MCS-2; *P. putida* GPp104 pBBR1MCS-2::AB, *P. putida* GPp104 pBBR1MCS-2::ABC and *P. putida* GPp104 pBBR1MCS-2::ABM were cultured on LB agar kanamycin (50 µg/ml) plates.

For the production of the rhamnolipids, the medium designated below as CMP medium was used. This consists of 2% (w/v) glucose, 0.007% (w/v) $KH_2PO_4$, 0.11% $Na_2HPO_4 \times 2\ H_2O$, 0.2% (w/v) $NaNO_3$, 0.04% (w/v) $MgSO_4 \times H_2O$, 0.01% (w/v) $CaCl_2 \times 2\ H_2O$ and 0.2% (v/v) of a trace element solution. This consists of 0.2% (w/v) $FeSO_4 \times 7\ H_2O$, 0.15% (w/v) $MnSO_4 \times H_2O$ and 0.06% (w/v) $(NH_4)MO_7O_{24} \times 4\ H_2O$. The pH of the medium was adjusted to 6.7 with NaOH and the medium was subsequently sterilized by means of an autoclave (121° C., 20 min). An adjustment of the pH during the culturing was not necessary.

For the investigation of the rhamnolipid production in the shaker flask a preculture was first prepared. For this, an inoculation loop of a strain freshly streaked on an LB agar plate was used and 10 ml of LB medium was inoculated into a 100 ml Erlenmeyer flask. All recombinant *P. putida* strains were in the LB medium, to which 50 µg/ml of kanamycin was added. The culturing of the strains took place overnight at 30° C. and 200 rpm.

The precultures were used to inoculate 50 ml of CMP medium in the 250 ml Erlenmeyer flask (start $OD_{600}$ 0.1). The cultures were cultured at 200 rpm and 30° C. for at most 120 h. At intervals of 24 h, a sample of 1 ml of broth was removed from the culture flask. The sample preparation for the following chromatographic analyses took place as follows:

Using a displacement pipette (Combitip), 1 ml of acetone was introduced into a 2 ml reaction vessel and the reaction vessel was immediately closed for the minimization of evaporation. The addition of 1 ml of broth followed. After vortexing of the broth/acetone mixture, this was centrifuged off for 3 min at 13,000 rpm, and 800 µl of the supernatant was transferred to an HPLC vessel.

For the detection and for the quantification of rhamnolipids, an evaporative light scattering detector (Sedex LT-ELSD Model 85LT) was used. The actual measurement was carried out by means of Agilent Technologies 1200 Series (Santa Clara, Calif.) and the Zorbax SB-C8 rapid resolution column (4.6×150 mm, 3.5 µm, Agilent). The injection volume was 5 µl and the runtime of the method was 20 min. As mobile phase, aqueous 0.1% TFA (trifluoroacetic acid, solution A) and methanol (solution B) was used. The column temperature was 40° C. The ELSD (detector temperature 60° C.) and the DAD (diode array, 210 nm) served as detectors. The gradient used in the method was:

| t [min] | Solution B vol. % | Flow [ml/min] |
|---|---|---|
| 0.00 | 70% | 1.00 |
| 15.00 | 100% | 1.00 |
| 15.01 | 70% | 1.00 |
| 20.00 | 70% | 1.00 |

Figure 2:
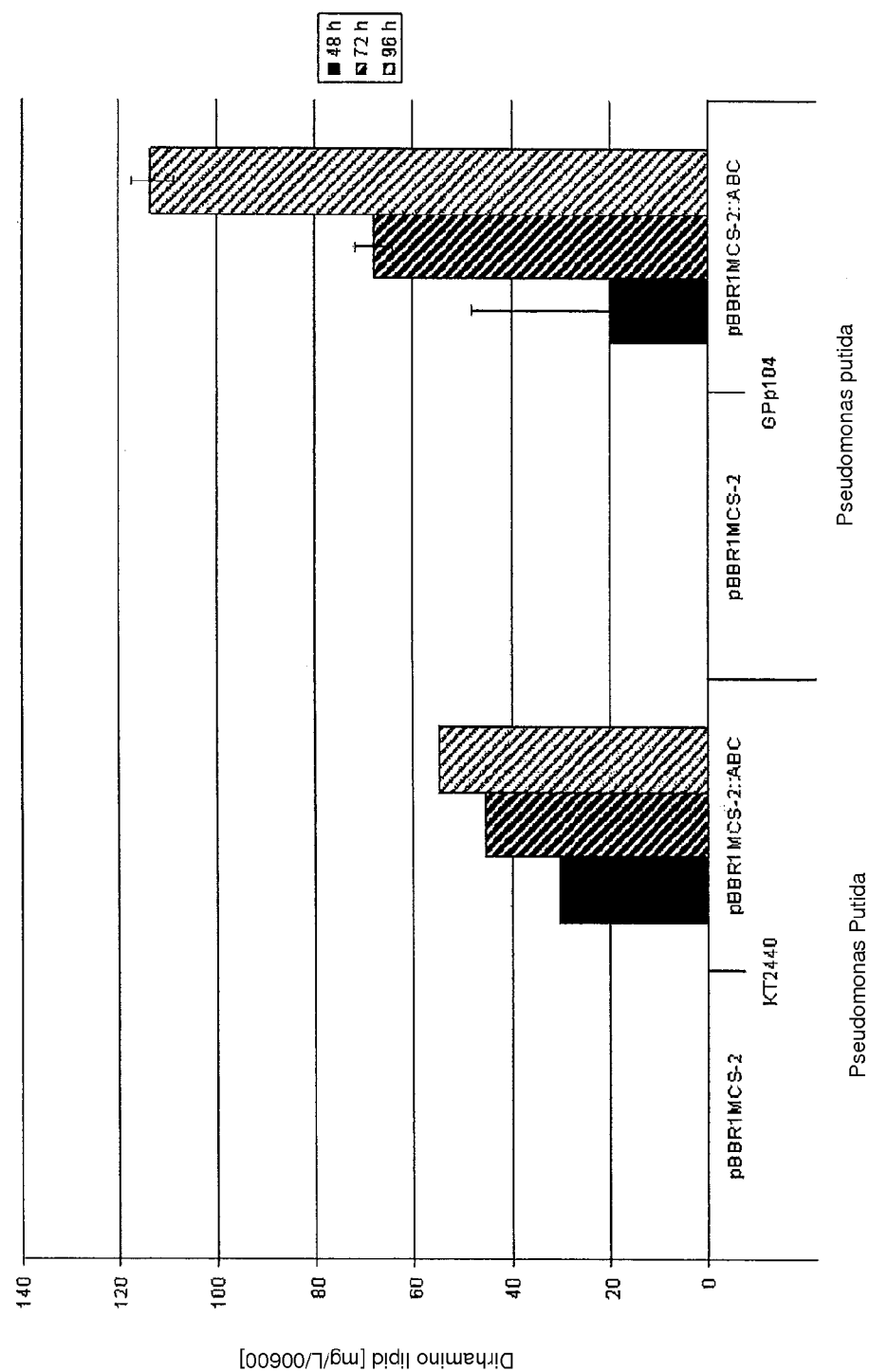
FIG. 2: Dirhamnosyl lipid formation (mg/l/OD 600 nm) of the recombinant strains *P. putida* KT2440 pBBR1MCS-2 and pBBR1MCS-2::ABC as well as GPp104 pBBR1MCS-2 and pBBR1MCS-2::ABC after 48 h, 72 h and 96 h culturing in CMP medium. The analysis of the rhamnolipid concentration took place by means of HPLC.
Figure 3:
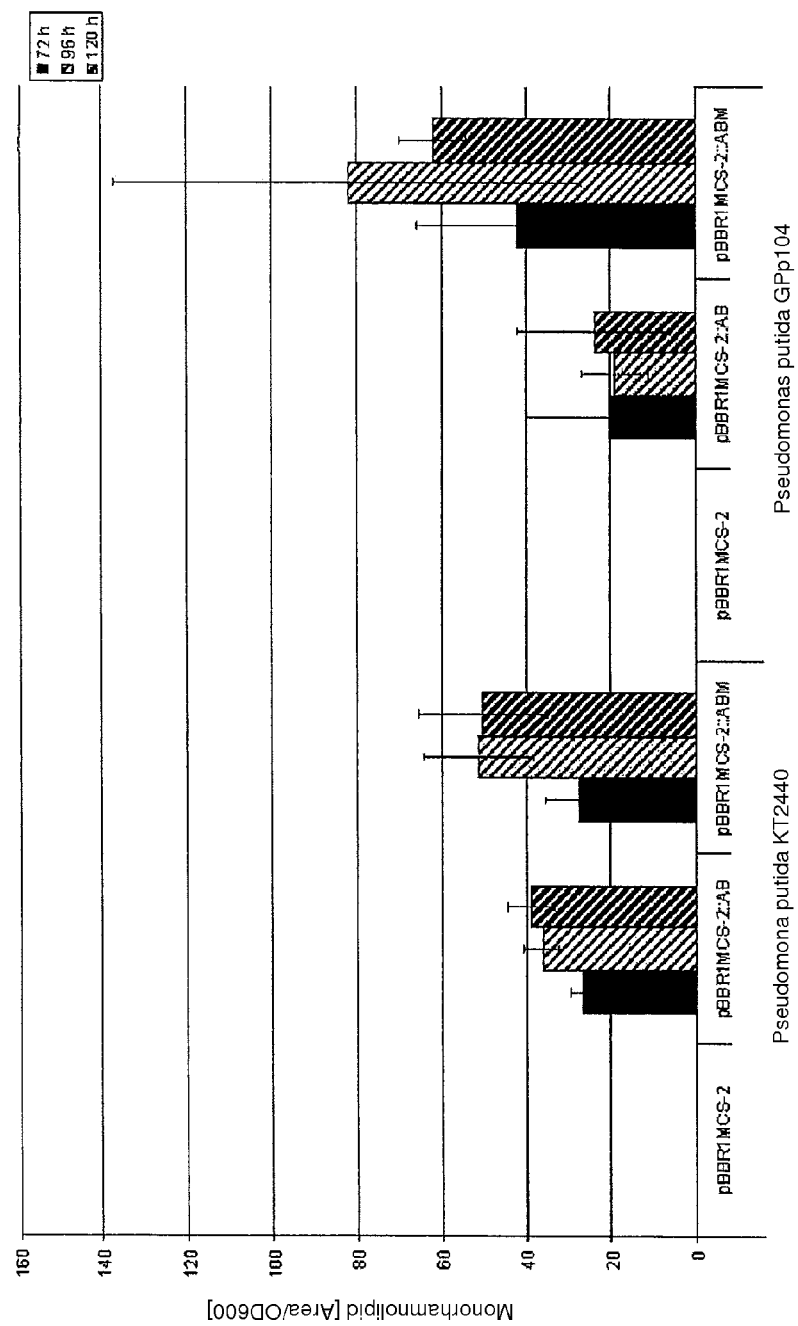
FIG. 3: Monorhamnosyl lipid formation (peakl area/OD 600 nm) of the recombinant strains *P. putida* KT2440 pBBR1MCS-2, pBBR1MCS-2::AB and pBBR1MCS-2::ABM as well as GPp104 pBBR1MCS-2, pBBR1MCS-2::AB and pBBR1MCS-2::ABM after 48 h, 72 h and 96 h culturing in CMP medium. The analysis of the rhamnolipid concentration took place by means of HPLC.

While *P. putida* KT2440 pBBR1MCS-2 and GPp104 pBBR1MCS-2 produced no rhamnolipids, in the recombinant strains *P. putida* KT2440 pBBR1MCS-2::AB, *P. putida* KT2440 pBBR1MCS-2::ABC, *P. putida* KT2440 pBBR1MCS-2::ABM, *P. putida* GPp104 pBBR1MCS-2::AB, *P. putida* GPp104 pBBR1MCS-2::ABC and *P. putida* GPp104 pBBR1MCS-2::ABM the formation of different rhamnolipid species was detectable (FIGS. 2 and 3).

By the incorporation of pBBR1MCS-2::AB and pBBR1MCS-2::ABM into *P. putida*, it was possible to generate monorhamnosyl lipids (FIG. 3). Since no reference material for monorhamnosyl lipids was present, the identification of the products took place by analysis of the corresponding mass traces and the $MS^2$ spectra in LC-MS.

If rhlC (pBBR1MCS-2::ABC) was additionally incorporated into the strains, mono- and dirhamnosyl lipids were produced (FIG. 2).

The direct comparison of the rhamnolipid formation by *P. putida* pBBR1MCS-2::AB and *P. putida* pBBR1MCS-2::ABM shows that the coexpression of *P. aeruginosa* p3111 with *P. aeruginosa* rhlAB leads to an improvement in the rhamnolipid biosynthesis (FIG. 3). While the strains *P. putida* KT2440 pBBR1MCS-2::AB and *P. putida* GPp104 pBBR1MCS-2::AB had produced about 39 (*P. putida* KT2440 pBBR1MCS-2::AB) and 23 peak areas rhamnolipids/OD 600 nm (*P. putida* GPp104 pBBR1MCS-2::AB)

after 120 h, the strains *P. putida* KT2440 pBBR1MCS-2::ABM and *P. putida* GPp104 pBBR1MCS-2::ABM formed about 50 (*P. putida* KT2440 pBBR1MCS-2::ABM) and 62 peak areas rhamnolipids/OD 600 nm (*P. putida* GPp104 pBBR1MCS-2::ABM) after 120 h.

If the monorhamnosyl lipid synthesis of the strains *P. putida* KT2440 pBBR1MCS-2::ABM and *P. putida* GPp104 pBBR1MCS-2::ABM was compared, it was possible in the PHA-negative mutant *P. putida* GPp104 pBBR1MCS-2::ABM to detect 62 peak areas/OD 600 nm (120 h culturing) and with *P. putida* KT2440 pBBR1MCS-2::ABM 50 area/OD 600 nm monorhamnosyl lipids (FIG. 3).

A comparative analysis of the dirhamnosyl lipid formation (mg/l/OD 600 nm) in the strains *P. putida* KT2440 and GPp104 likewise showed a greater formation of the dirhamnosyl lipids in the PHA-negative strain background of the *P. putida* GPp104. *P. putida* GPp104 pBBR1MCS-2::ABC formed on average 113 mg/l/OD 600 nm of dirhamnosyl lipids (96 h), whereas with *P. putida* KT2440 pBBR1MCS-2::ABC only 55 mg/l/OD 600 nm of dirhamnosyl lipids could be detected after 96 h (FIG. 2).

Thus it was possible to show that the use of a strain background attenuated with respect to PHA synthesis leads to an improvement in the rhamnolipid biosynthesis.

5. Construction of a Vector pBBR1MCS-2::ABMC for the Heterologous Expression of the *Pseudomonas aeruginosa* DSM1707 Genes rhIA, rhIB, pa1131 and rhIC in *Pseudomonas putida*

For the heterologous expression of the *Pseudomonas aeruginosa* DSM1707 genes rhIA, rhIB, pa1131 and rhIC, the plasmid pBBR1MCS-2::ABMC (Seq ID No. 51) was constructed. For this, the synthetic operon rhIAB-pa1131-rhIC (Seq ID No. 50) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::ABMC the synthetic operon was cleaved by means of BglII and XbaI from the vector and subsequently ligated into the expression vector pBBR1MCS-2 (Seq ID No. 49) cleaved with BamHI and XbaI (Kovach et al., 1995: Four new derivatives of the broad-host-range cloning vector pBBR1MCS carrying different antibiotic-resistance cassettes. Gene, 166:175-176). The resulting plasmid pBBR1MCS-2::ABMC (Seq ID No. 51) is 9663 base pairs in size. The ligation and the transformation of chemically competent *E. coli* DH5α cells (Gibco-BRL, Karlsruhe) took place in a manner known to the person skilled in the art. The authenticity of the insert was checked by DNA sequence analysis.

The transformation of *Pseudomonas putida* KT2440 and GPp104 using the vector pBBR1MCS-2::ABMC took place as previously described (Iwasaki et al. Biosci. Biotech. Biochem. 1994. 58(5):851-854). The plasmid DNA of every 10 clones was isolated and analyzed. The strains obtained carrying the plasmids were named *P. putida* KT2440 pBBR1MCS-2::ABMC and *P. putida* GPp104 pBBR1MCS-2::ABMC.

6. Qualitative Comparison of the Rhamnolipid Production by Recombinant *P. putida* Strains and *P. aeruginosa* Strains The recombinant strains *P. putida* GPp104 pBBR1MCS-2 and *P. putida* GPp104 pBBR1MCS-2::ABMC and *P. aeruginosa* DSM 19880 were cultured on LB agar kanamycin (50 µg/ml; *P. putida*) and LB agar plates (*P. aeruginosa*).

For the production of the rhamnolipids the medium below designated as CMP medium was used. This consists of 2% (w/v) glucose, 0.007% (w/v) $KH_2PO_4$, 0.11% $Na_2HPO_4 \times 2 H_2O$, 0.2% (w/v) $NaNO_3$, 0.04% (w/v) $MgSO_4 \times H_2O$, 0.01% (w/v) $CaCl_2 \times 2 H_2O$ and 0.2% (v/v) of a trace element solution. This consists of 0.2% (w/v) $FeSO_4 \times 7 H_2O$, 0.15% (w/v) $MnSO_4 \times H_2O$ and 0.06% (w/v) $(NH_4)MO_7O_{24} \times 4 H_2O$. The pH of the medium was adjusted to 6.7 using NaOH and the medium was subsequently sterilized by means of an autoclave (121° C., 20 min). An adjustment of the pH during the culturing was not necessary.

For the investigation of the rhamnolipid production in the shaker flask, a preculture was first prepared. For this, an inoculation loop of a strain freshly streaked on LB agar plate was used and 10 ml of LB medium was inoculated into a 100 ml Erlenmeyer flask. The recombinant *P. putida* strains were cultured in the LB medium, to which 50 µg/ml of kanamycin was added. *P. aeruginosa* was cultured in the LB medium. The culturing of the strains took place at 30° C. and 200 rpm overnight.

The precultures were used to inoculate 50 ml of CMP medium in the 250 ml Erlenmeyer flask (start $OD_{600}$ 0.1). The cultures were cultured at 200 rpm and 30° C. for at most 120 h. At intervals of 24 h, a sample of 1 ml of broth was removed from the culture flask. The sample preparation for the following chromatographic analyses took place as follows:

Using a displacement pipette (Combitip), 1 ml of acetone was introduced into a 2 ml reaction vessel and the reaction vessel was immediately closed for the minimization of evaporation. The addition of 1 ml of broth followed. After vortexing of the broth/acetone mixture, this was centrifuged off for 3 min at 13,000 rpm, and 800 µl of the supernatant were transferred to an HPLC vessel.

For the identification of the products formed, 5 µl were injected into an Accela UPLC unit (Thermo Scientific, Dreieich). The substances to be investigated were analyzed using a semi UPLC column "Pursuit XRs ULTRA (C8, 2.8 µm, 2.1×100 mm) (Varian, Darmstadt). The separation took place within 25 min by means of a gradient consisting of the mobile phase A1 ($H_2O$, 0.1% (v/v) TFA) and the mobile phase B1 (methanol, 0.1% (v/v) TFA) using a flow rate of 0.3 ml/min at 40° C. The time course of the gradient was the following:

| Time [min] | Mobile phase A1 [%] | Mobile phase B1 [%] |
|---|---|---|
| 0 | 30 | 70 |
| 15 | 0 | 100 |
| 25 | 0 | 100 |
| 25.01 | 30 | 70 |
| 32 | 30 | 70 |

Detection took place by means of DAD detector in the wavelength range from 200-600 nm and mass-selectively using a high-resolution FT-ICR LTQ-FT mass spectrometer (Thermo Scientific, Dreieich) in the scanning range m/e 100-1000. Ionization took place by means of ESI (electrospray ionization). Exact masses and empirical chemical formulae were determined with the aid of the FT-ICR mass analyzer, using a resolution of R=100000 and a mass accuracy of ≤2 ppm. The identification of the products takes place by analysis of the corresponding mass traces and the MS² spectra. To be able to compare the strains, the peak areas of the corresponding substances were contrasted.

As shown in FIG. 4, the strain P. putida GPp104 pBBR1MCS-2 formed no rhamnolipids at all. P. putida GPp104 pBBR1MCS-2::ABMC and P. aeruginosa DSM 19880 formed rhamnolipids, wherein the ratio between di- and monorhamnosyl lipids formed with P. putida GPp104 pBBR1MCS-2::ABMC was, for example, 4:1, with P. aeruginosa DSM 19880, for example, 2:1. Moreover, the strain P. putida GPp104 pBBR1MCS-2::ABMC in contrast to P. aeruginosa DSM 19880 formed no or only very few rhamnolipids having a radical determined by means of $R^1$ and $R^2$ derived from 3-hydroxyoctanoyl-3-hydroxydecanoic acid or 3-hydroxydecanoyl-3-hydroxyoctanoic acid.

7. Construction of a Vector pBBR1MCS-2::rfbBDAC and pBBR1MCS-2::ABC_rfbBDAC for Heterologous Expression in Pseudomonas putida At the company Trenzyme GmbH (Konstanz), the rhamnose biosynthesis operon rfbBDAC was amplified starting from chromosomal DNA of Pseudomonas putida KT2440. For this, the following primers were used:

```
RL1:
                                   (Seq ID No. 48)
5'-TATATATAGAATTCGCGTCATCTGTCTACGACAACAC-3'

RL2:
                                   (Seq ID No. 43)
5'-TATATATAGAATTCGGCTGCGCTACCGCAGCCCTTC-3'
```

The PCR product obtained was intercloned in Trenzyme's alligator cloning system and transformed in E. coli DH5α (New England Biolabs; Frankfurt). Vectors of different candidates were analyzed and sequenced. After successful and error-free DNA sequencing, the vector was cleaved by means of EcoRI and the target fragment rfbBDAC was isolated. For a further inter-cloning, the vector pBBR1MCS-2 (Kovach et al., 1995: Four new derivatives of the broad-host-range cloning vector pBBR1MCS carrying different antibiotic-resistance cassettes. Gene, 166:175-176) was cleaved in the same manner. The cleaved target fragment (rfbBDAC) and the cleaved vector (pBBR1MCS-2) were merged by conventional ligation. The resulting vector pBBR1MCS-2::rfbBDAC (Seq ID No. 45) was likewise transformed in E. coli DH5α (New England Biolabs; Frankfurt). Some candidates of the transformants were investigated with respect to the successful uptake of the plasmid.

The vector pBBR1MCS-2::rfbBDAC served as a matrix for a PCR. The following oligonucleotides were used:

```
RL_XbaI-fw:
                                   (Seq ID No. 44)
5'-TATATATATCTAGAATTAATGCAGCTGGCACGAC-3'

RL_Xba_rev:
                                   (Seq ID No. 46)
5'-GGCCGCTCTAGAACTAGTGGA-3'
```

The PCR was carried out using the Phusion™ High-Fidelity Master Mix of New England Biolabs (Frankfurt) polymerase. It was carried out in the manner known to the person skilled in the art. The target sequence (lac promoter and rfbBDAC) was intercloned in the Trenzyme alligator cloning system. E. coli DH5α (New England Biolabs; Frankfurt) transformants were selected and the plasmid DNA of different candidates was isolated and sequenced. After the sequence had been checked and investigated for correctness, the vector was cleaved using XbaI. The target fragment was ligated into the pBBR1MCS-2::ABC likewise cleaved using XbaI (see above) by means of conventional ligation methods. The target vector pBBR1MCS-2::AB-C_rfbBDAC obtained (Seq ID No. 47) has a size of 12249 base pairs. The insert of the vector was sequenced. The carrying-out of the PCR, the checking of the successful amplification of the PCR by means of agarose gel electrophoresis, ethidium bromide staining of the DNA, determination of the PCR fragment size, purification of the PCR products and DNA concentration determination took place in the manner known to the person skilled in the art.

The transformation of Pseudomonas putida KT2440 and GPp104 using the vector pBBR1MCS-2::ABC_rfbBDAC took place as previously described (Iwasaki et al. Biosci. Biotech. Biochem. 1994. 58(5):851-854). The plasmid DNA of every 10 clones was isolated and analyzed. The strains obtained carrying the plasmids are named P. putida KT2440 pBBR1MCS-2::ABC_rfbBDAC and P. putida GPp104 pBBR1MCS-2::ABC_rfbBDAC.

8. Quantification of the Rhamnolipid Production by Recombinant P. putida Strains with and without Overexpression of the rfbBDAC Operon The recombinant strains P. putida KT2440 pBBR1MCS-2; P. putida KT2440 pBBR1MCS-2::ABC, P. putida KT2440 pBBR1MCS-2::ABC_rfbBDAC, P. putida GPp104 pBBR1MCS-2, P. putida GPp104 pBBR1MCS-2::ABC and P. putida GPp104 pBBR1MCS-2::ABC_rfbBDAC are cultured on LB agar kanamycin (50 µg/ml) plates.

For the production of the rhamnolipids, the medium designated below as CMP medium is used. This consists of 2% (w/v) glucose, 0.007% (w/v) $KH_2PO_4$, 0.11% $Na_2HPO_4 \times 2$ $H_2O$, 0.2% (w/v) $NaNO_3$, 0.04% (w/v) $MgSO_4 \times H_2O$, 0.01% (w/v) $CaCl_2 \times 2$ $H_2O$ and 0.2% (v/v) of a trace element solution. This consists of 0.2% (w/v) $FeSO_4 \times 7$ $H_2O$, 0.15% (w/v) $MnSO_4 \times H_2O$ and 0.06% (w/v) $(NH_4)MO_7O_{24} \times 4$ $H_2O$. The pH of the medium is adjusted to 6.7 using NaOH and the medium is subsequently sterilized by means of an autoclave (121° C., 20 min). An adjustment of the pH during the culturing is not necessary.

For the investigation of the rhamnolipid production in the shaker flask, a preculture is first prepared. For this, an inoculation loop of a strain freshly streaked on LB agar plate is used and 10 ml of LB medium are inoculated into a 100 ml Erlenmeyer flask. All recombinant P. putida strains are cultured in the LB medium, to which 50 µg/ml of kanamycin is added. The culturing of the P. putida strains was carried out at 30° C. and 200 rpm overnight.

The precultures are used to inoculate 50 ml of CMP medium in the 250 ml Erlenmeyer flask (start $OD_{600}$ 0.1). The cultures are cultured at 200 rpm and 30° C. for at most 120 h. At intervals of 24 h, a sample of 1 ml broth is removed from the culture flask. The sample preparation for the following chromatographic analyses takes place as follows:

Using a displacement pipette (Combitip), 1 ml of acetone is introduced into a 2 ml reaction vessel and the reaction vessel is closed immediately for the minimization of evaporation. The addition of 1 ml of broth follows. After vortexing of the broth/acetone mixture, this is centrifuged off for 3 min at 13,000 rpm, and 800 µl of the supernatant are transferred to an HPLC vessel. For the detection and for the quantification of rhamnolipids, an evaporative light scattering detector (Sedex LT-ELSD Model 85LT) is used. The actual measurement is carried out by means of Agilent Technologies 1200 Series (Santa Clara, Calif.) and the Zorbax SB-C8 rapid resolution column (4.6×150 mm, 3.5 µm, Agilent). The injection volume is 5 µl and the runtime of the method is 20 min. As a mobile phase, aqueous 0.1% TFA (trifluoroacetic acid, solution A) and methanol (solution B) is used. The column temperature is 40° C. The ELSD (detector temperature 60° C.) and the DAD (diode array, 210 nm) serve as detectors. The gradient used in the method is:

| t [min] | Solution B vol. % | Flow [ml/min] |
|---|---|---|
| 0.00 | 70% | 1.00 |
| 15.00 | 100% | 1.00 |
| 15.01 | 70% | 1.00 |
| 20.00 | 70% | 1.00 |

While *P. putida* KT2440 pBBR1MCS-2 and GPp104 pBBR1MCS-2 produce no rhamnolipids, in the recombinant strains *P. putida* KT2440 pBBR1MCS-2::ABC, *P. putida* KT2440 pBBR1MCS-2::ABC_rfbBDAC; *P. putida* GPp104 pBBR1MCS-2::ABC and *P. putida* GPp104 pBBR1MCS-2::ABC_rfbBDAC the formation of rhamnolipids is detectable.

*P. putida* KT2440 pBBR1MCS-2::ABC_rfbBDAC shows in comparison to *P. putida* KT2440 pBBR1MCS-2::ABC and *P. putida* GPp104 pBBR1MCS-2::ABC_rfbBDAC shows in comparison to *P. putida* GPp104 pBBR1MCS-2::ABC an increased formation of the di- and monorhamnosyl lipids. This clearly shows the positive influence of the amplification of the expression of rfbBDAC on the formation of mono- and dirhamnosyl lipids.

If the mono- and dirhamnosyl lipid biosynthesis of the strains *P. putida* KT2440 pBBR1MCS-2::ABC_rfbBDAC and *P. putida* GPp104 pBBR1MCS-2::ABC_rfbBDAC is compared, an increased mono- and dirhamnosyl lipid synthesis is detected in the PHA-negative mutant *P. putida* GPp104 pBBR1MCS-2::ABC_rfbBDAC.

As already described above, the rhamnolipid biosynthesis is increased with the use of a strain background inactivated in the PHA synthesis.

9. Generation of Recombinant *E. coli* W3110 pBBR1MCS-2::ABC and *E. coli* W3110 pBBR1MCS-2::ABC_rfbBDAC The transformation of *E. coli* W3110 took place as previously described (Miller J H. A Short Course in Bacterial Genetics: A Laboratory Manual and Handbook for *Escherichia coli* and Related Bacteria. Plainview, N.Y.: Cold Spring Harbor Lab. Press; 1992) by means of electroporation. The plasmid DNA of every 10 clones was isolated and analyzed. The strains obtained carrying the plasmids were named *E. coli* W3110 pBBR1MCS-2::ABC_rfbBDAC and *E. coli* W3110 pBBR1MCS-2::ABC_rfbBDAC.

10. Quantification of the Rhamnolipid Production by Recombinant *E. coli* Strains with and without Overexpression of the rfbBDAC Operon The recombinant strains *E. coli* W3110 pBBR1MCS-2; *E. coli* W3110 pBBR1MCS-2::ABC and *E. coli* W3110 pBBR1MCS-2::ABC_rfbBDAC are cultured on LB agar kanamycin (50 µg/ml) plates.

For the production of the rhamnolipids, the medium designated in the following as CMP medium is used. This consists of 2% (w/v) glucose, 0.007% (w/v) $KH_2PO_4$, 0.11% $Na_2HPO_4 \times 2$ $H_2O$, 0.2% (w/v) $NaNO_3$, 0.04% (w/v) $MgSO_4 \times H_2O$, 0.01% (w/v) $CaCl_2 \times 2$ $H_2O$ and 0.2% (v/v) of a trace element solution. This consists of 0.2% (w/v) $FeSO_4 \times 7$ $H_2O$, 0.15% (w/v) $MnSO_4 \times H_2O$ and 0.06% (w/v) $(NH_4)MO_7O_{24} \times 4$ $H_2O$. The pH of the medium is adjusted to 6.7 using NaOH and the medium is subsequently sterilized by means of an autoclave (121° C., 20 min). An adjustment of the pH during the culturing is not necessary.

For the investigation of the rhamnolipid production in the shaker flask, a preculture is first prepared. For this, an inoculation loop of a strain freshly streaked on LB agar plate is used and 10 ml of LB medium is inoculated into a 100 ml Erlenmeyer flask. All recombinant *E. coli* strains are cultured in the LB medium, to which 50 µg/ml of kanamycin is added. The culturing of the *E. coli* strains took place at 37° C. and 200 rpm overnight.

The precultures are used to inoculate 50 ml of CMP medium in the 250 ml Erlenmeyer flask (start $OD_{600}$ 0.1). The cultures are cultured at 200 rpm and 30° C. for at most 120 h. At intervals of 24 h a sample of 1 ml of broth is removed from the culture flask. The sample preparation for the following chromatographic analyses takes place as follows:

Using a displacement pipette (Combitip), 1 ml of acetone is introduced into a 2 ml reaction vessel and the reaction vessel is closed immediately for the minimization of evaporation. The addition of 1 ml of broth follows. After vortexing of the broth/acetone mixture, this is centrifuged off for 3 min at 13,000 rpm, and 800 µl of the supernatant are transferred to an HPLC vessel. For detection and for the quantification of rhamnolipids, an evaporative light scattering detector (Sedex LT-ELSD Model 85LT) is used. The actual measurement is carried out by means of Agilent Technologies 1200 Series (Santa Clara, Calif.) and the Zorbax SB-C8 rapid resolution column (4.6×150 mm, 3.5 µm, Agilent). The injection volume is 5 µl and the runtime of the method is 20 min. Aqueous 0.1% TFA (trifluoroacetic acid, solution A) and methanol (solution B) is used as the mobile phase. The column temperature is 40° C. The ELSD (detector temperature 60° C.) and the DAD (diode array, 210 nm) serve as detectors. The gradient used in the method is:

| t [min] | Solution B vol. % | Flow [ml/min] |
|---|---|---|
| 0.00 | 70% | 1.00 |
| 15.00 | 100% | 1.00 |
| 15.01 | 70% | 1.00 |
| 20.00 | 70% | 1.00 |

While *E. coli* W3110 pBBR1MCS-2 produces no rhamnolipids, the formation of mono- and dirhamnosyl lipids is detectable in the recombinant strains *E. coli* W3110 pBBR1MCS-2::ABC and *E. coli* W3110 pBBR1MCS-2::ABC_rfbBDAC, wherein *E. coli* W3110 pBBR1MCS-2::ABC_rfbBDAC forms significantly more mono- and dirhamnosyl lipids than *E. coli* W3110 pBBR1MCS-2::ABC. This shows that the heterologous expression of rhlABC of *Pseudomonas aeruginosa* DSM1707 leads to the formation of mono- and dirhamnosyl lipids in *E. coli*. This furthermore shows the positive influence of the reinforcement of the expression of rfbBDAC on the formation of mono- and dirhamnosyl lipids.

11. Construction of a vector pBBR1MCS-2::ABC-BTH_II1077-II1080-II1081 for the Heterologous Expression of the *Pseudomonas aeruginosa* DSM1707 Genes rhIA, rhIB and rhIC and the *Burkholderia thailandensis* E264 Genes BTH_II1077, BT_II1080 and BT_II1081 in *Pseudomonas putida*

For the heterologous expression of the *Pseudomonas aeruginosa* DSM1707 genes rhIA, rhIB and rhIC and the *B. thailandensis* E264 genes BTH_II1077, BT_II1080 and BT_II1081 in *Pseudomonas putida*, the plasmid pBBR1MCS-2::ABC-BTH_II1077-II1080-II1081 (Seq ID No. 69) is constructed. For this, the synthetic operon BTH_II1077, BT_II1080 and BT_II1081 (Seq ID No. 70) is synthesized by the company DNA 2.0 (Menlo Park, Calif., USA) and intercloned in the commercial vector pJ294 (DNA 2.0; Menlo Park, Calif., USA). The basis for the synthesis is the genomic sequence of the strain *B. thailandensis* E264. Starting from the vector pJ294-BTH_II1077-II1080-II1081, the synthetic operon is cleaved from this vector by means of XbaI and subsequently ligated into the vector pBBR1MCS-2::ABC (Seq ID No. 40) likewise cleaved using XbaI. The target vector pBBR1MCS-2::ABC-BTH_II1077-II1080-II1081 (Seq ID No. 69) obtained has a size of 13768 base pairs. The insert of the vector is sequenced. The carrying-out of the PCR, the checking of the successful amplification of the PCR by means of agarose gel electrophoresis, ethidium bromide staining of the DNA, determination of the PCR fragment size, purification of the PCR products and DNA concentration determination takes place in the manner known to the person skilled in the art.

The transformation of *Pseudomonas putida* KT2440 and GPp104 using the vector pBBR1MCS-2::ABC-BTH_II1077-II1080-II1081 (Seq ID No. 69) takes place as previously described (Iwasaki et al. Biosci. Biotech. Biochem. 1994. 58(5):851-854). The plasmid DNA of every 10 clones is isolated and analyzed. The strains obtained carrying the plasmids are named *P. putida* KT2440 pBBR1MCS-2::ABC-BTH_II1077-II1080-II1081 and *P. putida* GPp104 pBBR1MCS-2::ABC-BTH_II1077-II1080-II1081.

12. Quantification of the Rhamnolipid Production by Recombinant *P. putida* Strains with and without Overexpression of the *B. thailandensis* E264 Genes BTH_II1077, BT_II1080 and BT_II1081

The recombinant strains *P. putida* strains *P. putida* KT2440 pBBR1MCS-2::AB, *P. putida* KT2440 pBBR1MCS-2::AB-BTH_II1077-II1080-II1081, *P. putida* GPp104 pBBR1MCS-2::AB, *P. putida* GPp104 pBBR1MCS-2::AB-BTH_II1077-II1080-II1081, *P. putida* KT2440 pBBR1MCS-2::ABC, *P. putida* KT2440 pBBR1MCS-2::ABC-BTH_II1077-II1080-II1081 *P. putida* GPp104 pBBR1MCS-2::ABC and *P. putida* GPp104 pBBR1MCS-2::ABC-BTH_II1077-II1080-II1081 generated in the Examples 1, 2 and 11 are cultured on LB agar kanamycin (50 µg/ml) plates.

For the production of the rhamnolipids, the medium designated in the following as M9 medium is used. This medium consists of 2% (w/v) glucose, 0.3% (w/v) $KH_2PO_4$, 0.679% $Na_2HPO_4$, 0.05% (w/v) NaCl, 0.2% (w/v) $NH_4Cl$, 0.049% (w/v) $MgSO_4 \times 7\ H_2O$ and 0.1% (v/v) of a trace element solution. This consists of 1.78% (w/v) $FeSO_4 \times 7\ H_2O$, 0.191% (w/v) $MnCl_2 \times 7\ H_2O$, 3.65% (w/v) HCl, 0.187% (w/v) $ZnSO_4 \times 7\ H_2O$, 0.084% (v/v) Na EDTA× $2H_2O$, 0.03% (v/v) $H_3BO_3$, 0.025% (w/v) $Na_2MoO_4 \times 2\ H_2O$ and 0.47% (w/v) $CaCl_2 \times 2\ H_2O$. The pH of the medium is adjusted to 7.4 using $NH_4OH$ and the medium is subsequently sterilized by means of an autoclave (121° C., 20 min). An adjustment of the pH during the culturing is not necessary. For the investigation of the rhamnolipid production in the shaker flask, a preculture is first prepared. For this, an inoculation loop of a strain freshly streaked on LB agar plate is used and 10 ml of LB medium are inoculated into a 100 ml Erlenmeyer flask. All recombinant *P. putida* strains are cultured in LB medium, to which 50 µg/ml of kanamycin was added. The culturing of the *P. putida* strains takes place at 37° C. and 200 rpm overnight.

The precultures are used to inoculate 50 ml of M9 medium (+50 µg/ml of kanamycin) in the 250 ml Erlenmeyer flask (start $OD_{600}$ 0,1). The cultures are cultured at 200 rpm and 30° C. At intervals of 24 h, a sample of 1 ml of broth is removed from the culture flask. The sample preparation for the following chromatographic analyses and the chromatographic analyses themselves are carried out as described in Example 4.

It is shown that the recombinant strains *P. putida* KT2440 pBBR1MCS-2::AB-BTH_II1077-II1080-II1081 and *P. putida* GPp104 pBBR1MCS-2::AB-BTH_II1077-II1080-II1081 form significantly more monorhamnosyl lipids than the strains *P. putida* KT2440 pBBR1MCS-2::AB and *P. putida* GPp104 pBBR1MCS-2::AB. This demonstrates that the amplification of BTH_II1077-II1080-II1081 from *B. thailandensis* E264 increases the formation of monorhamnosyl lipids in *P. putida* strains containing the *Pseudomonas aeruginosa* DSM1707 genes rhIAB.

It is furthermore shown that the recombinant strains *P. putida* KT2440 pBBR1MCS-2::ABC BTH_II1077-II1080-II1081 and *P. putida* GPp104 pBBR1MCS-2::ABC-BTH_II1077-II1080-II1081 form significantly more mono- and dirhamnosyl lipids than the strains *P. putida* KT2440 pBBR1MCS-2::ABC and *P. putida* GPp104 pBBR1MCS-2::ABC. This proves that the amplification of BTH_II1077-II1080-II1081 from *B. thailandensis* E264 increases the formation of mono- and dirhamnosyl lipids in *P. putida* strains containing the *Pseudomonas aeruginosa* DSM1707 genes rhIABC.

It is finally shown that the reduction of the polyhydroxybutyrate formation in the strain background *P. putida* GPp104 compared to the strain *P. putida* KT2440 leads to an increased rhamnolipid formation, as the strains *P. putida* KT2440 pBBR1MCS-2::AB, *P. putida* KT2440 pBBR1MCS-2::ABC, *P. putida* KT2440 pBBR1MCS-2::AB-BTH_II1077-II1080-II1081 and *P. putida* KT2440 pBBR1MCS-2::ABC-BTH_II1077-II1080-II1081 are able to form significantly fewer mono-( ) and mono- and dirhamnosyl lipids ( ) than the corresponding control strains *P. putida* GPp104 pBBR1MCS-2::AB, *P. putida* GPp104 pBBR1MCS-2::ABC, *P. putida* GPp104 pBBR1MCS-2::AB-BTH_II1077-II1080-II1081 and *P. putida* GPp104 pBBR1MCS-2::ABC-BTH_II1077-II1080-II1081.

13. Construction of a Vector pBBR1MCS-2::ABCM for the Heterologous Expression of the *Pseudomonas aeruginosa* DSM1707 Genes rhIA, rhIB, pa1131 and rhIC in *Pseudomonas putida*

For the heterologous expression of the *Pseudomonas aeruginosa* DSM1707 genes rhIA, rhIB, pa1131 and rhIC, the plasmid pBBR1MCS-2::ABCM (Seq ID No. 58) was constructed. For this, the gene pa1131 (Seq ID No. 59) was amplified starting from genomic DNA of the strain *Pseudomonas aeruginosa* PAO1 (DSM 1707) containing the oligonucleotides

```
MFS2.0_xbaI_fw:
                                        (Seq ID No. 60)
5'-AGGAAATCTAGATGAGAGGCCGGCAAGGATAC-3'

MFS2.0_XbaI_rev:
                                        (Seq ID No. 61)
5'-CCAGGTTCTAGACGCCAGGATTGAACAGTACC-3'.
```

The amplification of the PCR product (1483 base pairs) was carried out using the Phusion™ High-Fidelity Master Mix from New England Biolabs (Frankfurt) polymerase. The PCR product was cleaved using XbaI and ligated in the vector pBBR1MCS-2::ABC (Seq ID No. 40) likewise cleaved using XbaI by means of Fast Link Ligation Kit (Epicentre Technologies; Madison, Wis., USA). The target vector pBBR1MCS-2::ABCM (Seq ID No. 58) obtained has a size of 9892 base pairs. The insert of the vector was sequenced. The chromosomal DNA was isolated by means of DNeasy Blood and Tissue Kit (Qiagen; Hilden) according to manufacturer's instructions. The carrying-out of the PCR, the checking of the successful amplification of the PCR by means of agarose gel electrophoresis, ethidium bromide staining of the DNA, determination of the PCR fragment size, purification of the PCR products and DNA concentration determination took place in a manner known to the person skilled in the art. The transformation of *Pseudomonas putida* KT2440 and GPp104 using the vector pBBR1MCS-2::ABCM took place as previously described (Iwasaki et al. Biosci. Biotech. Biochem. 1994. 58(5):851-854). The plasmid DNA of every 10 clones was isolated and analyzed. The strains obtained carrying the plasmids were named *P. putida* KT2440 pBBR1MCS-2::ABCM and *P. putida* GPp104 pBBR1MCS-2::ABCM.

14. Quantification of the Rhamnolipid Production by Recombinant *P. putida* Strains with and without Overexpression of the *Pseudomonas aeruginosa* DSM1707 pa1131 Gene The recombinant strains *P. putida* strains *P. putida* KT2440 pBBR1MCS-2::ABC, *P. putida* KT2440 pBBR1MCS-2::ABCM, *P. putida* KT2440 pBBR1MCS-2::ABC and *P. putida* GPp104 pBBR1MCS-2::ABCM generated in the Examples 2 and 13 were cultured on LB agar kanamycin (50 µg/ml) plates. The subsequent culturing for the production of the rhamnolipids took place as described in Example 12.

The sample preparation for the following chromatographic analyses and the chromatographic analyses themselves took place as described in Example 4.

The results are shown in the following table.

Formation of di- and monorhamnosyl lipids by *P. putida* strains with and without overexpression of the *P. aeruginosa* gene pa1131 after 48 h incubation

| *P. putida* strains | Dirhamnosyl lipids [mg/l] | Monorhamnosyl lipids [peak area] |
|---|---|---|
| KT2440 pBBR1MCS-2::ABC | 310 | 19 |
| KT2440 pBBR1MCS-2::ABCM | 1053 | 314 |
| GPp104 pBBR1MCS-2::ABC | 689 | 127 |
| GPp104 pBBR1MCS-2::ABCM | 960 | 1090 |

The results show that the overexpression of the *P. aeruginosa* gene pa1131 in both strain backgrounds (KT2440: wild-type and GPp104 having inactivated polyhydroxybutyrate formation) leads to an increased formation of di- and monorhamnosyl lipids. The results furthermore show that the reduction of the polyhydroxybutyrate formation in GPp104 generally leads to an increased formation of rhamnosyl lipids.

15. Construction of a vector pEC-XT99A::AB for the heterologous expression of the genes rhlA and rhlB from *Pseudomonas aeruginosa* DSM1707 in *Corynebacterium glutamicum*

For the heterologous expression of the genes rhlA and rhlB from *Pseudomonas aeruginosa* DSM1707 in *Corynebacterium glutamicum*, the plasmid pEC-XT99A::AB (Seq ID No. 52) is constructed. For this, the synthetic operon rhlAB (Seq ID No. 37) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::AB, the synthetic operon is cleaved from the vector by means of BglII and XbaI and subsequently ligated into the expression vector pEC-XT99A (U.S. Pat. No. 7,118,904) cleaved using BamHI and XbaI. The resulting plasmid pEC-XT99A::AB (Seq ID No. 52) is 9793 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *C. glutamicum* ATCC13032 using the vector pEC-XT99A::AB takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented with 5 mg/l of tetracycline). The plates were incubated at 33° C. for two days. The strain obtained carrying the plasmid is named *C. glutamicum* pEC-XT99A::AB.

16. Construction of a Vector pEC-XT99A::ABC for the Heterologous Expression of the Genes rhlA, rhlB and rhlC from *Pseudomonas aeruginosa* DSM1707 in *Corynebacterium glutamicum*

For the heterologous expression of the genes rhlA, rhlB and rhlC from *Pseudomonas aeruginosa* DSM1707 in *Corynebacterium glutamicum*, the plasmid pEC-XT99A::ABC (Seq ID No. 53) is constructed. For this, the synthetic operon rhlABC (Seq ID No. 39) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::ABC, the synthetic operon is cleaved from the vector by means of BglII and XbaI and subsequently ligated into the expression vector pEC-XT99A (U.S. Pat. No. 7,118,904) cleaved using BamHI and XbaI. The resulting plasmid pEC-XT99A::ABC (Seq ID No. 53) is 10780 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *C. glutamicum* ATCC13032 using the vector pEC-XT99A::ABC takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented using 5 mg/l of tetracycline). The plates were incubated at 33° C. for two days. The strain obtained carrying the plasmid is named *C. glutamicum* pEC-XT99A::ABC.

17. Construction of a Vector pEC-XT99A::ABM for the Heterologous Expression of the Genes rhlA, rhlB and pa1131 from *Pseudomonas aeruginosa* DSM1707 in *Corynebacterium glutamicum*

For the heterologous expression of the genes rhlA, rhlB and pa1131 from *Pseudomonas aeruginosa* DSM1707 in *Corynebacterium glutamicum*, the plasmid pEC-XT99A::ABM (Seq ID No. 54) is constructed. For this, the synthetic operon rhlABM (Seq ID No. 41) was synthesized by the company GeneArt AG (Regensburg) and intercloned in the commercial vector pMA (GeneArt AG). The basis for the synthesis was the already known genomic sequence of the *Pseudomonas aeruginosa* DSM1707. Starting from the vector pMA::ABM, the synthetic operon is cleaved from the vector by means of BglII and XbaI and subsequently ligated into the expression vector pEC-XT99A (U.S. Pat. No. 7,118, 904) cleaved using BamHI and XbaI. The resulting plasmid pEC-XT99A::ABM (Seq ID No. 54) is 11073 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *C. glutamicum* ATCC13032 using the vector pEC-XT99A::ABM takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented with 5 mg/l of tetracycline). The plates were incubated at 33° C. for two days. The strain obtained carrying the plasmid is named *C. glutamicum* pEC-XT99A::ABM.

18. Construction of a Vector pEC-XT99A::ABCM for the Heterologous Expression of the Genes rhlA, rhlB, pa1131 and rhlC from *Pseudomonas aeruginosa* DSM1707 in *Corynebacterium glutamicum*

For the heterologous expression of the genes rhlA, rhlB, pa1131 and rhlC from *Pseudomonas aeruginosa* DSM1707 in *Corynebacterium glutamicum*, the plasmid pEC-XT99A::ABCM (Seq ID No. 55) is constructed. For this, the gene pa1131 (Seq ID No. 59) was amplified starting from genomic DNA of the strain *Pseudomonas aeruginosa* PAO1 (DSM 1707) using the oligonucleotides

```
MFS2.0_xbaI_fw:
                                     (Seq ID No. 60)
5'-AGGAAATCTAGATGAGAGGCCGGCAAGGATAC-3'

MFS2.0_XbaI_rev:
                                     (Seq ID No. 61)
5'-CCAGGTTCTAGACGCCAGGATTGAACAGTACC-3'.
```

The amplification of the PCR product (1483 base pairs) was carried out using the Phusion™ High-Fidelity Master Mix from New England Biolabs (Frankfurt) polymerase. The PCR product was cleaved using XbaI and ligated into the vector pBBR1MCS-2::ABC (Seq ID No. 40) likewise cleaved using XbaI by means of Fast Link Ligation Kit (Epicentre Technologies; Madison, Wis., USA). The target vector pEC-XT99A::ABCM (Seq ID No. 55) obtained has a size of 12263 base pairs. The insert of the vector was sequenced. The chromosomal DNA was isolated by means of DNeasy Blood and Tissue Kit (Qiagen; Hilden) according to manufacturer's instructions. The carrying-out of the PCR, the checking of the successful amplification of the PCR by means of agarose gel electrophoresis, ethidium bromide staining of the DNA, determination of the PCR fragment size, purification of the PCR products and DNA concentration determination took place in the manner known to the person skilled in the art.

The transformation of *C. glutamicum* ATCC13032 using the vector pEC-XT99A::ABCM takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented with 5 mg/l of tetracycline). The plates were incubated for two days at 33° C. The strain obtained carrying the plasmid is named *C. glutamicum* pEC-XT99A::ABCM.

19. Construction of a Vector pVWEX1::rfbBDAC for Heterologous Expression in *C. glutamicum*

For the heterologous expression of the genes rfbBDAC from *P. putida* under the control of the lac promoter in *C. glutamicum*, the vector pVWEX1::rfbBDAC (Seq ID No. 57) is constructed. For this, the vector pBBR1MCS-2:: rfbBDAC (Seq ID No. 45) is digested using XbaI and the fragment (3840 bp) containing the genes rfbBDAC from *P. putida* KT2440 and the lac promoter is ligated into the vector pVWEX1 (Seq ID No. 56) digested with XbaI. The resulting plasmid pVWEX1::rfbBDAC (Seq ID No. 57) is 12311 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *C. glutamicum* ATCC13032 pEC-XT99A, ATCC13032 pEC-XT99A::AB, ATCC13032 pEC-XT99A::ABM, ATCC13032 pEC-XT99A::ABC and ATCC13032 pEC-XT99A::ABCM using the vector pVWEX1::rfbBDAC takes place as previously described (Liebl et al., *FEMS Microbiol. Lett.* 53:299-303 (1989)). The selection of the transformants takes place on LBHIS agar plates (18.5 g/l of brain heart infusion broth, 0.5 M sorbitol, 5 g/l of Bacto tryptone, 2.5 g/l of Bacto yeast extract, 5 g/l of NaCl and 18 g/l of Bacto agar, supplemented with 5 mg/l of tetracycline and 25 mg/l of kanamycin). The plates were incubated at 33° C. for two days. The strains obtained carrying the plasmids are named *C. glutamicum* pEC- XT99A pVWEX1::rfbBDAC, *C. glutamicum* pEC-XT99A:: AB pVWEX1::rfbBDAC, *C. glutamicum* pEC-XT99A:: ABM pVWEX1::rfbBDAC, *C. glutamicum* pEC-XT99A:: ABC pVWEX1::rfbBDAC and *C. glutamicum* pEC-XT99A::ABCM pVWEX1::rfbBDAC.

20. Quantification of the Rhamnolipid Production by Recombinant *C. glutamicum* Strains The recombinant strains *C. glutamicum* strains generated in the Examples 15 to 19 *C. glutamicum* pEC-XT99A, *C. glutamicum* pEC-XT99A::AB, *C. glutamicum* pEC-XT99A::ABC, *C. glutamicum* pEC-XT99A::ABM, *C. glutamicum* pEC-XT99A::ABCM, *C. glutamicum* pEC-XT99A pVWEX1::rfbBDAC, *C. glutamicum* pEC-XT99A::AB pVWEX1::rfbBDAC, *C. glutamicum* pEC-XT99A::ABM pVWEX1::rfbBDAC, *C. glutamicum* pEC-XT99A::ABC pVWEX1::rfbBDAC and *C. glutamicum* pEC-XT99A:: ABCM pVWEX1::rfbBDAC are cultured on LBHIS agar plates using 5 mg/l of tetracycline and 5 mg/l of tetracycline and 25 mg/l of kanamycin. For the investigation of the rhamnolipid production in the shaker flask, precultures are first prepared. For this, an inoculation loop of a strain freshly streaked on an LBHIS agar plate is used and 10 ml of LBHIS medium (18.5 g/l of brain heart infusion broth, 0.5 M sorbitol, 5 g/l of Bacto tryptone, 2.5 g/l of Bacto yeast extract and 5 g/l of NaCl, supplemented with 5 mg/l of tetracycline or 5 mg/l of tetracycline and 25 mg/l of kanamycin) is inoculated into a 100 ml Erlenmeyer flask. The culturing of the strains takes place at 33° C. and 200 rpm overnight. The next morning, 50 ml of CGXII medium (containing 5 mg/l of tetracycline or 5 mg/l of tetracycline and 25 mg/l of kanamycin) are inoculated into a 500 ml Erlenmeyer flask containing baffles with 1 ml of the preculture (start $OD_{600}$ 0.1).

CGXII Medium:
    20 g/l of $(NH_4)_2SO_4$ (Merck)
    5 g/l of urea (Merck)
    1 g/l of $KH_2PO_4$ (Merck)
    1 g/l of $K_2HPO_4$ (Merck)
    0.25 g/l of $MgSO_4.7H_2O$ (Merck)
    10 mg/l of $CaCl_2$ (Merck)
    42 g/l of MOPS (Roth)
    0.2 mg/l of biotin (Merck)
    1 ml/l of trace salt solution
    adjust to pH 7 using NaOH
    after autoclaving add 1 ml/l of protocatechuic acid (30 g/l dissolved in dil. NaOH, sterile-filtered) and 40 g/l of glucose (Merck)
Trace Salt Solution:
    10 g/l of $FeSO_4.7H_2O$ (Merck)
    10 g/l of $MnSO_4.H_2O$ (Merck)
    1 g/l of $ZnSO_4.7H_2O$ (Merck)
    0.2 g/l of $CuSO_4.5H_2O$ (Merck)
    20 mg/l of $NiCl_2.6H_2O$ (Merck)
    to dissolve acidify to pH 1 using HCl The cultures are cultured at 200 rpm and 33° C. up to an optical density (600 nm) of 0.4-0.6. At this optical density, the cultures are induced by the addition of IPTG (isopropyl-β-D-thiogalactopyranoside; 1 mM final concentration). The subsequent expression likewise takes place at 33° C. and 200 rpm for 72 h. At intervals of 24 h, a sample of 1 ml of broth is removed from the culture flask. The sample preparation for the following chromatographic analyses and the chromatographic analyses themselves are carried out as described in Example 4.

While *C. glutamicum* pEC-XT99A produces no rhamnolipids, in the recombinant strains *C. glutamicum* pEC-XT99A::AB, *C. glutamicum* pEC-XT99A::ABC, *C. glutamicum* pEC-XT99A::ABM and *C. glutamicum* pEC-XT99A::ABCM the formation of rhamnolipids is detectable. With the aid of reference materials, it is shown that *C. glutamicum* pEC-XT99A::AB and *C. glutamicum* pEC-XT99A::ABM only form monorhamnosyl lipids, while *C. glutamicum* pEC-XT99A::ABC, *C. glutamicum* pEC-XT99A::ABM and *C. glutamicum* pEC-XT99A::ABCM are able to form dirhamnosyl lipids and monorhamnosyl lipids. Furthermore, it is shown that *C. glutamicum* pEC-XT99A:: ABM and *C. glutamicum* pEC-XT99A::ABCM are able to form more monorhamnosyl lipids or dirhamnosyl lipids and monorhamnosyl lipids than the respective reference strains *C. glutamicum* pEC-XT99A::AB and *C. glutamicum* pEC-XT99A::ABC without amplification of the pa1131 gene from *Pseudomonas aeruginosa*.

Moreover, it is shown that the strains *C. glutamicum* pEC-XT99A::AB pVWEX1::rfbBDAC, *C. glutamicum* pEC-XT99A::ABM pVWEX1::rfbBDAC, *C. glutamicum* pEC-XT99A::ABC pVWEX1::rfbBDAC and *C. glutamicum* pEC-XT99A::ABCM pVWEX1::rfbBDAC form significantly more mono- (*C. glutamicum* pEC-XT99A::AB pVWEX1::rfbBDAC and *C. glutamicum* pEC-XT99A:: ABM pVWEX1::rfbBDAC) or mono- and dirhamnosyl lipids (*C. glutamicum* pEC-XT99A::ABC pVWEX1::rfbBDAC and *C. glutamicum* pEC-XT99A::ABCM pVWEX1::rfbBDAC) than the strains, *C. glutamicum* pEC-XT99A::ABM, *C. glutamicum* pEC-XT99A::ABC and *C. glutamicum* pEC-XT99A::ABCM without amplification of the of the rfbBDA genes from *P. putida*.

21. Construction of *Pseudomonas* Strains that Carry the Plasmids pBBR1MCS-2, pBBR1MCS-2::AB, pBBR1MCS-2::ABC, pBBR1MCS-2::ABM and pBBR1MCS-2::ABCM The plasmids pBBR1MCS-2, pBBR1MCS-2::AB, pBBR1MCS-2::ABC, pBBR1MCS-2::ABM and pBBR1MCS-2::ABCM are incorporated in *Pseudomonas fluorescens* DSM 50090, *Pseudomonas fluorescens* DSM 9958, *Pseudomonas putida* DSM 6899, *Pseudomonas putida* DSM 50204, *Pseudomonas putida* 50194, *P. brassicacearum* DSM 13227, *P. stutzeri* DSM 10701, *Pseudomonas stutzeri* DSM 4166 and *Pseudomonas fulva* DSM 17717 by electroporation. The transformation of *Pseudomonas* strains takes place as described previously (Iwasaki et al. Biosci. Biotech. Biochem. 1994. 58(5):851-854). The selection of the transformants takes place on nutrient agar plates (5 g/l of peptone; 3 g/l of meat extract; 15 g/l of agar; pH 7; supplemented with 50 mg/l of kanamycin). The plates are incubated at 30° C. or rather 28° C. for two days. The strains obtained, carrying the plasmids, are named *Pseudomonas fluorescens* DSM 50090 pBBR1MCS-2, *Pseudomonas fluorescens* DSM 9958 pBBR1MCS-2, *Pseudomonas putida* DSM 6899 pBBR1MCS-2, *Pseudomonas putida* DSM 50204 pBBR1MCS-2, *Pseudomonas putida* 50194 pBBR1MCS-2, *P. brassicacearum* DSM 13227 pBBR1MCS-2, *P. stutzeri* DSM 10701 pBBR1MCS-2, *Pseudomonas stutzeri* DSM 4166 pBBR1MCS-2, *Pseudomonas fulva* DSM 17717 pBBR1MCS-2, *Pseudomonas fluorescens* DSM 50090 pBBR1MCS-2::AB, *Pseudomonas fluorescens* DSM 9958 pBBR1MCS-2::AB, *Pseudomonas putida* DSM 6899 pBBR1MCS-2::AB, *Pseudomonas putida* DSM 50204 pBBR1MCS-2::AB, *Pseudomonas putida* 50194 pBBR1MCS-2::AB, *P. brassicacearum DSM 13227 pBBR1MCS-2::AB, *P. stutzeri* DSM 10701 pBBR1MCS-2::AB, *Pseudomonas stutzeri* DSM 4166 pBBR1MCS-2::AB, *Pseudomonas fulva* DSM 17717 pBBR1MCS-2::AB, *Pseudomonas fluorescens* DSM 50090 pBBR1MCS-2::ABC, *Pseudomonas fluorescens* DSM 9958 pBBR1MCS-2::ABC, *Pseudomonas putida* DSM 6899 pBBR1MCS-2::ABC, *Pseudomonas putida* DSM 50204 pBBR1MCS-2::ABC, *Pseudomonas putida* 50194 pBBR1MCS-2::ABC, *P. brassicacearum* DSM 13227 pBBR1MCS-2::ABC, *P. stutzeri* DSM 10701 pBBR1MCS-2::ABC, *Pseudomonas stutzeri* DSM 4166 pBBR1MCS-2::ABC, *Pseudomonas fulva* DSM 17717 pBBR1MCS-2::ABC, *Pseudomonas fluorescens* DSM 50090 pBBR1MCS-2::ABCM, *Pseudomonas fluorescens* DSM 9958 pBBR1MCS-2::ABCM, *Pseudomonas putida* DSM 6899 pBBR1MCS-2::ABCM, *Pseudomonas putida* DSM 50204 pBBR1MCS-2::ABCM, *Pseudomonas putida* 50194 pBBR1MCS-2::ABCM, *P. brassicacearum* DSM 13227 pBBR1MCS-2::ABCM, *P. stutzeri* DSM 10701 pBBR1MCS-2::ABCM, *Pseudomonas stutzeri* DSM 4166 pBBR1MCS-2::ABCM, *Pseudomonas fulva* DSM 17717 pBBR1MCS-2::ABCM, *Pseudomonas fluorescens* DSM 50090 pBBR1MCS-2::ABM, *Pseudomonas fluorescens* DSM 9958 pBBR1MCS-2::ABM, *Pseudomonas putida* DSM 6899 pBBR1MCS-2::ABM, *Pseudomonas putida* DSM 50204 pBBR1MCS-2::ABM, *Pseudomonas putida* 50194 pBBR1MCS-2::ABM, *P. brassicacearum* DSM 13227 pBBR1MCS-2::ABM, *P. stutzeri* DSM 10701 pBBR1MCS-2::ABM, *Pseudomonas stutzeri* DSM 4166 pBBR1MCS-2::ABM and *Pseudomonas fulva* DSM 17717 pBBR1MCS-2::ABM.

22. Quantification of the Rhamnolipid Production by Recombinant *Pseudomonas* Strains The recombinant strains *Pseudomonas* strains *Pseudomonas fluorescens* DSM 50090, *Pseudomonas fluorescens* DSM 9958 pBBR1MCS-2, *Pseudomonas putida* DSM 6899 pBBR1MCS-2, *Pseudomonas putida* DSM 50204 pBBR1MCS-2, *Pseudomonas putida* 50194 pBBR1MCS-2, *P. brassicacearum* DSM 13227 pBBR1MCS-2, *P. stutzeri* DSM 10701 pBBR1MCS-2, *Pseudomonas stutzeri* DSM 4166 pBBR1MCS-2, *Pseudomonas fulva* DSM 17717 pBBR1MCS-2, *Pseudomonas fluorescens* DSM 50090 pBBR1MCS-2::AB, *Pseudomonas fluorescens* DSM 9958 pBBR1MCS-2::AB, *Pseudomonas putida* DSM 6899 pBBR1MCS-2::AB, *Pseudomonas putida* DSM 50204 pBBR1MCS-2::AB, *Pseudomonas putida* 50194 pBBR1MCS-2::AB, *P. brassicacearum* DSM 13227 pBBR1MCS-2::AB, *P. stutzeri* DSM 10701 pBBR1MCS-2::AB, *Pseudomonas stutzeri* DSM 4166 pBBR1MCS-2::AB, *Pseudomonas fulva* DSM 17717 pBBR1MCS-2::AB, *Pseudomonas fluorescens* DSM 50090 pBBR1MCS-2::ABC, *Pseudomonas fluorescens* DSM 9958 pBBR1MCS-2::ABC, *Pseudomonas putida* DSM 6899 pBBR1MCS-2::ABC, *Pseudomonas putida* DSM 50204 pBBR1MCS-2::ABC, *Pseudomonas putida* 50194 pBBR1MCS-2::ABC, *P. brassicacearum* DSM 13227 pBBR1MCS-2::ABC, *P. stutzeri* DSM 10701 pBBR1MCS-2::ABC, *Pseudomonas stutzeri* DSM 4166 pBBR1MCS-2::ABC, *Pseudomonas fulva* DSM 17717 pBBR1MCS-2::ABC, *Pseudomonas fluorescens* DSM 50090 pBBR1MCS-2::ABCM, *Pseudomonas fluorescens* DSM 9958 pBBR1MCS-2::ABCM, *Pseudomonas putida* DSM 6899 pBBR1MCS-2::ABCM, *Pseudomonas putida* DSM 50204 pBBR1MCS-2::ABCM, *Pseudomonas putida* 50194 pBBR1MCS-2::ABCM, *P. brassicacearum* DSM 13227 pBBR1MCS-2::ABCM, *P. stutzeri* DSM 10701 pBBR1MCS-2::ABCM, *Pseudomonas stutzeri* DSM 4166 pBBR1MCS-2::ABCM, *Pseudomonas fulva* DSM 17717 pBBR1MCS-2::ABCM, *Pseudomonas fluorescens* DSM 50090 pBBR1MCS-2::ABM, *Pseudomonas fluorescens* DSM 9958 pBBR1MCS-2::ABM, *Pseudomonas putida* DSM 6899 pBBR1MCS-2::ABM, *Pseudomonas putida* DSM 50204 pBBR1MCS-2::ABM, *Pseudomonas putida* 50194 pBBR1MCS-2::ABM, *P. brassicacearum* DSM 13227 pBBR1MCS-2::ABM, *P. stutzeri* DSM 10701 pBBR1MCS-2::ABM, *Pseudomonas stutzeri* DSM 4166 pBBR1MCS-2::ABM and *Pseudomonas fulva* DSM 17717 pBBR1MCS-2::ABM generated in Example 21 are cultured on LB agar kanamycin (50 µg/ml) plates. The subsequent culturing for the production of the rhamnolipids takes place as described in Example 12. The sample preparation for the following chromatographic analyses and the chromatographic analyses themselves are carried out as described in Example 4.

While the *Pseudomonas* strains *Pseudomonas fluorescens* DSM 50090, *Pseudomonas fluorescens* DSM 9958 pBBR1MCS-2, *Pseudomonas putida* DSM 6899 pBBR1MCS-2, *Pseudomonas putida* DSM 50204 pBBR1MCS-2, *Pseudomonas putida* 50194 pBBR1MCS-2, *P. brassicacearum* DSM 13227 pBBR1MCS-2, *P. stutzeri* DSM 10701 pBBR1MCS-2, *Pseudomonas stutzeri* DSM 4166 pBBR1MCS-2, *Pseudomonas fulva* DSM 17717 pBBR1MCS-2 produce no rhamnolipids, in the recombinant strains *Pseudomonas fluorescens* DSM 50090 pBBR1MCS-2::AB, *Pseudomonas fluorescens* DSM 9958 pBBR1MCS-2::AB, *Pseudomonas putida* DSM 6899 pBBR1MCS-2::AB, *Pseudomonas putida* DSM 50204 pBBR1MCS-2::AB, *Pseudomonas putida* 50194 pBBR1MCS-2::AB, *P. brassicacearum* DSM 13227 pBBR1MCS-2::AB, *P. stutzeri* DSM 10701 pBBR1MCS-2::AB, *Pseudomonas stutzeri* DSM 4166 pBBR1MCS-2::AB, *Pseudomonas fulva* DSM 17717 pBBR1MCS-2::AB, *Pseudomonas fluorescens* DSM 50090 pBBR1MCS-2::ABM, *Pseudomonas fluorescens* DSM 9958 pBBR1MCS-2::ABM, *Pseudomonas putida* DSM 6899 pBBR1MCS-2::ABM, *Pseudomonas putida* DSM 50204 pBBR1MCS-2::ABM, *Pseudomonas putida* 50194 pBBR1MCS-2::ABM, *P. brassicacearum* DSM 13227 pBBR1MCS-2::ABM, *P. stutzeri* DSM 10701 pBBR1MCS-2::ABM, *Pseudomonas stutzeri* DSM 4166 pBBR1MCS-2::ABM and *Pseudomonas fulva* DSM 17717 pBBR1MCS-2::ABM the formation of monorhamnosyl lipids and in the strains *Pseudomonas fluorescens* DSM 50090 pBBR1MCS-2::ABC, *Pseudomonas fluorescens* DSM 9958 pBBR1MCS-2::ABC, *Pseudomonas putida* DSM 6899 pBBR1MCS-2::ABC, *Pseudomonas putida* DSM 50204 pBBR1MCS-2::ABC, *Pseudomonas putida* 50194 pBBR1MCS-2::ABC, *P. brassicacearum* DSM 13227 pBBR1MCS-2::ABC, *P. stutzeri* DSM 10701 pBBR1MCS-2::ABC, *Pseudomonas stutzeri* DSM 4166 pBBR1MCS-2::ABC, *Pseudomonas fulva* DSM 17717 pBBR1MCS-2::ABC, *Pseudomonas fluorescens* DSM 50090 pBBR1MCS-2::ABCM, *Pseudomonas fluorescens* DSM 9958 pBBR1MCS-2::ABCM, *Pseudomonas putida* DSM 6899 pBBR1MCS-2::ABCM, *Pseudomonas putida* DSM 50204 pBBR1MCS-2::ABCM, *Pseudomonas putida* 50194 pBBR1MCS-2::ABCM, *P. Brassicacearum* DSM 13227 pBBR1MCS-2::ABCM, *P. stutzeri* DSM 10701 pBBR1MCS-2::ABCM, *Pseudomonas stutzeri* DSM 4166 pBBR1MCS-2::ABCM and *Pseudomonas fulva* DSM 17717 pBBR1MCS-2::ABCM the formation of mono- and dirhamnosyl lipids is detectable.

Moreover, fewer monorhamnosyl lipids are formed by the recombinant *Pseudomonas* strains *Pseudomonas fluorescens* DSM 50090 pBBR1MCS-2::ABM, *Pseudomonas fluore-* scens DSM 9958 pBBR1MCS-2::ABM, *Pseudomonas putida* DSM 6899 pBBR1MCS-2::ABM, *Pseudomonas putida* DSM 50204 pBBR1MCS-2::ABM, *Pseudomonas putida* 50194 pBBR1MCS-2::ABM, *P. brassicacearum* DSM 13227 pBBR1MCS-2::ABM, *P. stutzeri* DSM 10701 pBBR1MCS-2::ABM, *Pseudomonas stutzeri* DSM 4166 pBBR1MCS-2::ABM *Pseudomonas fulva* DSM 17717 pBBR1MCS-2::ABM and by the recombinant *Pseudomonas* strains *Pseudomonas fluorescens* DSM 50090 pBBR1MCS-2::ABCM, *Pseudomonas fluorescens* DSM 9958 pBBR1MCS-2::ABCM, *Pseudomonas putida* DSM 6899 pBBR1MCS-2::ABCM, *Pseudomonas putida* DSM 50204 pBBR1MCS-2::ABCM, *Pseudomonas putida* 50194 pBBR1MCS-2::ABCM, *P. brassicacearum* DSM 13227 pBBR1MCS-2::ABCM, *P. stutzeri* DSM 10701 pBBR1MCS-2::ABCM, *Pseudomonas stutzeri* DSM 4166 pBBR1MCS-2::ABCM and *Pseudomonas fulva* DSM 17717 pBBR1MCS-2::ABCM fewer mono- and dirhamnosyl lipids are formed than by the respective reference strains without the *P. aeruginosa* gene pa1131 *Pseudomonas fluorescens* DSM 50090 pBBR1MCS-2::AB, *Pseudomonas fluorescens* DSM 9958 pBBR1MCS-2::AB, *Pseudomonas putida* DSM 6899 pBBR1MCS-2::AB, *Pseudomonas putida* DSM 50204 pBBR1MCS-2::AB, *Pseudomonas putida* 50194 pBBR1MCS-2::AB, *P. brassicacearum* DSM 13227 pBBR1MCS-2::AB, *P. stutzeri* DSM 10701 pBBR1MCS-2::AB, *Pseudomonas stutzeri* DSM 4166 pBBR1MCS-2::AB and *Pseudomonas fulva* DSM 17717 pBBR1MCS-2::AB and *Pseudomonas fluorescens* DSM 50090 pBBR1MCS-2::ABC, *Pseudomonas fluorescens* DSM 9958 pBBR1MCS-2::ABC, *Pseudomonas putida* DSM 6899 pBBR1MCS-2::ABC, *Pseudomonas putida* DSM 50204 pBBR1MCS-2::ABC, *Pseudomonas putida* 50194 pBBR1MCS-2::ABC, *P. brassicacearum* DSM 13227 pBBR1MCS-2::ABC, *P. stutzeri* DSM 10701 pBBR1MCS-2::ABC, *Pseudomonas stutzeri* DSM 4166 pBBR1MCS-2::ABC and *Pseudomonas fulva* DSM 17717 pBBR1MCS-2::ABC without amplification of the pa1131 gene from *Pseudomonas aeruginosa*.

23. Construction of the Vectors pBBR1MCS-2::ABPAO1-C1 and pBBR1MCS-2::ABPA7-CE264 for the Heterologous Expression of Alternative rhIA, rhIB and rhIC Genes from *Pseudomonas aeruginosa* PAO1, *Pseudomonas aeruginosa* PA7, *Pseudomonas aeruginosa* 1 and *Burkholderia thailandensis* E264 in *P. putida*

For the heterologous expression of the genes rhIA, rhIB and rhIC from *Pseudomonas aeruginosa* PAO1 and *Pseudomonas aeruginosa* PA7, the plasmids pBBR1MCS-2::ABPAO1 (Seq ID No. 62) and pBBR1MCS-2::ABPA7 (Seq ID No. 63) are first constructed. For this, the synthetic operons rhIABPAO1 (Seq ID No. 64) and rhIABPA7 (Seq ID No. 65) are synthesized by the company DNA 2.0 (Menlo Park, Calif., U.S.A) and intercloned in the commercial vector pJ294 (DNA 2.0). The basis for the synthesis is the already known genomic sequence of the strains *Pseudomonas aeruginosa* PAO1 and *Pseudomonas aeruginosa* PA7. Starting from the vectors pJ294::ABPAO1 and pJ294::ABPA7, the synthetic operons are cleaved from the vectors by means of KpnI and XbaI and subsequently ligated into the expression vector pBBR1MCS-2 (Seq ID No. 49) (Kovach et al., 1995: Four new derivatives of the broad-host-range cloning vector pBBR1MCS carrying different antibiotic-resistance cassettes. Gene, 166:175-176) cleaved using KpnI and XbaI. The resulting plasmids pBBR1MCS-2::ABPAO1 (Seq ID No. 62) and pBBR1MCS-2::ABPA7 (Seq ID No. 63) are 7332 and 7354 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

In the second step, the plasmids pBBR1MCS-2::ABPAO1-C1 (Seq ID No. 66) and pBBR1MCS-2::ABPA7-CE264 (Seq ID No. 67) are produced. For this, the rhIC genes from *Pseudomonas aeruginosa* 1 (Seq ID No. 68) and *Burkholderia thailandensis* E264 (Seq ID No. 76) are synthesized by the company DNA 2.0 (Menlo Park, Calif., U.S.A) and intercloned in the commercial vector pJ294 (DNA 2.0). The basis for the synthesis is the already known genomic sequence of the strains *Pseudomonas aeruginosa* 1 and *Burkholderia thailandensis* E264. Starting from the vectors pJ294::C1 and pJ294::CE264, the rhIC genes are cleaved from the vectors by means of Xba and SacI and subsequently ligated into the vectors pBBR1MCS-2::ABPAO1 (Seq ID No. 62) and pBBR1MCS-2::ABPA7 (Seq ID No. 63) likewise cleaved using Xba and SacI. The resulting plasmids pBBR1MCS-2::ABPAO1-C1 (Seq ID No. 66) and pBBR1MCS-2::ABPA7-CE264 (Seq ID No. 67) are 8325 and 8335 base pairs in size. The ligation and the transformation of chemically competent *E. coli* DH5α cells (Gibco-BRL, Karlsruhe) takes place in the manner known to the person skilled in the art. The authenticity of the insert is checked by DNA sequence analysis.

The transformation of *Pseudomonas putida* KT2440 and GPp104 using the vectors pBBR1MCS-2, pBBR1MCS-2::ABPAO1-C1 and pBBR1MCS-2::ABPA7-CE264 takes place as previously described (Iwasaki et al. Biosci. Biotech. Biochem. 1994. 58(5):851-854). The plasmid DNA of every 10 clones was isolated and analyzed. The strains obtained carrying the plasmids are named *P. putida* KT2440 pBBR1MCS-2, *P. putida* KT2440 pBBR1MCS-2::ABPAO1-C1, *P. putida* KT2440 pBBR1MCS-2::ABPA7-CE264, *P. putida* GPp104 pBBR1MCS-2, *P. putida* GPp104 pBBR1MCS-2::ABPAO1-C1 and *P. putida* GPp104 pBBR1MCS-2::ABPA7-CE264.

24. Quantification of the Rhamnolipid Production by Recombinant *P. putida* Strains Having Alternative rhIA, rhIB and rhIC Genes from *Pseudomonas aeruginosa* PAO1, *Pseudomonas aeruginosa* PA7, *Pseudomonas aeruginosa* 1 and *Burkholderia thailandensis* E264

The recombinant strains *P. putida* strains generated in Example 23 are cultured on LB agar kanamycin (50 µg/ml) plates. The subsequent culturing for the production of the rhamnolipids takes place as described in Example 12. The sample preparation for the following chromatographic analyses and the chromatographic analyses themselves are carried out as described in Example 4.

While the strains *P. putida* KT2440 pBBR1MCS-2 and *P. putida* GPp104 pBBR1MCS-2 are not able to produce mono- and dirhamnosyl lipids, the strains *P. putida* KT2440 pBBR1MCS-2::ABPAO1-C1, *P. putida* KT2440 pBBR1MCS-2::ABPA7-CE264, *P. putida* GPp104 pBBR1MCS-2::ABPAO1-C1 and *P. putida* GPp104 pBBR1MCS-2::ABPA7-CE264 form both mono- as well as dirhamnosyl lipids. It is shown that the strains are able to produce more mono- and dirhamnosyl lipids with an attenuation of the polyhydroxybutyrate formation (*P. putida* GPp104 pBBR1MCS-2::ABPAO1-C1 and *P. putida*

GPp104 pBBR1MCS-2::ABPA7-CE264) than the strains without attenuation of the polyhydroxybutyrate formation (*P. putida* KT2440 pBBR1MCS-2::ABPAO1-C1 and *P. putida* KT2440 pBBR1MCS-2::ABPA7-CE264).

25. Construction of the Vectors pBBR1MCS-2::AB_rfbBDAC, pBBR1MCS-2::ABM_rfbBDAC and pBBR1MCS-2::ABMC_rfbBDAC for the Overexpression of the *P. putida* rfbBDAC Operon in *P. putida* and *E. coli*

For the construction of the vectors pBBR1MCS-2::AB_rfbBDAC, pBBR1MCS-2::ABM_rfbBDAC and pBBR1MCS-2::ABMC_rfbBDAC for the overexpression of the *P. putida* rfbBDAC operon in *P. putida* and *E. coli*, the *P. putida* rfbBDAC operon was first amplified by PCR. The vector pBBR1MCS-2::rfbBDAC (Seq ID No. 45) served as matrix for a PCR. The following oligonucleotides were used:

```
RL_AgeI-fw:
                                       (Seq ID No. 71)
5'-TATATATAACCGGTATTAATGCAGCTGGCACGAC-3'

RL_AgeI_rev:
                                       (Seq ID No. 72)
5'-GGCCGACCGGTACTAGTGGA-3'
```

The PCR was carried out using the Phusion™ High-Fidelity Master Mix of New England Biolabs (Frankfurt) polymerase. It took place in the manner known to the person skilled in the art. The target sequence (lac promoter and rfbBDAC) was intercloned in the Trenzyme alligator cloning system. *E. coli* DH5α (New England Biolabs; Frankfurt) transformants were selected and the plasmid DNA of different candidates was isolated and sequenced. After the sequence had been checked and examined for correctness, the vector was cleaved using AgeI. The target fragment was ligated into the vectors pBBR1MCS-2::AB (Seq ID No. 38), pBBR1MCS-2::ABM (Seq ID No. 42) and pBBR1MCS-2::ABMC (Seq ID No. 51) likewise cleaved using AgeI by means of conventional ligation methods. The resulting vectors pBBR1MCS-2::AB_rfbBDAC (Seq ID No. 73), pBBR1MCS-2::ABM_rfbBDAC (Seq ID No. 74) and pBBR1MCS-2::ABMC_rfbBDAC (Seq ID No. 75) have sizes of 11960, 13289 and 14250 base pairs. The inserts of the vectors were sequenced. The carrying-out of the PCR, the checking of the successful amplification of the PCR by means of agarose gel electrophoresis, ethidium bromide staining of the DNA, determination of the PCR fragment size, purification of the PCR products and DNA concentration determination took place in the manner known to the person skilled in the art. The transformation of *Pseudomonas putida* KT2440 using the vectors pBBR1MCS-2::AB_rfbBDAC, pBBR1MCS-2::ABM_rfbBDAC and pBBR1MCS-2::ABMC_rfbBDAC took place as previously described (Iwasaki et al. Biosci. Biotech. Biochem. 1994. 58(5):851-854). The plasmid DNA of every 10 clones was isolated and analyzed. The strains obtained carrying the plasmids are named *P. putida* KT2440 pBBR1MCS-2::AB_rfbBDAC, *P. putida* KT2440 pBBR1MCS-2::ABM_rfbBDAC and *P. putida* KT2440 pBBR1MCS-2::ABMC_rfbBDAC.

26. Quantification of the Rhamnolipid Production by Recombinant *P. putida* KT2440 pBBR1MCS-2::AB_rfbBDAC, *P. putida* KT2440 pBBR1MCS-2::ABM_rfbBDAC, *P. putida* KT2440 pBBR1MCS-2::ABC_rfbBDAC, *P. putida* KT2440 pBBR1MCS-2::ABMC_rfbBDAC, *P. putida* KT2440 pBBR1MCS-2::AB, *P. putida* KT2440 pBBR1MCS-2::ABM, *P. putida* KT2440 pBBR1MCS-2::ABC and *P. putida* KT2440 pBBR1MCS-2::ABMC The recombinant strains *P. putida* strains generated in the Examples 2, 7 and 25 are cultured on LB agar-kanamycin (50 µg/ml) plates. The subsequent culturing for the production of the rhamnolipids takes place as described in Example 12. The sample preparation for the following chromatographic analyses and the chromatographic analyses themselves take place as described in Example 4.

It is shown that *P. putida* KT2440 pBBR1MCS-2::AB_rfbBDAC, *P. putida* KT2440 pBBR1MCS-2::ABM_rfbBDAC, *P. putida* KT2440 pBBR1MCS-2::AB and *P. putida* KT2440 pBBR1MCS-2::ABM are able to form monorhamnosyl lipids, while *P. putida* KT2440 pBBR1MCS-2::ABMC_rfbBDAC, *P. putida* KT2440 pBBR1MCS-2::ABC_rfbBDAC, *P. putida* KT2440 pBBR1MCS-2::ABC and *P. putida* KT2440 pBBR1MCS-2::ABMC are able to form mono- and dirhamnosyl lipids.

Furthermore, it is shown that *P. putida* KT2440 pBBR1MCS-2::ABM_rfbBDAC, *P. putida* KT2440 pBBR1MCS-2::ABM, KT2440 pBBR1MCS-2::ABMC_rfbBDAC and KT2440 pBBR1MCS-2::ABMC are able to form more mono- and dirhamnosyl lipids than the corresponding control strains *P. putida* KT2440 pBBR1MCS-2::AB_rfbBDAC, *P. putida* KT2440 pBBR1MCS-2::AB, KT2440 pBBR1MCS-2::ABC_rfbBDAC and KT2440 pBBR1MCS-2::ABC without amplification of the *Pseudomonas aeruginosa* gene pa1131.

Finally, it is shown that *P. putida* KT2440 pBBR1MCS-2::AB_rfbBDAC, *P. putida* KT2440 pBBR1MCS-2::ABM_rfbBDAC, *P. putida* KT2440 pBBR1MCS-2::ABC_rfbBDAC, *P. putida* KT2440 pBBR1MCS-2::ABMC_rfbBDAC are able to form more mono- (*P. putida* KT2440 pBBR1MCS-2::AB_rfbBDAC and *P. putida* KT2440 pBBR1MCS-2::ABM_rfbBDAC) and mono- and dirhamnosyl lipids (*P. putida* KT2440 pBBR1MCS-2::ABC_rfbBDAC and *P. putida* KT2440 pBBR1MCS-2::ABMC_rfbBDAC) than the respective control strains *P. putida* KT2440 pBBR1MCS-2::AB, *P. putida* KT2440 pBBR1MCS-2::ABM, *P. putida* KT2440 pBBR1MCS-2::ABC, *P. putida* KT2440 pBBR1MCS-2::ABMC without amplification of the *P. putida* genes rfbBDAC.

27. Generation of Recombinant *E. coli* W3110 pBBR1MCS-2::AB, *E. coli* W3110 pBBR1MCS-2::ABM, *E. coli* W3110 pBBR1MCS-2::ABC, *E. coli* W3110 pBBR1MCS-2::ABCM, *E. coli* W3110 pBBR1MCS-2::AB_rfbBDAC, *E. coli* W3110 pBBR1MCS-2::ABM_rfbBDAC, *E. coli* W3110 pBBR1MCS-2::ABC_rfbBDAC and *E. coli* W3110 pBBR1MCS-2::ABCM_rfbBDAC The transformation of *E. coli* W3110 took place as described previously (Miller J H. A Short Course in Bacterial Genetics: A Laboratory Manual and Handbook for *Escherichia coli* and Related Bacteria. Plainview, N.Y.: Cold Spring Harbor Lab. Press; 1992) by means of electroporation. The plasmid DNA of every 10 clones was isolated and analyzed. The obtained strains carrying the plasmids were named *E. coli* W3110 pBBR1MCS-2::AB, *E. coli* W3110 pBBR1MCS-2::ABM, *E. coli* W3110 pBBR1MCS-2::ABC, *E. coli* W3110 pBBR1MCS-2::ABCM, *E. coli* W3110 pBBR1MCS-2::AB_rfbBDAC, *E. coli* W3110 pBBR1MCS-2::ABM_rfbBDAC, *E. coli* W3110 pBBR1MCS-2::ABC_rfbBDAC and *E. coli* W3110 pBBR1MCS-2::ABCM_rfbBDAC.

28. Quantification of the Rhamnolipid Production by Recombinant *E. coli* W3110 pBBR1MCS-2::AB, *E. coli* W3110 pBBR1MCS-2::ABM, *E. coli* W3110 pBBR1MCS-2::ABC, *E. coli* W3110 pBBR1MCS-2::ABCM, *E. coli* W3110 pBBR1MCS-2::AB_rfbBDAC, *E. coli* W3110 pBBR1MCS-2::ABM_rfbBDAC, *E. coli* W3110 pBBR1MCS-2::ABC_rfbBDAC and *E. coli* W3110 pBBR1MCS-2::ABCM_rfbBDAC The recombinant *E. coli* strains generated in Example 27 are cultured on LB agar kanamycin (50 µg/ml) plates. The subsequent culturing for the production of the rhamnolipids takes place as described in Example 10. The sample preparation for the following chromatographic analyses and the chromatographic analyses themselves take place as described in Example 4.

It is shown that *E. coli* W3110 pBBR1MCS-2::AB, *E. coli* W3110 pBBR1MCS-2::ABM, *E. coli* W3110 pBBR1MCS-2::AB_rfbBDAC and *E. coli* W3110 pBBR1MCS-2::ABM_rfbBDAC are able to form monorhamnosyl lipids, while *E. coli* W3110 pBBR1MCS-2::ABC, *E. coli* W3110 pBBR1MCS-2::ABCM, *E. coli* W3110 pBBR1MCS-2::AB-C_rfbBDAC and *E. coli* W3110 pBBR1MCS-2::ABCM_rfbBDAC are able to form mono- and dirhamnosyl lipids. Furthermore, it is shown that *E. coli* W3110 pBBR1MCS-2::ABM and *E. coli* W3110 pBBR1MCS-2::ABM_rfbBDAC form more monorhamnosyl lipids than *E. coli* W3110 pBBR1MCS-2::AB and *E. coli* W3110 pBBR1MCS-2::AB_rfbBDAC without amplification of the *Pseudomonas aeruginosa* gene pa1131.

Furthermore, it is shown that *E. coli* W3110 pBBR1MCS-2::ABCM and *E. coli* W3110 pBBR1MCS-2::ABCM_rfbBDAC form more mono- and dirhamnosyl lipids than *E. coli* W3110 pBBR1MCS-2::ABC and *E. coli* W3110 pBBR1MCS-2::ABC_rfbBDAC without amplification of the *Pseudomonas aeruginosa* gene pa1131. Furthermore, it is shown that *E. coli* W3110 pBBR1MCS-2::ABM and *E. coli* W3110 pBBR1MCS-2::ABM_rfbBDAC form more monorhamnosyl lipids than *E. coli* W3110 pBBR1MCS-2::AB and *E. coli* W3110 pBBR1MCS-2::AB_rfbBDAC without amplification of the *Pseudomonas aeruginosa* gene pa1131.

Finally, it is shown that *E. coli* W3110 pBBR1MCS-2::AB_rfbBDAC, *E. coli* W3110 pBBR1MCS-2::ABM_rfbBDAC, *E. coli* W3110 pBBR1MCS-2::ABC_rfbBDAC and *E. coli* W3110 pBBR1MCS-2::ABCM_rfbBDAC are able to form more mono- (*E. coli* W3110 pBBR1MCS-2::AB_rfbBDAC, *E. coli* W3110 pBBR1MCS-2::ABM_rfbBDAC) and mono- and dirhamnosyl lipids (*E. coli* W3110 pBBR1MCS-2::ABC_rfbBDAC and *E. coli* W3110 pBBR1MCS-2::ABCM_rfbBDAC) than the respective control strains *E. coli* W3110 pBBR1MCS-2::AB, *E. coli* W3110 pBBR1MCS-2::ABM, *E. coli* W3110 pBBR1MCS-2::ABC and *E. coli* W3110 pBBR1MCS-2::ABCM without amplification of the *P. putida* genes rfbBDAC.

---

The invention claimed is:
1. A genetically modified cell, which is able to form at least one rhamnolipid of general formula (I),

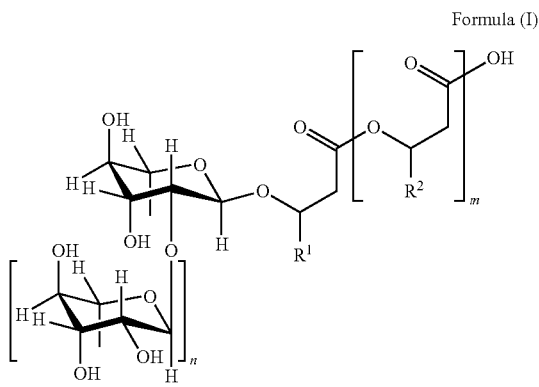

Formula (I)

wherein
m=2, 1 or 0,
n=1 or 0,
$R^1$ and $R^2$ are organic residues having 2 to 24 carbon atoms,
said cell having been genetically modified such that, compared to its wild-type, the cell has increased activity of at least one of the enzymes $E_1$, $E_2$ and $E_3$, wherein:
the enzyme $E_1$ has at least 95% amino acid identity to a sequence selected from SEQ ID NO: 18, 78, 80, 82, or 2;
the enzyme $E_2$ has at least 95% amino acid identity to a sequence selected from SEQ ID NO: 20, 84, 86, 88, or 4;
the enzyme $E_3$ has at least 95% amino acid identity to a sequence selected from SEQ ID NO: 22, 90, 92, or 6;
wherein said cell, compared to its wild-type further has increased activity of an enzyme $E_8$, which catalyses rhamnolipid export from the cell into the surrounding medium; and
wherein $E_8$ has at least 95% amino acid identity to SEQ ID NO: 8.

2. The genetically modified cell of claim 1, wherein said cell has increased activities of an enzyme combination selected from $E_1E_2$, $E_2E_3$ and $E_1E_2E_3$.

3. The genetically modified cell of claim 2, wherein said cell has an increased activity of the enzyme combination $E_1E_2E_3$ and n is =1.

4. The genetically modified cell of claim 1, wherein said cell is selected from a genus of the group consisting of Aspergillus, Corynebacterium, Brevibacterium, Bacillus, Acinetobacter, Alcaligenes, Lactobacillus, Paracoccus, Lactococcus, Candida, Pichia, Hansenula, Kluyveromyces, Saccharomyces, Escherichia, Zymomonas, Yarrowia, Methylobacterium, Ralstonia, Pseudomonas, Rhodospirillum, Rhodobacter, Burkholderia, Clostridium and Cupriavidus.

5. The genetically modified cell of claim 1, wherein said cell is a bacterial cell.

6. The genetically modified cell of claim 1, wherein the wild-type of said cell forms polyhydroxyalkanoates having chain lengths of $C_6$ to $C_{16}$.

7. The genetically modified cell of claim 6, wherein said cell, compared to its wild-type, has a decreased activity of at least one enzyme $E_9$ or $E_{10}$, wherein
$E_9$ has at least 95% identity to the amino acid sequence of SEQ ID NO: 30 or SEQ ID NO: 32, and
$E_{10}$ has at least 95% identity to the amino acid sequence of SEQ ID NO: 34 or SEQ ID NO: 36.

8. The genetically modified cell of claim 1, wherein said cell, compared to its wild-type, has increased activity of at least one enzyme selected from the group consisting of:
$E_4$, which has at least 95% amino acid identity to SEQ ID NO: 10,
$E_5$, which has at least 95% amino acid identity to SEQ ID NO: 12,
$E_6$, which has at least 95% amino acid identity to SEQ ID NO: 16, and
$E_7$, which has at least 95% amino acid identity to SEQ ID NO: 14.

9. The genetically modified cell of claim 8, wherein said cell has increased activity of each of the enzymes $E_4$, $E_5$, $E_6$, and $E_7$.

10. The genetically modified cell of claim 1, wherein said genetic modification comprises introduction into said cell of at least one vector comprising at least one nucleic acid sequence selected from:
a sequence with at least 95% identity to SEQ ID NO: 17, 77, 79, 81, or 1;
a sequence with at least 95% identity to SEQ ID NO: 19, 83, 85, 87, or 3; and
a sequence with at least 95% identity to SEQ ID NO: 21, 89, 91, or 5.

11. A method for producing rhamnolipids of general formula (I)

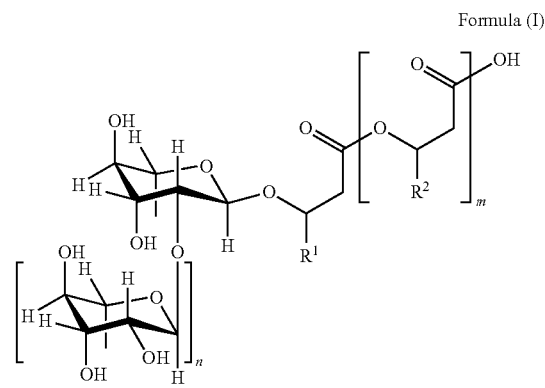

Formula (I)

wherein
m=2, 1 or 0,
n=1 or 0
$R^1$ and $R^2$ are organic residues having 2 to 24 carbon atoms,
said method comprising:
I) contacting the genetically modified cell of claim 1 with a medium containing a carbon source; and
II) culturing the cell under conditions in which the cell forms rhamnolipids from the carbon source.

* * * * *

UNITED STATES PATENT AND TRADEMARK OFFICE
CERTIFICATE OF CORRECTION

PATENT NO. : 9,580,720 B2  
APPLICATION NO. : 14/642879  
DATED : February 28, 2017  
INVENTOR(S) : Steffen Schaffer et al.

Page 1 of 1

It is certified that error appears in the above-identified patent and that said Letters Patent is hereby corrected as shown below:

Related U.S. Application Data should read:
(62) Division of application No. 13/812,625, filed as application No. PCT/EP2011/062441 on July 20, 2011, now Pat. No. 9,005,928.

Signed and Sealed this
Ninth Day of May, 2017

Michelle K. Lee
*Director of the United States Patent and Trademark Office*